US012735400B2

(12) United States Patent
Kysil et al.

(10) Patent No.: US 12,735,400 B2
(45) Date of Patent: Sep. 15, 2026

(54) BCL-2 INHIBITORS

(71) Applicant: Eil Therapeutics, Inc., Dover, DE (US)

(72) Inventors: Volodymyr Kysil, San Diego, CA (US); Vladislav Zenonovich Parchinsky, Moscow (RU); Alexei Pushechnikov, San Diego, CA (US); Alexandre Vasilievich Ivachtchenko, Hallandale Beach, FL (US); Ruben Abagyan, La Jolla, CA (US); Nikolay Savchuk, San Diego, CA (US)

(73) Assignee: Eli Therapeutics, Inc., Dover, DE (US)

( * ) Notice: Subject to any disclaimer, the term of this patent is extended or adjusted under 35 U.S.C. 154(b) by 272 days.

(21) Appl. No.: 18/725,057

(22) PCT Filed: Dec. 27, 2022

(86) PCT No.: PCT/US2022/054091
§ 371 (c)(1),
(2) Date: Jun. 27, 2024

(87) PCT Pub. No.: WO2023/129553
PCT Pub. Date: Jul. 6, 2023

(65) Prior Publication Data

US 2025/0115577 A1 Apr. 10, 2025

Related U.S. Application Data

(60) Provisional application No. 63/415,203, filed on Oct. 11, 2022, provisional application No. 63/294,646, filed on Dec. 29, 2021.

(51) Int. Cl.

| | |
|---|---|
| ***C07D 401/14*** | (2006.01) |
| ***A61K 31/5377*** | (2006.01) |
| ***C07D 401/10*** | (2006.01) |
| ***C07D 471/04*** | (2006.01) |

(52) U.S. Cl.
CPC ........ *C07D 401/14* (2013.01); *A61K 31/5377* (2013.01); *C07D 401/10* (2013.01); *C07D 471/04* (2013.01)

(58) Field of Classification Search
CPC .. C07D 401/14; C07D 401/10; C07D 471/04; A61K 31/5377
See application file for complete search history.

(56) References Cited

U.S. PATENT DOCUMENTS 10,265,323 B2 * 4/2019 Le Tiran ................ A61P 43/00
2017/0202851 A1 7/2017 Le Tiran et al.

FOREIGN PATENT DOCUMENTS

| | | |
|---|---|---|
| WO | WO2015/011397 | 1/2015 |
| WO | WO2015/011399 | 1/2015 |
| WO | WO2015/011400 | 1/2015 |

* cited by examiner

*Primary Examiner* — Kamal A Saeed
(74) *Attorney, Agent, or Firm* — Sergey Alyabyev

(57) ABSTRACT

The present invention is generally directed to inhibitors of BCL-2 proteins useful in the treatment of diseases and disorders modulated by said enzyme and having the Formula (I):

(I)

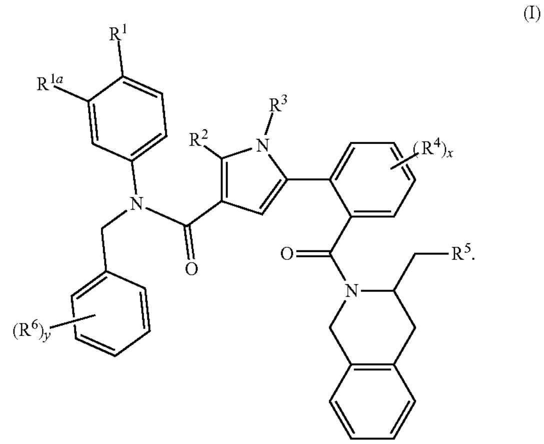

19 Claims, No Drawings

BCL-2 INHIBITORS

CROSS-REFERENCE TO RELATED APPLICATIONS

This application claims priority to, and the benefit of, U.S. Provisional Patent Application Ser. No. 63/294,646 filed Dec. 29, 2021 entitled "BCL-2 INHIBITORS" and U.S. Provisional Patent Application Ser. No. 63/415,203 filed Oct. 11, 2022 entitled "BCL-2 INHIBITORS," the disclosures of which are incorporated herein by reference in their entireties for all purposes.

FIELD OF INVENTION

The present invention is directed to inhibitors of B-cell lymphoma 2 (BCL-2) proteins. The inhibitors described herein can be useful in the treatment of diseases or disorders associated with BCL-2. In particular, the invention is concerned with compounds and pharmaceutical compositions inhibiting BCL-2, methods of treating diseases or disorders associated with BCL-2, and methods of synthesizing these compounds.

BACKGROUND OF THE INVENTION

Apoptosis, or programmed cell death, is a physiological process that is crucial for embryonic development and maintenance of tissue homeostasis (U.S. Pat. No. 9,120,791)

Deregulation of apoptosis is involved in certain pathologies. Increased apoptosis is associated with neurodegenerative diseases such as Parkinson's disease, Alzheimer's disease and ischaemia. Id. Conversely, deficits in the implementation of apoptosis play a significant role in the development of cancers and their chemoresistance, in autoimmune diseases, inflammatory diseases and viral infections. Accordingly, absence of apoptosis is one of the phenotypic signatures of cancer (Hanahan, D. et al, Cell, 2000, 100, 57-70)

The BCL-2 family of proteins plays a major role in tumorogenesis (WO 2018/102, 766). BCL-2 proteins are characterized based on the presence of Bel-2 homology (BH) domains. The anti-apoptotic proteins contain all the BH1-4 domains; the pro-apoptotic proteins contain either the BH3 domain only or multiple BH domains. The BH3 domain is necessary in executing the pro apoptotic function of these proteins. In anti-apoptotic proteins, the BH3 domain remains hidden or buried inside other BH domains and hence they exclusively function as protectors of cell survival. The BCL-2 proteins use BH domains to interact with each other. The anti-apoptotic BCL-2 proteins interact with pro-apoptotic members and inhibit their function to maintain cellular homeostasis. It is the shift in balance between anti-apoptotic and pro-apoptotic BCL-2 proteins that may decide the fate of cancer cells.

Cancer therapeutics targeting the BCL-2 family mainly have focused on neutralizing one or more anti-apoptotic members by inhibiting their function using small molecule inhibitors or by suppressing their expression utilizing antisense oligonucleotides (WO 2018/102,766). The concept was to inhibit the anti-apoptotic Bel-2 members' function and thus allowing pro-apoptotic members to induce cell death in cancer cells. Id. However, cancer cells treated with Bcl-2 inhibitors were found to upregulate other anti-apoptotic BCL-2 or non-BCL-2 family proteins involved in cell survival, resulting in therapeutic resistance.

There is a need for therapeutic agents that can induce cell death in tumors or cancers with increased expression of Bcl-2. This invention is intended to fill this unmet needs associated with current BCL-2 inhibition therapy.

SUMMARY OF THE INVENTION

A first aspect of the invention relates to compounds of Formula (I):

(I)

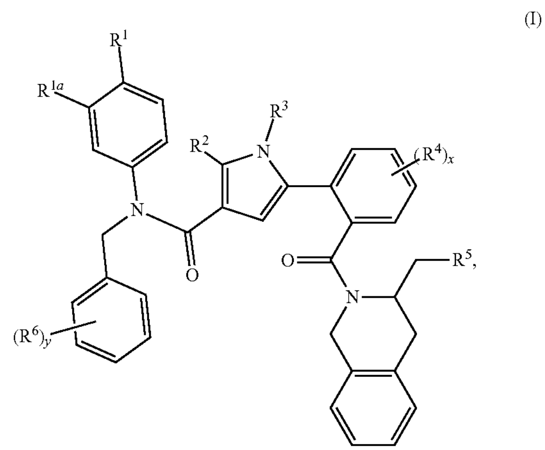

or a pharmaceutically acceptable salt, stereoisomer, solvate, prodrug, or tautomer thereof, wherein:

$R^1$ is selected from halogen, —OH, —CN, and —$CONH_2$;

$R^{1a}$ is H;

or $R^1$ and $R^{1a}$, together with the atom to which they are attached, come together to form a 3- to 10-membered heteroaryl ring further comprising 1, 2, or 3 heteroatoms selected from N, O, and S;

$R^2$ and $R^3$ each independently selected from $C_1$-$C_6$ alkyl;

or $R^2$ and $R^3$, together with the atom to which they are attached, come together to form a 3- to 10-membered heterocyclyl ring further comprising 1, 2, or 3 heteroatoms selected from N, O, and S;

each $R^4$ is independently selected from halogen, —OH, —CN, —$NO_2$, —COOH, —$CH_2CN$, $CH_2N(R^8)_2$, $C_1$-$C_6$ alkyl, $C_1$-$C_6$ alkoxy, $C_1$-$C_6$ halogenalkyl, $C_1$-$C_6$ halogenalkoxy, —O—($C_2$-$C_6$ alkenyl), —O—($C_2$-$C_6$ alkynyl), $C_2$-$C_6$ alkenyl, $C_2$-$C_6$ alkynyl, —OH, —OP(O)$(OH)_2$, —OC(O)($C_1$-$C_6$ alkyl), —C(O)($C_1$-$C_6$ alkyl), —OC(O)O($C_1$-$C_6$ alkyl), —$NH_2$, —NH($C_1$-$C_6$ alkyl), —N($C_1$-$C_6$ alkyl)$_2$, —NHC(O)($C_1$-$C_6$ alkyl), —C(O)$NH_2$, —C(O)NH($C_1$-$C_6$ alkyl), —S(O)$_2$ ($C_1$-$C_6$ alkyl), —S(O)NH($C_1$-$C_6$ alkyl), and S(O)N($C_1$-$C_6$ alkyl)$_2$;

$R^5$ is selected from

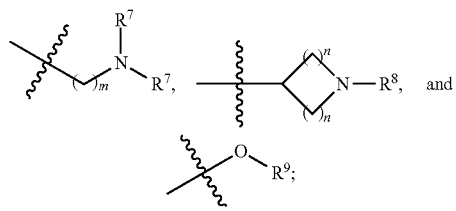

each $R^6$ is independently selected from halogen, —OH, —CN, —COOH, —$CH_2CN$, —$CH_2N(R^8)_2$, $C_1$-$C_6$ alkyl, $C_1$-$C_6$ alkoxy, $C_1$-$C_6$ halogenalkyl, $C_1$-$C_6$ halogenalkoxy, —O—($C_2$-$C_6$)alkenyl, —O—($C_2$-$C_6$)alkynyl, $C_2$-$C_6$ alkenyl, $C_2$-$C_6$ alkynyl, —OH, —OP(O)$(OH)_2$, —OC(O)($C_1$-$C_6$)alkyl, —C(O)($C_1$-$C_6$)alkyl, —OC(O)O($C_1$-$C_6$)alkyl, —$NH_2$, —NH($C_1$-$C_6$ alkyl), —N($C_1$-$C_6$ alkyl)$_2$, —NHC(O)($C_1$-$C_6$)alkyl, —C(O)NH($C_1$-$C_6$)alkyl, —S(O)$_2$ ($C_1$-$C_6$)alkyl, —S(O)NH($C_1$-$C_6$)alkyl, and S(O)N($C_1$-$C_6$ alkyl)$_2$;

each $R^7$ is independently selected from H, $C_{1-6}$ alkyl, $C_{2-6}$ alkenyl, $C_{2-6}$ alkynyl, aryl;

wherein alkyl or aryl is optionally substituted with one or more substituents independently selected from halogen, —OH, —CN, —COOH, —$CH_2CN$, —$CH_2N(R^8)_2$, $C_1$-$C_6$ alkyl, $C_1$-$C_6$ alkoxy, $C_1$-$C_6$ halogenalkyl, $C_1$-$C_6$ halogenalkoxy, —O—($C_2$-$C_6$)alkenyl, —O—($C_2$-$C_6$)alkynyl, $C_2$-$C_6$ alkenyl, $C_2$-$C_6$ alkynyl, —OH, —OP(O)$(OH)_2$, —OC(O)($C_1$-$C_6$)alkyl, —C(O)($C_1$-$C_6$)alkyl, —OC(O)O($C_1$-$C_6$)alkyl, —$NH_2$, —NH($C_1$-$C_6$ alkyl), —N($C_1$-$C_6$ alkyl)$_2$, —NHC(O)($C_1$-$C_6$)alkyl, —C(O)NH($C_1$-$C_6$)alkyl, —S(O)$_2$ ($C_1$-$C_6$)alkyl, —S(O)NH($C_1$-$C_6$)alkyl, and S(O)N($C_1$-$C_6$ alkyl)$_2$;

or two $R^7$ together with the nitrogen atom to which they are bound and any intervening atoms, form a heterocycle;

wherein heterocycle is optionally substituted with one or more substituents independently selected from halogen, —OH, —CN, —COOH, —$CH_2CN$, —$CH_2N(R^8)_2$, $C_1$-$C_6$ alkyl, $C_1$-$C_6$ alkoxy, $C_1$-$C_6$ halogenalkyl, $C_1$-$C_6$ halogenalkoxy, —O—($C_2$-$C_6$)alkenyl, —O—($C_2$-$C_6$)alkynyl, $C_2$-$C_6$ alkenyl, $C_2$-$C_6$ alkynyl, —OH, —OP(O)$(OH)_2$, —OC(O)($C_1$-$C_6$)alkyl, —C(O)($C_1$-$C_6$)alkyl, —OC(O)O($C_1$-$C_6$) alkyl, —$NH_2$, —NH($C_1$-$C_6$ alkyl), —N($C_1$-$C_6$ alkyl)$_2$, —NHC(O)($C_1$-$C_6$)alkyl, —C(O)NH($C_1$-$C_6$)alkyl, —S(O)$_2$ ($C_1$-$C_6$)alkyl, —S(O)NH($C_1$-$C_6$)alkyl, and S(O)N($C_1$-$C_6$ alkyl)$_2$;

$R^8$ is selected from H, $C_{1-6}$ alkyl, $C_{3-8}$ cycloalkyl, aryl, $C_{1-6}$ halogenalkyl;

$R^9$ is selected from $C_{1-6}$ alkyl, $C_{2-6}$ alkenyl, $C_{2-6}$ alkynyl, —$(CH_2)_{1-6}OR^8$, $C_{3-8}$ cycloalkyl, aryl, heterocycle;

wherein alkyl, cycloalkyl, aryl or heterocycle are optionally substituted with one or more substituents independently selected from halogen, —OH, —CN, —COOH, —$CH_2CN$, $C_1$-$C_6$ alkyl, $C_1$-$C_6$ alkoxy, $C_1$-$C_6$ halogenalkyl, $C_1$-$C_6$ halogenalkoxy, —O—($C_2$-$C_6$)alkenyl, —O—($C_2$-$C_6$)alkynyl, $C_2$-$C_6$ alkenyl, $C_2$-$C_6$ alkynyl, —OH, —OP(O)$(OH)_2$, —OC(O)($C_1$-$C_6$)alkyl, —C(O)($C_1$-$C_6$)alkyl, —OC(O)O($C_1$-$C_6$)alkyl, —$NH_2$, —NH($C_1$-$C_6$ alkyl), —N($C_1$-$C_6$ alkyl)$_2$, —NHC(O)($C_1$-$C_6$)alkyl, —C(O)NH($C_1$-$C_6$)alkyl, —S(O)$_2$ ($C_1$-$C_6$)alkyl, —S(O)NH($C_1$-$C_6$)alkyl, and S(O)N($C_1$-$C_6$ alkyl)$_2$;

wherein, x is an integer selected from 0, 1, 2, 3;

y is an integer selected from 0, 1, 2, 3;

m is an integer selected from 0, 1, and 2;

each n is an integer independently selected from 1, 2, 3;

aryl is cyclic, aromatic hydrocarbon groups that have 1 to 3 aromatic rings;

heterocycle is saturated or partially unsaturated 3-10 membered monocyclic, 7-12 membered bicyclic (fused, bridged, or spiro rings), or 11-14 membered tricyclic ring system (fused, bridged, or spiro rings) having one or more heteroatoms selected from O, N, S, P, Se, and B.

Another aspect of the invention is directed to pharmaceutical compositions comprising a compound of Formula (I), or a pharmaceutically acceptable salt, hydrate, solvate, prodrug, stereoisomer, or tautomer thereof and a pharmaceutically acceptable carrier. The pharmaceutical acceptable carrier may further include an excipient, diluent, or surfactant.

Another aspect of the invention relates to a method of treating a disease or disorder associated with modulation of BCL-2 proteins, such as Isoform 1 and Isoform 2. The method comprises administering to a patient in need of a treatment for diseases or disorders associated with modulation of BCL-2 proteins an effective amount of a compound of Formula (I), or a pharmaceutically acceptable salt, hydrate, solvate, prodrug, stereoisomer, tautomer, or pharmaceutical composition thereof.

Another aspect of the invention is directed to a method of inhibiting BCL-2 proteins including, but not limited to Isoform 1 and Isoform 2. The method involves administering to a patient in need thereof an effective amount of a compound of Formula (I), or a pharmaceutically acceptable salt, hydrate, solvate, prodrug, stereoisomer, tautomer, or pharmaceutical composition thereof.

Another aspect of the invention is directed to a method of treating or preventing a disease or disorder disclosed herein in a subject in need thereof. The method involves administering to a patient in need thereof an effective amount of a compound of Formula (I), or a pharmaceutically acceptable salt, hydrate, solvate, prodrug, stereoisomer, tautomer, or pharmaceutical composition thereof.

Another aspect of the present invention relates to compounds of Formula (I), and pharmaceutically acceptable salts, hydrates, solvates, prodrugs, stereoisomers, tautomers, or pharmaceutical compositions thereof, for use in the manufacture of a medicament for inhibiting BCL-2 proteins, such as Isoform 1 and Isoform 2.

Another aspect of the present invention relates to compounds of Formula (I), and pharmaceutically acceptable salts, hydrates, solvates, prodrugs, stereoisomers, tautomers, or pharmaceutical compositions thereof, for use in the manufacture of a medicament for treating or preventing a disease or disorder disclosed herein.

Another aspect of the present invention relates to the use of a compound of Formula (I), or a pharmaceutically acceptable salt, hydrate, solvate, prodrug, stereoisomer, tautomer, or pharmaceutical composition thereof, in the treatment of a disease associated with inhibiting BCL-2 proteins, such as Isoform 1 and Isoform 2.

Another aspect of the present invention relates to the use of a compound of Formula (I), or a pharmaceutically acceptable salt, hydrate, solvate, prodrug, stereoisomer, tautomer, or pharmaceutical composition thereof, in the treatment of a disease or disorder disclosed herein.

The present invention further provides methods of treating a disease or disorder associated with modulation of BCL-2 proteins including, cancer and metastasis, comprising administering to a patient suffering from at least one of said diseases or disorders a compound of Formula (I), or a pharmaceutically acceptable salt, hydrate, solvate, prodrug, stereoisomer, tautomer, or pharmaceutical composition thereof.

The present invention provides inhibitors of BCL-2 proteins that are therapeutic agents in the treatment of diseases such as cancer and metastasis.

The present invention further provides compounds and compositions with an improved efficacy and safety profile relative to known BCL-2 protein inhibitors. The present disclosure also provides agents with novel mechanisms of action toward BCL-2 protein in the treatment of various types of diseases including cancer and metastasis.

In some aspects, the present disclosure provides a compound obtainable by, or obtained by, a method for preparing compounds described herein (e.g., a method comprising one or more steps described in General Procedures).

In some aspects, the present disclosure provides an intermediate as described herein, being suitable for use in a method for preparing a compound as described herein (e.g., the intermediate is selected from the intermediates described in Preparations 1-168)

In some aspects, the present disclosure provides a method of preparing a compound of the present disclosure.

In some aspects, the present disclosure provides a method of preparing a compound, comprising one or more steps described herein.

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar or equivalent to those described herein can be used in the practice or testing of the present disclosure, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting. In the case of conflict between the chemical structures and names of the compounds disclosed herein, the chemical structures will control.

Other features and advantages of the disclosure will be apparent from the following detailed description and claims

DETAILED DESCRIPTION OF THE INVENTION

The present disclosure relates to compounds and compositions that are capable of inhibiting the activity BCL-2 proteins including, but not limited to Isoform 1 and Isoform 2. The disclosure features methods of treating, preventing or ameliorating a disease or disorder in which BCL-2 plays a role by administering to a patient in need thereof a therapeutically effective amount of a compound of Formula (I), or a pharmaceutically acceptable salt, hydrate, solvate, prodrug, stereoisomer, or tautomer thereof. The methods of the present invention can be used in the treatment of a variety of BCL-2 mediated diseases and disorders by inhibiting the activity of BCL-2 proteins. Inhibition of BCL-2 can be an effective approach to the treatment, prevention, or amelioration of diseases including, but not limited to, cancer and metastasis. Decreasing BCL-2 activity can suppress cancer mutagenesis, dampen tumor evolution, and/or decrease the probability of adverse outcomes, such as drug resistance and/or metastases.

In a first aspect of the invention, the compounds of Formula (I) are described:

(I)

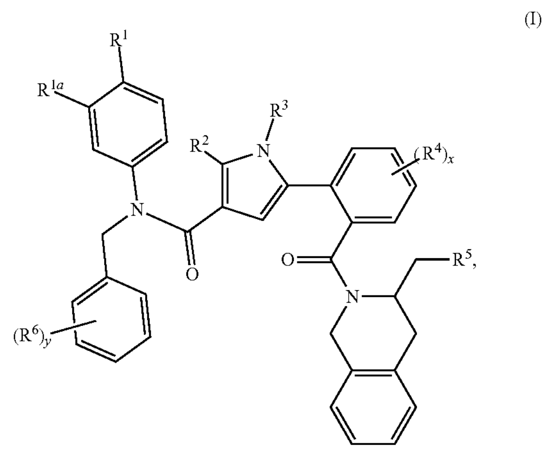

and pharmaceutically acceptable salts, hydrates, solvates, prodrugs, stereoisomers, and tautomers thereof, wherein $R^1$, $R^2$, $R^3$, $R^4$, $R^5$, $R^6$, x and y are described herein.

It is understood that, for a compound of Formula (I), $R^1$, $R^2$, $R^3$, $R^4$, $R^5$, $R^6$, x and y can each be, where applicable, selected from the groups described herein, and any group described herein for any of $R^1$, $R^2$, $R^3$, $R^4$, $R^5$, $R^6$, x and y can be combined, where applicable, with any group described herein for one or more of the remainder of $R^1$, $R^2$, $R^3$, $R^4$, $R^5$, $R^6$, x and y.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated herein by reference in their entireties.

Definitions

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

The term "optionally substituted" is understood to mean that a given chemical moiety (e.g., an alkyl group) can (but is not required to) be bonded other substituents (e.g., heteroatoms). For instance, an alkyl group that is optionally substituted can be a fully saturated alkyl chain (i.e., a pure hydrocarbon). Alternatively, the same optionally substituted alkyl group can have substituents different from hydrogen. For instance, it can, at any point along the chain be bounded to a halogen atom, a hydroxyl group, or any other substituent described herein. Thus the term "optionally substituted" means that a given chemical moiety has the potential to contain other functional groups, but does not necessarily have any further functional groups. Suitable substituents used in the optional substitution of the described groups include, without limitation, halogen, oxo, —OH, —CN, —COOH, —$CH_2CN$, —O—($C_1$-$C_6$)alkyl, ($C_1$-$C_6$)alkyl, ($C_1$-$C_6$)alkoxy, ($C_1$-$C_6$)haloalkyl, ($C_1$-$C_6$)haloalkoxy, —O—($C_2$-$C_6$)alkenyl, —O—($C_2$-$C_6$)alkynyl, ($C_2$-$C_6$)alkenyl, ($C_2$-$C_6$)alkynyl, —OH, —OP(O)$(OH)_2$, —OC(O)($C_1$-$C_6$)alkyl, —C(O)($C_1$-$C_6$)alkyl, —OC(O)O($C_1$-$C_6$)alkyl, —$NH_2$, —NH(($C_1$-$C_6$)alkyl), —N(($C_1$-$C_6$)alkyl)$_2$, —NHC(O)($C_1$-$C_6$)alkyl, —C(O)NH($C_1$-$C_6$)alkyl, —S(O)$_2$ ($C_1$-$C_6$) alkyl, —S(O)NH($C_1$-$C_6$)alkyl, and S(O)N(($C_1$-$C_6$)alkyl)$_2$. The substituents can themselves be optionally substituted. "Optionally substituted" as used herein also refers to substituted or unsubstituted whose meaning is described below.

As used herein, the term "substituted" means that the specified group or moiety bears one or more suitable substituents wherein the substituents may connect to the specified group or moiety at one or more positions. For example, an aryl substituted with a cycloalkyl may indicate that the cycloalkyl connects to one atom of the aryl with a bond or by fusing with the aryl and sharing two or more common atoms.

As used herein, the term "unsubstituted" means that the specified group bears no substituents.

Unless otherwise specifically defined, the term "aryl" refers to cyclic, aromatic hydrocarbon groups that have 1 to 3 aromatic rings, including monocyclic or bicyclic groups such as phenyl, biphenyl, or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. Exemplary substituents include, but are not limited to, —H, -halogen, —O—($C_1$-$C_6$)alkyl, ($C_1$-$C_6$)alkyl, —O—($C_2$-$C_6$)alkenyl, —O—($C_2$-$C_6$)alkynyl, ($C_2$-$C_6$)alkenyl, ($C_2$-$C_6$)alkynyl, —OH, —OP(O)$(OH)_2$, —OC(O)($C_1$-$C_6$)alkyl, —C(O)($C_1$-$C_6$)alkyl, —OC(O)O($C_1$-$C_6$)alkyl, —$NH_2$, NH(($C_1$-$C_6$)alkyl), N(($C_1$-$C_6$)alkyl)$_2$, —S(O)$_2$—($C_1$-$C_6$)alkyl, —S(O)NH($C_1$-$C_6$)alkyl, and —S(O)N(($C_1$-$C_6$)alkyl)$_2$. The substituents can themselves be optionally substituted. Furthermore, when containing two fused rings, the aryl groups herein defined may have a saturated or partially unsaturated ring fused with a fully unsaturated aromatic ring. Exemplary ring systems of these aryl groups include, but are not limited to, phenyl, biphenyl, naphthyl, anthracenyl, phenalenyl, phenanthrenyl, indanyl, indenyl, tetrahydronaphthalenyl, tetrahydrobenzoannulenyl, and the like.

Unless otherwise specifically defined, "heteroaryl" means a monovalent monocyclic or polycyclic aromatic radical of 5 to 24 ring atoms, containing one or more ring heteroatoms selected from N, O, S, P, Se, or B, the remaining ring atoms being C. Heteroaryl as herein defined also means a bicyclic heteroaromatic group wherein the heteroatom is selected from N, O, S, P, Se, or B. Heteroaryl as herein defined also means a tricyclic heteroaromatic group containing one or more ring heteroatoms selected from N, O, S, P, Se, or B. The aromatic radical is optionally substituted independently with one or more substituents described herein. Examples include, but are not limited to, furyl, thienyl, pyrrolyl, pyridyl, pyrazolyl, pyrimidinyl, imidazolyl, isoxazolyl, oxazolyl, oxadiazolyl, pyrazinyl, indolyl, thiophen-2-yl, quinolinyl, benzopyranyl, isothiazolyl, thiazolyl, thiadiazole, indazole, benzimidazolyl, thieno[3,2-b]thiophene, triazolyl, triazinyl, imidazo[1,2-b]pyrazolyl, furo[2,3-c]pyridinyl, imidazo[1,2-a]pyridinyl, indazolyl, pyrrolo[2,3-c]pyridinyl, pyrrolo[3,2-c]pyridinyl, pyrazolo[3,4-c]pyridinyl, thieno[3,2-c]pyridinyl, thieno[2,3-c]pyridinyl, thieno[2,3-b]pyridinyl, benzothiazolyl, indolyl, indolinyl, indolinonyl, dihydrobenzothiophenyl, dihydrobenzofuranyl, benzofuran, chromanyl, thiochromanyl, tetrahydroquinolinyl, dihydrobenzothiazine, quinolinyl, isoquinolinyl, 1,6-naphthyridinyl, benzo[de]isoquinolinyl, pyrido[4,3-b][1,6]naphthyridinyl, thieno[2,3-b]pyrazinyl, quinazolinyl, tetrazolo[1,5-a]pyridinyl, [1,2,4]triazolo[4,3-a]pyridinyl, isoindolyl, pyrrolo[2,3-b]pyridinyl, pyrrolo[3,4-b]pyridinyl, pyrrolo[3,2-b]pyridinyl, imidazo[5,4-b]pyridinyl, pyrrolo[1,2-alpyrimidinyl, tetrahydro pyrrolo[1,2-a]pyrimidinyl, 3,4-dihydro-2H-122-pyrrolo[2,1-b]pyrimidine, dibenzo[b,d]thiophene, pyridin-2-one, furo[3,2-c]pyridinyl, furo[2,3-c]pyridinyl, 1H-pyrido[3,4-b][1,4]thiazinyl, benzoxazolyl, benzisoxazolyl, furo[2,3-b]pyridinyl, benzothiophenyl, 1,5-naphthyridinyl, furo[3,2-b]pyridine, [1,2,4]triazolo[1,5-a]pyridinyl, benzo[1,2,3]triazolyl, imidazo[1,2-a]pyrimidinyl, [1,2,4]triazolo[4,3-b]pyridazinyl, benzo[c][1,2,5]thiadiazolyl, benzo[c][1,2,5]oxadiazole, 1,3-dihydro-2H-benzo[d]imidazol-2-one, 3,4-dihydro-2H-pyrazolo[1,5-b][1,2]oxazinyl, 4,5,6,7-tetrahydropyrazolo[1,5-a]pyridinyl, thiazolo[5,4-d]thiazolyl, imidazo[2,1-b][1,3,4]thiadiazolyl, thieno[2,3-b]pyrrolyl, 3H-indolyl, and derivatives thereof. Furthermore, when containing two or more fused rings, the heteroaryl groups defined herein may have one or more saturated or partially unsaturated ring fused with a fully unsaturated aromatic ring, e.g., a 5-membered heteroaromatic ring containing 1 to 3 heteroatoms selected from N, O, S, P, Se, or B, or a 6-membered heteroaromatic ring containing 1 to 3 nitrogens, wherein the saturated or partially unsaturated ring includes 0 to 4 heteroatoms selected from N, O, S, P, Se, or B, and is optionally substituted with one or more oxo. In heteroaryl ring systems containing more than two fused rings, a saturated or partially unsaturated ring may further be fused with a saturated or partially unsaturated ring described herein. Exemplary ring systems of these heteroaryl groups include, for example, indolinyl, indolinonyl, dihydrobenzothiophenyl, dihydrobenzofuran, chromanyl, thiochromanyl, tetrahydroquinolinyl, dihydrobenzothiazine, 3,4-dihydro-1H-isoquinolinyl, 2,3-dihydrobenzofuranyl, benzofuranonyl, indolinyl, oxindolyl, indolyl, 1,6-dihydro-7H-pyrazolo[3,4-c]pyridin-7-onyl, 7,8-dihydro-6H-pyrido[3,2-b]pyrrolizinyl, 8H-pyrido[3,2-b]pyrrolizinyl, 1,5,6,7-tetrahydrocyclopenta[b]pyrazolo[4,3-e]pyridinyl, 7,8-dihydro-6H-pyrido[3,2-b]pyrrolizine, pyrazolo[1,5-a]pyrimidin-7 (4H)-only, 3,4-dihydropyrazino[1,2-a]indol-1 (2H)-onyl, or benzo[c][1,2]oxaborol-1 (3H)-olyl.

"Halogen" or "halo" refers to fluorine, chlorine, bromine, or iodine.

"Alkyl" refers to a straight or branched chain saturated hydrocarbon containing 1-12 carbon atoms. Examples of a ($C_1$-$C_6$)alkyl group include, but are not limited to, methyl, ethyl, propyl, butyl, pentyl, hexyl, isopropyl, isobutyl, sec-butyl, tert-butyl, isopentyl, neopentyl, and isohexyl.

"Alkoxy" refers to a straight or branched chain saturated hydrocarbon containing 1-12 carbon atoms containing a terminal "O" in the chain, i.e., —O(alkyl). Examples of alkoxy groups include without limitation, methoxy, ethoxy, propoxy, butoxy, t-butoxy, or pentoxy groups.

"Alkenyl" refers to a straight or branched chain unsaturated hydrocarbon containing 2-12 carbon atoms. The "alkenyl" group contains at least one double bond in the chain. The double bond of an alkenyl group can be unconjugated or conjugated to another unsaturated group. Examples of alkenyl groups include ethenyl, propenyl, n-butenyl, isobutenyl, pentenyl, or hexenyl. An alkenyl group can be unsubstituted or substituted. Alkenyl, as herein defined, may be straight or branched.

"Alkynyl" refers to a straight or branched chain unsaturated hydrocarbon containing 2-12 carbon atoms. The "alkynyl" group contains at least one triple bond in the chain. Examples of alkenyl groups include ethynyl, propargyl, n-butynyl, iso-butynyl, pentynyl, or hexynyl. An alkynyl group can be unsubstituted or substituted.

The term "alkylene" or "alkylenyl" refers to a divalent alkyl radical. Any of the above-mentioned monovalent alkyl groups may be an alkylene by abstraction of a second hydrogen atom from the alkyl. As herein defined, alkylene may also be a $C_1$-$C_6$ alkylene. An alkylene may further be a $C_1$-$C_4$ alkylene. Typical alkylene groups include, but are not limited to, $—CH_2—$, $—CH(CH_3)—$, $—C(CH_3)_2—$, $—CH_2CH_2—$, $—CH_2CH(CH_3)—$, $—CH_2C(CH_3)_2—$, $—CH_2CH_2CH_2—$, $—CH_2CH_2CH_2CH_2—$, and the like.

"Cycloalkyl" means a saturated or partially unsaturated hydrocarbon monocyclic or polycyclic (e.g., fused, bridged, or spiro rings) system having 3 to 30 carbon atoms (e.g., $C_3$-$C_{12}$, $C_3$-$C_{10}$, or $C_3$-$C_8$). Examples of cycloalkyl groups include, without limitations, cyclopropyl, cyclobutyl, cyclopentyl, cyclohexyl, cycloheptanyl, cyclooctanyl, norboranyl, norborenyl, bicyclo[2.2.2]octanyl, bicyclo[2.2.2]octenyl, decahydronaphthalenyl, octahydro-1H-indenyl, cyclopentenyl, cyclohexenyl, cyclohexa-1,4-dienyl, cyclohexa-1,3-dienyl, 1,2,3,4-tetrahydronaphthalenyl, octahydropentalenyl, 3a,4,5,6,7,7a-hexahydro-1H-indenyl, 1,2,3,3a-tetrahydropentalenyl, bicyclo[3.1.0]hexanyl, bicyclo[2.1.0]pentanyl, spiro[3.3]heptanyl, bicyclo[2.2.1]heptanyl, bicyclo[2.2.1]hept-2-enyl, bicyclo[2.2.2]octanyl, 6-methylbicyclo[3.1.1]heptanyl, 2,6,6-trimethylbicyclo[3.1.1]heptanyl, adamantyl, and derivatives thereof. In the case of polycyclic cycloalkyl, only one of the rings in the cycloalkyl needs to be non-aromatic.

"Heterocyclyl", "heterocycle" or "heterocycloalkyl" refers to a saturated or partially unsaturated 3-10 membered monocyclic, 7-12 membered bicyclic (fused, bridged, or spiro rings), or 11-14 membered tricyclic ring system (fused, bridged, or spiro rings) having one or more heteroatoms (such as O, N, S, P, Se, or B), e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulfur, unless specified otherwise. Examples of heterocycloalkyl groups include, but are not limited to, piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, oxiranyl, azetidinyl, oxetanyl, thietanyl, 1,2,3,6-tetrahydropyridinyl, tetrahydropyranyl, dihydropyranyl, pyranyl, morpholinyl, tetrahydrothiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, 1,4-dioxa-8-azaspiro[4.5]decanyl, 1,4-dioxaspiro[4.5]decanyl, 1-oxaspiro[4.5]decanyl, 1-azaspiro[4.5]decanyl, 3'H-spiro[cyclohexane-1,1'-isobenzofuran]-yl, 7'H-spiro[cyclohexane-1,5'-furo[3,4-b]pyridin]-yl, 3'H-spiro[cyclohexane-1,1'-furo[3,4-c]pyridin]-yl, 3-azabicyclo[3.1.0]hexanyl, 3-azabicyclo[3.1.0]hexan-3-yl, 1,4,5,6-tetrahydropyrrolo[3,4-c]pyrazolyl, 3,4,5,6,7,8-hexahydropyrido[4,3-d]pyrimidinyl, 4,5,6,7-tetrahydro-1H-pyrazolo[3,4-c]pyridinyl, 5,6,7,8-tetrahydropyrido[4,3-d]pyrimidinyl, 2-azaspiro[3.3]heptanyl, 2-methyl-2-azaspiro[3.3]heptanyl, 2-azaspiro[3.5]nonanyl, 2-methyl-2-azaspiro[3.5]nonanyl, 2-azaspiro[4.5]decanyl, 2-methyl-2-azaspiro[4.5]decanyl, 2-oxa-azaspiro[3.4]octanyl, 2-oxa-azaspiro[3.4]octan-6-yl, and the like.

The term "haloalkyl" as used herein refers to an alkyl group, as defined herein, which is substituted one or more halogen. Examples of haloalkyl groups include, but are not limited to, trifluoromethyl, difluoromethyl, pentafluoroethyl, trichloromethyl, etc.

The term "haloalkoxy" as used herein refers to an alkoxy group, as defined herein, which is substituted one or more halogen. Examples of haloalkoxy groups include, but are not limited to, trifluoromethoxy, difluoromethoxy, pentafluoroethoxy, trichloromethoxy, etc.

The term "cyano" as used herein means a substituent having a carbon atom joined to a nitrogen atom by a triple bond, i.e., C≡N.

The term "amine" as used herein refers to primary ($R—NH_2$, $R\neq H$), secondary ($R^2—NH$, $R^2\neq H$) and tertiary ($R^3—N$, $R\neq H$) amines. A substituted amine is intended to mean an amine where at least one of the hydrogen atoms has been replaced by the substituent.

The term "amino" as used herein means a substituent containing at least one nitrogen atom. Specifically, $—NH_2$, —NH(alkyl) or alkylamino, $—N(alkyl)_2$ or dialkylamino, amide-, carbamide-, urea, and sulfamide substituents are included in the term "amino".

The term "solvate" refers to a complex of variable stoichiometry formed by a solute and solvent. Such solvents for the purpose of the invention may not interfere with the biological activity of the solute. Examples of suitable solvents include, but are not limited to, water, MeOH, EtOH, and AcOH. Solvates wherein water is the solvent molecule are typically referred to as hydrates. Hydrates include compositions containing stoichiometric amounts of water, as well as compositions containing variable amounts of water.

The term "isomer" refers to compounds that have the same composition and molecular weight but differ in physical and/or chemical properties. The structural difference may be in constitution (geometric isomers) or in the ability to rotate the plane of polarized light (stereoisomers). With regard to stereoisomers, the compounds of Formula (I) may have one or more asymmetric carbon atom and may occur as racemates, racemic mixtures and as individual enantiomers or diastereomers.

The present invention also contemplates isotopically-labelled compounds of Formula I (e.g., those labeled with $^2H$ and $^{14}C$). Deuterated (i.e., $^2H$ or D) and carbon-14 (i.e., $^{14}C$) isotopes are particularly preferred for their ease of preparation and detectability. Further, substitution with heavier isotopes such as deuterium may afford certain therapeutic advantages resulting from greater metabolic stability (e.g., increased in vivo half-life or reduced dosage requirements) and hence may be preferred in some circumstances. Isotopically labelled compounds of Formula I can generally be prepared by following procedures analogous to those disclosed in the Schemes and/or in the Examples herein below, by substituting an appropriate isotopically labelled reagent for a non-isotopically labelled reagent.

The disclosure also includes pharmaceutical compositions comprising an effective amount of a disclosed compound and a pharmaceutically acceptable carrier. Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumerate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

A "patient" or "subject" is a mammal, e.g., a human, mouse, rat, guinea pig, dog, cat, horse, cow, pig, or non-human primate, such as a monkey, chimpanzee, baboon or rhesus.

An "effective amount" when used in connection with a compound is an amount effective for treating or preventing a disease or disorder in a subject as described herein.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

The term "treating" with regard to a subject, refers to improving at least one symptom of the subject's disorder. Treating includes curing, improving, or at least partially ameliorating the disorder.

The term "disorder" is used in this disclosure to mean, and is used interchangeably with, the terms disease, condition, or illness, unless otherwise indicated.

The term "administer", "administering", or "administration" as used in this disclosure refers to either directly administering a disclosed compound or pharmaceutically acceptable salt of the disclosed compound or a composition to a subject, or administering a prodrug derivative or analog of the compound or pharmaceutically acceptable salt of the compound or composition to the subject, which can form an equivalent amount of active compound within the subject's body.

The term "prodrug," as used in this disclosure, means a compound which is convertible in vivo by metabolic means (e.g., by hydrolysis) to a disclosed compound.

The present invention relates to compounds or pharmaceutically acceptable salts, hydrates, solvates, prodrugs, stereoisomers, or tautomers thereof, capable of inhibiting BCL-2 proteins, such as Isoform 1 and Isoform 2, which are useful for the treatment of diseases and disorders associated with modulation of an BCL-2 protein. The invention further relates to compounds, or pharmaceutically acceptable salts, hydrates, solvates, prodrugs, stereoisomers, or tautomers thereof, which can be useful for inhibiting BCL-2.

In some embodiments, the compounds of Formula (I) have the structure of Formula (I'):

(I')

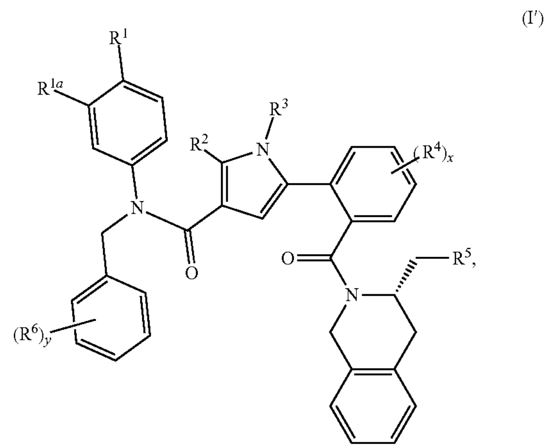

or pharmaceutically acceptable salts, prodrugs, solvates, hydrates, stereoisomers, or tautomers thereof.

In some embodiments, the compounds of Formula (I) have the structure of Formula (II):

(II)

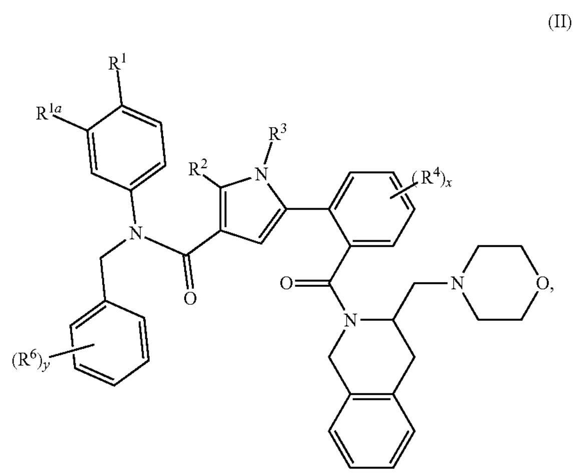

or pharmaceutically acceptable salts, prodrugs, solvates, hydrates, stereoisomers, or tautomers thereof.

In some embodiments, the compounds of Formula (I) have the structure of Formula (II):
(II')
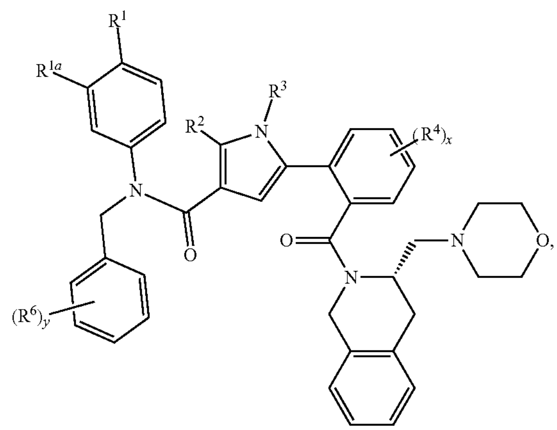
or pharmaceutically acceptable salts, prodrugs, solvates, hydrates, stereoisomers, or tautomers thereof.
In some embodiments, the compounds of Formula (I) have the structure of Formula (III-XI):
(III)
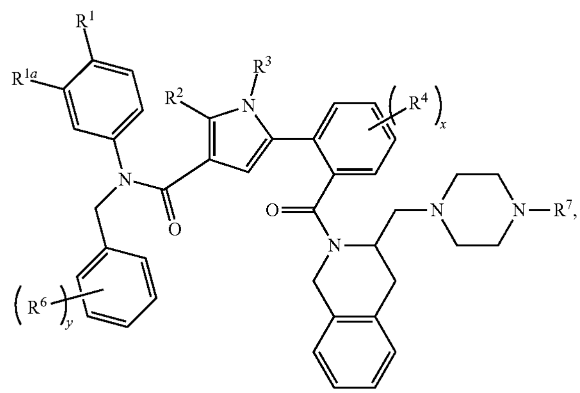
(IV)
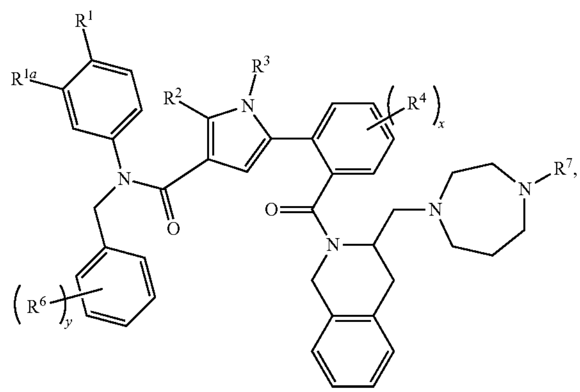
-continued
(V)
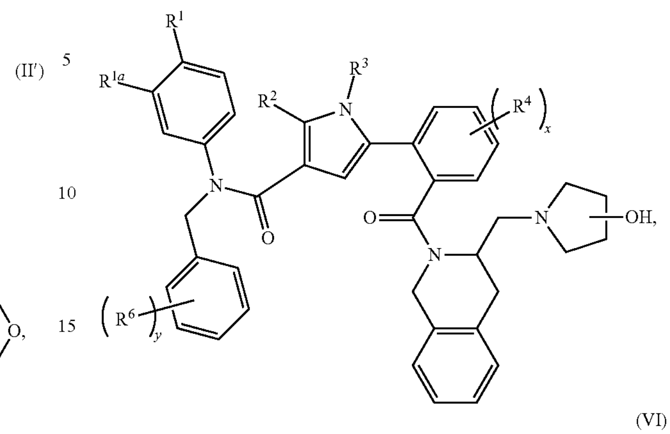
(VI)
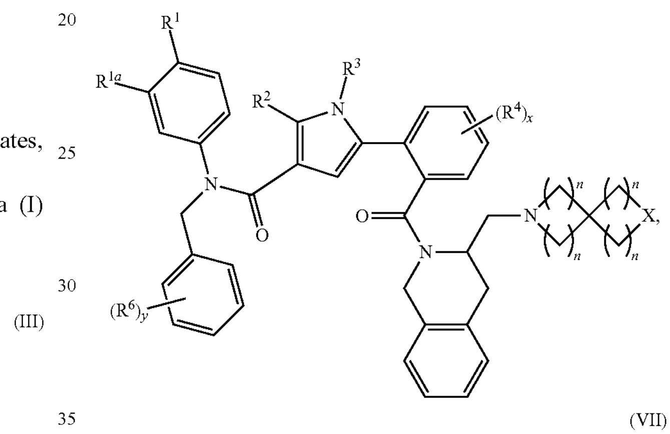
(VII)
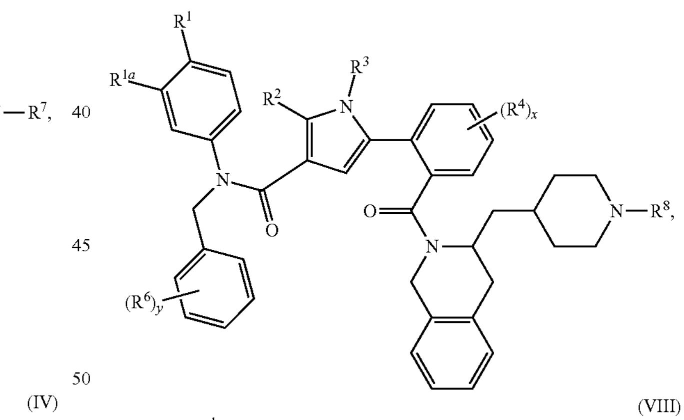
(VIII)
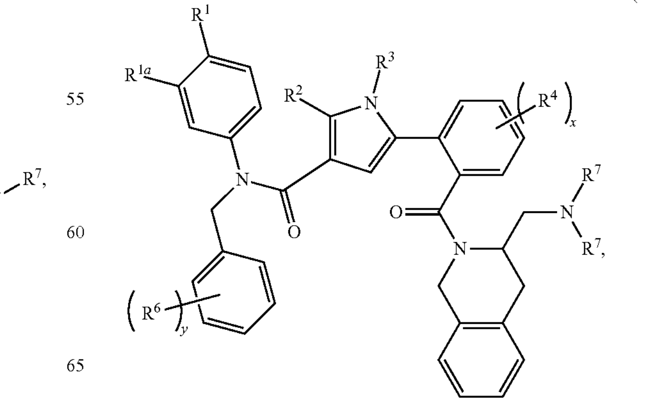

-continued (IX)

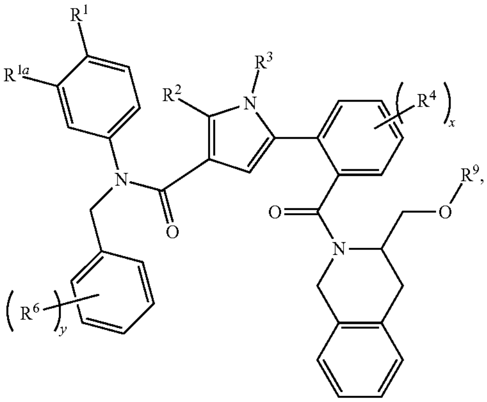

(X)

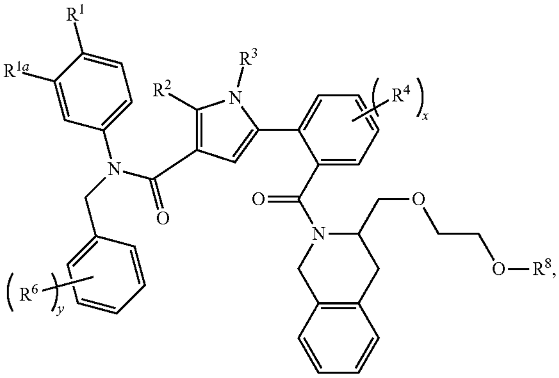

(XI)

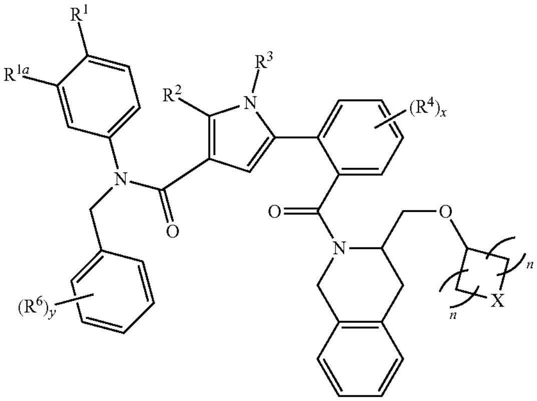

, wherein each n is independently selected from 1, 2, 3, and X is selected from $NR^9$, O, S, and pharmaceutically acceptable salts, prodrugs, solvates, hydrates, stereoisomers, or tautomers thereof.

In some embodiments, the compounds of Formula (I) have the structure of Formula (III).

In some embodiments, the compounds of Formula (I) have the structure of Formula (IV).

In some embodiments, the compounds of Formula (I) have the structure of Formula (V).

In some embodiments, the compounds of Formula (I) have the structure of Formula (VI).

In some embodiments, the compounds of Formula (I) have the structure of Formula (VII).

In some embodiments, the compounds of Formula (I) have the structure of Formula (VIII).

In some embodiments, the compounds of Formula (I) have the structure of Formula (IX).

In some embodiments, the compounds of Formula (I) have the structure of Formula (X).

In some embodiments, the compounds of Formula (I) have the structure of Formula (XI).

In some embodiments, the compounds of Formula (I) have the structure of Formula (III'—XI'):

(III')

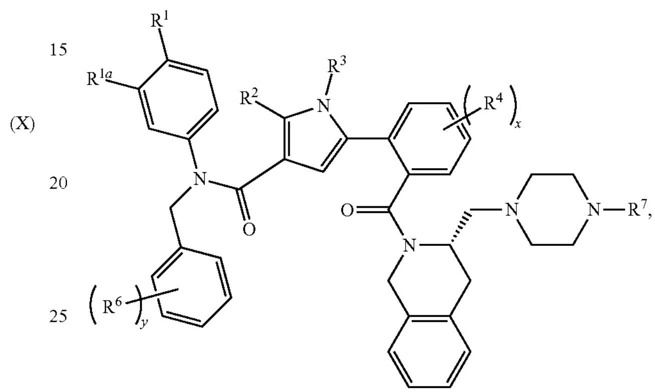

(IV')

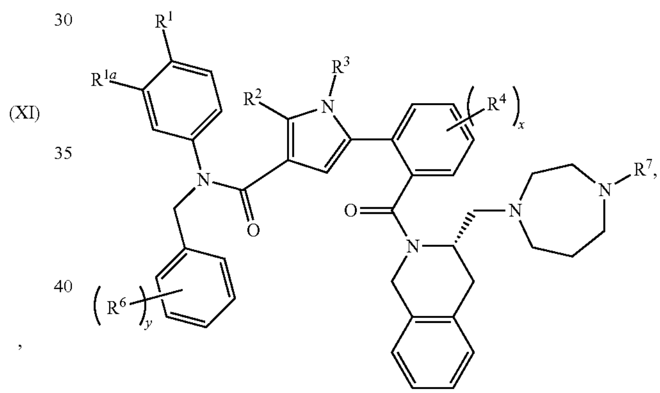

(V')

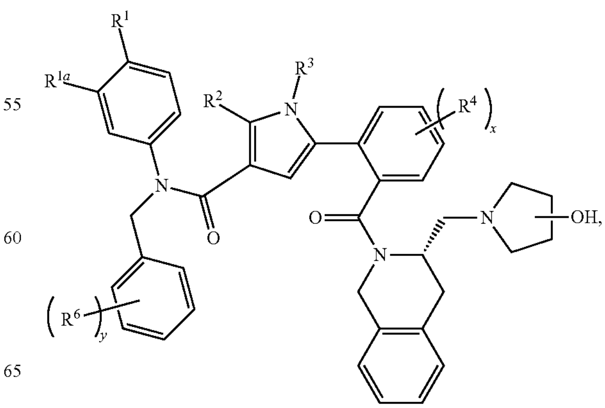

-continued (VI')

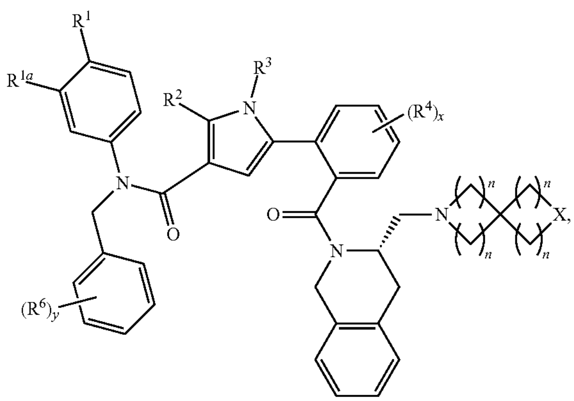

(VII')

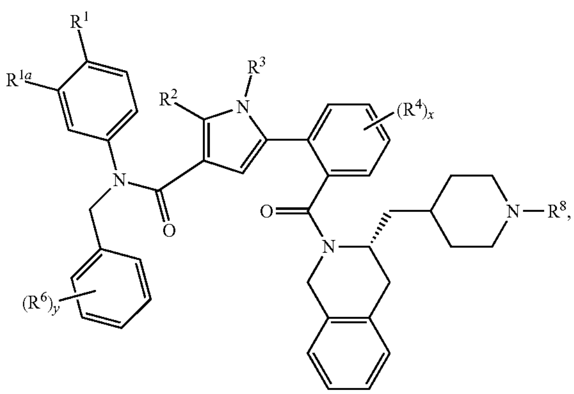

(VIII')

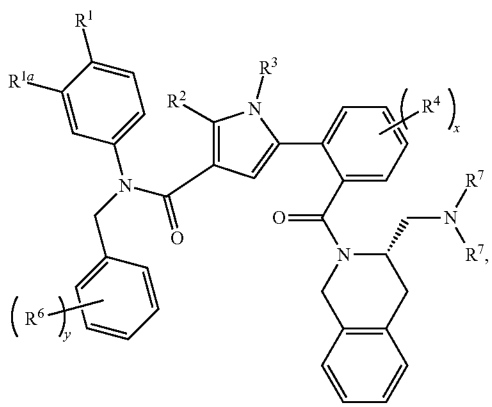

(IX')

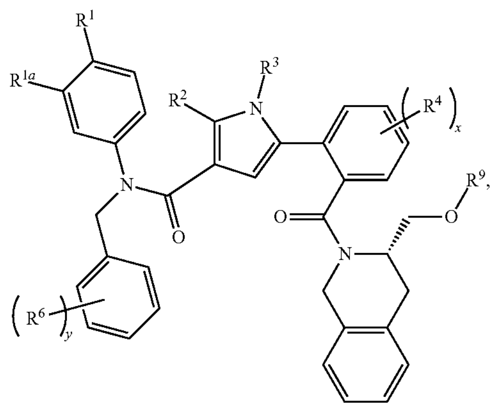

-continued (X')

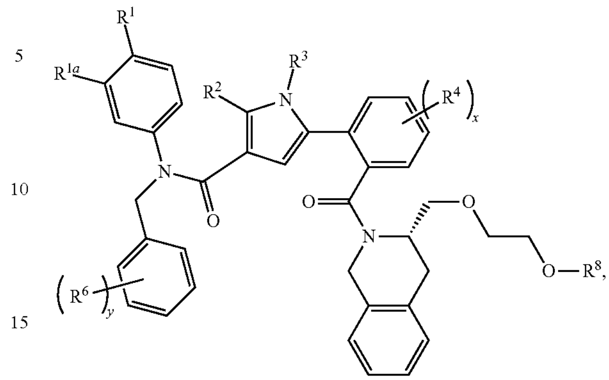

(XI')

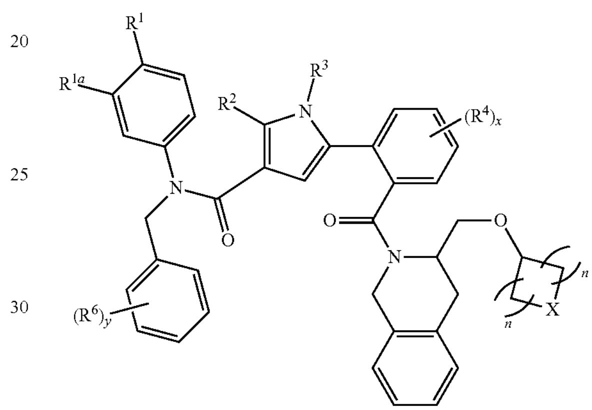

, wherein each n is independently selected from 1, 2, 3, and X is selected from $NR^9$, O, S, and pharmaceutically acceptable salts, prodrugs, solvates, hydrates, stereoisomers, or tautomers thereof.

In some embodiments, the compounds of Formula (I) have the structure of Formula (III').

In some embodiments, the compounds of Formula (I) have the structure of Formula (IV').

In some embodiments, the compounds of Formula (I) have the structure of Formula (V').

In some embodiments, the compounds of Formula (I) have the structure of Formula (VI').

In some embodiments, the compounds of Formula (I) have the structure of Formula (VII').

In some embodiments, the compounds of Formula (I) have the structure of Formula (VIII').

In some embodiments, the compounds of Formula (I) have the structure of Formula (IX').

In some embodiments, the compounds of Formula (I) have the structure of Formula (X').

In some embodiments, the compounds of Formula (I) have the structure of Formula (XI').

In some embodiments, the compounds of Formula (I) have the structure of Formula (I-1):

(I-1)

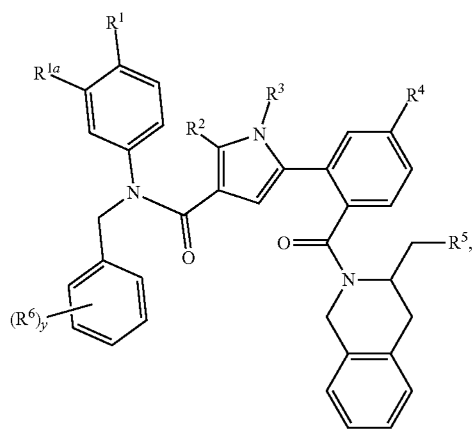

or pharmaceutically acceptable salts, prodrugs, solvates, hydrates, stereoisomers, or tautomers thereof.

In some embodiments, the compounds of Formula (I) have the structure of Formula (I-1'):

(I-1')

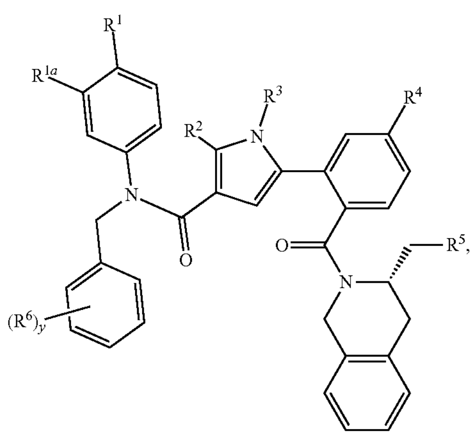

or pharmaceutically acceptable salts, prodrugs, solvates, hydrates, stereoisomers, or tautomers thereof.

In some embodiments, the compounds of Formula (I) have the structure of Formula (I-2):

(I-2)

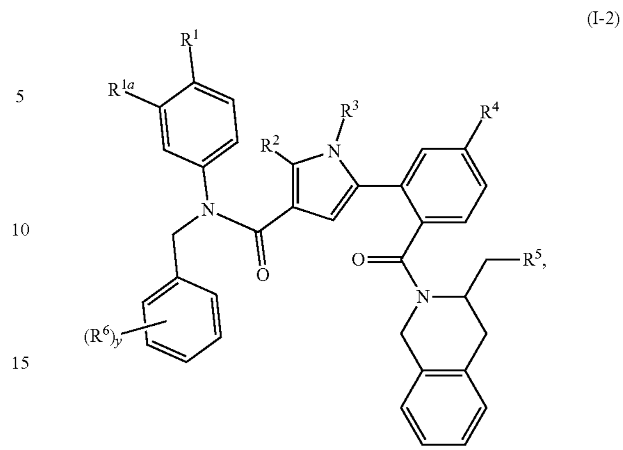

or pharmaceutically acceptable salts, prodrugs, solvates, hydrates, stereoisomers, or tautomers thereof.

In some embodiments, the compounds of Formula (I) have the structure of Formula (I-2'):

(I-2')

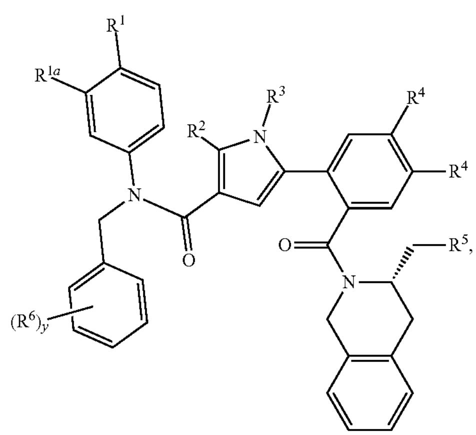

or pharmaceutically acceptable salts, prodrugs, solvates, hydrates, stereoisomers, or tautomers thereof.

In some embodiments, the compounds of Formula (I) have the structure of Formula (I-3):

(I-3)

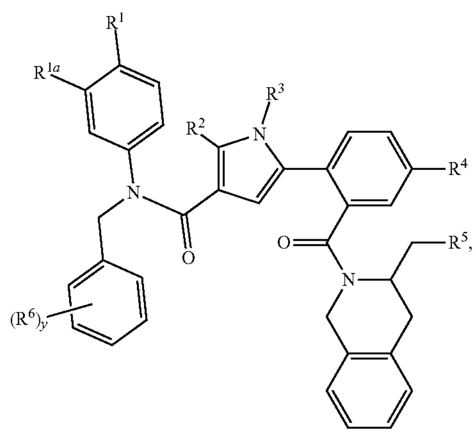

or pharmaceutically acceptable salts, prodrugs, solvates, hydrates, stereoisomers, or tautomers thereof.

In some embodiments, the compounds of Formula (I) have the structure of Formula (I-3'):

(I-3')

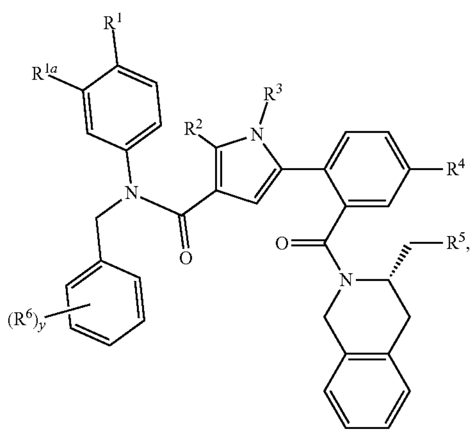

or pharmaceutically acceptable salts, prodrugs, solvates, hydrates, stereoisomers, or tautomers thereof.

In some embodiments, the compounds of Formula (I) have the structure of Formula (I-4):

(I-4)

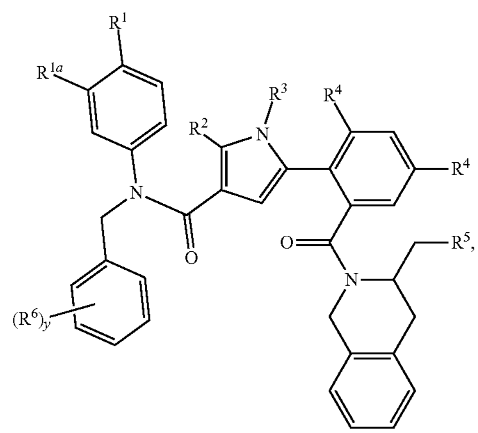

or pharmaceutically acceptable salts, prodrugs, solvates, hydrates, stereoisomers, or tautomers thereof.

In some embodiments, the compounds of Formula (I) have the structure of Formula (I-4'):

(I-4')

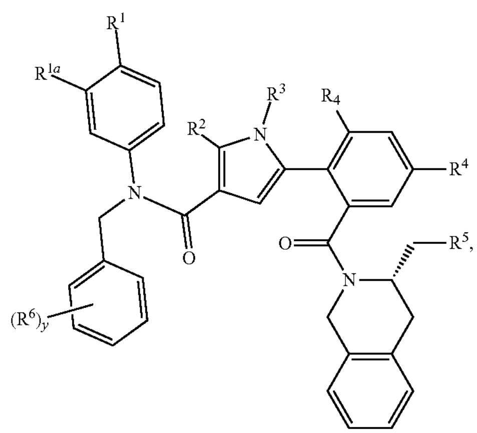

or pharmaceutically acceptable salts, prodrugs, solvates, hydrates, stereoisomers, or tautomers thereof.

In some embodiments, the compounds of Formula (I) have the structure of Formula (II-1):

(II-1)

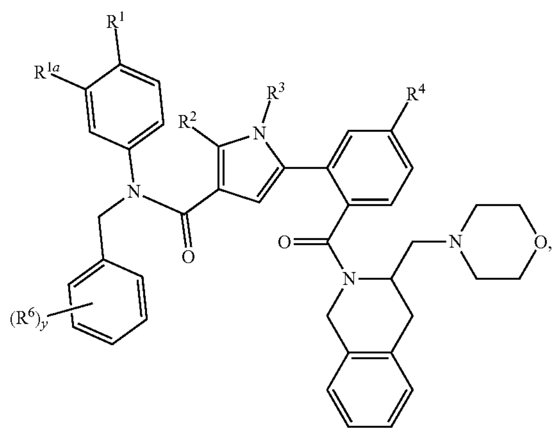

or pharmaceutically acceptable salts, prodrugs, solvates, hydrates, stereoisomers, or tautomers thereof. 1'):

(II-1′)

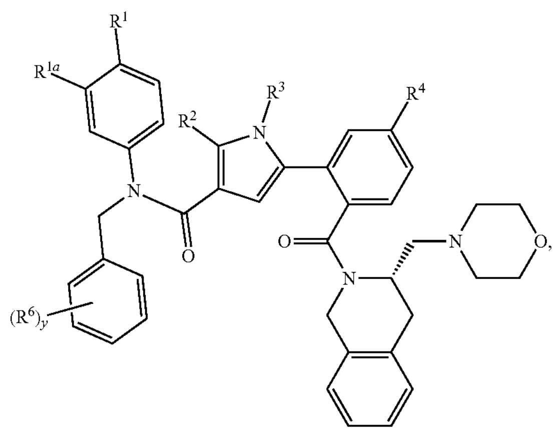

or pharmaceutically acceptable salts, prodrugs, solvates, hydrates, stereoisomers, or tautomers thereof.

In some embodiments, the compounds of Formula (I) have the structure of Formula (II-2):

(II-2)

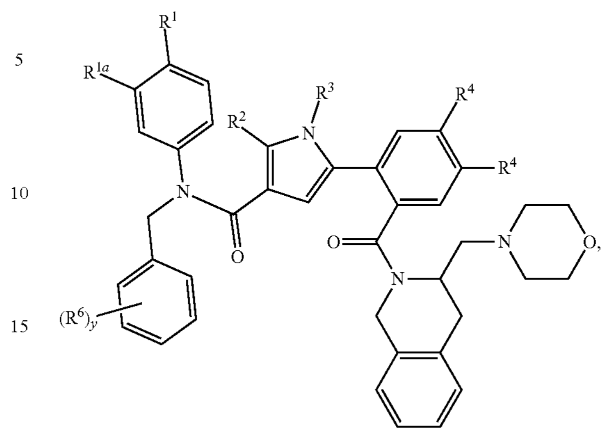

or pharmaceutically acceptable salts, prodrugs, solvates, hydrates, stereoisomers, or tautomers thereof. 2'):

(II-2′)

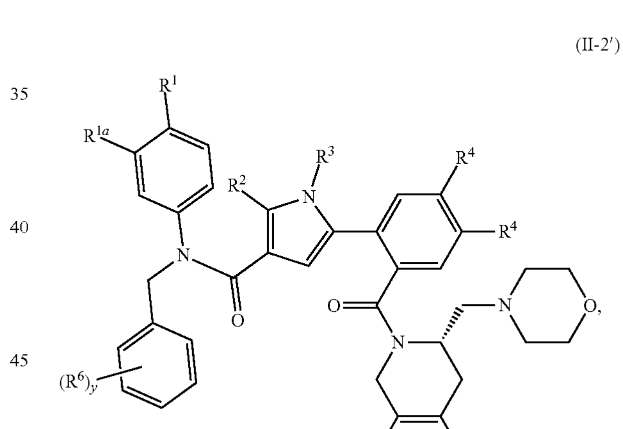

or pharmaceutically acceptable salts, prodrugs, solvates, hydrates, stereoisomers, or tautomers thereof.

In some embodiments, the compounds of Formula (I) have the structure of Formula (II-3):

(II-3)

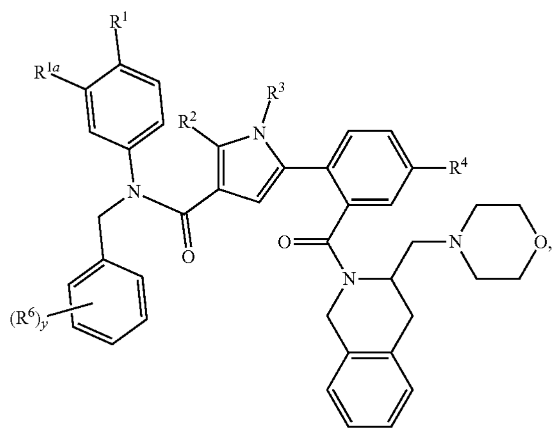

or pharmaceutically acceptable salts, prodrugs, solvates, hydrates, stereoisomers, or tautomers thereof. 3'):

(II-3')

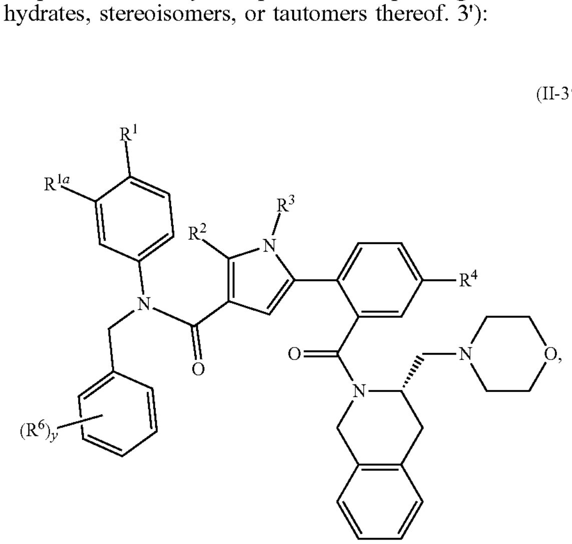

or pharmaceutically acceptable salts, prodrugs, solvates, hydrates, stereoisomers, or tautomers thereof.

In some embodiments, the compounds of Formula (I) have the structure of Formula (II-4):

(II-4)

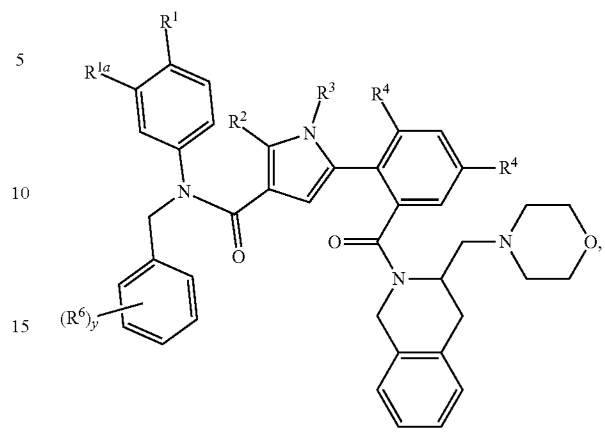

or pharmaceutically acceptable salts, prodrugs, solvates, hydrates, stereoisomers, or tautomers thereof. 4'):

(II-4')

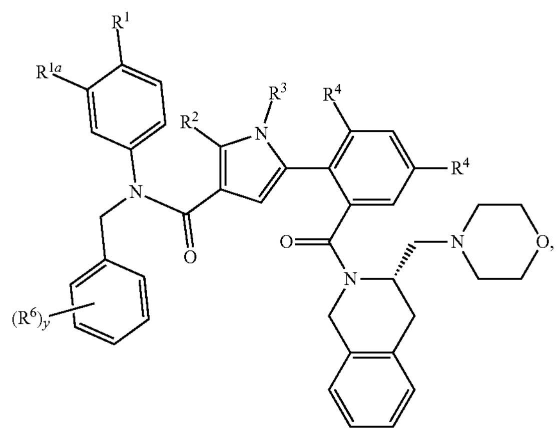

or pharmaceutically acceptable salts, prodrugs, solvates, hydrates, stereoisomers, or tautomers thereof.

In some embodiments, the compounds of Formula (I) have the structure of Formula (II-A):

(II-A)

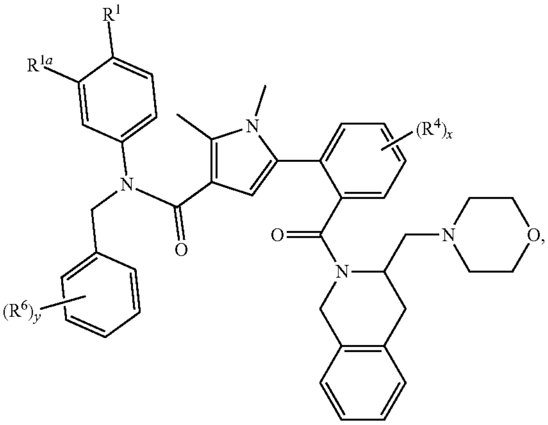

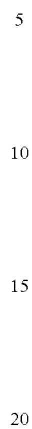

or pharmaceutically acceptable salts, prodrugs, solvates, hydrates, stereoisomers, or tautomers thereof.

In some embodiments, the compounds of Formula (I) have the structure of Formula (II—A-1):

(II-A-1)

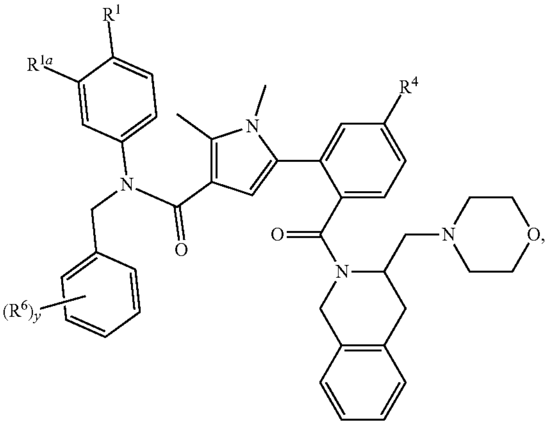

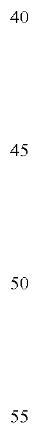

or pharmaceutically acceptable salts, prodrugs, solvates, hydrates, stereoisomers, or tautomers thereof.

In some embodiments, the compounds of Formula (I) have the structure of Formula (II-A-1'):

(II-A-1')

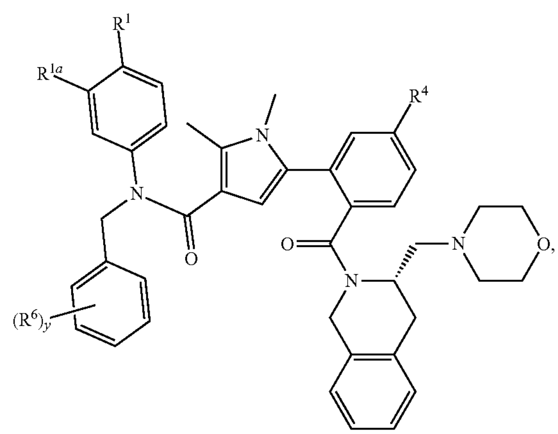

or pharmaceutically acceptable salts, prodrugs, solvates, hydrates, stereoisomers, or tautomers thereof.

In some embodiments, the compounds of Formula (I) have the structure of Formula (II—A-2):

(II-A-2)

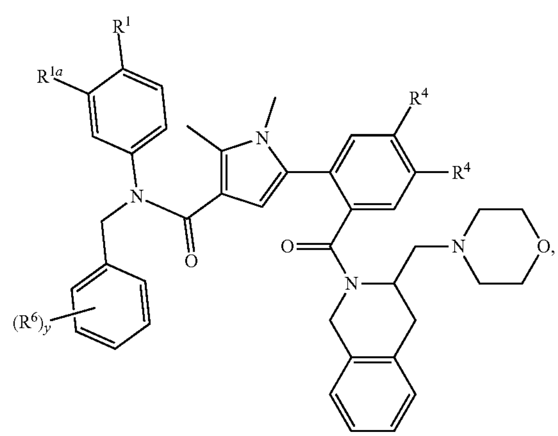

or pharmaceutically acceptable salts, prodrugs, solvates, hydrates, stereoisomers, or tautomers thereof.

In some embodiments, the compounds of Formula (I) have the structure of Formula (II-A-2'):

(II-A-2')

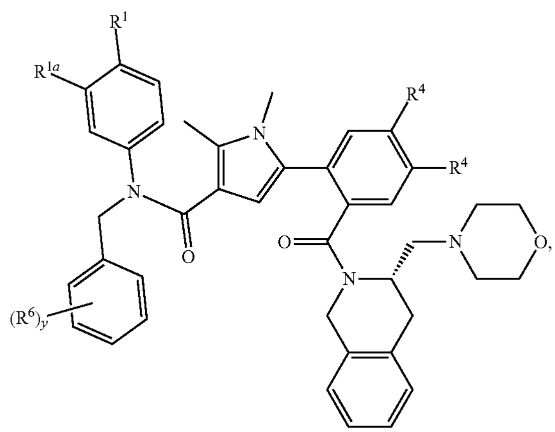

or pharmaceutically acceptable salts, prodrugs, solvates, hydrates, stereoisomers, or tautomers thereof.

In some embodiments, the compounds of Formula (I) have the structure of Formula (II-A-3):

(II-A-3)

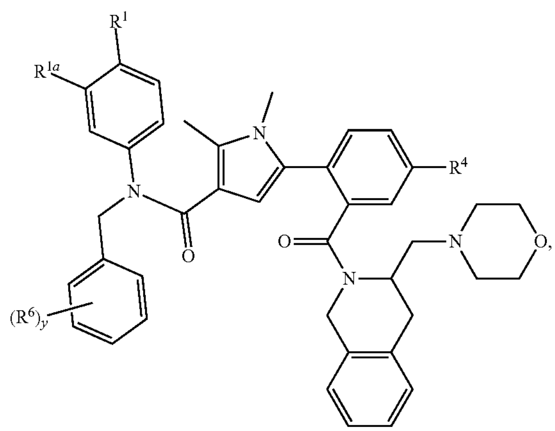

or pharmaceutically acceptable salts, prodrugs, solvates, hydrates, stereoisomers, or tautomers thereof.

In some embodiments, the compounds of Formula (I) have the structure of Formula (II-A-3'):

(II-A-3')

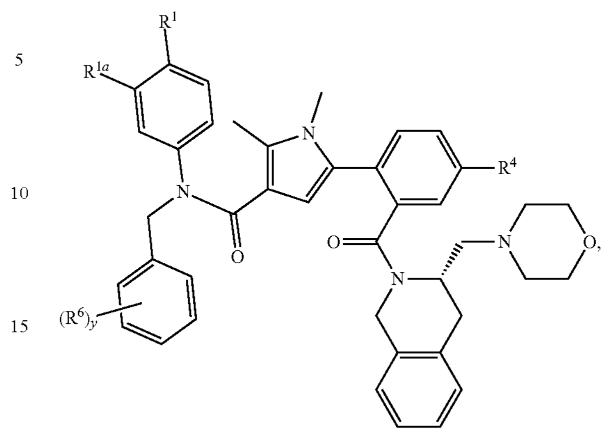

or pharmaceutically acceptable salts, prodrugs, solvates, hydrates, stereoisomers, or tautomers thereof.

In some embodiments, the compounds of Formula (I) have the structure of Formula (II-A-4):

(II-A-4)

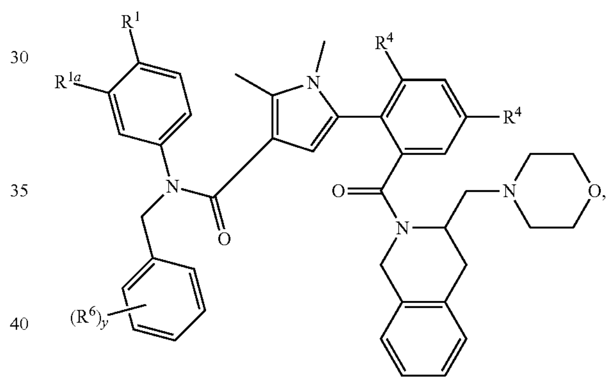

or pharmaceutically acceptable salts, prodrugs, solvates, hydrates, stereoisomers, or tautomers thereof.

In some embodiments, the compounds of Formula (I) have the structure of Formula (II-A-4'):

(II-A-4')

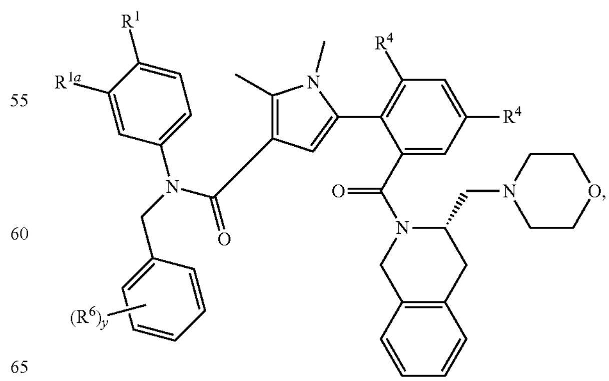

or pharmaceutically acceptable salts, prodrugs, solvates, hydrates, stereoisomers, or tautomers thereof. B):

(II-B)

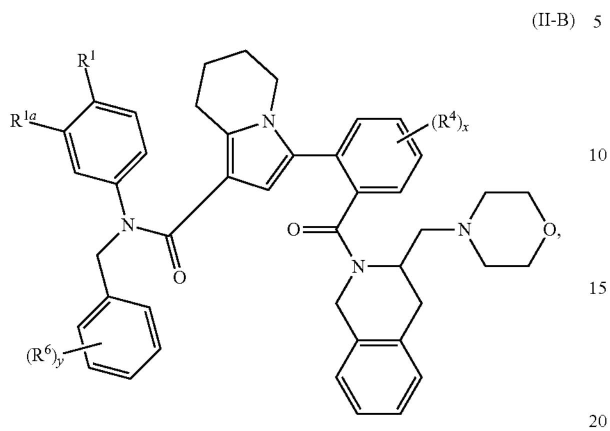

or pharmaceutically acceptable salts, prodrugs, solvates, hydrates, stereoisomers, or tautomers thereof.

In some embodiments, the compounds of Formula (I) have the structure of Formula (II-B-1):

(II-B-1)

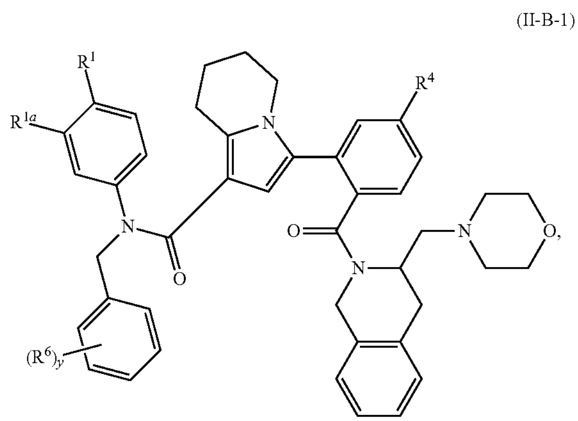

or pharmaceutically acceptable salts, prodrugs, solvates, hydrates, stereoisomers, or tautomers thereof. B-1'):

(II-B-1')

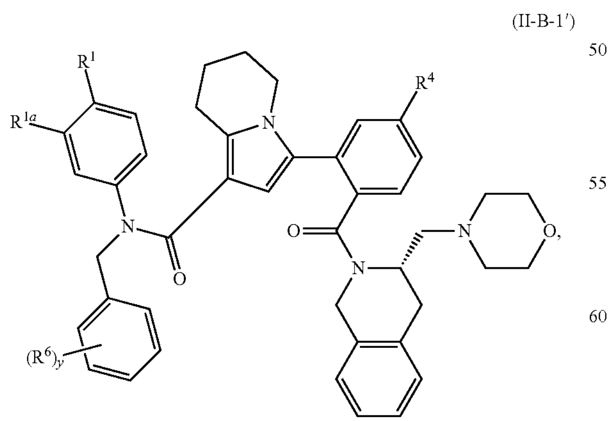

or pharmaceutically acceptable salts, prodrugs, solvates, hydrates, stereoisomers, or tautomers thereof.

In some embodiments, the compounds of Formula (I) have the structure of Formula (II-B-1):

(II-B-2)

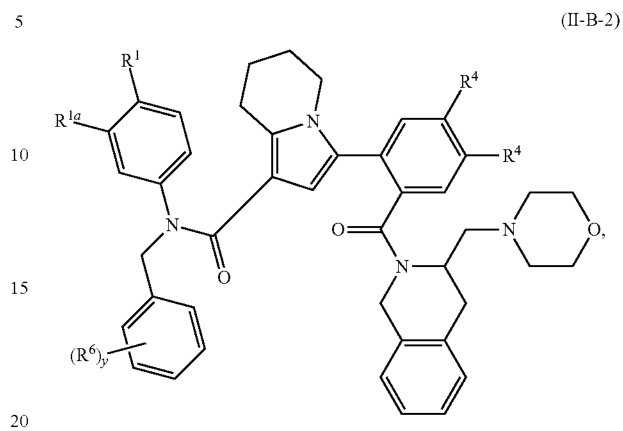

or pharmaceutically acceptable salts, prodrugs, solvates, hydrates, stereoisomers, or tautomers thereof. B-2'):

(II-B-2')

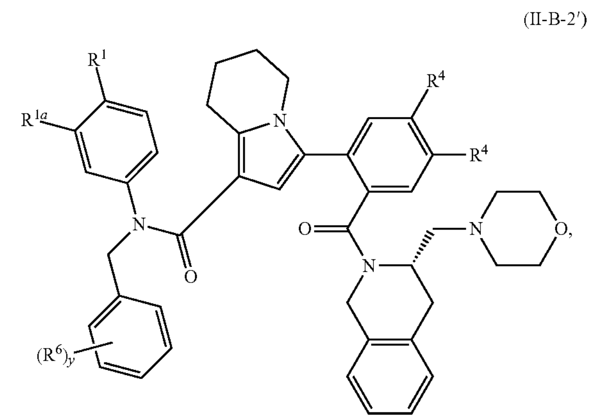

or pharmaceutically acceptable salts, prodrugs, solvates, hydrates, stereoisomers, or tautomers thereof.

In some embodiments, the compounds of Formula (I) have the structure of Formula (II-B-3):

(II-B-3)

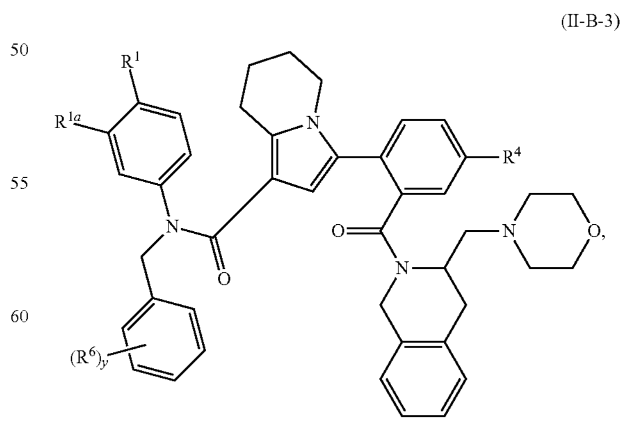

or pharmaceutically acceptable salts, prodrugs, solvates, hydrates, stereoisomers, or tautomers thereof. B-3'):

(II-B-3′)

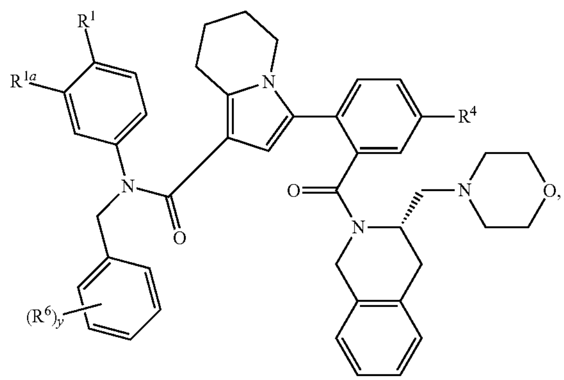

or pharmaceutically acceptable salts, prodrugs, solvates, hydrates, stereoisomers, or tautomers thereof.

In some embodiments, the compounds of Formula (I) have the structure of Formula (II-B-4):

(II-B-4)

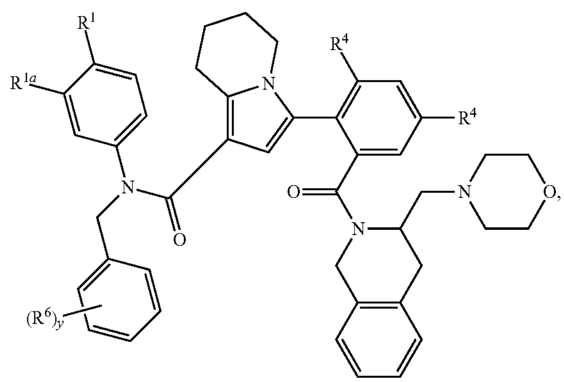

or pharmaceutically acceptable salts, prodrugs, solvates, hydrates, stereoisomers, or tautomers thereof. B-4'):

(II-B-4′)

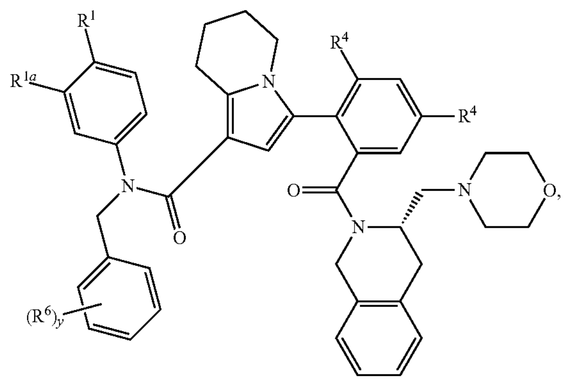

or pharmaceutically acceptable salts, prodrugs, solvates, hydrates, stereoisomers, or tautomers thereof.

In some embodiments, the compounds of Formula (I) have the structure of Formula (II-A-1-A):

(II-A-A)

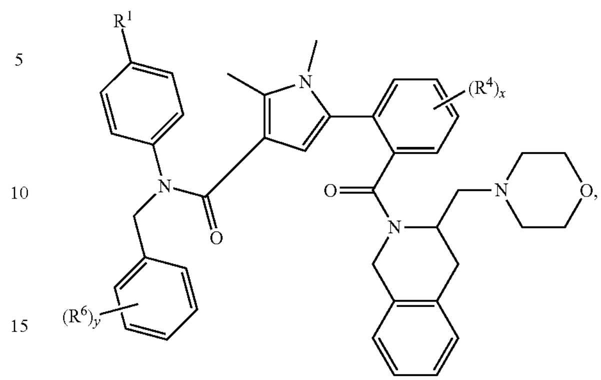

or pharmaceutically acceptable salts, prodrugs, solvates, hydrates, stereoisomers, or tautomers thereof.

In some embodiments, the compounds of Formula (I) have the structure of Formula (II-A-1-A):

(II-A-1-A)

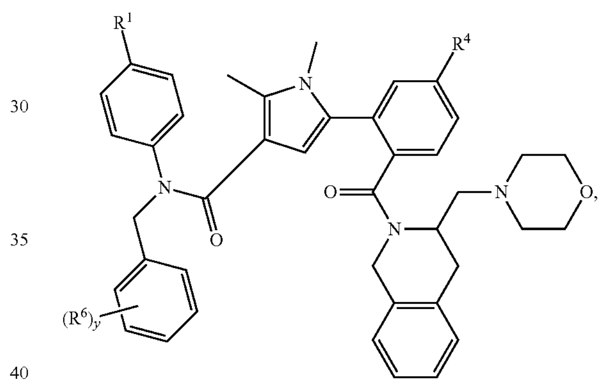

or pharmaceutically acceptable salts, prodrugs, solvates, hydrates, stereoisomers, or tautomers thereof.

In some embodiments, the compounds of Formula (I) have the structure of Formula (II-A-1-A'):

(II-A-1-A′)

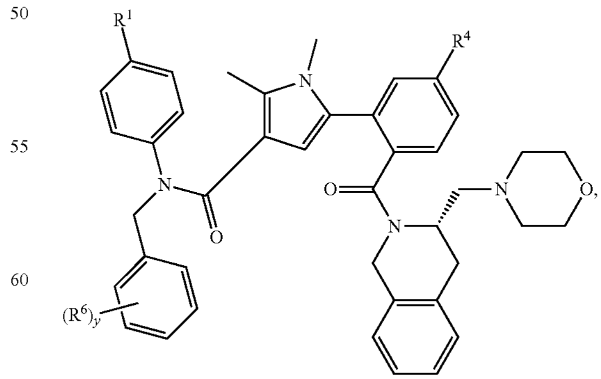

or pharmaceutically acceptable salts, prodrugs, solvates, hydrates, stereoisomers, or tautomers thereof.

In some embodiments, the compounds of Formula (I) have the structure of Formula (II-A-2-A):

(II-A-2-A)

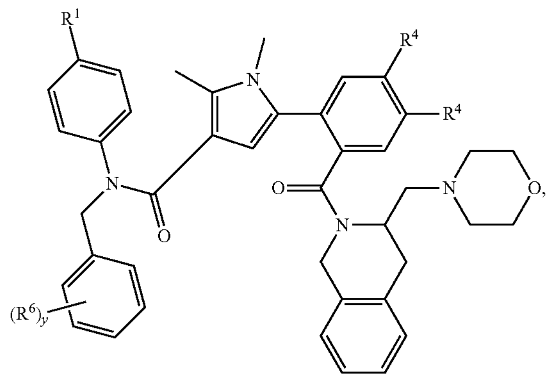

or pharmaceutically acceptable salts, prodrugs, solvates, hydrates, stereoisomers, or tautomers thereof.

In some embodiments, the compounds of Formula (I) have the structure of Formula (II-A-2-A'):

(II-A-2-A')

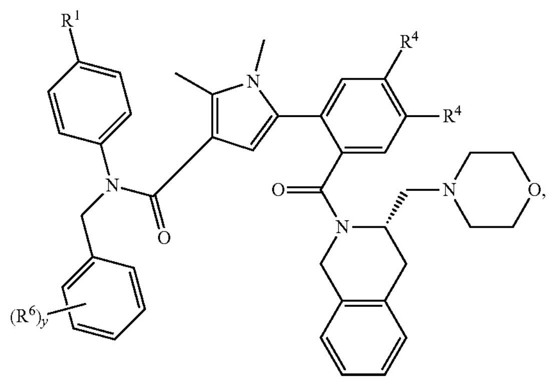

or pharmaceutically acceptable salts, prodrugs, solvates, hydrates, stereoisomers, or tautomers thereof.

In some embodiments, the compounds of Formula (I) have the structure of Formula (II-A-3-A):

(II-A-3-A)

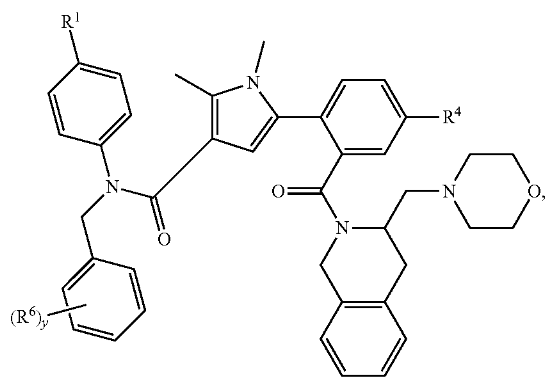

or pharmaceutically acceptable salts, prodrugs, solvates, hydrates, stereoisomers, or tautomers thereof.

In some embodiments, the compounds of Formula (I) have the structure of Formula (II-A-3-A'):

(II-A-3-A')

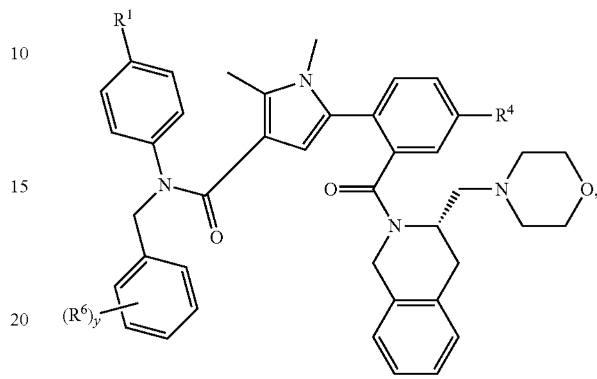

or pharmaceutically acceptable salts, prodrugs, solvates, hydrates, stereoisomers, or tautomers thereof.

In some embodiments, the compounds of Formula (I) have the structure of Formula (II-A-4-A):

(II-A-4-A)

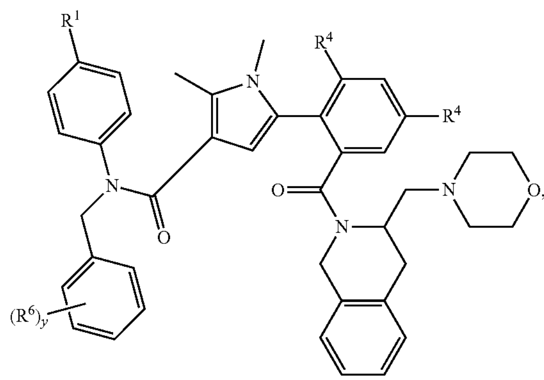

or pharmaceutically acceptable salts, prodrugs, solvates, hydrates, stereoisomers, or tautomers thereof.

In some embodiments, the compounds of Formula (I) have the structure of Formula (II-A-4-A'):

(II-A-4-A′)

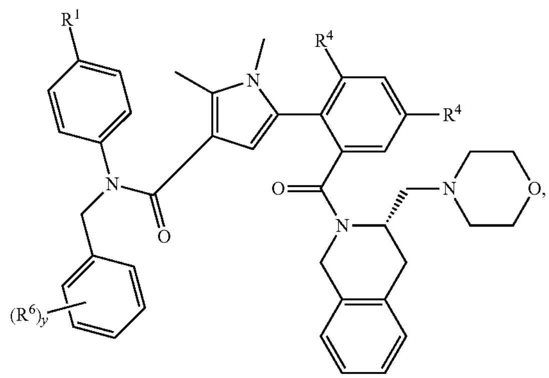

or pharmaceutically acceptable salts, prodrugs, solvates, hydrates, stereoisomers, or tautomers thereof. B-A):

(II-B-A)

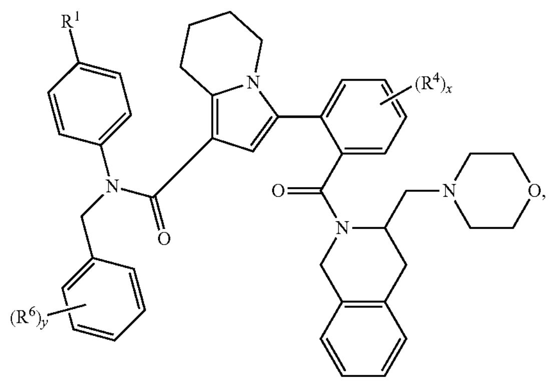

or pharmaceutically acceptable salts, prodrugs, solvates, hydrates, stereoisomers, or tautomers thereof.

In some embodiments, the compounds of Formula (I) have the structure of Formula (II-B-1-A):

(II-B-1-A)

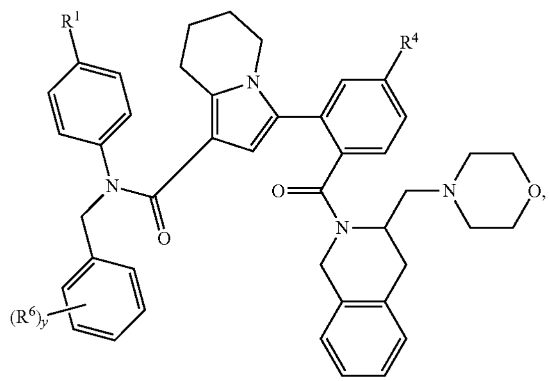

or pharmaceutically acceptable salts, prodrugs, solvates, hydrates, stereoisomers, or tautomers thereof. B-1-A'):

(II-B-1-A′)

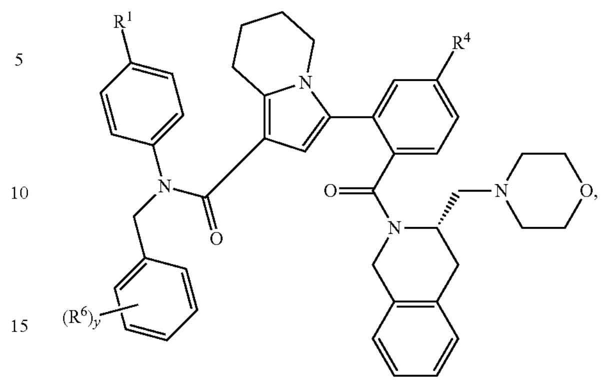

or pharmaceutically acceptable salts, prodrugs, solvates, hydrates, stereoisomers, or tautomers thereof.

In some embodiments, the compounds of Formula (I) have the structure of Formula (II-B-2-A):

(II-B-2-A)

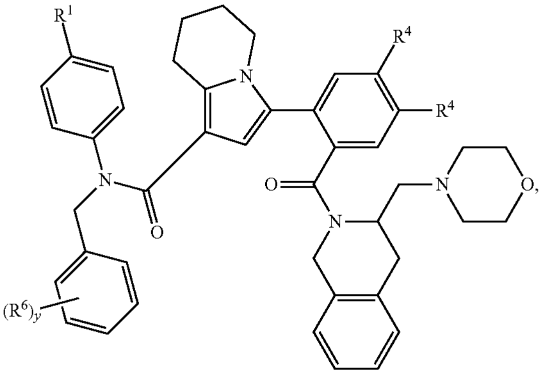

or pharmaceutically acceptable salts, prodrugs, solvates, hydrates, stereoisomers, or tautomers thereof. B-2-A'):

(II-B-2-A′)

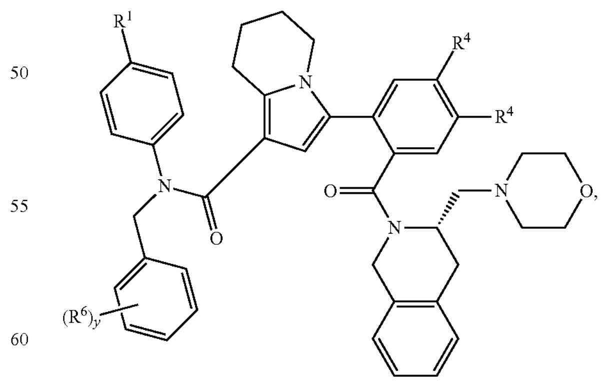

or pharmaceutically acceptable salts, prodrugs, solvates, hydrates, stereoisomers, or tautomers thereof.

In some embodiments, the compounds of Formula (I) have the structure of Formula (II-B-3-A):

(II-B-3-A)

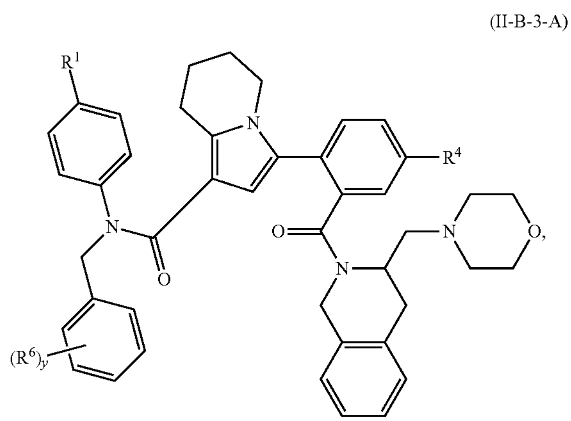

or pharmaceutically acceptable salts, prodrugs, solvates, hydrates, stereoisomers, or tautomers thereof. B-3-A'):

(II-B-3-A')

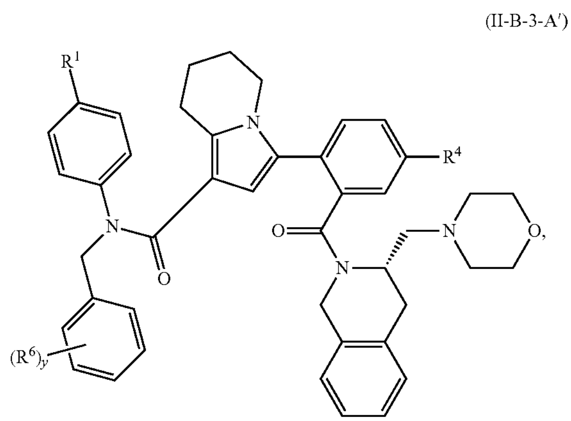

or pharmaceutically acceptable salts, prodrugs, solvates, hydrates, stereoisomers, or tautomers thereof.

In some embodiments, the compounds of Formula (I) have the structure of Formula (II-B-4-A):

(II-B-4-A)

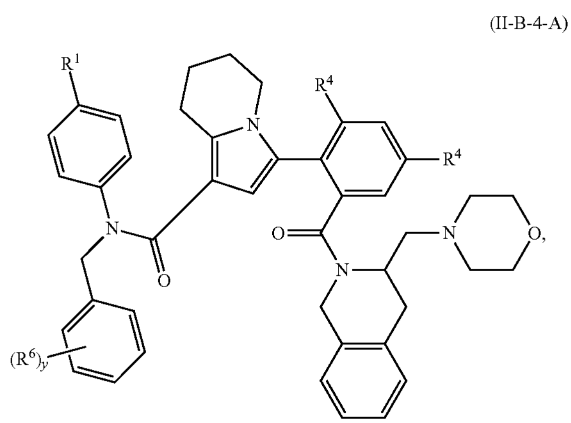

or pharmaceutically acceptable salts, prodrugs, solvates, hydrates, stereoisomers, or tautomers thereof. B-4-A'):

(II-B-4-A')

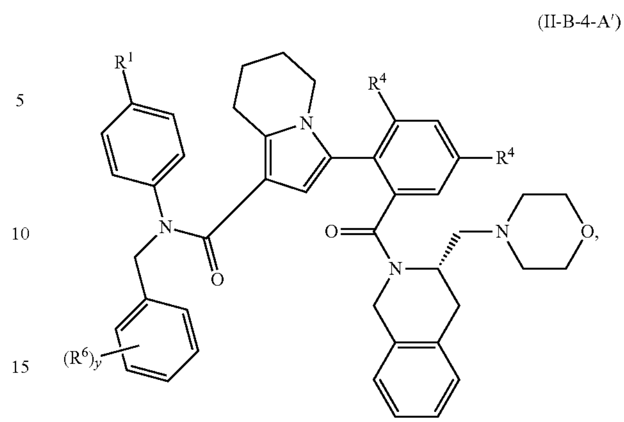

or pharmaceutically acceptable salts, prodrugs, solvates, hydrates, stereoisomers, or tautomers thereof.

In some embodiments, the compounds of Formula (I) have the structure of Formula (II-A-B):

(II-A-B)

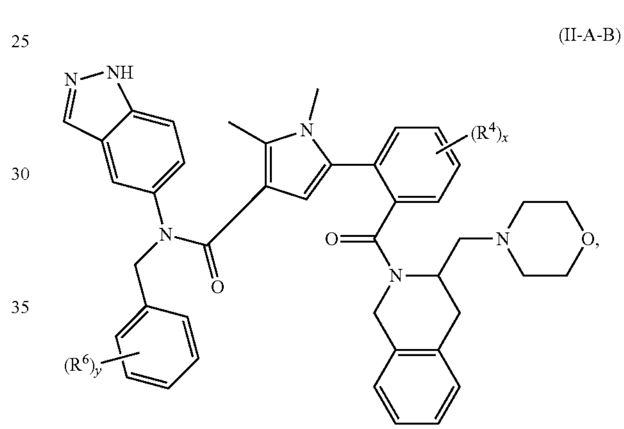

or pharmaceutically acceptable salts, prodrugs, solvates, hydrates, stereoisomers, or tautomers thereof.

In some embodiments, the compounds of Formula (I) have the structure of Formula (II-A-1-B):

(II-A-1-B)

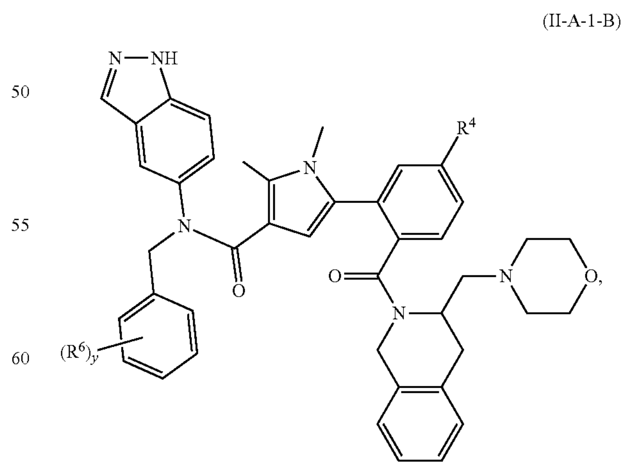

or pharmaceutically acceptable salts, prodrugs, solvates, hydrates, stereoisomers, or tautomers thereof.

In some embodiments, the compounds of Formula (I) have the structure of Formula (II-A-1-B'):

(II-A-1-B')

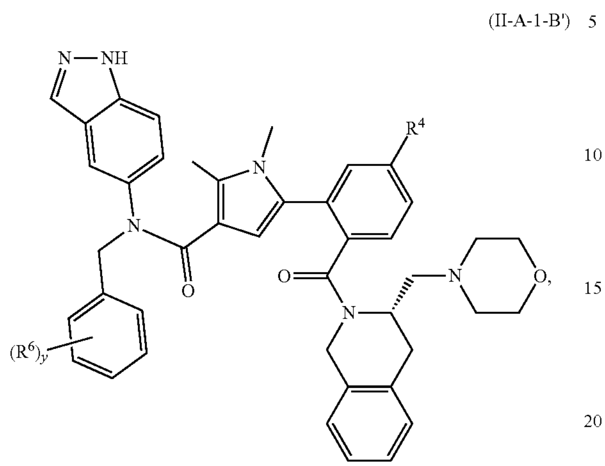

or pharmaceutically acceptable salts, prodrugs, solvates, hydrates, stereoisomers, or tautomers thereof.

In some embodiments, the compounds of Formula (I) have the structure of Formula (II-A-2-B):

(II-A-2-B)

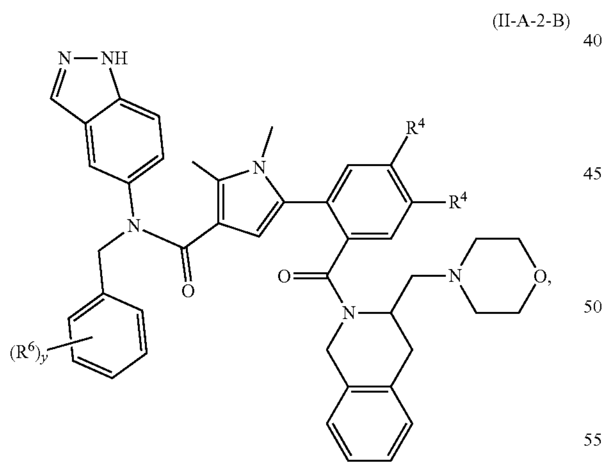

or pharmaceutically acceptable salts, prodrugs, solvates, hydrates, stereoisomers, or tautomers thereof.

In some embodiments, the compounds of Formula (I) have the structure of Formula (II-A-2-B'):

(II-A-2-B')

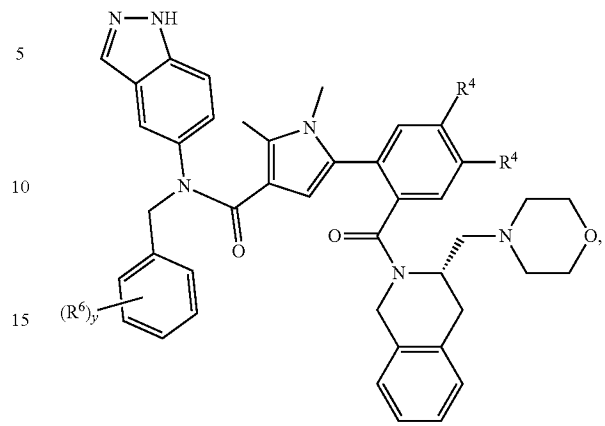

or pharmaceutically acceptable salts, prodrugs, solvates, hydrates, stereoisomers, or tautomers thereof.

In some embodiments, the compounds of Formula (I) have the structure of Formula (II-A-3-B):

(II-A-3-B)

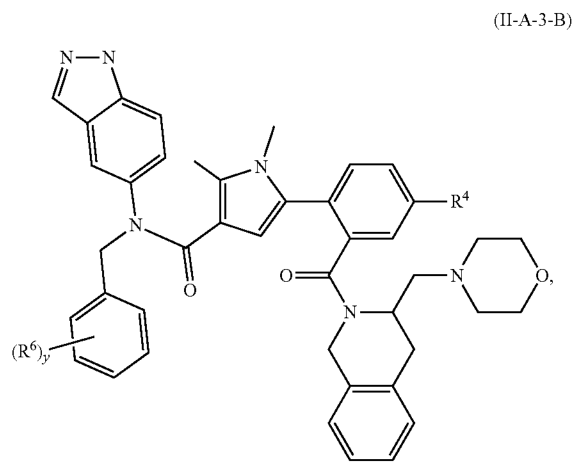

or pharmaceutically acceptable salts, prodrugs, solvates, hydrates, stereoisomers, or tautomers thereof.

In some embodiments, the compounds of Formula (I) have the structure of Formula (II-A-3-B'):

(II-A-3-B')

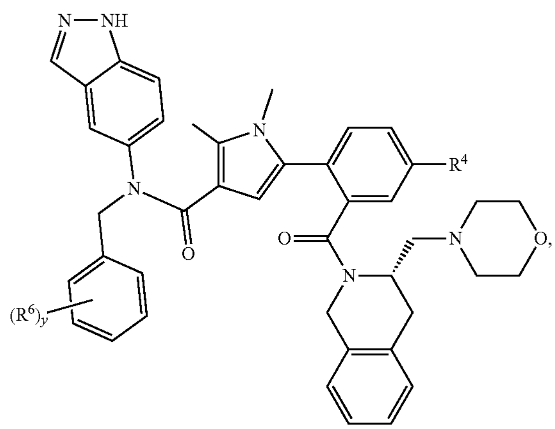

or pharmaceutically acceptable salts, prodrugs, solvates, hydrates, stereoisomers, or tautomers thereof.

In some embodiments, the compounds of Formula (I) have the structure of Formula (II-A-4-B):

(II-A-4-B)

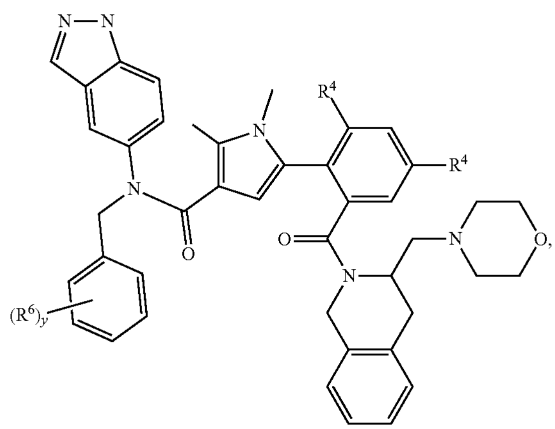

or pharmaceutically acceptable salts, prodrugs, solvates, hydrates, stereoisomers, or tautomers thereof.

In some embodiments, the compounds of Formula (I) have the structure of Formula (II-A-4-B'):

(II-A-4-B')

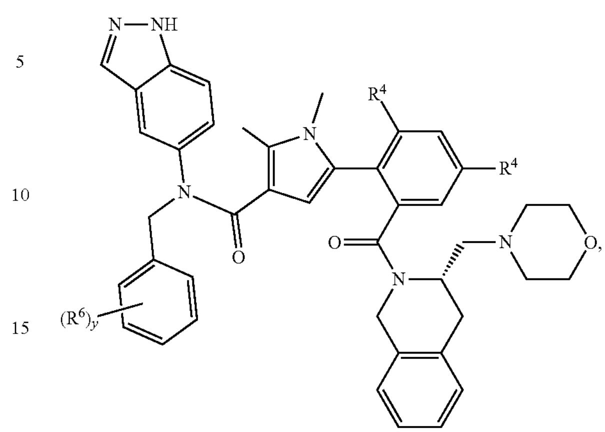

or pharmaceutically acceptable salts, prodrugs, solvates, hydrates, stereoisomers, or tautomers thereof. B—B):

(II-B-B)

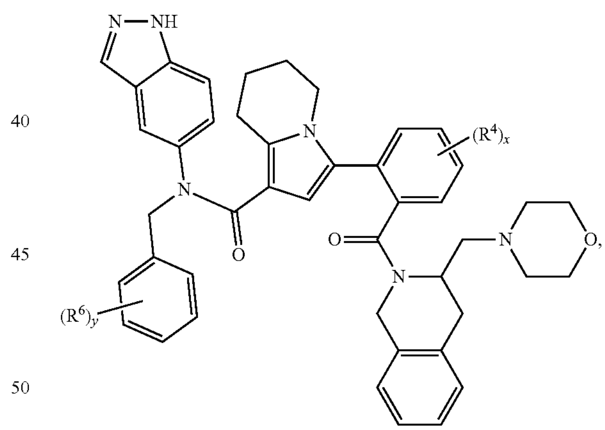

or pharmaceutically acceptable salts, prodrugs, solvates, hydrates, stereoisomers, or tautomers thereof.

In some embodiments, the compounds of Formula (I) have the structure of Formula (II-B-1-B):

(II-B-1-B)

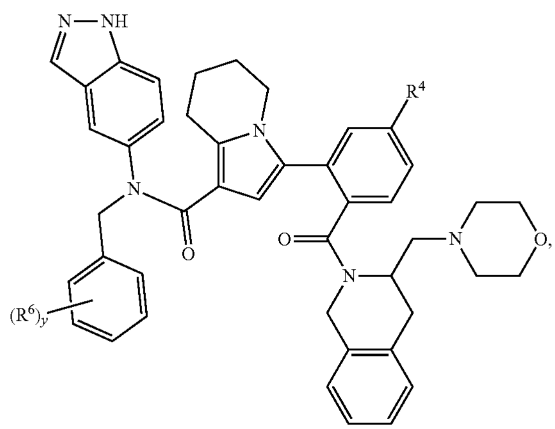

or pharmaceutically acceptable salts, prodrugs, solvates, hydrates, stereoisomers, or tautomers thereof. B-1-B'):

(II-B-1-B')

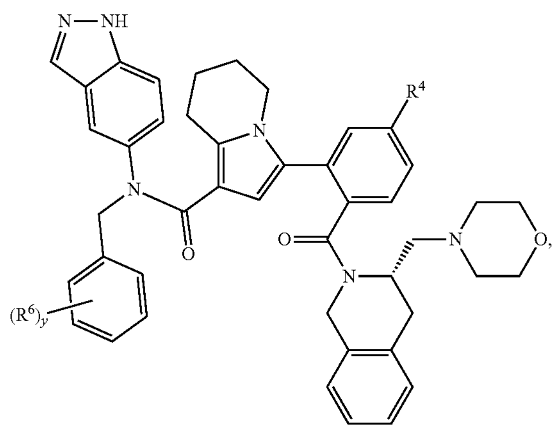

or pharmaceutically acceptable salts, prodrugs, solvates, hydrates, stereoisomers, or tautomers thereof.

In some embodiments, the compounds of Formula (I) have the structure of Formula (II-B-2-B):

(II-B-2-B)

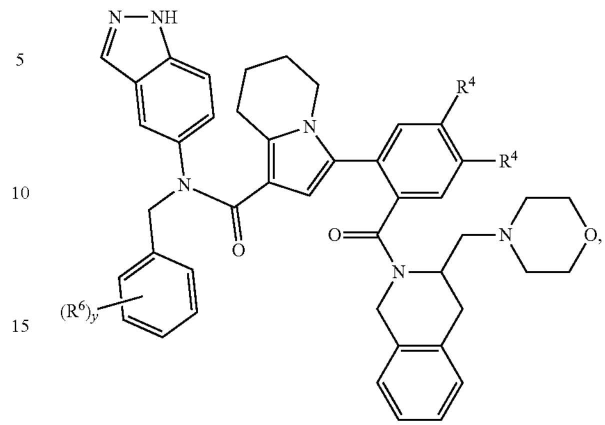

or pharmaceutically acceptable salts, prodrugs, solvates, hydrates, stereoisomers, or tautomers thereof. B-2-B'):

(II-B-2-B')

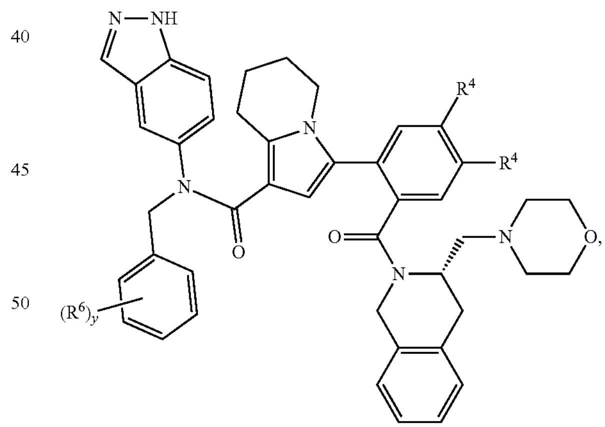

or pharmaceutically acceptable salts, prodrugs, solvates, hydrates, stereoisomers, or tautomers thereof.

In some embodiments, the compounds of Formula (I) have the structure of Formula (II-B-3-B):

(II-B-3-B)

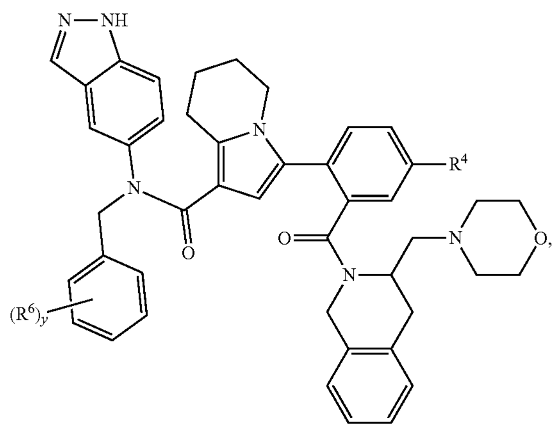

or pharmaceutically acceptable salts, prodrugs, solvates, hydrates, stereoisomers, or tautomers thereof. B-3-B'):

(II-B-3-B')

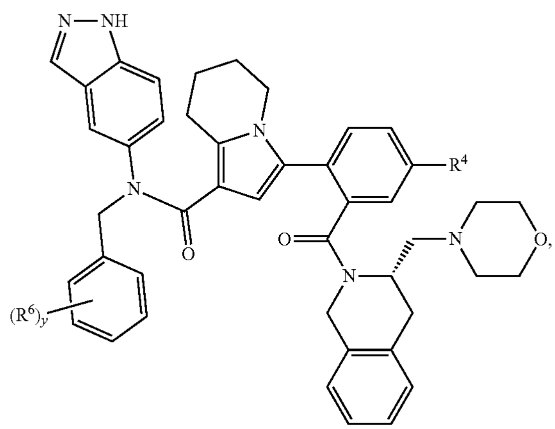

or pharmaceutically acceptable salts, prodrugs, solvates, hydrates, stereoisomers, or tautomers thereof.

In some embodiments, the compounds of Formula (I) have the structure of Formula (II-B-4-B):

(II-B-4-B)

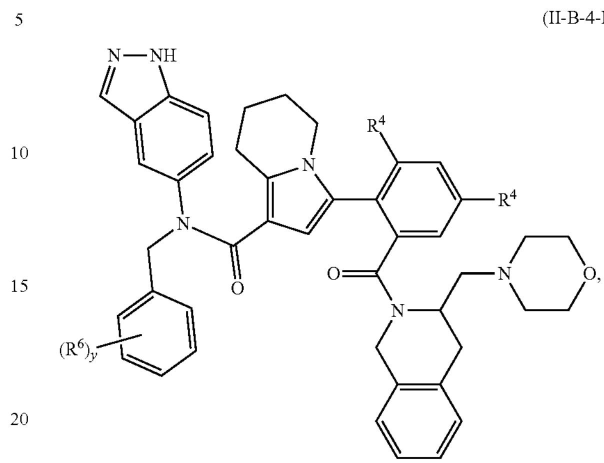

or pharmaceutically acceptable salts, prodrugs, solvates, hydrates, stereoisomers, or tautomers thereof. B-4-B'):

(II-B-4-B')

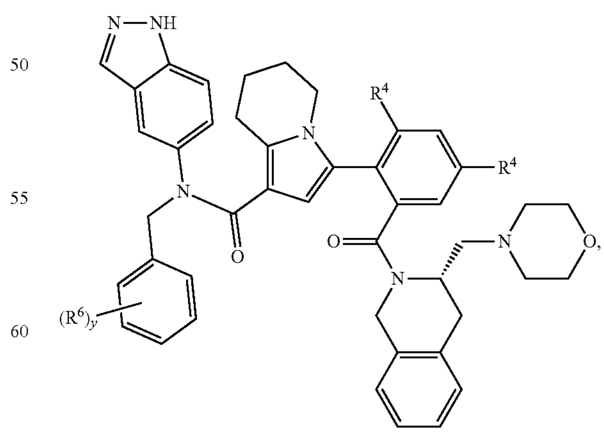

or pharmaceutically acceptable salts, prodrugs, solvates, hydrates, stereoisomers, or tautomers thereof.

In some embodiments, the compounds of Formula (I) have the structure of Formula (II-A-C):

(II-A-C)

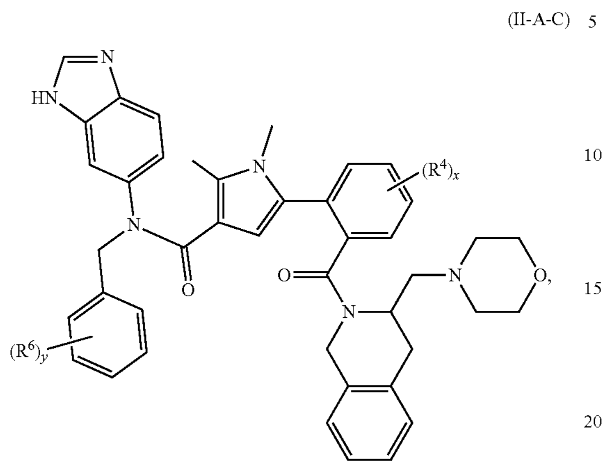

or pharmaceutically acceptable salts, prodrugs, solvates, hydrates, stereoisomers, or tautomers thereof.

In some embodiments, the compounds of Formula (I) have the structure of Formula (II-A-1-C):

(II-A-1-C)

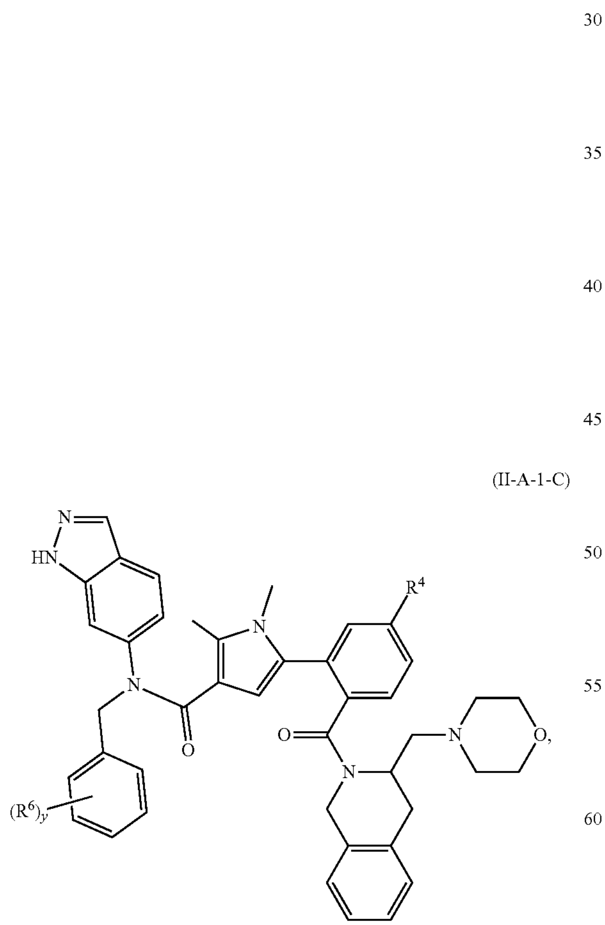

or pharmaceutically acceptable salts, prodrugs, solvates, hydrates, stereoisomers, or tautomers thereof.

In some embodiments, the compounds of Formula (I) have the structure of Formula (II-A-1-C'):

(II-A-1-C')

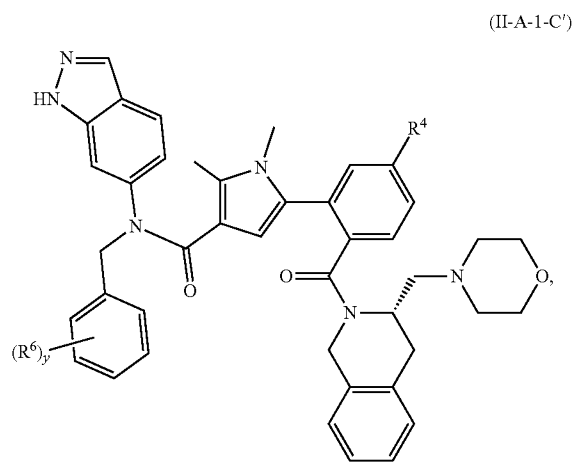

or pharmaceutically acceptable salts, prodrugs, solvates, hydrates, stereoisomers, or tautomers thereof.

In some embodiments, the compounds of Formula (I) have the structure of Formula (II-A-2-C):

(II-A-2-C)

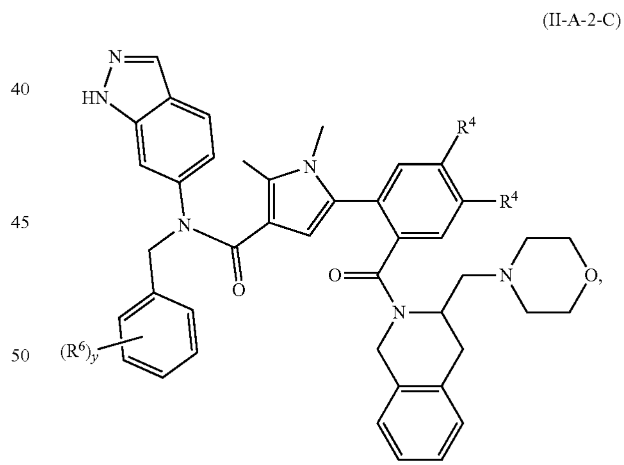

or pharmaceutically acceptable salts, prodrugs, solvates, hydrates, stereoisomers, or tautomers thereof.

In some embodiments, the compounds of Formula (I) have the structure of Formula (II-A-2-C'):

(II-A-2-C')

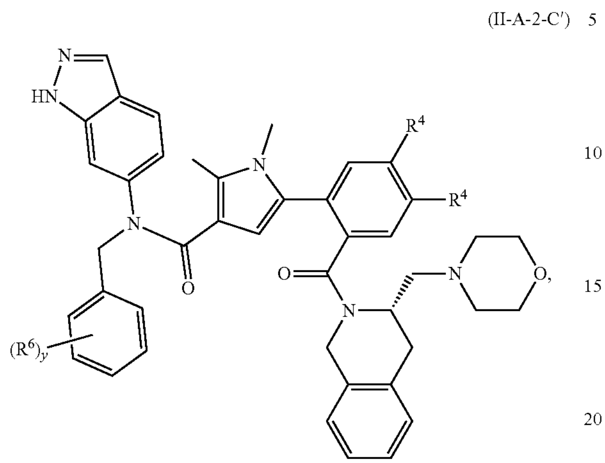

or pharmaceutically acceptable salts, prodrugs, solvates, hydrates, stereoisomers, or tautomers thereof.

In some embodiments, the compounds of Formula (I) have the structure of Formula (II-A-3-C):

(II-A-3-C)

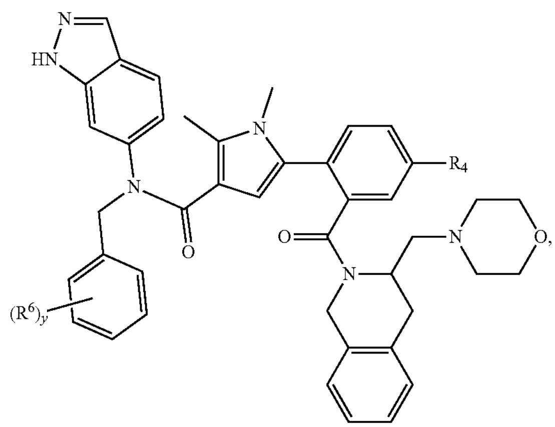

or pharmaceutically acceptable salts, prodrugs, solvates, hydrates, stereoisomers, or tautomers thereof.

In some embodiments, the compounds of Formula (I) have the structure of Formula (II-A-3-C'):

(II-A-3-C')

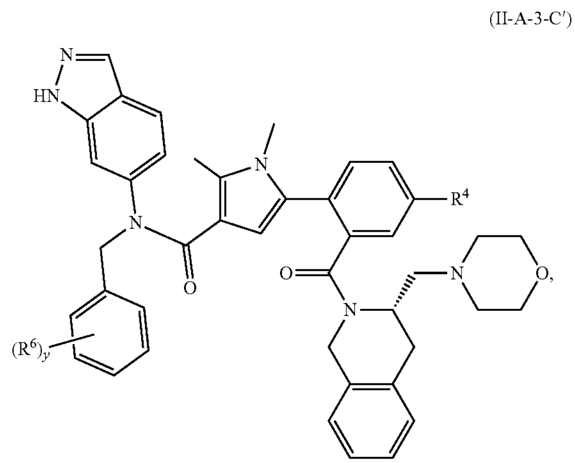

or pharmaceutically acceptable salts, prodrugs, solvates, hydrates, stereoisomers, or tautomers thereof.

In some embodiments, the compounds of Formula (I) have the structure of Formula (II-A-4-C):

(II-A-4-C)

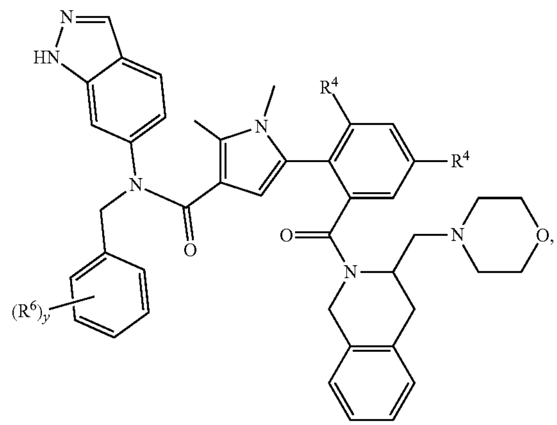

or pharmaceutically acceptable salts, prodrugs, solvates, hydrates, stereoisomers, or tautomers thereof.

In some embodiments, the compounds of Formula (I) have the structure of Formula (II-A-4-C'):

(II-A-4-C')

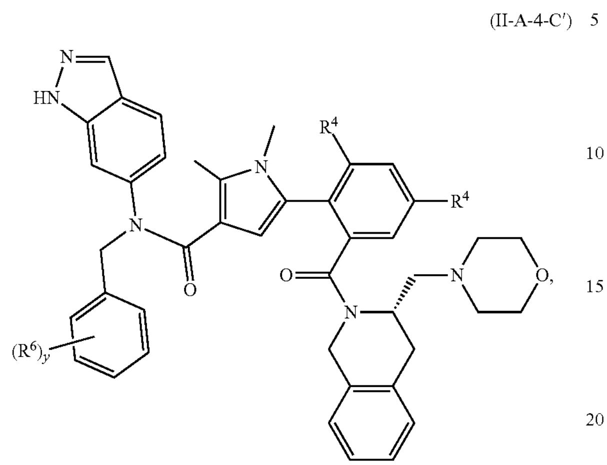

or pharmaceutically acceptable salts, prodrugs, solvates, hydrates, stereoisomers, or tautomers thereof. B—C):

(II-B-C)

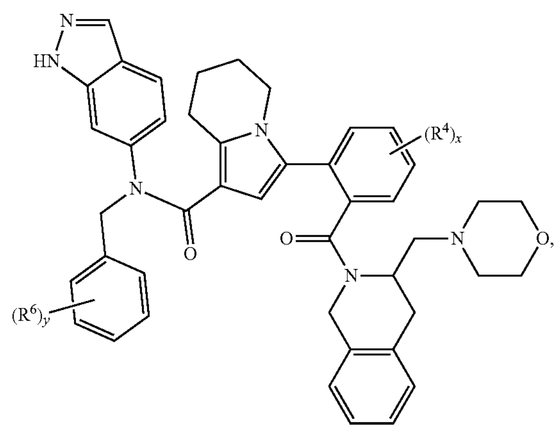

or pharmaceutically acceptable salts, prodrugs, solvates, hydrates, stereoisomers, or tautomers thereof.

In some embodiments, the compounds of Formula (I) have the structure of Formula (II-B-1-C):

(II-B-1-C)

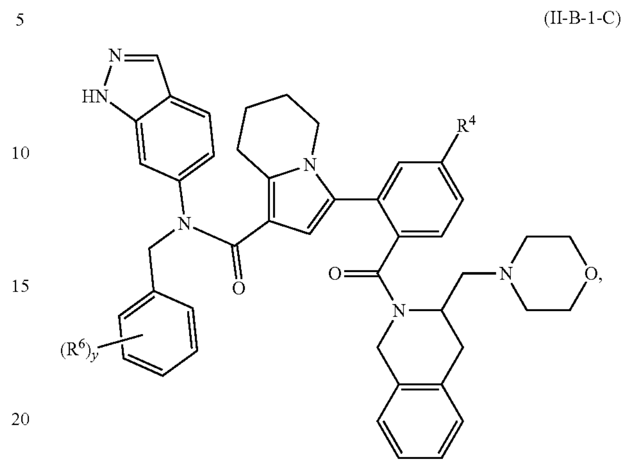

or pharmaceutically acceptable salts, prodrugs, solvates, hydrates, stereoisomers, or tautomers thereof. B-1-C'):

(II-B-1-C')

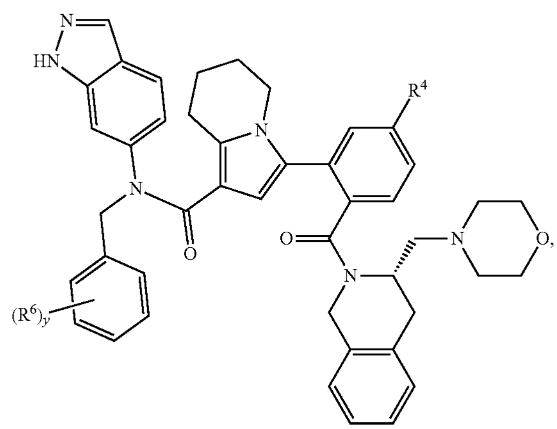

or pharmaceutically acceptable salts, prodrugs, solvates, hydrates, stereoisomers, or tautomers thereof.

In some embodiments, the compounds of Formula (I) have the structure of Formula (II-B-2-C):

(II-B-2-C)

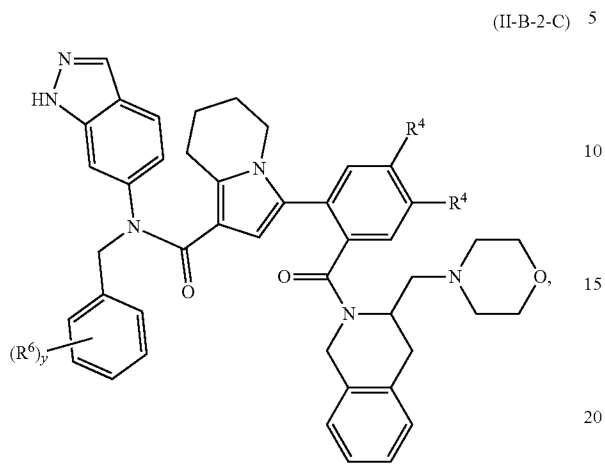

or pharmaceutically acceptable salts, prodrugs, solvates, hydrates, stereoisomers, or tautomers thereof. B-2-C'):

(II-B-2-C')

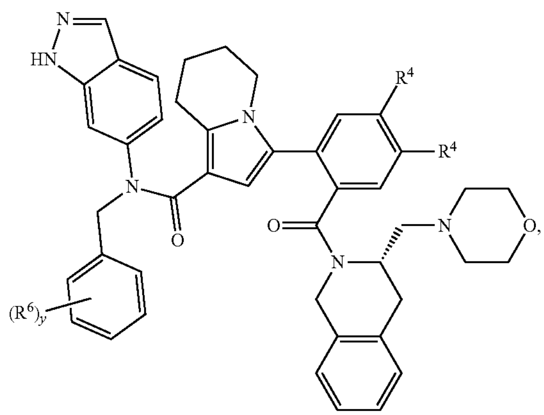

or pharmaceutically acceptable salts, prodrugs, solvates, hydrates, stereoisomers, or tautomers thereof.

In some embodiments, the compounds of Formula (I) have the structure of Formula (II-B-3-C):

(II-B-3-C)

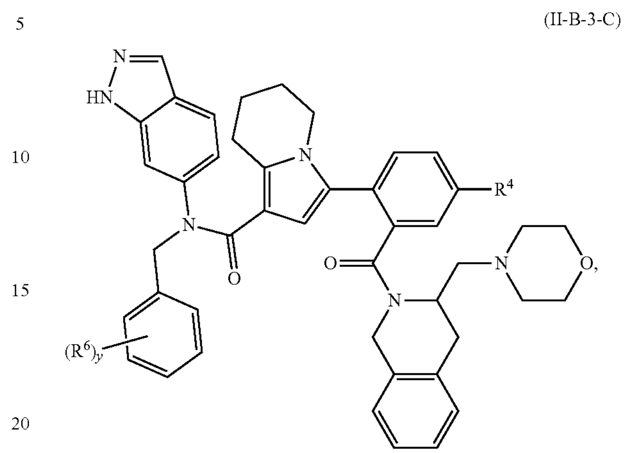

or pharmaceutically acceptable salts, prodrugs, solvates, hydrates, stereoisomers, or tautomers thereof. B-3-C'):

(II-B-3-C')

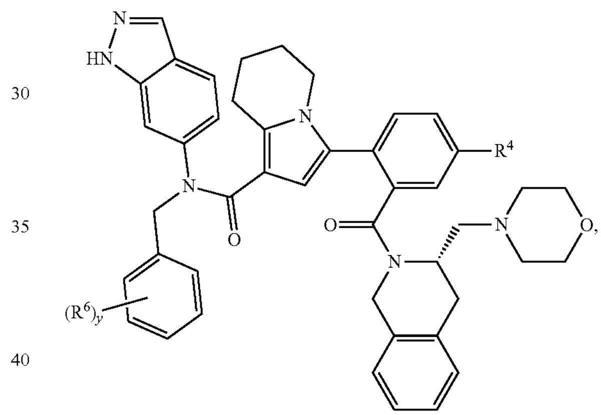

or pharmaceutically acceptable salts, prodrugs, solvates, hydrates, stereoisomers, or tautomers thereof.

In some embodiments, the compounds of Formula (I) have the structure of Formula (II-B-4-C):

(II-B-4-C)

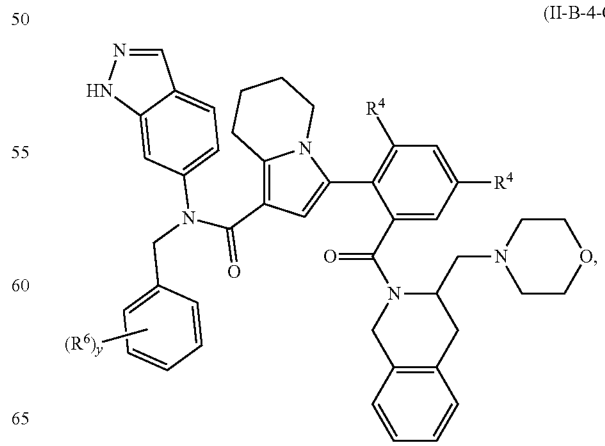

or pharmaceutically acceptable salts, prodrugs, solvates, hydrates, stereoisomers, or tautomers thereof. B-4-C'):

(II-B-4-C')

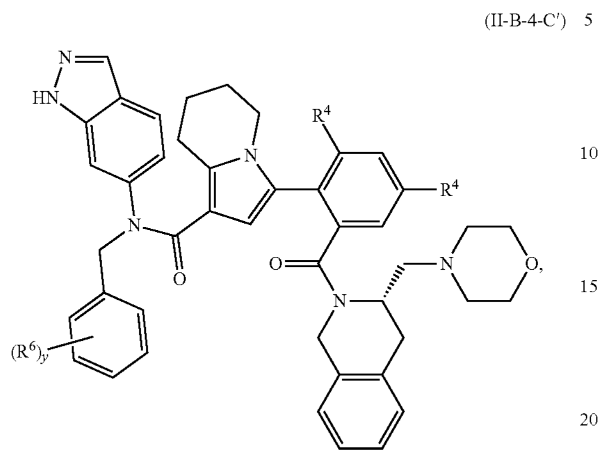

or pharmaceutically acceptable salts, prodrugs, solvates, hydrates, stereoisomers, or tautomers thereof.

In some embodiments, the compounds of Formula (I) have the structure of Formula (II-A-1-A-1):

(II-A-1-A-1)

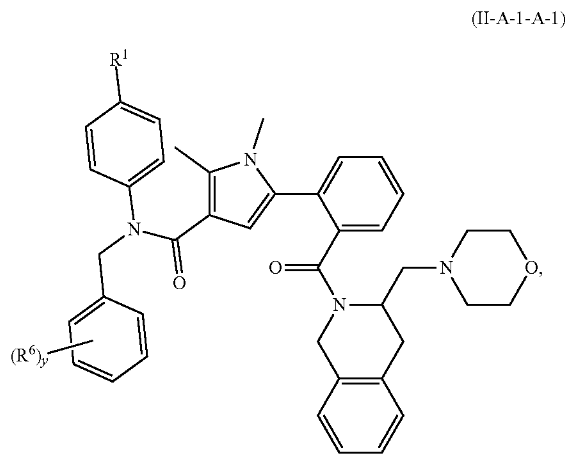

or pharmaceutically acceptable salts, prodrugs, solvates, hydrates, stereoisomers, or tautomers thereof.

In some embodiments, the compounds of Formula (I) have the structure of Formula (II-A-1-A'):

(II-A-1-A-1')

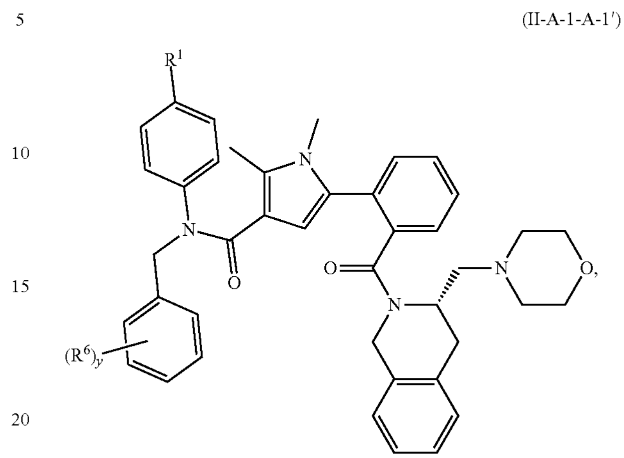

or pharmaceutically acceptable salts, prodrugs, solvates, hydrates, stereoisomers, or tautomers thereof.

In some embodiments, the compounds of Formula (I) have the structure of Formula (II-A-1-A-a):

(II-A-1-A-a)

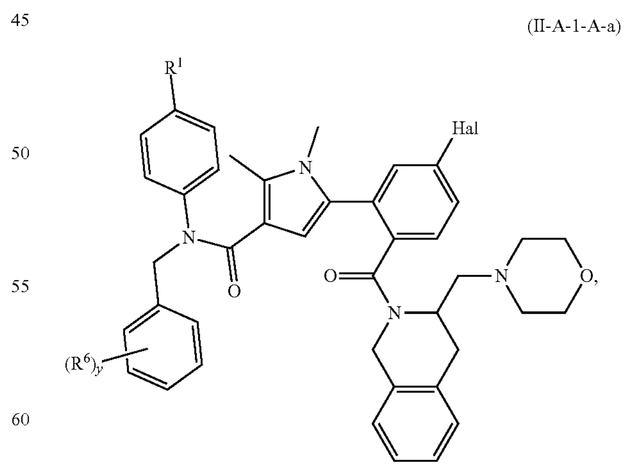

or pharmaceutically acceptable salts, prodrugs, solvates, hydrates, stereoisomers, or tautomers thereof wherein Hal is halogen and all ither variables are as defined herein. A-1-A-a'):

(II-A-1-A-a')

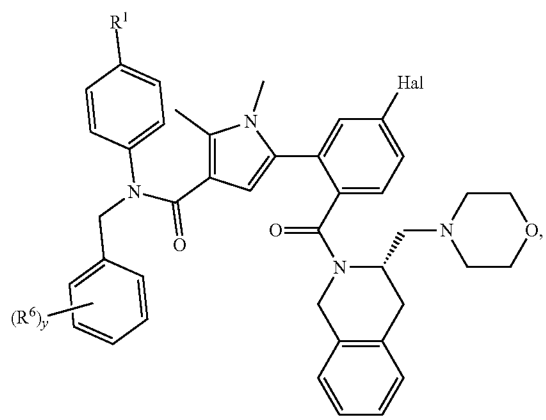

or pharmaceutically acceptable salts, prodrugs, solvates, hydrates, stereoisomers, or tautomers thereof, wherein Hal is halogen and all other variables are as defined herein.

In some embodiments, the compounds of Formula (I) have the structure of Formula (II-A-1-A-2):

(II-A-1-A-2)

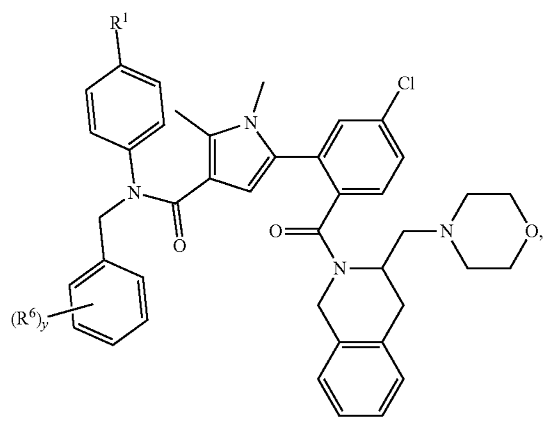

or pharmaceutically acceptable salts, prodrugs, solvates, hydrates, stereoisomers, or tautomers thereof.

In some embodiments, the compounds of Formula (I) have the structure of Formula (II-A-1-A-2'):

(II-A-1-A-2')

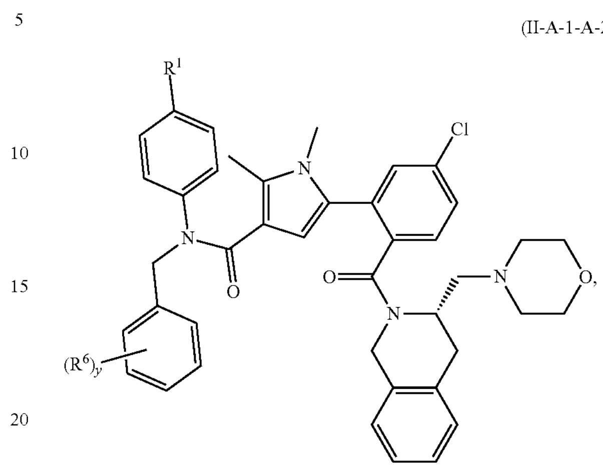

or pharmaceutically acceptable salts, prodrugs, solvates, hydrates, stereoisomers, or tautomers thereof.

In some embodiments, the compounds of Formula (I) have the structure of Formula (II-A-1-A-3):

(II-A-1-A-3)

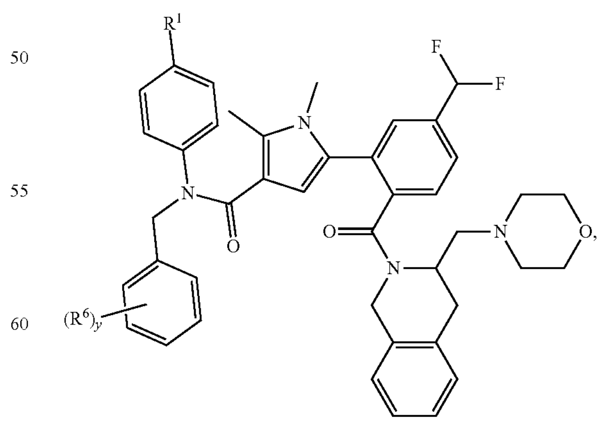

or pharmaceutically acceptable salts, prodrugs, solvates, hydrates, stereoisomers, or tautomers thereof.

In some embodiments, the compounds of Formula (I) have the structure of Formula (II-A-1-A-3'):

(II-A-1-A-3')

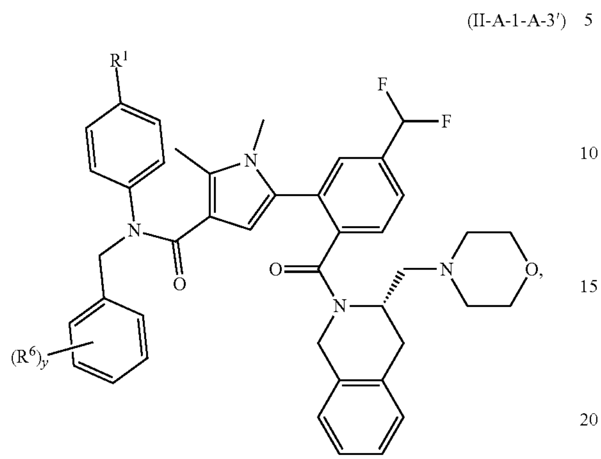

or pharmaceutically acceptable salts, prodrugs, solvates, hydrates, stereoisomers, or tautomers thereof.

In some embodiments, the compounds of Formula (I) have the structure of Formula (II-A-1-A-4):

(II-A-1-A-4)

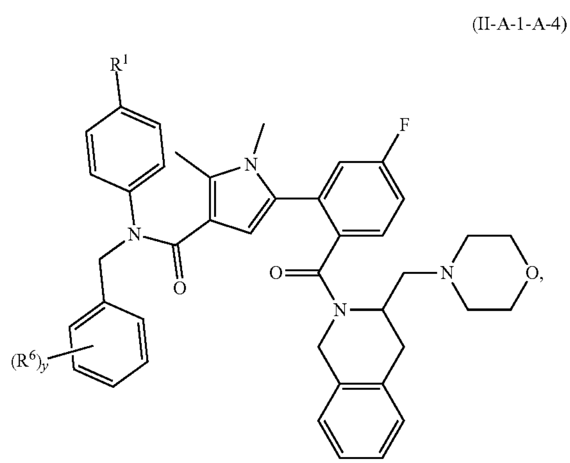

or pharmaceutically acceptable salts, prodrugs, solvates, hydrates, stereoisomers, or tautomers thereof.

In some embodiments, the compounds of Formula (I) have the structure of Formula (II-A-1-A-4'):

(II-A-1-A-4')

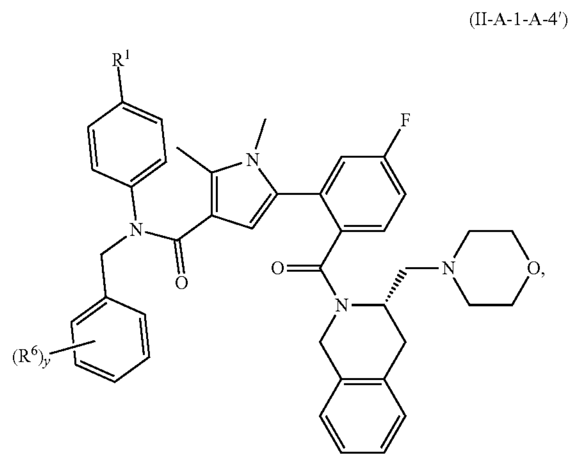

or pharmaceutically acceptable salts, prodrugs, solvates, hydrates, stereoisomers, or tautomers thereof.

In some embodiments, the compounds of Formula (I) have the structure of Formula (II-A-1-A-5):

(II-A-1-A-5)

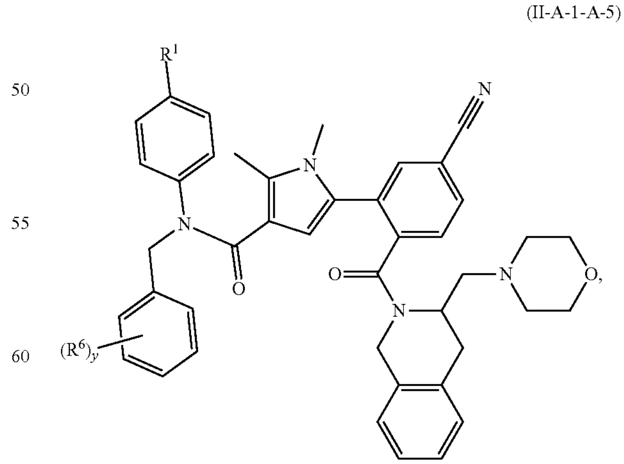

or pharmaceutically acceptable salts, prodrugs, solvates, hydrates, stereoisomers, or tautomers thereof.

In some embodiments, the compounds of Formula (I) have the structure of Formula (II-A-1-A-5'):

(II-A-1-A-5')

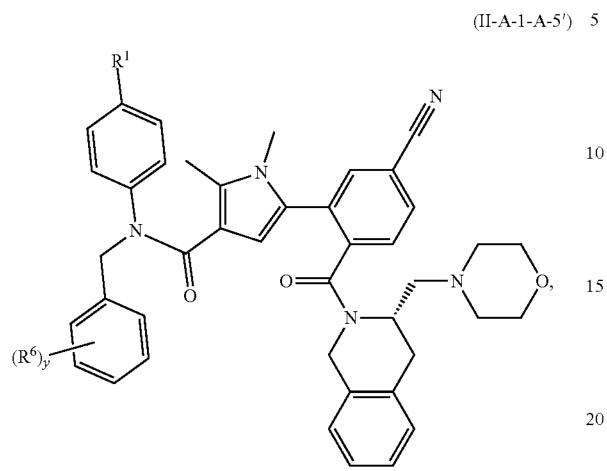

or pharmaceutically acceptable salts, prodrugs, solvates, hydrates, stereoisomers, or tautomers thereof.

In some embodiments, the compounds of Formula (I) have the structure of Formula (II-A-1-A-6):

(II-A-1-A-6)

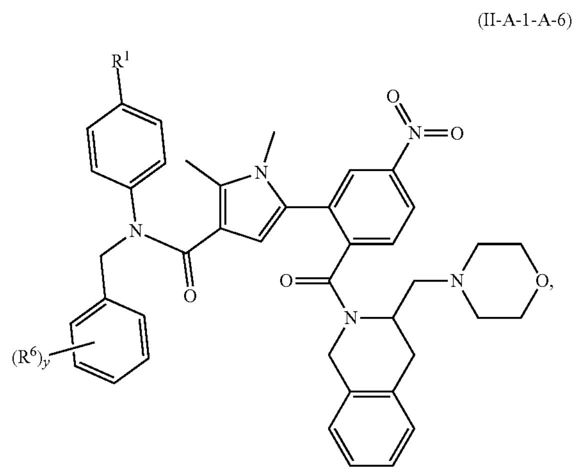

or pharmaceutically acceptable salts, prodrugs, solvates, hydrates, stereoisomers, or tautomers thereof.

In some embodiments, the compounds of Formula (I) have the structure of Formula (II-A-1-A-6'):

(II-A-1-A-6')

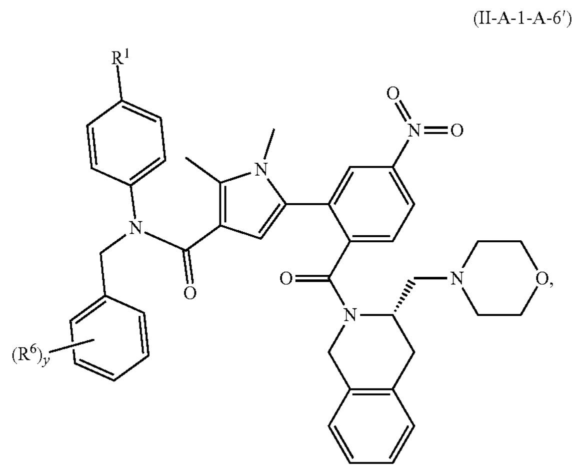

or pharmaceutically acceptable salts, prodrugs, solvates, hydrates, stereoisomers, or tautomers thereof.

In some embodiments, the compounds of Formula (I) have the structure of Formula (II-A-1-A-7):

(II-A-1-A-7)

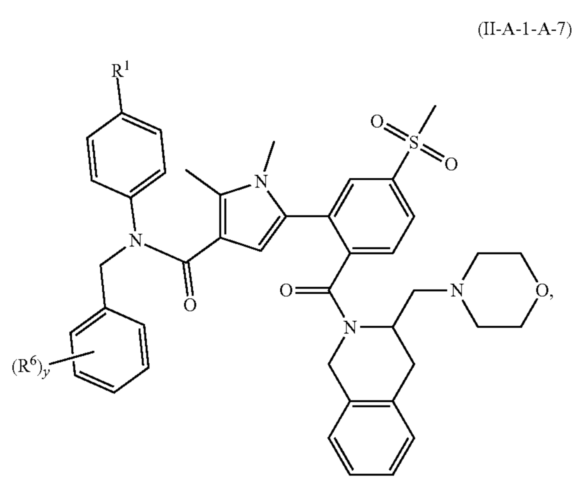

or pharmaceutically acceptable salts, prodrugs, solvates, hydrates, stereoisomers, or tautomers thereof.

In some embodiments, the compounds of Formula (I) have the structure of Formula (II-A-1-A-7'):

(II-A-1-A-7')

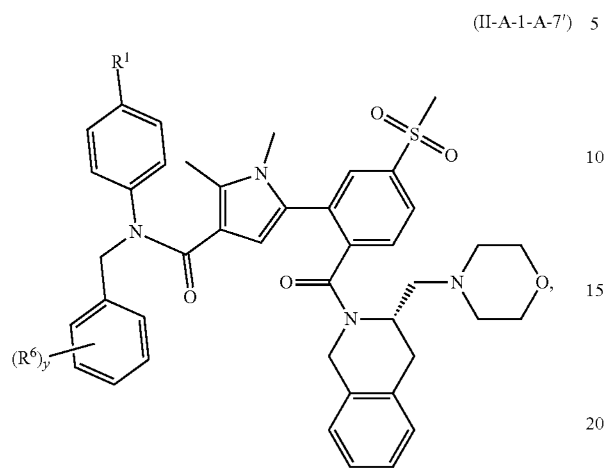

or pharmaceutically acceptable salts, prodrugs, solvates, hydrates, stereoisomers, or tautomers thereof.

In some embodiments, the compounds of Formula (I) have the structure of Formula (II-A-1-A-8):

(II-A-1-A-8)

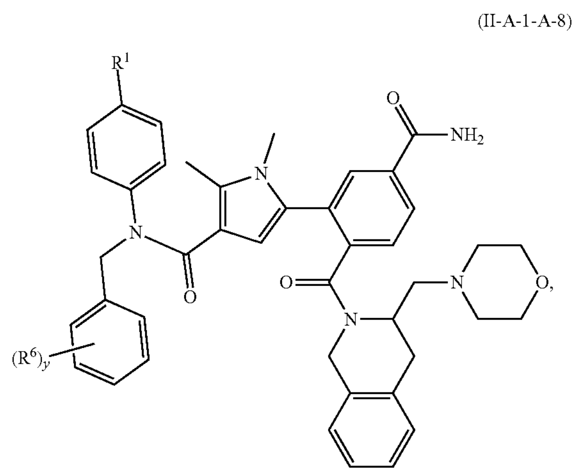

or pharmaceutically acceptable salts, prodrugs, solvates, hydrates, stereoisomers, or tautomers thereof.

In some embodiments, the compounds of Formula (I) have the structure of Formula (II-A-1-A-8'):

(II-A-1-A-8')

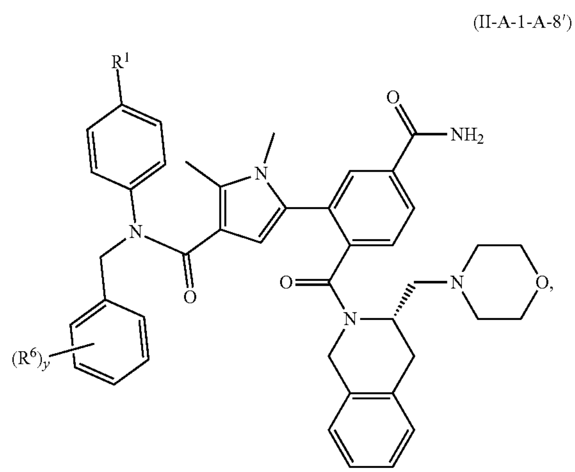

or pharmaceutically acceptable salts, prodrugs, solvates, hydrates, stereoisomers, or tautomers thereof.

In some embodiments, the compounds of Formula (I) have the structure of Formula (II-A-1-A-9):

(II-A-1-A-9)

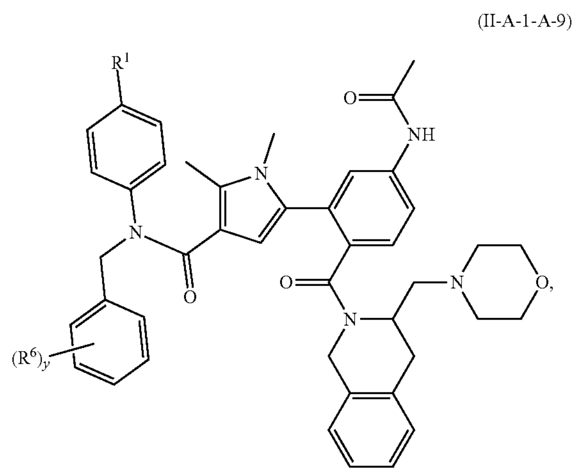

or pharmaceutically acceptable salts, prodrugs, solvates, hydrates, stereoisomers, or tautomers thereof.

In some embodiments, the compounds of Formula (I) have the structure of Formula (II-A-1-A-9'):

(II-A-1-A-9')

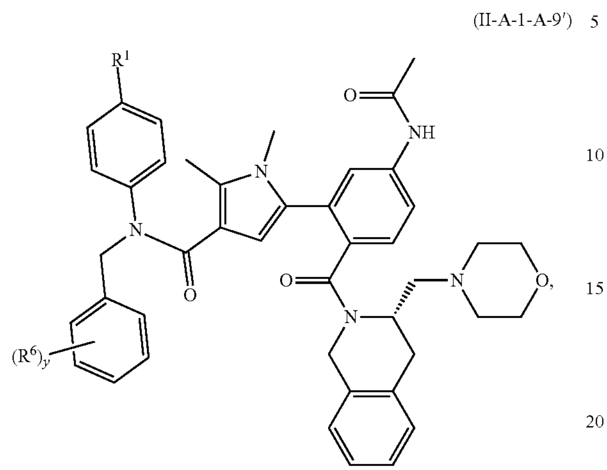

or pharmaceutically acceptable salts, prodrugs, solvates, hydrates, stereoisomers, or tautomers thereof.

In some embodiments, the compounds of Formula (I) have the structure of Formula (II-A-2-A-1):

(II-A-2-A-1)

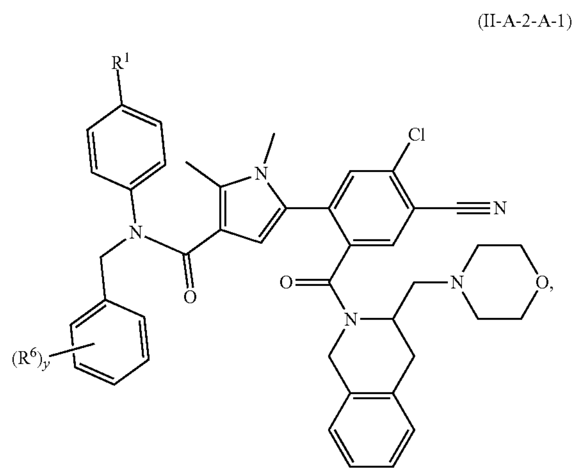

or pharmaceutically acceptable salts, prodrugs, solvates, hydrates, stereoisomers, or tautomers thereof.

In some embodiments, the compounds of Formula (I) have the structure of Formula (II-A-2-A-1'):

(II-A-2-A-1')

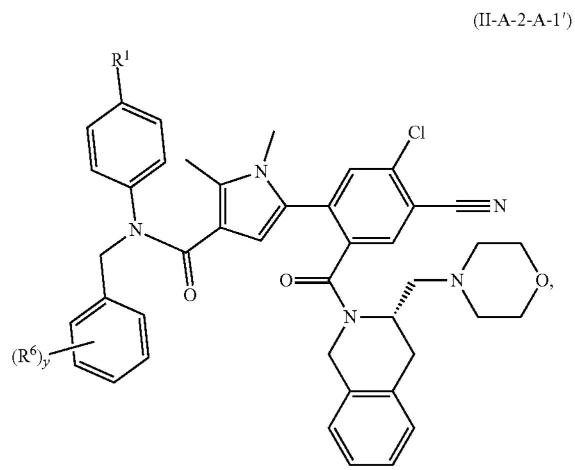

or pharmaceutically acceptable salts, prodrugs, solvates, hydrates, stereoisomers, or tautomers thereof.

In some embodiments, the compounds of Formula (I) have the structure of Formula (II-A-2-A-2):

(II-A-2-A-2)

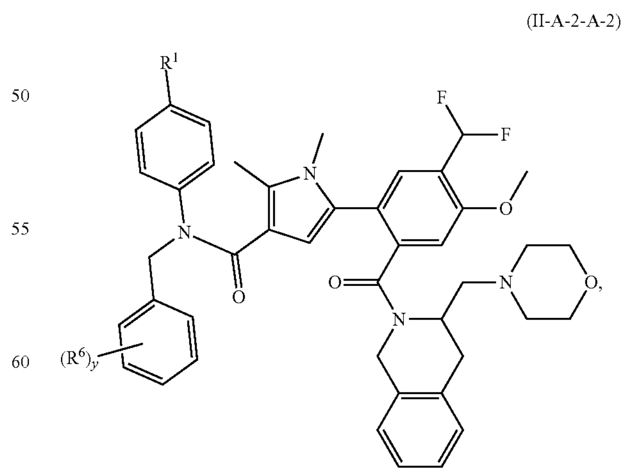

or pharmaceutically acceptable salts, prodrugs, solvates, hydrates, stereoisomers, or tautomers thereof.

In some embodiments, the compounds of Formula (I) have the structure of Formula (II-A-2-A-2'):

(II-A-2-A-2')

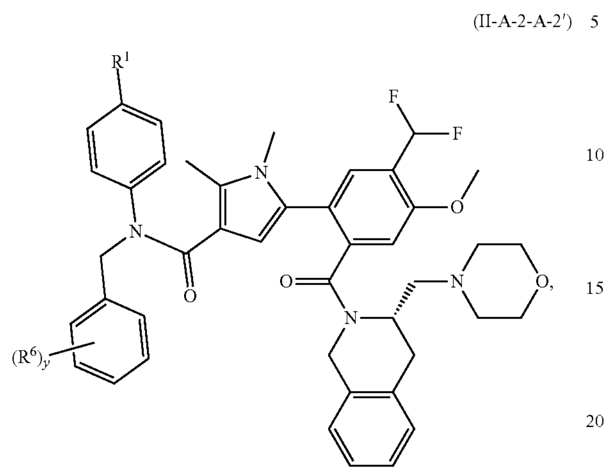

or pharmaceutically acceptable salts, prodrugs, solvates, hydrates, stereoisomers, or tautomers thereof.

In some embodiments, the compounds of Formula (I) have the structure of Formula (II-A-2-A-3):

(II-A-2-A-3)

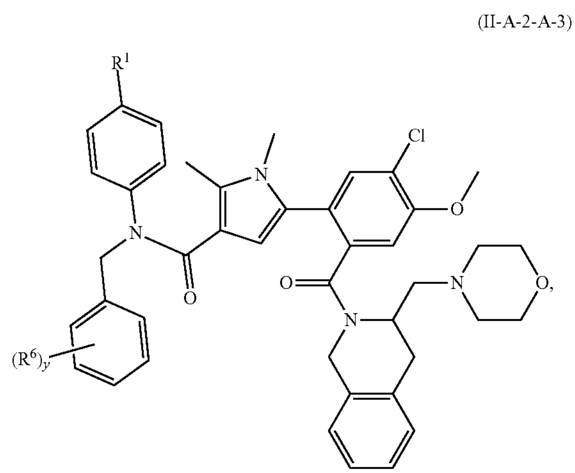

or pharmaceutically acceptable salts, prodrugs, solvates, hydrates, stereoisomers, or tautomers thereof.

In some embodiments, the compounds of Formula (I) have the structure of Formula (II-A-2-A-3'):

(II-A-2-A-3')

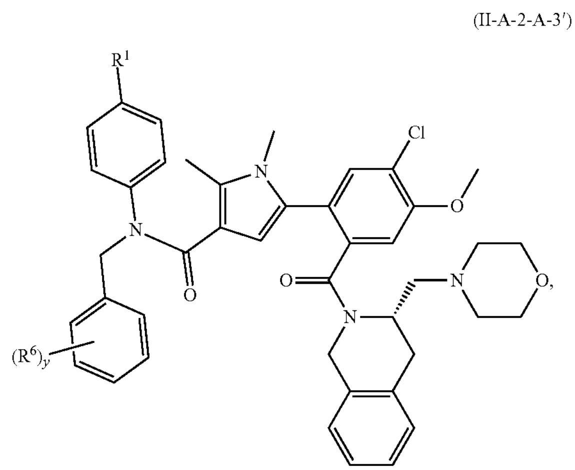

or pharmaceutically acceptable salts, prodrugs, solvates, hydrates, stereoisomers, or tautomers thereof.

In some embodiments, the compounds of Formula (I) have the structure of Formula (II-A-2-A-4):

(II-A-2-A-4)

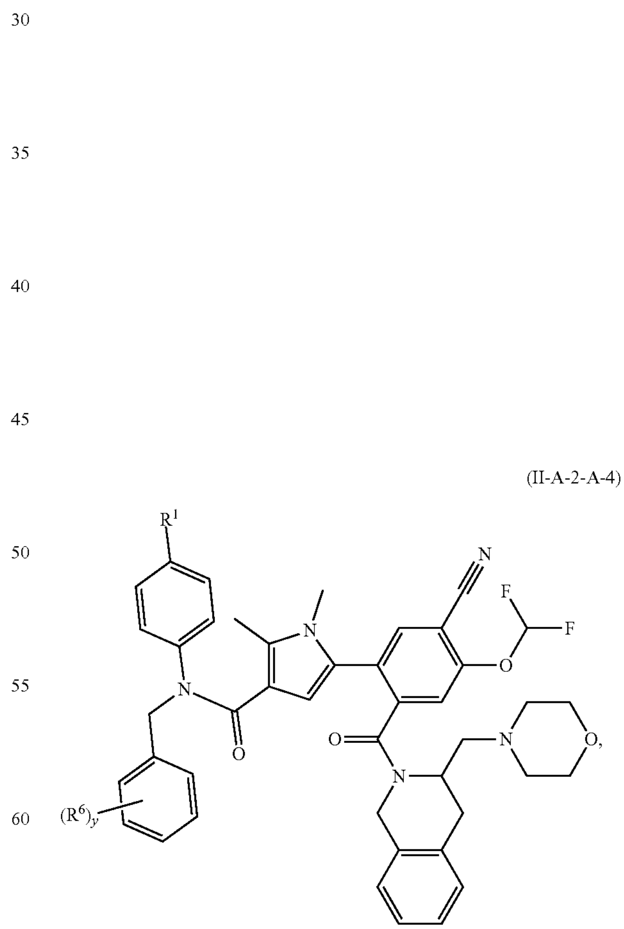

or pharmaceutically acceptable salts, prodrugs, solvates, hydrates, stereoisomers, or tautomers thereof.

In some embodiments, the compounds of Formula (I) have the structure of Formula (II-A-2-A-4'):

(II-A-2-A-4')

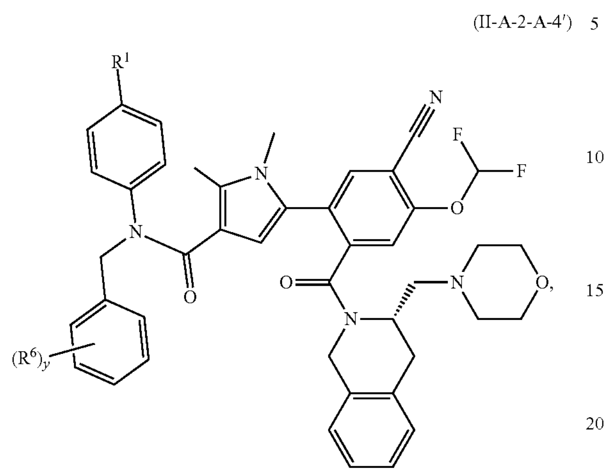

or pharmaceutically acceptable salts, prodrugs, solvates, hydrates, stereoisomers, or tautomers thereof.

In some embodiments, the compounds of Formula (I) have the structure of Formula (II-A-2-A-5):

(II-A-2-A-5)

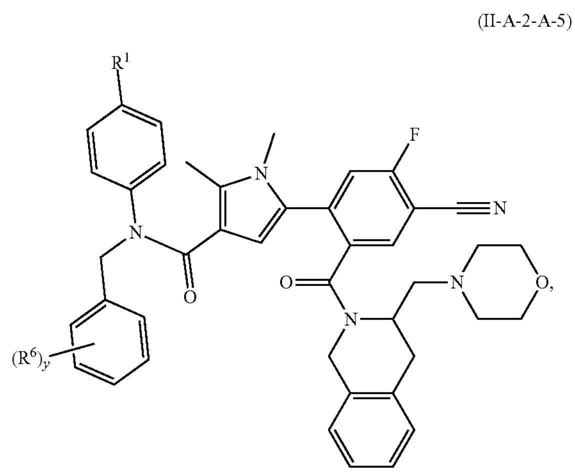

or pharmaceutically acceptable salts, prodrugs, solvates, hydrates, stereoisomers, or tautomers thereof.

In some embodiments, the compounds of Formula (I) have the structure of Formula (II-A-2-A-5'):

(II-A-2-A-5')

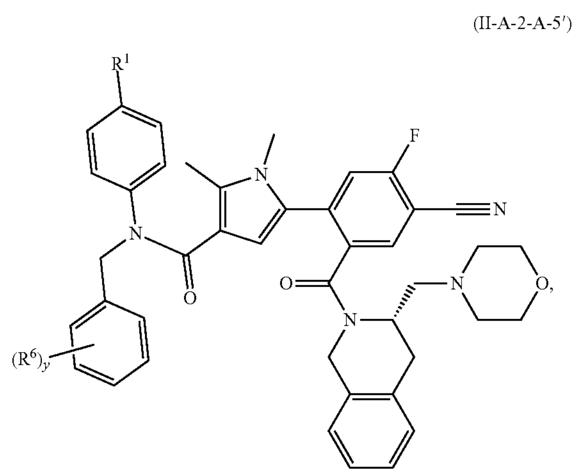

or pharmaceutically acceptable salts, prodrugs, solvates, hydrates, stereoisomers, or tautomers thereof.

In some embodiments, the compounds of Formula (I) have the structure of Formula (II-A-2-A-6):

(II-A-2-A-6)

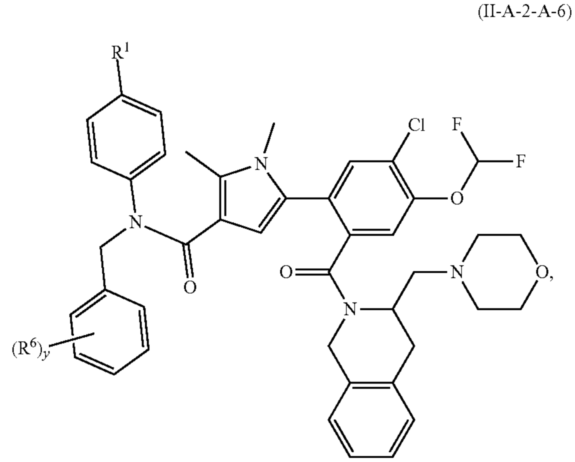

or pharmaceutically acceptable salts, prodrugs, solvates, hydrates, stereoisomers, or tautomers thereof.

In some embodiments, the compounds of Formula (I) have the structure of Formula (II-A-2-A-6'):

(II-A-2-A-6')

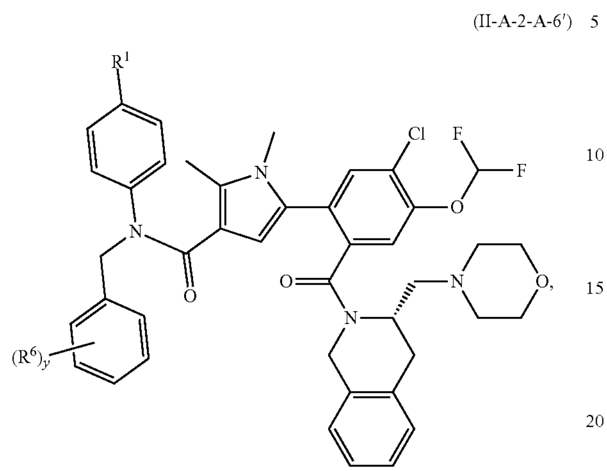

or pharmaceutically acceptable salts, prodrugs, solvates, hydrates, stereoisomers, or tautomers thereof.

In some embodiments, the compounds of Formula (I) have the structure of Formula (II-A-2-A-7):

(II-A-2-A-7)

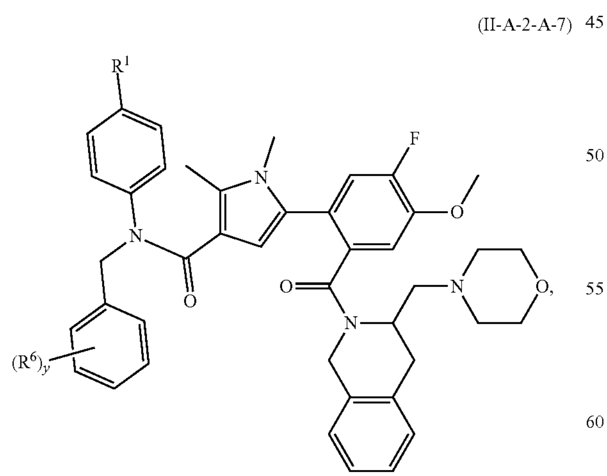

or pharmaceutically acceptable salts, prodrugs, solvates, hydrates, stereoisomers, or tautomers thereof.

In some embodiments, the compounds of Formula (I) have the structure of Formula (II-A-2-A-7'):

(II-A-2-A-7')

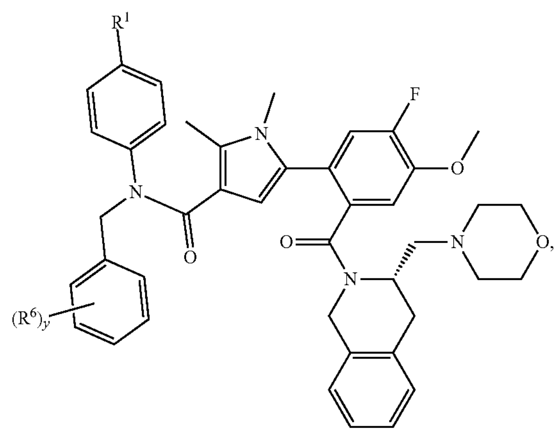

or pharmaceutically acceptable salts, prodrugs, solvates, hydrates, stereoisomers, or tautomers thereof.

In some embodiments, the compounds of Formula (I) have the structure of Formula (II-A-2-A-8):

(II-A-2-A-8)

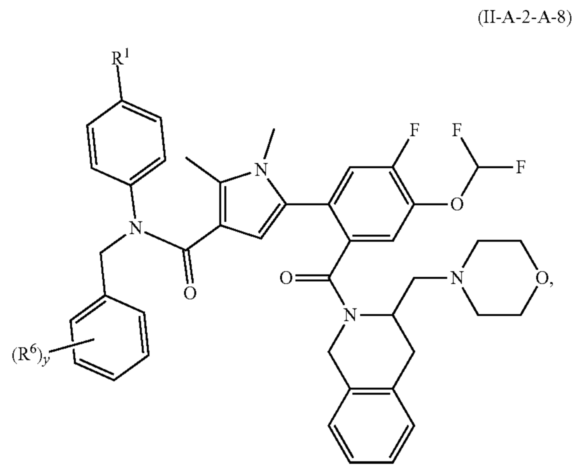

or pharmaceutically acceptable salts, prodrugs, solvates, hydrates, stereoisomers, or tautomers thereof.

In some embodiments, the compounds of Formula (I) have the structure of Formula (II-A-2-A-8'):

(II-A-2-A-8')

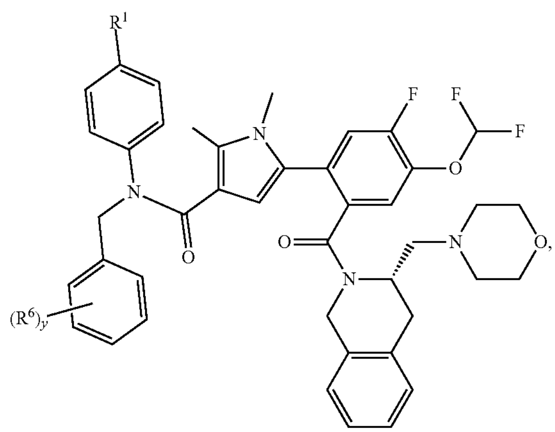

or pharmaceutically acceptable salts, prodrugs, solvates, hydrates, stereoisomers, or tautomers thereof.

In some embodiments, the compounds of Formula (I) have the structure of Formula (II-A-2-A-9):

(II-A-2-A-9)

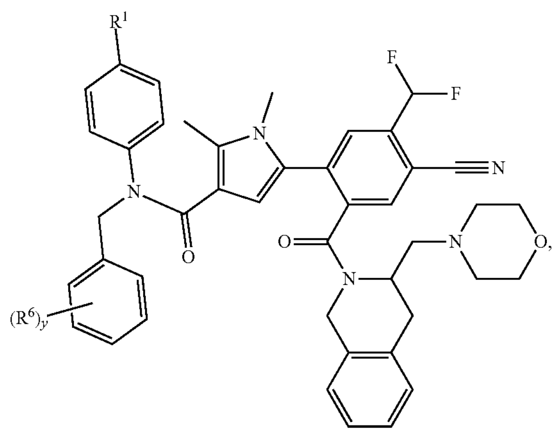

or pharmaceutically acceptable salts, prodrugs, solvates, hydrates, stereoisomers, or tautomers thereof.

In some embodiments, the compounds of Formula (I) have the structure of Formula (II-A-2-A-9'):

(II-A-2-A-9')

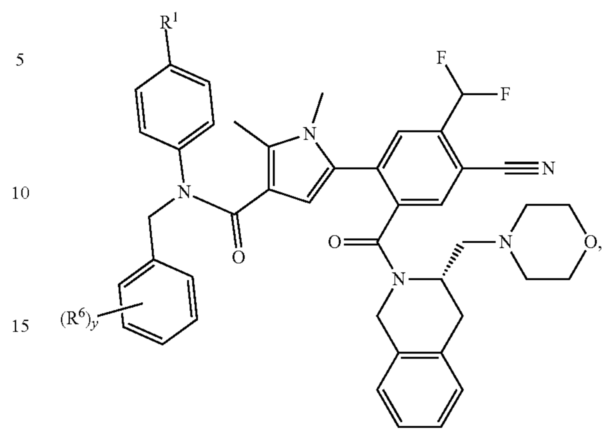

or pharmaceutically acceptable salts, prodrugs, solvates, hydrates, stereoisomers, or tautomers thereof.

In some embodiments, the compounds of Formula (I) have the structure of Formula (II-A-2-A-10):

(II-A-2-A-10)

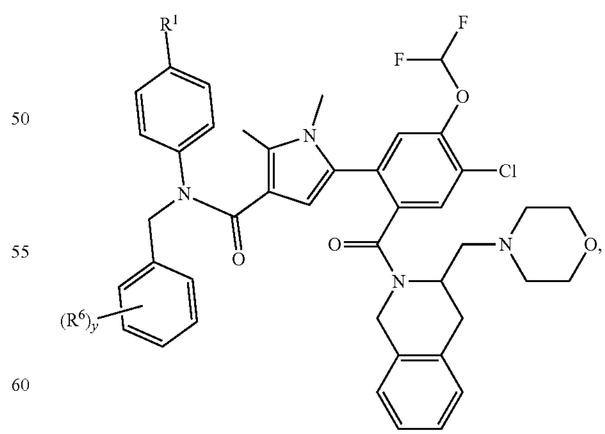

or pharmaceutically acceptable salts, prodrugs, solvates, hydrates, stereoisomers, or tautomers thereof.

In some embodiments, the compounds of Formula (I) have the structure of Formula (II-A-2-A-10'):

(II-A-2-A-10')

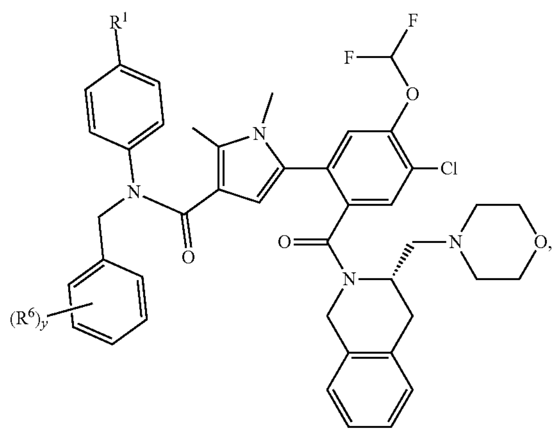

or pharmaceutically acceptable salts, prodrugs, solvates, hydrates, stereoisomers, or tautomers thereof.

In some embodiments, the compounds of Formula (I) have the structure of Formula (II-A-2-A-11):

(II-A-2-A-11)

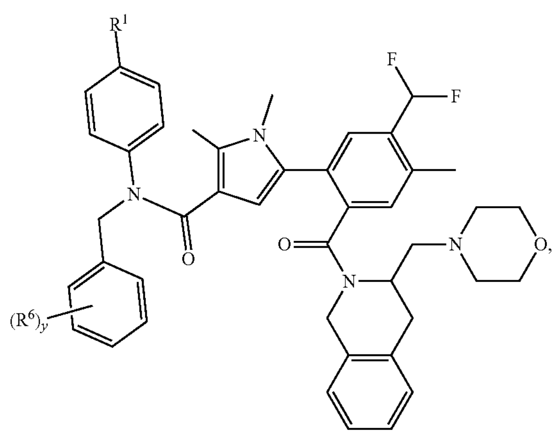

or pharmaceutically acceptable salts, prodrugs, solvates, hydrates, stereoisomers, or tautomers thereof.

In some embodiments, the compounds of Formula (I) have the structure of Formula (II-A-2-A-11'):

(II-A-2-A-11')

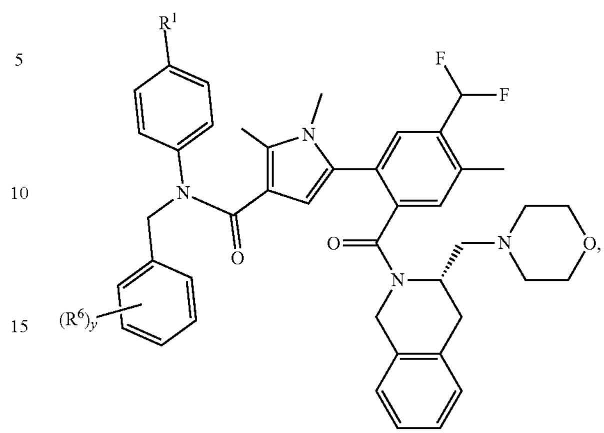

or pharmaceutically acceptable salts, prodrugs, solvates, hydrates, stereoisomers, or tautomers thereof.

In some embodiments, the compounds of Formula (I) have the structure of Formula (II-A-2-A-12):

(II-A-2-A-12)

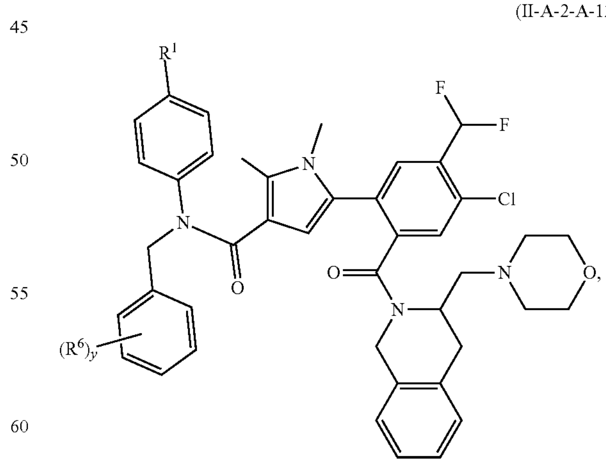

or pharmaceutically acceptable salts, prodrugs, solvates, hydrates, stereoisomers, or tautomers thereof.

In some embodiments, the compounds of Formula (I) have the structure of Formula (II-A-2-A-12'):

(II-A-2-A-12')

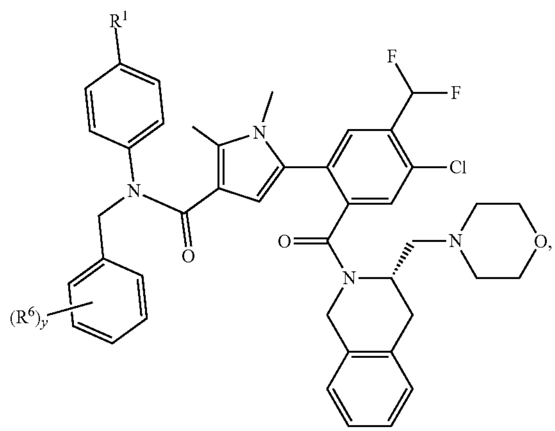

or pharmaceutically acceptable salts, prodrugs, solvates, hydrates, stereoisomers, or tautomers thereof.

In some embodiments, the compounds of Formula (I) have the structure of Formula (II-A-2-A-13):

(II-A-2-A-13)

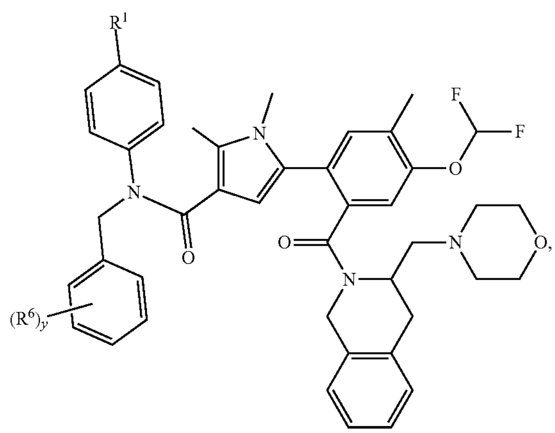

or pharmaceutically acceptable salts, prodrugs, solvates, hydrates, stereoisomers, or tautomers thereof.

In some embodiments, the compounds of Formula (I) have the structure of Formula (II-A-2-A-13'):

(II-A-2-A-13')

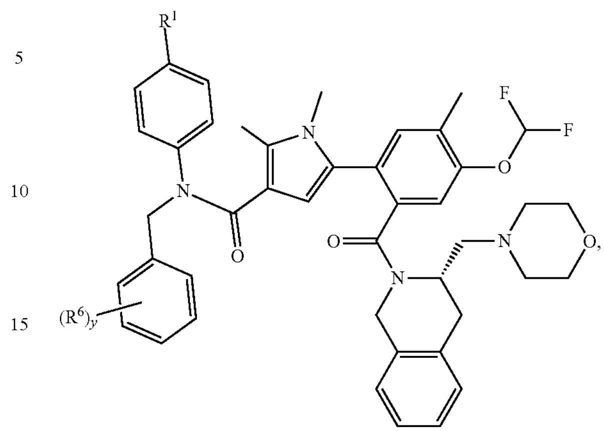

or pharmaceutically acceptable salts, prodrugs, solvates, hydrates, stereoisomers, or tautomers thereof.

In some embodiments, the compounds of Formula (I) have the structure of Formula (II-A-2-A-14):

(II-A-2-A-14)

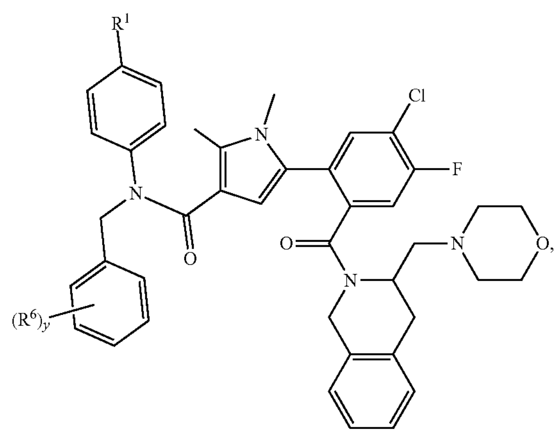

or pharmaceutically acceptable salts, prodrugs, solvates, hydrates, stereoisomers, or tautomers thereof.

In some embodiments, the compounds of Formula (I) have the structure of Formula (II-A-2-A-14'):

(II-A-2-A-14′)

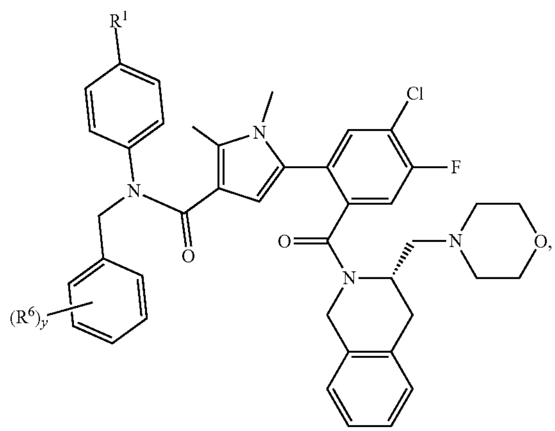

or pharmaceutically acceptable salts, prodrugs, solvates, hydrates, stereoisomers, or tautomers thereof.

In some embodiments, the compounds of Formula (I) have the structure of Formula (II-A-2-A-15):

(II-A-2-A-15)

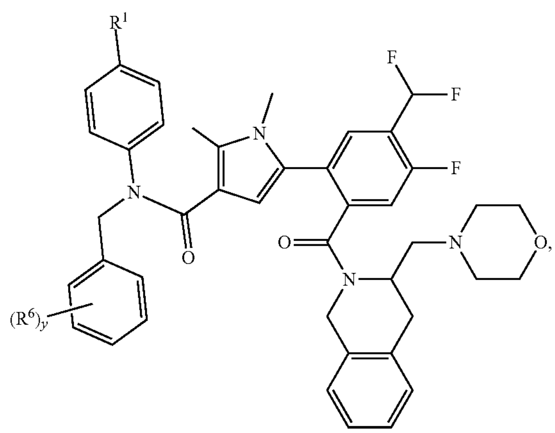

or pharmaceutically acceptable salts, prodrugs, solvates, hydrates, stereoisomers, or tautomers thereof.

In some embodiments, the compounds of Formula (I) have the structure of Formula (II-A-2-A-15'):

(II-A-2-A-15′)

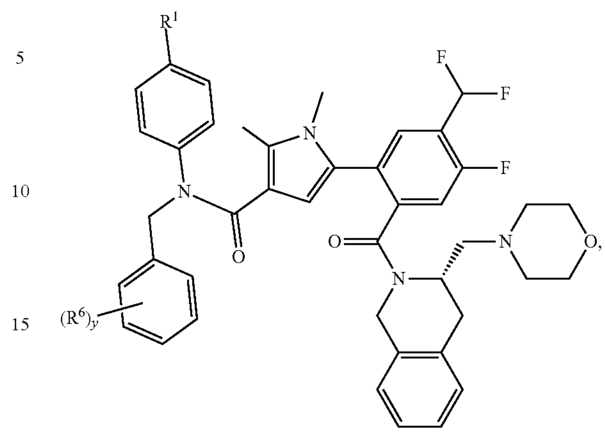

or pharmaceutically acceptable salts, prodrugs, solvates, hydrates, stereoisomers, or tautomers thereof.

In some embodiments, the compounds of Formula (I) have the structure of Formula (II-A-2-A-16):

(II-A-2-A-16)

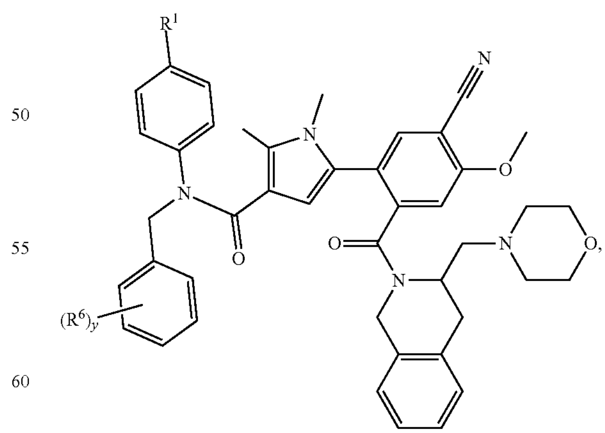

or pharmaceutically acceptable salts, prodrugs, solvates, hydrates, stereoisomers, or tautomers thereof.

In some embodiments, the compounds of Formula (I) have the structure of Formula (II-A-2-A-16'):

(II-A-2-A-16')

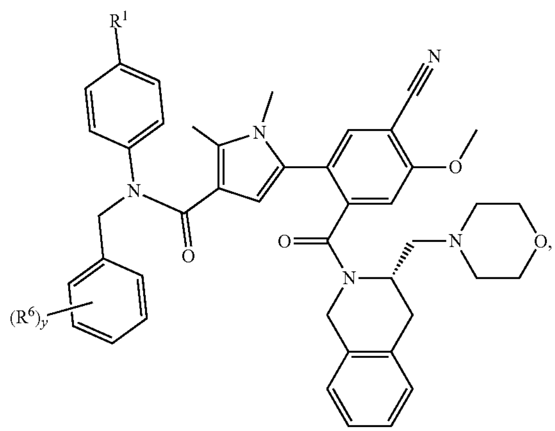

or pharmaceutically acceptable salts, prodrugs, solvates, hydrates, stereoisomers, or tautomers thereof.

In some embodiments, the compounds of Formula (I) have the structure of Formula (II-A-2-A-17):

(II-A-2-A-17)

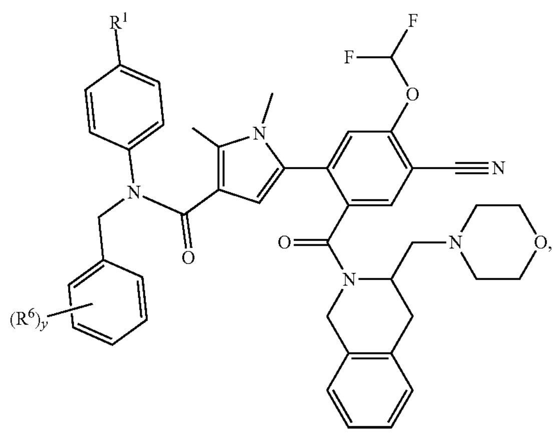

or pharmaceutically acceptable salts, prodrugs, solvates, hydrates, stereoisomers, or tautomers thereof.

In some embodiments, the compounds of Formula (I) have the structure of Formula (II-A-2-A-17'):

(II-A-2-A-17')

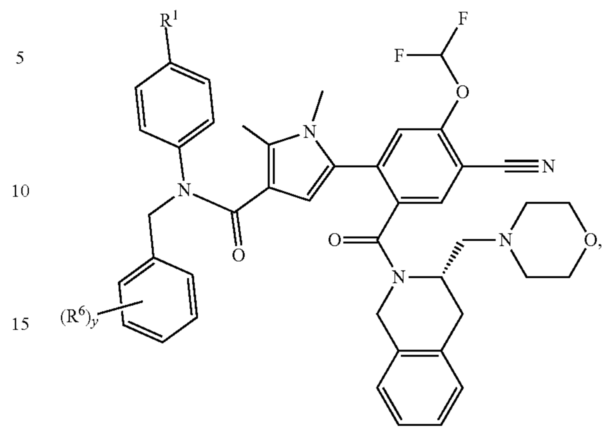

or pharmaceutically acceptable salts, prodrugs, solvates, hydrates, stereoisomers, or tautomers thereof.

In some embodiments, the compounds of Formula (I) have the structure of Formula (II-A-2-A-18):

(II-A-2-A-18)

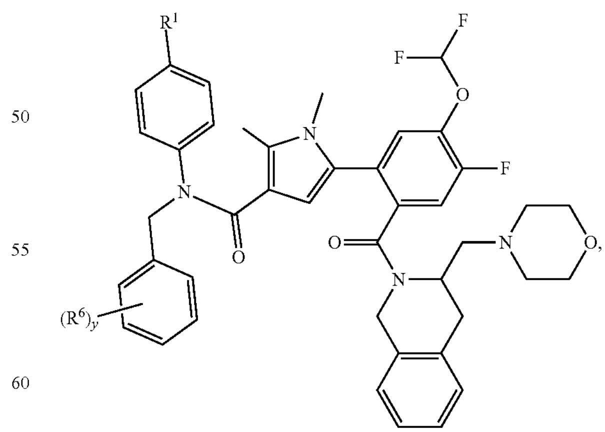

or pharmaceutically acceptable salts, prodrugs, solvates, hydrates, stereoisomers, or tautomers thereof.

In some embodiments, the compounds of Formula (I) have the structure of Formula (II-A-2-A-18'):

(II-A-2-A-18')

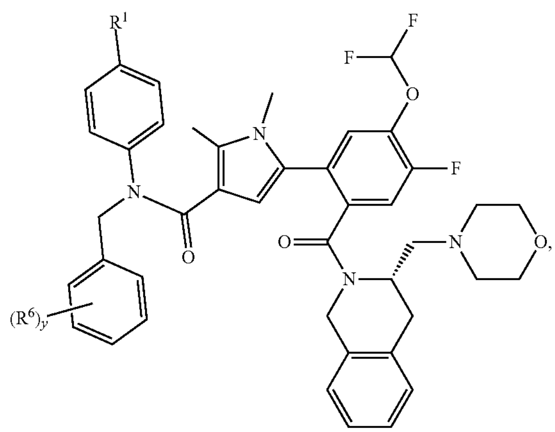

or pharmaceutically acceptable salts, prodrugs, solvates, hydrates, stereoisomers, or tautomers thereof.

In some embodiments, the compounds of Formula (I) have the structure of Formula (II-A-2-A-19):

(II-A-2-A-19)

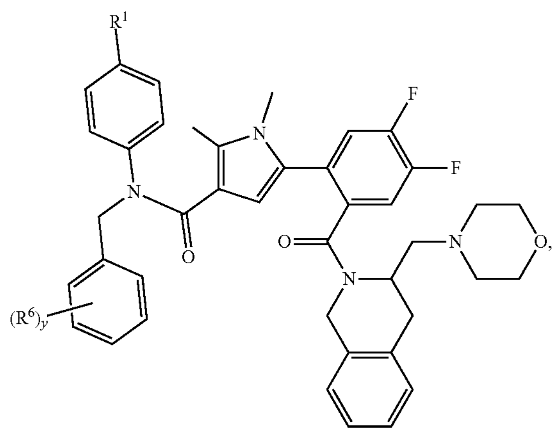

or pharmaceutically acceptable salts, prodrugs, solvates, hydrates, stereoisomers, or tautomers thereof.

In some embodiments, the compounds of Formula (I) have the structure of Formula (II-A-2-A-19'):

(II-A-2-A-19')

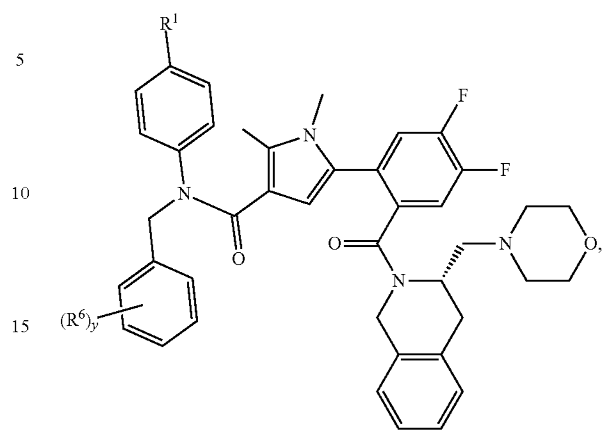

or pharmaceutically acceptable salts, prodrugs, solvates, hydrates, stereoisomers, or tautomers thereof.

In some embodiments, the compounds of Formula (I) have the structure of Formula (II-A-2-A-20):

(II-A-2-A-20)

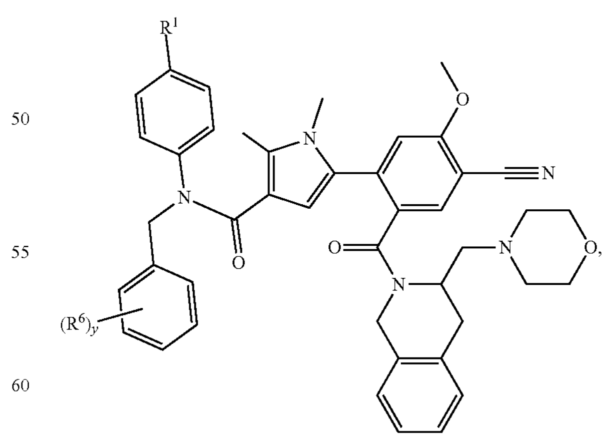

or pharmaceutically acceptable salts, prodrugs, solvates, hydrates, stereoisomers, or tautomers thereof.

In some embodiments, the compounds of Formula (I) have the structure of Formula (II-A-2-A-20'):

(II-A-2-A-20')

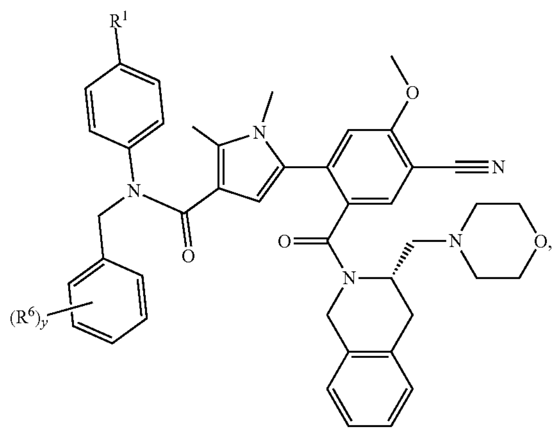

or pharmaceutically acceptable salts, prodrugs, solvates, hydrates, stereoisomers, or tautomers thereof.

In some embodiments, the compounds of Formula (I) have the structure of Formula (II-A-2-A-21):

(II-A-2-A-21)

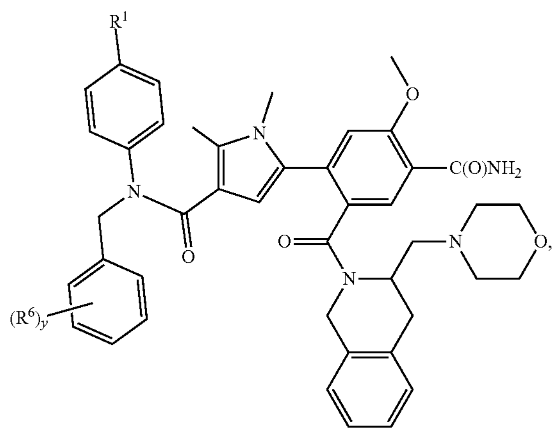

or pharmaceutically acceptable salts, prodrugs, solvates, hydrates, stereoisomers, or tautomers thereof.

In some embodiments, the compounds of Formula (I) have the structure of Formula (II-A-2-A-21'):

(II-A-2-A-21')

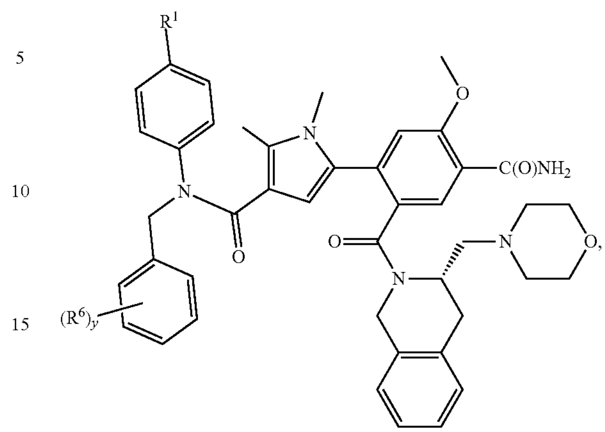

or pharmaceutically acceptable salts, prodrugs, solvates, hydrates, stereoisomers, or tautomers thereof.

In some embodiments, the compounds of Formula (I) have the structure of Formula (II-A-3-A-1):

(II-A-3-A-1)

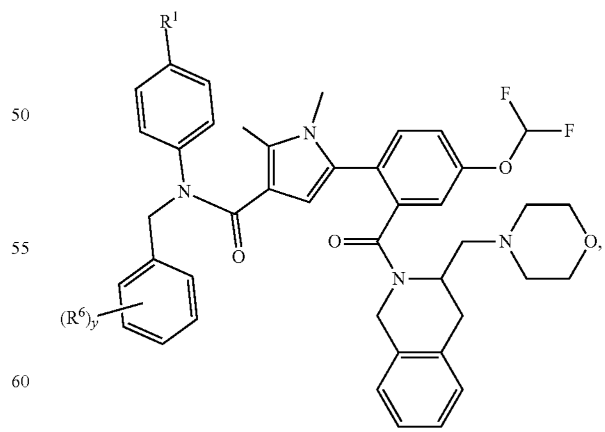

or pharmaceutically acceptable salts, prodrugs, solvates, hydrates, stereoisomers, or tautomers thereof.

In some embodiments, the compounds of Formula (I) have the structure of Formula (II-A-3-A-1'):

(II-A-3-A-1')

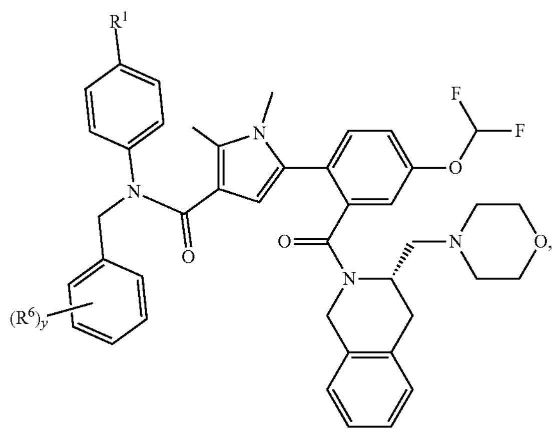

or pharmaceutically acceptable salts, prodrugs, solvates, hydrates, stereoisomers, or tautomers thereof.

In some embodiments, the compounds of Formula (I) have the structure of Formula (II-A-4-A-1):

(II-A-4-A-1)

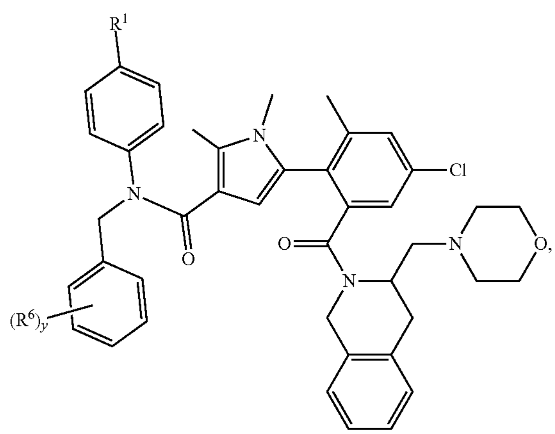

or pharmaceutically acceptable salts, prodrugs, solvates, hydrates, stereoisomers, or tautomers thereof.

In some embodiments, the compounds of Formula (I) have the structure of Formula (II-A-4-A-1'):

(II-A-4-A-1')

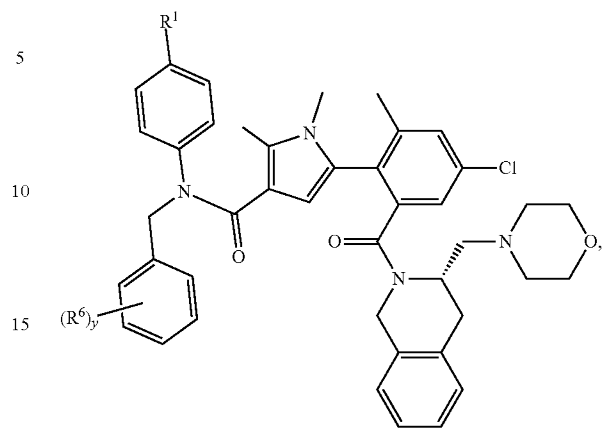

or pharmaceutically acceptable salts, prodrugs, solvates, hydrates, stereoisomers, or tautomers thereof.

In some embodiments, the compounds of Formula (I) have the structure of Formula (II-B-1-A-1):

(II-B-1-A-1)

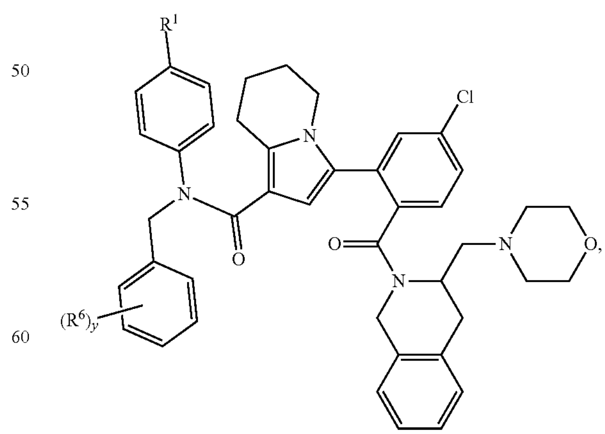

or pharmaceutically acceptable salts, prodrugs, solvates, hydrates, stereoisomers, or tautomers thereof. B-1-A-1'):

(II-B-1-A-1')

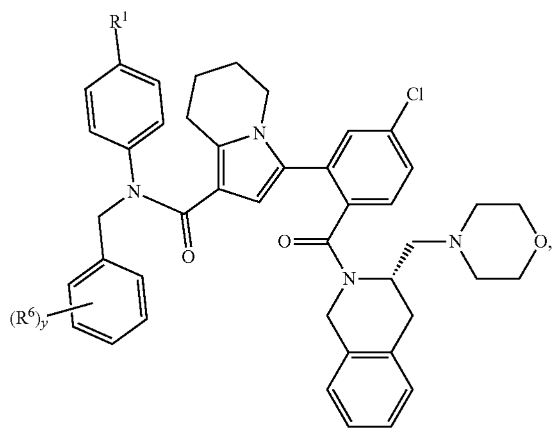

or pharmaceutically acceptable salts, prodrugs, solvates, hydrates, stereoisomers, or tautomers thereof.

In some embodiments, the compounds of Formula (I) have the structure of Formula (II-B-1-A-2):

(II-B-1-A-2)

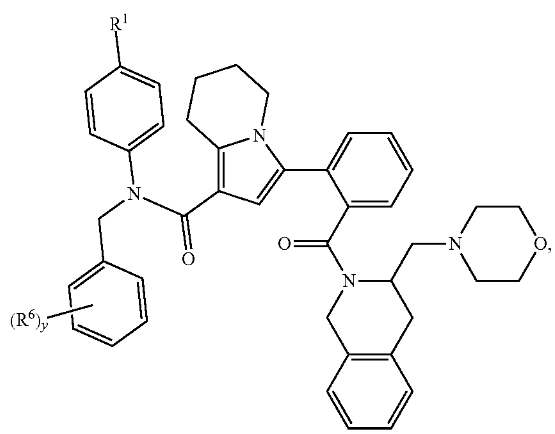

or pharmaceutically acceptable salts, prodrugs, solvates, hydrates, stereoisomers, or tautomers thereof. B-1-A-2'):

(II-B-1-A-2')

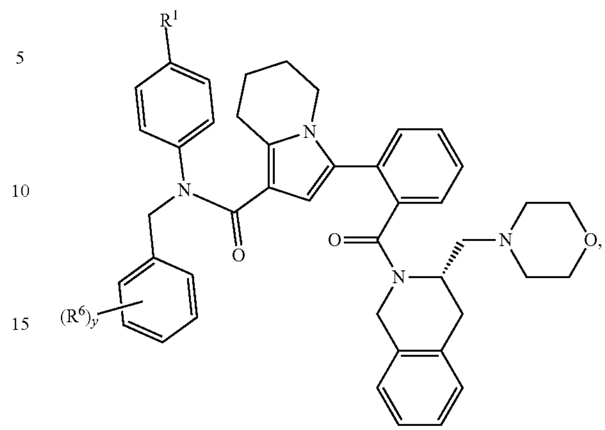

or pharmaceutically acceptable salts, prodrugs, solvates, hydrates, stereoisomers, or tautomers thereof.

In some embodiments, the compounds of Formula (I) have the structure of Formula (II-A-1-B-1):

(II-A-1-B-1)

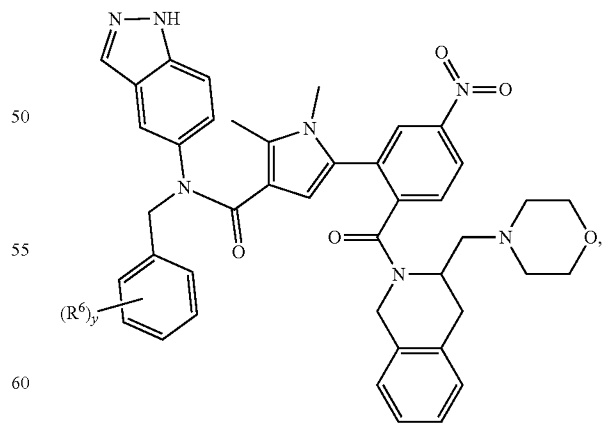

or pharmaceutically acceptable salts, prodrugs, solvates, hydrates, stereoisomers, or tautomers thereof.

In some embodiments, the compounds of Formula (I) have the structure of Formula (II-A-1-B-1'):

(II-A-1-B-1')

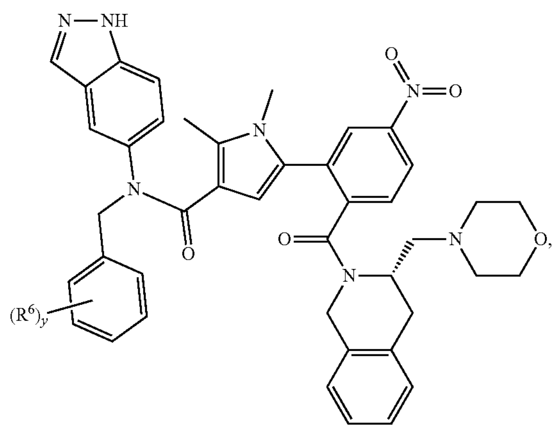

or pharmaceutically acceptable salts, prodrugs, solvates, hydrates, stereoisomers, or tautomers thereof.

In some embodiments, the compounds of Formula (I) have the structure of Formula (II-A-1-B-2):

(II-A-1-B-2)

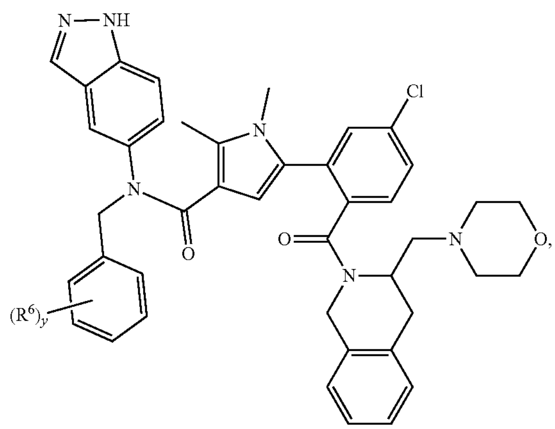

or pharmaceutically acceptable salts, prodrugs, solvates, hydrates, stereoisomers, or tautomers thereof.

In some embodiments, the compounds of Formula (I) have the structure of Formula (II-A-1-B-2'):

(II-A-1-B-2')

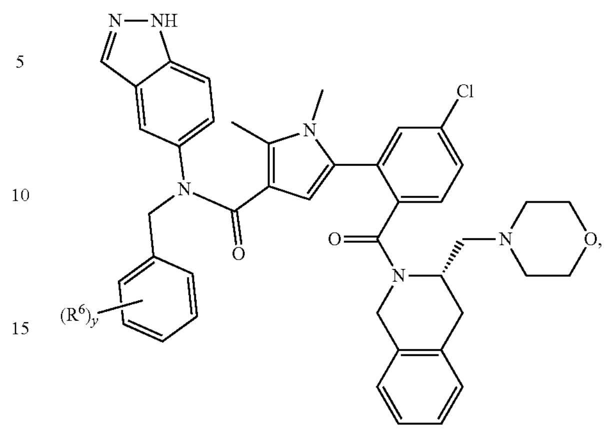

or pharmaceutically acceptable salts, prodrugs, solvates, hydrates, stereoisomers, or tautomers thereof.

In some embodiments, the compounds of Formula (I) have the structure of Formula (II-A-1-C-1):

(II-A-1-C-1)

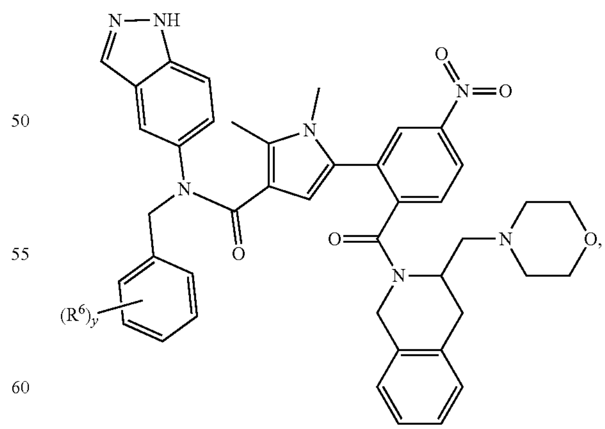

or pharmaceutically acceptable salts, prodrugs, solvates, hydrates, stereoisomers, or tautomers thereof.

In some embodiments, the compounds of Formula (I) have the structure of Formula (II-A-1-C-1'):

(II-A-1-C-1')

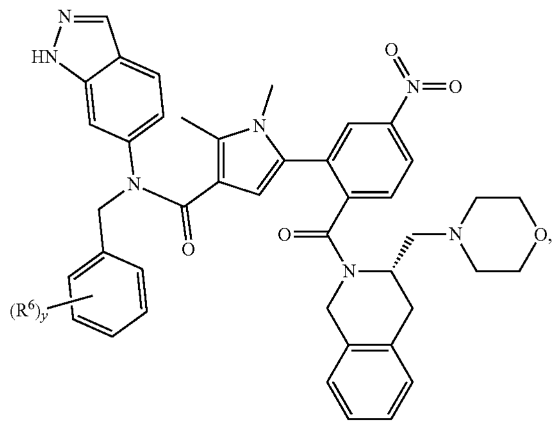

or pharmaceutically acceptable salts, prodrugs, solvates, hydrates, stereoisomers, or tautomers thereof.

A-A-1') or the structure of Formula (II-B-A-1'):

(II-A-A-1')

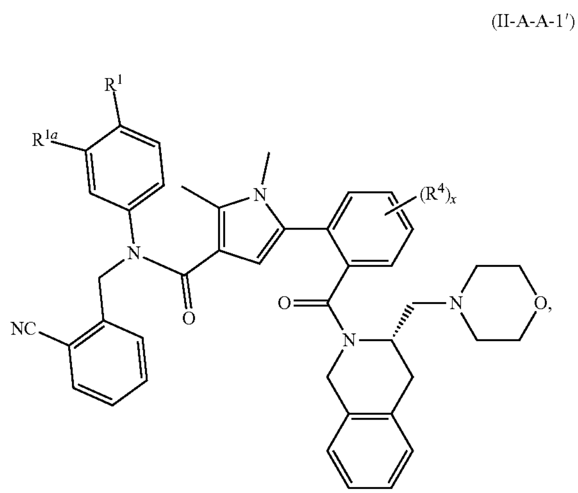

(II-B-A-1')

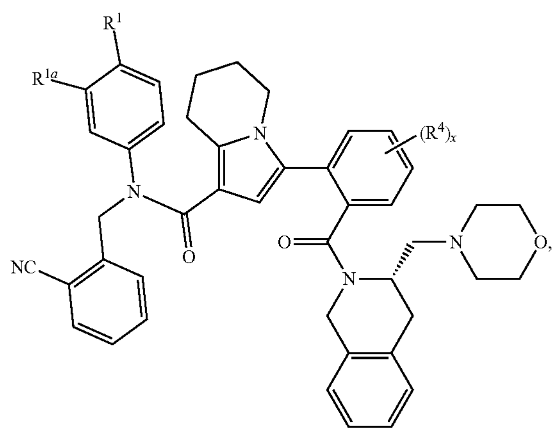

or pharmaceutically acceptable salts, prodrugs, solvates, hydrates, stereoisomers, or tautomers thereof.

In some embodiments, the compounds of Formula (I) have the structure of Formula (II-A-A-2') or the structure of Formula (II-B-A-2'):

(II-A-A-2')

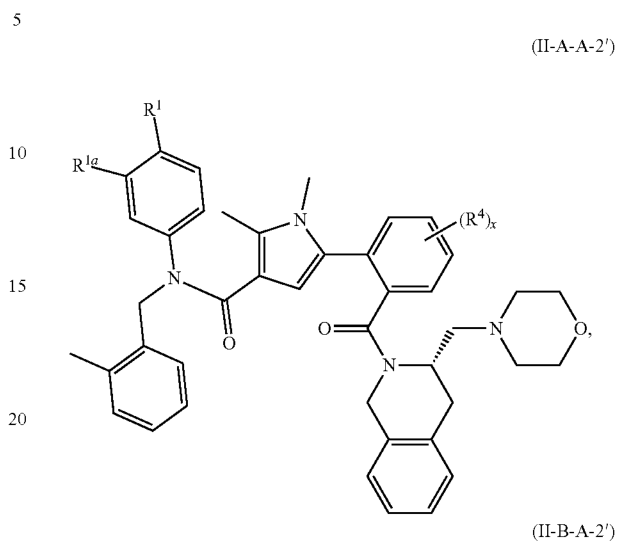

(II-B-A-2')

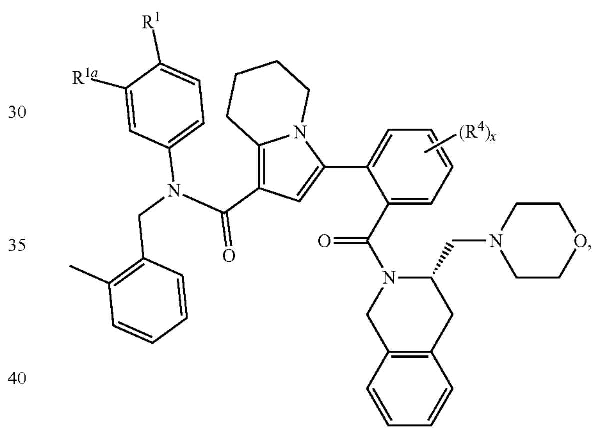

or pharmaceutically acceptable salts, prodrugs, solvates, hydrates, stereoisomers, or tautomers thereof.

A-A-3') or the structure of Formula (II-B-A-3'):

(II-A-A-3')

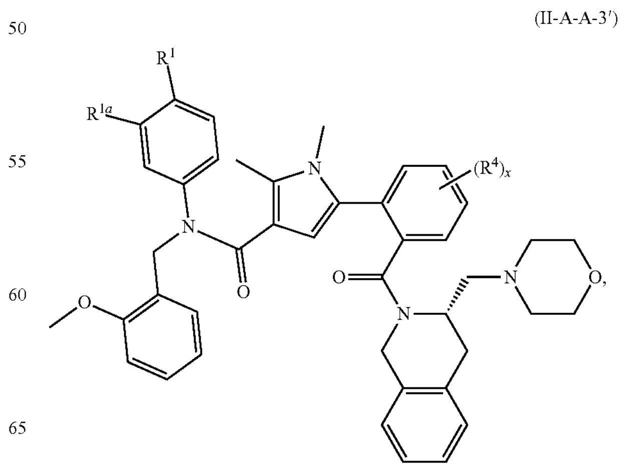

-continued (II-B-A-3')

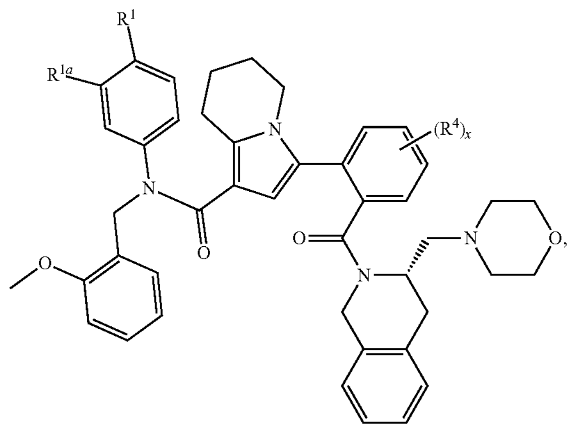

or pharmaceutically acceptable salts, prodrugs, solvates, hydrates, stereoisomers, or tautomers thereof.

A-A-4') or the structure of Formula (II-B-A-4'):

(II-A-A-4')

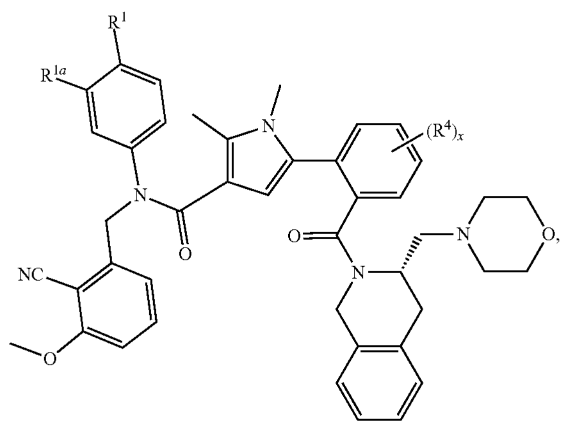

(II-B-A-4')

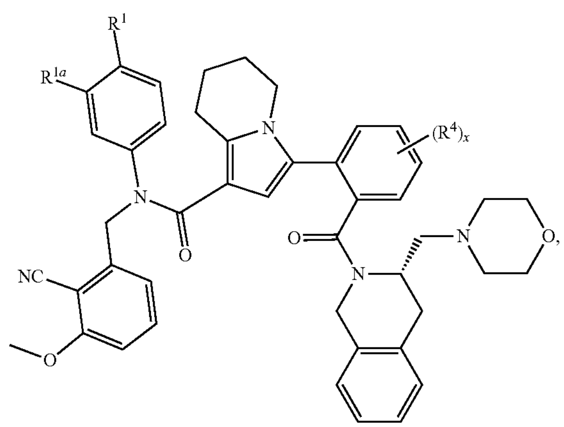

or pharmaceutically acceptable salts, prodrugs, solvates, hydrates, stereoisomers, or tautomers thereof.

A-A-5') or the structure of Formula (II-B-A-5'):

(II-A-A-5')

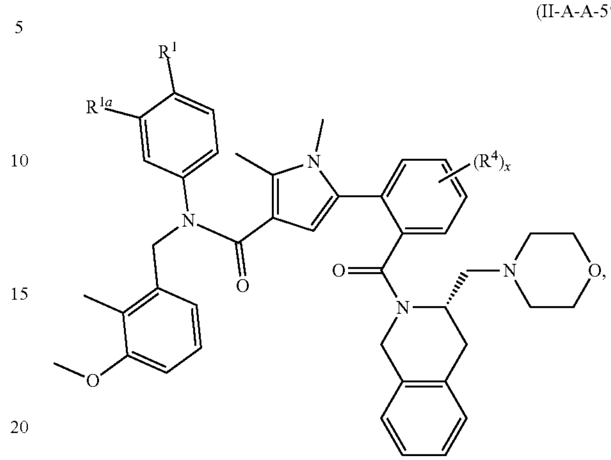

(II-B-A-5')

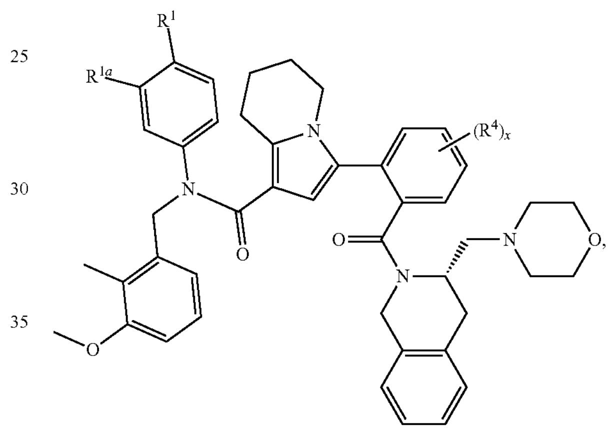

or pharmaceutically acceptable salts, prodrugs, solvates, hydrates, stereoisomers, or tautomers thereof.

In some embodiments, the compounds of Formula (I) have the structure of Formula (II-A-A-5-1') or the structure of Formula (II-B-A-5-1'):

(II-A-A-5-1')

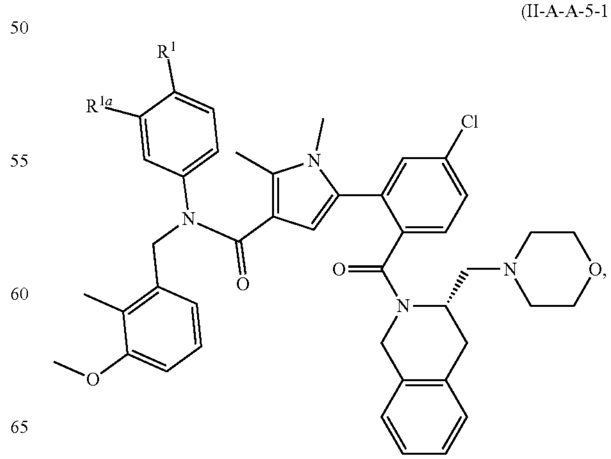

-continued (II-B-A-5-1')

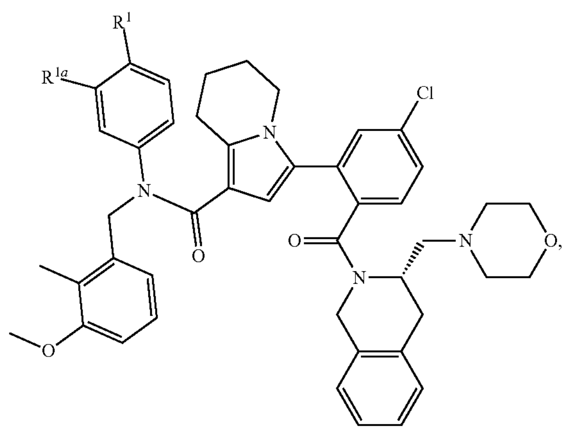

or pharmaceutically acceptable salts, prodrugs, solvates, hydrates, stereoisomers, or tautomers thereof.

A-A-6') or the structure of Formula (II-B-A-6'):

(II-A-A-6')

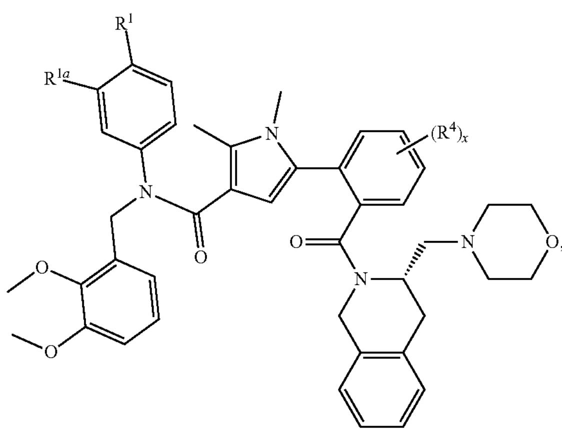

(II-B-A-6')

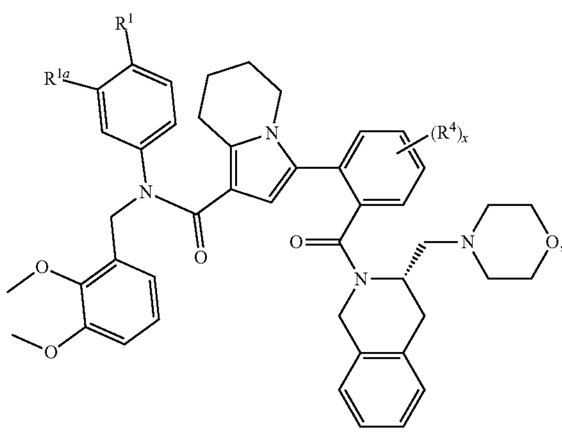

or pharmaceutically acceptable salts, prodrugs, solvates, hydrates, stereoisomers, or tautomers thereof.

In some embodiments, the compounds of Formula (I) have the structure of Formula (V-A), the structure of Formula (VI-A), or the structure of Formula (XI-A):

(V-A)

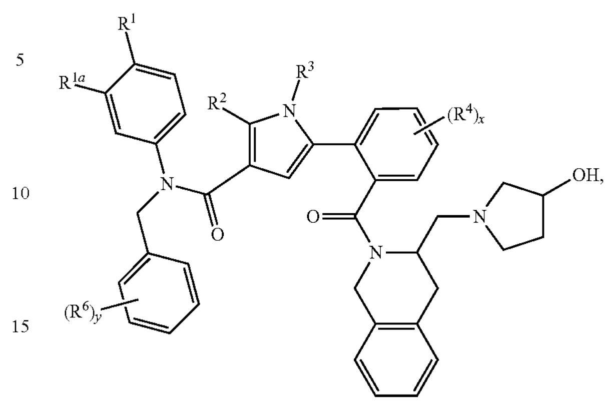

(VI-A)

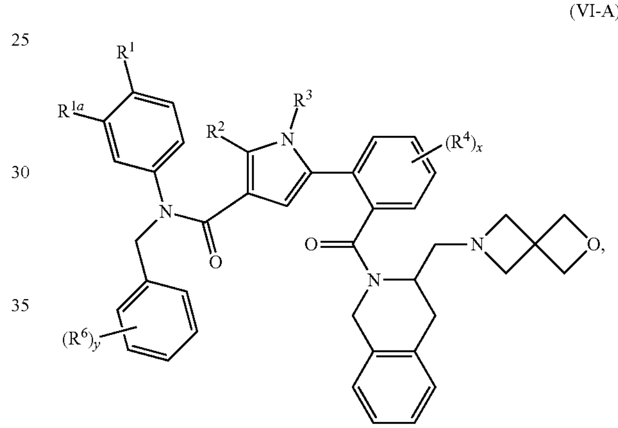

(XI-A)

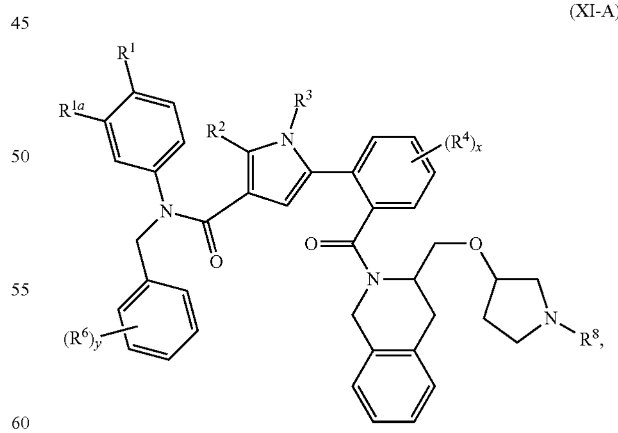

or pharmaceutically acceptable salts, prodrugs, solvates, hydrates, stereoisomers, or tautomers thereof.

In some embodiments, the compounds of Formula (I) have the structure of Formula (V-A'), the structure of Formula (VI-A'), or the structure of Formula (XI-A'):

(V-A')

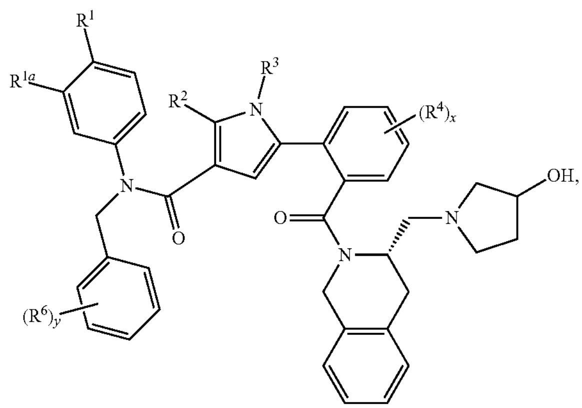

(VI-A')

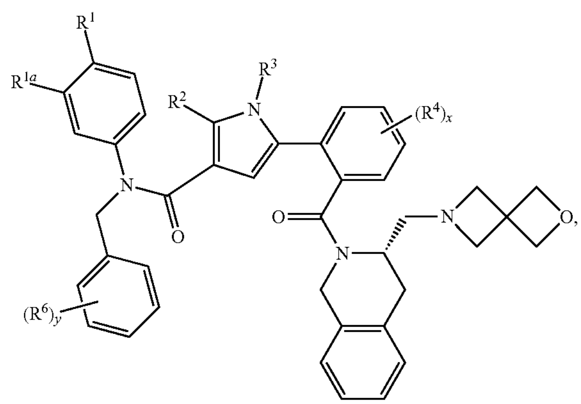

(XI-A')

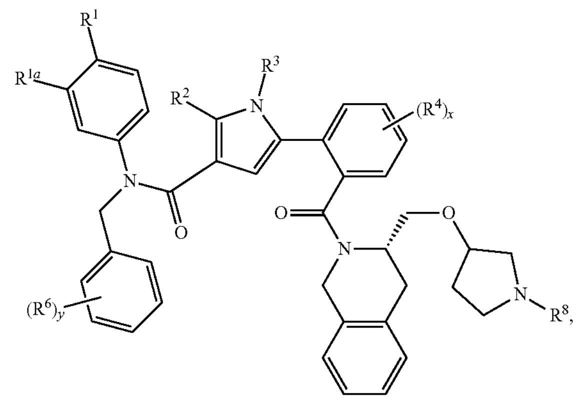

or pharmaceutically acceptable salts, prodrugs, solvates, hydrates, stereoisomers, or tautomers thereof.

In some embodiments, $R^1$ is halogen, —OH, —CN, or —$CONH_2$.

In some embodiments, $R^1$ is halogen.

In some embodiments, $R^1$ is fluoro.

In some embodiments, $R^1$ is chloro.

In some embodiments, $R^1$ is —OH.

In some embodiments, $R^1$ is —CN.

In some embodiments, $R^{1a}$ is H.

In some embodiments, $R^1$ and $R^{1a}$, together with the atom to which they are attached, come together to form a 3- to 10-membered heteroaryl ring further comprising 1, 2, or 3 heteroatoms selected from N, O, and S.

In some embodiments, $R^1$ and $R^{1a}$, together with the atom to which they are attached, come together to form a 5-membered heteroaryl ring further comprising 1, 2, or 3 heteroatoms selected from N, O, and S.

In some embodiments, $R^1$ and Ra, together with the atom to which they are attached, come together to form a 5-membered heteroaryl ring further comprising 2 heteroatoms selected from N, O, and S.

In some embodiments, $R^1$ and $R^{1a}$, together with the atom to which they are attached, come together to form a 5-membered heteroaryl ring further comprising 2 nitrogen atoms.

In some embodiments, $R^2$ is $C_1$-$C_6$ alkyl.

In some embodiments, $R^2$ is —$CH_3$.

In some embodiments, $R^3$ is $C_1$-$C_6$ alkyl.

In some embodiments, $R^3$ is —$CH_3$.

In some embodiments, $R^2$ and $R^3$, together with the atom to which they are attached, come together to form a 3- to 10-membered heterocyclyl ring further comprising 1, 2, or 3 heteroatoms selected from N, O, and S.

In some embodiments, $R^2$ and $R^3$, together with the atom to which they are attached, come together to form a 5-membered heterocyclyl ring comprising 1 nitrogen atom.

In some embodiments, $R^2$ and $R^3$, together with the atom to which they are attached, come together to form a 6-membered heterocyclyl ring comprising 1 nitrogen atom.

In some embodiments, $R^2$ and $R^3$, together with the atom to which they are attached, come together to form a 7-membered heterocyclyl ring comprising 1 nitrogen atom.

In some embodiments each $R^4$ is independently selected from halogen, —OH, —CN, —$NO_2$, —COOH, —$CH_2CN$, $CH_2N(R^8)_2$, $C_1$-$C_6$ alkyl, $C_1$-$C_6$ alkoxy, $C_1$-$C_6$ halogenalkyl, $C_1$-$C_6$ halogenalkoxy, —O—($C_2$-$C_6$ alkenyl), —O—($C_2$-$C_6$ alkynyl), $C_2$-$C_6$ alkenyl, $C_2$-$C_6$ alkynyl, —OH, —OP(O)$(OH)_2$, —OC(O)($C_1$-$C_6$ alkyl), —C(O)($C_1$-$C_6$ alkyl), —OC(O)O($C_1$-$C_6$ alkyl), —$NH_2$, —NH($C_1$-$C_6$ alkyl), —N($C_1$-$C_6$ alkyl)$_2$, —NHC(O)($C_1$-$C_6$ alkyl), —C(O)$NH_2$, —C(O)NH($C_1$-$C_6$ alkyl), —S(0)$_2$ ($C_1$-$C_6$ alkyl), —S(O)NH($C_1$-$C_6$ alkyl), and S(O)N($C_1$-$C_6$ alkyl)$_2$.

In some embodiments, $R^4$ is halogen.

In some embodiments, $R^4$ is F.

In some embodiments, $R^4$ is $C_1$.

In some embodiments, $R^4$ is —CN.

In some embodiments, $R^4$ is —$NO_2$.

In some embodiments, $R^4$ is —C(O)$NH_2$.

In some embodiments, $R^4$ is —$C_1$-$C_6$ alkyl.

In some embodiments, $R^4$ is —$CH_3$.

In some embodiments, $R^4$ is $C_1$-$C_6$ halogenalkyl.

In some embodiments, $R^4$ is —$CHF_2$.

In some embodiments, $R^4$ is $C_1$-$C_6$ alkoxy.

In some embodiments, $R^4$-s-$OCH_3$.

In some embodiments, $R^4$ is $C_1$-$C_6$ halogenalkoxy.

In some embodiments, $R^4$ is —$OCHF_2$.

In some embodiments, $R^4$ is —NHC(O)($C_1$-$C_6$ alkyl).

In some embodiments, $R^4$ is —NHC(O) $CH_3$.

In some embodiments, $R^4$ is $S(O)_2$ ($C_1$-$C_6$ alkyl).

In some embodiments, $R^4$ is $S(O)_2CH_3$.

In some embodiments, x is an integer selected from 0, 1, 2 and 3.

In some embodiments, x is 0.

In some embodiments, x is 1.

In some embodiments, x is 2.

In some embodiments, x is 3.

In some embodiments, $R^5$ is selected from

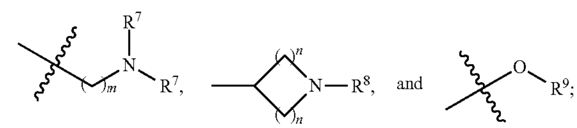

In some embodiments, $R^5$ is

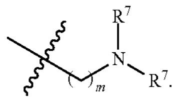

In some embodiments, $R^5$ is

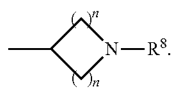

In some embodiments, $R^5$ is

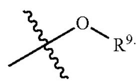

In some embodiments, $R^5$ is selected from

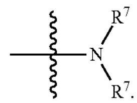

In some embodiments, $R^5$ is selected from

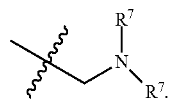

In some embodiments, $R^5$ is selected from

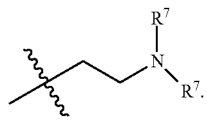

In some embodiments $R^5$ is selected from

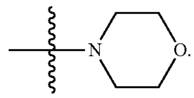

In some embodiments, $R^5$ is selected from the group consisting

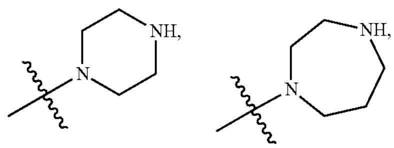

-continued

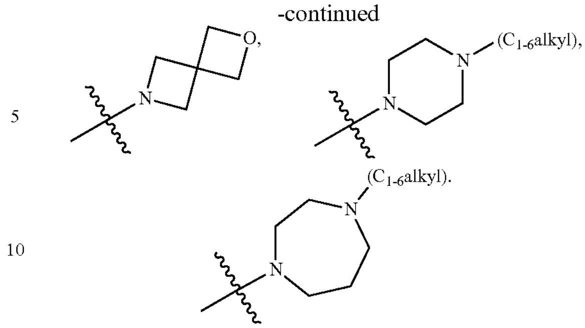

In some embodiments, $R^5$ is selected from the group consisting

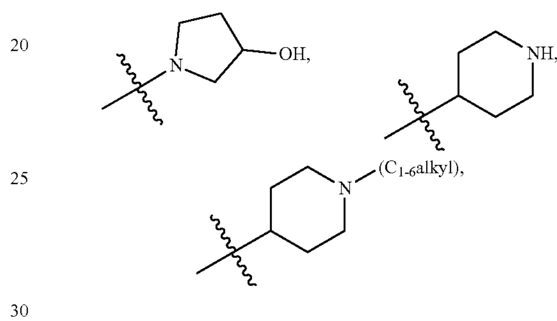

In some embodiments, $R^5$ is selected from the group consisting

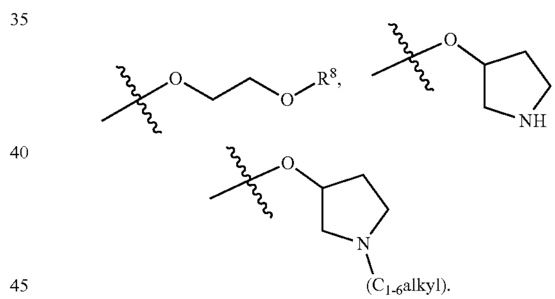

In some embodiments, m is selected from 0, 1, and 2.

In some embodiments, m is 0.

In some embodiments, m is 1.

In some embodiments, m is 2.

In some embodiments, each n is an integer independently selected from 1, 2, 3.

In some embodiments each $R^6$ is independently selected from halogen, —OH, —CN, —COOH, —$CH_2$CN, —CON$(R^8)_2$, $C_1$-$C_6$ alkyl, $C_1$-$C_6$ alkoxy, $C_1$-$C_6$ halogenalkyl, $C_1$-$C_6$ halogenalkoxy, —O—($C_2$-$C_6$ alkenyl), —O—($C_2$-$C_6$ alkynyl), $C_2$-$C_6$ alkenyl, $C_2$-$C_6$ alkynyl, —OH, —OP(O)$(OH)_2$, —OC(O)($C_1$-$C_6$ alkyl), —C(O)($C_1$-$C_6$ alkyl), —OC(O)O($C_1$-$C_6$ alkyl), —$NH_2$, —NH($C_1$-$C_6$ alkyl), —N($C_1$-$C_6$ alkyl)$_2$, —NHC(O)($C_1$-$C_6$ alkyl), —C(O)NH($C_1$-$C_6$ alkyl), —S(O)$_2$ ($C_1$-$C_6$ alkyl), —S(O)NH($C_1$-$C_6$ alkyl), and S(O)N($C_1$-$C_6$ alkyl)$_2$.

In some embodiments, each $R^6$ is independently selected from CN, CO$(NR^8)_2$, $C_1$-$C_6$ alkyl, $C_1$-$C_6$ alkoxy, $C_1$-$C_6$ halogenalkyl, $C_1$-$C_6$ halogenalkoxy.

In some embodiments, $R^6$ is —$CH_3$.

In some embodiments, $R^6$ is —$OCH_3$.

In some embodiments, $R^6$ is —CN.

In some embodiments, $R^6$ is —$C(O)NH_2$.

In some embodiments, y is an integer selected from 0, 1, 2, 3.

In some embodiments, y is 0.

In some embodiments, y is 1.

In some embodiments, y is 2.

In some embodiments, y is 3.

In some embodiments, each $R^7$ is independently selected from H, $C_{1-6}$ alkyl, $C_{2-6}$ alkenyl, $C_{2-6}$ alkynyl, and aryl.

In some embodiments two $R^7$ together with the nitrogen atom to which they are bound and any intervening atoms, form a heterocycle.

In some embodiments two $R^7$ together with the nitrogen atom to which they are bound and any intervening atoms, form a 6-membered heterocycle.

In some embodiments two $R^7$ together with the nitrogen atom to which they are bound and any intervening atoms, form a 6-membered heterocycle comprising N and O.

In some embodiments $R^8$ is selected from H, $C_{1-6}$ alkyl, $C_{3-8}$ cycloalkyl, $C_{1-6}$ halogenalkyl.

In some embodiments $R^8$ is selected from H and $C_{1-6}$ alkyl.

In some embodiments, $R^9$ is selected from $C_{1-6}$ alkyl, $C_{2-6}$ alkenyl, $C_{2-6}$ alkynyl, —$(CH_2)_{1-6}OR^8$, $C_{3-8}$ cycloalkyl, aryl, heterocycle.

In some embodiments, $R^9$ is $C_{1-6}$ alkyl, or $C_{1-6}$ Halogenalkyl.

In some embodiments, $R^9$ is $C_{1-4}$ alkyl. In some embodiments, $R^9$ is $C_{1-4}$ Halogenalkyl.

In some embodiments, $R^9$ is —$CH_3$. In some embodiments $R^9$ is —$CH_2F$. In some embodiments, $R^9$ is —$CHF_2$. In some embodiments, $R^9$ is —$CF_3$.

Non-limiting illustrative compounds of the present disclosure include the compounds, presented in the Table 1, or a pharmaceutically acceptable salt, isomer, solvate, prodrug, or tautomer thereof.

TABLE 1

| Examples of the Compound (I) | | |
|---|---|---|
| Compound # | Structure | IUPAC name |
| 1 | 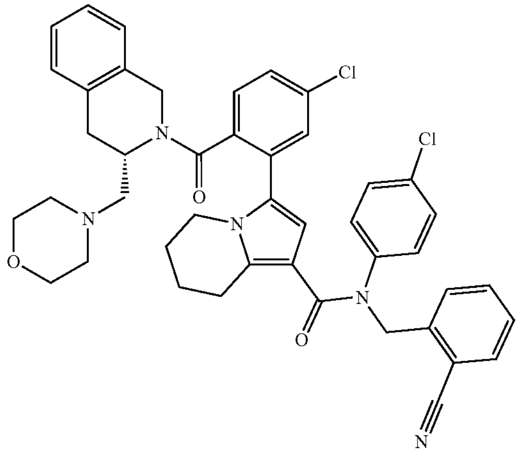 [SMILES: N#Cc1ccccc1CN(C(=O)c1cc(-c2cc(Cl)ccc2C(=O)N2Cc3ccccc3C[C@H]2CN2CCOCC2)n2c1CCCC2)c1ccc(Cl)cc1] | 3-[5-chloro-2-[(3S)-3-(morpholinomethyl)-3,4-dihydro-1H-isoquinoline-2-carbonyl]phenyl]-N-(4-chlorophenyl)-N-[(2-cyanophenyl)methyl]-5,6,7,8-tetrahydroindolizine-1-carboxamide |
| 2 | 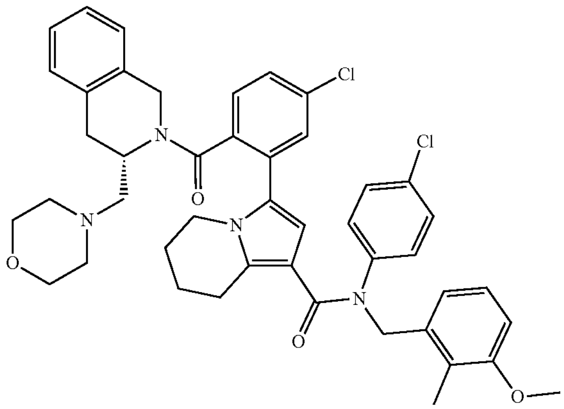 [SMILES: COc1cccc(CN(C(=O)c2cc(-c3cc(Cl)ccc3C(=O)N3Cc4ccccc4C[C@H]3CN3CCOCC3)n3c2CCCC3)c2ccc(Cl)cc2)c1C] | 3-[5-chloro-2-[(3S)-3-(morpholinomethyl)-3,4-dihydro-1H-isoquinoline-2-carbonyl]phenyl]-N-(4-chlorophenyl)-N-[(3-methoxy-2-methyl-phenyl)methyl]-5,6,7,8-tetrahydroindolizine-1-carboxamide |

TABLE 1-continued

| Examples of the Compound (I) | | |
|---|---|---|
| Compound # | Structure | IUPAC name |
| 3 | 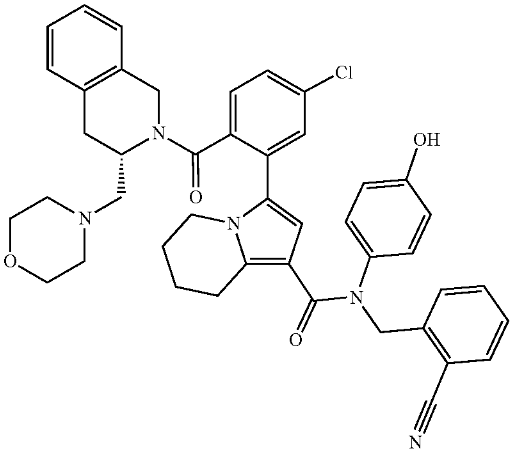 [SMILES: N#Cc1ccccc1CN(C(=O)c1cc(-c2cc(Cl)ccc2C(=O)N2Cc3ccccc3C[C@H]2CN2CCOCC2)n2c1CCCC2)c1ccc(O)cc1] | 3-[5-chloro-2-[(3S)-3-(morpholinomethyl)-3,4-dihydro-1H-isoquinoline-2-carbonyl]phenyl]-N-[(2-cyanophenyl)methyl]-N-(4-hydroxyphenyl)-5,6,7,8-tetrahydroindolizine-1-carboxamide |
| 4 | 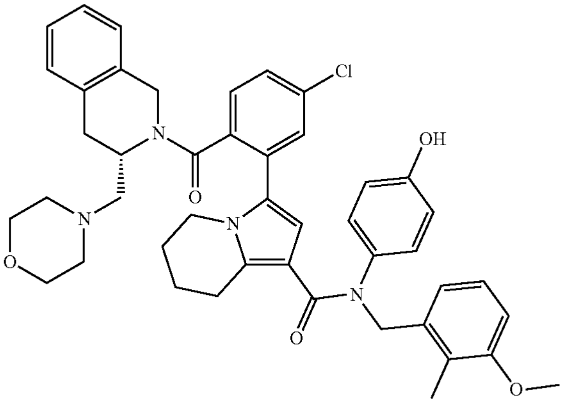 [SMILES: COc1cccc(CN(C(=O)c2cc(-c3cc(Cl)ccc3C(=O)N3Cc4ccccc4C[C@H]3CN3CCOCC3)n3c2CCCC3)c2ccc(O)cc2)c1C] | 3-[5-chloro-2-[(3S)-3-(morpholinomethyl)-3,4-dihydro-1H-isoquinoline-2-carbonyl]phenyl]-N-(4-hydroxyphenyl)-N-[(3-methoxy-2-methyl-phenyl)methyl]-5,6,7,8-tetrahydroindolizine-1-carboxamide |
| 5 | 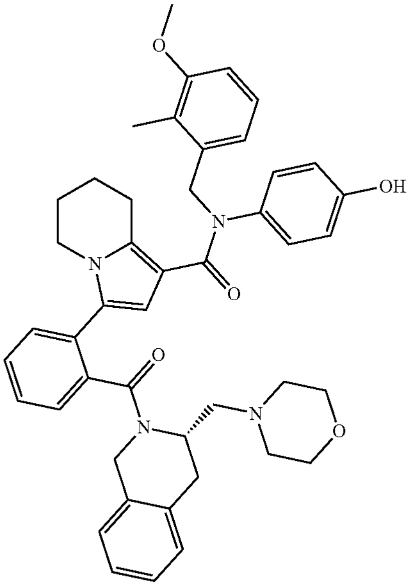 [SMILES: COc1cccc(CN(C(=O)c2cc(-c3ccccc3C(=O)N3Cc4ccccc4C[C@H]3CN3CCOCC3)n3c2CCCC3)c2ccc(O)cc2)c1C] | N-(4-hydroxyphenyl)-N-[(3-methoxy-2-methyl-phenyl)methyl]-3-[2-[(3S)-3-(morpholinomethyl)-3,4-dihydro-1H-isoquinoline-2-carbonyl]phenyl]-5,6,7,8-tetrahydroindolizine-1-carboxamide |

TABLE 1-continued

| Examples of the Compound (I) | | |
|---|---|---|
| Compound # | Structure | IUPAC name |
| 6 | 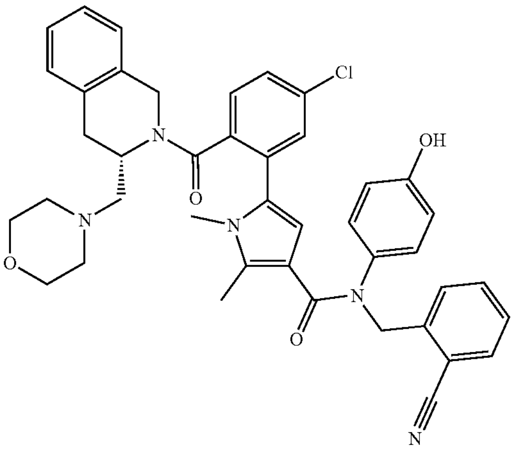 [SMILES: Cc1c(C(=O)N(Cc2ccccc2C#N)c2ccc(O)cc2)cc(-c2cc(Cl)ccc2C(=O)N2Cc3ccccc3C[C@H]2CN2CCOCC2)n1C] | 5-[5-chloro-2-[(3S)-3-(morpholinomethyl)-3,4-dihydro-1H-isoquinoline-2-carbonyl]phenyl]-N-[(2-cyanophenyl)methyl]-N-(4-hydroxyphenyl)-1,2-dimethyl-pyrrole-3-carboxamide |
| 7 | 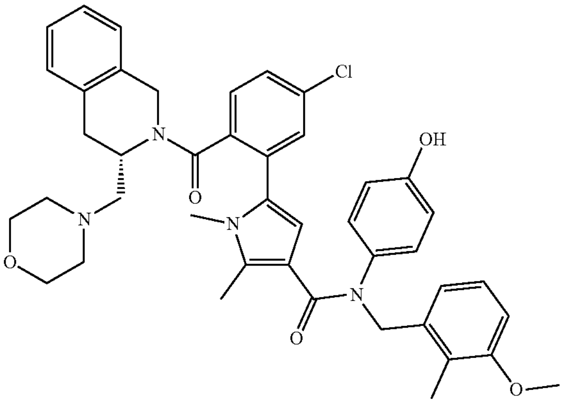 [SMILES: COc1cccc(CN(C(=O)c2cc(-c3cc(Cl)ccc3C(=O)N3Cc4ccccc4C[C@H]3CN3CCOCC3)n(C)c2C)c2ccc(O)cc2)c1C] | 5-[5-chloro-2-[(3S)-3-(morpholinomethyl)-3,4-dihydro-1H-isoquinoline-2-carbonyl]phenyl]-N-(4-hydroxyphenyl)-N-[(3-methoxy-2-methyl-phenyl)methyl]-1,2-dimethyl-pyrrole-3-carboxamide |
| 8 | 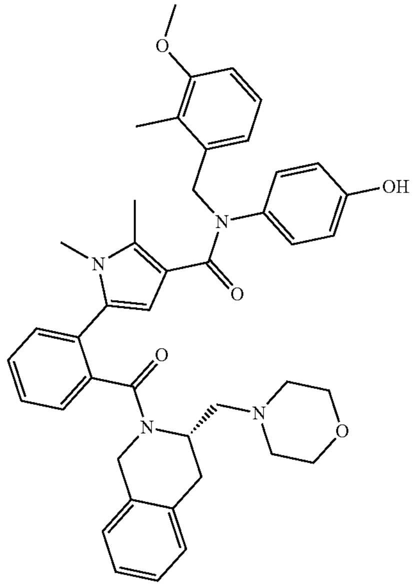 [SMILES: COc1cccc(CN(C(=O)c2cc(-c3ccccc3C(=O)N3Cc4ccccc4C[C@H]3CN3CCOCC3)n(C)c2C)c2ccc(O)cc2)c1C] | N-(4-hydroxyphenyl)-N-[(3-methoxy-2-methyl-phenyl)methyl]-1,2-dimethyl-5-[2-[(3S)-3-(morpholinomethyl)-3,4-dihydro-1H-isoquinoline-2-carbonyl]phenyl]pyrrole-3-carboxamide |

TABLE 1-continued

| Examples of the Compound (I) | | |
|---|---|---|
| Compound # | Structure | IUPAC name |
| 9 | 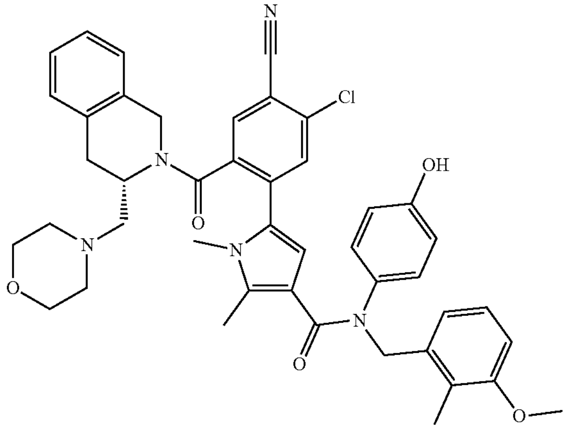 [SMILES: COc1cccc(CN(C(=O)c2cc(-c3cc(Cl)c(C#N)cc3C(=O)N3Cc4ccccc4C[C@H]3CN3CCOCC3)n(C)c2C)c2ccc(O)cc2)c1C] | 5-[5-chloro-4-cyano-2-[(3S)-3-(morpholinomethyl)-3,4-dihydro-1H-isoquinoline-2-carbonyl]phenyl]-N-(4-hydroxyphenyl)-N-[(3-methoxy-2-methyl-phenyl)methyl]-1,2-dimethyl-pyrrole-3-carboxamide |
| 10 | 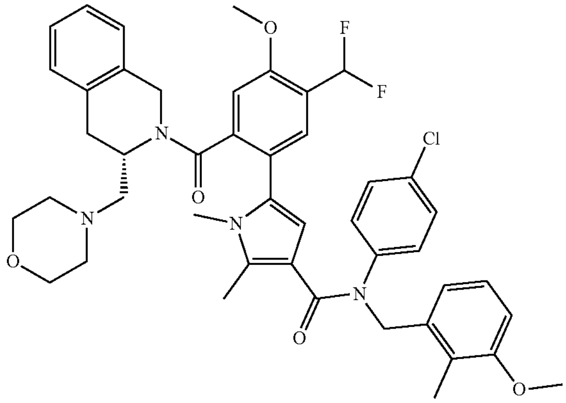 [SMILES: COc1cc(C(=O)N2Cc3ccccc3C[C@H]2CN2CCOCC2)c(-c2cc(C(=O)N(Cc3cccc(OC)c3C)c3ccc(Cl)cc3)c(C)n2C)cc1C(F)F] | N-(4-chlorophenyl)-5-[5-(difluoromethyl)-4-methoxy-2-[(3S)-3-(morpholinomethyl)-3,4-dihydro-1H-isoquinoline-2-carbonyl]phenyl]-N-[(3-methoxy-2-methyl-phenyl)methyl]-1,2-dimethyl-pyrrole-3-carboxamide |
| 11 | 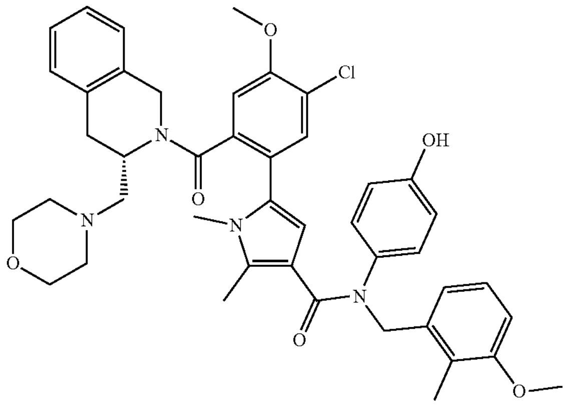 | 5-[5-chloro-4-methoxy-2-[(3S)-3-(morpholinomethyl)-3,4-dihydro-1H-isoquinoline-2-carbonyl]phenyl]-N-(4-hydroxyphenyl)-N-[(3-methoxy-2-methyl-phenyl)methyl]-1,2-dimethyl-pyrrole-3-carboxamide |

TABLE 1-continued

| Examples of the Compound (I) | | |
|---|---|---|
| Compound # | Structure | IUPAC name |
| 12 | 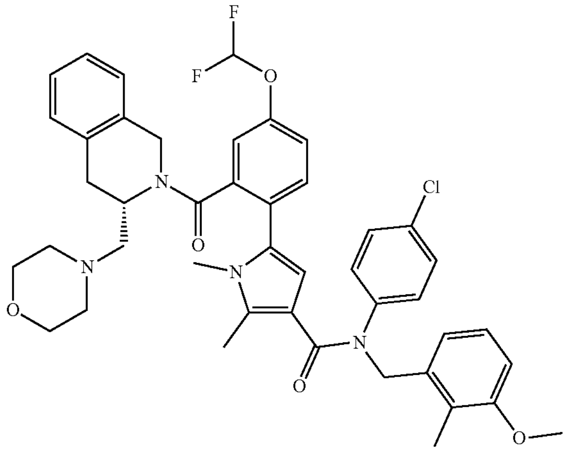 [SMILES: COc1cccc(CN(C(=O)c2cc(-c3ccc(OC(F)F)cc3C(=O)N3Cc4ccccc4C[C@H]3CN3CCOCC3)n(C)c2C)c2ccc(Cl)cc2)c1C] | N-(4-chlorophenyl)-5-[4-(difluoromethoxy)-2-[(3S)-3-(morpholinomethyl)-3,4-dihydro-1H-isoquinoline-2-carbonyl]phenyl]-N-[(3-methoxy-2-methyl-phenyl)methyl]-1,2-dimethyl-pyrrole-3-carboxamide |
| 13 | 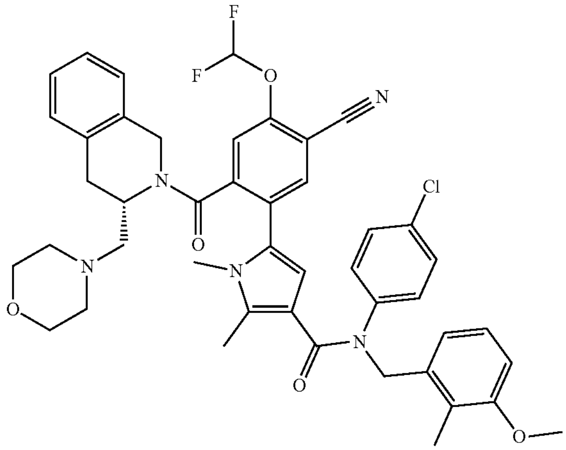 [SMILES: COc1cccc(CN(C(=O)c2cc(-c3cc(C#N)c(OC(F)F)cc3C(=O)N3Cc4ccccc4C[C@H]3CN3CCOCC3)n(C)c2C)c2ccc(Cl)cc2)c1C] | N-(4-chlorophenyl)-5-[5-cyano-4-(difluoromethoxy)-2-[(3S)-3-(morpholinomethyl)-3,4-dihydro-1H-isoquinoline-2-carbonyl]phenyl]-N-[(3-methoxy-2-methyl-phenyl)methyl]-1,2-dimethyl-pyrrole-3-carboxamide |
| 14 | 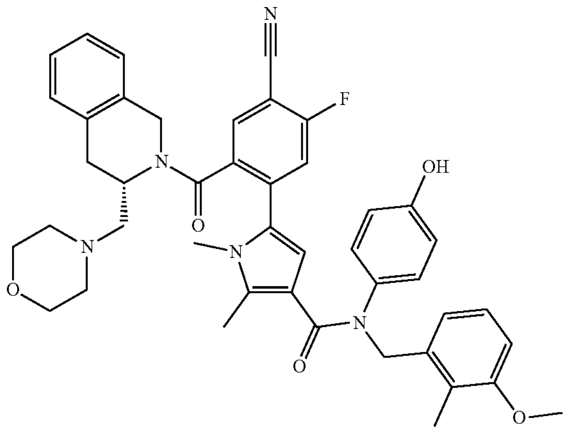 [SMILES: COc1cccc(CN(C(=O)c2cc(-c3cc(F)c(C#N)cc3C(=O)N3Cc4ccccc4C[C@H]3CN3CCOCC3)n(C)c2C)c2ccc(O)cc2)c1C] | 5-[4-cyano-5-fluoro-2-[(3S)-3-(morpholinomethyl)-3,4-dihydro-1H-isoquinoline-2-carbonyl]phenyl]-N-(4-hydroxyphenyl)-N-[(3-methoxy-2-methyl-phenyl)methyl]-1,2-dimethyl-pyrrole-3-carboxamide |

TABLE 1-continued

| Examples of the Compound (I) | | |
|---|---|---|
| Compound # | Structure | IUPAC name |
| 15 | 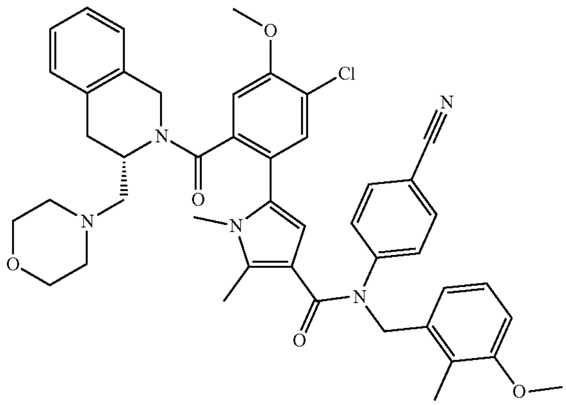 [SMILES: COc1cc(C(=O)N2Cc3ccccc3C[C@H]2CN2CCOCC2)c(-c2cc(C(=O)N(Cc3cccc(OC)c3C)c3ccc(C#N)cc3)c(C)n2C)cc1Cl] | 5-[5-chloro-4-methoxy-2-[(3S)-3-(morpholinomethyl)-3,4-dihydro-1H-isoquinoline-2-carbonyl]phenyl]-N-(4-cyanophenyl)-N-[(3-methoxy-2-methyl-phenyl)methyl]-1,2-dimethyl-pyrrole-3-carboxamide |
| 16 | 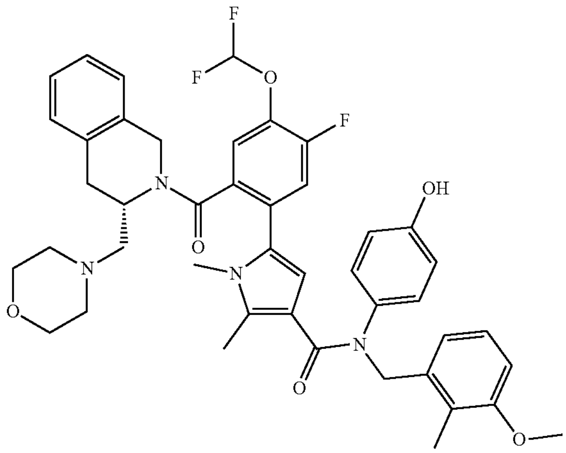 [SMILES: COc1cccc(CN(C(=O)c2cc(-c3cc(F)c(OC(F)F)cc3C(=O)N3Cc4ccccc4C[C@H]3CN3CCOCC3)n(C)c2C)c2ccc(O)cc2)c1C] | 5-[4-(difluoromethoxy)-5-fluoro-2-[(3S)-3-(morpholinomethyl)-3,4-dihydro-1H-isoquinoline-2-carbonyl]phenyl]-N-(4-hydroxyphenyl)-N-[(3-methoxy-2-methyl-phenyl)methyl]-1,2-dimethyl-pyrrole-3-carboxamide |
| 17 | 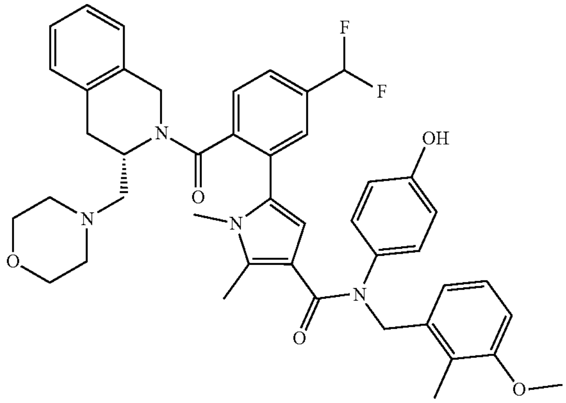 [SMILES: COc1cccc(CN(C(=O)c2cc(-c3cc(C(F)F)ccc3C(=O)N3Cc4ccccc4C[C@H]3CN3CCOCC3)n(C)c2C)c2ccc(O)cc2)c1C] | 5-[5-(difluoromethyl)-2-[(3S)-3-(morpholinomethyl)-3,4-dihydro-1H-isoquinoline-2-carbonyl]phenyl]-N-(4-hydroxyphenyl)-N-[(3-methoxy-2-methyl-phenyl)methyl]-1,2-dimethyl-pyrrole-3-carboxamide |

TABLE 1-continued

| Examples of the Compound (I) | | |
|---|---|---|
| Compound # | Structure | IUPAC name |
| 18 | 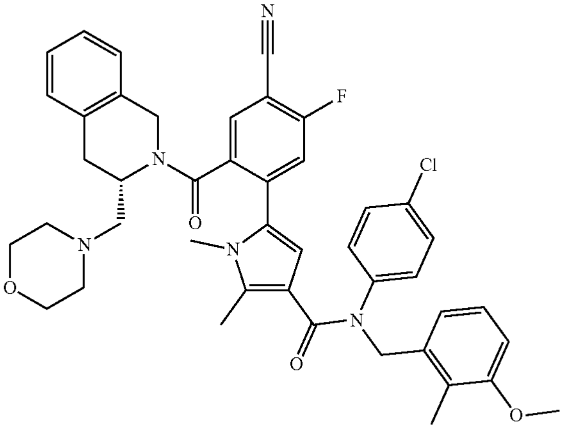 [SMILES: COc1cccc(CN(C(=O)c2cc(-c3cc(F)c(C#N)cc3C(=O)N3Cc4ccccc4C[C@H]3CN3CCOCC3)n(C)c2C)c2ccc(Cl)cc2)c1C] | N-(4-chlorophenyl)-5-[4-cyano-5-fluoro-2-[(3S)-3-(morpholinomethyl)-3,4-dihydro-1H-isoquinoline-2-carbonyl]phenyl]-N-[(3-methoxy-2-methyl-phenyl)methyl]-1,2-dimethyl-pyrrole-3-carboxamide |
| 19 | 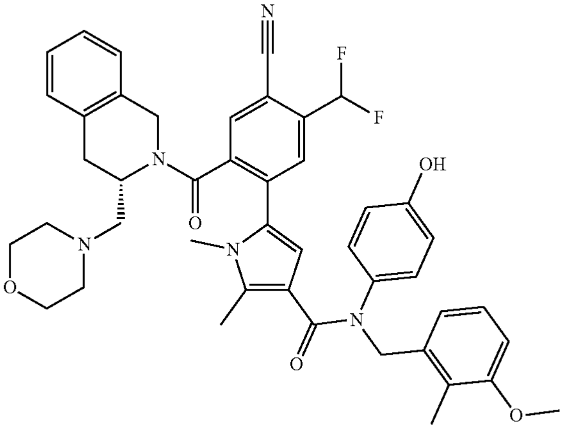 [SMILES: COc1cccc(CN(C(=O)c2cc(-c3cc(C(F)F)c(C#N)cc3C(=O)N3Cc4ccccc4C[C@H]3CN3CCOCC3)n(C)c2C)c2ccc(O)cc2)c1C] | 5-[4-cyano-5-(difluoromethyl)-2-[(3S)-3-(morpholinomethyl)-3,4-dihydro-1H-isoquinoline-2-carbonyl]phenyl]-N-(4-hydroxyphenyl)-N-[(3-methoxy-2-methyl-phenyl)methyl]-1,2-dimethyl-pyrrole-3-carboxamide |
| 20 | 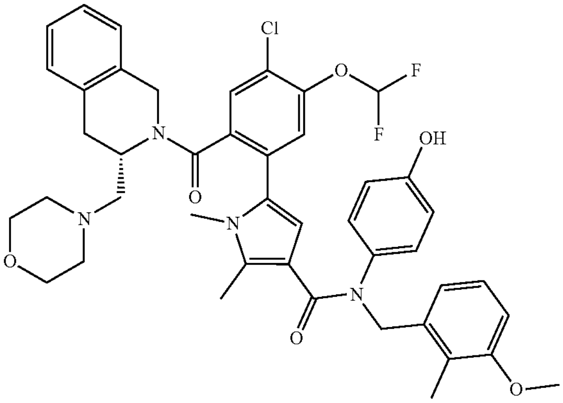 [SMILES: COc1cccc(CN(C(=O)c2cc(-c3cc(OC(F)F)c(Cl)cc3C(=O)N3Cc4ccccc4C[C@H]3CN3CCOCC3)n(C)c2C)c2ccc(O)cc2)c1C] | 5-[4-chloro-5-(difluoromethoxy)-2-[(3S)-3-(morpholinomethyl)-3,4-dihydro-1H-isoquinoline-2-carbonyl]phenyl]-N-(4-hydroxyphenyl)-N-[(3-methoxy-2-methyl-phenyl)methyl]-1,2-dimethyl-pyrrole-3-carboxamide |

TABLE 1-continued

| Examples of the Compound (I) | | |
|---|---|---|
| Compound # | Structure | IUPAC name |
| 21 | 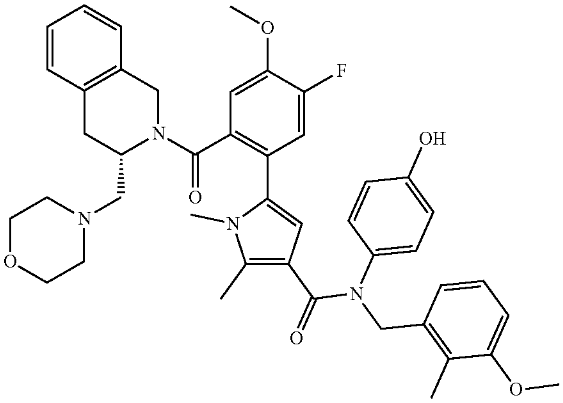 [SMILES: COc1cc(C(=O)N2Cc3ccccc3C[C@H]2CN2CCOCC2)c(-c2cc(C(=O)N(Cc3cccc(OC)c3C)c3ccc(O)cc3)c(C)n2C)cc1F] | 5-[5-fluoro-4-methoxy-2-[(3S)-3-(morpholinomethyl)-3,4-dihydro-1H-isoquinoline-2-carbonyl]phenyl]-N-(4-hydroxyphenyl)-N-[(3-methoxy-2-methyl-phenyl)methyl]-1,2-dimethyl-pyrrole-3-carboxamide |
| 22 | 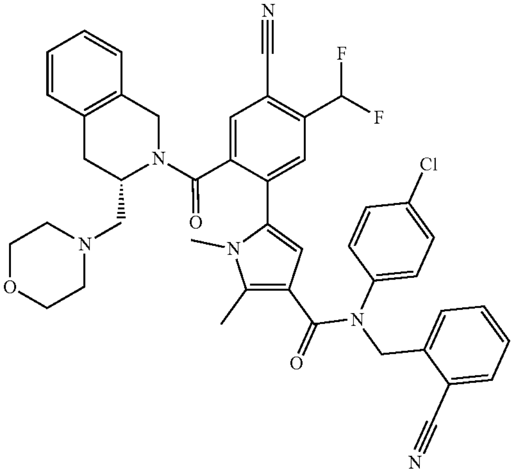 [SMILES: Cc1c(C(=O)N(Cc2ccccc2C#N)c2ccc(Cl)cc2)cc(-c2cc(C(F)F)c(C#N)cc2C(=O)N2Cc3ccccc3C[C@H]2CN2CCOCC2)n1C] | N-(4-chlorophenyl)-5-[4-cyano-5-(difluoromethyl)-2-[(3S)-3-(morpholinomethy1)-3,4-dihydro-1H-isoquinoline-2-carbonyl]phenyl]-N-[(2-cyanophenyl)methyl]-1,2-dimethyl-pyrrole-3-carboxamide |
| 23 | 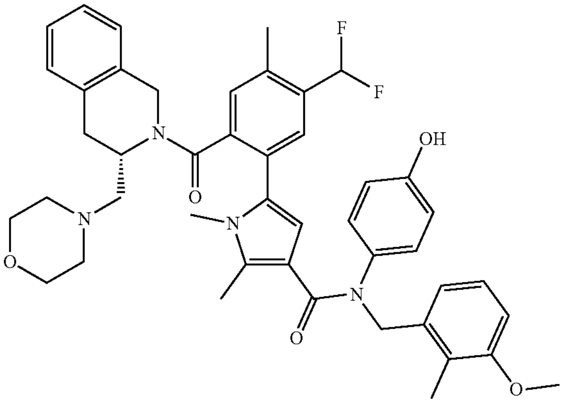 | 5-[5-(difluoromethyl)-4-methyl-2-[(3S)-3-(morpholinomethyl)-3,4-dihydro-1H-isoquinoline-2-carbonyl]phenyl]-N-(4-hydroxyphenyl)-N-[(3-methoxy-2-methyl-phenyl)methyl]-1,2-dimethyl-pyrrole-3-carboxamide |

TABLE 1-continued

| Examples of the Compound (I) | | |
|---|---|---|
| Compound # | Structure | IUPAC name |
| 24 | 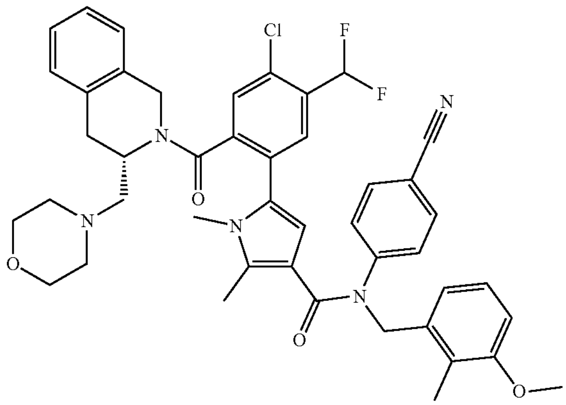 [SMILES: COc1cccc(CN(C(=O)c2cc(-c3cc(C(F)F)c(Cl)cc3C(=O)N3Cc4ccccc4C[C@H]3CN3CCOCC3)n(C)c2C)c2ccc(C#N)cc2)c1C] | 5-[4-chloro-5-(difluoromethyl)-2-[(3S)-3-(morpholinomethyl)-3,4-dihydro-1H-isoquinoline-2-carbonyl]phenyl]-N-(4-cyanophenyl)-N-[(3-methoxy-2-methyl-phenyl)methyl]-1,2-dimethyl-pyrrole-3-carboxamide |
| 25 | 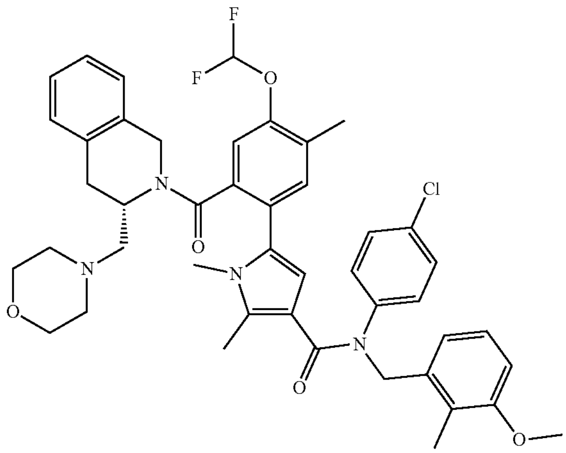 [SMILES: COc1cccc(CN(C(=O)c2cc(-c3cc(C)c(OC(F)F)cc3C(=O)N3Cc4ccccc4C[C@H]3CN3CCOCC3)n(C)c2C)c2ccc(Cl)cc2)c1C] | N-(4-chlorophenyl)-5-[4-(difluoromethoxy)-5-methyl-2-[(3S)-3-(morpholinomethyl)-3,4-dihydro-1H-isoquinoline-2-carbonyl]phenyl]-N-[(3-methoxy-2-methyl-phenyl)methyl]-1,2-dimethyl-pyrrole-3-carboxamide |
| 26 | 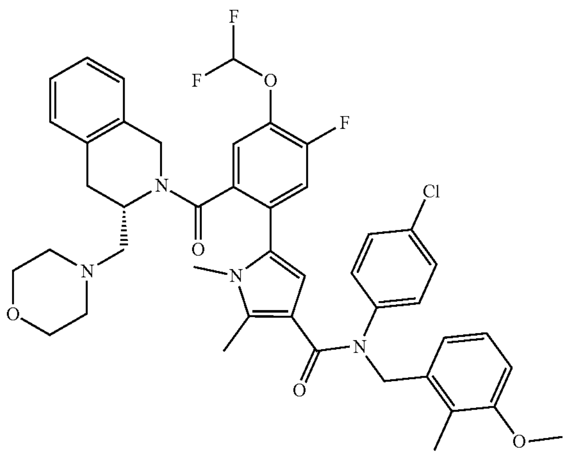 [SMILES: COc1cccc(CN(C(=O)c2cc(-c3cc(F)c(OC(F)F)cc3C(=O)N3Cc4ccccc4C[C@H]3CN3CCOCC3)n(C)c2C)c2ccc(Cl)cc2)c1C] | N-(4-chlorophenyl)-5-[4-(difluoromethoxy)-5-fluoro-2-[(3S)-3-(morpholinomethyl)-3,4-dihydro-1H-isoquinoline-2-carbonyl]phenyl]-N-[(3-methoxy-2-methyl-phenyl)methyl]-1,2-dimethyl-pyrrole-3-carboxamide |

TABLE 1-continued

| Examples of the Compound (I) | | |
|---|---|---|
| Compound # | Structure | IUPAC name |
| 27 | 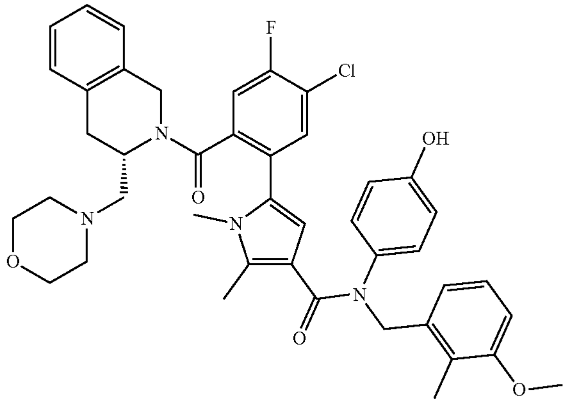 [SMILES: COc1cccc(CN(C(=O)c2cc(-c3cc(Cl)c(F)cc3C(=O)N3Cc4ccccc4C[C@H]3CN3CCOCC3)n(C)c2C)c2ccc(O)cc2)c1C] | 5-[5-chloro-4-fluoro-2-[(3S)-3-(morpholinomethyl)-3,4-dihydro-1H-isoquinoline-2-carbonyl]phenyl]-N-(4-hydroxyphenyl)-N-[(3-methoxy-2-methyl-phenyl)methyl]-1,2-dimethyl-pyrrole-3-carboxamide |
| 28 | 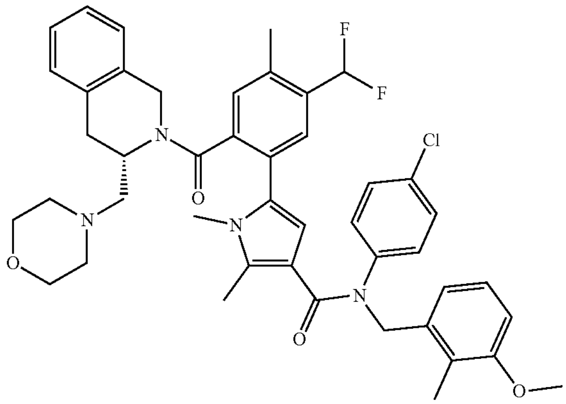 [SMILES: COc1cccc(CN(C(=O)c2cc(-c3cc(C(F)F)c(C)cc3C(=O)N3Cc4ccccc4C[C@H]3CN3CCOCC3)n(C)c2C)c2ccc(Cl)cc2)c1C] | N-(4-chlorophenyl)-5-[5-(difluoromethyl)-4-methyl-2-[(3S)-3-(morpholinomethyl)-3,4-dihydro-1H-isoquinoline-2-carbonyl]phenyl]-N-[(3-methoxy-2-methyl-phenyl)methyl]-1,2-dimethyl-pyrrole-3-carboxamide |
| 29 | 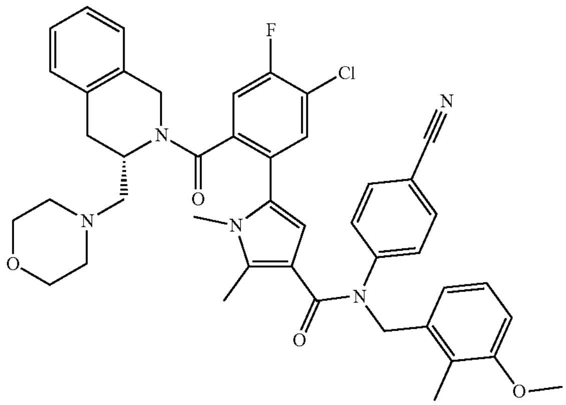 [SMILES: COc1cccc(CN(C(=O)c2cc(-c3cc(Cl)c(F)cc3C(=O)N3Cc4ccccc4C[C@H]3CN3CCOCC3)n(C)c2C)c2ccc(C#N)cc2)c1C] | 5-[5-chloro-4-fluoro-2-[(3S)-3-(morpholinomethyl)-3,4-dihydro-1H-isoquinoline-2-carbonyl]phenyl]-N-(4-cyanophenyl)-N-[(3-methoxy-2-methyl-phenyl)methyl]-1,2-dimethyl-pyrrole-3-carboxamide |

TABLE 1-continued

| Examples of the Compound (I) | | |
|---|---|---|
| Compound # | Structure | IUPAC name |
| 30 | 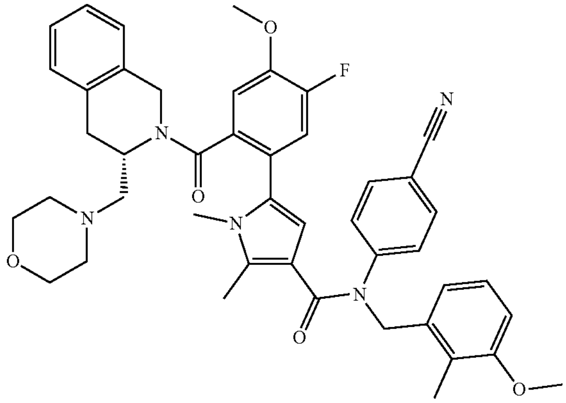 [SMILES: COc1cc(C(=O)N2Cc3ccccc3C[C@H]2CN2CCOCC2)c(-c2cc(C(=O)N(Cc3cccc(OC)c3C)c3ccc(C#N)cc3)c(C)n2C)cc1F] | N-(4-cyanophenyl)-5-[5-fluoro-4-methoxy-2-[(3S)-3-(morpholinomethyl)-3,4-dihydro-1H-isoquinoline-2-carbonyl]phenyl]-N-[(3-methoxy-2-methyl-phenyl)methyl]-1,2-dimethyl-pyrrole-3-carboxamide |
| 31 | 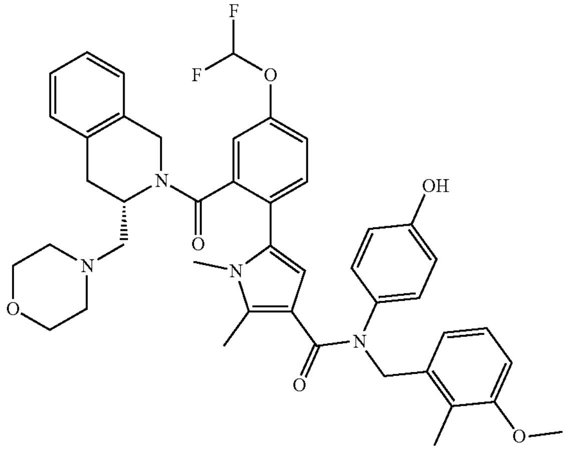 | 5-[4-(difluoromethoxy)-2-[(3S)-3-(morpholinomethyl)-3,4-dihydro-1H-isoquinoline-2-carbonyl]phenyl]-N-(4-hydroxyphenyl)-N-[(3-methoxy-2-methyl-phenyl)methyl]-1,2-dimethyl-pyrrole-3-carboxamide |
| 32 | 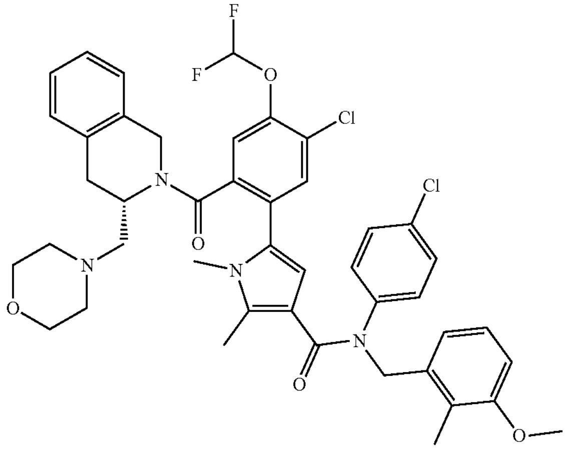 | 5-[5-chloro-4-(difluoromethoxy)-2-[(3S)-3-(morpholinomethyl)-3,4-dihydro-1H-isoquinoline-2-carbonyl]phenyl]-N-(4-chlorophenyl)-N-[(3-methoxy-2-methyl-phenyl)methyl]-1,2-dimethyl-pyrrole-3-carboxamide |

TABLE 1-continued

| Examples of the Compound (I) | | |
|---|---|---|
| Compound # | Structure | IUPAC name |
| 33 | 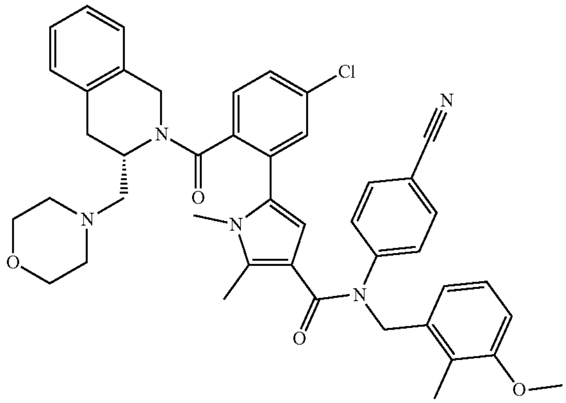 [SMILES: COc1cccc(CN(C(=O)c2cc(-c3cc(Cl)ccc3C(=O)N3Cc4ccccc4C[C@H]3CN3CCOCC3)n(C)c2C)c2ccc(C#N)cc2)c1C] | 5-[5-chloro-2-[(3S)-3-(morpholinomethyl)-3,4-dihydro-1H-isoquinoline-2-carbonyl]phenyl]-N-(4-cyanophenyl)-N-[(3-methoxy-2-methyl-phenyl)methyl]-1,2-dimethyl-pyrrole-3-carboxamide |
| 34 | 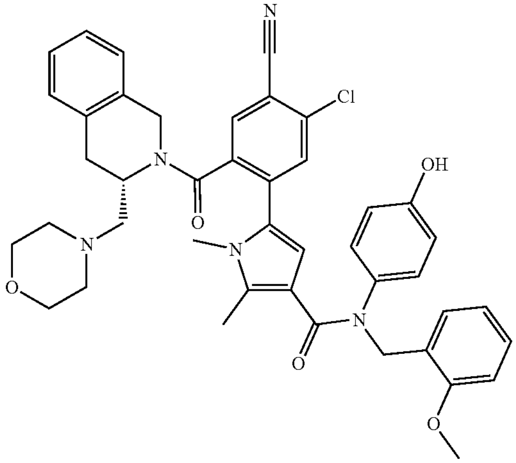 [SMILES: COc1ccccc1CN(C(=O)c1cc(-c2cc(Cl)c(C#N)cc2C(=O)N2Cc3ccccc3C[C@H]2CN2CCOCC2)n(C)c1C)c1ccc(O)cc1] | 5-[5-chloro-4-cyano-2-[(3S)-3-(morpholinomethyl)-3,4-dihydro-1H-isoquinoline-2-carbonyl]phenyl]-N-(4-hydroxyphenyl)-N-[(2-methoxyphenyl)methyl]-1,2-dimethyl-pyrrole-3-carboxamide |
| 35 | 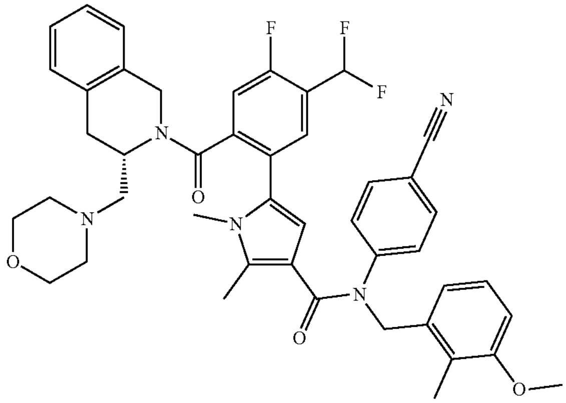 | N-(4-cyanophenyl)-5-[5-(difluoromethyl)-4-fluoro-2-[(3S)-3-(morpholinomethyl)-3,4-dihydro-1H-isoquinoline-2-carbonyl]phenyl]-N-[(3-methoxy-2-methyl-phenyl)methyl]-1,2-dimethyl-pyrrole-3-carboxamide |

TABLE 1-continued

| Examples of the Compound (I) | | |
|---|---|---|
| Compound # | Structure | IUPAC name |
| 36 | 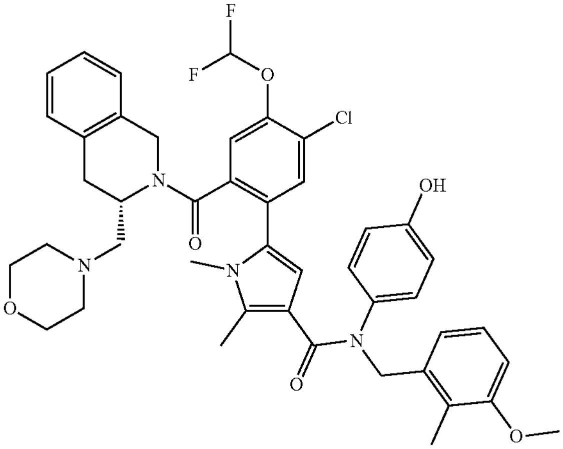 [SMILES: COc1cccc(CN(C(=O)c2cc(-c3cc(Cl)c(OC(F)F)cc3C(=O)N3Cc4ccccc4C[C@H]3CN3CCOCC3)n(C)c2C)c2ccc(O)cc2)c1C] | 5-[5-chloro-4-(difluoromethoxy)-2-[(3S)-3-(morpholinomethyl)-3,4-dihydro-1H-isoquinoline-2-carbonyl]phenyl]-N-(4-hydroxyphenyl)-N-[(3-methoxy-2-methyl-phenyl)methyl]-1,2-dimethyl-pyrrole-3-carboxamide |
| 37 | 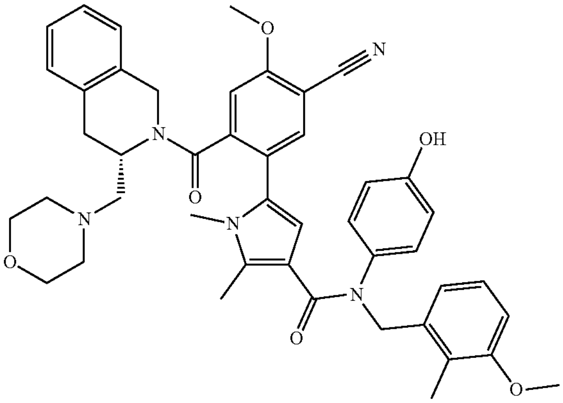 [SMILES: COc1cc(C(=O)N2Cc3ccccc3C[C@H]2CN2CCOCC2)c(-c2cc(C(=O)N(Cc3cccc(OC)c3C)c3ccc(O)cc3)c(C)n2C)cc1C#N] | 5-[5-cyano-4-methoxy-2-[(3S)-3-(morpholinomethyl)-3,4-dihydro-1H-isoquinoline-2-carbonyl]phenyl]-N-(4-hydroxyphenyl)-N-[(3-methoxy-2-methyl-phenyl)methyl]-1,2-dimethyl-pyrrole-3-carboxamide |
| 38 | 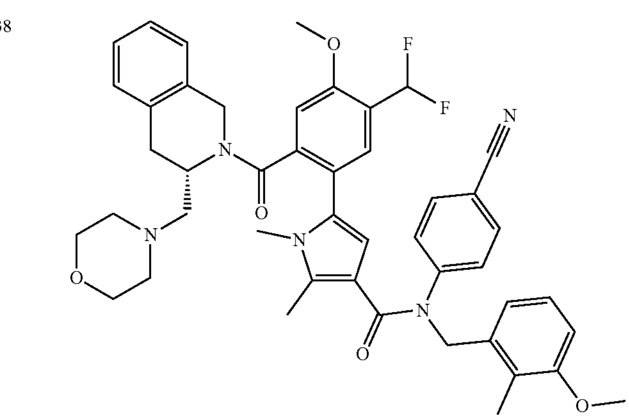 | N-(4-cyanophenyl)-5-[5-(difluoromethyl)-4-methoxy-2-[(3S)-3-(morpholinomethyl)-3,4-dihydro-1H-isoquinoline-2-carbonyl]phenyl]-N-[(3-methoxy-2-methyl-phenyl)methyl]-1,2-dimethyl-pyrrole-3-carboxamide |

TABLE 1-continued

| Examples of the Compound (I) | | |
|---|---|---|
| Compound # | Structure | IUPAC name |
| 39 | 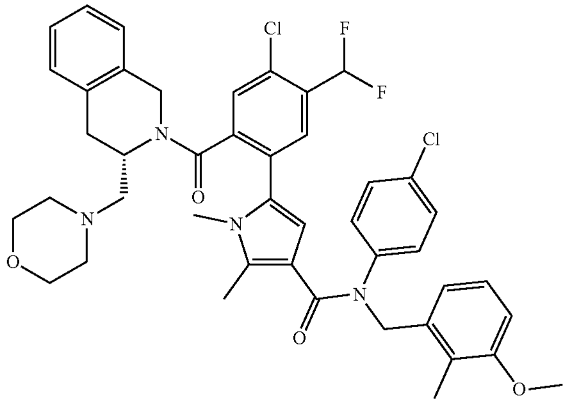 [SMILES: COc1cccc(CN(C(=O)c2cc(-c3cc(C(F)F)c(Cl)cc3C(=O)N3Cc4ccccc4C[C@H]3CN3CCOCC3)n(C)c2C)c2ccc(Cl)cc2)c1C] | 5-[4-chloro-5-(difluoromethyl)-2-[(3S)-3-(morpholinomethyl)-3,4-dihydro-1H-isoquinoline-2-carbonyl]phenyl]-N-(4-chlorophenyl)-N-[(3-methoxy-2-methyl-phenyl)methyl]-1,2-dimethyl-pyrrole-3-carboxamide |
| 40 | 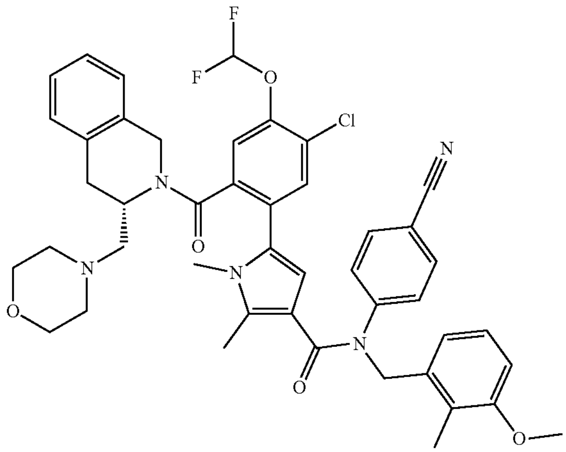 [SMILES: COc1cccc(CN(C(=O)c2cc(-c3cc(Cl)c(OC(F)F)cc3C(=O)N3Cc4ccccc4C[C@H]3CN3CCOCC3)n(C)c2C)c2ccc(C#N)cc2)c1C] | 5-[5-chloro-4-(difluoromethoxy)-2-[(3S)-3-(morpholinomethyl)-3,4-dihydro-1H-isoquinoline-2-carbonyl]phenyl]-N-(4-cyanophenyl)-N-[(3-methoxy-2-methyl-phenyl)methyl]-1,2-dimethyl-pyrrole-3-carboxamide |
| 41 | 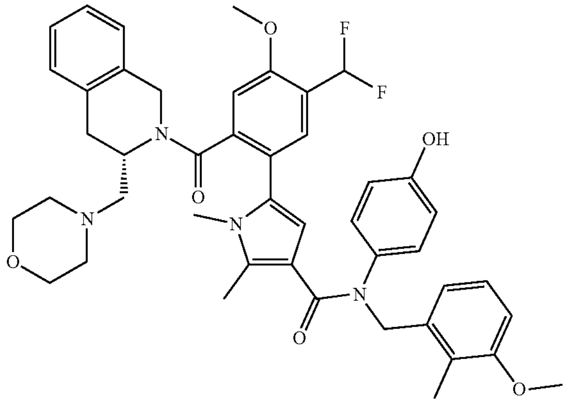 [SMILES: COc1cc(C(=O)N2Cc3ccccc3C[C@H]2CN2CCOCC2)c(-c2cc(C(=O)N(Cc3cccc(OC)c3C)c3ccc(O)cc3)c(C)n2C)cc1C(F)F] | 5-[5-(difluoromethyl)-4-methoxy-2-[(3S)-3-(morpholinomethyl)-3,4-dihydro-1H-isoquinoline-2-carbonyl]phenyl]-N-(4-hydroxyphenyl)-N-[(3-methoxy-2-methyl-phenyl)methyl]-1,2-dimethyl-pyrrole-3-carboxamide |

TABLE 1-continued

| Examples of the Compound (I) | | |
|---|---|---|
| Compound # | Structure | IUPAC name |
| 42 | 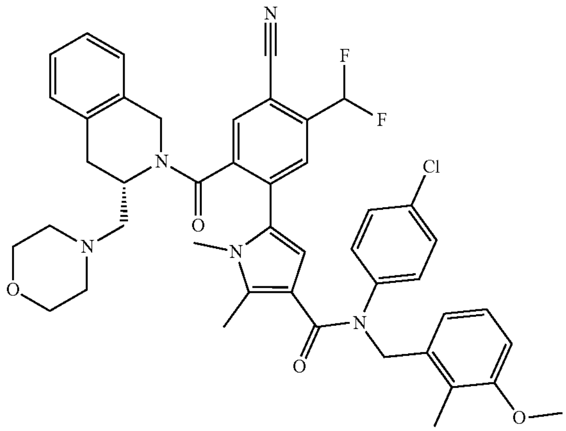 [SMILES: COc1cccc(CN(C(=O)c2cc(-c3cc(C(F)F)c(C#N)cc3C(=O)N3Cc4ccccc4C[C@H]3CN3CCOCC3)n(C)c2C)c2ccc(Cl)cc2)c1C] | N-(4-chlorophenyl)-5-[4-cyano-5-(difluoromethyl)-2-[(3S)-3-(morpholinomethyl)-3,4-dihydro-1H-isoquinoline-2-carbonyl]phenyl]-N-[(3-methoxy-2-methyl-phenyl)methyl]-1,2-dimethyl-pyrrole-3-carboxamide |
| 43 | 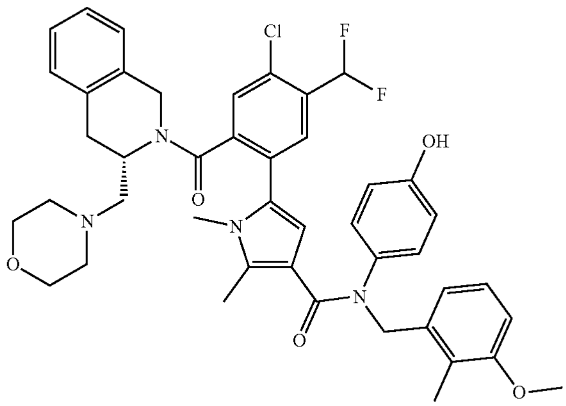 | 5-[4-chloro-5-(difluoromethyl)-2-[(3S)-3-(morpholinomethyl)-3,4-dihydro-1H-isoquinoline-2-carbonyl]phenyl]-N-(4-hydroxyphenyl)-N-[(3-methoxy-2-methyl-phenyl)methyl]-1,2-dimethyl-pyrrole-3-carboxamide |
| 44 | 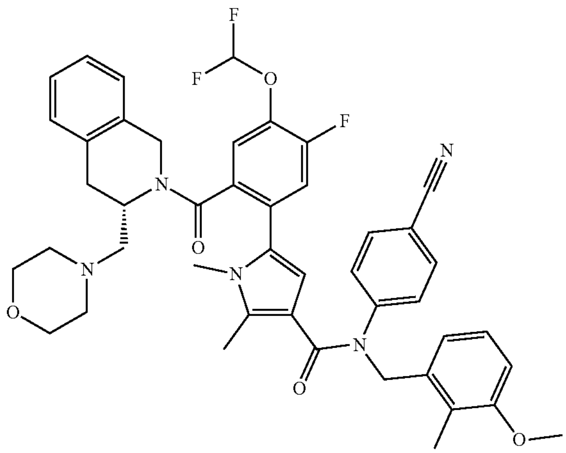 [SMILES: COc1cccc(CN(C(=O)c2cc(-c3cc(F)c(OC(F)F)cc3C(=O)N3Cc4ccccc4C[C@H]3CN3CCOCC3)n(C)c2C)c2ccc(C#N)cc2)c1C] | N-(4-cyanophenyl)-5-[4-(difluoromethoxy)-5-fluoro-2-[(3S)-3-(morpholinomethyl)-3,4-dihydro-1H-isoquinoline-2-carbonyl]phenyl]-N-[(3-methoxy-2-methyl-phenyl)methyl]-1,2-dimethyl-pyrrole-3-carboxamide |

TABLE 1-continued

| Examples of the Compound (I) | | |
|---|---|---|
| Compound # | Structure | IUPAC name |
| 45 | 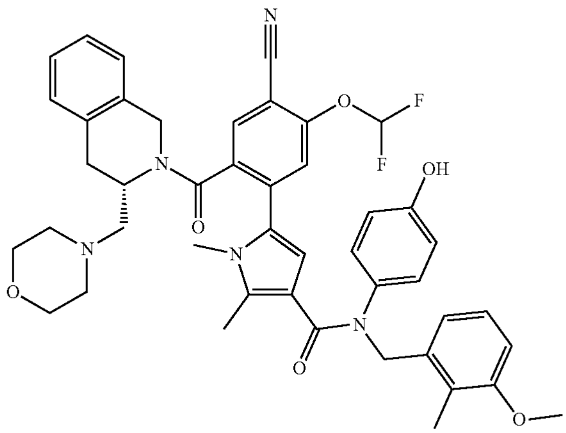 [SMILES: COc1cccc(CN(C(=O)c2cc(-c3cc(OC(F)F)c(C#N)cc3C(=O)N3Cc4ccccc4C[C@H]3CN3CCOCC3)n(C)c2C)c2ccc(O)cc2)c1C] | 5-[4-cyano-5-(difluoromethoxy)-2-[(3S)-3-(morpholinomethyl)-3,4-dihydro-1H-isoquinoline-2-carbonyl]phenyl]-N-(4-hydroxyphenyl)-N-[(3-methoxy-2-methyl-phenyl)methyl]-1,2-dimethyl-pyrrole-3-carboxamide |
| 46 | 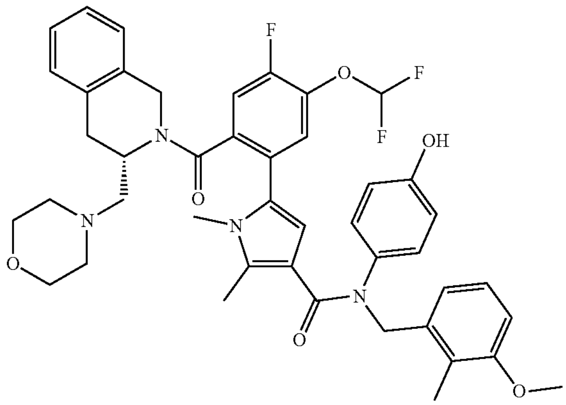 [SMILES: COc1cccc(CN(C(=O)c2cc(-c3cc(OC(F)F)c(F)cc3C(=O)N3Cc4ccccc4C[C@H]3CN3CCOCC3)n(C)c2C)c2ccc(O)cc2)c1C] | 5-[5-(difluoromethoxy)-4-fluoro-2-[(3S)-3-(morpholinomethyl)-3,4-dihydro-1H-isoquinoline-2-carbonyl]phenyl]-N-(4-hydroxyphenyl)-N-[(3-methoxy-2-methyl-phenyl)methyl]-1,2-dimethyl-pyrrole-3-carboxamide |
| 47 | 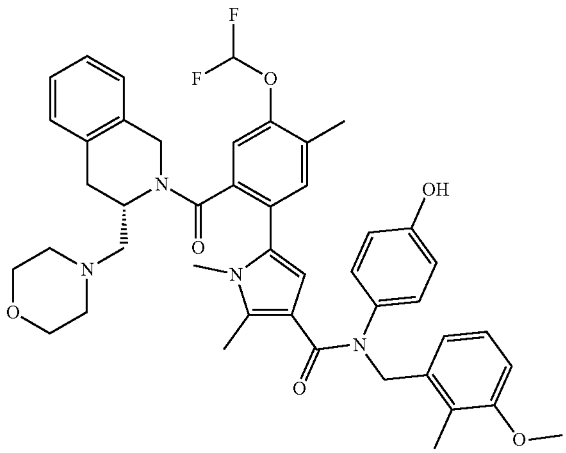 [SMILES: COc1cccc(CN(C(=O)c2cc(-c3cc(C)c(OC(F)F)cc3C(=O)N3Cc4ccccc4C[C@H]3CN3CCOCC3)n(C)c2C)c2ccc(O)cc2)c1C] | 5-[4-(difluoromethoxy)-5-methyl-2-[(3S)-3-(morpholinomethyl)-3,4-dihydro-1H-isoquinoline-2-carbonyl]phenyl]-N-(4-hydroxyphenyl)-N-[(3-methoxy-2-methyl-phenyl)methyl]-1,2-dimethyl-pyrrole-3-carboxamide |

TABLE 1-continued

| Examples of the Compound (I) | | |
|---|---|---|
| Compound # | Structure | IUPAC name |
| 48 | 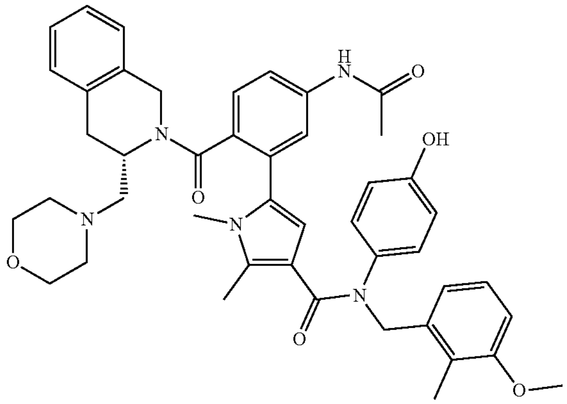 [SMILES: COc1cccc(CN(C(=O)c2cc(-c3cc(NC(C)=O)ccc3C(=O)N3Cc4ccccc4C[C@H]3CN3CCOCC3)n(C)c2C)c2ccc(O)cc2)c1C] | 5-[5-acetamido-2-[(3S)-3-(morpholinomethyl)-3,4-dihydro-1H-isoquinoline-2-carbonyl]phenyl]-N-(4-hydroxyphenyl)-N-[(3-methoxy-2-methyl-phenyl)methyl]-1,2-dimethyl-pyrrole-3-carboxamide |
| 49 | 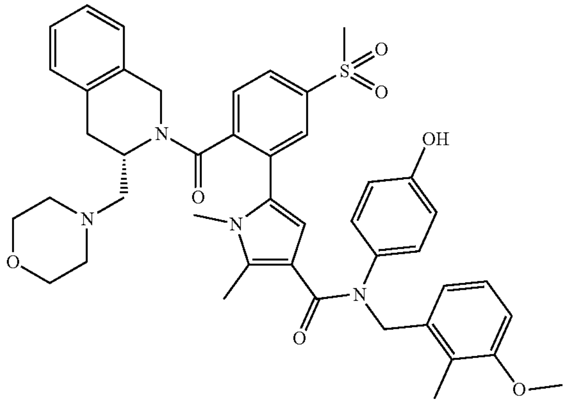 [SMILES: COc1cccc(CN(C(=O)c2cc(-c3cc(S(C)(=O)=O)ccc3C(=O)N3Cc4ccccc4C[C@H]3CN3CCOCC3)n(C)c2C)c2ccc(O)cc2)c1C] | N-(4-hydroxyphenyl)-N-[(3-methoxy-2-methyl-phenyl)methyl]-1,2-dimethyl-5-[5-methylsulfonyl-2-[(3S)-3-(morpholinomethyl)-3,4-dihydro-1H-isoquinoline-2-carbonyl]phenyl]pyrrole-3-carboxamide |
| 50 | 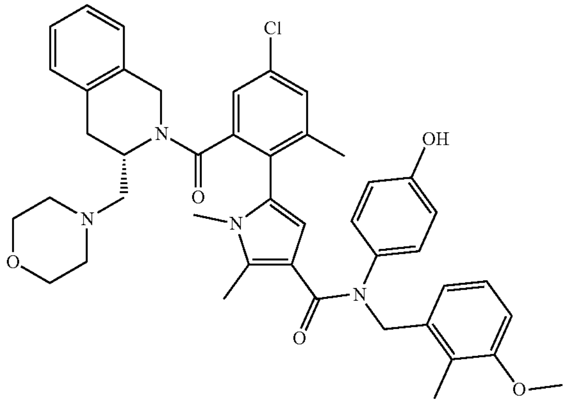 [SMILES: COc1cccc(CN(C(=O)c2cc(-c3c(C)cc(Cl)cc3C(=O)N3Cc4ccccc4C[C@H]3CN3CCOCC3)n(C)c2C)c2ccc(O)cc2)c1C] | 5-[4-chloro-2-methyl-6-[(3S)-3-(morpholinomethyl)-3,4-dihydro-1H-isoquinoline-2-carbonyl]phenyl]-N-(4-hydroxyphenyl)-N-[(3-methoxy-2-methyl-phenyl)methyl]-1,2-dimethyl-pyrrole-3-carboxamide |

TABLE 1-continued

| Examples of the Compound (I) | | |
|---|---|---|
| Compound # | Structure | IUPAC name |
| 51 | 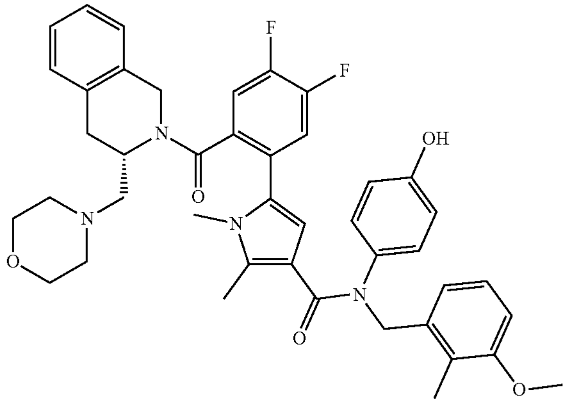 [SMILES: COc1cccc(CN(C(=O)c2cc(-c3cc(F)c(F)cc3C(=O)N3Cc4ccccc4C[C@H]3CN3CCOCC3)n(C)c2C)c2ccc(O)cc2)c1C] | 5-[4,5-difluoro-2-[(3S)-3-(morpholinomethyl)-3,4-dihydro-1H-isoquinoline-2-carbonyl]phenyl]-N-(4-hydroxyphenyl)-N-[(3-methoxy-2-methyl-phenyl)methyl]-1,2-dimethyl-pyrrole-3-carboxamide |
| 52 | 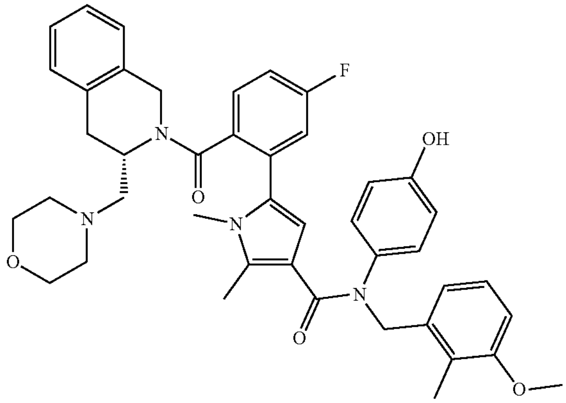 | 5-[5-fluoro-2-[(3S)-3-(morpholinomethyl)-3,4-dihydro-1H-isoquinoline-2-carbonyl]phenyl]-N-(4-hydroxyphenyl)-N-[(3-methoxy-2-methyl-phenyl)methyl]-1,2-dimethyl-pyrrole-3-carboxamide |
| 53 | 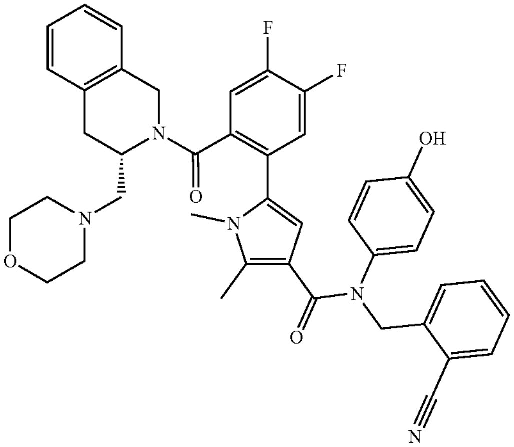 [SMILES: Cc1c(C(=O)N(Cc2ccccc2C#N)c2ccc(O)cc2)cc(-c2cc(F)c(F)cc2C(=O)N2Cc3ccccc3C[C@H]2CN2CCOCC2)n1C] | N-[(2-cyanophenyl)methyl]-5-[4,5-difluoro-2-[(3S)-3-(morpholinomethyl)-3,4-dihydro-1H-isoquinoline-2-carbonyl]phenyl]-N-(4-hydroxyphenyl)-1,2-dimethyl-pyrrole-3-carboxamide |

TABLE 1-continued

| Examples of the Compound (I) | | |
|---|---|---|
| Compound # | Structure | IUPAC name |
| 54 | 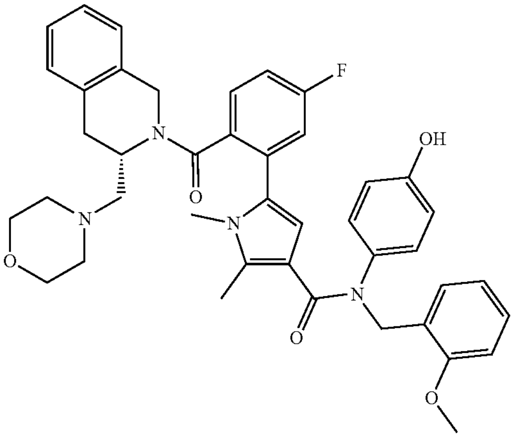 [SMILES: COc1ccccc1CN(C(=O)c1cc(-c2cc(F)ccc2C(=O)N2Cc3ccccc3C[C@H]2CN2CCOCC2)n(C)c1C)c1ccc(O)cc1] | 5-[5-fluoro-2-[(3S)-3-(morpholinomethyl)-3,4-dihydro-1H-isoquinoline-2-carbonyl]phenyl]-N-(4-hydroxyphenyl)-N-[(2-methoxyphenyl)methyl]-1,2-dimethyl-pyrrole-3-carboxamide |
| 55 | 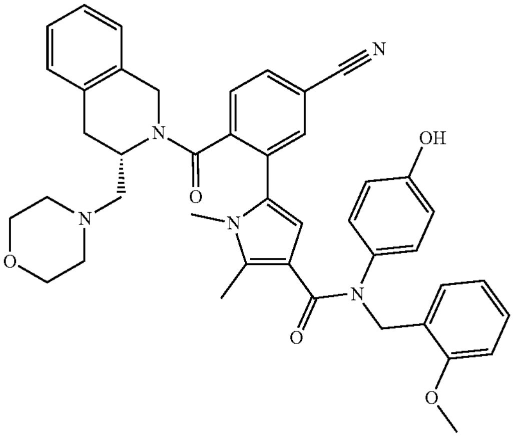 [SMILES: COc1ccccc1CN(C(=O)c1cc(-c2cc(C#N)ccc2C(=O)N2Cc3ccccc3C[C@H]2CN2CCOCC2)n(C)c1C)c1ccc(O)cc1] | 5-[5-cyano-2-[(3S)-3-(morpholinomethyl)-3,4-dihydro-1H-isoquinoline-2-carbonyl]phenyl]-N-(4-hydroxyphenyl)-N-[(2-methoxyphenyl)methyl]-1,2-dimethyl-pyrrole-3-carboxamide |
| 56 | 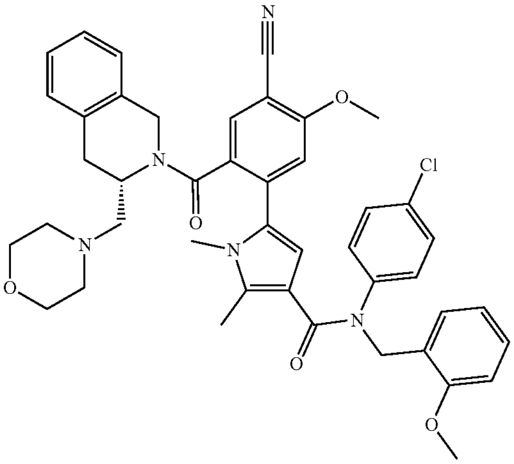 [SMILES: COc1cc(-c2cc(C(=O)N(Cc3ccccc3OC)c3ccc(Cl)cc3)c(C)n2C)c(C(=O)N2Cc3ccccc3C[C@H]2CN2CCOCC2)cc1C#N] | N-(4-chlorophenyl)-5-[4-cyano-5-methoxy-2-[(3S)-3-(morpholinomethyl)-3,4-dihydro-1H-isoquinoline-2-carbonyl]phenyl]-N-[(2-methoxyphenyl)methyl]-1,2-dimethyl-pyrrole-3-carboxamide |

TABLE 1-continued

| Examples of the Compound (I) | | |
|---|---|---|
| Compound # | Structure | IUPAC name |
| 57 | 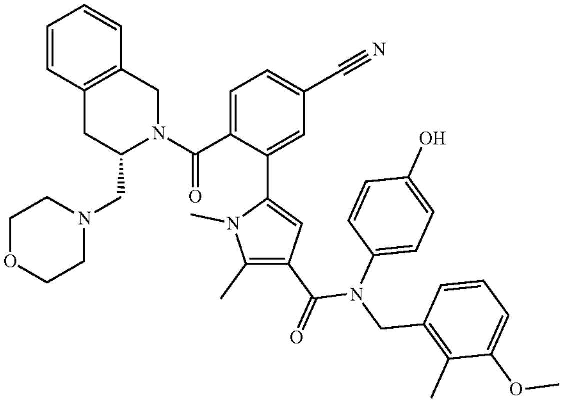 [SMILES: COc1cccc(CN(C(=O)c2cc(-c3cc(C#N)ccc3C(=O)N3Cc4ccccc4C[C@H]3CN3CCOCC3)n(C)c2C)c2ccc(O)cc2)c1C] | 5-[5-cyano-2-[(3S)-3-(morpholinomethyl)-3,4-dihydro-1H-isoquinoline-2-carbonyl]phenyl]-N-(4-hydroxyphenyl)-N-[(3-methoxy-2-methyl-phenyl)methyl]-1,2-dimethyl-pyrrole-3-carboxamide |
| 58 | 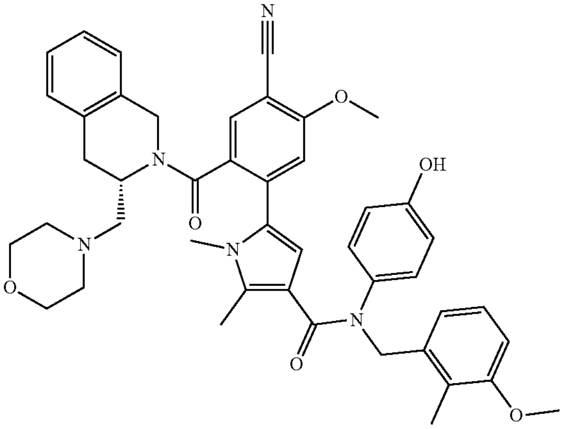 | 5-[4-cyano-5-methoxy-2-[(3S)-3-(morpholinomethyl)-3,4-dihydro-1H-isoquinoline-2-carbonyl]phenyl]-N-(4-hydroxyphenyl)-N-[(3-methoxy-2-methyl-phenyl)methyl]-1,2-dimethyl-pyrrole-3-carboxamide |
| 59 | 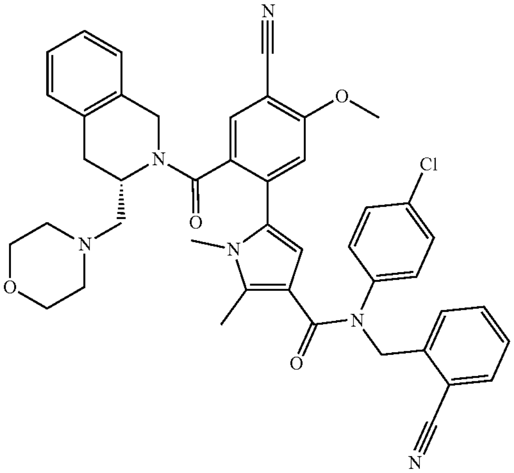 [SMILES: COc1cc(-c2cc(C(=O)N(Cc3ccccc3C#N)c3ccc(Cl)cc3)c(C)n2C)c(C(=O)N2Cc3ccccc3C[C@H]2CN2CCOCC2)cc1C#N] | N-(4-chlorophenyl)-5-[4-cyano-5-methoxy-2-[(3S)-3-(morpholinomethyl)-3,4-dihydro-1H-isoquinoline-2-carbonyl]phenyl]-N-[(2-cyanophenyl)methyl]-1,2-dimethyl-pyrrole-3-carboxamide |

TABLE 1-continued

| Examples of the Compound (I) | | |
|---|---|---|
| Compound # | Structure | IUPAC name |
| 60 | 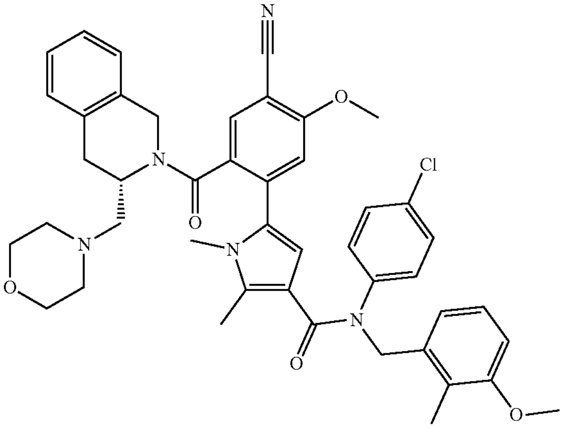 [SMILES: COc1cc(-c2cc(C(=O)N(Cc3cccc(OC)c3C)c3ccc(Cl)cc3)c(C)n2C)c(C(=O)N2Cc3ccccc3C[C@H]2CN2CCOCC2)cc1C#N] | N-(4-chlorophenyl)-5-[4-cyano-5-methoxy-2-[(3S)-3-(morpholinomethyl)-3,4-dihydro-1H-isoquinoline-2-carbonyl]phenyl]-N-[(3-methoxy-2-methyl-phenyl)methyl]-1,2-dimethyl-pyrrole-3-carboxamide |
| 61 | 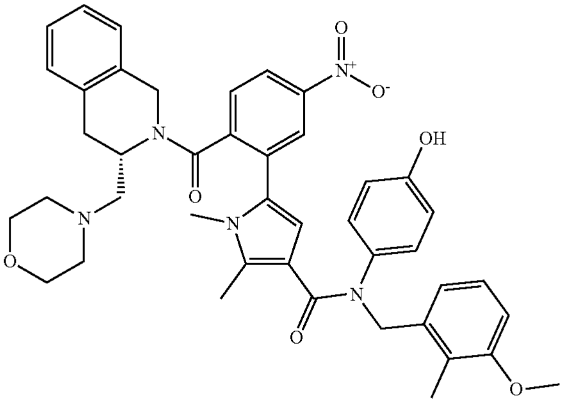 | N-(4-hydroxyphenyl)-N-[(3-methoxy-2-methyl-phenyl)methyl]-1,2-dimethyl-5-[2-[(3S)-3-(morpholinomethyl)-3,4-dihydro-1H-isoquinoline-2-carbonyl]-5-nitro-phenyl]pyrrole-3-carboxamide |
| 62 | 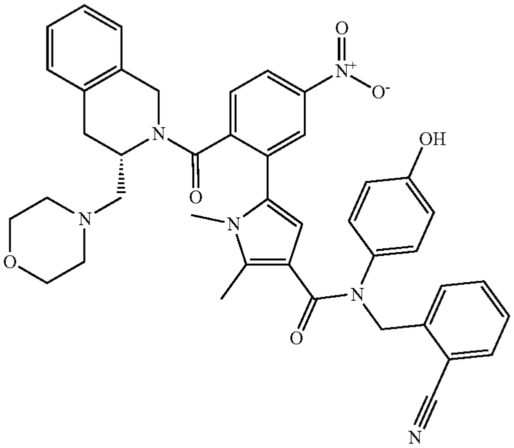 [SMILES: Cc1c(C(=O)N(Cc2ccccc2C#N)c2ccc(O)cc2)cc(-c2cc([N+](=O)[O-])ccc2C(=O)N2Cc3ccccc3C[C@H]2CN2CCOCC2)n1C] | N-[(2-cyanophenyl)methyl]-N-(4-hydroxyphenyl)-1,2-dimethyl-5-[2-[(3S)-3-(morpholinomethyl)-3,4-dihydro-1H-isoquinoline-2-carbonyl]-5-nitro-phenyl]pyrrole-3-carboxamide |

TABLE 1-continued

| Examples of the Compound (I) | | |
|---|---|---|
| Compound # | Structure | IUPAC name |
| 63 | 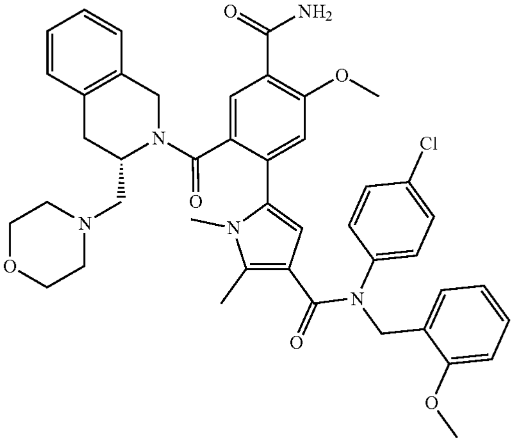 [SMILES: COc1ccccc1CN(C(=O)c1cc(-c2cc(OC)c(C(N)=O)cc2C(=O)N2Cc3ccccc3C[C@H]2CN2CCOCC2)n(C)c1C)c1ccc(Cl)cc1] | 5-[4-carbamoyl-5-methoxy-2-[(3S)-3-(morpholinomethyl)-3,4-dihydro-1H-isoquinoline-2-carbonyl]phenyl]-N-(4-chlorophenyl)-N-[(2-methoxyphenyl)methyl]-1,2-dimethyl-pyrrole-3-carboxamide |
| 64 | 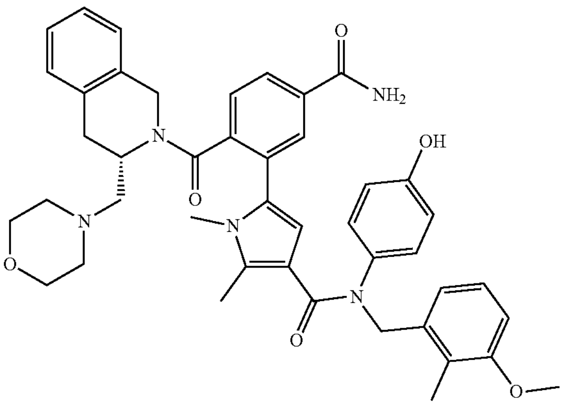 [SMILES: COc1cccc(CN(C(=O)c2cc(-c3cc(C(N)=O)ccc3C(=O)N3Cc4ccccc4C[C@H]3CN3CCOCC3)n(C)c2C)c2ccc(O)cc2)c1C] | 5-[5-carbamoyl-2-[(3S)-3-(morpholinomethyl)-3,4-dihydro-1H-isoquinoline-2-carbonyl]phenyl]-N-(4-hydroxyphenyl)-N-[(3-methoxy-2-methyl-phenyl)methyl]-1,2-dimethyl-pyrrole-3-carboxamide |
| 65 | 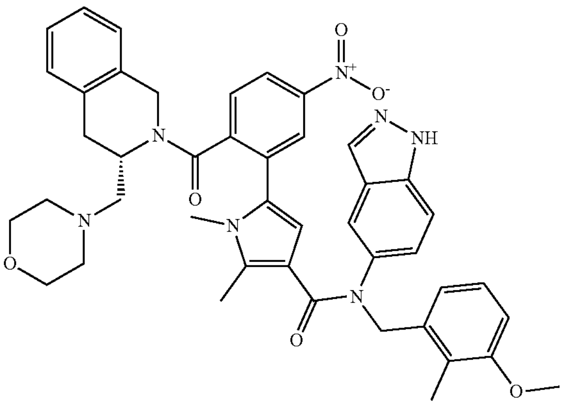 [SMILES: COc1cccc(CN(C(=O)c2cc(-c3cc([N+](=O)[O-])ccc3C(=O)N3Cc4ccccc4C[C@H]3CN3CCOCC3)n(C)c2C)c2ccc3[nH]ncc3c2)c1C] | N-(1H-indazol-5-yl)-N-[(3-methoxy-2-methyl-phenyl)methyl]-1,2-dimethyl-5-[2-[(3S)-3-(morpholinomethyl)-3,4-dihydro-1H-isoquinoline-2-carbonyl]-5-nitro-phenyl]pyrrole-3-carboxamide |

TABLE 1-continued

Examples of the Compound (I)

| Compound # | Structure | IUPAC name |
|---|---|---|
| 66 | 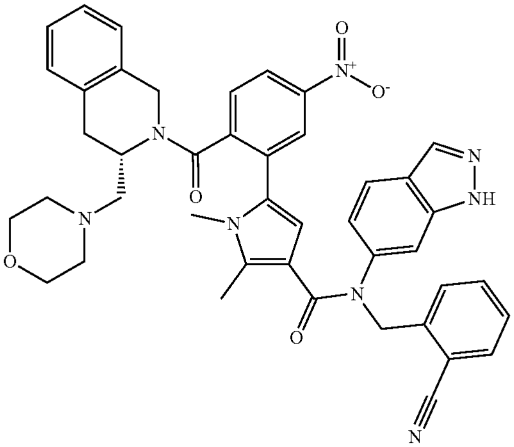 [SMILES: Cc1c(C(=O)N(Cc2ccccc2C#N)c2ccc3cn[nH]c3c2)cc(-c2cc([N+](=O)[O-])ccc2C(=O)N2Cc3ccccc3C[C@H]2CN2CCOCC2)n1C] | N-[(2-cyanophenyl)methyl]-N-(1H-indazol-6-yl)-1,2-dimethyl-5-[2-[(3S)-3-(morpholinomethyl)-3,4-dihydro-1H-isoquinoline-2-carbonyl]-5-nitro-phenyl]pyrrole-3-carboxamide |
| 67 | 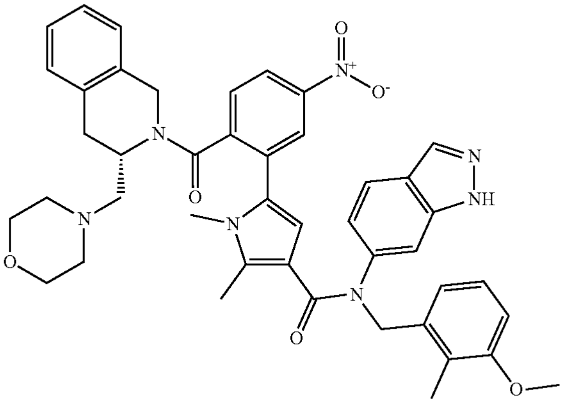 [SMILES: COc1cccc(CN(C(=O)c2cc(-c3cc([N+](=O)[O-])ccc3C(=O)N3Cc4ccccc4C[C@H]3CN3CCOCC3)n(C)c2C)c2ccc3cn[nH]c3c2)c1C] | N-(1H-indazol-6-yl)-N-[(3-methoxy-2-methyl-phenyl)methyl]-1,2-dimethyl-5-[2-[(3S)-3-(morpholinomethyl)-3,4-dihydro-1H-isoquinoline-2-carbonyl]-5-nitro-phenyl]pyrrole-3-carboxamide |
| 68 | 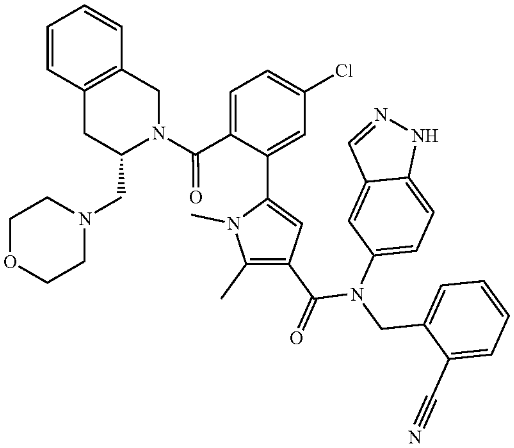 [SMILES: Cc1c(C(=O)N(Cc2ccccc2C#N)c2ccc3[nH]ncc3c2)cc(-c2cc(Cl)ccc2C(=O)N2Cc3ccccc3C[C@H]2CN2CCOCC2)n1C] | 5-[5-chloro-2-[(3S)-3-(morpholinomethyl)-3,4-dihydro-1H-isoquinoline-2-carbonyl]phenyl]-N-[(2-cyanophenyl)methyl]-N-(1H-indazol-5-yl)-1,2-dimethyl-pyrrole-3-carboxamide |

TABLE 1-continued

| Examples of the Compound (I) | | |
|---|---|---|
| Compound # | Structure | IUPAC name |
| 69 | 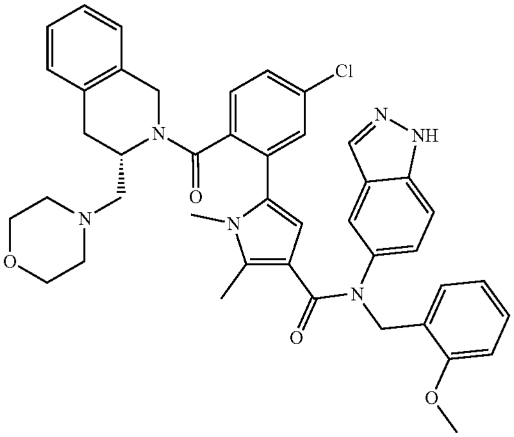 [SMILES: COc1ccccc1CN(C(=O)c1cc(-c2cc(Cl)ccc2C(=O)N2Cc3ccccc3C[C@H]2CN2CCOCC2)n(C)c1C)c1ccc2[nH]ncc2c1] | 5-[5-chloro-2-[(3S)-3-(morpholinomethyl)-3,4-dihydro-1H-isoquinoline-2-carbonyl]phenyl]-N-(1H-indazol-5-yl)-N-[(2-methoxyphenyl)methyl]-1,2-dimethyl-pyrrole-3-carboxamide |
| 70 | 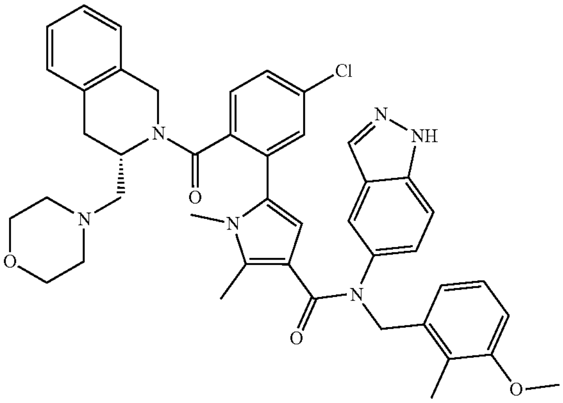 [SMILES: COc1cccc(CN(C(=O)c2cc(-c3cc(Cl)ccc3C(=O)N3Cc4ccccc4C[C@H]3CN3CCOCC3)n(C)c2C)c2ccc3[nH]ncc3c2)c1C] | 5-[5-chloro-2-[(3S)-3-(morpholinomethyl)-3,4-dihydro-1H-isoquinoline-2-carbonyl]phenyl]-N-(1H-indazol-5-yl)-N-[(3-methoxy-2-methyl-phenyl)methyl]-1,2-dimethyl-pyrrole-3-carboxamide |
| 71 | 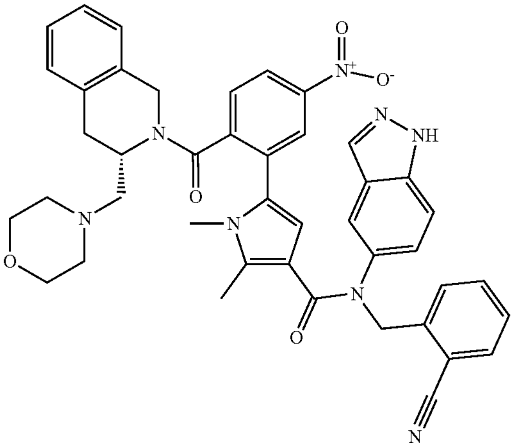 [SMILES: Cc1c(C(=O)N(Cc2ccccc2C#N)c2ccc3[nH]ncc3c2)cc(-c2cc([N+](=O)[O-])ccc2C(=O)N2Cc3ccccc3C[C@H]2CN2CCOCC2)n1C] | N-[(2-cyanophenyl)methyl]-N-(1H-indazol-5-yl)-1,2-dimethyl-5-[2-[(3S)-3-(morpholinomethyl)-3,4-dihydro-1H-isoquinoline-2-carbonyl]-5-nitro-phenyl]pyrrole-3-carboxamide |

TABLE 1-continued

| Examples of the Compound (I) | | |
| --- | --- | --- |
| Compound # | Structure | IUPAC name |
| 72 | 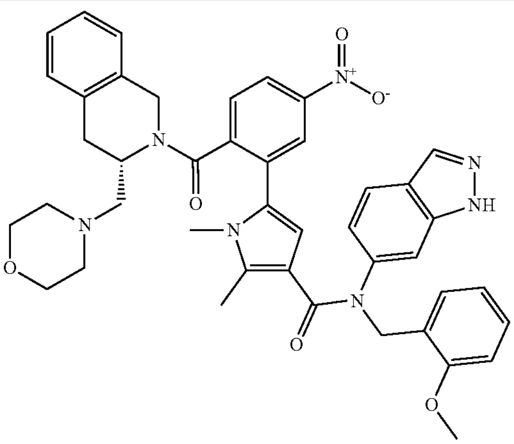 [SMILES: COc1ccccc1CN(C(=O)c1cc(-c2cc([N+](=O)[O-])ccc2C(=O)N2Cc3ccccc3C[C@H]2CN2CCOCC2)n(C)c1C)c1ccc2cn[nH]c2c1] | N-(1H-indazol-6-yl)-N-[(2-methoxyphenyl)methyl]-1,2-dimethyl-5-[2-[(3S)-3-(morpholinomethyl)-3,4-dihydro-1H-isoquinoline-2-carbonyl]-5-nitro-phenyl]pyrrole-3-carboxamide |
| 73 | 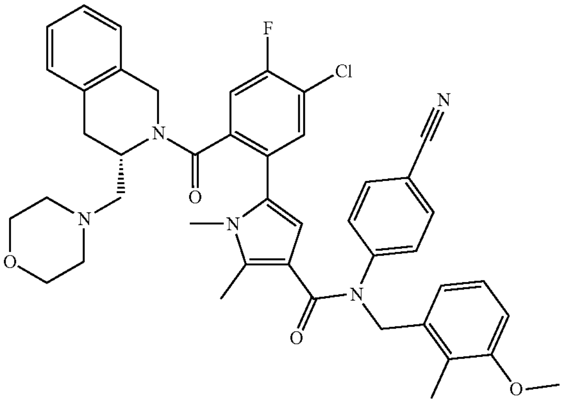 [SMILES: COc1cccc(CN(C(=O)c2cc(-c3cc(Cl)c(F)cc3C(=O)N3Cc4ccccc4C[C@H]3CN3CCOCC3)n(C)c2C)c2ccc(C#N)cc2)c1C] | 5-[5-chloro-4-fluoro-2-[(3S)-3-(morpholinomethyl)-3,4-dihydro-1H-isoquinoline-2-carbonyl]phenyl]-N-(4-cyanophenyl)-N-[(3-methoxy-2-methyl-phenyl)methyl]-1,2-dimethyl-pyrrole-3-carboxamide |
| 74 | 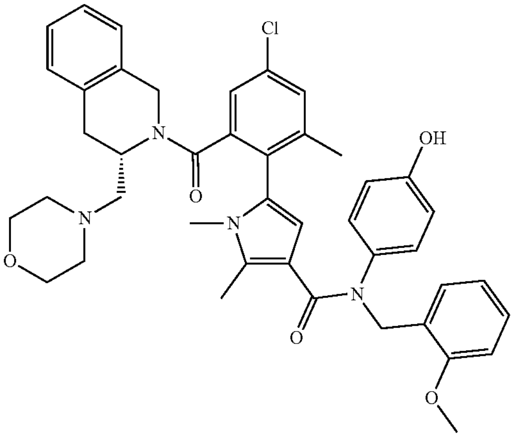 [SMILES: COc1ccccc1CN(C(=O)c1cc(-c2c(C)cc(Cl)cc2C(=O)N2Cc3ccccc3C[C@H]2CN2CCOCC2)n(C)c1C)c1ccc(O)cc1] | 5-[4-chloro-2-methyl-6-[(3S)-3-(morpholinomethyl)-3,4-dihydro-1H-isoquinoline-2-carbonyl]phenyl]-N-(4-hydroxyphenyl)-N-[(2-methoxyphenyl)methyl]-1,2-dimethyl-pyrrole-3-carboxamide |

In some embodiments, the compound is a pharmaceutically acceptable salt.

In some embodiments, the compound is a salt of hydrochloric acid.

It should be understood that all isomeric forms are included within the present invention, including mixtures thereof. If the compound contains a double bond, the substituent may be in the E- or Z-configuration. If the compound contains a disubstituted cycloalkyl, the cycloalkyl substituent may have a cis- or trans-configuration. All tautomeric forms are also intended to be included.

Compounds of the invention, and pharmaceutically acceptable salts, hydrates, solvates, stereoisomers and prodrugs thereof may exist in their tautomeric form (for example, as an amide or imino ether). All such tautomeric forms are contemplated herein as part of the present invention.

The compounds of the invention may contain asymmetric or chiral centers, and, therefore, exist in different stereoisomeric forms. It is intended that all stereoisomeric forms of the compounds of the invention as well as mixtures thereof, including racemic mixtures, form part of the present invention. In addition, the present invention embraces all geometric and positional isomers. For example, if a compound of the invention incorporates a double bond or a fused ring, both the cis- and trans-forms, as well as mixtures, are embraced within the scope of the invention. each compound herein disclosed includes all the enantiomers that conform to the general structure of the compound. The compounds may be in a racemic or enantiomerically pure form, or any other form in terms of stereochemistry. The assay results may reflect the data collected for the racemic form, the enantiomerically pure form, or any other form in terms of stereochemistry.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the invention may be atropisomers (e.g., substituted biaryls) and are considered as part of this invention. Enantiomers can also be separated by use of a chiral HPLC column.

It is also possible that the compounds of the invention may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula (I) incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester," "prodrug" and the like, is intended to equally apply to the salt, solvate, ester and prodrug of enantiomers, stereoisomers, rotamers, tautomers, positional isomers, racemates or prodrugs of the inventive compounds.

The compounds of Formula I may form salts which are also within the scope of this invention. Reference to a compound of the Formula herein is understood to include reference to salts thereof, unless otherwise indicated.

The present invention relates to compounds which are modulators of BCL-2 proteins. In one embodiment, the compounds of the present invention are inhibitors of BCL-2 proteins. In another embodiment, the BCL-2 proteins is Isoform 1. In another embodiment, the BCL-2 proteins is Isoform 2.

The invention is directed to compounds as described herein and pharmaceutically acceptable salts, hydrates, solvates, prodrugs, stereoisomers, or tautomers thereof, and pharmaceutical compositions comprising one or more compounds as described herein, or pharmaceutically acceptable salts, hydrates, solvates, prodrugs, stereoisomers, or tautomers thereof.

Method of Synthesizing the Compounds

The compounds of the present invention may be made by a variety of methods, including standard chemistry. Suitable synthetic routes are depicted in the Schemes given below.

The compounds of Formula (I) may be prepared by methods known in the art of organic synthesis as set forth in part by the following synthetic schemes. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of those skilled in the art will recognize if a stereocenter exists in the compounds of Formula (I). Accordingly, the present invention includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994)

The compounds described herein may be made from commercially available starting materials or synthesized using known organic, inorganic, and/or enzymatic processes.

Preparation of Compounds

The compounds of the present invention can be prepared in a number of ways well known to those skilled in the art of organic synthesis. By way of example, compounds of the present invention can be synthesized using the methods described below, together with synthetic methods known in the art of synthetic organic chemistry, or variations thereon as appreciated by those skilled in the art. Preferred methods include but are not limited to those methods described below. Compounds of the present invention can be synthesized by following the steps outlined in General Schemes 1 which comprise different sequences of assembling intermediates or compounds. Starting materials are either commercially available or made by known procedures in the reported literature or as illustrated below. Presented General Scheme 1 has only illustrative propose and it obvious to skilled in the art that it could be modified in case of preparation each specific compound of Formula (I).

General Scheme 1
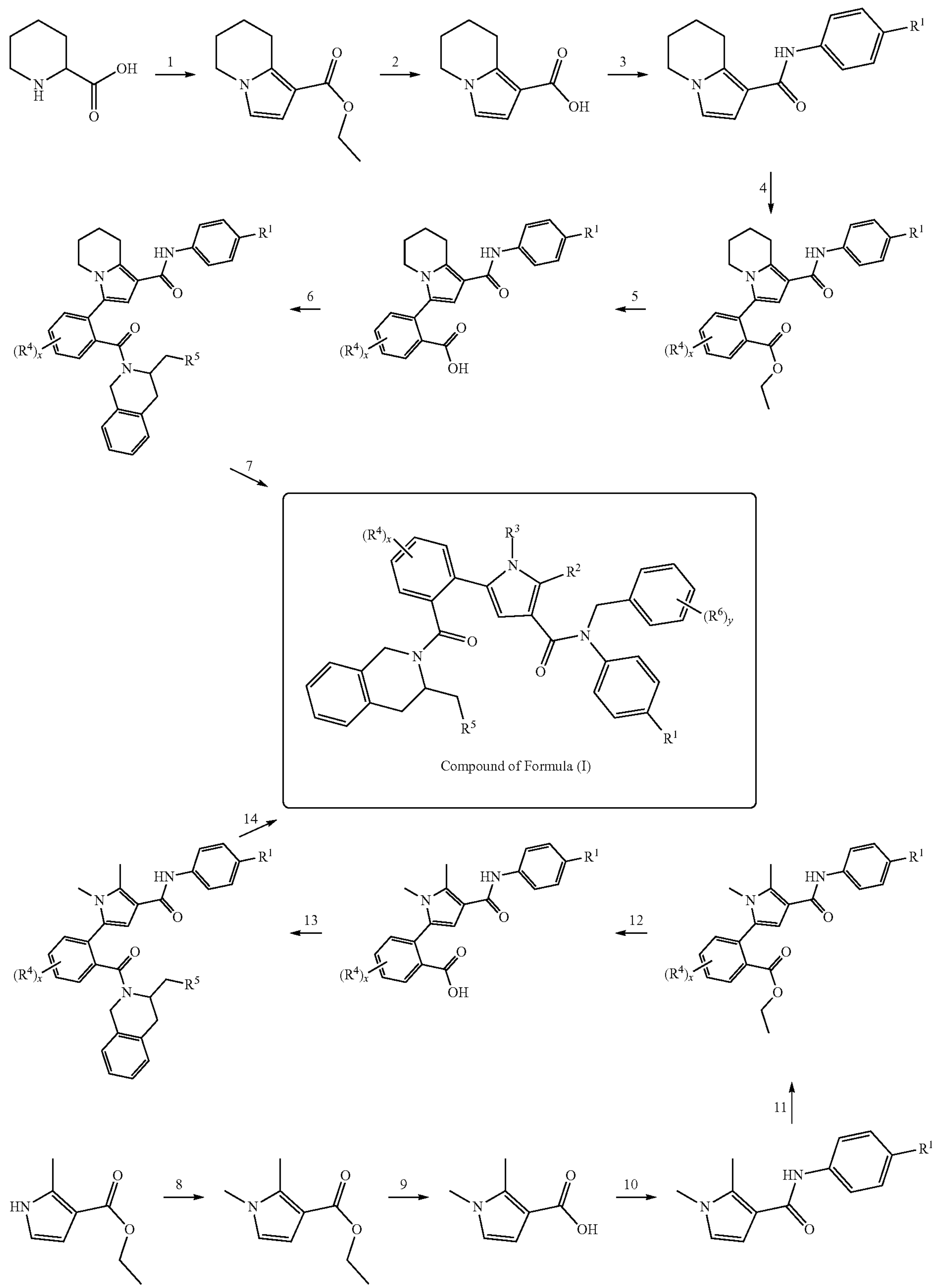
Compound of Formula (I)

The Table 2 presents the non-limiting illustrative conditions for the reactions described in the General Scheme 1.

TABLE 2

| Reaction step | Co-Reagent | Conditions |
| --- | --- | --- |
| 1 | Ethyl propiolate | Propionic anhydride, formic acid, 0° C.→ambient temperature→100° C., $Na_2CO_3$, 6 h |
| 2 | KOH | $H_2O$, MeOH, HCl, 50° C., 5 h |
| 3, 10 | 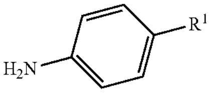 | $Et_3N$, TBTU, DCM, ambient temperature, overnight |
| 4, 11 | 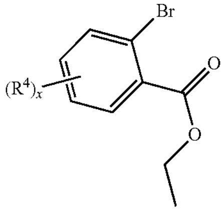 | $K_3PO_4$, pivalic acid, N,N-dimethylacetamide, $PdCl_2(PPh_3)_2$, 135° C., 45 min |
| 5, 9, 12 | NaOH | $H_2O$/EtOH, HCl, ambient temperature-50° C., 5-12 h |
| 6, 13 | 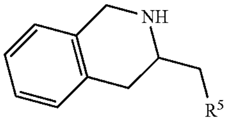 | DIPEA, TBTU, DMF, 60° C., overnight |
| 7, 14 | 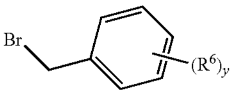 | tert-BuOK, tert-BuOH, 50-60° C., 1.5 h |
| 8 | $CH_3I$ | DMF, NaH, 0° C.→ambient temperature, 16 h |

It obvious to skilled in the art that for some transformation may be use appropriate protecting groups. Non-limiting list of protecting group useful in the preparation of compounds of Formula I includes: Acetyl (Ac), Benzoyl (Bz), Benzyl (Bn), Methoxymethyl ether (MOM), p-Methoxybenzyl ether (PMB), Pivaloyl (Piv), Trityl (Tr), Carbobenzyloxy group (Cbz), tert-Butyloxycarbonyl (Boc), Tosyl (Ts).

Such example of using protective group presented in the preparation of the compound 3:

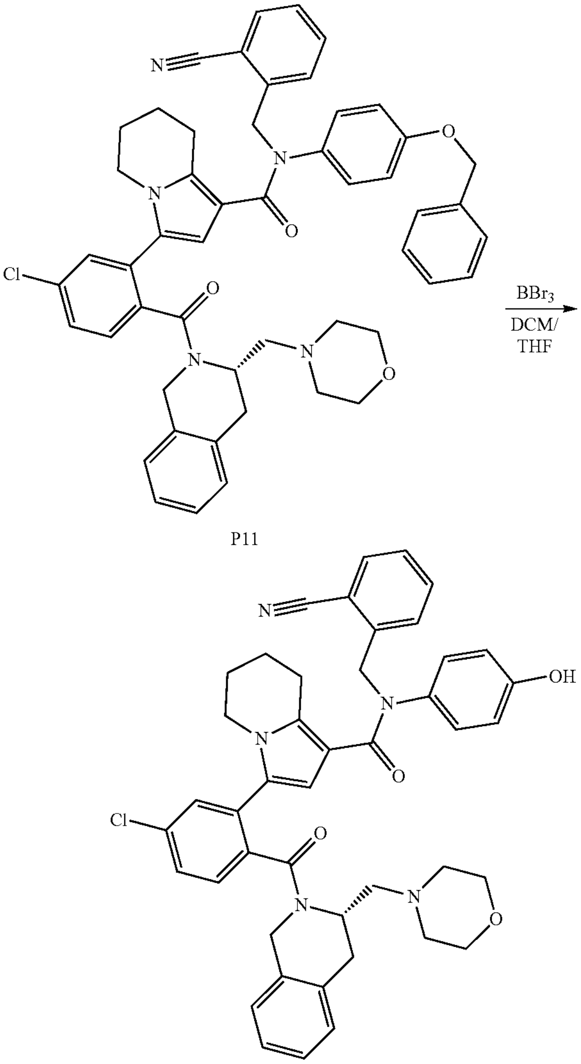

P11

3

Methods of Using the Disclosed Compounds

Another aspect of the invention relates to a method of treating a disease or disorder associated with modulation of BCL-2 proteins. The method comprises administering to a patient in need of a treatment for diseases or disorders associated with modulation of BCL-2 proteins an effective amount the compositions and compounds of Formula (I).

In another aspect, the present invention is directed to a method of inhibiting BCL-2 proteins. The method involves administering to a patient in need thereof an effective amount of a compound of Formula (I).

Another aspect of the present invention relates to a method of treating, preventing, inhibiting or eliminating a disease or disorder in a patient associated with the inhibition of BCL-2 proteins, the method comprising administering to a patient in need thereof an effective amount of a compound of Formula (I). In one embodiment, the disease may be, but not limited to, cancer and metastasis.

The present invention also relates to the use of an inhibitor of BCL-2 proteins for the preparation of a medicament used in the treatment, prevention, inhibition or elimination of a disease or condition mediated by BCL-2 proteins, wherein the medicament comprises a compound of Formula (I).

In another aspect, the present invention relates to a method for the manufacture of a medicament for treating, preventing, inhibiting, or eliminating a disease or condition mediated by BCL-2 proteins, wherein the medicament comprises a compound of Formula (I).

Another aspect of the present invention relates to a compound of Formula (I) for use in the manufacture of a medicament for treating a disease associated with inhibiting BCL-2 proteins.

In another aspect, the present invention relates to the use of a compound of Formula (I) in the treatment of a disease associated with inhibiting BCL-2 proteins.

Another aspect of the invention relates to a method of treating cancer. The method comprises administering to a patient in need thereof an effective amount of a compound of Formula (I).

Another aspect of the invention relates to a method of treating or preventing cancer. The method comprises administering to a patient in need thereof an effective amount of a compound of Formula (I).

In one embodiment, the present invention relates to the use of an inhibitor of BCL-2 proteins for the preparation of a medicament used in treatment, prevention, inhibition or elimination of a disease or disorder associated with cancer.

In another embodiment, the present invention relates to a compound of Formula (I) or a pharmaceutical composition comprising a compound of the present invention and a pharmaceutically acceptable carrier used for the treatment of cancers including, but not limited to, selected from bladder cancer, bone cancer, brain cancer, breast cancer, cardiac cancer, cervical cancer, colon cancer, colorectal cancer, esophageal cancer, fibrosarcoma, gastric cancer, gastrointestinal cancer, head, spine and neck cancer, Kaposi's sarcoma, kidney cancer, leukemia, liver cancer, lymphoma, melanoma, multiple myeloma, pancreatic cancer, penile cancer, testicular germ cell cancer, thymoma carcinoma, thymic carcinoma, lung cancer, ovarian cancer, and prostate cancer.

Another aspect of the invention is directed to pharmaceutical compositions comprising a compound of Formula (I) and a pharmaceutically acceptable carrier. The pharmaceutical acceptable carrier may further include an excipient, diluent, or surfactant.

In one embodiment, are provided methods of treating a disease or disorder associated with modulation of BCL-2 proteins including, cancer or cell proliferative disorder, comprising administering to a patient suffering from at least one of said diseases or disorder a compound of Formula (I).

One therapeutic use of the compounds or compositions of the present invention which inhibit BCL-2 proteins is to provide treatment to patients or subjects suffering from a cancer or cell proliferative disorder.

The disclosed compounds of the invention can be administered in effective amounts to treat or prevent a disorder and/or prevent the development thereof in subjects.

Administration of the disclosed compounds can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, the disclosed compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, and all using forms well known to those skilled in the pharmaceutical arts.

Illustrative pharmaceutical compositions are tablets and gelatin capsules comprising a Compound of the Invention and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, the disclosed compound is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

The disclosed compounds can be also formulated as a suppository that can be prepared from fatty emulsions or suspensions; using polyalkylene glycols such as propylene glycol, as the carrier.

The disclosed compounds can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564 which is hereby incorporated by reference in its entirety.

Disclosed compounds can also be delivered by the use of monoclonal antibodies as individual carriers to which the disclosed compounds are coupled. The disclosed compounds can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxidepolylysine substituted with palmitoyl residues. Furthermore, the Disclosed compounds can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In one embodiment, disclosed compounds are not covalently bound to a polymer, e.g., a polycarboxylic acid polymer, or a polyacrylate.

Parenteral injectable administration is generally used for subcutaneous, intramuscular or intravenous injections and infusions. Injectables can be prepared in conventional forms, either as liquid solutions or suspensions or solid forms suitable for dissolving in liquid prior to injection.

Another aspect of the invention is directed to pharmaceutical compositions comprising a compound of Formula (I) and a pharmaceutically acceptable carrier. The pharmaceutical acceptable carrier may further include an excipient, diluent, or surfactant. In some embodiments, the pharmaceutical composition can further comprise an additional pharmaceutically active agent.

Compositions can be prepared according to conventional mixing, granulating or coating methods, respectively, and the present pharmaceutical compositions can contain from about 0.1% to about 99%, from about 5% to about 90%, or from about 1% to about 20% of the disclosed compound by weight or volume.

The dosage regimen utilizing the disclosed compound is selected in accordance with a variety of factors including type, species, age, weight, sex and medical condition of the patient; the severity of the condition to be treated; the route of administration; the renal or hepatic function of the patient; and the particular disclosed compound employed. A physician or veterinarian of ordinary skill in the art can readily determine and prescribe the effective amount of the drug required to prevent, counter or arrest the progress of the condition.

Effective dosage amounts of the disclosed compounds, when used for the indicated effects, range from about 0.5 mg to about 5000 mg of the disclosed compound as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed compound, or, in a range of from one amount to another amount in the list of doses. In one embodiment, the compositions are in the form of a tablet that can be scored.

EXAMPLES

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Abbreviations used in the following examples and elsewhere herein are:

anh. anhydrous
atm atmosphere
br. broad
aq. aqueous
conc. concentrated
DCM dichloromethane
DIPEA N,N-diisopropylethylamine
DMEM Dulbecco's modified eagle medium
DMF N,N-dimethyl formamide
DMSO dimethyl sulfoxide
ESI electrospray ionization
EtOAc ethyl acetate
EtOH ethanol
h hour(s)
HPLC high pressure (or performance) liquid chromatography
LAH lithium aluminium hidride
LCMS liquid chromatography mass spectrometry
M molar
m multiplet
MHz megahertz
min minutes
NMR nuclear magnetic resonance
ppm parts per million
TBTU 2-(1H-Benzotriazole-1-yl)-1,1,3,3-tetramethylaminium tetrafluoroborate
THF tetrahydrofuran
TLC thin layer chromatography

Examples

Analysis and Purification
Preparative HPLC

Neutral conditions are as follows: YMC-Pack ODS-AQ 250×20 mm, S-10 μm, pore size 12 nm, gradient water-acetonitrile.

Standard, acidic, conditions are as follows: YMC-Pack ODS-AQ 250×20 mm, S-10 μm, pore size 12 nm, gradient A solution-B solution; A: 1000 ml water-226 μl trifluoroacetic acid, B: 1000 ml $CH_3CN$-226 μl trifluoroacetic acid.

Analytical Data, LCMS Conditions:

C18 column 100× 4.6 mm, 5.0 μm, pore size 100 Å, water-acetonitrile+0.1% trifluoroacetic acid, gradient 5 to 87% for 10 min

Synthesis of Intermediates

N-(4-Chlorophenyl)-5,6,7,8-tetrahydroindolizine-1-carboxamide (P3)

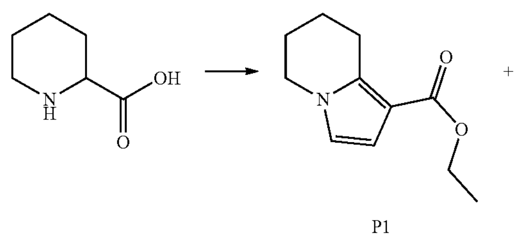

P1

-continued

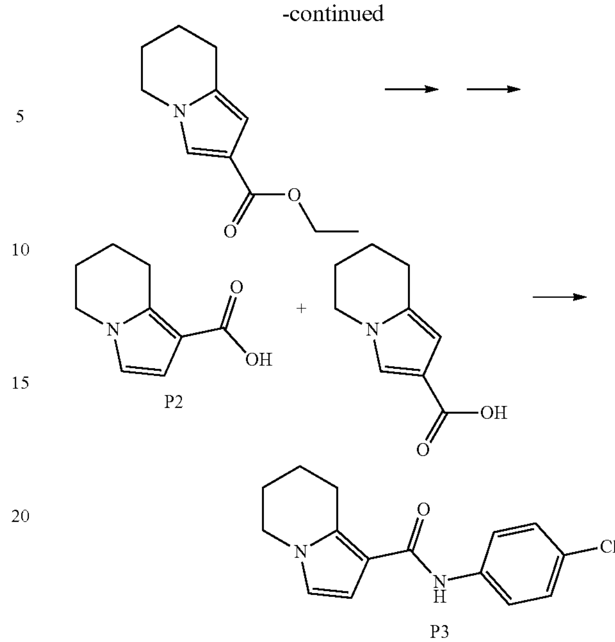

P2

P3

Preparation 1: Ethyl 5,6,7,8-tetrahydroindolizine-1-carboxylate P1 (as a mixture with ethyl 5,6,7,8-tetrahydroindolizine-2-carboxylate)

Propionic anhydride (90 mL) was added to a stirred solution of piperidine-2-carboxylic acid (21 g, 162 mmol) in formic acid (70 mL) maintaining temperature 0° C. The reaction mixture was allowed to warm to ambient temperature, then stirred for 3 h, and evaporated to dryness on rotary evaporator under reduced pressure. The residue was dissolved in propionic anhydride (150 mL), ethyl propiolate (78 g, 800 mmol) was added in one portion, and the resulted mixture was stirred and heated at 100° C. for 1 h. Volatiles were removed under reduced pressure, and the residue was stirred with 20% aq. solution of $Na_2CO_3$ for 2 h. The product was extracted with DCM (2×200 mL). Combined organic layers were washed with brine, dried over $Na_2SO_4$, and concentrated on rotary evaporator under reduced pressure to afford 28 g (89%) of crude product as a mixture of isomers ethyl 5,6,7,8-tetrahydroindolizine-1-carboxylate (P1) and ethyl 5,6,7,8-tetrahydroindolizine-2-carboxylates in ratio 5:1 that was used for the next step without further purification and separation.

Preparation 2:5,6,7,8-Tetrahydroindolizine-1-carboxylic acid P2 (as a mixture with 5,6,7,8-tetrahydroindolizine-2-carboxylic acid)

A solution of KOH (31.3 g, 560 mmol) in 100 mL of water was added to a solution of the obtained in the Preparation 1 mixture of esters (28 g, 140 mmol) in methanol (300 mL). The resulted mixture was stirred and heated at 50° C. for 5 h (TLC monitoring). Volatiles were removed under reduced pressure. The residue was diluted with water (400 mL) and acidified with conc. HCl to pH=2. Formed precipitate was filtered off, washed with water, and dried by lyophilization to afford 23 g (77%) of crude product as a mixture of isomers 5,6,7,8-tetrahydroindolizine-1-carboxylic acid (P2) and 5,6, 7,8-tetrahydroindolizine-2-carboxylic acid that was used for the next step without further purification and separation.

Preparation 3: N-(4-Chlorophenyl)-5,6,7,8-tetrahydroindolizine-1-carboxamide (P3)

A mixture of the crude product obtained in the Preparation 2 (5.0 g, 30.3 mmol), 4-chloroaniline (3.8 g, 30.3 mmol), Et3N(6.5 mL, 45.5 mmol), and TBTU (11.6 g, 36.3 mmol) in DCM (250 mL) was stirred at ambient temperature overnight and quenched with water (200 mL). The organic layer was separated, washed with brine, dried over $Na_2SO_4$, filtered, and the filtrate was evaporated under reduced pressure. The residue after evaporation was subjected to silica flash chromatography eluting with a mixture of EtOAc (0→10%) and $CCl_4$ to afford 800 mg (10%) of the title compound P3.

4-Chloro-2-(1-{[(4-chlorophenyl)amino]carbonyl}-5,6,7,8-tetrahydroindolizin-3-yl)benzoic acid (P5)

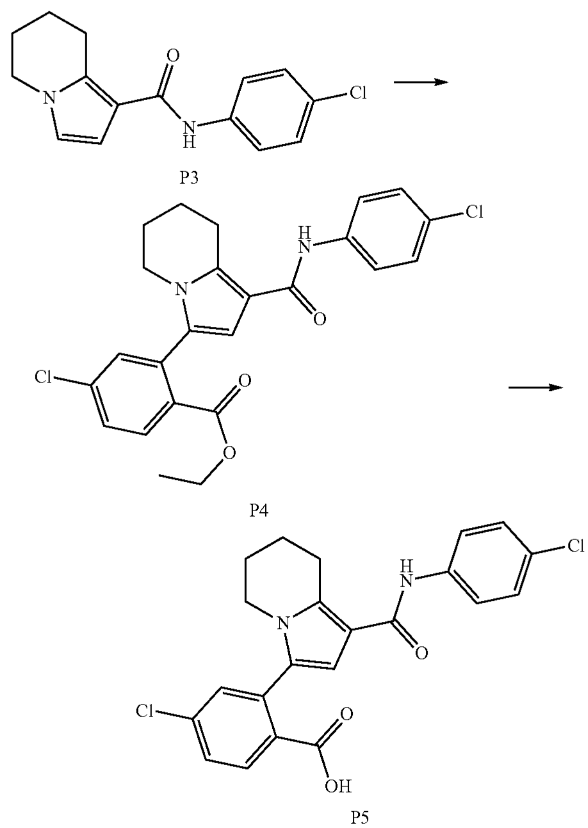

P3

P4

P5

Preparation 4: Ethyl 4-chloro-2-(1-{[(4-chlorophenyl)amino]carbonyl}-5,6,7,8-tetrahydroindolizin-3-yl)benzoate (P4)

A mixture of N-(4-chlorophenyl)-5,6,7,8-tetrahydroindolizine-1-carboxamide P3 (800 mg, 2.9 mmol), ethyl 6-bromo-1,3-benzodioxole-5-carboxylate (1.5 g, 5.8 mmol), $K_3PO_4$ (3.08 g, 14.5 mmol), and pivalic acid (0.09 g, 0.8 mmol) in N,N-dimethylacetamide (10 mL) was stirred at 135° C. for 15 min, then $PdCl_2(PPh_3)_2$ (0.4 g, 0.58 mmol) was added. The resulting mixture was stirred at 135° C. for 30 min. Upon completion of the reaction mixture was diluted with water (20 mL) and EtOAC (20 mL). The organic layer was separated, washed with brine, dried over sodium sulfate, filtered, and concentrated under reduced pressure. The residue was subjected to silica flash chromatography eluting with a mixture of EtOAc (0→20%) and DCM to afford 1.0 g (76%) of the title compound P4. ESI LCMS $[MH]^+$: 457, 458.

Preparation 5:4-Chloro-2-(1-{[(4-chlorophenyl)amino]carbonyl}-5,6,7,8-tetrahydroindolizin-3-yl)benzoic acid (P5)

A solution of ester P4 (1000 mg, 2.2 mmol) and NaOH (440 mg, 10.9 mol) in a mixture of EtOH (20 mL) and water (5 mL) was stirred at ambient temperature for 12 h. The volatiles were removed under reduced pressure, and water (20 mL) was added to the residue. The solution was acidified with 6M HCl to pH 1 and extracted with DCM (2×20 mL); the combined organic layers were dried over $Na_2SO_4$ and evaporated to dryness under reduced pressure to afford 900 mg (97%) of the title compound P5 that was pure enough to be used further for the next step. ESI LCMS $[MH]^+$: 429, 430.

3-(5-Chloro-2-{[(3S)-3-(morpholin-4-ylmethyl)-3,4-dihydroisoquinolin-2 (1H)-yl]carbonyl}phenyl)-N-(4-chlorophenyl)-5,6,7,8-tetrahydroindolizine-1-carboxamide (P6)

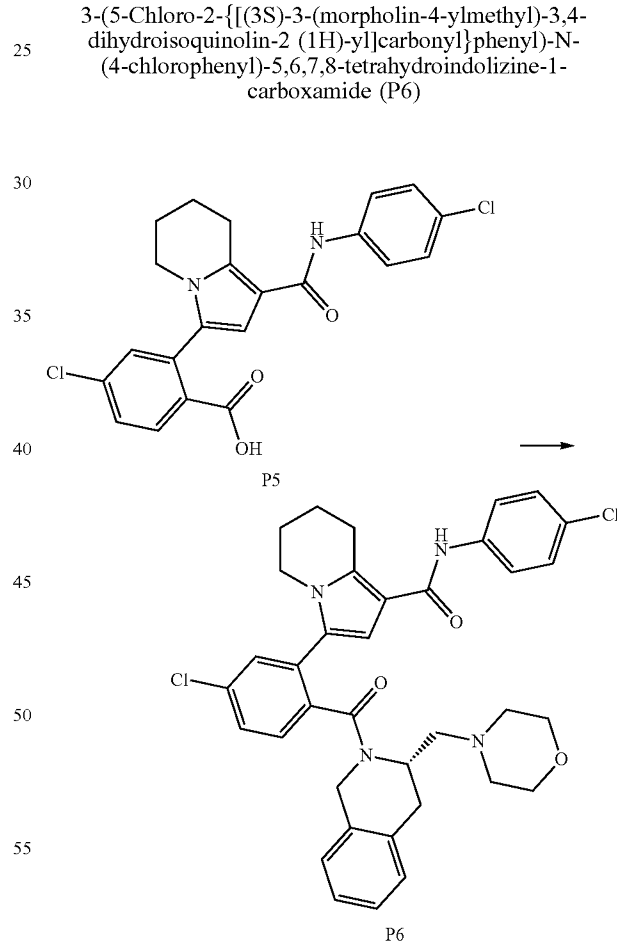

P5

P6

Preparation 6:3-(5-Chloro-2-{[(3S)-3-(morpholin-4-ylmethyl)-3,4-dihydroisoquinolin-2 (1H)-yl]carbonyl}phenyl)-N-(4-chlorophenyl)-5,6,7,8-tetrahydroindolizine-1-carboxamide (P6)

A mixture of 4-chloro-2-(1-{[(4-chlorophenyl)amino]carbonyl}-5,6,7,8-tetrahydroindolizin-3-yl)benzoic acid P5

(900 mg, 2.1 mmol), (3S)-3-(morpholin-4-ylmethyl)-1,2,3,4-tetrahydroisoquinoline (0.53 g, 2.3 mmol), DIPEA (0.55 mL, 3.1 mmol), and TBTU (0.8 g, 2.5 mmol), and DMF (10 mL) was stirred at 60° C. overnight. The reaction mixture was diluted with water (20 mL) and EtOAc (50 ml). The organic layer was separated, washed with brine, dried over $Na_2SO_4$, filtered, and concentrated under reduced pressure. The residue was subjected to silica flash chromatography eluting with a mixture of EtOAc (0→100%) and DCM to afford 880 mg (65%) of the title compound P6. ESI LCMS $[MH]^+$: 643, 645, 644.

N-[4-(benzyloxy)phenyl]-5,6,7,8-tetrahydroindolizine-1-carboxamide (P7)

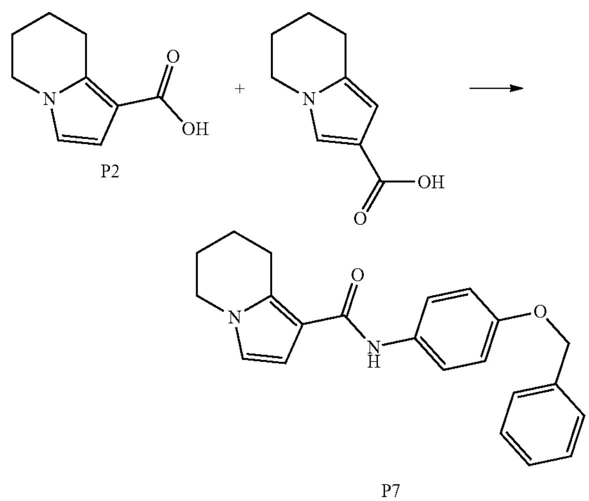

P2

P7

Preparation 7: N-[4-(benzyloxy)phenyl]-5,6,7,8-tetrahydroindolizine-1-carboxamide (P7)

A mixture of the crude product P2 (17.0 g, 100 mol), [4-(benzyloxy)phenyl]amine (18.0 g, 90 mmol), Et3N(22 mL, 150 mmol), and TBTU (36.0 g, 110 mmol) in DCM (250 mL) was stirred at ambient temperature overnight and quenched with water (200 mL). The organic layer was separated, washed with brine, dried over $Na_2SO_4$, filtered, and the filtrate was evaporated under reduced pressure. The residue after evaporation was subjected to silica flash chromatography eluting with a mixture of EtOAc (0→10%) and DCM to afford 14.5 g (41%) of the title compound P7. ESI LCMS $[MH]^+$: 347.

2-[1-({[4-(benzyloxy)phenyl]amino}carbonyl)-5,6,7,8-tetrahydroindolizin-3-yl]-4-chlorobenzoic acid (P9)

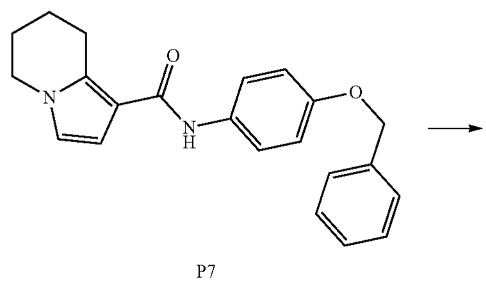

P7

-continued

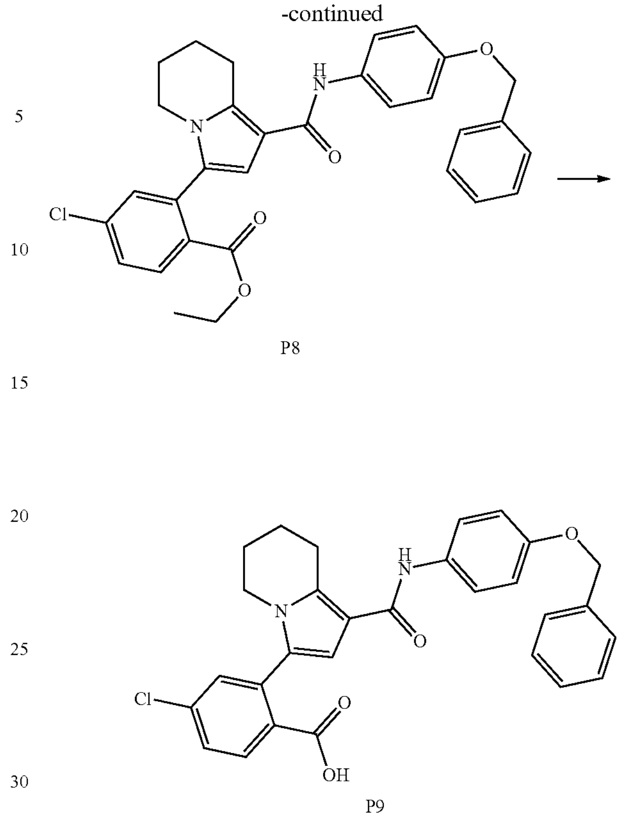

P8

P9

Preparation 8: Ethyl 2-[1-({[4-(benzyloxy)phenyl]amino}carbonyl)-5,6,7,8-tetrahydroindolizin-3-yl]-4-chlorobenzoate (P8)

A mixture of N-[4-(benzyloxy)phenyl]-5,6,7,8-tetrahydroindolizine-1-carboxamide (P7, 500 mg, 1.44 mmol), ethyl 2-bromo-4-chloro-benzoate (0.76 g, 2.9 mmol), $K_3PO_4$ (1.53 g, 7.2 mmol), pivalic acid (0.04 g, 0.4 mmol) in N,N-dimethylacetamide (10 mL) was stirred at 135° C. for 15 min, then $PdCl_2$ $(PPh_3)_2$ (0.2 g, 0.29 mmol) was added. The resulting mixture was stirred at 135° C. for 30 min. Upon completion of the reaction mixture was diluted with water (20 mL) and EtOAc (20 mL). The organic layer was separated, washed with brine, dried over sodium sulfate, filtered, and concentrated under reduced pressure. The residue was subjected to silica flash chromatography eluting with a mixture of EtOAc (0→20%) and DCM to afford 450 mg (59%) of the title compound P8. ESI LCMS $[MH]^+$: 529.

Preparation 9:2-[1-({[4-(Benzyloxy)phenyl]amino}carbonyl)-5,6,7,8-tetrahydroindolizin-3-yl]-4-chlorobenzoic acid (P9)

A solution of ester (P8, 450 mg, 0.85 mmol) and NaOH (170 mg, 4.2 mol) in a mixture of EtOH (20 mL) and water (5 mL) was stirred at ambient temperature for 12 h. The volatiles were removed under reduced pressure, and water (20 mL) was added to the residue. The solution was acidified with 6M HCl to pH 1 and extracted with DCM (2×20 mL); the combined organic layers were dried over $Na_2SO_4$ and evaporated to dryness under reduced pressure to afford 400 mg (94%) of the title compound P9 that was pure enough to be used further for the next step. ESI LCMS $[MH]^+$: 501.

N-[4-(benzyloxy)phenyl]-3-(5-chloro-2-{[(3S)-3-(morpholin-4-ylmethyl)-3,4-dihydroisoquinolin-2 (1H)-yl]carbonyl}phenyl)-5,6,7,8-tetrahydroindolizine-1-carboxamide

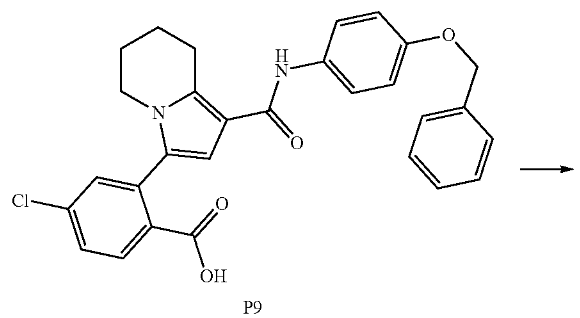

P9

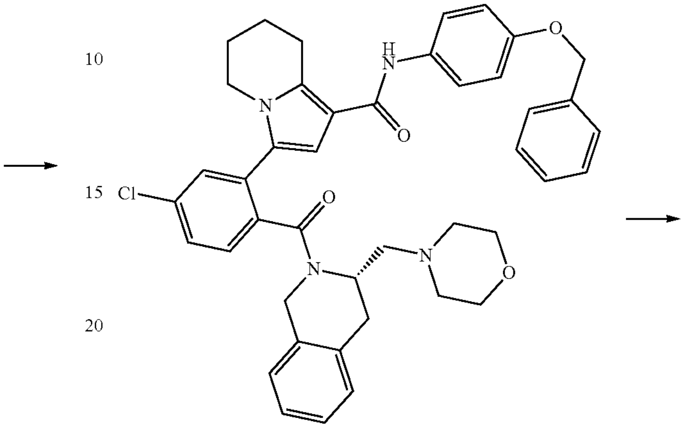

P10

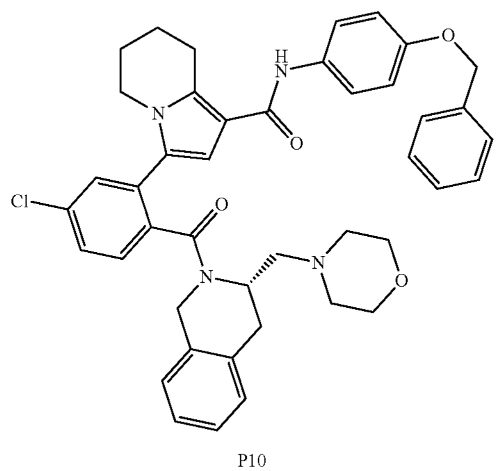

P10

Preparation 10: N-[4-(benzyloxy)phenyl]-3-(5-chloro-2-{[(3S)-3-(morpholin-4-ylmethyl)-3,4-dihydroisoquinolin-2 (1H)-yl]carbonyl}phenyl)-5,6,7,8-tetrahydroindolizine-1-carboxamide (P10)

A mixture of 2-[1-({[4-(benzyloxy)phenyl] amino}carbonyl)-5,6,7,8-tetrahydroindolizin-3-yl]-4-chlorobenzoic acid (P9, 450 mg, 0.8 mmol), (3S)-3-(morpholin-4-ylmethyl)-1,2,3,4-tetrahydroisoquinoline (0.23 g, 1.0 mmol), DIPEA (0.2 mL, 1.2 mmol), and TBTU (0.3 g, 0.9 mmol), and DMF (10 mL) was stirred at 60° C. overnight. The reaction mixture was diluted with water (20 mL) and EtOAc (50 ml). The organic layer was separated, washed with brine, dried over $Na_2SO_4$, filtered, and concentrated under reduced pressure. The residue was subjected to silica flash chromatography eluting with a mixture of EtOAc (0→100%) and DCM to afford 400 mg (70%) of the title compound P10. ESI LCMS $[MH]^+$: 715.

N-[4-(benzyloxy)phenyl]-3-(5-chloro-2-{[(3S)-3-(morpholin-4-ylmethyl)-3,4-dihydroisoquinolin-2 (1H)-yl]carbonyl}phenyl)-N-(2-cyanobenzyl)-5,6,7,8-tetrahydroindolizine-1-carboxamide (P11)

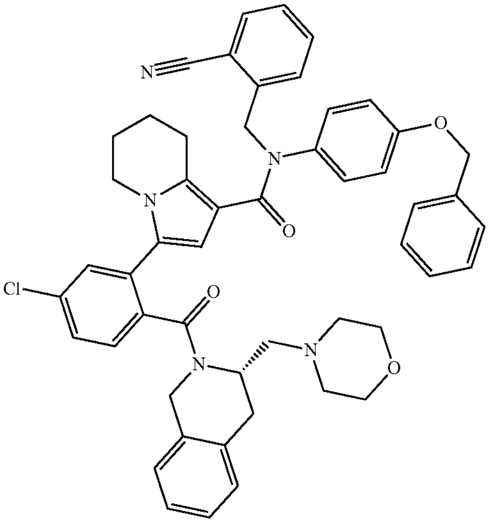

P11

Preparation 11. N-[4-(benzyloxy)phenyl]-3-(5-chloro-2-{[(3S)-3-(morpholin-4-ylmethyl)-3,4-dihydroisoquinolin-2 (1H)-yl]carbonyl}phenyl)-N-(2-cyanobenzyl)-5,6,7,8-tetrahydroindolizine-1-carboxamide (P11)

A mixture of N-[4-(benzyloxy)phenyl]-3-(5-chloro-2-{[(3S)-3-(morpholin-4-ylmethyl)-3,4-dihydroisoquinolin-2 (1H)-yl]carbonyl}phenyl)-5,6,7,8-tetrahydroindolizine-1-carboxamide (P10, 200 mg, 0.28 mmol), tert-BuOK (125 mg 1.1 mmol), and tert-BuOH (5 mL) was stirred at 50° C. for 30 min, then 2-(bromomethyl)benzonitrile (110 mg, 0.56 mmol) was added. The reaction mixture was stirred at 60° C. for 1 h and then partitioned between EtOAc and water. The organic layer was separated, washed with brine, dried over $Na_2SO_4$, filtered, and concentrated under reduced pressure. The residue was subjected to silica flash chromatography eluting with a mixture of EtOAc (0→100%) and DCM to afford 180 mg (78%) of the title compound P11. ESI LCMS $[MH]^+$: 830.

N-[4-(benzyloxy)phenyl]-3-(5-chloro-2-{[(3S)-3-(morpholin-4-ylmethyl)-3,4-dihydroisoquinolin-2 (1H)-yl]carbonyl}phenyl)-N-(3-methoxy-2-methylbenzyl)-5,6,7,8-tetrahydroindolizine-1-carboxamide (P12)

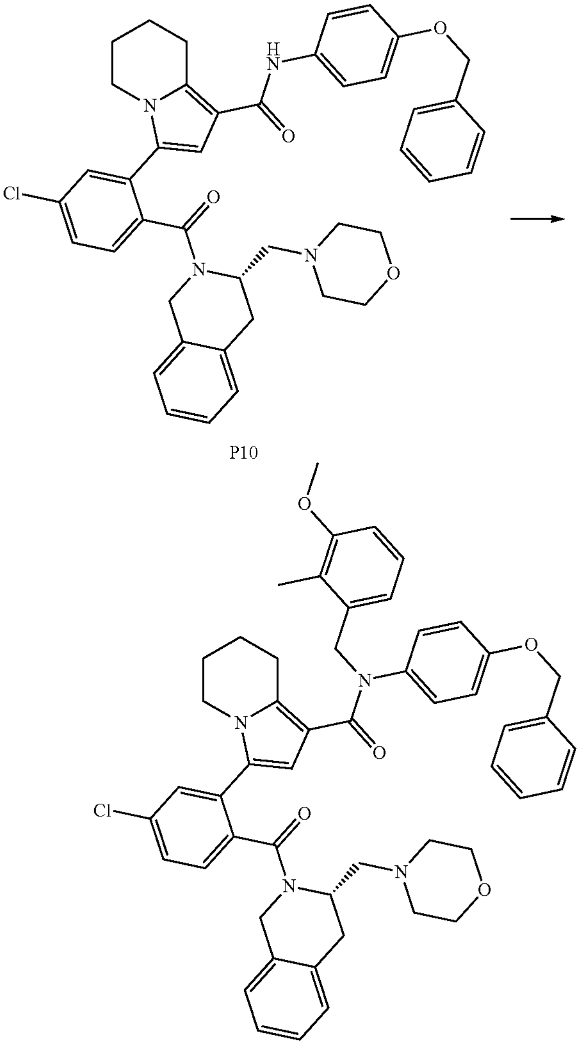

P10

P12

Preparation 12. N-[4-(benzyloxy)phenyl]-3-(5-chloro-2-{[(3S)-3-(morpholin-4-ylmethyl)-3,4-dihydroisoquinolin-2 (1H)-yl]carbonyl}phenyl)-N-(3-methoxy-2-methylbenzyl)-5,6,7,8-tetrahydroindolizine-1-carboxamide (P12)

A mixture of N-[4-(benzyloxy)phenyl]-3-(5-chloro-2-{[(3S)-3-(morpholin-4-ylmethyl)-3,4-dihydroisoquinolin-2 (1H)-yl]carbonyl}phenyl)-5,6,7,8-tetrahydroindolizine-1-carboxamide (P10, 200 mg, 0.28 mmol), tert-BuOK (125 mg 1.1 mmol), and tert-BuOH (5 mL) was stirred at 50° C. for 30 min, then 3-methoxy-2-methylbenzyl methanesulfonate (130 mg, 0.56 mmol) was added. The reaction mixture was stirred at 60° C. for 1 h and then partitioned between EtOAc and water. The organic layer was separated, washed with brine, dried over $Na_2SO_4$, filtered, and concentrated under reduced pressure. The residue was subjected to silica flash chromatography eluting with a mixture of EtOAc (0→100%) and DCM to afford 200 mg (84%) of the title compound P12. ESI LCMS $[MH]^+$: 849.

N-(4-Cyanophenyl)-1,2-dimethyl-1H-pyrrole-3-carboxamide (P13)

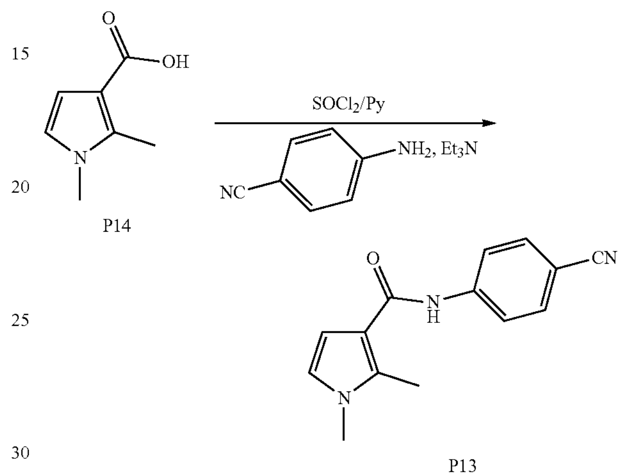

P14

P13

Preparation 13. N-(4-cyanophenyl)-1,2-dimethyl-1H-pyrrole-3-carboxamide (P13)

To a stirred solution of P14 (1.0 g, 7.2 mmol) in pyridine (5 mL) neat $SOCl_2$ (0.55 mL, 7.6 mmol) was added dropwise at 0° C. and the reaction mixture was stirred at 0° C. for 3 h. Then 4-aminobenzonitrile (0.85 g, 7.2 mmol) in DIPEA (1.4 mL, 7.96 mmol) was added dropwise, keeping the temperature at 0° C. After the reaction was warmed up to ambient temperature, then stirred at ambient temperature for 16 h. Volatiles were removed under reduced pressure. The residue was diluted with water and Et20. The organic layer separated, washed with water, brine, dried over dried over anhydrous sodium sulfate, filtered, and concentrated under reduced pressure. The residue was subjected to a silica gel flash chromatography eluting with a mixture of EtOAc (0→20%) and DCM to afford 850 mg (50%) of the title compound. $^1H$ NMR (400 MHZ, DMSO-$d_6$), δ:9.70 (br. s, 1H), 7.95 (d, 1H, J=8.7 Hz,), 7.7.73 (d, 1H, J=8.7 Hz), 6.73-6.64 (m, 1H), 3.54 (s, 3H), 2.47 (s, 3H). LCMS(ESI+) m/z 240 $[M+H]^+$.

N-[4-(Benzyloxy)phenyl]-1,2-dimethyl-1H-pyrrole-3-carboxamide (P15)

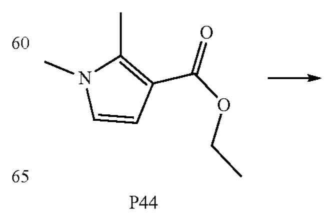

P44

-continued

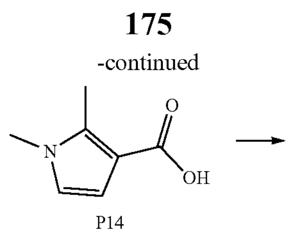

P14

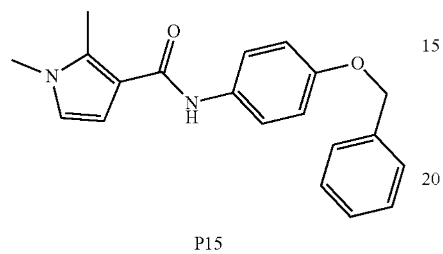

P15

Preparation 14. 1,2-Dimethyl-1H-pyrrole-3-carboxylic acid (P14)

A solution of NaOH (6.5 g, 163 mmol) in 10 mL of water was added to a solution of P13 in ethanol (50 mL). The resulted mixture was stirred and heated at 50° C. for 5 h (TLC monitoring). Volatiles were removed under reduced pressure. The residue was diluted with water (50 mL) and acidified with conc. HCl to pH=2. Formed precipitate was filtered off, washed with water, and dried by lyophilization to afford 4.0 g of P14 (88%). ESI+ LCMS $[MH]^+$: 140.

Preparation 15. N-[4-(benzyloxy)phenyl]-1,2-dimethyl-1H-pyrrole-3-carboxamide (P15)

A mixture of P14 (2.0 g, 14.4 mmol), [4-(benzyloxy) phenyl]amine (3.1 g, 15.58 mmol), Et3N(3.1 mL, 21.5 mmol), and TBTU (5.5 g, 17.2 mmol) in DCM (250 mL) was stirred at ambient temperature overnight and quenched with water (20 mL). The organic layer was separated, washed with brine, dried over $Na_2SO_4$, filtered, and the filtrate was evaporated under reduced pressure. The residue after evaporation was subjected to silica flash chromatography eluting with a mixture of EtOAc (0→20%) and DCM to afford 2.5 g (54%) of P15. ESI+ LCMS $[MH]^+$: 321. 2-[4-({[4-(Benzyloxy)phenyl]amino}carbonyl)-1,5-dimethyl-1H-pyrrol-2-yl]-4-chlorobenzoic acid (P17)

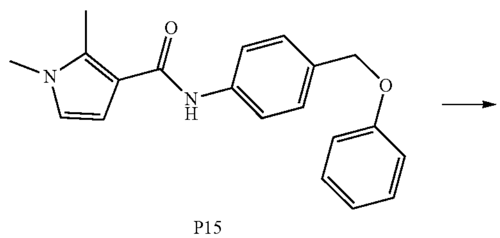

P15

-continued

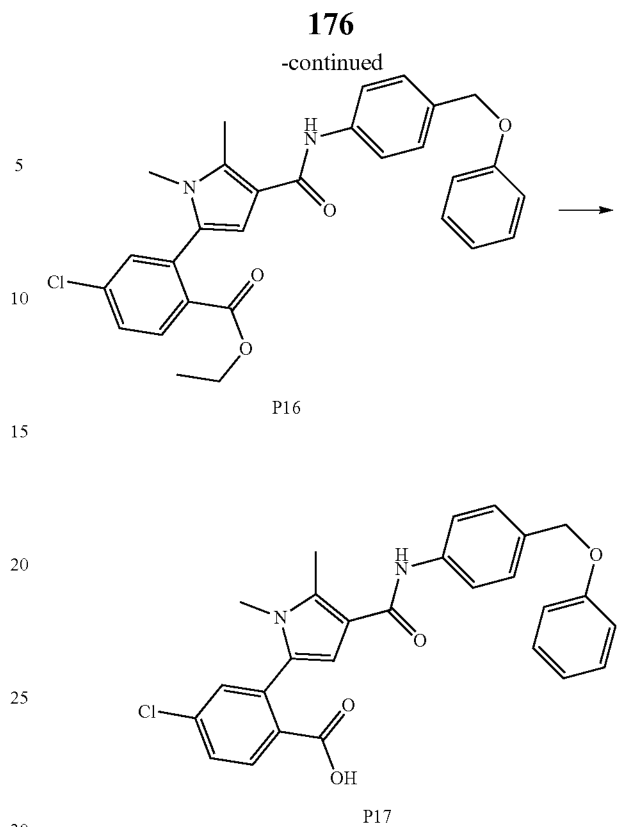

P16

P17

Preparation 16. Ethyl 2-[4-({[4-(benzyloxy)phenyl] amino}carbonyl)-1,5-dimethyl-1H-pyrrol-2-yl]-4-chlorobenzoate (P16)

A mixture of N-[4-(benzyloxy)phenyl]-1,2-dimethyl-1H-pyrrole-3-carboxamide (P15, 1.0 g, 3.1 mmol), ethyl 6-bromo-1,3-benzodioxole-5-carboxylate (1.0 g, 3.1 mmol), $K_3PO_4$ (3.3 g, 15.6 mmol), pivalic acid (0.1 g, 0.9 mmol) in N,N-dimethylacetamide (10 mL) was stirred at 135° C. for 15 min, then $PdCl_2(PPh_3)_2$ (0.44 g, 0.6 mmol) was added. The resulting mixture was stirred at 135° C. for 30 min. Upon completion of the reaction mixture was diluted with water (20 mL) and EtOAc (20 mL). The organic layer was separated, washed with brine, dried over sodium sulfate, filtered, and concentrated under reduced pressure. The residue was subjected to silica flash chromatography eluting with a mixture of EtOAc (0→20%) and DCM to afford 1.1 g (70%) of P16. ESI+ LCMS $[MH]^+$: 503.

Preparation 17. 2-[4-({[4-(Benzyloxy)phenyl] amino}carbonyl)-1,5-dimethyl-1H-pyrrol-2-yl]-4-chlorobenzoic acid (P17)

A solution of P16 (1100 mg, 2.2 mmol) and NaOH (440 mg, 10.9 mol) in a mixture of EtOH (20 mL) and water (5 mL) was stirred at ambient temperature for 12 h. The volatiles were removed under reduced pressure, and water (20 mL) was added to the residue. The solution was acidified with 6M HCl to pH 1 and extracted with DCM (2×20 mL); the combined organic layers were dried over $Na_2SO_4$ and evaporated to dryness under reduced pressure to afford 900 mg (90%) of P17 that was pure enough to be used further for the next step. ESI+ LCMS $[MH]^+$: 475.

N-[4-(benzyloxy)phenyl]-5-(5-chloro-2-{[(3S)-3-(morpholin-4-ylmethyl)-3,4-dihydroisoquinolin-2 (1H)-yl]carbonyl}phenyl)-1,2-dimethyl-1H-pyrrole-3-carboxamide N-[4-(benzyloxy)phenyl]-5-(5-chloro-2-{[(3S)-3-(morpholin-4-ylmethyl)-3,4-dihydroisoquinolin-2 (1H)-yl]carbonyl}phenyl)-N-(2-cyanobenzyl)-1,2-dimethyl-1H-pyrrole-3-carboxamide (P19)

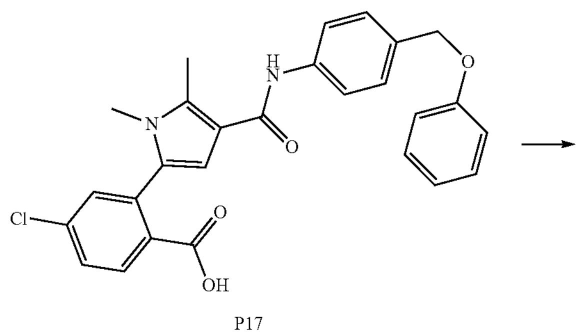

P17

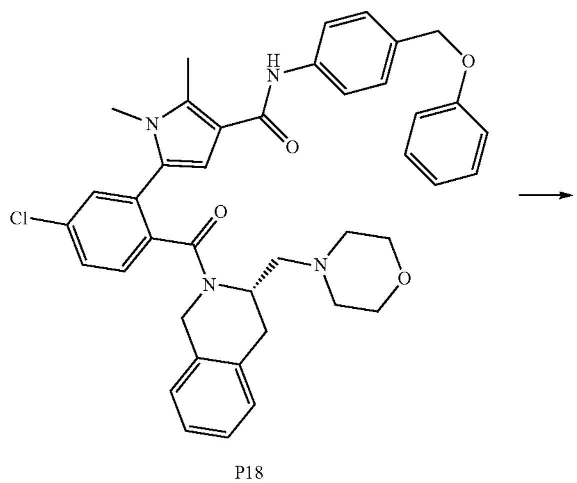

P18

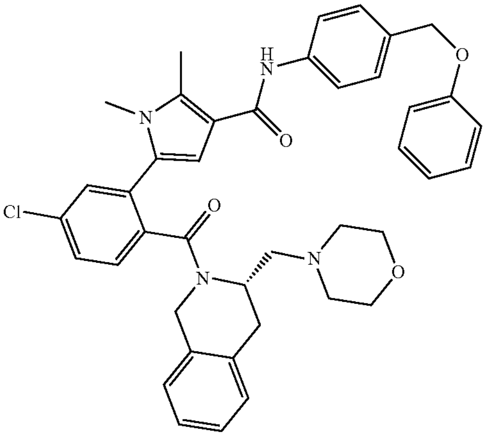

P18

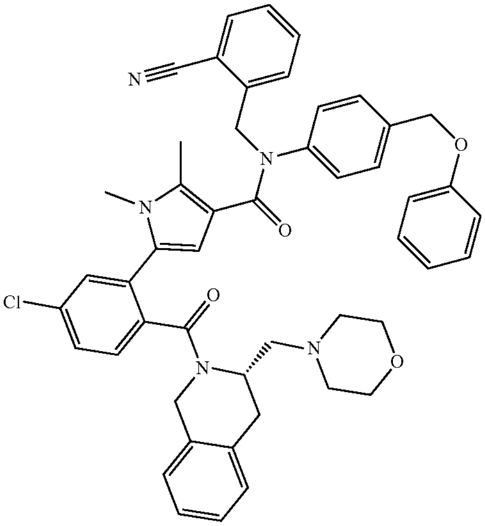

P19

Preparation 18. N-[4-(benzyloxy)phenyl]-5-(5-chloro-2-{[(3S)-3-(morpholin-4-ylmethyl)-3,4-dihydroisoquinolin-2 (1H)-yl]carbonyl}phenyl)-1,2-dimethyl-1H-pyrrole-3-carboxamide (P18)

A mixture of 2-[4-({[4-(benzyloxy)phenyl] amino}carbonyl)-1,5-dimethyl-1H-pyrrol-2-yl]-4-chlorobenzoic acid (P17, 900 mg, 1.9 mmol), (3S)-3-(morpholin-4-ylmethyl)-1,2,3,4-tetrahydroisoquinoline (0.48 g, 2.1 mmol), DIPEA (0.5 mL, 2.8 mmol), TBTU (0.73 g, 2.3 mmol), and DMF (10 mL) was stirred at 60° C. overnight. The reaction mixture was diluted with water (20 mL) and EtOAc (50 ml). The organic layer was separated, washed with brine, dried over $Na_2SO_4$, filtered, and concentrated under reduced pressure. The residue was subjected to silica flash chromatography eluting with a mixture of EtOAc (0→100%) and DCM to afford 700 mg (54%) of P18. ESI LCMS $[MH]^+$: 689.

Preparation 19. N-[4-(benzyloxy)phenyl]-5-(5-chloro-2-{[(3S)-3-(morpholin-4-ylmethyl)-3,4-dihydroisoquinolin-2 (1H)-yl]carbonyl}phenyl)-N-(2-cyanobenzyl)-1,2-dimethyl-1H-pyrrole-3-carboxamide (P19)

A mixture of N-[4-(benzyloxy)phenyl]-5-(5-chloro-2-{[(3S)-3-(morpholin-4-ylmethyl)-3,4-dihydroisoquinolin-2 (1H)-yl]carbonyl}phenyl)-1,2-dimethyl-1H-pyrrole-3-carboxamide (P18, 150 mg, 0.2 mmol), tert-BuOK (92 mg 0.8 mmol), and tert-BuOH (5 mL) was stirred at 50° C. for 30 min, then 2-(bromomethyl)benzonitrile (85 mg, 0.4 mmol) was added. The reaction mixture was stirred at 60° C. for 1 h and then partitioned between EtOAc and water. The organic layer was separated, washed with brine, dried over $Na_2SO_4$, filtered, and concentrated under reduced pressure. The residue was subjected to silica flash chromatography eluting with a mixture of EtOAc (0→100%) and DCM to afford 100 mg (57%) of P19. ESI LCMS $[MH]^+$: 804. N-[4-(benzyloxy)phenyl]-5-(5-chloro-2-{[(3S)-3-(morpholin-4-ylmethyl)-3,4-dihydroisoquinolin-2 (1H)-yl]carbonyl}phenyl)-N-(3-methoxy-2-methylbenzyl)-1,2-dimethyl-1H-pyrrole-3-carboxamide (P20)

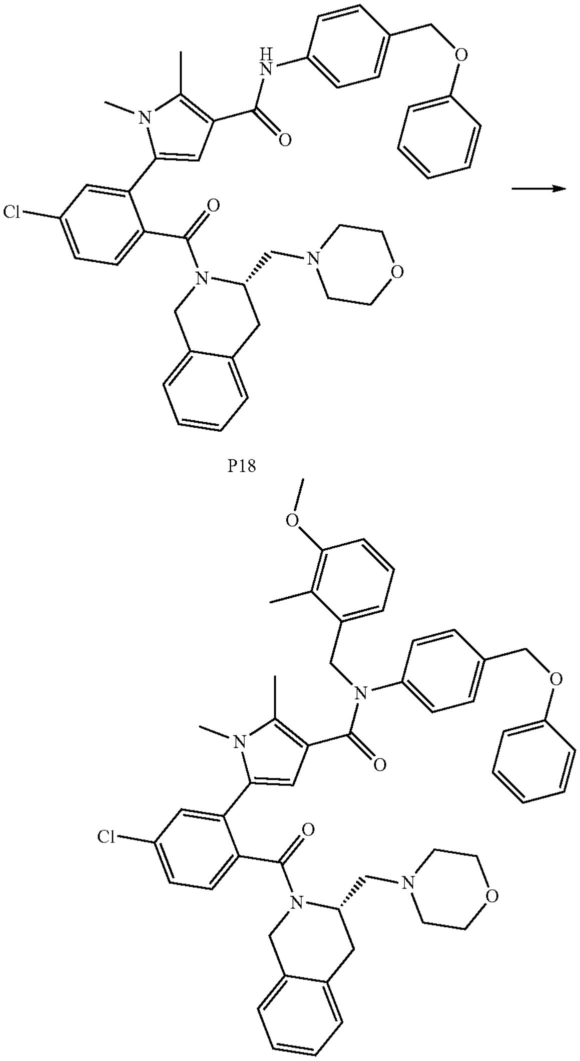

P18

P20

Preparation 20. N-[4-(benzyloxy)phenyl]-5-(5-chloro-2-{[(3S)-3-(morpholin-4-ylmethyl)-3,4-dihydroisoquinolin-2 (1H)-yl]carbonyl}phenyl)-N-(3-methoxy-2-methylbenzyl)-1,2-dimethyl-1H-pyrrole-3-carboxamide (P20)

A mixture of N-[4-(benzyloxy)phenyl]-5-(5-chloro-2-{[(3S)-3-(morpholin-4-ylmethyl)-3,4-dihydroisoquinolin-2 (1H)-yl]carbonyl}phenyl)-1,2-dimethyl-1H-pyrrole-3-carboxamide (P18, 150 mg, 0.2 mmol), tert-BuOK (92 mg 0.8 mmol), and tert-BuOH (5 mL) was stirred at 50° C. for 30 min, then 3-methoxy-2-methylbenzyl methanesulfonate (98 mg, 0.4 mmol) was added. The reaction mixture was stirred at 60° C. for 12 h and then partitioned between EtOAc and water. The organic layer was separated, washed with brine, dried over $Na_2SO_4$, filtered, and concentrated under reduced pressure. The residue was subjected to silica flash chromatography eluting with a mixture of EtOAc (0→100%) and DCM to afford 120 mg (67%) of P20.

4-chloro-N-(3-methoxy-2-methylbenzyl) aniline (P23)

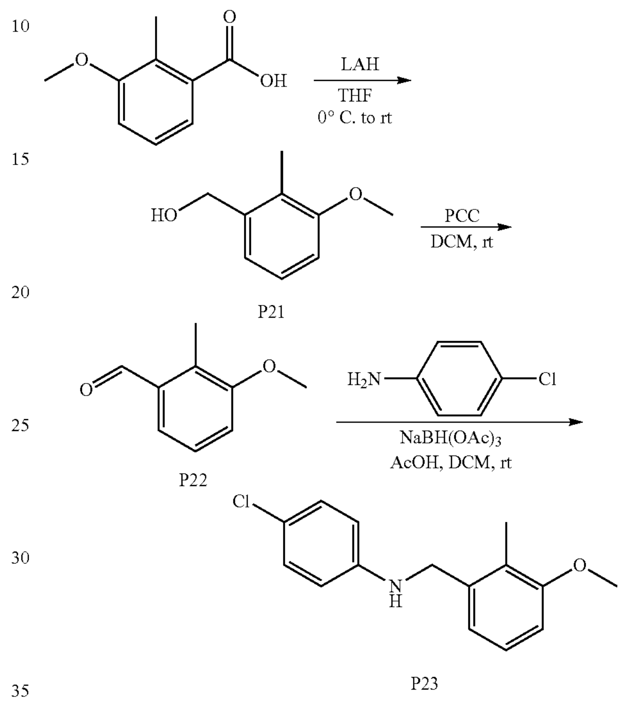

P21

P22

P23

Preparation 21. 1-(chloromethyl)-3-methoxy-2-methylbenzene (P21)

To a solution of 3-methoxy-2-methylbenzoic acid (10.0 g, 60.2 mmol, 1 eq) in anh. THF (200 mL) was added lithium aluminum hydride (72.0 mL, 72.2 mmol, 1.2 eq, 1 M solution in THF) at 0° C. After the solution was stirred at rt for 16 h, the mixture was diluted with water and NaOH (aq) (15%, 3 mL), and filtered through a pad of celite. The filtrate was concentrated under reduced pressure to give P21 (9.0 g, 98% yield) as a white solid which was used in the next step without further purification. $^1H$ NMR (400 MHZ, $CDCl_3$), δ: 7.18 (dd, J=8.2, 7.8 Hz, 1H), 6.98 (d, J=7.8 Hz, 1H), 6.83 (d, J=8.2 Hz, 1H), 4.68 (s, 2H), 3.84 (s, 3H), 2.22 (s, 3H).

Preparation 22. 3-Methoxy-2-methylbenzaldehyde (P22)

To a solution of pyridinium chlorochromate (10.6 g, 49.3 mmol, 1.5 eq) in DCM (83 mL) was added the solution of P21 (5.0 g, 32.9 mmol, 1.0 eq) in DCM (83 mL). After the solution was stirred at rt for 6 h, the mixture was diluted with diethyl ether (80 mL), filtered through a pad of celite, and washed with diethyl ether. The filtrate was concentrated under reduced pressure. The residue was purified by silica gel column chromatography (0-100% EtOAc in n-hexane) to give P22 (3.6 g, 72% yield) as a yellow solid. $^1H$ NMR (400 MHZ, $CDCl_3$), δ: 10.32 (s, 1H), 7.42 (d, J=7.8 Hz, 1H), 7.30 (dd, J=8.0, 7.8 Hz, 1H), 7.07 (d, J=8.0 Hz, 1H), 3.87 (s, 3H), 2.54 (s, 3H).

Preparation 23. 4-Chloro-N-(3-methoxy-2-methylbenzyl) aniline (P23)

To a solution of P22 (292 mg, 1.90 mmol, 1.0 eq), 4-chloroaniline (247 mg, 1.90 mmol, 1.0 eq) and AcOH (11 mg, 0.18 mmol, 0.1 eq) in DCM (13 mL) was added NaBH(OAc) 3 (990 mg, 4.67 mmol, 2.5 eq) at rt and it was stirred at rt for 16 h. The mixture was treated with $NaHCO_3$ $_{(aq)}$ and extracted with EtOAc. The combined organic layers were dried over $Na_2SO_4$, filtered, and concentrated. The residue was purified by silica gel column (0-50% EtOAc in n-hexane) to give P23 (350 mg, 70% yield) as a yellow solid. $^1$H NMR (400 MHZ, $CDCl_3$), δ: 7.18-7.09 (m, 3H), 6.93 (d, J=7.8 Hz, 1H), 6.82 (d, J=8.4 Hz, 1H), 6.54 (d, J=8.8 Hz, 2H), 4.24 (d, J=5.2 Hz, 2H), 3.84 (s, 4H, OMe and NH), 2.22 (s, 3H); LRMS(ESI+) m/z: 262.0 $[M+H]^+$. (S)-5-(4-(difluoromethoxy)-5-fluoro-2-(3-(morpholinomethyl)-1,2,3,4-tetrahydroisoquinoline-2-carbonyl)phenyl)-1,2-dimethyl-1H-pyrrole-3-carbonyl chloride (P28)

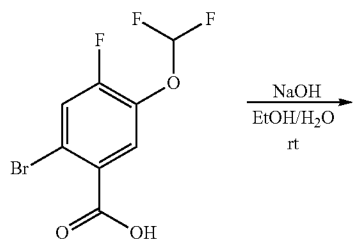

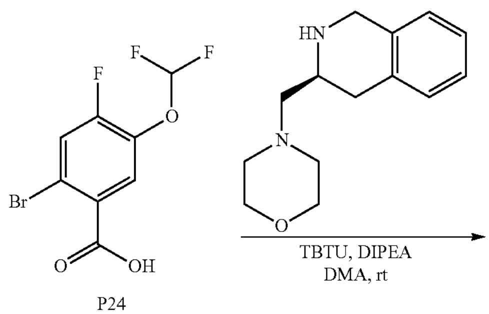

P24

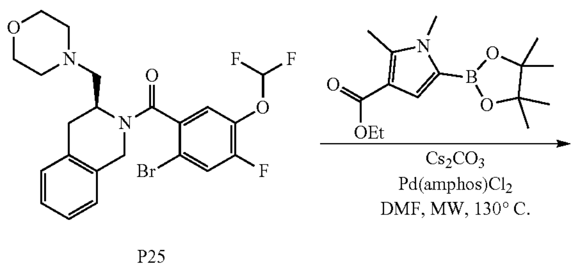

P25

-continued

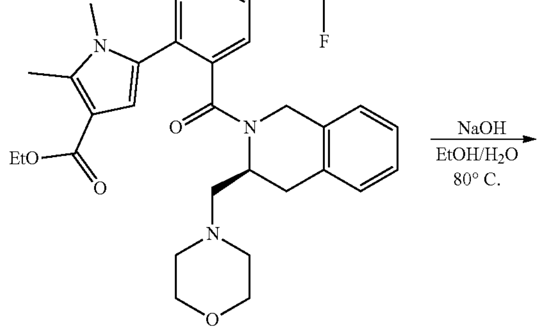

P26

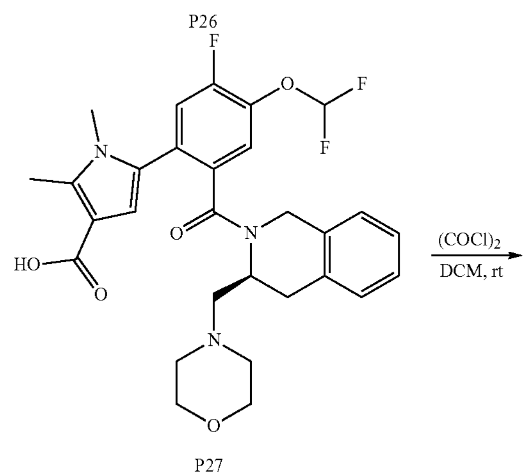

P27

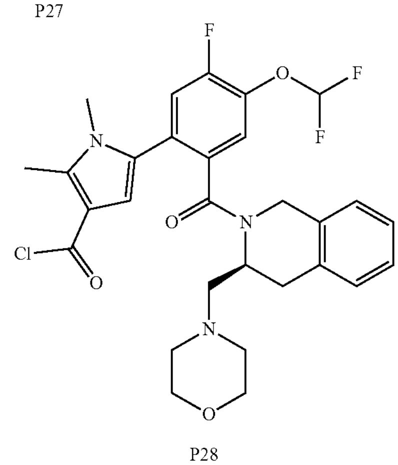

P28

Preparation 24. 2-Bromo-5-(difluoromethoxy)-4-fluorobenzoic acid (P24)

To a solution of ethyl 2-bromo-5-(difluoromethoxy)-4-fluoro-benzoate (800 mg, 2.56 mmol) in EtOH/$H_2O$(4:1, 25 mL) was added sodium hydroxide (511 mg, 12.8 mmol) and then it was stirred at rt for 3 h. The mixture was adjusted pH value (pH=5) with 2N HCl (aq) and extracted with EtOAc. The combined organic layers were dried over $MgSO_4$, filtered, and concentrated in vacuo to give P24 (709 mg, 97%) as a white solid which was used in the next step without purification.

$^1$H NMR (400 MHZ, $CD_3OD$), δ: 7.81 (d, J=8.4 Hz, 1H), 7.69 (d, J=9.6 Hz, 1H), 6.93 (t, $^2J_{H-F}$=72.8 Hz, 1H); LCMS (ESI) m/z calcd for $C_8H_4BrF_3O_3$ 283.93; found, 282.8 $[M-H]^-$.

Preparation 25. (S)-(2-Bromo-5-(difluoromethoxy)-4-fluorophenyl) (3-(morpholinomethyl)-3,4-dihydroisoquinolin-2 (1H)-yl)methanone (P25)

To a solution of P24 (700 mg, 2.46 mmol) and (3S)-3-(morpholin-4-ylmethyl)-1,2,3,4-tetrahydroisoquinoline (627 mg, 2.70 mmol) in N,N-dimethylacetamide (25 mL) was added N,N-diisopropylethylamine (0.64 mL, 3.7 mmol) and 2-(1H-benzotriazole-1-yl)-1,1,3,3-tetramethyluronium tetrafluoroborate (946 mg, 2.95 mmol). After the reaction was stirred at rt for 1 h, the mixture was treated with water and extracted with EtOAc. The combined organic layers were dried over $MgSO_4$, filtered, and concentrated under reduced pressure. The residue was purified by silica gel column chromatography (0-80% EtOAc in n-hexane) to give P25 (1.18 g, 96%) as a white solid. $^1$H NMR (400 MHZ, $CDCl_3$), δ: 7.58-7.29 (m, 2H), 7.26-7.02 (m, 3H), 7.02-6.30 (m, 2H), 5.39-5.22 (m, 1H), 4.56-4.17 (m, 2H), 3.89-3.56 (m, 4H), 3.34-3.09 (m, 1H), 2.87-2.11 (m, 7H); LCMS(ESI) m/z calcd for $C_{22}H_{22}BrF_3N_2O_3$ 498.08; found, 499.2 $[M+H]^+$.

Preparation 26. Ethyl(S)-5-(4-(difluoromethoxy)-5-fluoro-2-(3-(morpholinomethyl)-1,2,3,4-tetrahydroisoquinoline-2-carbonyl)phenyl)-1,2-dimethyl-1H-pyrrole-3-carboxylate (P26)

A solution of P25 (680 mg, 1.36 mmol), ethyl 1,2-dimethyl-5-(4,4,5,5-tetramethyl-1,3,2-dioxaborolan-2-yl) pyrrole-3-carboxylate (600 mg, 2.04 mmol), and cesium carbonate (887 mg, 2.72 mmol) in N,N-dimethylformamide (10 mL) was degassed by argon for 30 min. The mixture was then treated with bis(di-tert-butyl (4-dimethylaminophenyl) phosphine) dichloropalladium (II) (48 mg, 0.068 mmol) and then degassed by argon again. The mixture was stirred at 130° C. for 2 h under microwave irradiation. The reaction was treated with water and extracted with EtOAc. The combined organic layers were dried over $MgSO_4$, filtered, and concentrated under reduced pressure. The residue was purified by silica gel column chromatography (0-50% EtOAc in n-hexane) to give P26 (818 mg, 77%) as a yellow powder. $^1$H NMR (400 MHZ, $CDCl_3$), δ: 7.52-7.31 (m, 1H), 7.22-6.17 (m, 7H), 5.29-4.81 (m, 1H), 4.36-4.02 (m, 3H), 3.82-3.50 (m, 4H), 3.45-3.21 (m, 2H), 3.06-2.42 (m, 6H), 2.42-1.84 (m, 8H), 1.29-1.25 (m, 3H); LCMS(ESI) m/z calcd for $C_{31}H_{34}F_3N_3O_5$ 585.25; found, 586.8 $[M+H]^+$.

Preparation 27. (S)-5-(4-(Difluoromethoxy)-5-fluoro-2-(3-(morpholinomethyl)-1,2,3,4-tetrahydroisoquinoline-2-carbonyl)phenyl)-1,2-dimethyl-1H-pyrrole-3-carboxylic acid (P27)

To a solution of P26 (610 mg, 1.04 mmol) in ethanol (4.0 mL) and water (1.0 mL) was added sodium hydroxide (208 mg, 5.21 mmol) and then it was stirred at 80° C. for 16 h. The mixture was adjusted pH value to 5 with 2N HCl (aq) and extracted with EtOAc. The combined organic layers were dried over $MgSO_4$, filtered, and concentrated under reduced pressure. The residue was purified by silica gel column chromatography (0-10% MeOH in DCM containing 1% $NH_4OH$ (aq)) to give P27 (500 mg, 86%) as a white solid. $^1$H NMR (400 MHZ, $CDCl_3$), δ: 7.23-6.91 (m, 5H), 6.91-6.24 (m, 3H), 5.51-5.35 (m, 1H), 4.36-4.16 (m, 2H), 4.06-3.67 (m, 4H), 3.64-3.11 (m, 5H), 3.00-2.34 (m, 7H), 2.26-2.06 (m, 3H); LCMS(ESI) m/z calcd for $C_{29}H_{30}F_3N_3O_5$ 557.21; found, 556.2 $[M-H]^+$.

Preparation 28. (S)-5-(4-(difluoromethoxy)-5-fluoro-2-(3-(morpholinomethyl)-1,2,3,4-tetrahydroisoquinoline-2-carbonyl)phenyl)-1,2-dimethyl-1H-pyrrole-3-carbonyl chloride (P28)

To a solution of P27 (100 mg, 0.179 mmol) in DCM (4.0 mL) was added oxalyl chloride (31 μL, 0.36 mmol) at rt. The mixture was stirred at rt for 1 h. The mixture was concentrated to remove solvent to give P28 as a crude product which was used in next step without purification.

2-Cyclopropyl-6-(5-isopropoxy-1H-indazol-3-yl)-4-morpholinopyridazin-3 (2H)-one (P34)

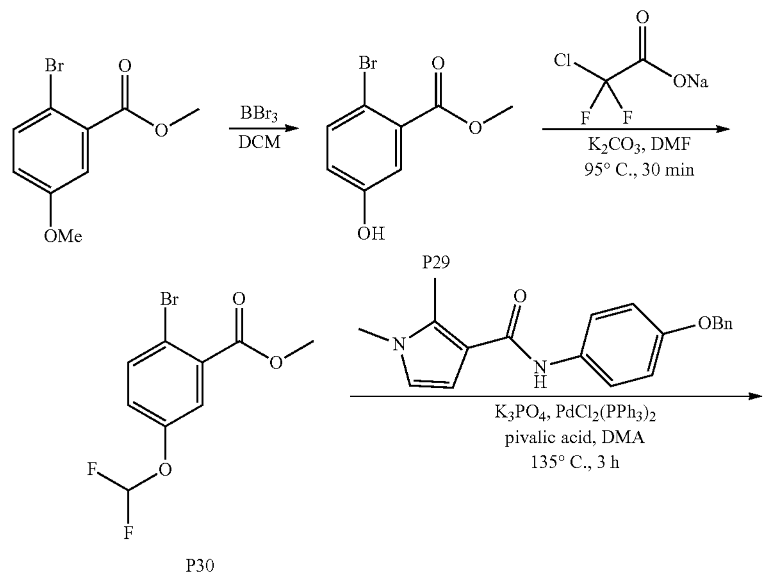

P29

P30

-continued
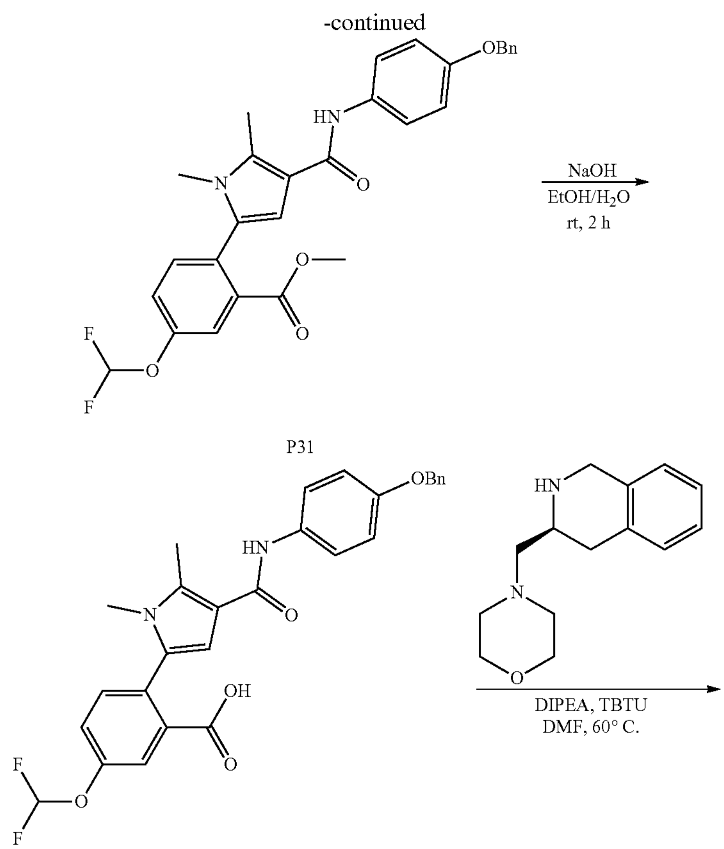
P31
P32
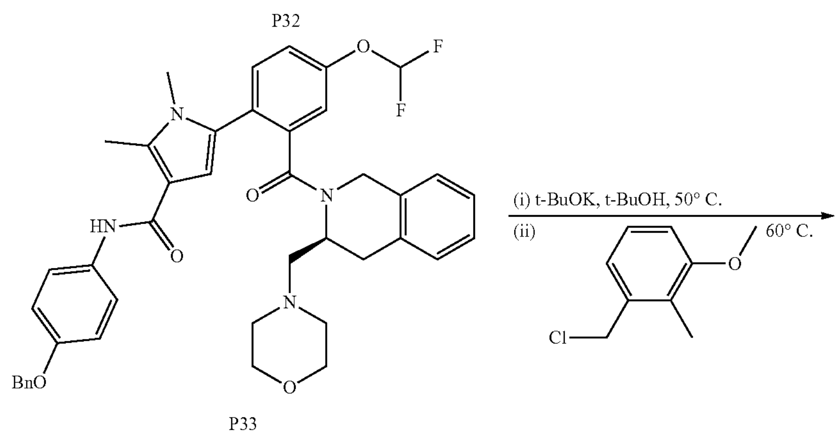
P33
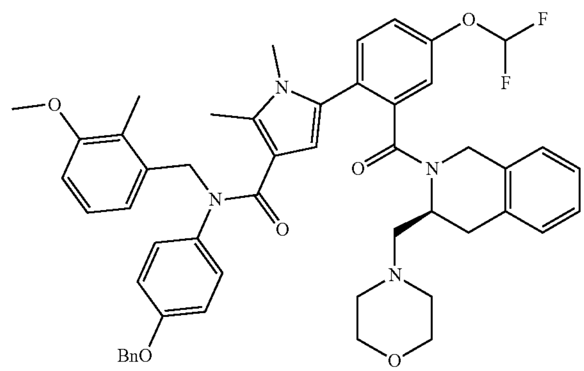
P34

Preparation 29. Methyl 2-bromo-5-hydroxybenzoate (P29)

To a solution of methyl 2-bromo-5-methoxy-benzoate (20.0 g, 81.6 mmol) in anh. DCM (300 mL) was added boron tribromide (48 mL, 0.50 mmol) at −78° C. After the mixture was stirred at −78° C. to rt for 6 h, the reaction was cooled to 0° C. and quenched with MeOH. The solution was concentrated under reduced pressure. The residue was diluted with EtOAc and washed with sodium bicarbonate aqueous solution. The organic layer was dried over $MgSO_4$, filtered, and concentrated under reduced pressure to give P28 (3.20 g, 68%) as a white solid which was used in the next step without further purification. $^1$H NMR (400 MHZ, $CD_3OD$), δ: 7.45 (d, J=8.8 Hz, 1H), 7.15 (d, J=3.0 Hz, 1H), 6.83 (dd, J=8.8, 3.0 Hz, 1H), 3.88 (s, 3H); LCMS(ESI) m/z calcd for $C_8H_7BrO_3$229.96; found, 230.7 [M+H]$^+$.

Preparation 30. Methyl 2-bromo-5-(difluoromethoxy)benzoate (P30)

To a solution of potassium carbonate (14.2 g, 102 mmol) in anh. DMF (45 mL) at 95° C. was added a mixture of P29 (15.8 g, 68.4 mmol) and sodium chlorodifluoroacetate (20.9 g, 136 mmol) in anh. DMF (90 mL). After the mixture was stirred at 95° C. for 30 min, the mixture was diluted with EtOAc and washed with $H_2O$ and brine. The organic layer was dried over $MgSO_4$, filtered, and concentrated under reduced pressure. The residue was purified by silica gel chromatography (0-50% EtOAc in n-hexane) to give P30 (8.2 g, 45%) as white gum. $^1$H NMR (400 MHZ, $CD_3OD$), δ: 7.73 (d, J=8.8 Hz, 1H), 7.54 (d, J=2.8 Hz, 1H), 7.23 (dd, J=8.8, 2.8 Hz, 1H), 6.90 (t, $J_{H-F}$=73.6 Hz, 1H), 3.92 (s, 3H).

Preparation 31. Methyl 2-(4-((4-(benzyloxy)phenyl) carbamoyl)-1,5-dimethyl-1H-pyrrol-2-yl)-5-(difluoromethoxy)benzoate (P31)

A solution of P30 (200 mg, 0.624 mmol), N-(4-benzyloxyphenyl)-1,2-dimethyl-pyrrole-3-carboxamide (263 mg, 0.936 mmol), pivalic acid (19 mg, 0.19 mmol) and potassium phosphate (662 mg, 3.12 mmol) in N,N-dimethylacetamide (42 mL) was degassed with argon for 15 min. Then bis(triphenylphosphine) palladium (II) dichloride (88 mg, 0.13 mmol) was added to the mixture and the reaction was degassed with argon again for 15 min. After the mixture was stirred at 135° C. for 3 h, the mixture was diluted with EtOAc and washed with brine. The organic layer was dried over $MgSO_4$, filtered, and concentrated under reduced pressure. The residue was purified by reverse phase chromatography (0-100% MeOH in $H_2O$) to give P31 (219 mg, 59%) as a yellow solid. $^1$H NMR (400 MHZ, $CDCl_3$), δ: 7.74 (s, 1H), 7.50-7.27 (m, 10H), 6.94 (d, J=8.8 Hz, 2H), 6.61 (t, $J_{H-F}$=73.2 Hz, 1H), 6.22 (s, 1H), 5.05 (s, 2H), 3.77 (s, 3H), 3.26 (s, 3H), 2.64 (s, 3H); LCMS(ESI) m/z calcd for $C_{29}H_{26}F_2N_2O_5$520.18; found, 521.6 [M+H]$^+$. Note: The degassing step is crucial for the yield.

Preparation 32. 2-(4-((4-(Benzyloxy)phenyl) carbamoyl)-1,5-dimethyl-1H-pyrrol-2-yl)-5-(difluoromethoxy)benzoic acid (P32)

To a solution of P31 (218 mg, 0.419 mmol) in EtOH (3.2 mL) and $H_2O$(0.80 mL) was added sodium hydroxide (84 mg, 2.1 mmol) and then stirred at rt for 2 h. The mixture was adjusted to pH 5 with 2N HCl (aq) and extracted with EtOAc. The combined organic layers were dried over $MgSO_4$, filtered, and concentrated under reduced pressure. The residue was purified by silica gel column chromatography (0-10% MeOH in DCM) to give P32 (148 mg, 70%) as a white solid.

$^1$H NMR (400 MHZ, $CD_3OD$), δ: 7.70 (s, 1H), 7.51-7.26 (m, 9H), 7.17-6.74 (m, 3H), 6.49 (s, 1H), 5.07 (s, 2H), 3.30 (s, 3H, overlapped with solvent residual of d-methanol), 2.57 (s, 3H); LCMS (ESI) m/z calcd for $C_{28}H_{24}F_2N_2O_5$506.17; found, 507.4 [M+H]$^+$.

Preparation 33 (S)—N-(4-(Benzyloxy)phenyl)-5-(4-(difluoromethoxy)-2-(3-(morpholinomethyl)-1,2,3,4-tetrahydroisoquinoline-2-carbonyl)phenyl)-1,2-dimethyl-1H-pyrrole-3-carboxamide (P33)

To a solution of P32 (145 mg, 0.286 mmol) and 4-[[(3S)-1,2,3,4-tetrahydroisoquinolin-3-yl]methyl]morpholine (72.9 mg, 0.315 mmol) in DMF (1.5 mL) was added N,N-diisopropylethylamine (0.075 mL, 0.43 mmol) and 2-(1H-benzotriazole-1-yl)-1,1,3,3-tetramethyluronium tetrafluoroborate (110 mg, 0.344 mmol). After the reaction was stirred at 60° C. for overnight, the mixture was treated with water and extracted with EtOAc. The combined organic layers were dried over $Na_2SO_4$, filtered, and concentrated under reduced pressure. The residue was purified by silica gel column chromatography (30% EtOAc in DCM) to give P33 (105 mg, 51%) as a colorless gum. $^1$H NMR (400 MHZ, $CDCl_3$), δ: 7.47-7.28 (m, 8H), 7.22-7.08 (m, 3H), 7.00-6.86 (m, 4H), 6.75-6.51 (m, 2H), 5.08-5.04 (m, 2H), 4.36-4.16 (m, 2H), 3.77-3.63 (m, 3H), 3.59-3.54 (m, 1H), 3.49 (s, 1H), 3.20 (s, 3H), 2.78-2.69 (m, 1H), 2.68-2.60 (m, 2H), 2.55-2.44 (m, 2H), 2.38-2.30 (m, 4H), 2.28-2.20 (m, 1H); LCMS (ESI) m/z calcd for $C_{42}H_{42}F_2N_4O_5$720.31; found, 721.9 [M+H]$^+$.

Preparation 34. 2-Cyclopropyl-6-(5-isopropoxy-1H-indazol-3-yl)-4-morpholinopyridazin-3 (2H)-one (P34)

A solution of P33 (100 mg, 0.139 mmol) and 1-BuOK (93 mg, 0.83 mmol) in 1-BuOH (3.5 mL) was stirred at 50° C. for 30 min, and then (3-methoxy-2-methyl-phenyl)methyl methanesulfonate (128 mg, 0.555 mmol) was added to the mixture. After the mixture was stirred at 60° C. for overnight, the mixture was cooled, diluted with EtOAc and washed with brine. The organic layer was dried over $MgSO_4$, filtered, and concentrated under reduced pressure. The residue was purified by silica gel chromatography (30% EtOAc in n-hexane with 3% TEA) to give P34 (24 mg, 20%) as a colorless gum. $^1$H NMR (400 MHZ, $CDCl_3$), δ: 7.42-7.36 (m, 1H), 7.35-7.27 (m, 3H), 7.20-6.94 (m, 8H), 6.89-6.62 (m, 5H), 6.62-6.40 (m, 3H), 5.23-5.00 (m, 2H), 4.99-4.90 (m, 2H), 4.82-4.63 (m, 1H), 4.31-3.93 (m, 1H), 3.86-3.75 (m, 3H), 3.72-3.60 (m, 3H), 3.55-3.48 (m, 1H), 3.27-3.19 (m, 1H), 3.10 (s, 1H), 2.94-2.74 (m, 1H), 2.71-2.36 (m, 4H), 2.35-2.20 (m, 4H), 2.20-2.03 (m, 4H), 2.02-1.87 (m, 2H).; LCMS(ESI) m/z calcd for $C_{51}H_{52}F_2N_4O_6$854.39; found, 856.0 [M+H]$^+$.

1-(Chloromethyl)-3-methoxy-2-methylbenzene (P35)

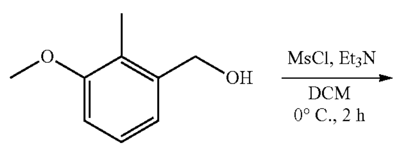

-continued

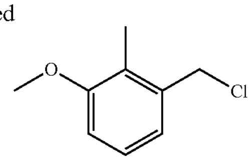

P35

Preparation 35. 1-(Chloromethyl)-3-methoxy-2-methylbenzene (P35)

To a solution of (3-methoxy-2-methyl-phenyl)methanol (73.3 mg, 0.481 mmol) in DCM (1.5 mL) was added methanesulfonyl chloride (56.0 μL, 0.722 mmol) and triethylamine (134 μL, 0.963 mmol) at 0° C. After the reaction solution was stirred at 0° C. for 2 h, quenched with $H_2O$, and extracted with EtOAc. The organic layers were dried over $MgSO_{4(s)}$, filtered and concentrated under reduced pressure to give P35 (82.2 mg) which was used in next step without purification.

$^1$H NMR (400 MHZ, $CDCl_3$), δ: 7.20 (t, J=7.6 Hz, 1H), 7.00-6.90 (m, 2H), 5.28 (s, 2H), 3.84 (s, 3H), 2.87 (s, 3H).

(S)—N-(4-(benzyloxy)phenyl)-5-(5-chloro-4-(difluoromethoxy)-2-(3-(morpholinomethyl)-1,2,3,4-tetrahydroisoquinoline-2-carbonyl)phenyl)-N-(3-methoxy-2-methylbenzyl)-1,2-dimethyl-1H-pyrrole-3-carboxamide (P38)

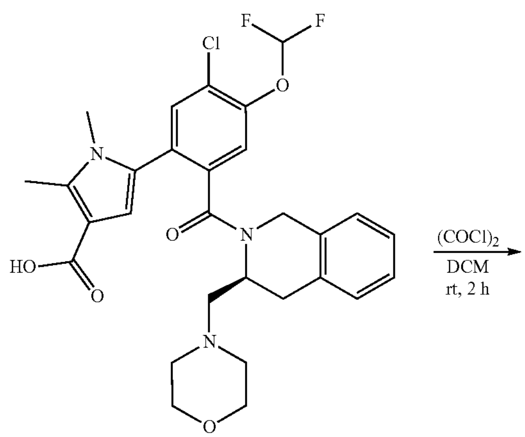

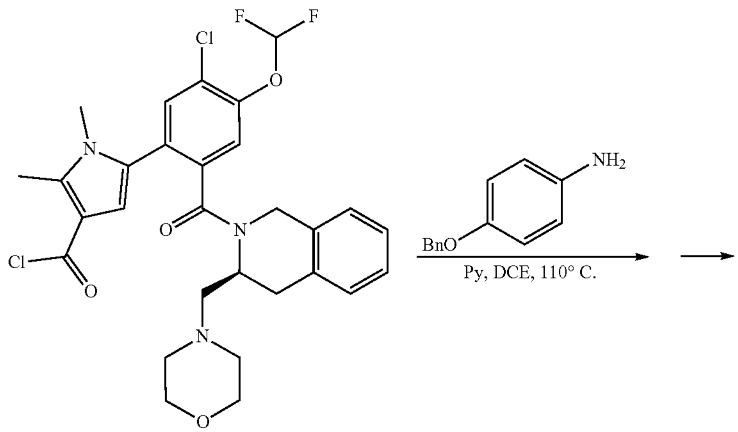

P36

-continued

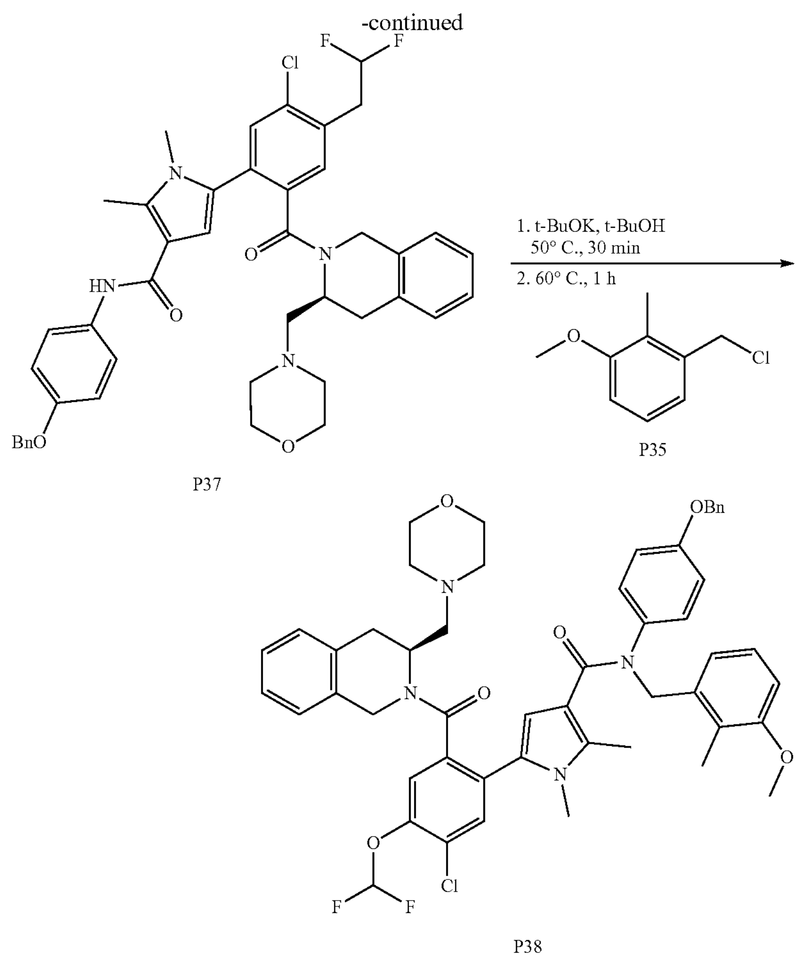

P37

P35

P38

Preparation 36. (S)-5-(5-Chloro-4-(difluoromethoxy)-2-(3-(morpholinomethyl)-1,2,3,4-tetrahydroisoquinoline-2-carbonyl)phenyl)-1,2-dimethyl-1H-pyrrole-3-carbonyl chloride (P36)

To a solution of 5-[5-chloro-4-(difluoromethoxy)-2-[(3S)-3-(morpholinomethyl)-3,4-dihydro-1H-isoquinoline-2-carbonyl]phenyl]-1,2-dimethyl-pyrrole-3-carboxylic acid (100 mg, 0.174 mmol) in anh. DCM (2.0 mL) was added oxalyl chloride (30 μL, 0.348 mmol) dropwise at 0° C. The reaction solution was stirred at rt for 2 h. TLC analysis indicated the starting material was consumed. The solution was concentrated to remove solvent to give the crude product P36 which was used in next step without purification.

Preparation 37. (S)—N-(4-(Benzyloxy)phenyl)-5-(5-chloro-4-(difluoromethoxy)-2-(3-(morpholinomethyl)-1,2,3,4-tetrahydroisoquinoline-2-carbonyl)phenyl)-1,2-dimethyl-1H-pyrrole-3-carboxamide (P37)

To a solution of crude P36 in 1,2-dichloroethane (2.0 mL) was added pyridine (42.1 μL, 0.522 mmol) and 4-(benzyloxy) aniline (38.2 mg, 0.191 mmol) at rt. After the reaction solution was stirred at 110° C. for 16 h and cooled to rt, the solution quenched with $H_2O$ and extracted with EtOAc. The organic layers were dried over $MgSO_{4(s)}$, filtered and concentrated under reduced pressure. The residue was purified by silica-gel column chromatography (DCM: EtOAc=1:1) to give P37 (91.0 mg, 69% yield) as a grey solid. $^1H$ NMR (400 MHZ, $CDCl_3$), δ: 7.82-7.28 (m, 7H), 7.18-6.76 (m, 7H), 6.66-6.36 (m, 2H), 5.91-5.21 (m, 2H), 5.06 (s, 2H), 4.72-4.17 (m, 3H), 3.69-3.45 (m, 5H), 3.24-2.98 (m, 4H), 2.83-2.60 (m, 2H), 2.53-2.47 (m, 1H), 2.37 (m, 3H), 2.26-2.21 (m, 1H), 2.12-2.07 (m, 1H); LCMS(ESI) m/z calcd for $C_{42}H_{41}ClF_2N_4O_5$754.27; found, 755.3 $[M+H]^+$.

Preparation 38. (S)—N-(4-(Benzyloxy)phenyl)-5-(5-chloro-4-(difluoromethoxy)-2-(3-(morpholinomethyl)-1,2,3,4-tetrahydroisoquinoline-2-carbonyl)phenyl)-N-(3-methoxy-2-methylbenzyl)-1,2-dimethyl-1H-pyrrole-3-carboxamide (P38)

To a solution of P37 (91.0 mg, 0.120 mmol) in tert-butanol (1.5 mL) was added potassium tert-butoxide (88.3 mg, 0.723 mmol) at rt. After the reaction solution was stirred at 50° C. for 30 min, to the solution was added P35 (82.2 mg, 0.482 mmol) and it was stirred at 60° C. for another 1 h. The reaction solution was cooled, quenched with $H_2O$ and extracted with EtOAc. The organic layers were dried over $MgSO_{4(s)}$, filtered and concentrated under reduced pressure. The residue was purified by silica-gel column chromatography (dichloromethane: EtOAc=1:1) to give P38 (40.0 mg, 37% yield) as a pale solid. $^1H$ NMR (400 MHz, $CDCl_3$), δ: 7.71-7.29 (m, 7H), 7.25-6.40 (m, 12H), 5.52-5.47 (m, 1H), 5.15-4.92 (m, 3H), 4.79-4.61 (m, 1H), 4.36-3.93 (m, 4H), 3.83-3.66 (m, 6H), 3.57-3.41 (m, 2H), 3.27-3.12 (m, 4H), 2.33-2.04 (m, 10H); LCMS(ESI) m/z calcd for $C_{51}H_{51}ClF_2N_4O_6$888.35; found, 889.4 [M+H]$^+$.

5-[4-chloro-5-(difluoromethyl)-2-[(3S)-3-(morpholinomethyl)-3,4-dihydro-1H-isoquinoline-2-carbonyl]phenyl]-1,2-dimethyl-pyrrole-3-carbonyl chloride

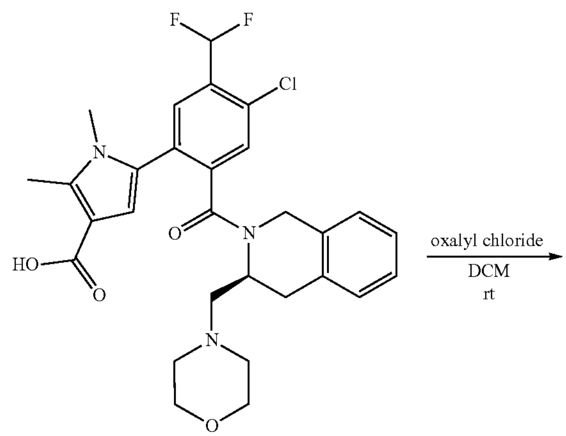

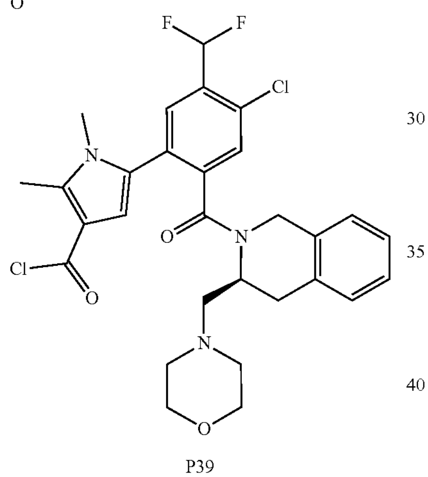

P39

Preparation 39. 5-[4-chloro-5-(difluoromethyl)-2-[(3S)-3-(morpholinomethyl)-3,4-dihydro-1H-isoquinoline-2-carbonyl]phenyl]-1,2-dimethyl-pyrrole-3-carbonyl chloride (P39)

To a solution of 5-[4-chloro-5-(difluoromethyl)-2-[(3S)-3-(morpholinomethyl)-3,4-dihydro-1H-isoquinoline-2-carbonyl]phenyl]-1,2-dimethyl-pyrrole-3-carboxylic acid (150 mg, 0.27 mmol, 1.0 eq) in DCM (3.0 mL) was added oxalyl chloride (46 μL, 0.54 mmol, 2.0 eq) at ice bath. The reaction mixture was stirred at rt for 1 h. The reaction mixture was concentrated in vacuo to give a crude P39 which was used for the next step without further separation.

(S)—N-(4-(benzyloxy)phenyl)-5-(4-chloro-5-(difluoromethyl)-2-(3-(morpholinomethyl)-1,2,3,4-tetrahydroisoquinoline-2-carbonyl)phenyl)-N-(3-methoxy-2-methylbenzyl)-1,2-dimethyl-1H-pyrrole-3-carboxamide

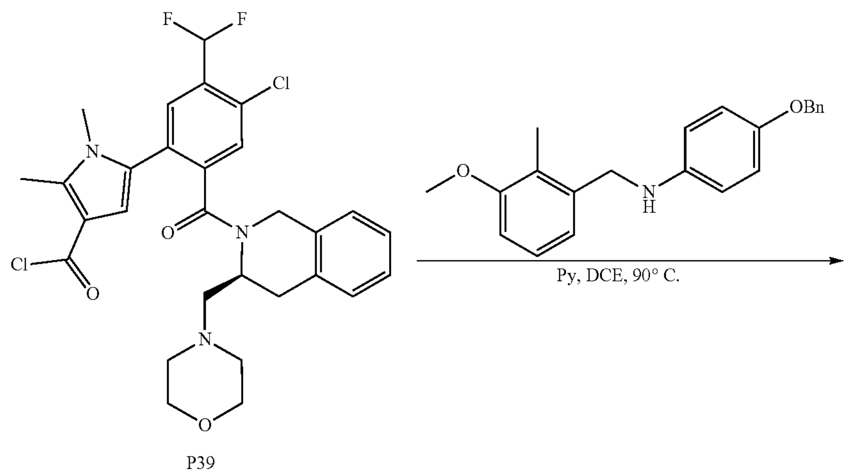

P39

-continued

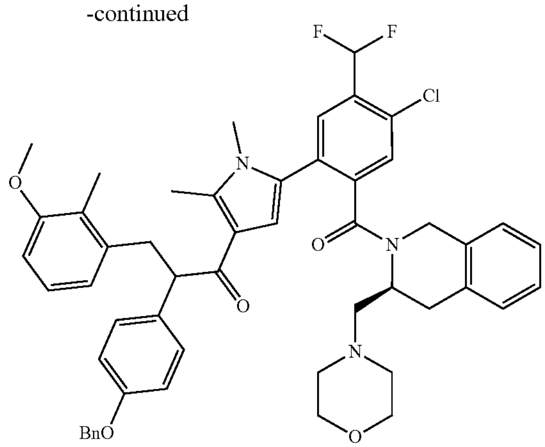

P40

Preparation 40. (S)—N-(4-(benzyloxy)phenyl)-5-(4-chloro-5-(difluoromethyl)-2-(3-(morpholinomethyl)-1,2,3,4-tetrahydroisoquinoline-2-carbonyl)phenyl)-N-(3-methoxy-2-methylbenzyl)-1,2-dimethyl-1H-pyrrole-3-carboxamide (P40)

To a solution of P39 (143 mg, 0.430 mmol) in dichloroethane (2.0 mL) was added a solution of pyridine (86 μL, 1.08 mmol) and 4-benzyloxy-N-[(3-methoxy-2-methyl-phenyl)methyl]aniline (crude, 0.358 mmol) in dichloroethane (4.0 mL) at rt. The mixture was stirred at 90° C. for 6 h. The reaction was quenched with $NaHCO_{3(aq)}$ and extracted with DCM. The organic layers were dried over $MgSO_{4(s)}$, filtered, and concentrated. The crude was purified by silica gel column chromatography (0-100% EtOAc in n-hexane containing 3% triethylamine) to give P40 (65.9 mg, 21%) as a white solid. $^1H$ NMR (400 MHz, $CDCl_3$), δ: 7.45-7.26 (m, 7H), 7.20-6.97 (m, 5H), 6.97-6.63 (m, 6H), 6.60-6.45 (m, 2H), 5.19-5.08 (m, 1H), 5.07-4.89 (m, 3H), 4.88-4.71 (m, 1H), 4.28-3.90 (m, 1H), 3.87-3.76 (m, 3H), 3.75-3.60 (m, 3H), 3.59-3.46 (m, 2H), 3.29-3.20 (m, 1H), 3.10 (s, 2H), 2.71-2.48 (m, 3H), 2.47-2.37 (m, 1H), 2.37-2.27 (m, 2H), 2.26-2.12 (m, 3H), 2.11-1.86 (m, 5H); LCMS(ESI) m/z calcd for $C_{51}H_{51}ClF_2N_4O_5$872.35; found, 873.4 $[M+H]^+$.

(S)-4-((1,2,3,4-tetrahydroisoquinolin-3-yl)methyl)morpholine (43)

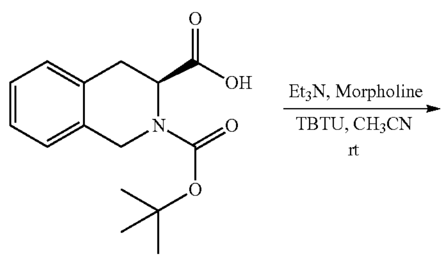

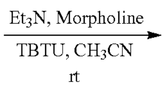

-continued

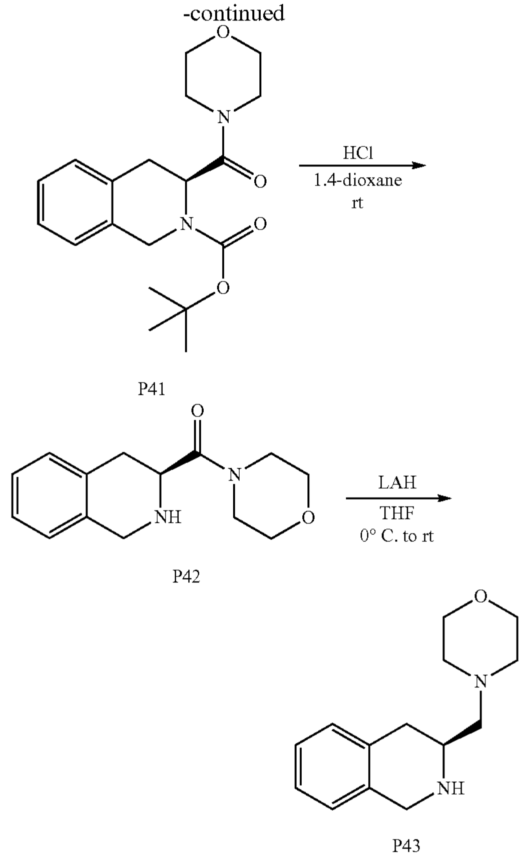

P41

P42

P43

Preparation 41. tert-Butyl(S)-3-(morpholine-4-carbonyl)-3,4-dihydroisoquinoline-2 (1H)-carboxylate (P41)

To a solution of tert-butyl (3S)-3-(morpholine-4-carbonyl)-3,4-dihydro-1H-isoquinoline-2-carboxylate (10 g, 36.06 mmol) in acetonitrile (100 mL) was added morpholine (3.98 mL, 46.16 mmol) and triethylamine (6.02 mL, 43.3 mmol) at rt and it was stirred for 20 min. ( ) (Benzotriazol-1-yl)-N,N,N',N'-tetramethyluronium tetrafluoroborate (TBTU) was added to the reaction mixture at rt. The reaction was stirred at rt overnight. The mixture was concentrated to give a residue. The residue was diluted with EtOAc and then treated with aq. sodium bicarbonate solution. The organic layer was dried over $MgSO_4$, filtered, and concentrated to get the product P41 (11.97 g, 94%) as a yellow solid which was used in the next step without purification. $^1$H NMR (400 MHZ, $CDCl_3$), δ: 7. 18-7.09 (m, 4H), 5.27 (br s, 1H), 4.94-4.82 (br m, 1H), 4.46-4.38 (br m, 1H), 3.69-3.58 (br m, 8H), 3.13-2.94 (m, 2H), 1.48 (br m, 9H).; LCMS(ESI) m/z calcd for $C_{19}H_{26}N_2O_4$ 346.19; found, 347.1 $[M+H]^+$.

Preparation 42. (S)-morpholino (1,2,3,4-tetrahydroisoquinolin-3-yl)methanone (P42)

To a solution of P41 (9.07 g, 26.18 mmol) in 1,4-dioxane (25 mL) was added a solution of 4M HCl in 1,4-dioxane (50 mL). The reaction was stirred at rt for 2 h. The solution was quenched by saturated $Na_2CO_{3\ (aq)}$ and extracted with DCM. The organic layers were was dried over $MgSO_4$, filtered, and concentrated to give P42 (5.1 g, 79%) as a white solid. $^1$H NMR (400 MHZ, DMSO-$d_6$), δ:7.10-7.07 (m, 3H), 7.01-6.99 (m, 1H), 3.88 (s, 2H), 3.87-3.83 (m, 1H), 3.71-3.37 (m, 9H), 2.85-2.78 (m, 1H), 2.69-2.64 (m, 1H); LCMS(ESI) m/z calcd for $C_{14}H_{18}N_2O_2$ 246.14; found, 247.3 $[M+H]^+$ Preparation 43. (S)-4-((1,2,3,4-tetrahydroisoquino-lin-3-yl)methyl) morpholine (P43)

To a solution of P42 (1.85 g, 7.51 mmol) in anh. THF (10 mL) was added LAH (15.02 mL, 15.02 mmol, 1 M in THF) at 0° C. The reaction was stirred at rt for overnight and then quenched by water (0.60 mL) and 15% NaOH (aq) (0.60 mL) at 0° C. The solution was filtered through a pad of celite and washed with THF. The filtrate was collected and concentrated to give the product P43 (1.20 g, 69%) as an orange oil. $^1$H NMR (400 MHZ, $CDCl_3$), δ: 7.15-7.08 (m, 3H), 7.06-7.04 (m, 1H), 4.09 (s, 2H), 3.76-3.73 (m, 4H), 3.10-3.03 (m, 1H), 2.73-2.55 (m, 4H), 2.50-2.40 (m, 4H).; LCMS (ESI) m/z calcd for $C_{14}H_{20}N_2O$ 232.16; found, 233.2 $[M+H]^+$.

Ethyl 1,2-dimethyl-5-(4,4,5,5-tetramethyl-1,3,2-dioxaborolan-2-yl)-1H-pyrrole-3-carboxylate

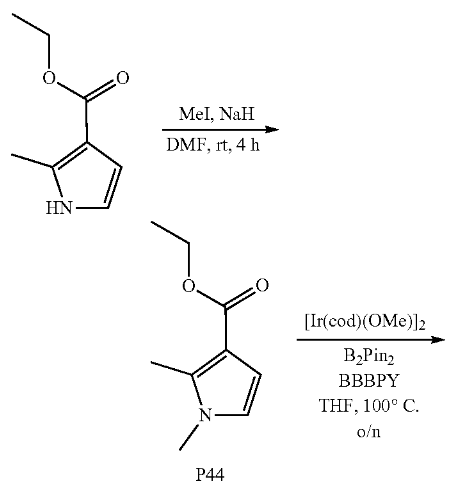

P44

-continued

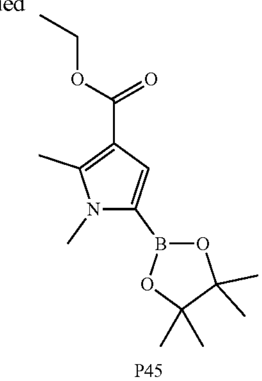

P45

Preparation 44. Ethyl 1,2-dimethyl-1H-pyrrole-3-carboxylate (P44)

To a solution of 2-methyl-1H-pyrrole-3-carboxylic acid ethyl ester (25.0 g, 163 mmol) in anh. DMF (200 mL) was slowly added sodium hydride (7.2 g, 18.0 mmol) at 0° C. and then it was stirred at rt for 30 min. After the mixture was treated with methyl iodide (11 mL, 18.0 mmol) at 0° C., it was stirred at rt for 16 h. The mixture was treated with water in ice bath and extracted with EtOAc. The combined organic layers were dried over $Na_2SO_4$, filtered, and concentrated under reduced pressure to give P44 (25.0 g, 91%) as an orange oil which was used in the next step without further purification. $^1$H NMR (400 MHZ, $CDCl_3$), δ: 6.50 (d, J=3.0 Hz, 1H), 6.45 (d, J=3.0 Hz, 1H), 4.25 (q, J=7.2 Hz, 2H), 3.52 (s, 3H), 2.50 (s, 3H), 1.33 (t, J=7.2 Hz, 3H); LCMS(ESI) m/z calcd for $C_9H_{13}NO_2$167.09; found, 168.1 $[M+H]^+$.

Preparation 45. Ethyl 1,2-dimethyl-5-(4,4,5,5-tetramethyl-1,3,2-dioxaborolan-2-yl)-1H-pyrrole-3-carboxylate (P45)

To a solution of P44 (5.0 g, 30 mmol) and bis (pinacolato) diboron (8.4 g, 33 mmol) in THF (75 mL) was added 4,4'-di-tert-butyl-2,2'-bipyridyl (482 mg, 1.8 mmol) and (1,5-cyclooctadiene)(methoxy) iridium (I) dimer (595 mg, 0.90 mmol) at rt. After the reaction was stirred at 100° C. for 16 h under nitrogen, the mixture was concentrated under reduced pressure to give P45 (12.5 g, <99%) as a red solid which was used in next step without further purification.

$^1$H NMR (400 MHZ, $CDCl_3$), δ: 7.21 (s, 1H), 4.23 (q, J=7.2 Hz, 2H), 3.70 (s, 3H), 2.52 (s, 3H), 1.30-1.26 (m, 15H); LCMS(ESI) m/z calcd for $C_{15}H_{24}BNO_4$293.18; found, 294.1 $[M+H]^+$.

(S)-(2-bromo-4-chlorophenyl) (3-(morpholinomethyl)-3,4-dihydroisoquinolin-2 (1H)—yl)-methanone (P46)

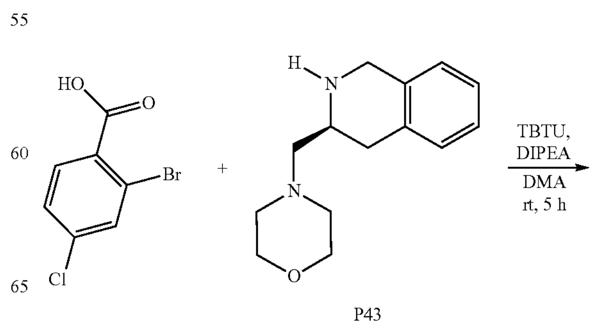

P43

-continued

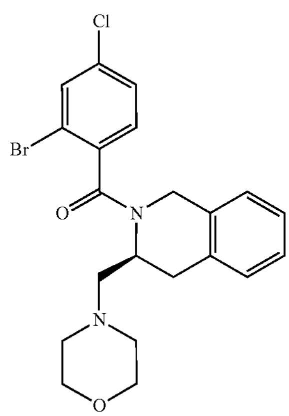

P46

Preparation 46. (S)-(2-bromo-4-chlorophenyl) (3-(morpholinomethyl)-3,4-dihydroisoquinolin-2 (1H)-yl)methanone (P46)

To a solution of 2-bromo-4-chlorobenzoic acid (3.00 g, 12.7 mmol) and P43 (3.30 g, 14.0 mmol) in N,N-dimethylacetamide (42 mL) was added N,N-diisopropylethylamine (3.3 mL, 19.1 mmol) and 2-(1H-benzotriazole-1-yl)-1,1,3,3-tetramethyluronium tetrafluoroborate (4.9 g, 15. mmol). After the reaction was stirred at rt for 5 h, the mixture was treated with water and extracted with EtOAc. The combined organic layers were dried over $Na_2SO_4$, filtered, and concentrated under reduced pressure. The residue was purified by silica gel column chromatography (0-80% EtOAc in n-hexane) to give P46 (4.9 g, 85%) as a yellow solid. $^1H$ NMR (400 MHZ, $CDCl_3$), δ: 7.68-7.60 (m, 1H), 7.43-7.29 (m, 2H), 7.24-7.11 (m, 3H), 6.92-6.88 (m, 1H), 5.46-5.28 (m, 1H), 4.49-4.34 (m, 1H), 4.25-4.20 (m, 1H), 3.72-3.69 (m, 3H), 3.64-3.54 (m, 2H), 3.35-3.12 (m, 1H), 2.94-2.74 (m, 1H), 2.68-2.40 (m, 2H), 2.35-2.22 (m, 1H), 2.21-2.09 (m, 2H); LCMS(ESI) m/z calcd for $C_{21}H_{22}BrClN_2O_2$ 448.06; found, 449.2 $[M+H]^+$.

(S)-5-(5-chloro-2-(3-(morpholinomethyl)-1,2,3,4-tetrahydroisoquinoline-2-carbonyl)phenyl)-1,2-dimethyl-1H-pyrrole-3-carboxylic acid (P48)

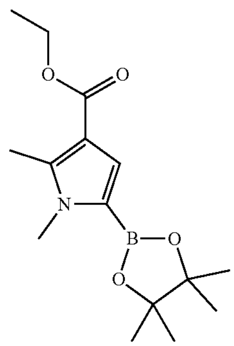

P45

+

-continued

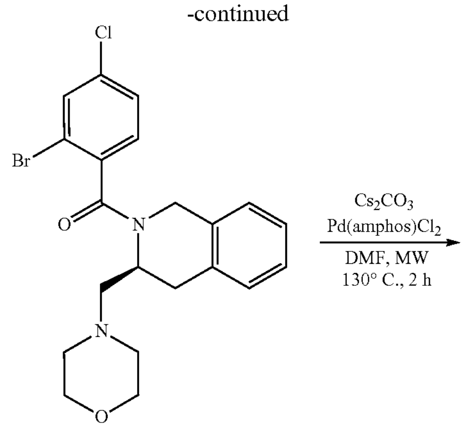

P46

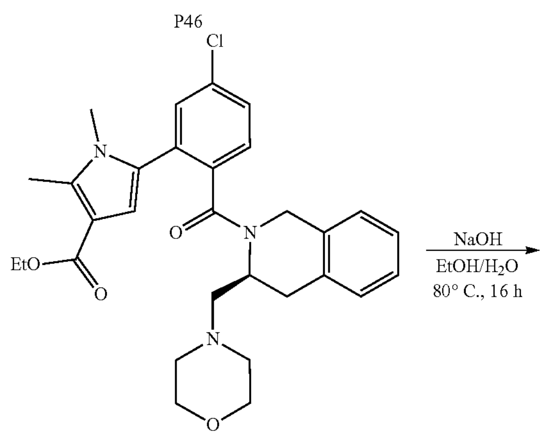

P47

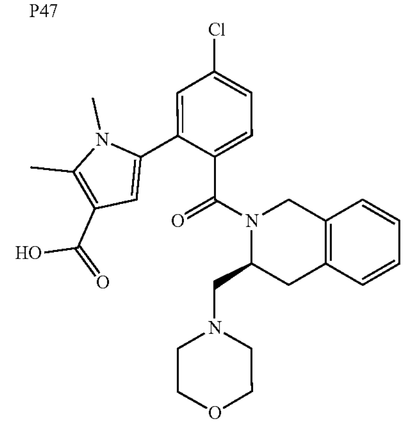

P48

Preparation 47. Ethyl(S)-5-(5-chloro-2-(3-(morpholinomethyl)-1,2,3,4-tetrahydroisoquinoline-2-carbonyl)phenyl)-1,2-dimethyl-1H-pyrrole-3-carboxylate (P47)

A solution of P45 (559 mg, 1.3 mmol), P46 (500 mg, 1.1 mmol), and cesium carbonate (723 mg, 2.2 mmol) in DMF (5.5 mL) was degassed by argon for 30 min. The mixture was then treated with bis(di-tert-butyl (4-dimethylamino-phenyl)phosphine) dichloropalladium (II) (39 mg, 0.06 mmol) and then degassed by argon again. The mixture was stirred at 130° C. for 2 h under microwave irradiation. The reaction was treated with water and extracted with EtOAc. The combined organic layers were dried over $Na_2SO_4$, filtered, and concentrated under reduced pressure. The residue was purified by silica gel column chromatography (0-80% EtOAc in n-hexane) to give P47 (350 mg, 58%) as a yellow solid. $^1$H NMR (400 MHZ, $CDCl_3$), δ: 7.44-7.38 (m, 2H), 7.13-7.05 (m, 3H), 6.98-6.96 (m, 1H), 6.83-6.76 (m, 1H), 6.20 (s, 1H), 5.28-5.22 (m, 1H), 4.31-4.14 (m, 4H), 3.71-3.52 (m, 5H), 3.38-3.31 (m, 1H), 3.23 (s, 3H), 3.00-2.75 (m, 1H), 2.55-2.38 (m, 4H), 2.24-2.16 (m, 4H), 2.03-1.98 (m, 2H), 1.26-1.19 (m, 3H); LCMS(ESI) m/z calcd for $C_{30}H_{34}ClN_3O_4$ 535.22; found, 536.4 $[M+H]^+$.

Preparation 48. (S)-5-(5-chloro-2-(3-(morpholinomethyl)-1,2,3,4-tetrahydroisoquinoline-2-carbonyl)phenyl)-1,2-dimethyl-1H-pyrrole-3-carboxylic acid (P48)

To a solution of P47 (350 mg, 0.65 mmol) in ethanol (5.2 mL) and water (1.3 mL) was added sodium hydroxide (131 mg, 3.3 mmol) and then stirred at 80° C. for 16 h. The mixture was adjusted pH value to 5 with 4N HCl (aq) and extracted with EtOAc. The combined organic layers were dried over $Na_2SO_4$, filtered, and concentrated under reduced pressure. The residue was purified by silica gel column chromatography (0-60% EtOAc in n-hexane) to give P48 (300 mg, 90%) as an orange solid. $^1$H NMR (400 MHZ, $CDCl_3$), δ: 7.60-7.53 (m, 2H), 7.42 (s, 1H), 7.13-7.11 (m, 2H), 6.97-6.88 (m, 2H), 6.36 (s, 1H), 5.36 (br s, 1H), 4.30-4.16 (m, 2H), 3.89-3.79 (br m, 4H), 3.59-3.47 (m, 1H), 3.21-3.07 (m, 5H), 2.94-2.88 (m, 4H), 2.55-2.46 (m, 2H), 2.08 (s, 3H); LCMS(ESI) m/z calcd for $C_{28}H_{30}ClN_3O_4$ 507.19; found, 508.4 $[M+H]^+$.

N-(3-Methoxy-2-methylbenzyl)-1-(tetrahydro-2H-pyran-2-yl)-1H-indazol-5-amine (P51)

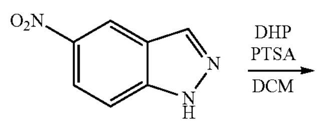

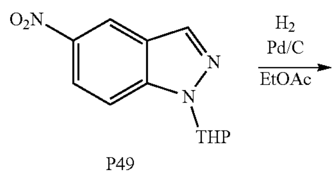

P49

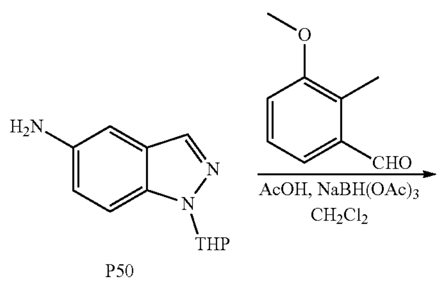

P50

-continued

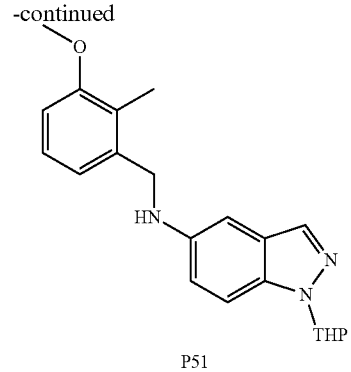

P51

Preparation 49. 5-Nitro-1-(tetrahydro-2H-pyran-2-yl)-1H-indazole (P48)

To a solution of 5-nitro-1H-indazole (2.00 g, 12.3 mmol) in DCM (60 mL) was added 2,3-dihydropyran (2.34 ml, 24.5 mmol) and 4-methylbenzenesulfonic acid (471 mg, 2.45 mmol). After the mixture was stirred at rt for overnight, the mixture was concentrated to remove solvent. The residue was treated with water and extracted with EtOAc. The organic layers were dried over $Na_2SO_{4(s)}$, filtered, and concentrated. The crude was purified by silica gel column chromatography (0-80% EtOAc in n-hexane) to give P49 (3.0 g, 99%). $^1$H NMR (400 MHZ, $CDCl_3$), δ: 8.71 (d, J=2.0 Hz, 1H), 8.27 (d, J=9.2 Hz, 1H), 8.21 (s, 1H), 7.69 (d, J=9.2 Hz, 1H), 5.77 (dd, J=8.8, 2.4 Hz, 1H), 4.04-3.99 (m, 1H), 3.80-3.74 (m, 1H), 2.56-2.47 (m, 1H), 2.18-2.08 (m, 2H), 1.83-1.67 (m, 3H).

Preparation 50. 1-(Tetrahydro-2H-pyran-2-yl)-1H-indazol-5-amine (P50)

To a solution of P49 (3.00 g, 12.1 mmol) in EtOAc (120 mL) was added palladium on carbon (300 mg) at rt. The mixture was purged with $H_2$ (g) over 5 min. The mixture was stirred at rt for overnight under $H_2$ atmosphere. The mixture was filtered through a pad of celite. The filtrate was then concentrated to give P50 (2.94 g, 100%) which was used in next step without purification. 1H NMR (400 MHZ, $CDCl_3$), δ: 7.82 (s, 1H), 7.41 (d, J=8.8 Hz, 1H), 6.93 (s, 1H), 6.89-6.87 (m, 1H), 5.64 (dd, J=9.2, 2.8 Hz, 1H), 4.04-4.00 (m, 1H), 3.76-3.69 (m, 1H), 2.59-2.50 (m, 1H), 2.16-2.11 (m, 1H), 2.09-2.06 (m, 1H), 1.81-1.68 (m, 3H).

Preparation 51. N-(3-Methoxy-2-methylbenzyl)-1-(tetrahydro-2H-pyran-2-yl)-1H-indazol-5-amine (P51)

To a solution of P50 (600 mg, 2.77 mmol) and 3-methoxy-2-methylbenzaldehyde (347 mg, 2.31 mmol) in DCM (15 mL) was added AcOH (1 drop). The mixture was stirred at rt for 16 h and concentrated to remove solvent. The residue was purified by silica gel column chromatography (10-80% EtOAc in n-hexane) to give P51 (610 mg, 75%). $^1$H NMR (400 MHZ, $CDCl_3$), δ: 7.84 (s, 1H), 7.42 (d, J=8.8 Hz, 1H), 7.14 (t, J=8.0 Hz, 1H), 6.99 (d, J=8.0 Hz, 1H), 6.85-6.79 (m, 3H), 5.64 (dd, J=9.2, 2.8 Hz, 1H), 4.29 (s, 2H), 4.04-3.99 (m, 1H), 3.85 (s, 3H), 3.75-3.68 (m, 1H), 2.59-2.50 (m, 1H), 2.25 (s, 3H), 2.16-2.12 (m, 1H), 2.09 (s, 1H), 2.08-2.07 (m, 1H), 1.81-1.69 (m, 2H), 1.67-1.60 (m, 1H).

5-(5-Chloro-2-((S)-3-(morpholinomethyl)-1,2,3,4-tetrahydroisoquinoline-2-carbonyl)phenyl)-N-(3-methoxy-2-methylbenzyl)-1,2-dimethyl-N-(1-(tetrahydro-2H-pyran-2-yl)-1H-indazol-5-yl)-1H-pyrrole-3-carboxamide (P53)

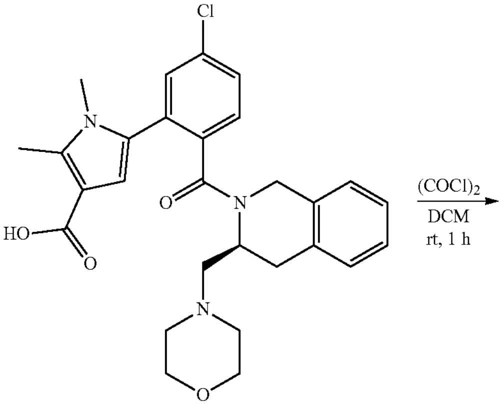

P48

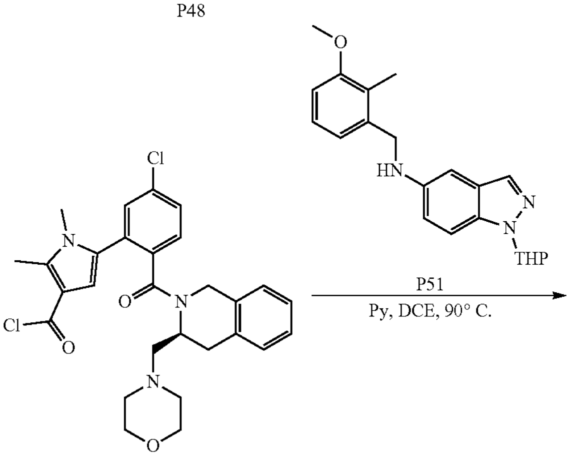

P52

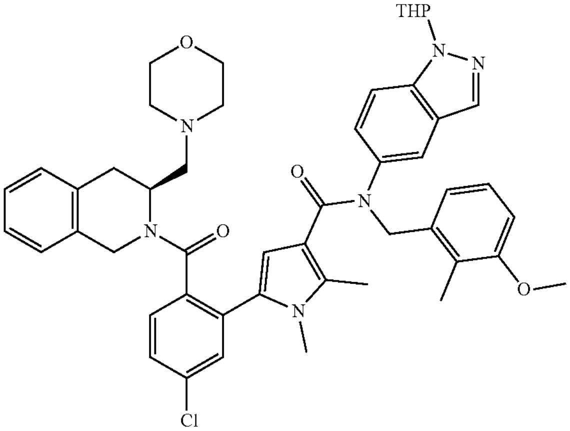

P53

Preparation 52. (S)-5-(5-Chloro-2-(3-(morpholinomethyl)-1,2,3,4-tetrahydroisoquinoline-2-carbonyl)phenyl)-1,2-dimethyl-1H-pyrrole-3-carbonyl chloride (P52). To a solution of P48 (200 mg, 0.390 mmol) in DCM (10 mL) was added oxalyl chloride (67 µl, 0.78 mmol) at rt. The mixture was stirred at rt for 1 h. The mixture was concentrated to remove solvent to give P52 as a crude product which was used in next step without purification Preparation 53. 5-(5-Chloro-2-((S)-3-(morpholinomethyl)-1,2,3,4-tetrahydroisoquinoline-2-carbonyl)phenyl)-N-(3-methoxy-2-methylbenzyl)-1,2-dimethyl-N-(1-(tetrahydro-2H-pyran-2-yl)-1H-indazol-5-yl)-1H-pyrrole-3-carboxamide (P53)

To a solution of P51 (137 mg, 0.390 mmol) and P52 (0.390 mmol) in dichloroethane (6.5 mL) was added pyridine (94 µl, 1.17 mmol) at rt. The mixture was stirred at 90° C. for overnight. The reaction was quenched with $NaHCO_{3\,(aq)}$ and extracted with DCM. The organic layers were dried over $Na_2SO_{4(s)}$, filtered and concentrated. The crude was purified by silica gel column chromatography (0-10% MeOH in dichloromethane) to give P53 (212 mg, 65%). $^1H$ NMR (400 MHz, $CDCl_3$), δ: 7.89-7.84 (m, 1H), 7.42-7.28 (m, 2H), 7.23-6.90 (m, 8H), 6.81-6.66 (m, 4H), 5.47 (br s, 1H), 5.15-4.88 (m, 4H), 3.82-3.79 (m, 3H), 3.72-3.61 (m, 3H), 3.49-3.47 (m, 2H), 3.30-3.23 (m, 2H), 3.05 (s, 2H), 2.78-2.72 (m, 1H), 2.64-2.57 (m, 1H), 2.54-2.48 (m, 2H), 2.37-2.28 (m, 2H), 2.24 (br m, 2H), 2.17 (br m, 1H), 2.07 (s, 2H), 2.04 (br s, 3H), 1.99-1.82 (m, 3H), 1.68 (br s, 3H); LCMS(ESI) m/z 841.5 $[M+H]^+$.

2-(((1-(Tetrahydro-2H-pyran-2-yl)-1H-indazol-5-yl)amino) methyl)benzonitrile (P54)

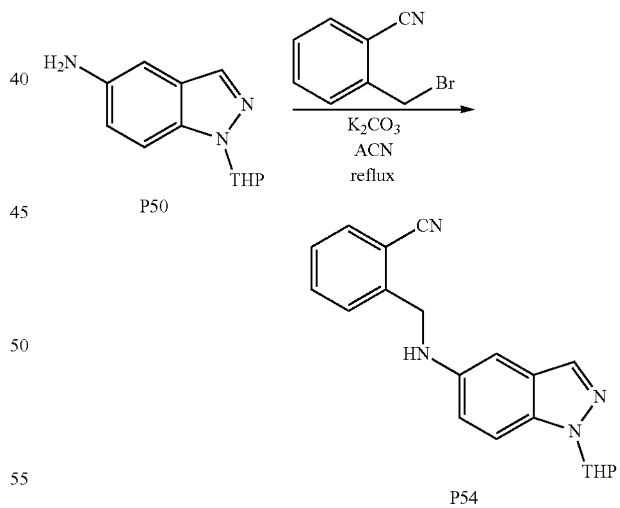

P50

P54

Preparation 54. 2-(((1-(tetrahydro-2H-pyran-2-yl)-1H-indazol-5-yl)amino) methyl)benzonitrile (P54)

To a solution of P50 (274 mg, 1.26 mmol) and 2-(bromomethyl)benzonitrile (247 mg, 1.26 mmol) in acetonitrile (18 mL) was added potassium carbonate (261 mg, 1.87 mmol). The mixture was stirred at 90° C. for 16 h. The mixture was concentrated to remove solvent. The residue was purified by silica gel column chromatography (10-70%

EtOAc in n-hexane) to give P54 (307 mg, 73%). $^1$H NMR (400 MHZ, DMSO-$d_6$), δ:7.79 (s, 1H), 7.68-7.66 (m, 1H), 7.55-7.32 (m, 4H), 6.88-6.85 (m, 1H), 6.69 (d, J=2.4 Hz, 1H), 5.61 (dd, J=9.2, 2.8 Hz, 1H), 4.60 (s, 2H), 4.02-3.98 (m, 1H), 3.74-3.68 (m, 1H), 2.56-2.47 (m, 1H), 2.15-2.10 (m, 2H), 1.76-1.60 (m, 3H); LRMS(ESI) m/z 333.6 [M+H]$^+$.

5-(5-Chloro-2-((S)-3-(morpholinomethyl)-1,2,3,4-tetrahydroisoquinoline-2-carbonyl)phenyl)-N-(2-cyanobenzyl)-1,2-dimethyl-N-(1-(tetrahydro-2H-pyran-2-yl)-1H-indazol-5-yl)-1H-pyrrole-3-carboxamide (P55)

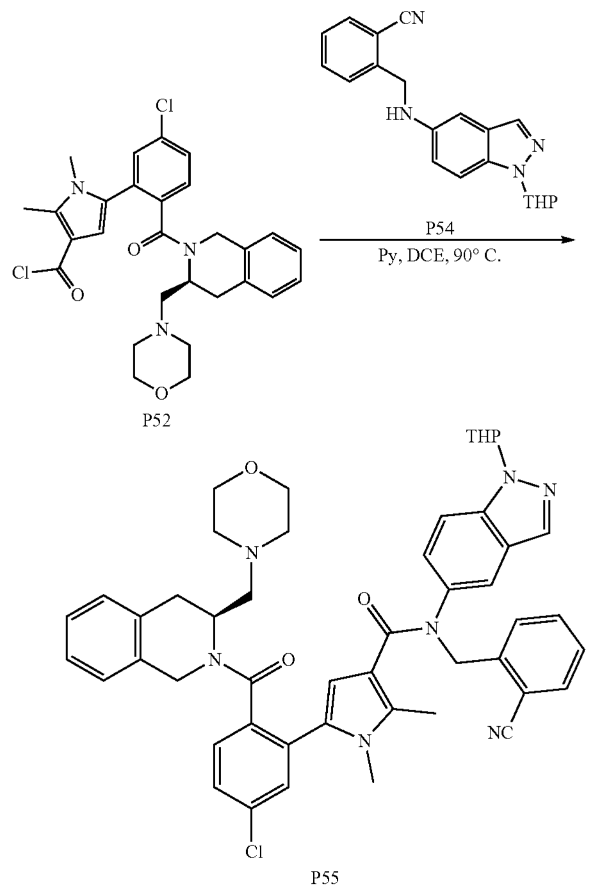

P52

P55

Preparation 55. 5-(5-Chloro-2-((S)-3-(morpholinomethyl)-1,2,3,4-tetrahydroisoquinoline-2-carbonyl)phenyl)-N-(2-cyanobenzyl)-1,2-dimethyl-N-(1-(tetrahydro-2H-pyran-2-yl)-1H-indazol-5-yl)-1H-pyrrole-3-carboxamide (P55)

To a solution of P54 (143 mg, 0.430 mmol) and P52 (crude, 0.390 mmol) in dichloroethane (6.5 mL) was added pyridine (94 μL, 1.17 mmol) at rt. The mixture was stirred at 90° C. for overnight. The reaction was quenched with $NaHCO_{3(aq)}$ and extracted with DCM. The organic layers were dried over $Na_2SO_{4(s)}$, filtered, and concentrated. The crude was purified by silica gel column chromatography (0-10% MeOH in dichloromethane) to give P55 (40 mg, 12%). $^1$H NMR (400 MHz, $CDCl_3$), δ: 7.88-7.81 (m, 1H), 7.66-7.60 (m, 1H), 7.56-7.48 (m, 3H), 7.42-7.33 (m, 1H), 7.31-7.27 (m, 2H), 7.24-7.16 (m, 3H), 7.15-7.08 (m, 3H), 7.00-6.87 (m, 2H), 6.82-6.77 (m, 2H), 5.68-5.58 (m, 1H), 5.37-5.27 (m, 1H), 5.11-4.96 (m, 2H), 4.26-4.09 (m, 1H), 3.98-3.86 (m, 2H), 3.72-3.62 (m, 6H), 3.54-3.47 (m, 1H), 3.26-3.22 (m, 2H), 3.10 (s, 3H), 2.81-2.40 (m, 2H), 2.32-2.25 (m, 4H), 2.16-1.94 (m, 1H), 1.77-1.64 (m, 2H), 1.31-1.23 (m, 1H); LRMS(ESI) m/z 822.4 [M+H]$^+$.

N-(2-Methoxybenzyl)-1-(tetrahydro-2H-pyran-2-yl)-1H-indazol-5-amine (P56)

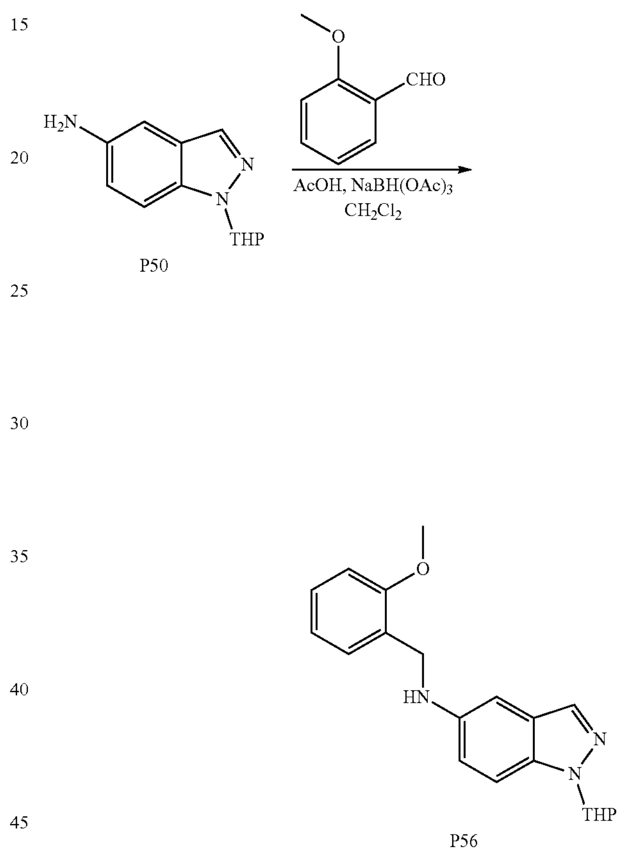

P50

P56

Preparation 56. N-(2-methoxybenzyl)-1-(tetrahydro-2H-pyran-2-yl)-1H-indazol-5-amine (P56)

To a solution of P50 (600 mg, 2.77 mmol) and 2-methoxybenzaldehyde (315 mg, 2.31 mmol) in DCM (15 mL) was added AcOH (1 drop) and sodium triacetoxyborohydride (1.17 g, 5.54 mmol). The mixture was stirred at rt for overnight and concentrated to remove solvent. The residue was purified by silica gel column chromatography (10-80% EtOAc in n-hexane) to give P56 (850 mg, 91%). $^1$H NMR (400 MHZ, $CDCl_3$), δ: 7.80 (s, 1H), 7.38 (d, J=8.8 Hz, 1H), 7.31-7.21 (m, 2H), 6.90-6.80 (m, 4H), 5.61 (dd, J=9.2, 2.8 Hz, 1H), 4.31 (s, 2H), 4.01-3.97 (m, 1H), 3.86 (s, 3H), 3.73-3.67 (m, 1H), 2.53-2.49 (m, 1H), 2.16-2.00 (m, 2H), 1.76-1.60 (m, 3H); LCMS(ESI) m/z 338.2 [M+H]$^+$.

5-(5-Chloro-2-((S)-3-(morpholinomethyl)-1,2,3,4-tetrahydroisoquinoline-2-carbonyl)phenyl)-N-(2-methoxybenzyl)-1,2-dimethyl-N-(1-(tetrahydro-2H-pyran-2-yl)-1H-indazol-5-yl)-1H-pyrrole-3-carboxamide (P57)

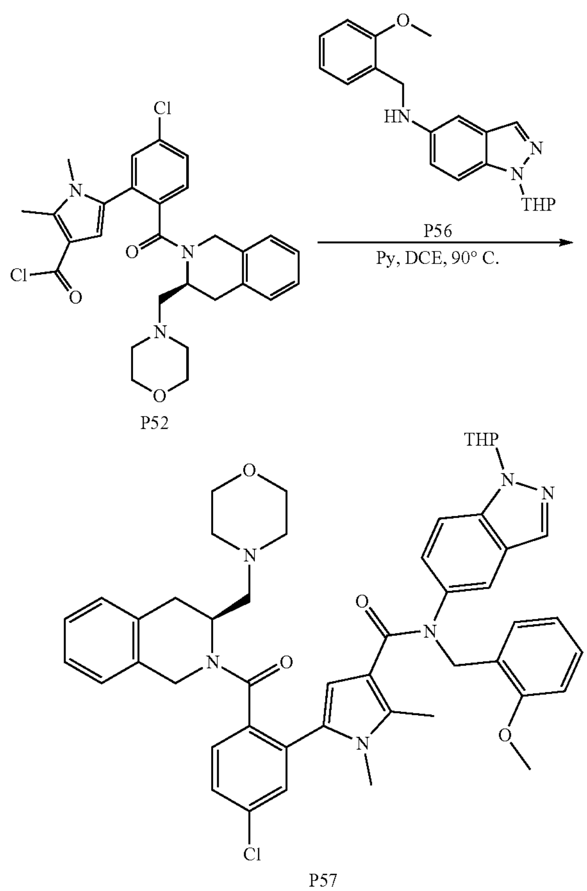

P52

P57

Preparation 57. 5-(5-Chloro-2-((S)-3-(morpholinomethyl)-1,2,3,4-tetrahydroisoquinoline-2-carbonyl)phenyl)-N-(2-methoxybenzyl)-1,2-dimethyl-N-(1-(tetrahydro-2H-pyran-2-yl)-1H-indazol-5-yl)-1H-pyrrole-3-carboxamide (P57)

To a solution of N-(2-methoxybenzyl)-1-(tetrahydro-2H-pyran-2-yl)-1H-indazol-5-amine (P56, 238 mg, 0.71 mmol) and pyridine (140 mg, 1.77 mmol) in 1,2-dichloroethane (3.0 mL) was added a solution of P52 (311 mg, 0.59 mmol) in 1,2-dichloroethane (6.0 mL). The reaction was stirred at 80° C. for 16 h. The solution was quenched by saturated $NaHCO_{3(aq)}$ solution and extracted with EtOAc. The combined organic layers were dried over $Na_2SO_{4(s)}$, filtered, and concentrated to give a residue. The residue was purified by silica-gel column chromatography (dichloromethane: methanol=20:1) to give P57 (315 mg, 65% yield) as an orange solid. LCMS(ESI) m/z calcd for $C_{48}H_{51}ClN_6O_5$ 826.36; found, 827.4 $[M+H]^+$.

5-[5-chloro-4-cyano-2-[(3S)-3-(morpholinomethyl)-3,4-dihydro-1H-isoquinoline-2-carbonyl]phenyl]-N-[(3-methoxy-2-methyl-phenyl)methyl]-1,2-dimethyl-N-[4-(2-trimethylsilylethoxymethoxy)phenyl]pyrrole-3-carboxamide (P61)

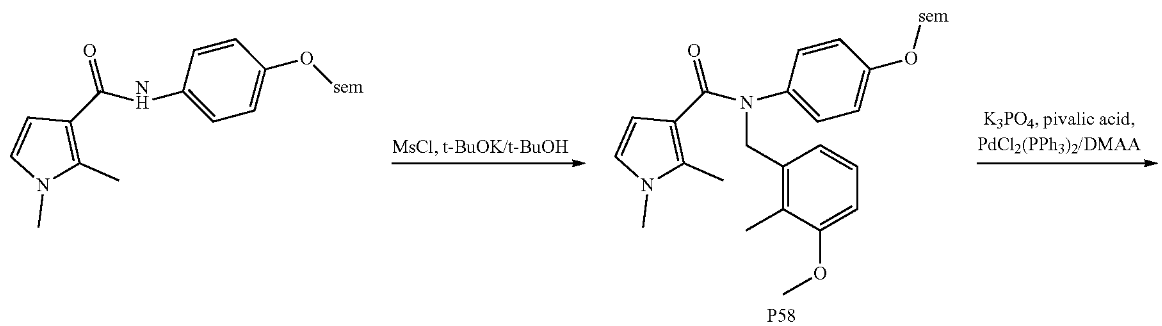

P58

-continued

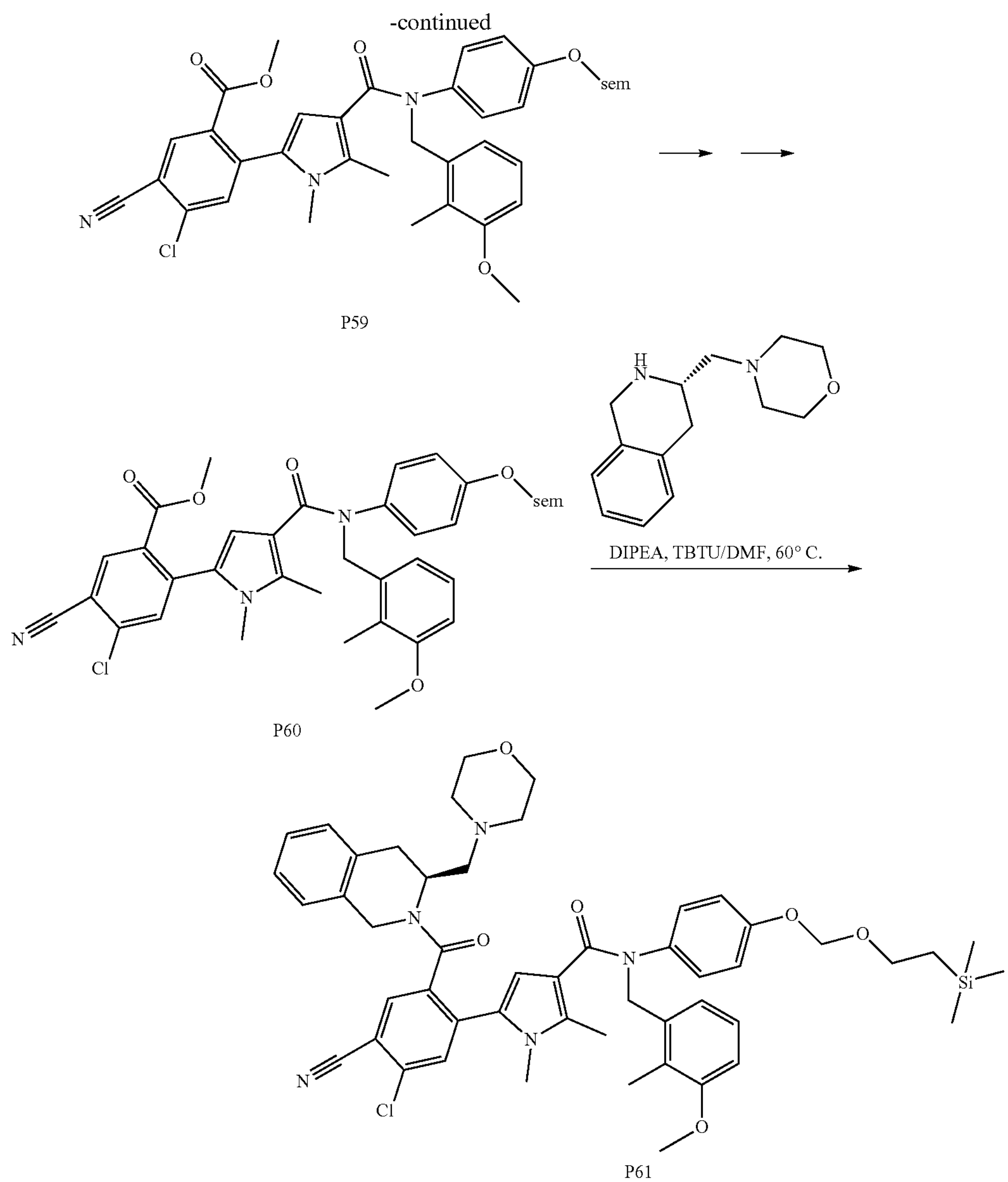

P59

P60

P61

Preparation 58. $N^3$-(3-methoxy-2-methylbenzyl)-1,2-dimethyl-$N^3$-(4-[2-(1,1,1-trimethylsilylethoxy] methoxyphenyl)-1H-pyrrole-3-carboxamide (P58)

A mixture of 1,2-dimethyl-$N^3$-(4-[2-(1,1,1-trimethylsilylethoxy]methoxyphenyl)-1H-pyrrole-3-carboxamide (0.85 g, 2.3 mmol), tert-BuOK (1 g, 8.9 mmol), and tert-BuOH (10 mL) was stirred at 60° C., then 3-methoxy-2-methylbenzyl methanesulfonate (1.1 g, 4.4 mmol) was added. The reaction mixture was stirred at 60° C. for 3 h and then partitioned between EtOAc and water. The organic layer was separated, washed with brine, dried over anhydrous sodium sulfate, filtered, and concentrated under reduced pressure. The residue was subjected to a silica gel flash chromatography eluting with a mixture of EtOAc (0→100%) and DCM to afford 0.95 g (82%) of the title compound. LCMS(ESI+) m/z 495 $[M+H]^+$.

Preparation 59. Methyl 4-chloro-5-cyano-2-4-[((3-methoxy-2-methylbenzyl)-4-[2-(1,1,1-trimethylsilylethoxy]methoxyanilino) carbonyl]-1,5-dimethyl-1H-pyrrol-2-ylbenzoate (P59)

A mixture of P58 (0.27 g, 0.5 mmol), methyl-2-bromo-4-chloro-5-cyanobenzoate (P63, 0.3 g, 1 mmol), $K_3PO_4$ (0.58 g, 2.7 mmol), pivalic acid (17 mg, 0.3 eq), PdC12 $(PPh_3)_2$ (77 mg, 0.2 eq) in N,N-dimethylacetamide (10 mL) was heated to 135° C. The resulting mixture was stirred at 135° C. for 30 min, then the reaction mixture was cooled to ambient temperature. Upon completion of the reaction, the mixture was diluted with water and EtOAc. The organic layer was separated, washed with brine, dried over dried over anhydrous sodium sulfate, filtered, and concentrated under reduced pressure. The residue was subjected to a silica gel flash chromatography eluting with a mixture of EtOAc (0→20%) and DCM to afford 70 mg (19%) of the title compound. LCMS (ESI+) m/z 689 $[M+H]^+$.

Preparation 60. 4-Chloro-5-cyano-2-4-[((3-methoxy-2-methylbenzyl)-4-[2-(1,1,1-trimethylsilylethoxy]methoxyanilino) carbonyl]-1,5-dimethyl-1H-pyrrol-2-ylbenzoic acid (P60)

A solution of P59 (70 mg, 0.1 mmol) and NaOH (20 mg, 5 eq) in a mixture of MeOH (2 mL) and water (0.2 mL) was stirred at ambient temperature for 12 h. The volatiles were removed under reduced pressure, and water (2 mL) was added to the residue. The solution was acidified with 6M HCl to pH 1 and extracted with DCM (2×3 mL), the combined organic layers were dried over anhydrous sodium sulfate and evaporated to dryness under reduced pressure to afford 67 mg (99%) of the title compound that was pure enough to be used for the next step. LCMS(ESI+) m/z 675 $[M+H]^+$ Preparation 61. 5-(5-Chloro-4-cyano-2-[(3R)-3-(morpholinomethyl)-3,4-dihydro-2 (1H)-isoquinolinyl]carbonylphenyl)-$N^3$-(3-methoxy-2-methylbenzyl)-1,2-dimethyl-$N^3$-(4-[2-(1,1,1-trimethylsilylethoxy]methoxyphenyl)-1H-pyrrole-3-carboxamide (P61)

A mixture of P60 (67 mg, 0.1 mmol), P43 (40 mg, 0.11 mol), DIPEA (0.04 mL, 0.15 mmol), TBTU (55 mg, 0.11 mmol), and DMF (2 mL) was stirred at 60° C. overnight. The reaction mixture was diluted with water (4 mL) and EtOAc (20 mL). The organic layer was separated, washed with brine, dried with anh. sodium sulfate, filtered, and concentrated under reduced pressure to afford 81 mg of the crude compound that was pure enough to be used for the next step. LCMS(ESI+) m/z 889 $[M+H]^+$

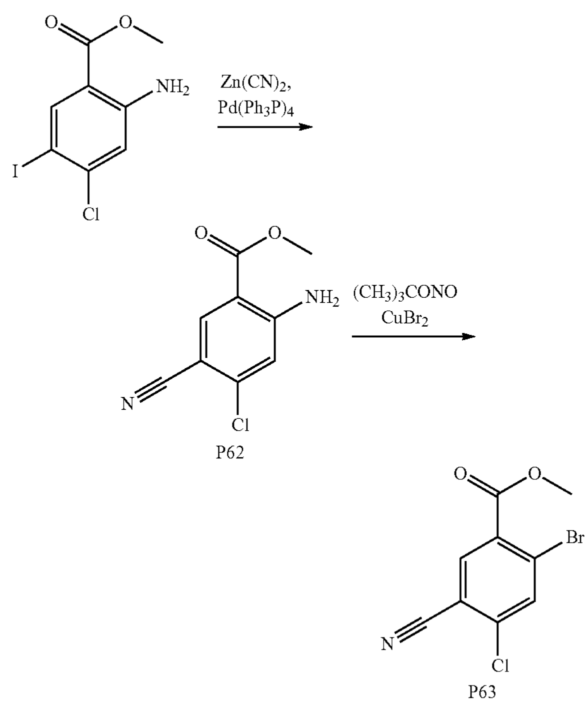

P62

P63

Preparation 62. Methyl 2-amino-4-chloro-5-cyano-benzoate (P62)

To a stirred solution of methyl 2-amino-4-chloro-5-(13-iodanylidynemethyl)benzoate (1 g, 3.2 mmol) in DMF (10 mL) $Zn(CN)_2$ (0.23 g, 1.97 mmol) and $Pd(Ph_3P)_4$ (0.19 g, 0.16 mmol) were added. Then reaction mixture was stirred at 120° C. for 2 h under microwave irradiation and then treated with water (20 mL) and extracted with $Et_2O$+EtOAc. The combined organic layers were dried over anhydrous sodium sulfate, filtered and the filtrate was evaporated under reduced pressure. The residue was subjected to a silica gel flash chromatography eluting with a mixture of DCM to afford 600 mg (89%) of compound P62.

Preparation 63. Methyl 2-bromo-4-chloro-5-cyano-benzoate (P63)

To a stirred solution of P62 (150 mg, 0.7 mmol) in $CH_3CN$(3 mL) $(CH_3)_3CNO_2$ (0.182 g, 1.8 eq) and CuBr2 (0.15 ml, 1.8 eq) were added. Then reaction mixture was stirred at rt for 3 h under microwave irradiation and then treated with water (1 mL) and extracted with EtOAc. The combined organic layers were dried over anh. sodium sulfate, filtered and the filtrate was evaporated under reduced pressure. The residue was subjected to a silica gel flash chromatography eluting with a mixture of $CCl_4$: DCM to afford 0.27 g (99%) of the title compound.

2-[4-({[4-(benzyloxy)phenyl]amino}carbonyl)-1,5-dimethyl-1H-pyrrol-2-yl]-4-chloro-5-methoxybenzoic acid (P65)

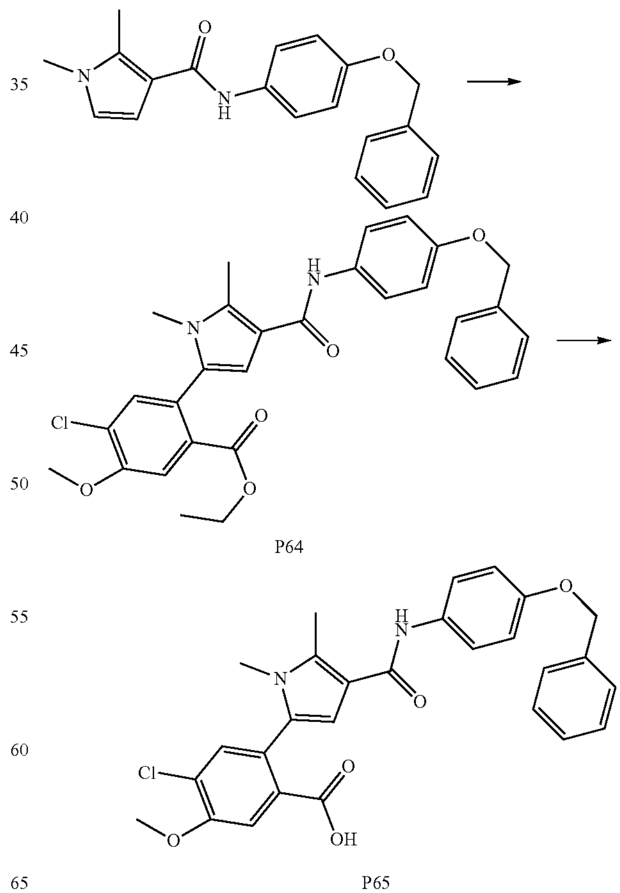

P64

P65

Preparation 64. Ethyl 2-[4-({[4-(benzyloxy)phenyl] amino}carbonyl)-1,5-dimethyl-1H-pyrrol-2-yl]-4-chloro-5-methoxybenzoate (P64)

A mixture of N-[4-(benzyloxy)phenyl]-1,2-dimethyl-1H-pyrrole-3-carboxamide (P15, 500 mg, 1.6 mmol), methyl 2-bromo-4-chloro-5-methoxybenzoate (870 mg, 3.1 mmol), $K_3PO_4$ (1.6 g, 7.8 mmol), pivalic acid (50 mg, 0.4 mmol) in N,N-dimethylacetamide (10 mL) was stirred at 135° C. for 15 min, then PdC12 $(PPh_3)_2$ (0.22 g, 0.3 mmol) was added. The resulting mixture was stirred at 135° C. for 30 min. Upon completion of the reaction the mixture was diluted with water (20 mL) and EtOAC (20 mL). The organic layer was separated, washed with brine, dried over sodium sulfate, filtered, and concentrated under reduced pressure. The residue was subjected to silica flash chromatography eluting with a mixture of EtOAc (0→20%) and DCM to afford 150 mg (19%) of the title compound.

Preparation 65. 2-[4-({[4-(Benzyloxy)phenyl] amino}carbonyl)-1,5-dimethyl-1H-pyrrol-2-yl]-4-chloro-5-methoxybenzoic acid (P65)

A solution of P64 (150 mg, 0.29 mmol) and NaOH (58 mg, 1.4 mol) in a mixture of EtOH (10 mL) and water (2 mL) was stirred at ambient temperature for 12 h. The volatiles were removed under reduced pressure, and water (20 mL) was added to the residue. The solution was acidified with 6M HCl to pH 1 and extracted with DCM (2×10 mL), the combined organic layers were dried over $Na_2SO_4$ and evaporated to dryness under reduced pressure to afford 130 mg (90%) of the title compound that was pure enough to be used in the next step.

N-[4-(benzyloxy)phenyl]-5-(5-chloro-4-methoxy-2-{[(3S)-3-(morpholin-4-ylmethyl)-3,4-dihydroisoquinolin-2 (1H)-yl]carbonyl}phenyl)-1,2-dimethyl-1H-pyrrole-3-carboxamide (P66)

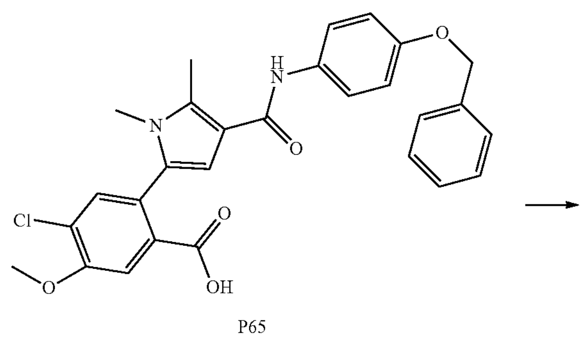

P65

-continued

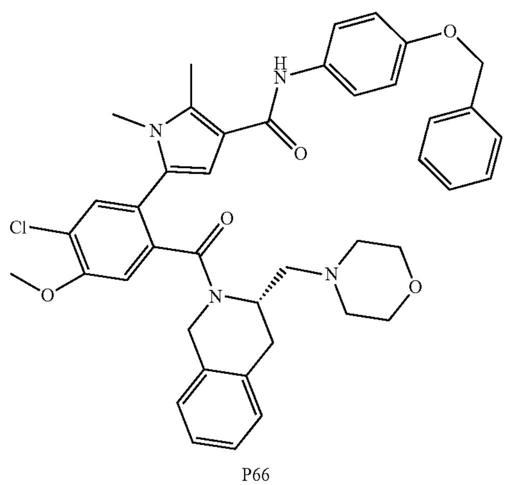

P66

Preparation 66. N-[4-(benzyloxy)phenyl]-5-(5-chloro-4-methoxy-2-{[(3S)-3-(morpholin-4-ylmethyl)-3,4-dihydroisoquinolin-2 (1H)-yl] carbonyl}phenyl)-1,2-dimethyl-1H-pyrrole-3-carboxamide (P66)

A mixture of P65 (130 mg, 0.26 mmol), P43 (72 mg, 0.3 mmol), DIPEA (0.07 mL, 0.39 mmol), and TBTU (100 mg, 0.3 mmol), and DMF (5 mL) was stirred at 60° C. overnight. The reaction mixture was diluted with water (20 mL) and EtOAc (10 ml). The organic layer was separated, washed with brine, dried over $Na_2SO_4$, filtered, and concentrated under reduced pressure. The residue was subjected to silica flash chromatography eluting with a mixture of EtOAc (0→100%) and DCM to afford 80 mg (43%) of the title compound.

N-[4-(benzyloxy)phenyl]-5-(5-chloro-4-methoxy-2-{[(3S)-3-(morpholin-4-ylmethyl)-3,4-dihydroisoquinolin-2 (1H)-yl]carbonyl}phenyl)-1,2-dimethyl-1H-pyrrole-3-carboxamide (P67)

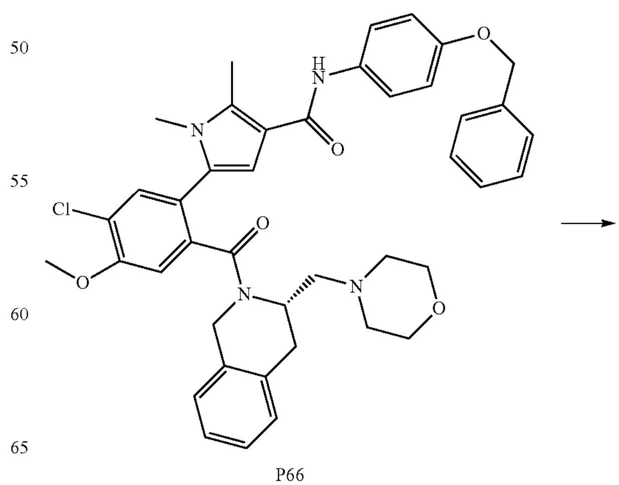

P66

-continued

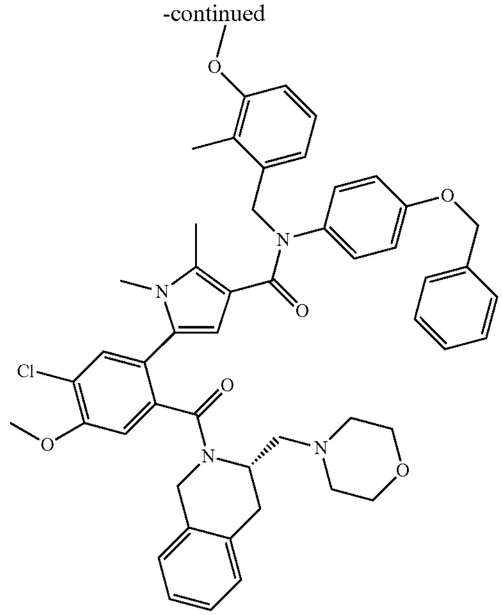

P67

Preparation 67. N-[4-(benzyloxy)phenyl]-5-(5-chloro-4-methoxy-2-{[(3S)-3-(morpholin-4-ylmethyl)-3,4-dihydroisoquinolin-2 (1H)-yl] carbonyl}phenyl)-1,2-dimethyl-1H-pyrrole-3-carboxamide (P67)

A mixture of P66 (80 mg, 0.1 mmol), tert-BuOK (50 mg 0.4 mmol), and tert-BuOH (5 mL) was stirred at 50° C. for 30 min, then 3-methoxy-2-methylbenzyl methanesulfonate (46 mg, 0.2 mmol) was added. The reaction mixture was stirred at 60° C. for 1 h and then partitioned between EtOAc and water. The organic layer was separated, washed with brine, dried over $Na_2SO_4$, filtered, and concentrated under reduced pressure. The residue was subjected to silica flash chromatography eluting with a mixture of EtOAc (0→100%) and DCM to afford 80 mg (84%) of the title compound.

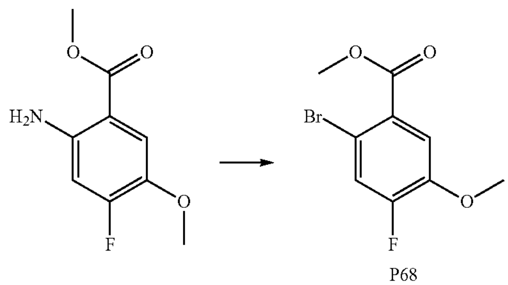

P68

Preparation 68. Methyl 2-bromo-4-fluoro-5-methoxybenzoate (P68)

To a solution of methyl 2-amino-4-fluoro-5-methoxybenzoate (0.6 g, 0.003 mol) and tert-butyl nitrite (0.55 g, 0.0054 mol) in acetonitrile (20 ml) was added CuBr2 (1.2 g, 0.0054 mol) at 0° C. and the reaction mixture was stirred at rt overnight. The reaction mixture was treated with water and extracted with EtOAc. The combined organic layers were dried over anh. sodium sulfate, filtered and the filtrate was evaporated under reduced pressure The residue was subjected to a silica gel flash chromatography eluting with a of DCM to afford 228 mg (29%) of the title compound. LCMS (ESI+) m/z 264 $[M+H]^+$. $^1H$ NMR (400 MHZ, $CDCl_3$), δ: 7.70 (d, J=5.4 Hz, 1H), 7.54 (d, J=4. 8 Hz, 1H), 3.88 (s, 3H), 3.86 (s, 3H).

2-[4-({[4-(benzyloxy)phenyl]amino}carbonyl)-1,5-dimethyl-1H-pyrrol-2-yl]-4-fluoro-5-methoxybenzoic acid (P70)

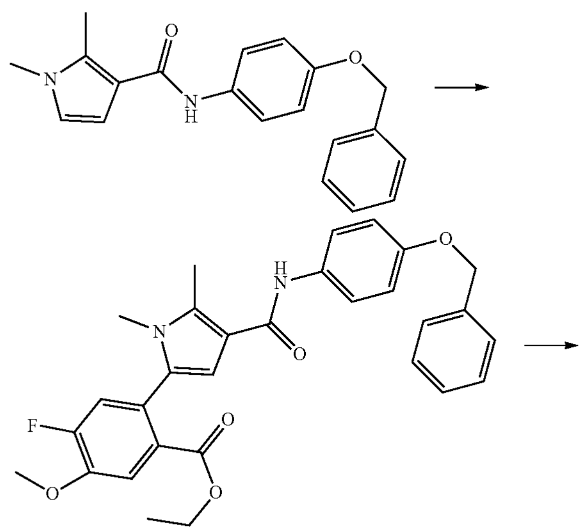

P69

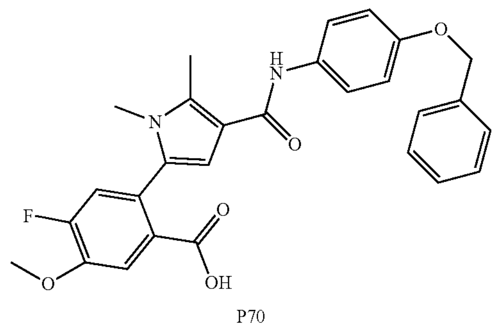

P70

Preparation 69. Ethyl 2-[4-({[4-(benzyloxy)phenyl] amino}carbonyl)-1,5-dimethyl-1H-pyrrol-2-yl]-4-chloro-5-methoxybenzoate (P69)

A mixture of P15 (220 mg, 0.86 mmol), methyl 2-bromo-4-fluoro-5-methoxybenzoate (228 mg, 0.86 mmol), $K_3PO_4$ (919 mg, 3.44 mmol), pivalic acid (26 mg, 0.2 mmol) in N,N-dimethylacetamide (10 mL) was stirred at 135° C. for 15 min, then PdC12 $(PPh_3)_2$ (150 mg, 0.17 mmol) was added. The resulting mixture was stirred at 135° C. for 30 min. Upon completion of the reaction the mixture was diluted with water (20 mL) and EtOAC (20 mL). The organic layer was separated, washed with brine, dried over sodium sulfate, filtered, and concentrated under reduced pressure. The residue was subjected to silica flash chromatography eluting with a mixture of EtOAc (0→20%) and DCM to afford 180 mg (41%) of the title compound.

Preparation 70. 2-[4-({[4-(Benzyloxy)phenyl] amino}carbonyl)-1,5-dimethyl-1H-pyrrol-2-yl]-4-fluoro-5-methoxybenzoic acid (P70)

A solution of P69 (365 mg, 0.729 mmol) and LiOH (174 mg, 7.29 mmol) in a mixture of THF (16 mL) and water (4 mL) was stirred at ambient temperature for 12 h. The volatiles were removed under reduced pressure, and water (20 mL) was added to the residue. The solution was acidified with 6M HCl to pH 1 and extracted with DCM (2×10 mL), the combined organic layers were dried over $Na_2SO_4$ and evaporated to dryness under reduced pressure to afford 160 mg (55%) of the title compound that was pure enough to be used further in the next step.

N-[4-(benzyloxy)phenyl]-5-(5-fluoro-4-methoxy-2-{[(3S)-3-(morpholin-4-ylmethyl)-3,4-dihydroisoquinolin-2 (1H)-yl]carbonyl}phenyl)-1,2-dimethyl-1H-pyrrole-3-carboxamide (P71)

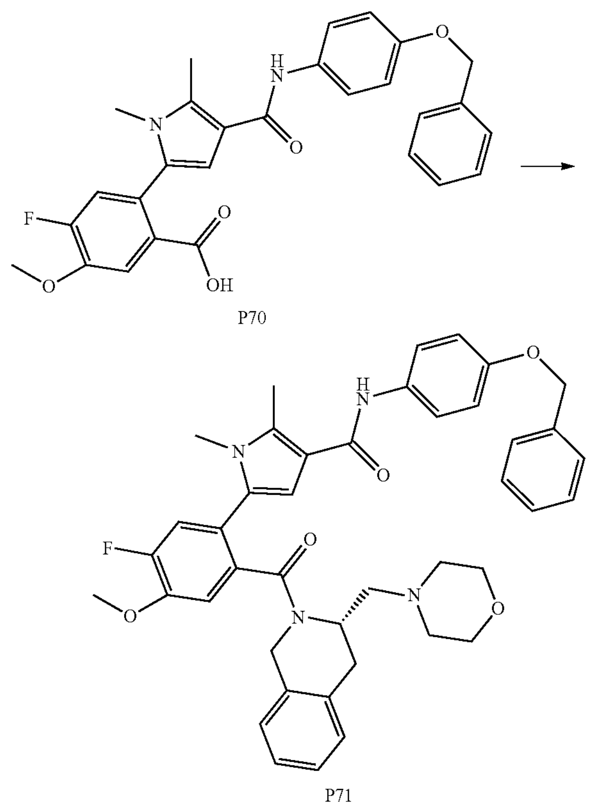

P70

P71

Preparation 71. N-[4-(benzyloxy)phenyl]-5-(5-fluoro-4-methoxy-2-{[(3S)-3-(morpholin-4-ylmethyl)-3,4-dihydroisoquinolin-2 (1H)-yl] carbonyl}phenyl)-1,2-dimethyl-1H-pyrrole-3-carboxamide (P71)

A mixture of P70 (150 mg, 0.31 mmol), P43 (86 mg, 0.37 mmol), DIPEA (0.08 mL, 0.46 mmol), and TBTU (118 mg, 0.37 mmol), and DMF (8 mL) was stirred at 60° C. overnight. The reaction mixture was diluted with water (20 mL) and EtOAc (10 mL). The organic layer was separated, washed with brine, dried over $Na_2SO_4$, filtered, and concentrated under reduced pressure. The residue was subjected to silica flash chromatography eluting with a mixture of EtOAc (0-+100%) and DCM to afford 50 mg (23%) of the title compound.

N-[4-(benzyloxy)phenyl]-5-(5-fluoro-4-methoxy-2-{[(3S)-3-(morpholin-4-ylmethyl)-3,4-dihydroisoquinolin-2 (1H)-yl]carbonyl}phenyl)-1,2-dimethyl-1H-pyrrole-3-carboxamide (P72)

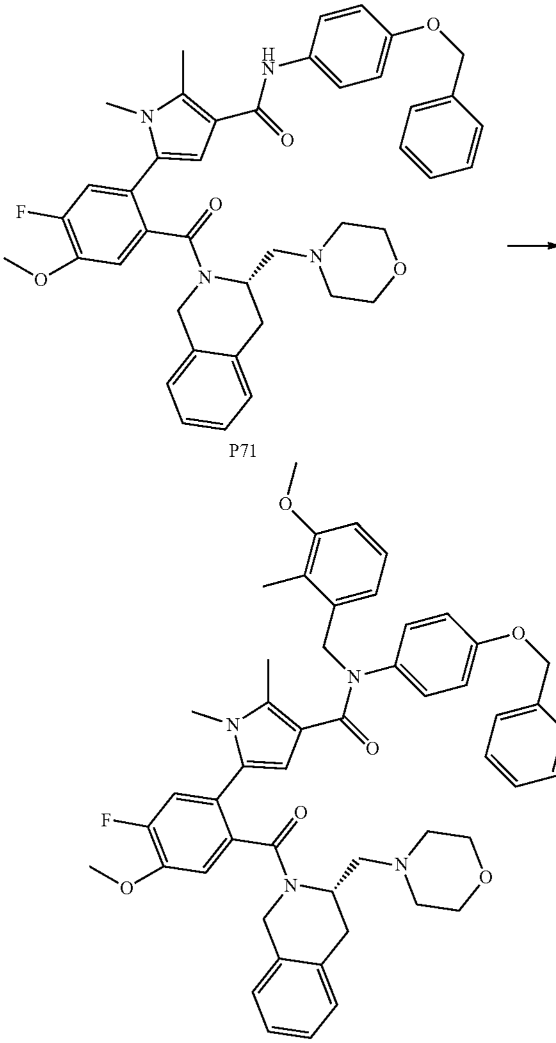

P71

P72

Preparation 72 N-[4-(benzyloxy)phenyl]-5-(5-fluoro-4-methoxy-2-{[(3S)-3-(morpholin-4-ylmethyl)-3,4-dihydroisoquinolin-2 (1H)-yl] carbonyl}phenyl)-1,2-dimethyl-1H-pyrrole-3-carboxamide (P72)

A mixture of P71 (50 mg, 0.071 mmol), tert-BuOK (32 mg, 0.28 mmol), and tert-BuOH (5 mL) was stirred at 50° C. for 30 min, then 3-methoxy-2-methylbenzyl methanesulfonate (33 mg, 0.14 mmol) was added. The reaction mixture was stirred at 60° C. for 1 h and then partitioned between EtOAc and water. The organic layer was separated, washed with brine, dried over $Na_2SO_4$, filtered, and concentrated under reduced pressure. The residue was subjected to silica flash chromatography eluting with a mixture of EtOAc (0→100%) and DCM to afford 33 mg (55%) of the title compound.

N-(4-chlorophenyl)-1,2-dimethyl-1H-pyrrole-3-carboxamide (P73)

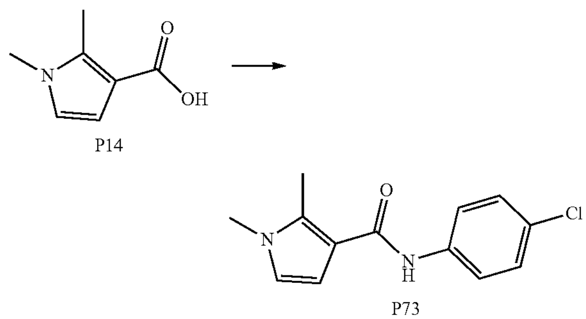

P14

P73

Preparation 73. N-(4-chlorophenyl)-1,2-dimethyl-1H-pyrrole-3-carboxamide (P73)

To a stirred solution of P14 (1.0 g, 7.2 mmol) in pyridine (5 mL) $SOCl_2$ (0.55 mL, 7.6 mmol) was added dropwise at 0° C. and the reaction mixture was stirred at 0° C. for 3 h. Then (4-chlorophenyl)amine (0.85 g, 7.2 mmol) in DIPEA (1.4 mL, 7.96 mmol) was added dropwise, keeping the temperature at 0° C. After the reaction was warmed up to ambient temperature, then stirred at ambient temperature for 16 h. Volatiles were removed under reduced pressure. The residue was diluted with water and Et20. The organic layer separated, washed with water, brine, dried over dried over anh. sodium sulfate, filtered, and concentrated under reduced pressure. The residue was subjected to a silica gel flash chromatography eluting with a mixture of EtOAc (0→20%) and DCM to afford 850 mg (50%) of the title compound.

Methyl 2-bromo-5-cyano-4-fluorobenzoate (P77)

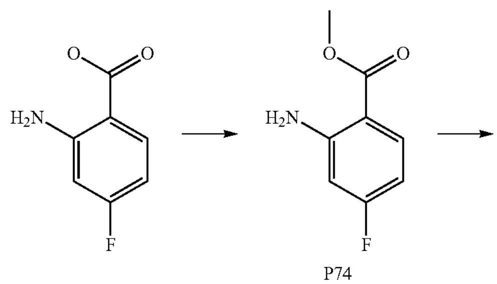

P74

-continued

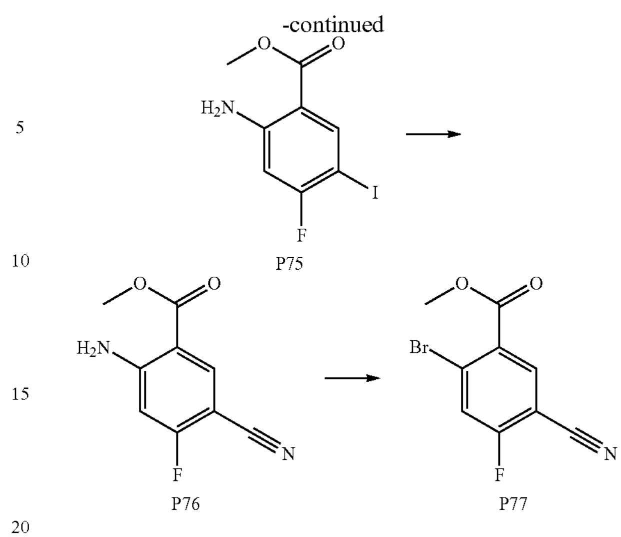

P75

P76

P77

Preparation 74. Methyl 2-amino-4-fluorobenzoate (P74)

$SOCl_2$ (15.52 mL, 0.21 mol) was added to a solution of 2-amino-4-fluoro-benzoic acid (30.0 g, 0.19 mol) in MeOH (0.3 L) in 15 min at 0-5° C. After completion of the addition, the reaction was heated under reflux for additional 16 h. MeOH was evaporated under reduced pressure. To the residue was added 2M aqueous $Na_2CO_3$ (300 mL), and the resulting mixture was extracted with EtOAc (400 mL). The combined organic layers were washed with brine (400 mL), dried over anhydrous $Na_2SO_4$, filtered, and concentrated to afford 18.1 g (56%) of the compound P74.

Preparation 75. Methyl 2-amino-4-fluoro-5-iodobenzoate (P75)

Potassium iodide (10.7 g, 64.5 mmol) in water (22.5 mL) was added dropwise into acetic acid (203.2 mL) containing compound P74 (10 g, 64.5 mmol), sodium periodate (13.7 g, 64.5 mmol) and sodium chloride (0.69 g, 129 mmol) over a 2 h period. The mixture was left stirring at rt overnight, after which was poured into ice water (30 mL), quenched with excess of sodium thiosulfate solution and the solution extracted with DCM (6×50 mL). The pH of the solution was adjusted to 5 with addition of 1N NaOH. The solution was decolorized with addition of $NaHSO_3$ and DCM layer was evaporated to yield a brownish solid. The solid was washed with water and after drying in the vacuum oven 12.56 g (69%) of P75 as brown solid.

Preparation 76. Methyl 2-amino-5-cyano-4-fluorobenzoate (P76)

P75 (1.25 g, 4.14 mmol) was dissolved in N,N-dimethylformamide (10 ml), zinc cyanide (0.268 g, 2.4 mmol) and tetrakis(triphenylphosphine) palladium (0.254 g, 0.2 mmol) were added and reacted at rt for 0.5 h, 120° C. for 2 h in MW. After reaction was completed, hot reaction mixture was filtered, The filtrate was poured into the ice water and formed precipitate was filtered off, The precipitate was heated with a small amount of n-hexane (3 mL) and the target product was filtered off to give P76 (0.6 g, 74.2%).

Preparation 77. Methyl 2-bromo-5-cyano-4-fluorobenzoate (P77)

To a solution of methyl 2-amino-5-cyano-4-fluorobenzoate (0.4 g, 2.06 mmol) and tert-butyl nitrite (0.32 g, 3.12 mmol) in acetonitrile (7 ml) was added CuBr2 (0.69 g, 3.12 mmol) at 0° C. and the reaction mixture was stirred at rt overnight. The reaction mixture was treated with water and extracted with EtOAc. The combined organic layers were dried over anhydrous sodium sulfate, filtered and the filtrate was evaporated under reduced pressure The residue was subjected to a silica gel flash chromatography eluting with DCM to afford 500 mg (94%) of the title compound. LCMS (ESI+) m/z 259 $[M+H]^+$. $^1H$ NMR (400 MHZ, $CDCl_3$), δ: 8.38 (d, J=3.6 Hz, 1H), 8.15 (d, J=4.6 Hz, 1H), 3.88 (s, 3H).

2-[4-{[(4chlorophenyl)amino]carbonyl}-carbonyl)-1,5-dimethyl-1H-pyrrol-2-yl]-5-cyano-4-methoxybenzoic acid (P80)

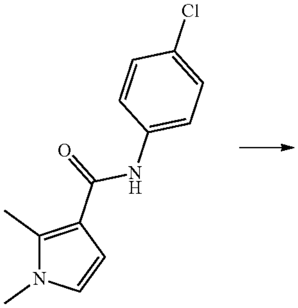

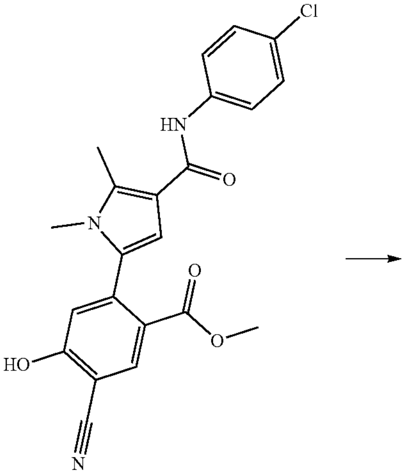

P78

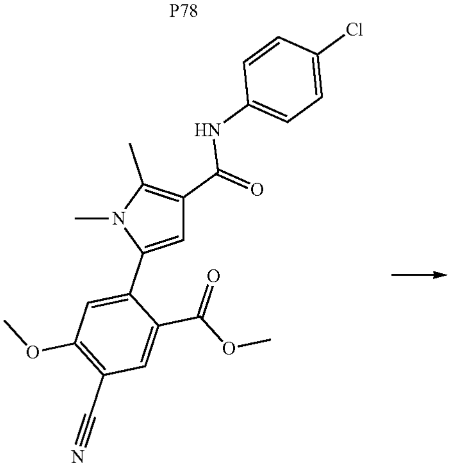

P79

-continued

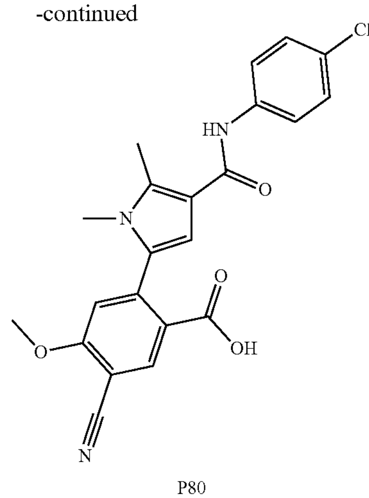

P80

Preparation 78. Methyl 2-[4-{[(4chlorophenyl)amino]carbonyl}-1,5-dimethyl-1H-pyrrol-2-yl]-5-cyano-4-hydroxybenzoate (P78)

A mixture of P73 (1.3 g, 5.2 mmol), methyl 2-bromo-5-cyano-4-fluorobenzoate (2.7 g, 10.4 mmol), $K_3PO_4$ (5 55 g, 26 mmol), pivalic acid (0.16 g, 1.5 mmol) in N,N-dimethylacetamide (125 mL) was stirred at 135° C. for 15 min, then $PdCl_2$ $(PPh_3)_2$ (0.92 g, 1.07 mmol) was added. The resulting mixture was stirred at 135° C. for 30 min. Upon completion of the reaction the mixture was diluted with water (70 mL) and EtOAC (120 mL). The organic layer was separated, washed with brine, dried over sodium sulfate, filtered, and concentrated under reduced pressure. The residue was subjected to silica flash chromatography eluting with a mixture of EtOAc (0→20%) and DCM to afford 800 mg (36%) of the title compound.

Preparation 79. Methyl 2-[4-{[(4chlorophenyl)amino]carbonyl}-carbonyl)-1,5-dimethyl-1H-pyrrol-2-yl]-5-cyano-4-methoxybenzoate (P79)

A suspension of P78 (0.8 g, 2.03 mmol) and $K_2CO_3$ (0.421 g, 3.05 mmol) in DMF (10 ml) was treated with $CH_3I$ (0.46 g, 3.1 mmol). The mixture was stirred for overnight at rt, the reaction mixture was poured into cold water. The resulting precipitate was filtered off, washed with water, Et20 and air-dried to afford 300 mg (34%) of the title compound.

Preparation 80. 2-[4-{[(4-Chlorophenyl)amino]carbonyl}-carbonyl)-1,5-dimethyl-1H-pyrrol-2-yl]-5-cyano-4-methoxybenzoic acid (P80)

A solution of P79 (300 mg, 0.77 mmol) and LiOH (18 mg, 7.7 mmol) in a mixture of THF (8 mL) and water (2 mL) was stirred at ambient temperature for 12 h. The volatiles were removed under reduced pressure, and water (20 mL) was added to the residue. The solution was acidified with 6M HCl to pH 1 and extracted with DCM (2×10 mL), the combined organic layers were dried over $Na_2SO_4$ and evaporated to dryness under reduced pressure to afford 280 mg (97%) of the title compound that was pure enough to be used in the next step.

N-(4-chlorophenyl)-5-(4-cyano-5-methoxy-2-{[(3S)-3-(morpholin-4-ylmethyl)-3,4-dihydroisoquinolin-2 (1H)-yl]carbonyl}phenyl)-1,2-dimethyl-1H-pyrrole-3-carboxamide (P81)

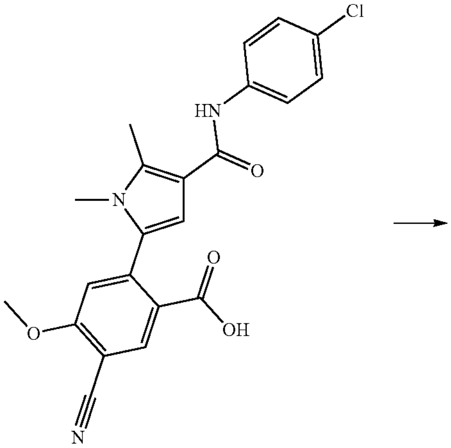

P80

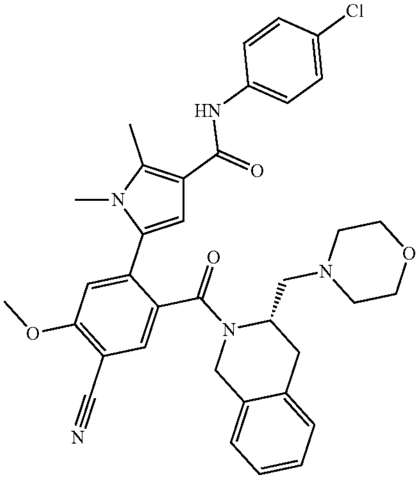

P81

Preparation 81. N-(4-chlorophenyl)-5-(4-cyano-5-methoxy-2-{[(3S)-3-(morpholin-4-ylmethyl)-3,4-dihydroisoquinolin-2 (1H)-yl]carbonyl}phenyl)-1,2-dimethyl-1H-pyrrole-3-carboxamide (P81)

A mixture of P80 (320 mg, 0.75 mmol), P43 (210 mg, 1.0 mmol), DIPEA (0.2 mL, 0.110 mmol), TBTU (292 mg, 1.0 mmol), and DMF (15 mL) was stirred at 60° C. overnight. The reaction mixture was diluted with water (20 mL) and EtOAc (10 ml). The organic layer was separated, washed with brine, dried over $Na_2SO_4$, filtered, and concentrated under reduced pressure. The residue was subjected to silica flash chromatography eluting with a mixture of EtOAc (0→100%) and DCM to afford 300 mg (78%) of the title compound.

2-[4-({[4-(benzyloxy)phenyl]amino}carbonyl)-1,5-dimethyl-1H-pyrrol-2-yl]-4-chloro-5-fluorobenzoic acid

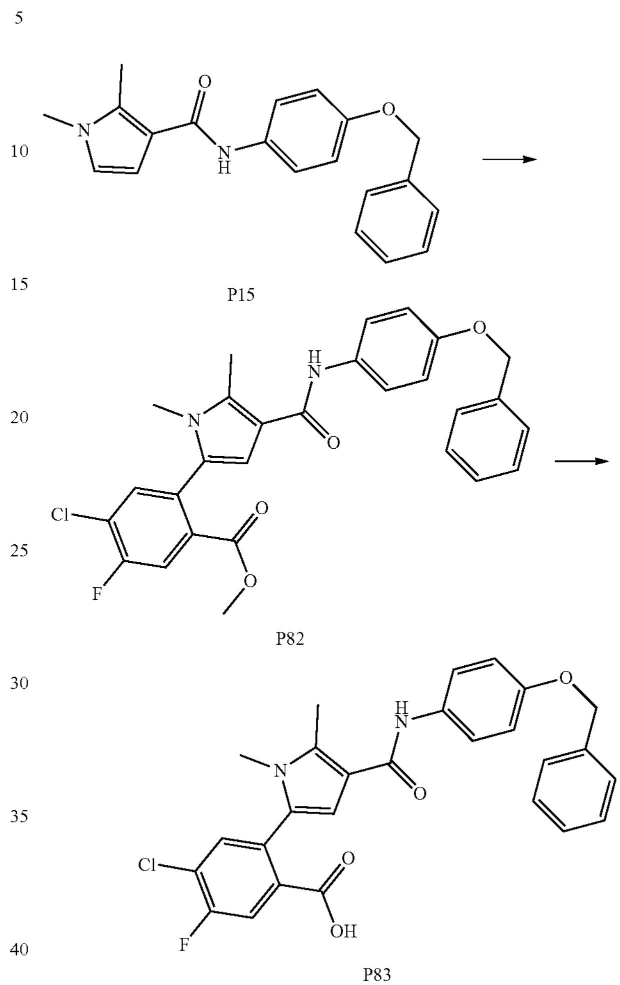

P15

P82

P83

Preparation 82. Methyl 2-[4-({[4-(benzyloxy)phenyl]amino}carbonyl)-1,5-dimethyl-1H-pyrrol-2-yl]-4-chloro-5-fluorobenzoate (P82)

A mixture of P15 (500 mg, 1.6 mmol), methyl 2-bromo-4-chloro-5-fluorobenzoate (835 mg, 3.1 mmol), $K_3PO_4$ (1.6 g, 7.8 mmol), pivalic acid (50 mg, 0.4 mmol) in N,N-dimethylacetamide (10 mL) was stirred at 135° C. for 15 min, then $PdCl_2$ $(PPh_3)_2$ (0.22 g, 0.3 mmol) was added. The resulting mixture was stirred at 135° C. for 30 min. Upon completion of the reaction mixture was diluted with water (20 mL) and EtOAC (20 mL). The organic layer was separated, washed with brine, dried over sodium sulfate, filtered, and concentrated under reduced pressure. The residue was subjected to silica flash chromatography eluting with a mixture of EtOAc (0→20%) and DCM to afford 360 mg (46%) of the title compound.

Preparation 83. 2-[4-({[4-(Benzyloxy)phenyl]amino}carbonyl)-1,5-dimethyl-1H-pyrrol-2-yl]-4-chloro-5-fluorobenzoic acid (P83)

A solution of P82 (360 mg, 0.7 mmol) and LiOH (82 mg, 3.5 mmol) in a mixture of THF (10 mL) and water (2 mL) was stirred at ambient temperature for 12 h. The volatiles were removed under reduced pressure, and water (20 mL) was added to the residue. The solution was acidified with 6M HCl to pH 1 and extracted with DCM (2×10 mL), the combined organic layers were dried over $Na_2SO_4$ and evaporated to dryness under reduced pressure to afford 350 mg (99%) of the title compound that was pure enough to be used further for the next step.

N-[4-(benzyloxy)phenyl]-5-(5-chloro-4-fluoro-2-{[(3S)-3-(morpholin-4-ylmethyl)-3,4-dihydroisoquinolin-2 (1H)-yl]carbonyl}phenyl)-1,2-dimethyl-1H-pyrrole-3-carboxamide (P84)

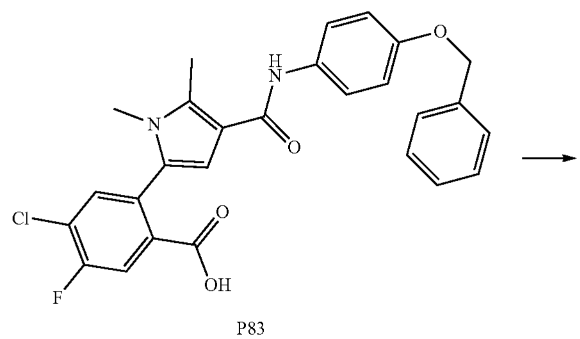

P83

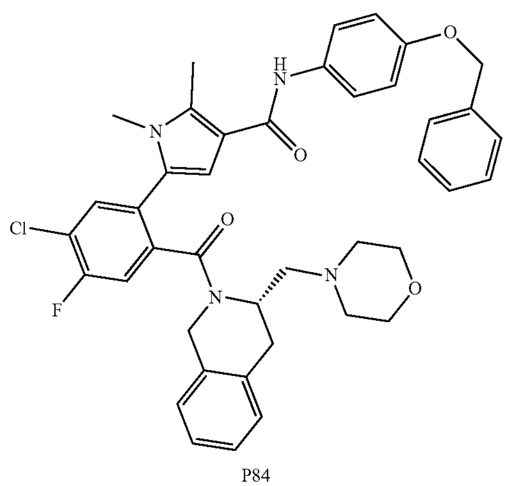

P84

Preparation 84 N-[4-(benzyloxy)phenyl]-5-(5-chloro-4-fluoro-2-{[(3S)-3-(morpholin-4-ylmethyl)-3,4-dihydroisoquinolin-2 (1H)-yl]carbonyl}phenyl)-1,2-dimethyl-1H-pyrrole-3-carboxamide (P84)

A mixture of P83 (350 mg, 0.7 mmol), P43 (198 mg, 0.85 mmol), DIPEA (0.18 mL, 1.1 mmol), TBTU (100 mg, 0.3 mmol), and DMF (5 mL) was stirred at 60° C. overnight. The reaction mixture was diluted with water (20 mL) and EtOAc (10 mL). The organic layer was separated, washed with brine, dried over $Na_2SO_4$, filtered, and concentrated under reduced pressure. The residue was subjected to silica flash chromatography eluting with a mixture of EtOAc (0→100%) and DCM to afford 420 mg (84%) of the title compound.

5-(5-chloro-4-fluoro-2-{[(3S)-3-(morpholin-4-ylmethyl)-3,4-dihydroisoquinolin-2 (1H)-yl]carbonyl}phenyl)-N-(3-methoxy-2-methylbenzyl)-1,2-dimethyl-N-(4-{[2-(trimethylsilylethoxy]methoxy}phenyl)-1H-pyrrole-3-carboxamide (P87)

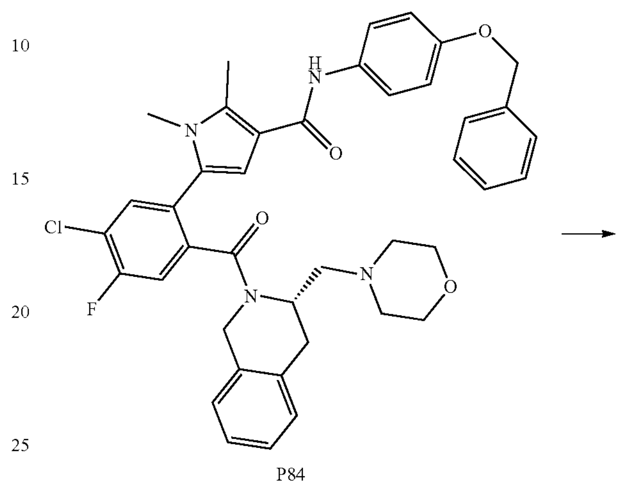

P84

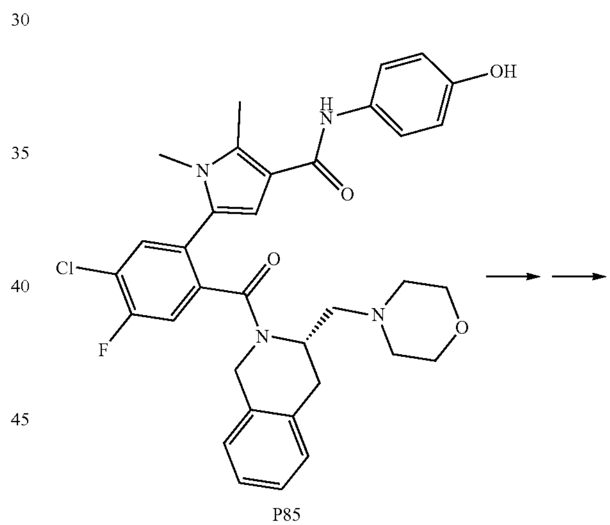

P85

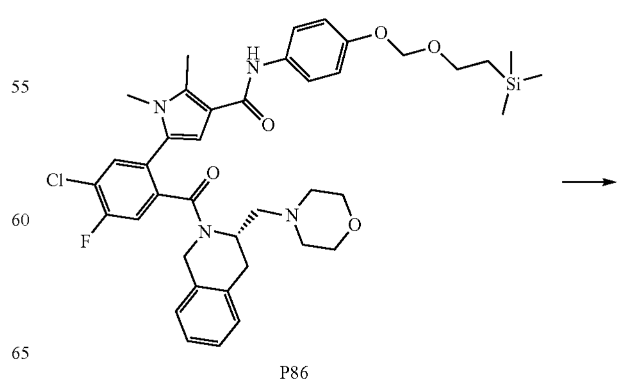

P86

-continued

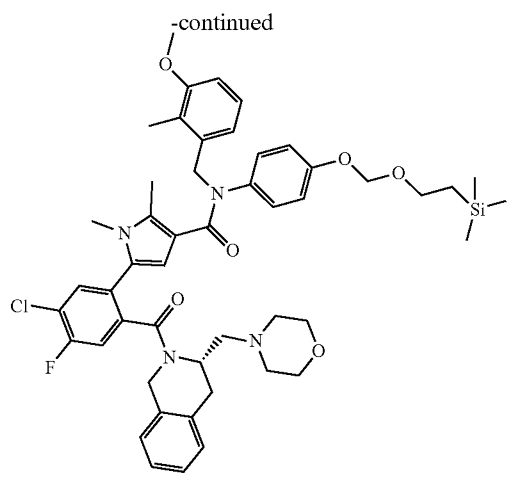

P87

Preparation 85. 5-[5-Chloro-4-fluoro-2-[(3S)-3-(morpholinomethyl)-3,4-dihydro-1H-isoquinoline-2-carbonyl]phenyl]-N-(4-hydroxyphenyl)-1,2-dimethyl-pyrrole-3-carboxamide (P85)

A solution of P84 (420 mg, 0.6 mmol) in DCM (5 mL) was cooled to −78° C., and a solution of $BBr_3$ (300 mg, 1.2 mmol) in THF (1 mL) was added over 5 min. The reaction mixture was stirred at to −78° C. for 1 h and then was diluted with saturated aq. solution of sodium bicarbonate $NaHCO_3$. The organic layer was separated, washed with brine, dried over $Na_2SO_4$, filtered, and concentrated under reduced pressure. The residue was subjected to HPLC purification to afford 270 mg (75%) of the title compound.

Preparation 86. 5-[5-Chloro-4-fluoro-2-[(3S)-3-(morpholinomethyl)-3,4-dihydro-1H-isoquinoline-2-carbonyl]phenyl]-1,2-dimethyl-N-[4-(2-trimethylsilylethoxymethoxy)phenyl]pyrrole-3-carboxamide (P86)

NaH (21 mg, 0.5 mmol, 60%) was added to a stirred solution of P85 (270 mg, 0.44 mmol) in DMF (5 mL) maintaining temperature 0° C. and stirred 30 min. Then [2-(chloromethoxy)ethyl](trimethyl) silane (80 mg, 0.5 mmol) was added. The reaction mixture was stirred at ambient temperature overnight and then partitioned between EtOAc and water. The organic layer was separated, washed with brine, dried over $Na_2SO_4$, filtered, and concentrated under reduced pressure. The residue was subjected to silica flash chromatography eluting with a mixture of EtOAc (0→100%) and DCM to afford 130 mg (40%) of the title compound.

Preparation 87. 5-(5-Chloro-4-fluoro-2-{[(3S)-3-(morpholin-4-ylmethyl)-3,4-dihydroisoquinolin-2(1H)-yl]carbonyl}phenyl)-N-(3-methoxy-2-methylbenzyl)-1,2-dimethyl-N-(4-{[2-(trimethylsilylethoxy]methoxy}phenyl)-1H-pyrrole-3-carboxamide (P87)

A mixture of P86 (130 mg, 0.17 mmol), tert-BuOK (78 mg, 0.7 mmol), and tert-BuOH (5 mL) was stirred at 50° C. for 30 min, then 3-methoxy-2-methylbenzyl methanesulfonate (80 mg, 0.35 mmol) was added. The reaction mixture was stirred at 60° C. for 1 h and then partitioned between EtOAc and water. The organic layer was separated, washed with brine, dried over $Na_2SO_4$, filtered, and concentrated under reduced pressure. The residue was subjected to silica flash chromatography eluting with a mixture of EtOAc (0→100%) and DCM to afford 120 mg (78%) of the title compound.

2-[4-({[4-(Benzyloxy)phenyl]amino}carbonyl)-1,5-dimethyl-1H-pyrrol-2-yl]-5-cyano-4-methoxybenzoic acid (P90)

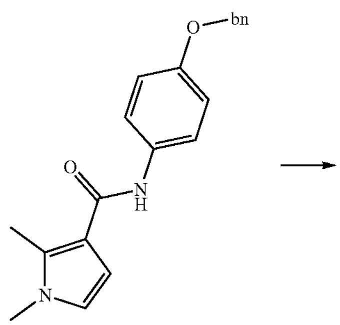

P15

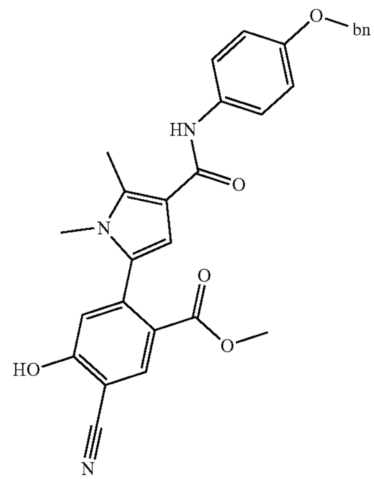

P88

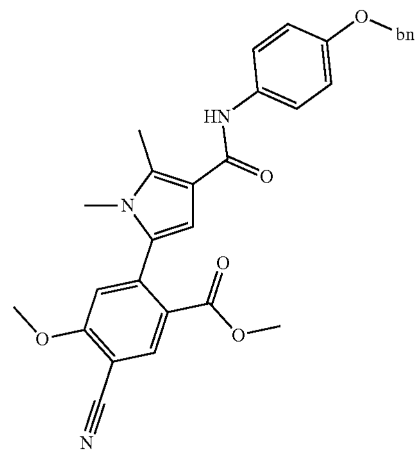

P89

-continued

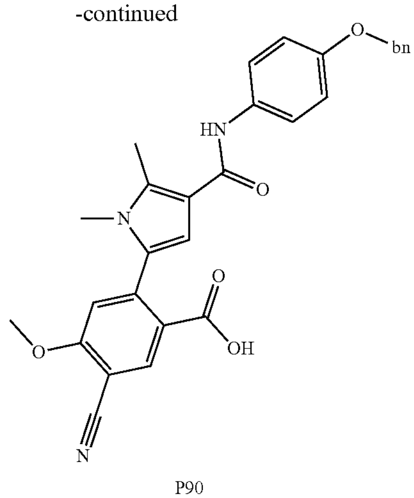

P90

Preparation 88. Methyl 2-[4-({[4-(benzyloxy)phenyl]amino}carbonyl)-1,5-dimethyl-1H-pyrrol-2-yl]-5-cyano-4-hydroxybenzoate (P88)

A mixture of P15 (500 mg, 1.56 mmol), methyl 2-bromo-5-cyano-4-fluorobenzoate (806 mg, 3.12 mmol), $K_3PO_4$ (1.66 g, 7.8 mmol), pivalic acid (47.6 mg, 0.5 mmol) in N,N-dimethylacetamide (25 mL) was stirred at 135° C. for 15 min, then $PdCl_2$ $(PPh_3)_2$ (0.32 g, 0.3 mmol) was added. The resulting mixture was stirred at 135° C. for 30 min. Upon completion of the reaction mixture was diluted with water (70 mL) and EtOAC (120 mL). The organic layer was separated, washed with brine, dried over sodium sulfate, filtered, and concentrated under reduced pressure. The residue was subjected to silica flash chromatography eluting with a mixture of EtOAc (0→20%) and DCM to afford 520 mg (61%) of the title compound.

Preparation 89. Methyl 2-[4-({[4-(benzyloxy)phenyl]amino}carbonyl)-1,5-dimethyl-1H-pyrrol-2-yl]-5-cyano-4-methoxybenzoate (P89)

A suspension of P88 (0.5 g, 1.18 mmol), and $K_2CO_3$ (0.245 g, 1.8 mmol) in DMF (6 ml) was treated with $CH_3I$ (0.33 g, 1.8 mmol). The mixture was stirred for overnight at rt, reaction mixture poured into cold water. Formed precipitate was filtered off, washed with water, $Et_2O$ and air-dried to afford 240 mg (44%) of the title compound.

Preparation 90. 2-[4-({[4-(Benzyloxy)phenyl]amino}carbonyl)-1,5-dimethyl-1H-pyrrol-2-yl]-5-cyano-4-methoxybenzoic acid (P90)

A solution of P89 (240 mg, 0.47 mmol) and LiOH (113 mg, 4.7 mmol) in a mixture of THF (8 mL) and water (2 mL) was stirred at ambient temperature for 12 h. The volatiles were removed under reduced pressure, and water (20 mL) was added to the residue. The solution was acidified with 6M HCl to pH 1 and extracted with DCM (2×10 mL), the combined organic layers were dried over $Na_2SO_4$ and evaporated to dryness under reduced pressure to afford 158 mg (67%) of the title compound that was pure enough to be used further for the next step.

N-[4-(benzyloxy)phenyl]-5-(4-cyano-5-methoxy-2-{[(3S)-3-(morpholin-4-ylmethyl)-3,4-dihydroisoquinolin-2 (1H)-yl]carbonyl}phenyl)-N-(3-methoxy-2-methylbenzyl)-1,2-dimethyl-1H-pyrrole-3-carboxamide (P92)

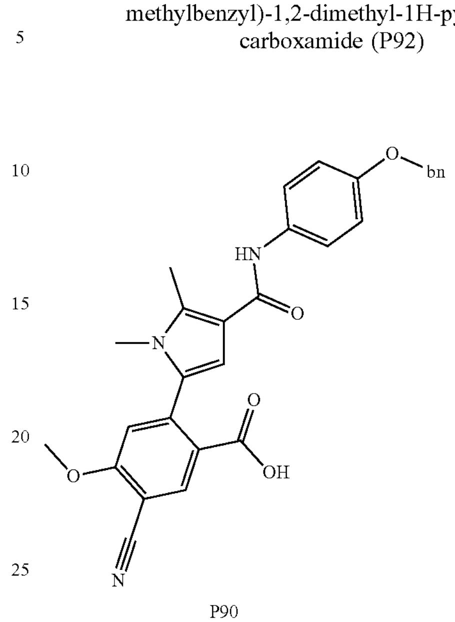

P90

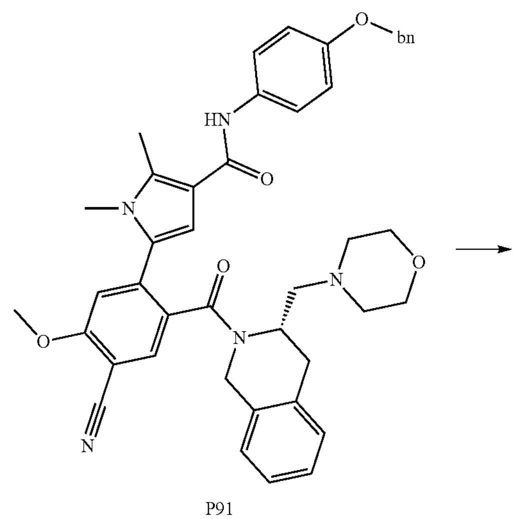

P91

-continued

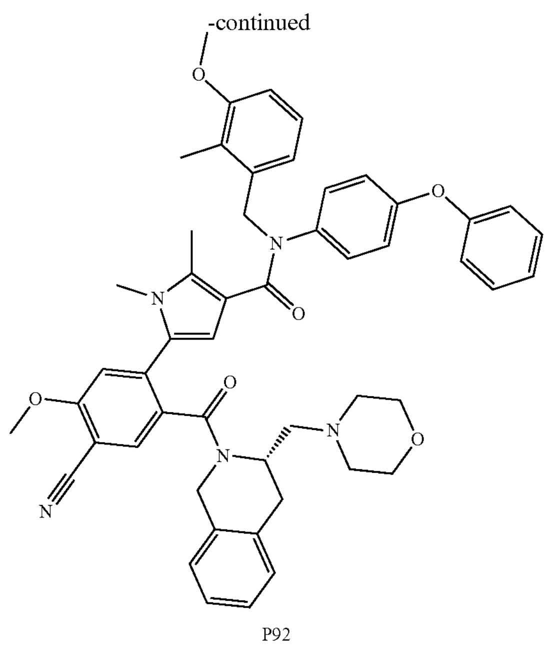

P92

Preparation 91. N-[4-(benzyloxy)phenyl]-5-(4-cyano-5-methoxy-2-{[(3S)-3-(morpholin-4-ylmethyl)-3,4-dihydroisoquinolin-2 (1H)-yl]carbonyl}phenyl)-1,2-dimethyl-1H-pyrrole-3-carboxamide (P91)

A mixture of P90 (158 mg, 0.31 mmol), P43 (89 mg, 0.39 mmol), DIPEA (0.08 mL, 0.46 mmol), and TBTU (123 mg, 0.39 mmol), and DMF (8 mL) was stirred at 60° C. overnight. The reaction mixture was diluted with water (20 mL) and EtOAc (10 mL). The organic layer was separated, washed with brine, dried over $Na_2SO_4$, filtered, and concentrated under reduced pressure. The residue was subjected to silica flash chromatography eluting with a mixture of EtOAc (0→100%) and DCM to afford 200 mg (88%) of the title compound.

Preparation 92. N-[4-(benzyloxy)phenyl]-5-(4-cyano-5-methoxy-2-{[(3S)-3-(morpholin-4-ylmethyl)-3,4-dihydroisoquinolin-2 (1H)-yl]carbonyl}phenyl)-N-(3-methoxy-2-methylbenzyl)-1,2-dimethyl-1H-pyrrole-3-carboxamide (P92)

A mixture of P91 (200 mg, 0.28 mmol), tert-BuOK (127 mg 1.12 mmol), and tert-BuOH (25 mL) was stirred at 50° C. for 30 min, then 3-methoxy-2-methylbenzyl methanesulfonate (130 mg, 0.56 mmol) was added. The reaction mixture was stirred at 60° C. for 1 h and then partitioned between EtOAc and water. The organic layer was separated, washed with brine, dried over $Na_2SO_4$, filtered, and concentrated under reduced pressure. The residue was subjected to silica flash chromatography eluting with a mixture of EtOAc (0→100%) and DCM to afford 160 mg (65%) of the title compound.

5-(5-Nitro-2-[(3R)-3-(morpholinomethyl)-3,4-dihydro-2 (1H)-isoquinolinyl]carbonylphenyl)-N$^3$-(3-methoxy-2-methylbenzyl)-1,2-dimethyl-N$^3$-(1-tetrahydro-2H-pyran-2-yl-1H-indazol-5-yl)-1H-pyrrole-3-carboxamide (P97)

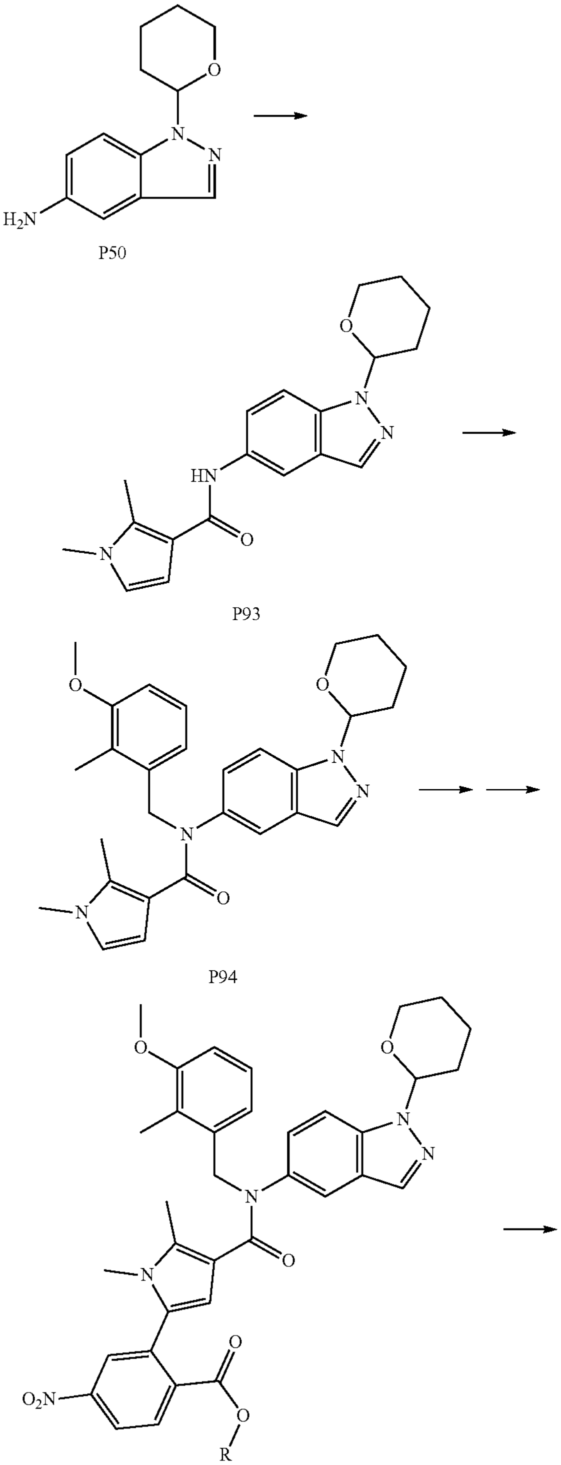

P50

P93

P94

P95 R = Me;
P96 R = H

-continued

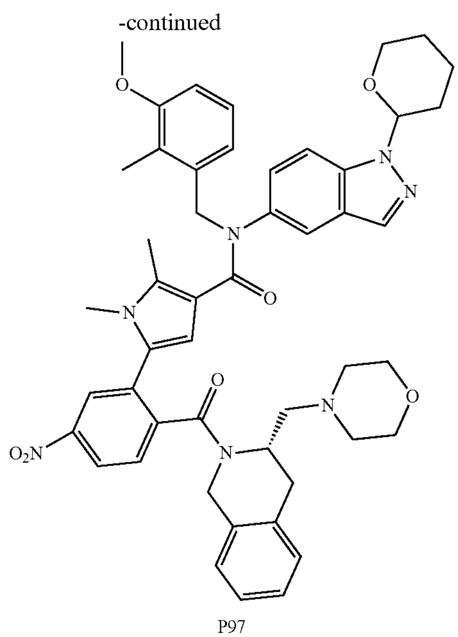

P97

Preparation 93. 1,2-Dimethyl-$N^3$-(1-tetrahydro-2H-pyran-2-yl-1H-indazol-5-yl)-1H-pyrrole-3-carboxamide (P93)

To a solution of acid (0.74 g, 5 mmol), amine P50 (1.1 g, 5 mmol), DMAP (0.8 g, 6.5 mmol), Et3N (3 ml, 5 eq), in DCM (40 ml) was added EDC×HCl (1.2 g, 6 mmol). The reaction mixture was stirred at ambient temperature overnight, then diluted with water (40 mL). The organic layer was separated, washed with brine, dried over $Na_2SO_4$, filtered, and concentrated under reduced pressure. The residue was subjected to silica flash chromatography eluting with a mixture of EtOAc (0→100%) and $CCl_4$ to afford 1.35 g (75%) of P93. LCMS(ESI+) m/z 339 $[M+H]^+$ Preparation 94. $N^3$-(3-methoxy-2-methylbenzyl)-1,2-dimethyl-$N^3$-(1-tetrahydro-2H-pyran-2-yl-1H-indazol-5-yl)-1H-pyrrole-3-carboxamide (P94)

A mixture of P93 (100 mg, 0.3 mmol), tert-BuOK (132 mg, 4 eq), and tert-BuOH (2 mL) was stirred at 50° C. for 5 min, then 3-methoxy-2-methylbenzyl methanesulfonate (146 mg, 2 eq) was added. The reaction mixture was stirred at 80° C. for 2 h and then partitioned between DCM and water. The organic layer was separated, washed with brine, dried over $Na_2SO_4$, filtered, and concentrated under reduced pressure. The residue was subjected to silica flash chromatography eluting with a mixture of EtOAc (0→100%) and DCM to afford 50 mg of compound P94. LCMS (ESI+) m/z 473 $[M+H]^+$.

Preparation 95. Methyl 4-nitro-2-(4-[(3-methoxy-2-methylbenzyl) (1-tetrahydro-2H-pyran-2-yl-1H-indazol-5-yl)amino]carbonyl-1,5-dimethyl-1H-pyrrol-2-yl)benzoate (P95)

A mixture of compound P94 (400 mg, 0.8 mmol), bromide (430 mg, 1.66 mmol), $K_3PO_4$ (896 mg, 5 eq), pivalic acid (26 mg, 0.3 eq), $PdCl_2$ $(PPh_3)_2$ (118 mg, 0.2 eq) in N,N-dimethylacetamide (15 mL) was stirred at 130° C. for 2 h. Upon completion of the reaction mixture was diluted with water (25 mL) and EtOAC (100 mL). The organic layer was separated, washed with brine, dried over sodium sulfate, filtered, and concentrated under reduced pressure. The residue was subjected to silica flash chromatography eluting with a mixture of EtOAc (0→20%) and DCM to afford 220 mg (45%) of the title compound. LCMS(ESI+) m/z 652 $[M+H]^+$.

Preparation 96. 4-Nitro-2-(4-[(3-methoxy-2-methylbenzyl) (1-tetrahydro-2H-pyran-2-yl-1H-indazol-5-yl)amino]carbonyl-1,5-dimethyl-1H-pyrrol-2-yl) benzoic acid (P96)

A solution of ester P95 (220 mg, 0.3 mmol) and NaOH (50 mg, 4 eq) in a mixture of MeOH/$H_2O$ was stirred at ambient temperature for 12 h. The volatiles were removed under reduced pressure, and water (3 mL) was added to the residue. The solution was acidified with 6M HCl to pH 1 and extracted with DCM (2×5 mL), the combined organic layers were dried over $Na_2SO_4$ and evaporated to dryness under reduced pressure to afford 180 mg (99%) of P96.

Preparation 97. 5-(5-Nitro-2-[(3R)-3-(morpholinomethyl)-3,4-dihydro-2 (1H)-isoquinolinyl]carbonylphenyl)-$N^3$-(3-methoxy-2-methylbenzyl)-1,2-dimethyl-$N^3$-(1-tetrahydro-2H-pyran-2-yl-1H-indazol-5-yl)-1H-pyrrole-3-carboxamide (P97)

A mixture of P96 (180 mg, 0.28 mmol), P43 (72 mg, 0.3 mmol), DIPEA (0.0744 mL, 1.5 eq), and TBTU (0.10 g, 0.3 mmol) and DMF (4 mL) was stirred at 60° C. overnight. The reaction mixture was diluted with water (10 mL), precipitate was filtered and dried to afford 180 mg of crude product P97. LCMS(ESI+) m/z 852 $[M+H]^+$.

5-(5-Nitro-2-[(3R)-3-(morpholinomethyl)-3,4-dihydro-2 (1H)-isoquinolinyl]carbonylphenyl)-$N^3$-(2-cyanobenzyl)-1,2-dimethyl-$N^3$-(1-tetrahydro-2H-pyran-2-yl-1H-indazol-5-yl)-1H-pyrrole-3-carboxamide (P101)

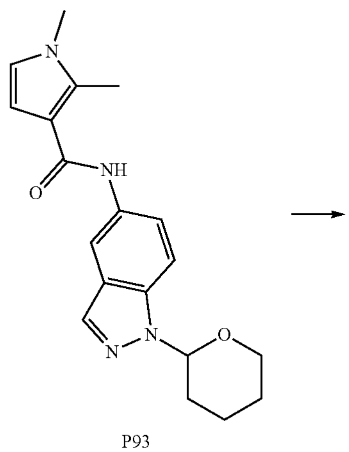

P93

-continued

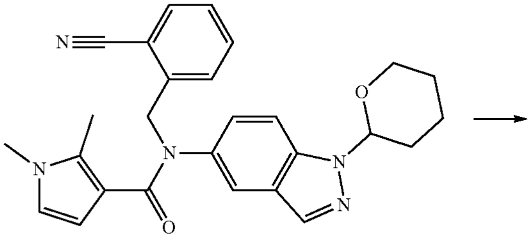

P98

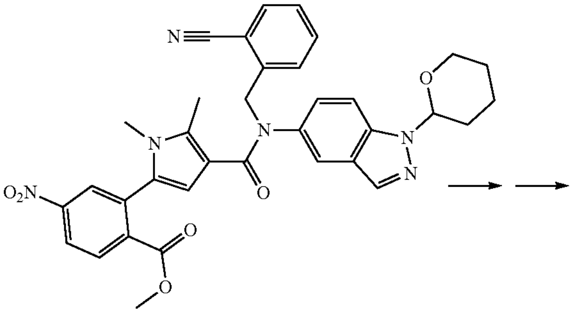

P99

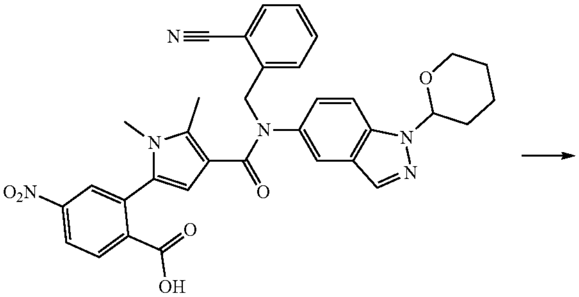

P100

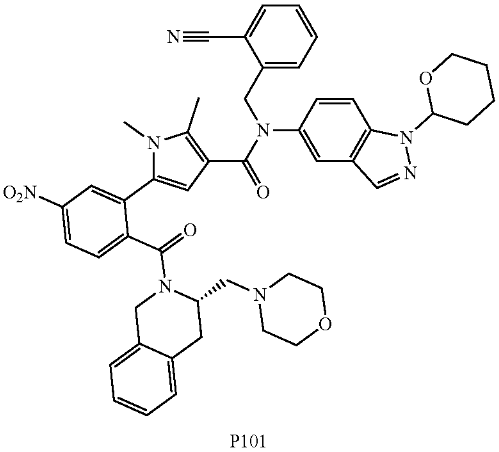

P101

Preparation 98. $N^3$-(2-Cyanobenzyl)-1,2-dimethyl-$N^3$-(1-tetrahydro-2H-pyran-2-yl-1H-indazol-5-yl)-1H-pyrrole-3-carboxamide (P98)

A mixture of P93 (800 mg, 2.3 mmol), tert-BuOK (1.06 g, 4 eq), and tert-BuOH (10 mL) was stirred at 50° C. for 5 min, then 2-(bromomethyl)benzonitrile (928 mg, 2 eq) was added. The reaction mixture was stirred at 80° C. for 2 h and then partitioned between DCM and water. The organic layer was separated, washed with brine, dried over $Na_2SO_4$, filtered, and concentrated under reduced pressure. The residue was subjected to silica flash chromatography eluting with a mixture of EtOAc (0→100%) and DCM to afford 950 mg (89%) of P98. LCMS(ESI+) m/z 454 $[M+H]^+$.

Preparation 99. Methyl 4-nitro-2-(4-[(2-cyanobenzyl) (1-tetrahydro-2H-pyran-2-yl-1H-indazol-5-yl) amino]carbonyl-1,5-dimethyl-1H-pyrrol-2-yl)benzoate (P99)

A mixture of P98 (950 mg, 2 mmol), bromide (1.08 g, 4 mmol), $K_3PO_4$ (2.2 g, 5 eq), pivalic acid (64 mg, 0.3 eq), $PdCl_2$ (74 mg, 0.2 eq), $PPh_3$ (109 mg, 0.2 eq) in N,N-dimethylacetamide (40 mL) was stirred at 130° C. for 2 h. Upon completion of the reaction mixture was diluted with water (40 mL) and EtOAC (150 mL). The organic layer was separated, washed with brine, dried over sodium sulfate, filtered, and concentrated under reduced pressure. The residue was subjected to silica flash chromatography eluting with a mixture of EtOAc (0→20%) and DCM to afford 800 mg (62%) of P99. LCMS(ESI+) m/z 633 $[M+H]^+$.

Preparation 100. 4-Nitro-2-(4-[(2-cyanobenzyl) (1-tetrahydro-2H-pyran-2-yl-1H-indazol-5-yl)amino] carbonyl-1,5-dimethyl-1H-pyrrol-2-yl)benzoic acid (P100)

A solution of ester P99 (800 mg, 1.3 mmol) and NaOH (300 mg, 6 eq) in a mixture of MeOH/$H_2O$ was stirred at ambient temperature for 12 h. The volatiles were removed under reduced pressure, and water (3 mL) was added to the residue. The solution was acidified with 6M HCl to pH 1 and extracted with DCM (2×10 mL), the combined organic layers were dried over $Na_2SO_4$ and evaporated to dryness under reduced pressure to afford 700 mg (90%) of P100.

Preparation 101. 5-(5-Nitro-2-[(3R)-3-(morpholinomethyl)-3,4-dihydro-2 (1H)-isoquinolinyl]carbonylphenyl)-$N^3$-(2-cyanobenzyl)-1,2-dimethyl-$N^3$-(1-tetrahydro-2H-pyran-2-yl-1H-indazol-5-yl)-1H-pyrrole-3-carboxamide (P101)

A mixture of acid P100 (690 mg, 1.1 mmol), P43 (288 mg, 1.2 mmol), DIPEA (0.3 mL, 1.5 eq), and TBTU (0.4 g, 1.2 mmol) and DMF (7 mL) was stirred at 60° C. overnight. The reaction mixture was diluted with water (10 mL), precipitate filtered and dried to afford 800 mg of P101. LCMS (ESI+) m/z 833 $[M+H]^+$ 4-cyano-2-(4-{[(2-methoxybenzyl) (4-{[2-(trimethylsilylethoxy]methoxy}phenyl)amino]carbonyl}-1,5-dimethyl-1H-pyrrol-2-yl)benzoic acid (P105)
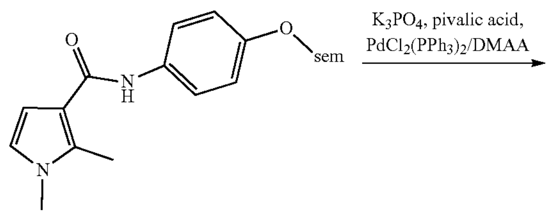
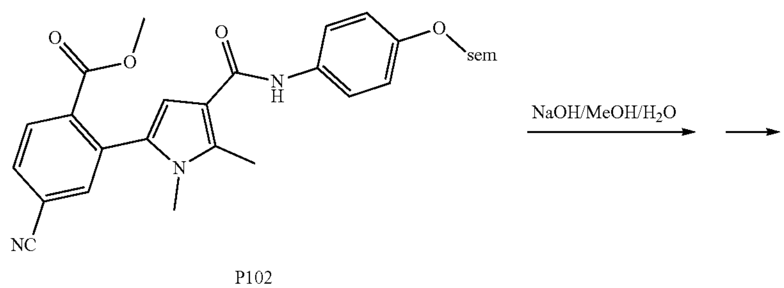
P102
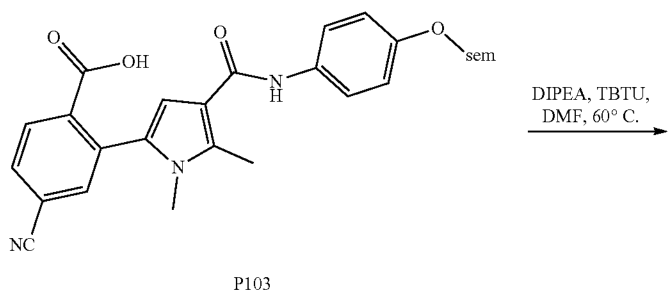
P103
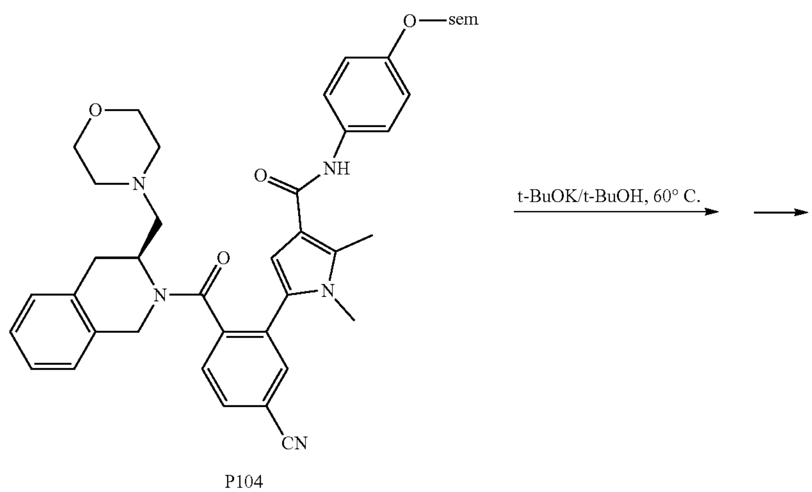
P104

-continued

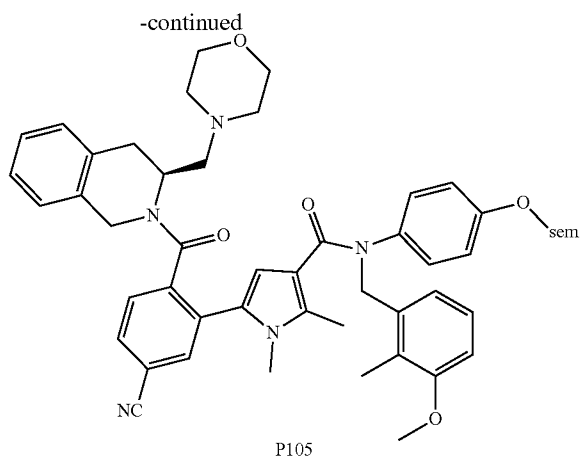

P105

Preparation 102. Methyl 4-cyano-2-(1,5-dimethyl-4-{[(4-{[2-(trimethylsilylethoxy]methoxy}phenyl) amino]carbonyl}-1H-pyrrol-2-yl)benzoate (P102)

A mixture of 1,2-dimethyl-N-(4-{[2-(trimethylsilylethoxy]methoxy}phenyl)-1H-pyrrole-3-carboxamide (300 g, 0.83 mmol), methyl 2-bromo-5-cyanobenzoate (400 mg, 1.66 mol), $K_3PO_4$ (880 g, 4.2 mmol), pivalic acid (254 g, 0.25 mmol), $PdCl_2$ $(PPh_3)_2$ (1.2 g, 0.17 mmol) in N,N-dimethylacetamide (10 mL) was heated to 135° C. The resulting mixture was stirred at 135° C. for 30 min, after that the reaction mixture was cooled to ambient temperature. Upon completion of the reaction, the mixture was diluted with water (30 mL) and $Et_2O$(30 mL). The organic layer was separated, washed with brine, dried over dried over anhydrous sodium sulfate, filtered, and concentrated under reduced pressure. The residue was subjected to a silica gel flash chromatography eluting with a mixture of EtOAc (0→20%) and DCM to afford 140 mg (33%) of the title compound. LCMS(ESI+) m/z 520 $[M+H]^+$.

Preparation 103. 4-Cyano-2-(1,5-dimethyl-4-{[(4-{[2-(trimethylsilylethoxy]methoxy}phenyl)amino] carbonyl}-1H-pyrrol-2-yl)benzoic acid (P103)

A solution of P102 (140 mg, 0.27 mmol) and NaOH (54 mg, 1.4 mmol) in a mixture of EtOH (10 mL) and water (2 mL) was stirred at ambient temperature for 12 h. The volatiles were removed under reduced pressure, and water (10 mL) was added to the residue. The solution was acidified with 6M HCl to pH 1 and extracted with DCM (2×20 mL), the combined organic layers were dried over anh. sodium sulfate and evaporated to dryness under reduced pressure to afford 120 mg (88%) of the title compound that was pure enough to be used for the next step. LCMS(ESI+) m/z 506 $[M+H]^+$.

Preparation 104. 5-(5-Cyano-2-{[(3S)-3-(morpholin-4-ylmethyl)-3,4-dihydroisoquinolin-2 (1H)-yl] carbonyl}phenyl)-1,2-dimethyl-N-(4-{[2-(trimethylsilylethoxy]methoxy}phenyl)-1H-pyrrole-3-carboxamide (P104)

A mixture of P103 (120 mg, 0.24 mmol), P43 (65 mg, 0.28 mmol), DIPEA (0.06 mL, 0.35 mmol), and TBTU (90 mg, 0.28 mmol), and DMF (10 mL) was stirred at 60° C. overnight. The reaction mixture was diluted with water (20 mL) and EtOAc (20 mL). The organic layer was separated, washed with brine, dried with anh. sodium sulfate, filtered, and concentrated under reduced pressure. The residue was subjected to asilica gel flash chromatography eluting with a mixture of EtOAc (0→100%) and DCM to afford 140 mg (82%) of the title compound. LCMS(ESI+) m/z 719 $[M+H]^+$.

Preparation 105. 4-Cyano-2-(4-{[(2-methoxybenzyl) (4-{[2-(trimethylsilylethoxy]methoxy}phenyl) amino]carbonyl}-1,5-dimethyl-1H-pyrrol-2-yl)benzoic acid (P105)

A mixture of P104 (140 mg, 0.19 mmol), tert-BuOK (87 mg 0.8 mmol), and tert-BuOH (20 mL) was stirred at 50° C. for 30 min, then 1-(chloromethyl)-2-methoxybenzene (60 mg, 0.4 mmol) was added. The reaction mixture was stirred at 60° C. for 1 h and then partitioned between EtOAc and water. The organic layer was separated, washed with brine, dried over anh. sodium sulfate, filtered, and was concentrated under reduced pressure. The residue was subjected to a silica gel flash chromatography eluting with a mixture of EtOAc (0-+100%) and DCM to afford 110 mg (94%) of the title compound. LCMS(ESI+) m/z 863 $[M+H]^+$.

N-(3-methoxy-2-methylbenzyl)-1,2-dimethyl-5-(5-(methylsulfonyl)-2-{[(3S)-3-(morpholin-4-ylm-ethyl)-3,4-dihydroisoquinolin-2 (1H)-yl] carbonyl}phenyl)-N-(4-{[2-(trimethylsilylethoxy] methoxy}phenyl)-1H-pyrrole-3-carboxamide (P109)
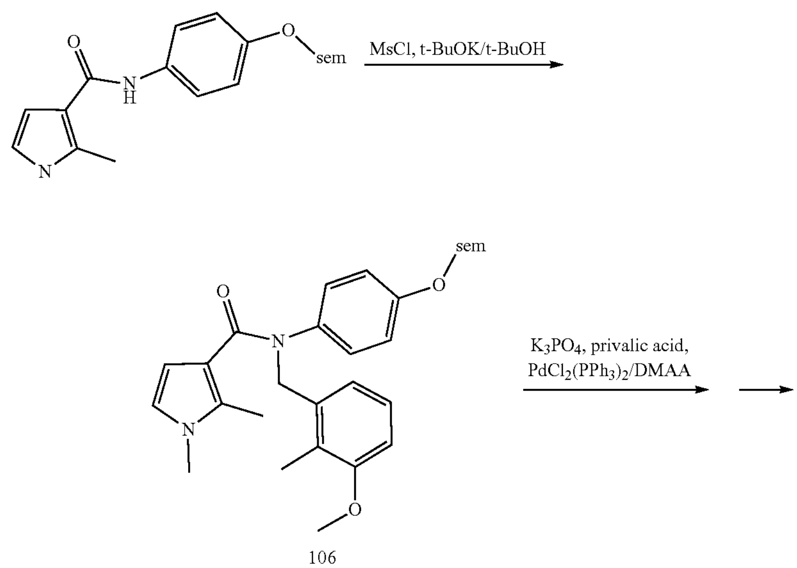
106
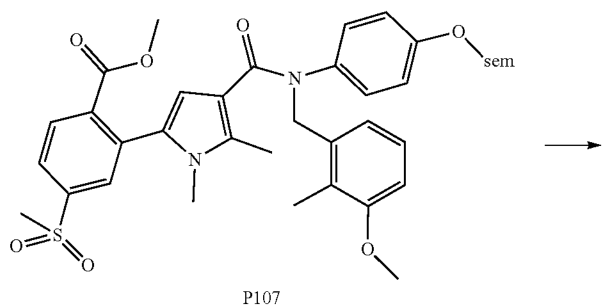
P107
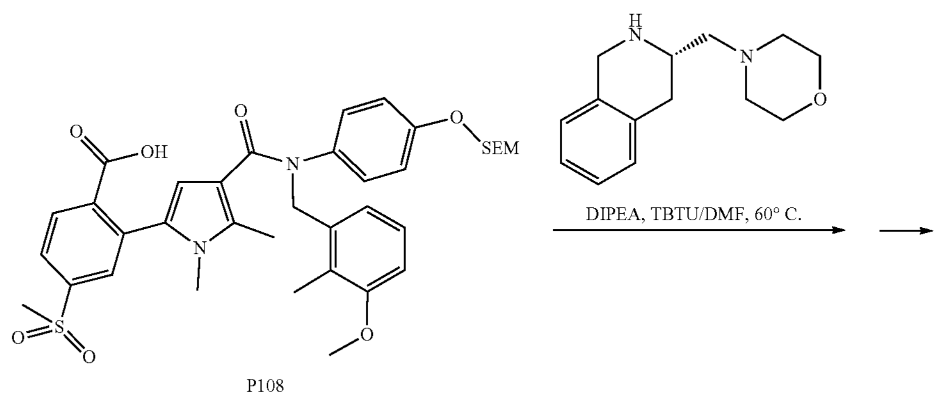
P108

-continued

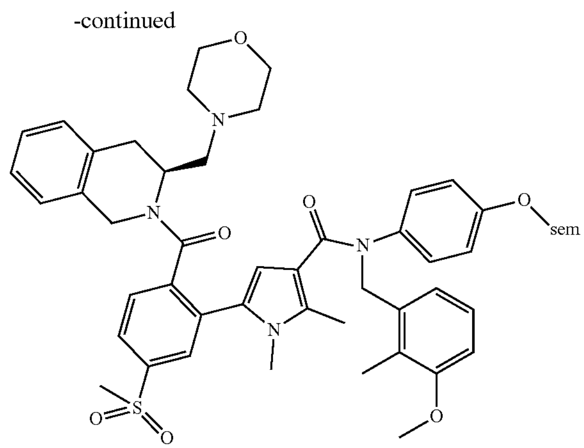

P109

Preparation 106. $N^3$-(3-methoxy-2-methylbenzyl)-1,2-dimethyl-$N^3$-(4-[2-(1,1,1-trimethylsilylethoxy]methoxyphenyl)-1H-pyrrole-3-carboxamide (P106)

A mixture of 1,2-dimethyl-N-(4-{[2-(trimethylsilylethoxy]methoxy}phenyl)-1H-pyrrole-3-carboxamide (0.85 g, 2.3 mmol), tert-BuOK (1 g, 8.9 mmol), and tert-BuOH (10 mL) was stirred at 60° C., then 3-methoxy-2-methylbenzyl methanesulfonate (1.1 g, 4.4 mmol) was added. The reaction mixture was stirred at 60° C. for 3 h and then partitioned between EtOAc and water. The organic layer was separated, washed with brine, dried over anh. sodium sulfate, filtered, and was concentrated under reduced pressure. The residue was subjected to a silica gel flash chromatography eluting with a mixture of EtOAc (0→100%) and DCM to afford 0.95 g (82%) of the title compound. LCMS(ESI+) m/z 495 $[M+H]^+$.

Preparation 107. Methyl 2-(4-{[(3-methoxy-2-methylbenzyl) (4-{[2-(trimethylsilylethoxy]methoxy}phenyl)amino]carbonyl}-1,5-dimethyl-1H-pyrrol-2-yl)-4-(methylsulfonyl)benzoate (P107)

A mixture of P106 (0.3 g, 0.6 mmol), methyl-2-bromo-4-chloro-5-cyanobenzoate (0.3 g, 1.2 mmol), $K_3PO_4$ (0.58 g, 2.7 mmol), pivalic acid (17 mg, 0.3 eq), $PdCl_2$ $(PPh_3)_2$ (77 mg, 0.2 eq) in N,N-dimethylacetamide (10 mL) was heated to 135° C. The resulting mixture was stirred at 135° C. for 30 min, after that the reaction mixture was cooled to ambient temperature. Upon completion of the reaction, the mixture was diluted with water and EtOAc. The organic layer was separated, washed with brine, dried over dried over anhydrous sodium sulfate, filtered, and concentrated under reduced pressure. The residue was subjected to a silica gel flash chromatography eluting with a mixture of EtOAc (0→20%) and DCM to afford 200 mg (48%) of the title compound. LCMS(ESI+) m/z 706 $[M+H]^+$.

Preparation 108. 2-(4-{[(3-methoxy-2-methylbenzyl) (4-{[2-(trimethylsilylethoxy]methoxy}phenyl) amino]carbonyl}-1,5-dimethyl-1H-pyrrol-2-yl)-4-(methylsulfonyl)benzoic acid (P108)

A solution of P107 (200 mg, 0.28 mmol) and LiOH (32 mg, 1.4 mmol) in a mixture of THF (2 mL) and water (0.2 mL) was stirred at ambient temperature for 12 h. The volatiles were removed under reduced pressure, and water (2 mL) was added to the residue. The solution was acidified with 6M HCl to pH 1 and extracted with DCM (2×3 mL), the combined organic layers were dried over anhydrous sodium sulfate and evaporated to dryness under reduced pressure to afford 180 mg (92%) of the title compound that was pure enough to be used for the next step. LCMS(ESI+) m/z 692 $[M+H]^+$.

Preparation 109. N-(3-Methoxy-2-methylbenzyl)-1,2-dimethyl-5-(5-(methylsulfonyl)-2-{[(3S)-3-(morpholin-4-ylmethyl)-3,4-dihydroisoquinolin-2 (1H)-yl]carbonyl}phenyl)-N-(4-{[2-(trimethylsilylethoxy]methoxy}phenyl)-1H-pyrrole-3-carboxamide (P109)

A mixture of P108 (180 mg, 0.26 mmol), P43 (72 mg, 0.3 mol), DIPEA (0.07 mL, 0.4 mmol), TBTU (100 mg, 0.3 mmol), and DMF (2 mL) was stirred at 60° C. overnight. The reaction mixture was diluted with water (4 mL) and EtOAc (20 mL). The organic layer was separated, washed with brine, dried anhydrous sodium sulfate, filtered, and concentrated under reduced pressure to afford 160 mg of the crude compound that was pure enough to be used for the next step. LCMS(ESI+) m/z 908 $[M+H]^+$.

1-(Tetrahydro-2H-pyran-2-yl)-1H-indazol-6-amine (P111)

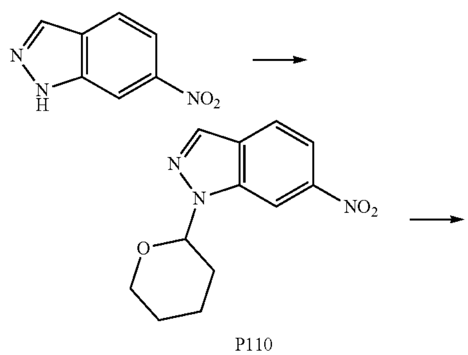

P110

-continued

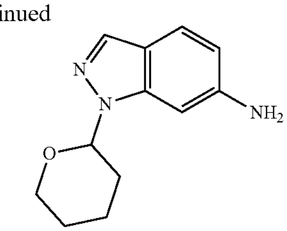

P111

Preparation 110. 6-Nitro-1-(tetrahydro-2H-pyran-2-yl)-1H-indazole (P110)

To a stirred solution of 6-nitro-1H-indazole (10.0 g, 0.06 mol) and dihydropyran (15.5 g, 0.18 mol) in DCM (250 mL) was added p-toluenesulfonic acid (1.06 g, 6 mmol). After mixture was stirred at rt for 8 h, then diluted with DCM (100 mL), washed with saturated sodium bicarbonate solution, and purified by column chromatography (DCM: hexane=1: 2-1:1) to afford 11.6 g (76%) of the title compound as a pale yellow pricipitate.

Preparation 111. 1-(Tetrahydro-2H-pyran-2-yl)-1H-indazol-6-amine (P111)

P110 (11.6 g, 0.47 mol) was dissolved in ethanol (300 mL). Pd/C (1.1 g, 10% w/w) was added and the mixture was stirred under hydrogen at 20 bar for 3 h. The catalyst was removed by filtration and the solution was evaporated under reduced pressure to afford 10 g (98%) of the title compound. $^1$H NMR (400 MHZ, $CDCl_3$), δ: 7.74 (s, 1H), 7.36 (d, 1H, J=4 Hz,) 6.61 (s, 1H), 6.53 (d, 1H, J=4.4 Hz), 5.53 (d, 1H, J=3.8 Hz), 5.34 (s, 1H), 3.87 (d, 1H, J=6 Hz), 3.68-3.62 (m, 1H), 2.42-2.32 (m, 1H), 2.03-1.99 (m, 1H), 1.92-1.88 (m, 1H), 1.75-1.66 (m, 1H), 1.57-1.52 (m, 1H). 1,2-Dimethyl-N-[1-(tetrahydro-2H-pyran-2-yl)-1H-indazol-6-yl]-1H-pyrrole-3-carboxamide

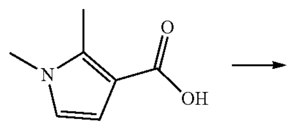

P14

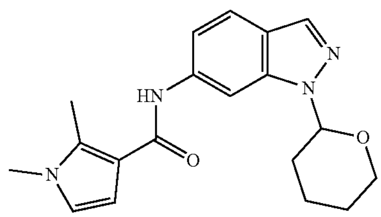

P112

Preparation 112. 1,2-dimethyl-N-[1-(tetrahydro-2H-pyran-2-yl)-1H-indazol-6-yl]-1H-pyrrole-3-carboxamide (P112)

To a stirred solution of P14 (7.1 g, 50.2 mmol), P111 (8.9 g, 40.1 mmol), DMAP (7.5 g, 60.1 mmol), and Et3N(20 g, 28.5 ml, 0.2 mol) in DCM (50 mL) was added EDC*HCl (11.7 g, 60.1 mmol). The reaction mixture was stirred at ambient temperature overnight. After reaction completion (LCMS monitiring), the mixture was quenched with water (100 ml), the organic layer separated, washed with water, brine, dried over dried over anh. sodium sulfate, filtered, and concentrated under reduced pressure. The residue was subjected to a silica gel flash chromatography eluting with a mixture of EtOAc (0→20%) and DCM to afford 8.4 g (60%) of the title compound.

N-(3-Methoxy-2-methylbenzyl)-1,2-dimethyl-5-(2-{[(3S)-3-(morpholin-4-ylmethyl)-3,4-dihydroisoquinolin-2 (1H)-yl]carbonyl}-5-nitrophenyl)-N-[1-(tetrahydro-2H-pyran-2-yl)-1H-indazol-6-v11-1H-pyrrole-3-carboxamide (P116)

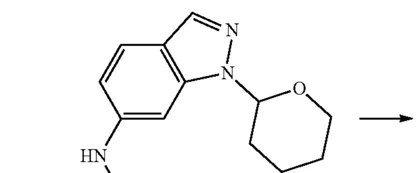

P112

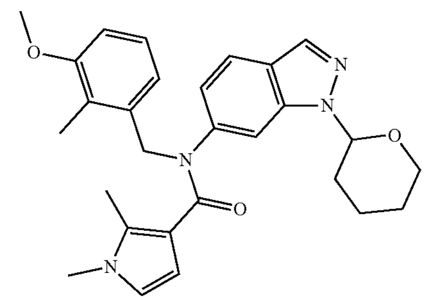

P113

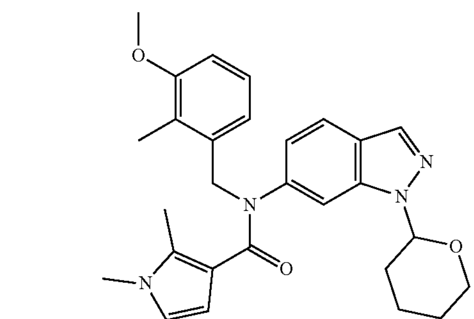

P114

-continued

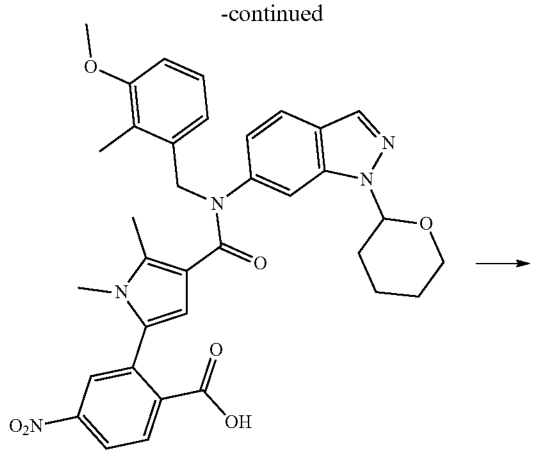

P115

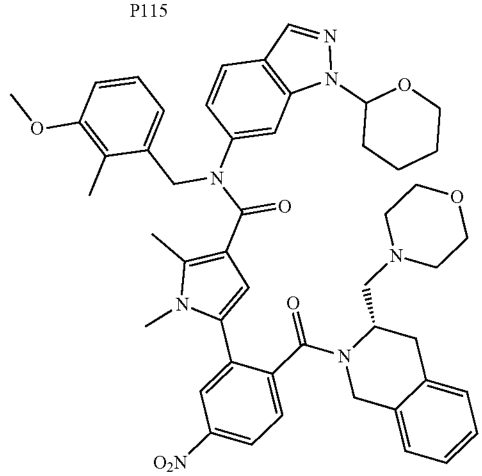

P116

Preparation 113. N-(3-Methoxy-2-methylbenzyl)-1,2-dimethyl-N-[1-(tetrahydro-2H-pyran-2-yl)-1H-indazol-6-yl]-1H-pyrrole-3-carboxamide (P113)

A mixture of P112 (1.5 g, 4.4 mmol), tert-BuOK (1.98 g, 17.6 mmol), and tert-BuOH (12 mL) was stirred at 50° C. for 30 min, then 3-methoxy-2-methylbenzyl methanesulfonate (1.5 g, 8.8 mmol) was added. The reaction mixture was stirred at 60° C. for 1 h and then partitioned between EtOAc and water. The organic layer was separated, washed with brine, dried over $Na_2SO_4$, filtered, and concentrated under reduced pressure. The residue was subjected to silica flash chromatography eluting with a mixture of EtOAc (0→100%) and DCM to afford 1.64 g (78%) of P113. LCMS (ESI+) m/z 473 $[M+H]^+$.

Preparation 114. Ethyl 2-[4-({(3-methoxy-2-methylbenzyl) [1-(tetrahydro-2H-pyran-2-yl)-1H-indazol-6-yl]amino}carbonyl)-1,5-dimethyl-1H-pyrrol-2-yl]-4-nitrobenzoate (P114)

A mixture of P113 (800 mg, 1.7 mmol), ethyl 2-bromo-4-nitrobenzoate (0.93 mg, 3.4 mmol), $K_3PO_4$ (1.4 g, 6.8 mmol), pivalic acid (52 mg, 0.51 mmol), $PdCl_2(PPh_3)_2$ (151 mg, 0.34 mmol) in N,N-dimethylacetamide (15 mL) was stirred at 130° C. for 2 h. Upon completion of the reaction mixture was diluted with water (25 mL) and EtOAC (100 mL). The organic layer was separated, washed with brine, dried over sodium sulfate, filtered, and concentrated under reduced pressure. The residue was subjected to silica flash chromatography eluting with a mixture of EtOAc (0-+20%) and DCM to afford 300 mg (27%) of the title compound. LCMS(ESI+) m/z 652 $[M+H]^+$.

Preparation 115. 2-[4-({(3-Methoxy-2-methylbenzyl) [1-(tetrahydro-2H-pyran-2-yl)-1H-indazol-6-yl] amino}carbonyl)-1,5-dimethyl-1H-pyrrol-2-yl]-4-nitrobenzoic acid (P115)

A solution of P114 (330 mg, 0.5 mmol) and NaOH (55 mg, 1.5 mmol) in a mixture of $MeOH/H_2O$ was stirred at ambient temperature for 12 h. The volatiles were removed under reduced pressure, and water (20 mL) was added to the residue. The solution was acidified with 6M HCl to pH 1 and extracted with DCM (2×10 mL), the combined organic layers were dried over $Na_2SO_4$ and evaporated to dryness under reduced pressure to afford 170 mg (53%) of the title compound that was pure enough to be used in the next step.

Preparation 116. N-(3-Methoxy-2-methylbenzyl)-1,2-dimethyl-5-(2-{[(3S)-3-(morpholin-4-ylmethyl)-3,4-dihydroisoquinolin-2 (1H)-yl]carbonyl}-5-nitrophenyl)-N-[1-(tetrahydro-2H-pyran-2-yl)-1H-indazol-6-yl]-1H-pyrrole-3-carboxamide (P116)

A mixture of P115 (170 mg, 0.26 mmol), P43 (68 mg, 0.28 mmol), DIPEA (0.07 mL, 0.39 mmol), and TBTU (94 mg, 0.28 mmol) and DMF (5 mL) was stirred at 60° C. overnight. The reaction mixture was diluted with water (10 mL), precipitate filtered and dried to afford 230 mg of crude product. LCMS(ESI+) m/z 853 $[M+H]^+$.

N-(2-Methoxybenzyl)-1,2-dimethyl-5-(2-{[(3S)-3-(morpholin-4-ylmethyl)-3,4-dihydroisoquinolin-2 (1H)-yl]carbonyl}-5-nitrophenyl)-N-[1-(tetrahydro-2H-pyran-2-yl)-1H-indazol-6-yl]-1H-pyrrole-3-carboxamide

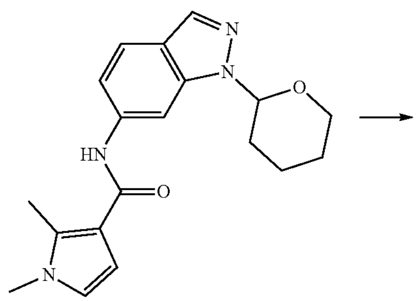

P112

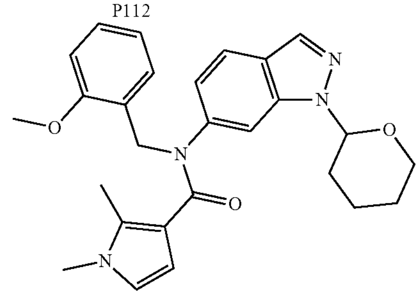

P117

-continued

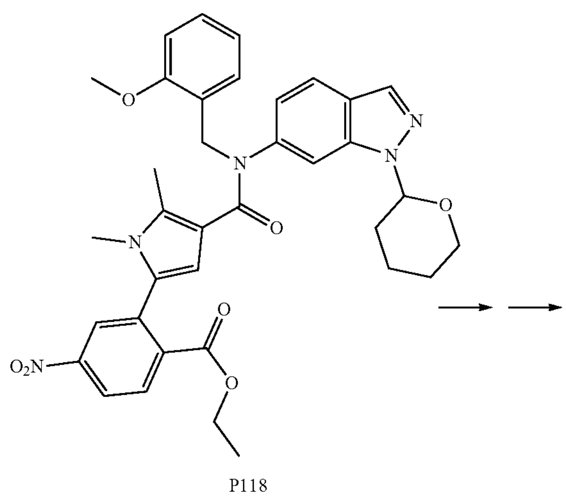

P118

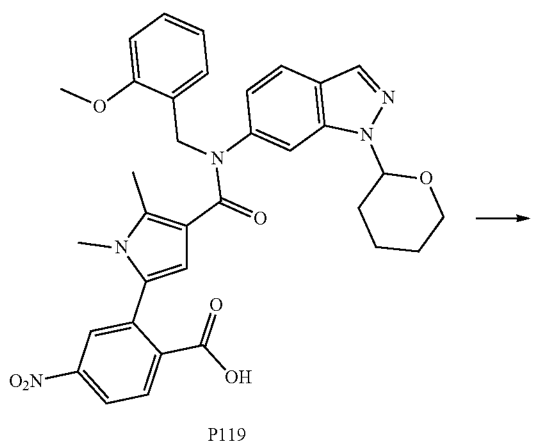

P119

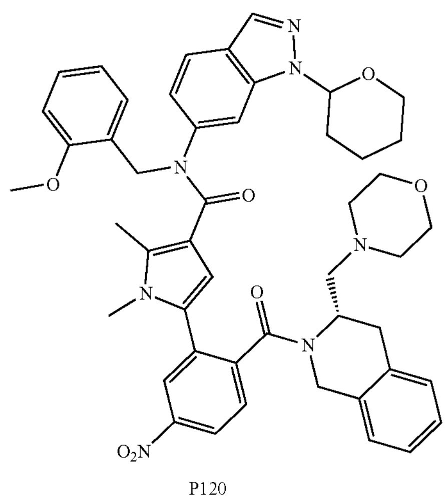 [SMILES: "P120" ; COc1ccccc1CN(C(=O)c1cc(-c2cc([N+](=O)[O-])ccc2C(=O)N2Cc3ccccc3C[C@H]2CN2CCOCC2)n(C)c1C)c1ccc2cnn(C3CCCCO3)c2c1]

P120

Preparation 117. N-(2-Methoxybenzyl)-1,2-dimethyl-N-[1-(tetrahydro-2H-pyran-2-yl)-1H-indazol-6-yl]-1H-pyrrole-3-carboxamide (P117)

A mixture of P112 (1.2 g, 3.5 mmol), tert-BuOK (1.6 g, 14.0 mmol), and tert-BuOH (12 mL) was stirred at 50° C. for 30 min, then 2-methoxybenzyl chloride (1.1 g, 7.0 mmol) was added. The reaction mixture was stirred at 60° C. for 1 h and then partitioned between EtOAc and water. The organic layer was separated, washed with brine, dried over $Na_2SO_4$, filtered, and concentrated under reduced pressure. The residue was subjected to silica flash chromatography eluting with a mixture of EtOAc (0→100%) and DCM to afford 0.6 g (37%) of P117. LCMS(ESI+) m/z 459 $[M+H]^+$ Preparation 118. Ethyl 2-[4-({(2-methoxybenzyl) [1-(tetrahydro-2H-pyran-2-yl)-1H-indazol-6-yl] amino}carbonyl)-1,5-dimethyl-1H-pyrrol-2-yl]-4-nitrobenzoate (P118)

A mixture of P117 (600 mg, 1.3 mmol), ethyl 2-bromo-4-nitrobenzoate (0.71 mg, 2.6 mmol), $K_3PO_4$ (1.1 g, 5.2 mmol), pivalic acid (40 mg, 0.39 mmol), $PdCl_2(PPh_3)_2$ (174 mg, 0.26 mmol) in N,N-dimethylacetamide (15 mL) was stirred at 130° C. for 2 h. Upon completion of the reaction mixture was diluted with water (25 mL) and EtOAC (100 mL). The organic layer was separated, washed with brine, dried over sodium sulfate, filtered, and concentrated under reduced pressure.

The residue was subjected to silica flash chromatography eluting with a mixture of EtOAc (0→20%) and DCM to afford 700 mg (83%) of the title compound. LCMS(ESI+) m/z 638 $[M+H]^+$.

Preparation 119. 2-[4-({(2-Methoxybenzyl) [1-(tetrahydro-2H-pyran-2-yl)-1H-indazol-6-yl] amino}carbonyl)-1,5-dimethyl-1H-pyrrol-2-yl]-4-nitrobenzoic acid (P119)

A solution of ethyl 2-[4-({(2-methoxybenzyl) [1-(tetrahydro-2H-pyran-2-yl)-1H-indazol-6-yl]amino}carbonyl)-1,5-dimethyl-1H-pyrrol-2-yl]-4-nitrobenzoate (700 mg, 1.1 mmol) and NaOH (440 mg, 11.0 mmol) in a mixture of $MeOH/H_2O$ was stirred at ambient temperature for 12 h. The volatiles were removed under reduced pressure, and water (20 mL) was added to the residue. The solution was acidified with 6M HCl to pH 1 and extracted with DCM (2×50 mL), the combined organic layers were dried over $Na_2SO_4$ and evaporated to dryness under reduced pressure to afford 300 mg (44%) of the title compound that was pure enough to be used further for the next step.

Preparation 120. N-(2-Methoxybenzyl)-1,2-dimethyl-5-(2-{[(3S)-3-(morpholin-4-ylmethyl)-3,4-dihydroisoquinolin-2 (1H)-yl]carbonyl}-5-nitrophenyl)-N-[1-(tetrahydro-2H-pyran-2-yl)-1H-indazol-6-yl]-1H-pyrrole-3-carboxamide (P120)

A mixture P119 (300 mg, 0.48 mmol), P43 (123 mg, 0.96 mmol), DIPEA (0.125 mL, 1.43 mmol), and TBTU (174 mg, 0.72 mmol) and DMF (15 mL) was stirred at 60° C. overnight. The reaction mixture was diluted with water (100 mL), precipitate filtered and dried to afford 350 mg of crude product. LCMS(ESI+) m/z 838 $[M+H]^+$.

N-(2-Cyanobenzyl)-1,2-dimethyl-5-(2-{[(3S)-3-(morpholin-4-ylmethyl)-3,4-dihydroisoquinolin-2(1H)-yl]carbonyl}-5-nitrophenyl)-N-[1-(tetrahydro-2H-pyran-2-yl)-1H-indazol-6-yl]-1H-pyrrole-3-carboxamide (P124)

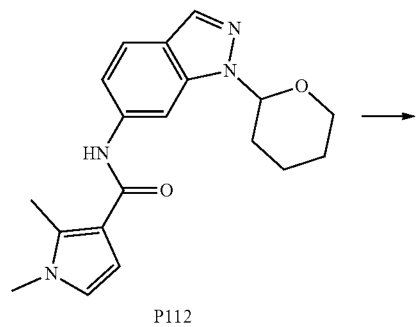

P112

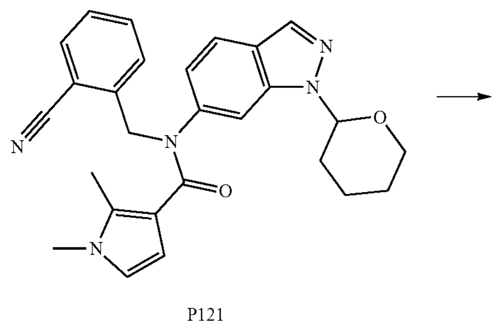

P121

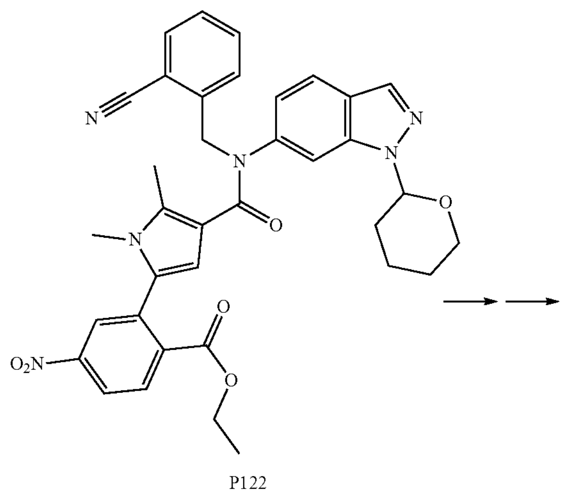

P122

-continued

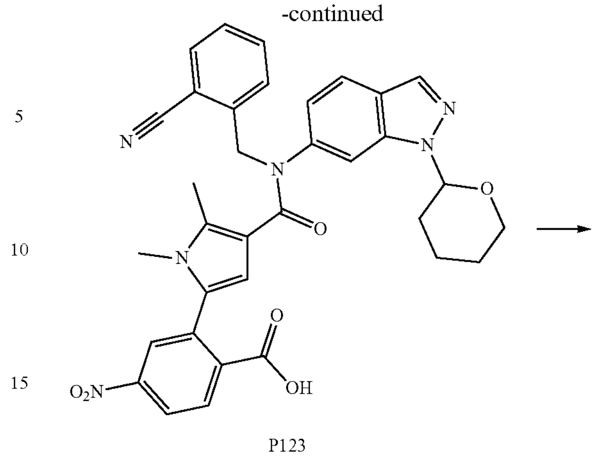

P123

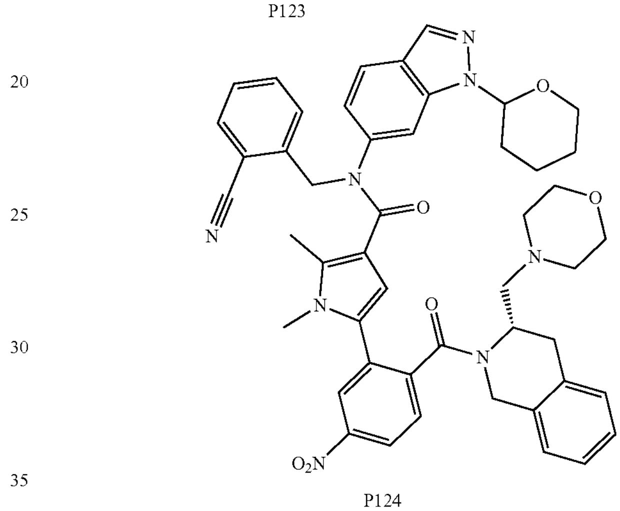

P124

Preparation 121. N-(2-Cyanobenzyl)-1,2-dimethyl-N-[1-(tetrahydro-2H-pyran-2-yl)-1H-indazol-6-yl]-1H-pyrrole-3-carboxamide (P121)

A mixture of P112 (1.5 g, 4.4 mmol), tert-BuOK (1.9 g, 17.6 mmol), and tert-BuOH (12 mL) was stirred at 50° C. for 30 min, then 2-(bromomethyl)benzonitrile (1.7 g, 8.8 mmol) was added. The reaction mixture was stirred at 60° C. for 1 h and then partitioned between EtOAc and water. The organic layer was separated, washed with brine, dried over $Na_2SO_4$, filtered, and concentrated under reduced pressure. The residue was subjected to silica flash chromatography eluting with a mixture of EtOAc (0→100%) and DCM to afford 1.0 g (49%) of P121. LCMS(ESI+) m/z 454 $[M+H]^+$.

Preparation 122. Ethyl 2-[4-({(2-cyanobenzyl) [1-(tetrahydro-2H-pyran-2-yl)-1H-indazol-6-yl] amino}carbonyl)-1,5-dimethyl-1H-pyrrol-2-yl]-4-nitrobenzoate (P122)

A mixture of P121 (1 g, 2.2 mmol), ethyl 2-bromo-4-nitrobenzoate (1.2 g, 4.4 mmol), $K_3PO_4$ (1.8 g, 8.8 mmol), pivalic acid (67 mg, 0.66 mmol), $PdCl_2$ $(PPh_3)_2$ (250 mg, 0.44 mmol) in N,N-dimethylacetamide (25 mL) was stirred at 130° C. for 2 h. Upon completion of the reaction mixture was diluted with water (25 mL) and EtOAC (100 mL). The organic layer was separated, washed with brine, dried over sodium sulfate, filtered, and concentrated under reduced pressure. The residue was subjected to silica flash chromatography eluting with a mixture of EtOAc (0→20%) and DCM to afford 500 mg (36%) of the title compound. LCMS(ESI+) m/z 633 $[M+H]^+$.

Preparation 123. 2-[4-({(2-Cyanobenzyl) [1-(tetrahydro-2H-pyran-2-yl)-1H-indazol-6-yl] amino}carbonyl)-1,5-dimethyl-1H-pyrrol-2-yl]-4-nitrobenzoic acid (P123)

A solution of P122 (500 mg, 0.8 mmol) and NaOH (340 mg, 9.0 mmol) in a mixture of $MeOH/H_2O$ was stirred at ambient temperature for 12 h. The volatiles were removed under reduced pressure, and water (20 mL) was added to the residue. The solution was acidified with 6M HCl to pH 1 and extracted with DCM (2×50 mL), the combined organic layers were dried over $Na_2SO_4$ and evaporated to dryness under reduced pressure to afford 440 mg (94%) of the title compound that was pure enough to be used further for the next step.

Preparation 124. N-(2-Cyanobenzyl)-1,2-dimethyl-5-(2-{[(3S)-3-(morpholin-4-ylmethyl)-3,4-dihydroisoquinolin-2 (1H)-yl]carbonyl}-5-nitrophenyl)-N-[1-(tetrahydro-2H-pyran-2-yl)-1H-indazol-6-yl]-1H-pyrrole-3-carboxamide (P124)

A mixture of P123 (440 mg, 0.71 mmol), P43 (182 mg, 0.81 mmol), DIPEA (0.186 mL, 1.13 mmol), and TBTU (251 mg, 0.82 mmol) and DMF (15 mL) was stirred at 60° C. overnight. The reaction mixture was diluted with water (100 mL), precipitate filtered and dried to afford 350 mg of crude product. LCMS(ESI+) m/z 833 $[M+H]^+$.

5-(5-Chloro-4-fluoro-2-{[(3S)-3-(morpholin-4-ylmethyl)-3,4-dihydroisoquinolin-2 (1H)-yl] carbonyl}phenyl)-N-(4-cyanophenyl)-1,2-dimethyl-1H-pyrrole-3-carboxamide (P127)

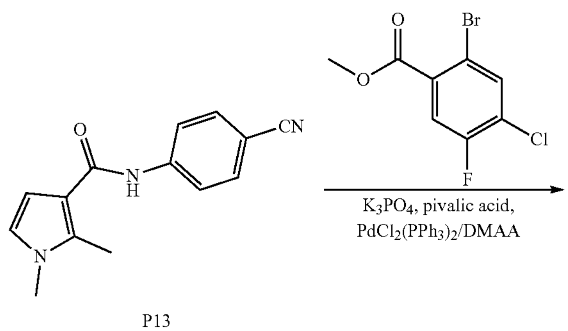

P13

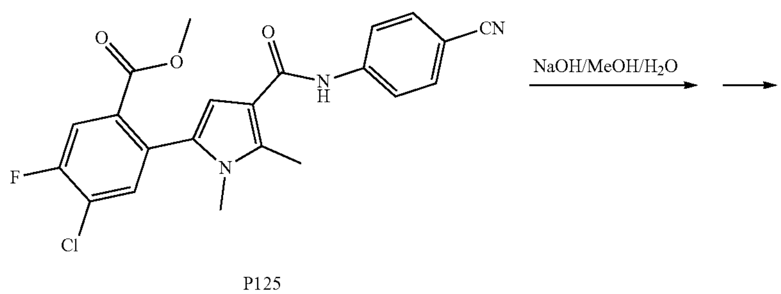

P125

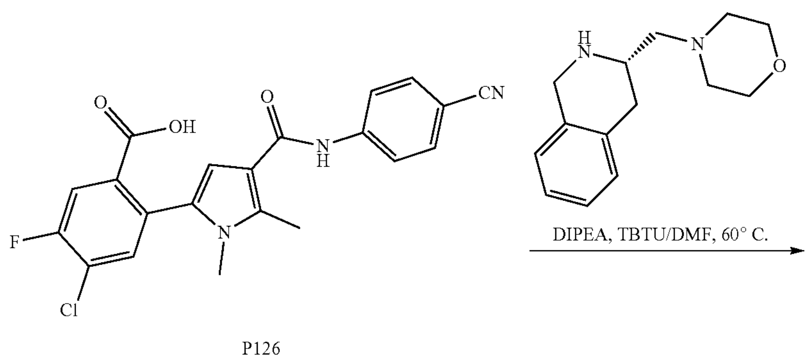

P126

-continued

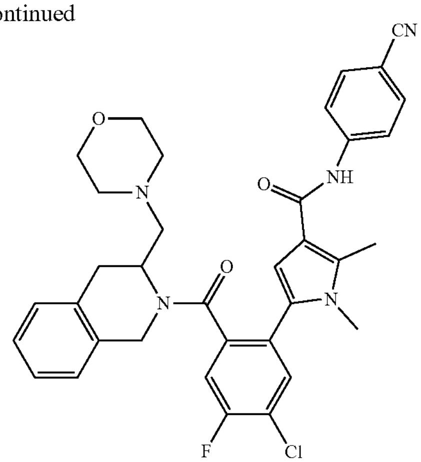

P127

Preparation 125. Methyl 4-chloro-2-(4-{[(4-cyanophenyl)amino]carbonyl}-1,5-dimethyl-1H-pyrrol-2-yl)-5-fluorobenzoate (P125)

A mixture of P13 (250 mg, 1.0 mmol), methyl 2-bromo-4-chloro-5-fluorobenzoate (560 mg, 2.0 mmol), $K_3PO_4$ (1.1 g, 5.2 mmol), pivalic acid (32 mg, 0.3 mmol), $PdCl_2(PPh_3)_2$ (147 mg, 0.2 mmol) in N,N-dimethylacetamide (3 mL) was heated to 135° C. The resulting mixture was stirred at 135° C. for 30 min, after that the reaction mixture was cooled to ambient temperature. Upon completion of the reaction, the mixture was diluted with water (10 mL) and $Et_2O$(10 mL). The organic layer was separated, washed with brine, dried over dried over anh. sodium sulfate, filtered, and concentrated under reduced pressure. The residue was subjected to a silica gel flash chromatography eluting with a mixture of EtOAc (0-+20%) and DCM to afford 100 mg (23%) of the title compound. LCMS(ESI+) m/z 426 $[M+H]^+$.

Preparation 126. 4-Chloro-2-(4-{[(4-cyanophenyl)amino]carbonyl}-1,5-dimethyl-1H-pyrrol-2-yl)-5-fluorobenzoic acid (P126)

A solution of P125 (100 mg, 0.2 mmol) and LiOH (28 mg, 1.2 mmol) in a mixture of THF (10 mL) and water (2 mL) was stirred at ambient temperature for 12 h. The volatiles were removed under reduced pressure, and water (20 mL) was added to the residue. The solution was acidified with 6M HCl to pH 1 and extracted with DCM (2×20 mL), the combined organic layers were dried over anh. sodium sulfate and evaporated to dryness under reduced pressure to afford 80 mg (82%) of the title compound that was pure enough to be used in the next step. LCMS(ESI+) m/z 413 $[M+H]^+$.

Preparation 127. 5-(5-Chloro-4-fluoro-2-{[(3S)-3-(morpholin-4-ylmethyl)-3,4-dihydroisoquinolin-2(1H)-yl]carbonyl}phenyl)-N-(4-cyanophenyl)-1,2-dimethyl-1H-pyrrole-3-carboxamide (P127)

A mixture of P126 (80 mg, 0.05 mmol), P43 (54 mg, 0.23 mmol), DIPEA (0.050 mL, 0.3 mmol), and TBTU (75 mg, 0.23 mmol), and DMF (5 mL) was stirred at 60° C. overnight. The reaction mixture was diluted with water (200 mL) and EtOAc (200 mL). The organic layer was separated, washed with brine, dried anh. sodium sulfate, filtered, and concentrated under reduced pressure. The residue was subjected to asilica gel flash chromatography eluting with a mixture of EtOAc (0→100%) and DCM to afford 90 mg (75%) of the title compound. LCMS(ESI+) m/z 627 $[M+H]^+$. 2-(4-{[(4-Chlorophenyl)amino]carbonyl}-1,5-dimethyl-1H-pyrrol-2-yl)-5-cyano-4-methoxybenzoic acid (P130)

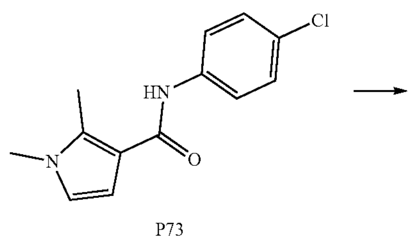

P73

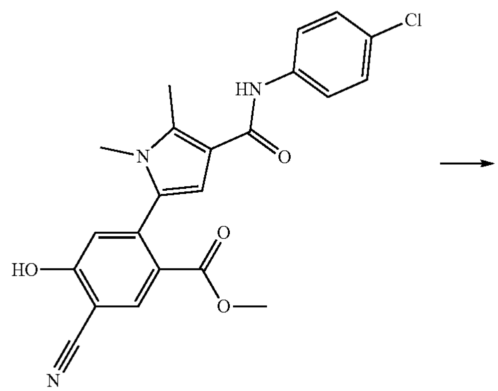

P128

-continued

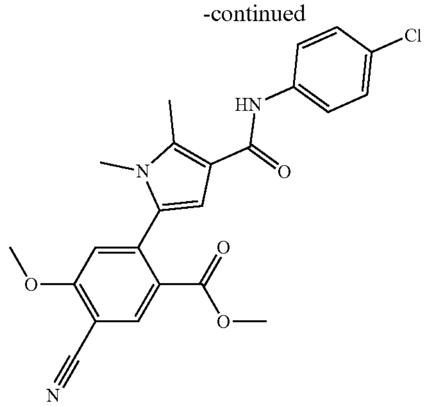

P128

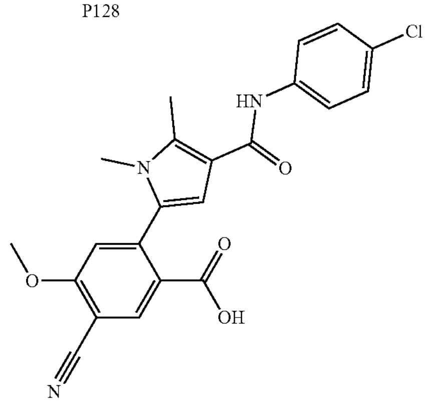

P130

Preparation 128. Methyl 2-(4-{[(4-chlorophenyl) amino]carbonyl}-1,5-dimethyl-1H-pyrrol-2-yl)-5-cyano-4-hydroxybenzoate (P128)

A mixture of P73 (1.3 g, 5.2 mmol), P77 (2.7 g, 10.4 mmol), $K_3PO_4$ (5.5 g, 26.0 mmol), pivalic acid (0.16 g, 1.5 mmol) in N,N-dimethylacetamide (50 mL) was stirred at 135° C. for 15 min, then $PdCl_2(PPh_3)_2$ (0.9 g, 1.02 mmol) was added. The resulting mixture was stirred at 135° C. for 30 min. Upon completion of the reaction the mixture was diluted with water (70 mL) and EtOAC (120 mL). The organic layer was separated, washed with brine, dried over sodium sulfate, filtered, and concentrated under reduced pressure. The residue was subjected to silica flash chromatography eluting with a mixture of EtOAc (0→20%) and DCM to afford 800 mg (36%) of the title compound.

Preparation 129. Methyl 2-(4-{[(4-chlorophenyl) amino]carbonyl}-1,5-dimethyl-1H-pyrrol-2-yl)-5-cyano-4-methoxybenzoate (P129)

A suspension of methyl P128 (0.86 g, 2.03 mmol), and $K_2CO_3$ (0.42 g, 3.0 mmol) in DMF (6 ml) was treated with $CH_3I$ (0.46 g, 3.2 mmol). The mixture was stirred for overnight at rt, reaction mixture poured into cold water. The resulting precipitate was filtered off, washed with water, Et20 and air-dried to afford 300 mg (34%) of the title compound.

Preparation 130. 2-(4-{[(4-Chlorophenyl)amino] carbonyl}-1,5-dimethyl-1H-pyrrol-2-yl)-5-cyano-4-methoxybenzoic acid (P130)

A solution of P129 (100 mg, 0.223 mmol) and LiOH (55 mg, 2.23 mmol) in a mixture of THF (8 mL) and water (2 mL) was stirred at ambient temperature for 12 h. The volatiles were removed under reduced pressure, and water (20 mL) was added to the residue. The solution was acidified with 6M HCl to pH 1 and extracted with DCM (2×10 mL), the combined organic layers were dried over $Na_2SO_4$ and evaporated to dryness under reduced pressure to afford 90 mg (93%) of the title compound that was pure enough to be used further for the next step.

N-(4-Chlorophenyl)-5-(4-cyano-5-methoxy-2-{[(3S)-3-(morpholin-4-ylmethyl)-3,4-dihydroisoquinolin-2 (1H)-yl]carbonyl}phenyl)-1,2-dimethyl-1H-pyrrole-3-carboxamide (P131)

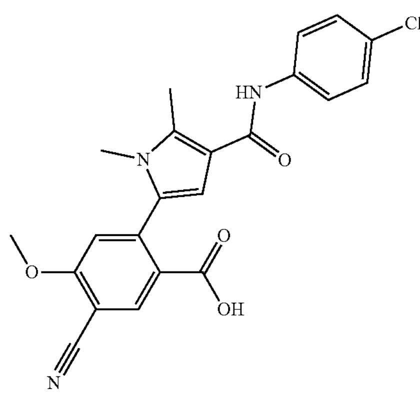

P130

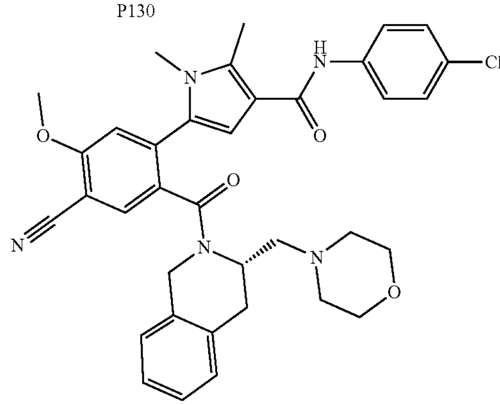

P131

Preparation 131. N-(4-Chlorophenyl)-5-(4-cyano-5-methoxy-2-{[(3S)-3-(morpholin-4-ylmethyl)-3,4-dihydroisoquinolin-2 (1H)-yl]carbonyl}phenyl)-1,2-dimethyl-1H-pyrrole-3-carboxamide (P131)

A mixture of P130 (150 mg, 0.31 mmol), P43 (86 mg, 0.37 mmol), DIPEA (0.08 mL, 0.46 mmol), and TBTU (118 mg, 0.37 mmol), and DMF (8 mL) was stirred at 60° C. overnight. The reaction mixture was diluted with water (20 mL) and EtOAc (10 mL). The organic layer was separated, washed with brine, dried over $Na_2SO_4$, filtered, and concentrated under reduced pressure. The residue was subjected to silica flash chromatography eluting with a mixture of EtOAc (0→100%) and DCM to afford 50 mg (23%) of the title compound.

Methyl 2-bromo-4-cyanobenzoate (P132)

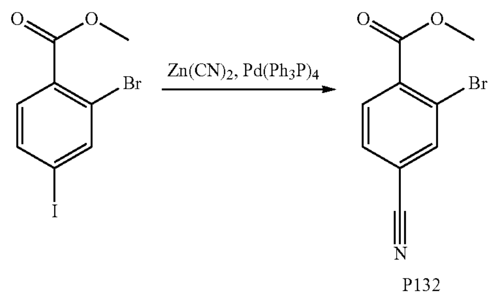

P132

Preparation 132. Methyl 2-bromo-4-cyanobenzoate (P132)

To a stirred solution of methyl 2-bromo-4-(iodomethyl) benzoate (1 g, 0.0028 mol) in DMF (10 mL) $Zn(CN)_2$ (0.329 g, 0.0028 mol) and $Pd(Ph_3P)_4$ (0.325 g, 0.1 eq) were added. Then reaction mixture was stirred at 100° C. overnight and then treated with water (20 mL) and extracted with EtOAc. The combined organic layers were dried over anhydrous sodium sulfate, filtered and the filtrate was evaporated under reduced pressure. The residue was subjected to a silica gel flash chromatography eluting with a mixture of DCM: $ClC_4$ to afford 670 mg (99%) of the title compound. $^1H$ NMR (400 MHZ, $CDCl_3$), δ: 7.97 (s, 1H), 7.88 (dd, J=2.3 Hz, J=8.0 Hz, 1H), 7.68 (dd, J=2.4 Hz, J=8.1 Hz, 1H), 3.98 (s, 3H).

2-(4-[4-(Benzyloxy) anilino]carbonyl-1,5-dimethyl-1H-pyrrol-2-yl)-4-cyanobenzoic acid (P134)

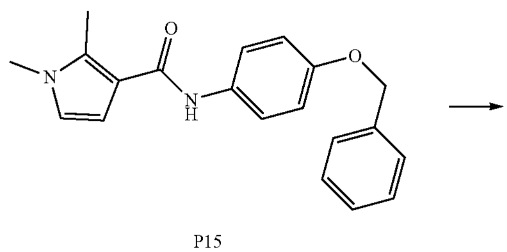

P15

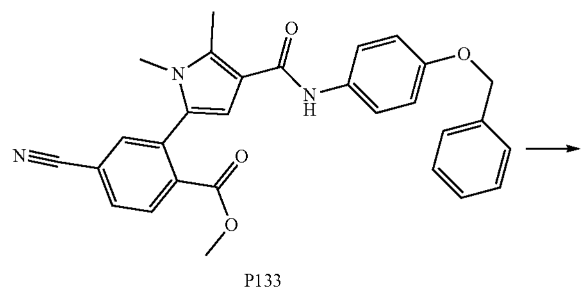

P133

-continued

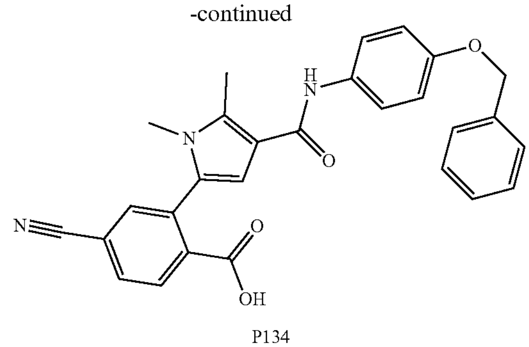

P134

Preparation 133. Methyl 2-(4-[4-(benzyloxy) anilino]carbonyl-1,5-dimethyl-1H-pyrrol-2-yl)-4-cyanobenzoate (P133)

A mixture of P15 (300 mg, 0.9 mmol), P132 (450 mg, 1.8 mmol), $K_3PO_4$ (993 mg, 5 eq), pivalic acid (29 mg, 0.3 eq) and $PdCl_2$ $(PPh_3)_2$ (131 mg, 0.2 eq) in N,N-dimethylacetamide (15 mL) was stirred at 130° C. for 2 h. Upon completion of the reaction mixture was diluted with water (25 mL) and EtOAC (100 mL). The organic layer was separated, washed with brine, dried over sodium sulfate, filtered, and concentrated under reduced pressure. The residue was subjected to silica flash chromatography eluting with a mixture of EtOAc (0→20%) and DCM to afford 266 mg (59%) of P133. LCMS(ESI+) m/z 480 $[M+H]^+$ Preparation 134. 2-(4-[4-(Benzyloxy) anilino]carbonyl-1,5-dimethyl-1H-pyrrol-2-yl)-4-cyanobenzoic acid (P134)

A solution of ester P133 (290 mg, 0.6 mmol) and LiOH (150 mg, 10 eq) in a mixture of $THF/H_2O$ was stirred at ambient temperature for 12 h. The volatiles were removed under reduced pressure, and water (3 mL) was added to the residue. The solution was acidified with 6M HCl to pH 1 and extracted with DCM (2×5 mL), the combined organic layers were dried over $Na_2SO_4$ and evaporated to dryness under reduced pressure to afford 280 mg (99%) of the title acid P134 that was pure enough to be used further for the next step. LCMS(ESI+) m/z 466 $[M+H]^+$.

$N^3$-[4-(benzyloxy)phenyl]-5-(5-cyano-2-[3-(morpholinomethyl)-3,4-dihydro-2 (1H)-isoquinolinyl] carbonylphenyl)-1,2-dimethyl-1H-pyrrole-3-carboxamide (P135)

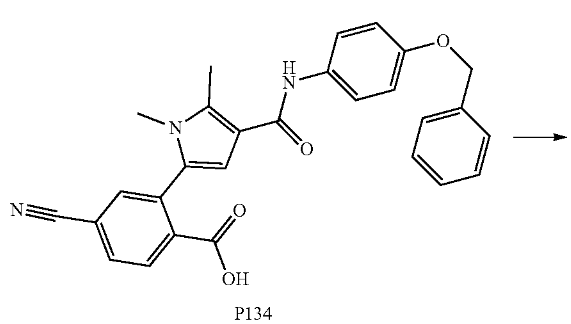

P134

-continued

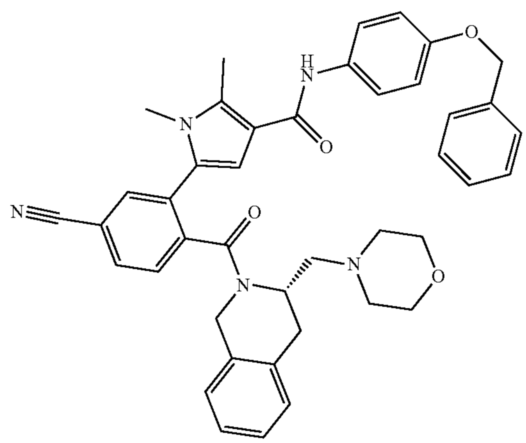

P135

-continued

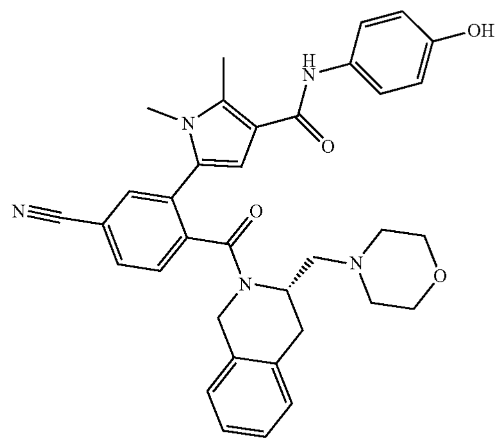

P136

Preparation 135. $N^3$-[4-(benzyloxy)phenyl]-5-(5-cyano-2-[3-(morpholinomethyl)-3,4-dihydro-2 (1H)-isoquinolinyl]carbonylphenyl)-1,2-dimethyl-1H-pyrrole-3-carboxamide (P135)

A mixture of acid P134 (280 mg, 0.6 mmol), P43 (0.14 g, 0.66 mmol), DIPEA (0.14 mL, 1.5 eq), and TBTU (0.199 g, 0.66 mmol), and DMF (4 mL) was stirred at 60° C. overnight. The reaction mixture was diluted with water (6 mL) and EtOAc (50 ml). The organic layer was separated, washed with brine, dried over $Na_2SO_4$, filtered, and concentrated under reduced pressure. The residue was subjected to silica flash chromatography eluting with a mixture of EtOAc (0→100%) and DCM to afford 221 mg (54%) of the title compound. LCMS(ESI+) m/z 680 $[M+H]^+$. 5-(5-Cyano-2-[3-(morpholinomethyl)-3,4-dihydro-2 (1H)-isoquinolinyl]carbonylphenyl)-$N^3$-(4-hydroxynhenyl)-1,2-dimethyl-1H-pyrrole-3-carboxamide (P136)

Preparation 136. $N^3$-[4-(benzyloxy)phenyl]-5-(5-cyano-2-[3-(morpholinomethyl)-3,4-dihydro-2 (1H)-isoquinolinyl]carbonylphenyl)-1,2-dimethyl-1H-pyrrole-3-carboxamide (P136)

A solution of the compound P135 (220 mg, 0.3 mmol) in DCM (5 mL) was cooled to −78° C., and a solution of $BBr_3$ (0.09 ml, 0.6 mmol) was added over 5 min. The reaction mixture was stirred at to −78° C. for 1 h and then was diluted with saturated aqueous solution of sodium bicarbonate $NaHCO_3$. The organic layer was separated, washed with brine, dried over $Na_2SO_4$, filtered, and concentrated under reduced pressure. The residue was subjected to silica flash chromatography eluting with a mixture of EtOAc to afford 202 mg (98%) of the title compound.LCMS(ESI+) m/z 590 $[M+H]^+$.

5-(5-Cyano-2-[3-(morpholinomethyl)-3,4-dihydro-2 (1H)-isoquinolinyl]carbonylphenyl)-1,2-dimethyl-$N^3$-(4-[2-(1,1,1-trimethylsilylethoxy]methoxyphenyl)-1H-pyrrole-3-carboxamide (P137)

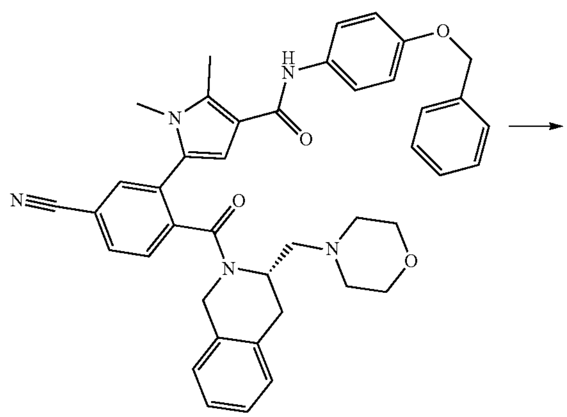

P135

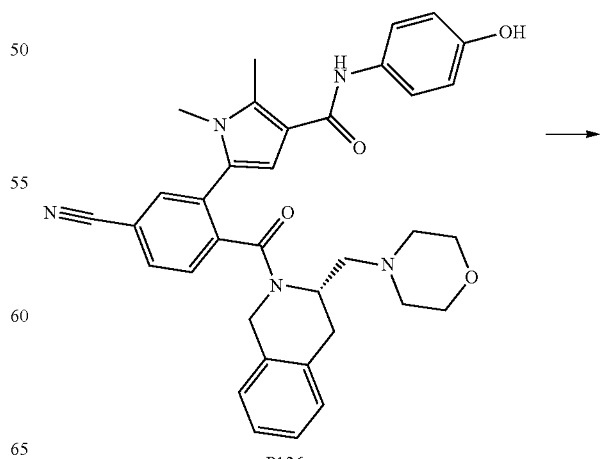

P136

-continued

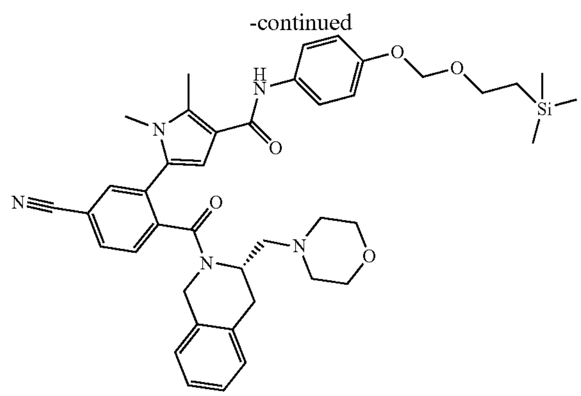

P137

Preparation 137. 5-(5-Cyano-2-[3-(morpholinomethyl)-3,4-dihydro-2 (1H)-isoquinolinyl]carbonylphenyl)-1,2-dimethyl-$N^3$-(4-[2-(1,1,1-trimethylsilylethoxy]methoxyphenyl)-1H-pyrrole-3-carboxamide (P137)

NaH (16 mg, 60%) was added to a stirred solution of P136 (200 mg, 0.3 mmol) in DMF (5 mL) maintaining temperature 0° C. and stirred 30 min Then [2-(chloromethoxy)ethyl](trimethyl) silane (0.1 mL, 0.45 mmol) was added. The reaction mixture was stirred at ambient temperature overnight and then partitioned between EtOAc and water. The organic layer was separated, washed with brine, dried over $Na_2SO_4$, filtered, and concentrated under reduced pressure. The residue was subjected to silica flash chromatography eluting with a mixture of EtOAc (0→100%) and DCM to afford 123 mg (50%) of the title compound. LCMS(ESI+) m/z 720 $[M+H]^+$.

5-(5-Cyano-2-[3-(morpholinomethyl)-3,4-dihydro-2 (1H)-isoquinolinyl]carbonylphenyl)-$N^3$-(3-methoxy-2-methylbenzyl)-1,2-dimethyl-$N^3$-(4-[2-(1,1,1-trimethylsilylethoxy]methoxyphenyl)-1H-pyrrole-3-carboxamide (P138)

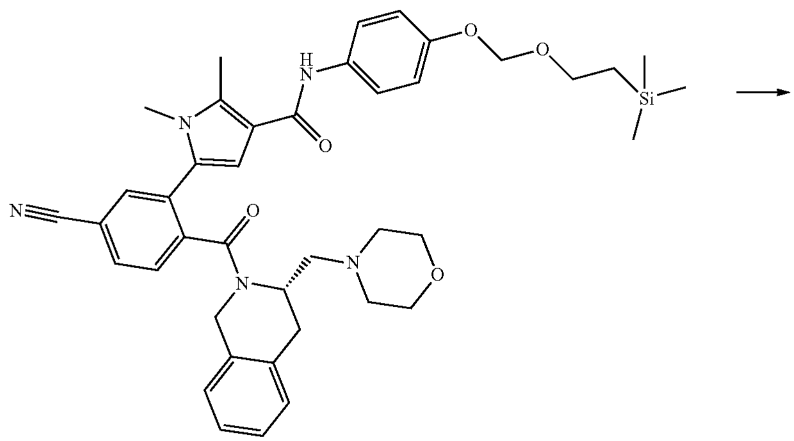

P137

-continued

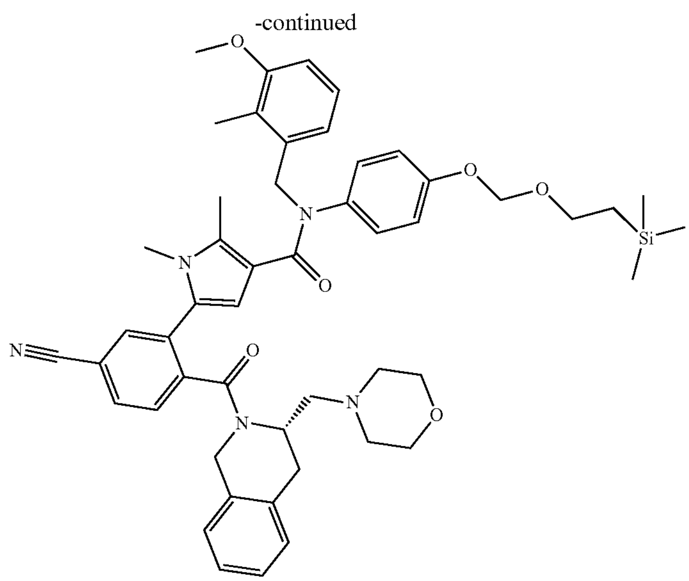

P138

Preparation 138. 5-(5-Cyano-2-[3-(morpholinomethyl)-3,4-dihydro-2 (1H)-isoquinolinyl]carbonylphenyl)-$N^3$-(3-methoxy-2-methylbenzyl)-1,2-dimethyl-$N^3$-(4-[2-(1,1,1-trimethylsilylethoxy]methoxyphenyl)-1H-pyrrole-3-carboxamide (P138)

A mixture of P137 (120 mg, 0.16 mmol), tert-BuOK (80 mg, 4 eq), and tert-BuOH (3 mL) was stirred at 50° C. for 5 min, then 3-methoxy-2-methylbenzyl methanesulfonate (80 mg, 2 eq) was added. The reaction mixture was stirred at 80° C. for 0.5 h and then partitioned between EtOAc and water. The organic layer was separated, washed with brine, dried over $Na_2SO_4$, filtered, and concentrated under reduced pressure. The residue was subjected to silica flash chromatography eluting with a mixture of EtOAc (0→100%) and DCM to afford 50 mg of P138. LCMS(ESI+) m/z 854 $[M+H]^+$.

5-(5-(Aminocarbonyl)-2-[3-(morpholinomethyl)-3,4-dihydro-2 (1H)-isoquinolinyl]carbonylphenyl)-$N^3$-(3-methoxy-2-methylbenzyl)-1,2-dimethyl-$N^3$-(4-[2-(1,1,1-trimethylsilylethoxy]methoxyphenyl)-1H-pyrrole-3-carboxamide (P139)

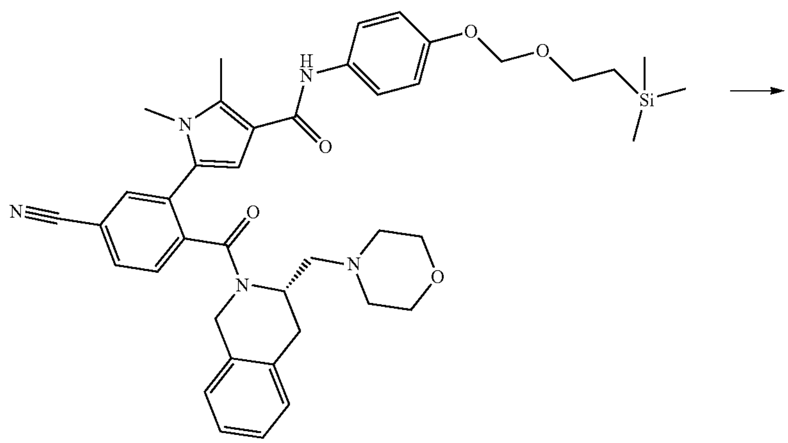

P138

-continued

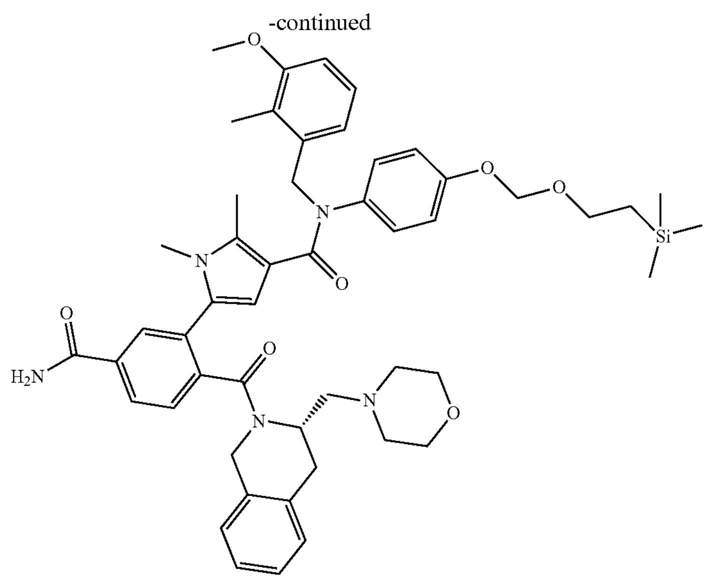

P139

Preparation 139. 5-(5-(Aminocarbonyl)-2-[3-(morpholinomethyl)-3,4-dihydro-2 (1H)-isoquinolinyl]carbonylphenyl)-$N^3$-(3-methoxy-2-methylbenzyl)-1,2-dimethyl-$N^3$-(4-[2-(1,1,1-trimethylsilylethoxy]methoxyphenyl)-1H-pyrrole-3-carboxamide (P139)

A mixture of P138 (120 mg, 0.16 mmol), tert-BuOK (80 mg, 4 eq), and tert-BuOH (3 mL) was stirred at 50° C. for 30 min, then 3-methoxy-2-methylbenzyl methanesulfonate (80 mg, 2 eq) was added. The reaction mixture was stirred at 60° C. for 3 h and then partitioned between EtOAc and water. The organic layer was separated, washed with brine, dried over $Na_2SO_4$, filtered, and concentrated under reduced pressure. The residue was subjected to silica flash chromatography eluting with a mixture of EtOAc (0→100%) and DCM to afford 70 mg of compound P139. LCMS(ESI+) m/z 872 $[M+H]^+$.

5-(5-Chloro-2-{[(3S)-3-(morpholin-4-ylmethyl)-3,4-dihydroisoquinolin-2 (1H)-yl]carbonyl}phenyl)-N-(4-cyanophenyl)-1,2-dimethyl-1H-pyrrole-3-carboxamide (P142)

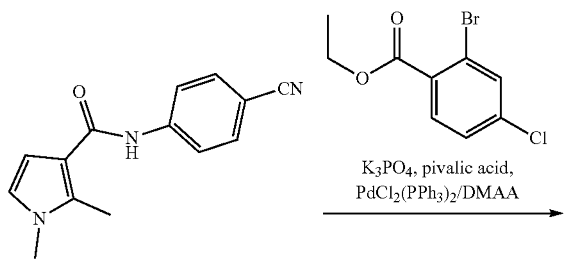

P13

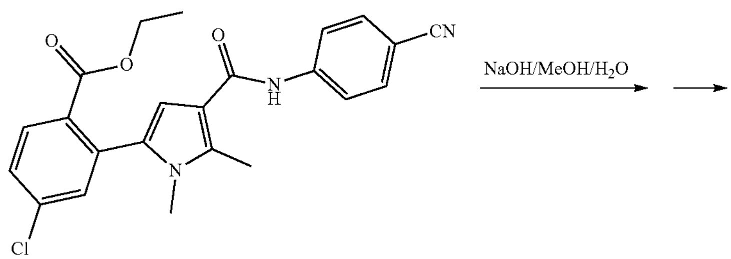

P140

-continued

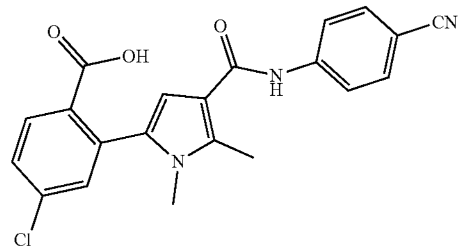

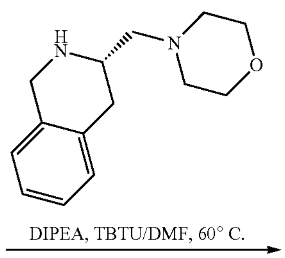

DIPEA, TBTU/DMF, 60° C.

P141

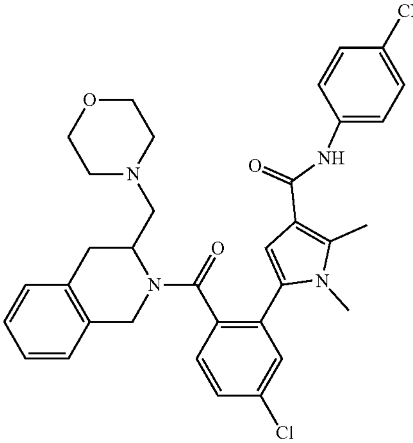

P142

Preparation 140. N-(4-cyanophenyl)-1,2-dimethyl-1H-pyrrole-3-carboxamide (P140)

To a stirred solution of P13 (1.0 g, 7.2 mmol) in pyridine (5 mL) neat $SOCl_2$ (0.55 mL, 7.6 mmol) was added dropwise at 0° C. and the reaction mixture was stirred at 0° C. for 3 h. Then 4-aminobenzonitrile (0.85 g, 7.2 mmol) in DIPEA (1.4 mL, 7.96 mmol) was added dropwise, keeping the temperature at 0° C. After the reaction was warmed up to ambient temperature, then stirred at ambient temperature for 16 h. Volatiles were removed under reduced pressure. The residue was diluted with water and Et20. The organic layer separated, washed with water, brine, dried over dried over anh. sodium sulfate, filtered, and concentrated under reduced pressure. The residue was subjected to a silica gel flash chromatography eluting with a mixture of EtOAc (0→20%) and DCM to afford 850 mg (50%) of the title compound. $^1$H NMR (400 MHZ, DMSO-$d_6$), δ: 9.70 (br. s, 1H), 7.95 (d, 1H, J=8.7 Hz,), 7.73 (d, 1H, J=8.7 Hz), 6.73-6.64 (m, 1H), 3.54 (s, 3H), 2.47 (s, 3H). LCMS(ESI+) m/z 240 [M+H]*.

Preparation 141. 4-Chloro-2-(4-{[(4-cyanophenyl)amino]carbonyl}-1,5-dimethyl-1H-pyrrol-2-yl)benzoic acid (P141)

A solution of P140 (200 mg, 0.47 mmol) and LiOH (54 mg, 2.4 mmol) in a mixture of EtOH (10 mL) and water (2 mL) was stirred at ambient temperature for 12 h. The volatiles were removed under reduced pressure, and water (20 mL) was added to the residue. The solution was acidified with 6M HCl to pH 1 and extracted with DCM (2×20 mL), the combined organic layers were dried over anh. sodium sulfate and evaporated to dryness under reduced pressure to afford 180 mg (96%) of the title compound that was pure enough to be used for the next step. LCMS(ESI+) m/z 394 $[M+H]^+$.

Preparation 142. 5-(5-Chloro-2-{[(3S)-3-(morpholin-4-ylmethyl)-3,4-dihydroisoquinolin-2 (1H)-yl]carbonyl}phenyl)-N-(4-cyanophenyl)-1,2-dimethyl-1H-pyrrole-3-carboxamide (P142)

A mixture of P141 (180 mg, 0.45 mmol), P43 (127 mg, 0.55 mmol), DIPEA (0.12 mL, 0.69 mmol), and TBTU (176 mg, 0.55 mmol), and DMF (5 mL) was stirred at 60° C. overnight. The reaction mixture was diluted with water (200 mL) and EtOAc (200 mL). The organic layer was separated, washed with brine, dried anh. sodium sulfate, filtered, and concentrated under reduced pressure. The residue was subjected to asilica gel flash chromatography eluting with a mixture of EtOAc (0→100%) and DCM to afford 170 mg (61%) of the title compound. LCMS(ESI+) m/z 609 $[M+H]^+$.

N-(2-cyanobenzyl)-1,2-dimethyl-5-(2-{[(3S)-3-(morpholin-4-ylmethyl)-3,4-dihydroisoquinolin-2(1H)-yl]carbonyl}-5-nitrophenyl)-N-(4-{[2-(trimethylsilylethoxy]methoxy}phenyl)-1H-pyrrole-3-carboxamide (P146)
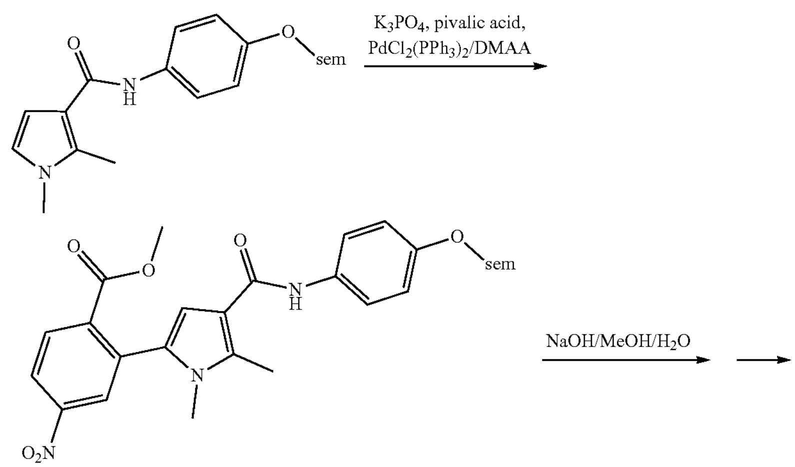
P143
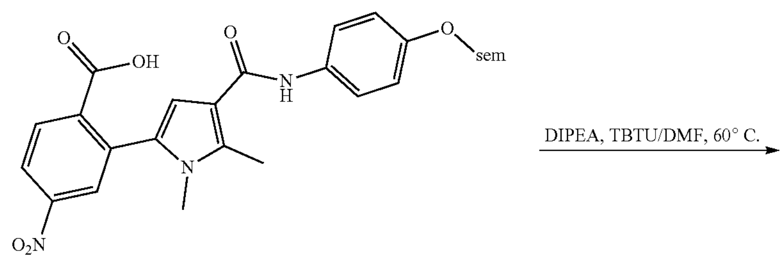
P144
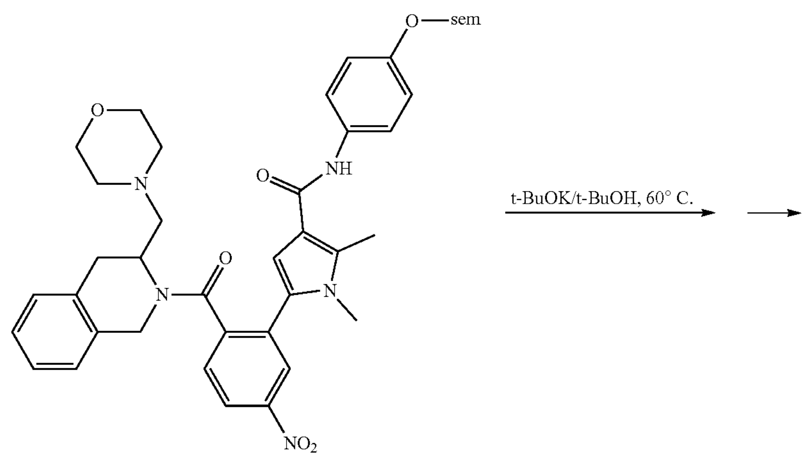
P145

-continued

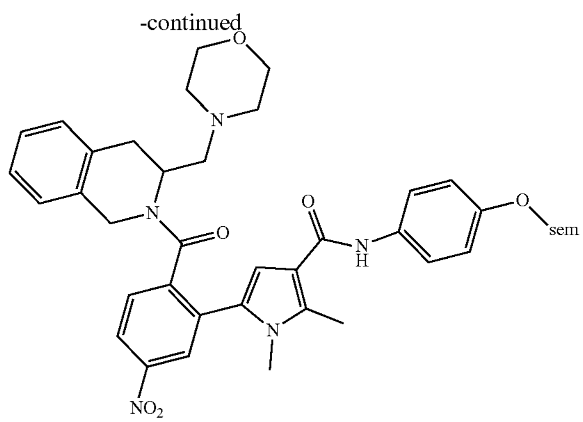

P146

Preparation 143. Methyl 2-(1,5-dimethyl-4-{[(4-{[2-(trimethylsilylethoxy]methoxy}phenyl)amino]carbonyl}-1H-pyrrol-2-yl)-4-nitrobenzoate (P143)

A mixture of 1,2-dimethyl-N-(4-{[2-(trimethylsilylethoxy]methoxy}phenyl)-1H-pyrrole-3-carboxamide (500 g, 1.4 mmol), methyl 2-bromo-4-nitrobenzoate (720 mg, 2.8 mol), $K_3PO_4$ (1.47 g, 6.9 mmol), pivalic acid (42 mg, 0.4 mmol), $PdCl_2$ $(PPh_3)_2$ (194 mg, 0.28 mmol) in N,N-dimethylacetamide (50 mL) was heated to 135° C. The resulting mixture was stirred at 135° C. for 30 min, after that the reaction mixture was cooled to ambient temperature. Upon completion of the reaction, the mixture was diluted with water (50 mL) and $Et_2O$(50 mL). The organic layer was separated, washed with brine, dried over dried over anhydrous sodium sulfate, filtered, and concentrated under reduced pressure. The residue was subjected to a silica gel flash chromatography eluting with a mixture of EtOAc (0→20%) and DCM to afford 40 mg (59%) of the title compound. LCMS(ESI+) m/z 540 $[M+H]^+$.

Preparation 144. 2-(1,5-dimethyl-4-{[(4-{[2-(trimethylsilylethoxy]methoxy}phenyl)amino]carbonyl}-1H-pyrrol-2-yl)-4-nitrobenzoic acid (P144)

A solution of P143 (440 mg, 0.8 mmol) and NaOH (162 mg, 4.0 mmol) in a mixture of EtOH (40 mL) and water (5 mL) was stirred at ambient temperature for 12 h. The volatiles were removed under reduced pressure, and water (50 mL) was added to the residue. The solution was acidified with 6M HCl to pH 1 and extracted with DCM (2×40 mL), the combined organic layers were dried over anh. sodium sulfate and evaporated to dryness under reduced pressure to afford 400 mg (94%) of the title compound that was pure enough to be used for the next step. LCMS(ESI+) m/z 525 $[M+H]^+$.

Preparation 145. 1,2-dimethyl-5-(2-{[(3S)-3-(morpholin-4-ylmethyl)-3,4-dihydroisoquinolin-2 (1H)-yl]carbonyl}-5-nitrophenyl)-N-(4-{[2-(trimethylsilylethoxy]methoxy}phenyl)-1H-pyrrole-3-carboxamide (P145)

A mixture of P144 (400 mg, 0.76 mmol), P43 (210 mg, 0.9 mmol), DIPEA (0.2 mL, 1.15 mmol), and TBTU (290 mg, 0.9 mmol), and DMF (10 mL) was stirred at 60° C. overnight. The reaction mixture was diluted with water (20 mL) and EtOAc (20 mL). The organic layer was separated, washed with brine, dried anh. sodium sulfate, filtered, and concentrated under reduced pressure. The residue was subjected to asilica gel flash chromatography eluting with a mixture of EtOAc (0→100%) and DCM to afford 450 mg (80%) of the title compound. LCMS(ESI+) m/z 740 $[M+H]^+$.

Preparation 146. N-(2-Cyanobenzyl)-1,2-dimethyl-5-(2-{[(3S)-3-(morpholin-4-ylmethyl)-3,4-dihydroisoquinolin-2 (1H)-yl]carbonyl}-5-nitrophenyl)-N-(4-{[2-(trimethylsilylethoxy]methoxy}phenyl)-1H-pyrrole-3-carboxamide (P146)

A mixture of P146 (150 mg, 0.2 mmol), tert-BuOK (87 mg 0.8 mmol), and tert-BuOH (20 mL) was stirred at 50° C. for 30 min, then 2-(bromomethyl)benzonitrile (80 mg, 0.4 mmol) was added. The reaction mixture was stirred at 60° C. for 1 h and then partitioned between EtOAc and water. The organic layer was separated, washed with brine, dried over anh. sodium sulfate, filtered, and was concentrated under reduced pressure. The residue was subjected to a silica gel flash chromatography eluting with a mixture of EtOAc (0→100%) and DCM to afford 120 mg (70%) of the title compound. LCMS(ESI+) m/z 856 $[M+H]^+$.

N-(3-methoxy-2-methylbenzyl)-1,2-dimethyl-5-(2-{[(3S)-3-(morpholin-4-ylmethyl)-3,4-dihydroisoquinolin-2 (1H)-yl]carbonyl}-5-nitrophenyl)-N-(4-{[2-(trimethylsilylethoxy]methoxy}phenyl)-1H-pyrrole-3-carboxamide (P147)

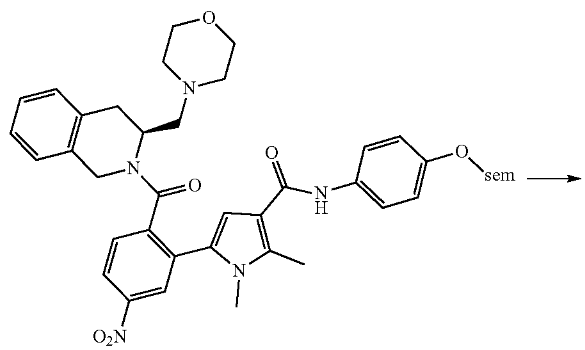

P145

-continued

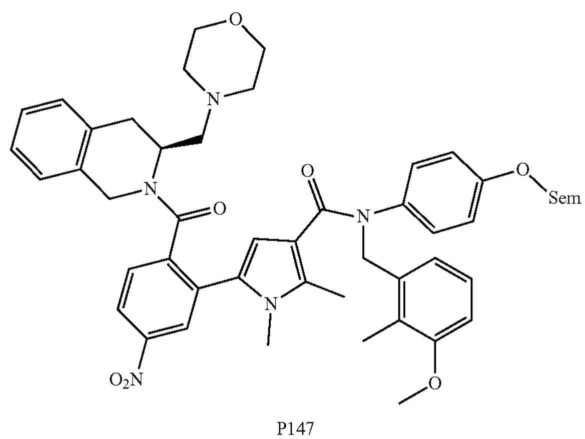

P147

Preparation 147. N-(3-methoxy-2-methylbenzyl)-1,2-dimethyl-5-(2-{[(3S)-3-(morpholin-4-ylmethyl)-3,4-dihydroisoquinolin-2 (1H)-yl]carbonyl}-5-nitrophenyl)-N-(4-{[2-(trimethylsilylethoxy]methoxy}phenyl)-1H-pyrrole-3-carboxamide (P146)

A mixture of P145 (200 mg, 0.27 mmol), tert-BuOK (120 mg, 1.1 mmol), and tert-BuOH (20 mL) was stirred at 50° C. for 30 min, then 3-methoxy-2-methylbenzyl methanesulfonate (124 mg, 0.54 mmol) was added. The reaction mixture was stirred at 60° C. for 1 h and then partitioned between EtOAc and water. The organic layer was separated, washed with brine, dried over anh. sodium sulfate, filtered, and concentrated under reduced pressure. The residue was subjected to a silica gel flash chromatography eluting with a mixture of EtOAc (0→100%) and DCM to afford 210 mg (89%) of the title compound. LCMS(ESI+) m/z 875 $[M+H]^+$.

5-(5-(Acetylamino)-2-{[(3S)-3-(morpholin-4-ylmethyl)-3,4-dihydroisoquinolin-2 (1H)-yl]carbonyl}phenyl)-N-(3-methoxy-2-methylbenzyl)-1,2-dimethyl-N-(4-{[2-(trimethylsilylethoxy]methoxy}phenyl)-1H-pyrrole-3-carboxamide (P149)

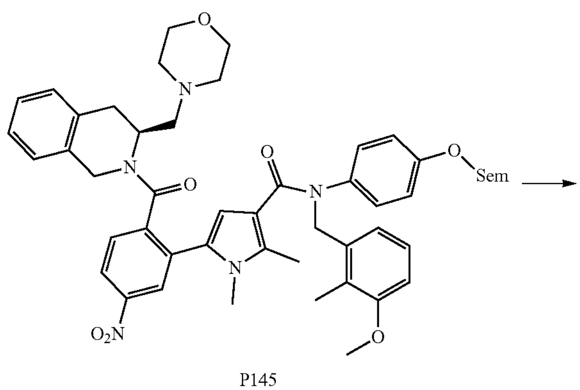

P145

-continued

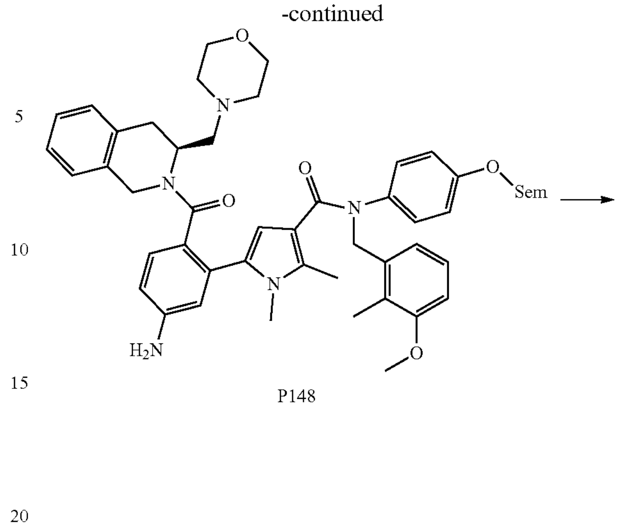

P148

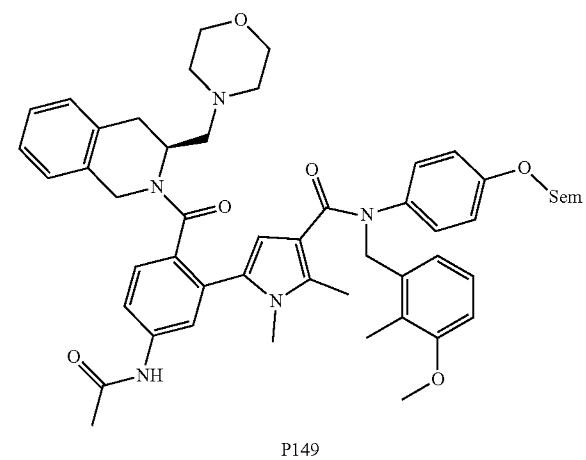

P149

Preparation 148. 5-(5-Amino-2-{[(3S)-3-(morpholin-4-ylmethyl)-3,4-dihydroisoquinolin-2 (1H)-yl]carbonyl}phenyl)-N-(3-methoxy-2-methylbenzyl)-1,2-dimethyl-N-(4-{[2-(trimethylsilylethoxy]methoxy}phenyl)-1H-pyrrole-3-carboxamide (P148). A stirred mixture of P145 (200 mg, 0.2 mmol), catalyst (5 mg of 5% Pd on charcoal), and tret-butanol (2 mL) was hydrogenated under $H_2$20 atmosphere for 56 h. The catalyst was filtered off, and the filtrate was evaporated to dryness to afford 180 mg (93%) of the title compound.

Preparation 149. 5-(5-(Acetylamino)-2-{[(3S)-3-(morpholin-4-ylmethyl)-3,4-dihydroisoquinolin-2 (1H)-yl]carbonyl}phenyl)-N-(3-methoxy-2-methylbenzyl)-1,2-dimethyl-N-(4-{[2-(trimethylsilylethoxy]methoxy}phenyl)-1H-pyrrole-3-carboxamide (P149). A stirred mixture of P148 (180 mg, 0.21 mmol), $C_2O$ (22 mg, 0.21 mmol), and DCM (2 mL) was stirred at ambient temperature for 3 h and then partitioned between EtOAc and water. The organic layer was separated, washed with brine, dried over anhydrous sodium sulfate, filtered, and was concentrated under reduced pressure. The residue was subjected to a silica gel flash chromatography eluting with a mixture of EtOAc (0→100%) and DCM to afford 150 mg (80%) of the title compound. LCMS(ESI+) m/z 887 $[M+H]^+$.

2-[4-({[4-(benzyloxy)phenyl]amino}carbonyl)-1,5-dimethyl-1H-pyrrol-2-yl]-4,5-difluorobenzoic acid (P151)

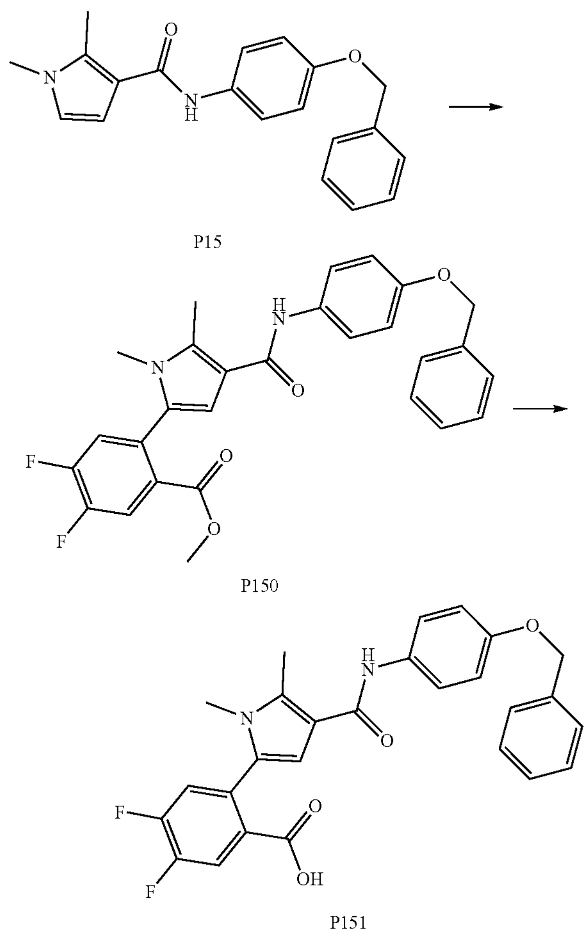

P15

P150

P151

Preparation 150. Methyl 2-[4-({[4-(benzyloxy)phenyl]amino}carbonyl)-1,5-dimethyl-1H-pyrrol-2-yl]-4,5-difluorobenzoate (P150)

A mixture of N-[4-(benzyloxy)phenyl]-1,2-dimethyl-1H-pyrrole-3-carboxamide P15 (500 mg, 1.6 mmol), methyl 2-bromo-4,5-difluorobenzoate (785 mg, 3.1 mmol), $K_3PO_4$ (1.6 g, 7.8 mmol), pivalic acid (50 mg, 0.4 mmol) in N,N-dimethylacetamide (10 mL) was stirred at 135° C. for 15 min, then $PdCl_2$ $(PPh_3)_2$ (0.22 g, 0.3 mmol) was added. The resulting mixture was stirred at 135° C. for 30 min. Upon completion of the reaction mixture was diluted with water (20 mL) and EtOAC (20 mL). The organic layer was separated, washed with brine, dried over sodium sulfate, filtered, and concentrated under reduced pressure. The residue was subjected to silica flash chromatography eluting with a mixture of EtOAc (0→20%) and DCM to afford 400 mg (53%) of the title compound.

Preparation 151. 2-[4-({[4-(Benzyloxy)phenyl]amino}carbonyl)-1,5-dimethyl-1H-pyrrol-2-yl]-4,5-difluorobenzoic acid (P151)

A solution of P150 (400 mg, 0.8 mmol) and NaOH (165 mg, 4.0 mmol) in a mixture of MeOH (10 mL) and water (2 mL) was stirred at ambient temperature for 12 h. The volatiles were removed under reduced pressure, and water (20 mL) was added to the residue. The solution was acidified with 6M HCl to pH 1 and extracted with DCM (2×10 mL), the combined organic layers were dried over $Na_2SO_4$ and evaporated to dryness under reduced pressure to afford 380 mg (98%) of the title compound that was pure enough to be used further for the next step.

N-[4-(benzyloxy)phenyl]-5-(4,5-difluoro-2-{[(3S)-3-(morpholin-4-ylmethyl)-3,4-dihydroisoquinolin-2(1H)-yl]carbonyl}phenyl)-1,2-dimethyl-1H-pyrrole-3-carboxamide (P152)

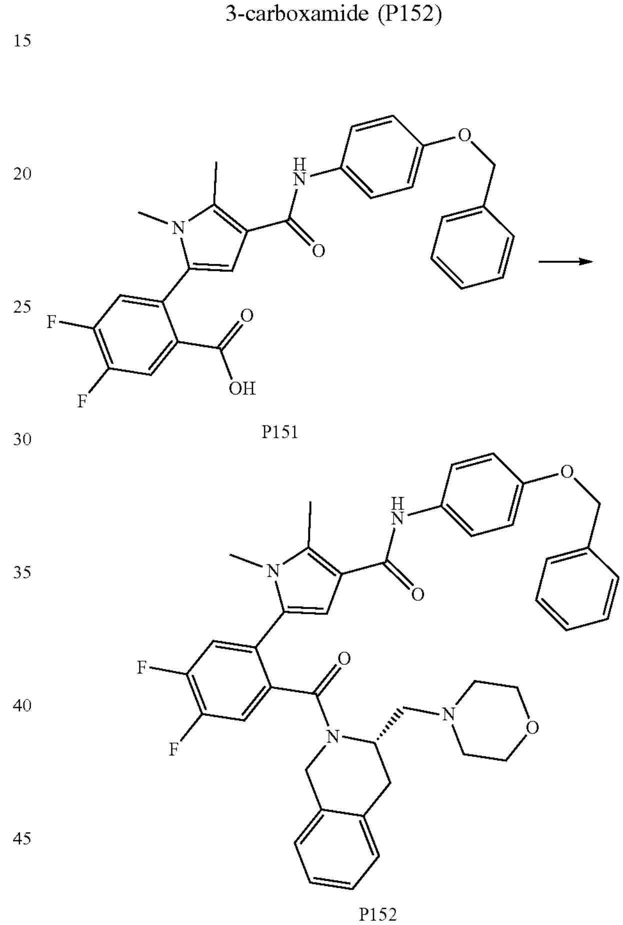

P151

P152

Preparation 152. N-[4-(benzyloxy)phenyl]-5-(4,5-difluoro-2-{[(3S)-3-(morpholin-4-ylmethyl)-3,4-dihydroisoquinolin-2 (1H)-yl]carbonyl}phenyl)-1,2-dimethyl-1H-pyrrole-3-carboxamide (P152)

A mixture of P151 (380 mg, 0.8 mmol), P43 (220 mg, 0.95 mmol), DIPEA (0.2 mL, 1.2 mmol), TBTU (300 mg, 0.95 mmol), and DMF (5 mL) was stirred at 60° C. overnight. The reaction mixture was diluted with water (20 mL) and EtOAc (10 mL). The organic layer was separated, washed with brine, dried over $Na_2SO_4$, filtered, and concentrated under reduced pressure. The residue was subjected to silica flash chromatography eluting with a mixture of EtOAc (0→100%) and DCM to afford 300 mg (55%) of the title compound.

N-[4-(benzyloxy)phenyl]-5-(4,5-difluoro-2-{[(3S)-3-(morpholin-4-ylmethyl)-3,4-dihydroisoquinolin-2 (1H)-yl]carbonyl}phenyl)-N-(3-methoxy-2-methyl-benzyl)-1,2-dimethyl-1H-pyrrole-3-carboxamide (P153)

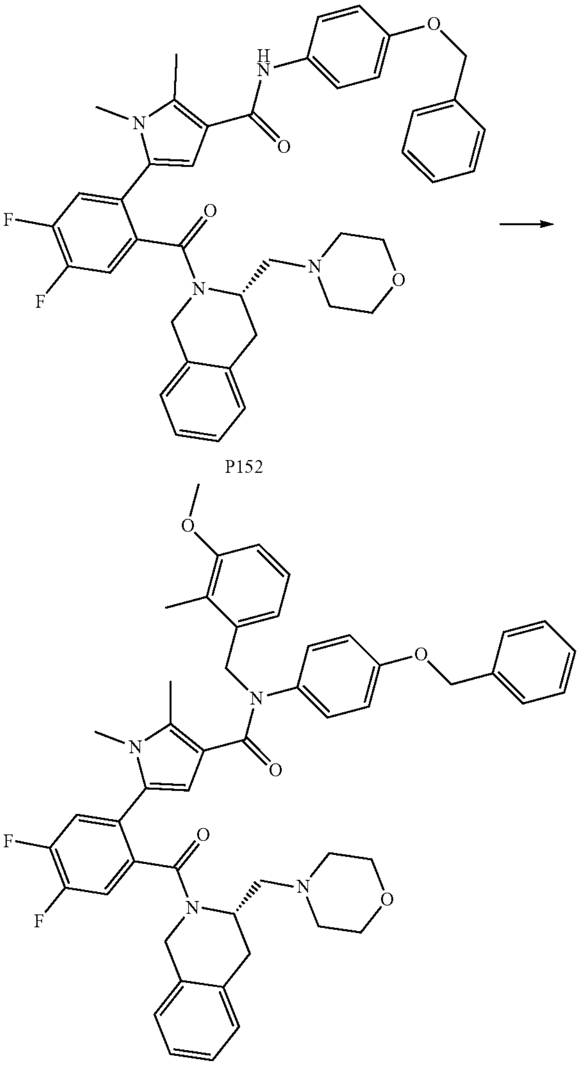

P152

P153

Preparation 153. N-[4-(benzyloxy)phenyl]-5-(4,5-difluoro-2-{[(3S)-3-(morpholin-4-ylmethyl)-3,4-dihydroisoquinolin-2 (1H)-yl]carbonyl}phenyl)-N-(3-methoxy-2-methylbenzyl)-1,2-dimethyl-1H-pyrrole-3-carboxamide (P153)

A mixture of P152 (100 mg, 0.14 mmol), tert-BuOK (65 mg 0.56 mmol), and tert-BuOH (5 mL) was stirred at 50° C. for 30 min, then 3-methoxy-2-methylbenzyl methane-sulfonate (67 mg, 0.28 mmol) was added. The reaction mixture was stirred at 60° C. for 1 h and then partitioned between EtOAc and water. The organic layer was separated, washed with brine, dried over $Na_2SO_4$, filtered, and concentrated under reduced pressure. The residue was subjected to silica flash chromatography eluting with a mixture of EtOAc (0→100%) and DCM to afford 70 mg (58%) of the title compound.

N-[4-(benzyloxy)phenyl]-5-(4,5-difluoro-2-{[(3S)-3-(morpholin-4-ylmethyl)-3,4-dihydroisoquinolin-2 (1H)-yl]carbonyl}phenyl)-N-(3-methoxy-2-methyl-benzyl)-1,2-dimethyl-1H-pyrrole-3-carboxamide (P154)

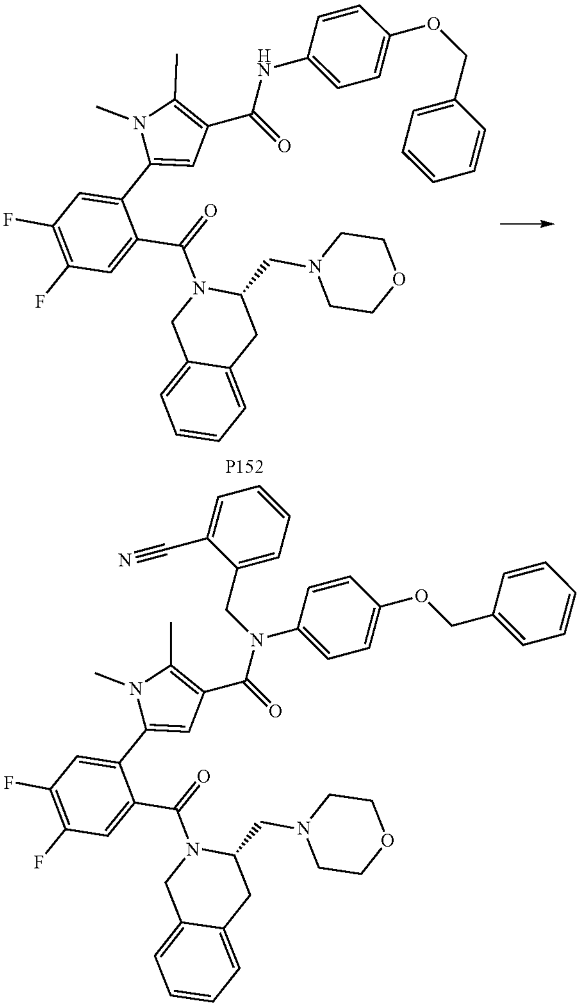

P152

P154

Preparation 154. N-[4-(benzyloxy)phenyl]-5-(4,5-difluoro-2-{[(3S)-3-(morpholin-4-ylmethyl)-3,4-dihydroisoquinolin-2 (1H)-yl]carbonyl}phenyl)-N-(3-methoxy-2-methylbenzyl)-1,2-dimethyl-1H-pyrrole-3-carboxamide (P154)

A mixture of P152 (100 mg, 0.14 mmol), tert-BuOK (65 mg 0.56 mmol), and tert-BuOH (5 mL) was stirred at 50° C. for 30 min, then 2-(bromomethyl)benzonitrile (57 mg, 0.28 mmol) was added. The reaction mixture was stirred at 60° C. for 1 h and then partitioned between EtOAc and water. The organic layer was separated, washed with brine, dried over $Na_2SO_4$, filtered, and concentrated under reduced pressure.

The residue was subjected to silica flash chromatography eluting with a mixture of EtOAc (0→100%) and DCM to afford 100 mg (86%) of the title compound.

(4-{[2-(trimethylsilylethoxy]methoxy}phenyl)amine (P156)

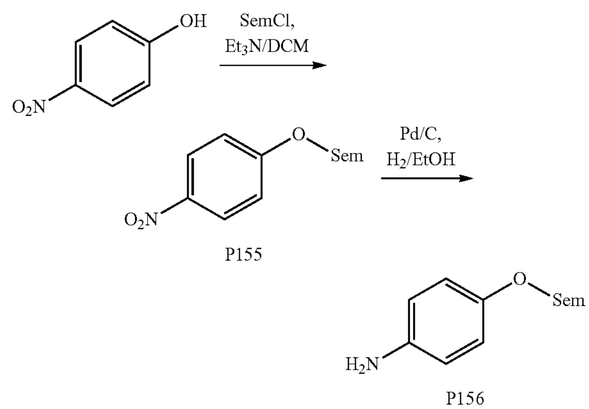

P155

P156

Preparation 155. Trimethyl {2-[(4-nitrophenoxy) methoxy]ethyl}silane (P155)

To a stirred solution of 4-nitrophenol (50.0 g, 0.36 mol) and Et3N(78 mL, 0.54 mol) in DCM (500 mL) SemCl (100 mL, 0.40 mol, 70%) was added dropwise at 0° C. and the reaction mixture was stirred at 0° C. for 30 min. After the reaction was warmed up to ambient temperature, then stirred at ambient temperature for 4 h. Water was added and the organic layer separated, washed with brine, dried over anh. sodium sulfate, filtered and the filtrate was evaporated under reduced pressure. The residue was used for the next step without further purification and separation.

Preparation 156. 4-{[2-(Trimethylsilylethoxy] methoxy}aniline (P156)

P155 (97 g, 0.36 mol) was dissolved in ethanol (1000 mL). Pd/C (5.0 g, 10% w/w) was added and the mixture was stirred under hydrogen at 20 bar for 3 h. The catalyst was removed by filtration and the solution was evaporated under reduced pressure. The residue was subjected to a silica gel flash chromatography eluting with a mixture of EtOAc (0→10%) and DCM to afford 60 g (70%) of the title compound. $^1$H NMR (400 MHZ, $CDCl_3$), δ: 6.90-6.89 (m, 4H), 6.73-6.56 (m, 4H), 5.13 (s, 2H), 3.82-3.69 (m, 2H), 3.59-3.19 (m, 2H), 1.03-0.90 (m, 2H), 0.08--0.07 (m, 9H).

1,2-dimethyl-N-(4-{[2-(trimethylsilylethoxy] methoxy}phenyl)-1H-pyrrole-3-carboxamide (P157)

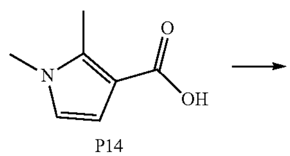

P14

-continued

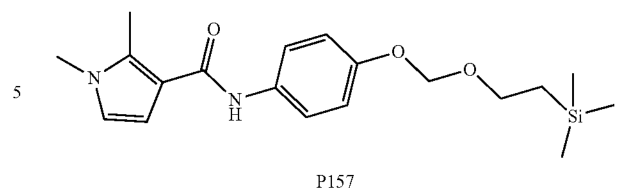

P157

Preparation 157. 1,2-dimethyl-N-(4-{[2-(trimethylsilylethoxy]methoxy}phenyl)-1H-pyrrole-3-carboxamide (P157)

To a stirred solution of P14 (45.0 g, 0.32 mol) in pyridine (500 mL) neat $SOCl_2$ (28 mL, 0.39 mol) was added dropwise at 0° C. and the reaction mixture was stirred at 0° C. for 3 h. Then P156 (61.8 g, 0.26 mmol) in Et3N(117 mL, 0.8 mol) was added dropwise, keeping the temperature at 0° C. After the reaction was warmed up to ambient temperature, then stirred at ambient temperature for 16 h. Volatiles were removed under reduced pressure. The residue was diluted with water and $Et_2O$. The organic layer separated, washed with water, brine, dried over dried over anh. sodium sulfate, filtered, and concentrated under reduced pressure. The residue was subjected to a silica gel flash chromatography eluting with a mixture of EtOAc (0→20%) and DCM to afford 48 g (42%) of the title compound. $^1$H NMR (400 MHZ, DMSO-$d_6$), δ:9.21 (s, 1H), 7.91 (d, J=9.0 Hz, 1H), 7.76-7.65 (m, 3H), 6.65 (dd, J=13.8, 3.0 Hz, 1H), 6.96-9.62 (m, 2H), 6.70 (s, 1H), 5.16 (s, 2H), 3.75-3.61 (m, 5H), 3.24 (s, 3H), 2.46 (s, 3H), 0.98-0.80 (m, 2H), 0.00 (s, 9H). LCMS(ESI+) m/z 361 $[M+H]^+$.

5-Chloro-2-(1,5-dimethyl-4-{[(4-{[2-(trimethylsilylethoxy]methoxy}phenyl)amino]carbonyl}-1H-pyrrol-2-yl)-3-methylbenzoic acid (P159)

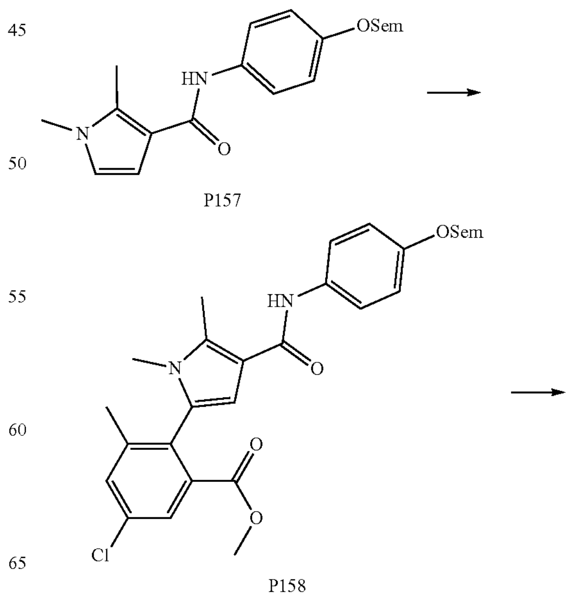

P157

P158

-continued

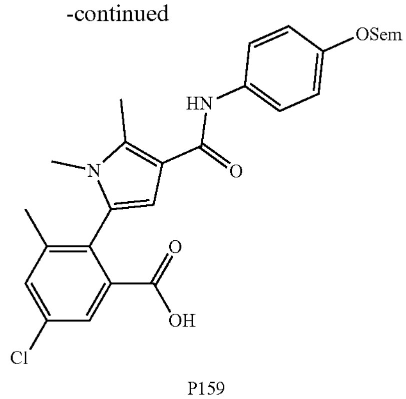

P159

Preparation 158. Methyl 5-chloro-2-(1,5-dimethyl-4-{[(4-{[2-(trimethylsilylethoxy]methoxy}phenyl) amino]carbonyl}-1H-pyrrol-2-yl)-3-methylbenzoate (P158)

A mixture of P157 (0.5 g, 1.38 mmol), methyl 2-bromo-5-chloro-3-methylbenzoate (0.7 g, 2.76 mmol), $K_3PO_4$ (1.18 g, 5.6 mmol), pivalic acid (0.04 g, 0.4 mmol) in N,N-dimethylacetamide (10 mL) was stirred at 135° C. for 15 min, then $PdCl_2$ $(PPh_3)_2$ (0.25 g, 0.1 mmol) was added. The resulting mixture was stirred at 135° C. for 30 min. Upon completion of the reaction the mixture was diluted with water (70 mL) and EtOAC (120 mL). The organic layer was separated, washed with brine, dried over sodium sulfate, filtered, and concentrated under reduced pressure. The residue was subjected to silica flash chromatography eluting with a mixture of EtOAc (0→20%) and DCM to afford 200 mg (26%) of the title compound.

Preparation 159. 5-Chloro-2-(1.5-dimethyl-4-{[(4-{[2-(trimethylsilylethoxy]methoxy}phenyl)amino]carbonyl}-1H-pyrrol-2-yl)-3-methylbenzoic acid (P159)

A solution of P158 (200 mg, 0.136 mmol) and LiOH (88 mg, 1.36 mmol) in a mixture of THF (8 mL) and water (2 mL) was stirred at ambient temperature for 12 h. The volatiles were removed under reduced pressure, and water (20 mL) was added to the residue. The solution was acidified with 6M HCl to pH 1 and extracted with DCM (2×10 mL), the combined organic layers were dried over $Na_2SO_4$ and evaporated to dryness under reduced pressure to afford 190 mg (97%) of the title compound that was pure enough to be used further for the next step.

5-(4-Chloro-2-methyl-6-{[(3S)-3-(morpholin-4-ylmethyl)-3,4-dihydroisoquinolin-2 (1H)-yl]carbonyl}phenyl)-1,2-dimethyl-N-(4-{[2-(trimethylsilylethoxy]methoxy}phenyl)-1H-pyrrole-3-carboxamide (P160)

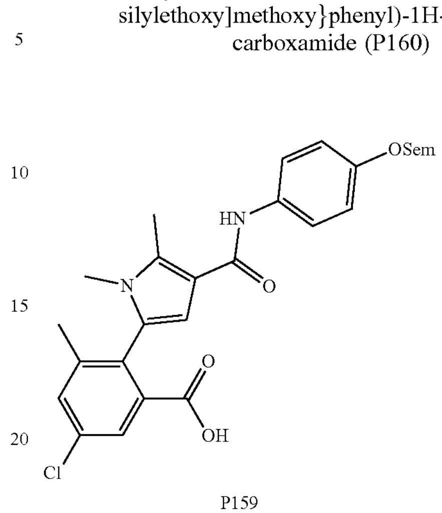

P159

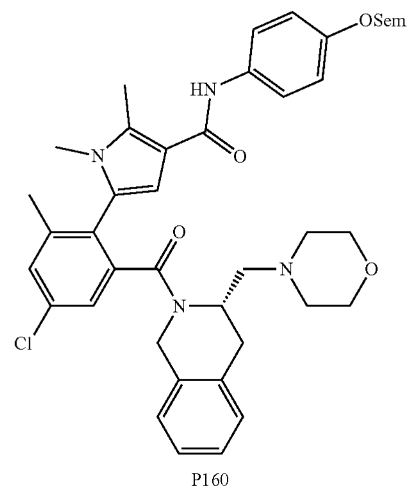

P160

Preparation 160. 5-(4-chloro-2-methyl-6-{[(3S)-3-(morpholin-4-ylmethyl)-3,4-dihydroisoquinolin-2 (1H)-yl]carbonyl}phenyl)-1,2-dimethyl-N-(4-{[2-(trimethylsilylethoxy]methoxy}phenyl)-1H-pyrrole-3-carboxamide (P160)

A mixture of P159 (190 mg, 0.378 mmol), P43 (105 mg, 0.42 mmol), DIPEA (0.098 mL, 0.56 mmol), TBTU (146 mg, 0.42 mmol), and DMF (15 mL) was stirred at 60° C. overnight. The reaction mixture was diluted with water (20 mL) and EtOAc (10 mL). The organic layer was separated, washed with brine, dried over $Na_2SO_4$, filtered, and concentrated under reduced pressure. The residue was subjected to silica flash chromatography eluting with a mixture of EtOAc (0→100%) and DCM to afford 200 mg (72%) of the title compound.

5-(4-Chloro-2-methyl-6-{[(3S)-3-(morpholin-4-ylmethyl)-3,4-dihydroisoquinolin-2 (1H)-yl] carbonyl}phenyl)-N-(3-methoxy-2-methylbenzyl)-1, 2-dimethyl-N-(4-{[2-(trimethylsilylethoxy] methoxy}phenyl)-1H-pyrrole-3-carboxamide (P161)

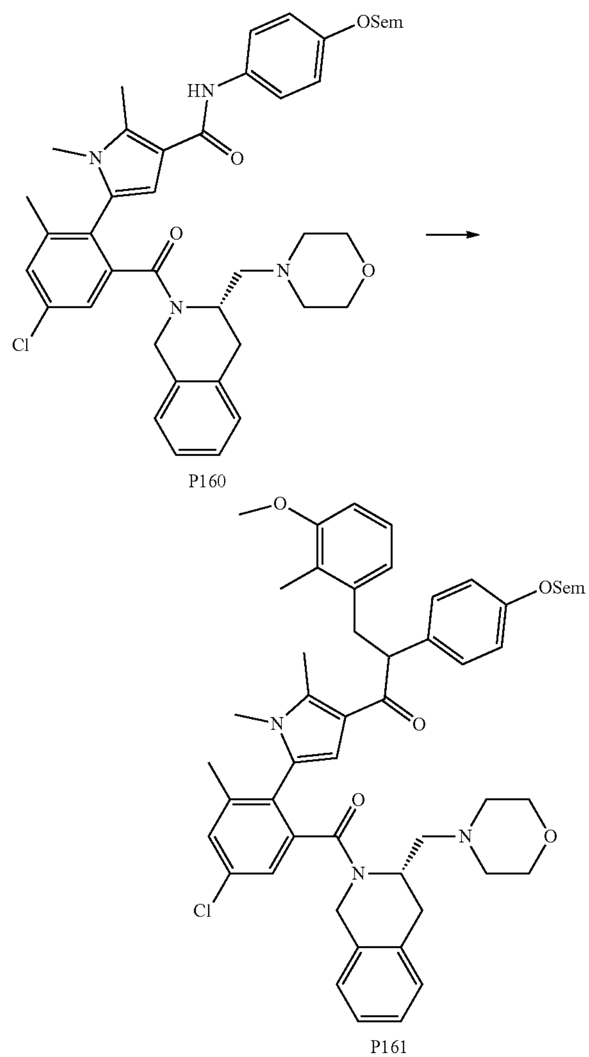

P160

P161

Preparation 161. 5-(4-Chloro-2-methyl-6-{[(3S)-3-(morpholin-4-ylmethyl)-3,4-dihydroisoquinolin-2 (1H)-yl]carbonyl}phenyl)-N-(3-methoxy-2-methylbenzyl)-1,2-dimethyl-N-(4-{[2-(trimethylsilylethoxy]methoxy}phenyl)-1H-pyrrole-3-carboxamide (P161)

A mixture of P160 (80 mg, 0.112 mmol), tert-BuOK (51 mg, 0.448 mmol), and tert-BuOH (9 mL) was stirred at 50° C. for 30 min, then 3-methoxy-2-methylbenzyl methanesulfonate (53 mg, 0.224 mmol) was added. The reaction mixture was stirred at 60° C. for 1 h and then partitioned between EtOAc and water. The organic layer was separated, washed with brine, dried over $Na_2SO_4$, filtered, and concentrated under reduced pressure. The residue was subjected to silica flash chromatography eluting with a mixture of EtOAc (0→100%) and DCM to afford 30 mg (21%).

5-(4-Chloro-2-methyl-6-{[(3S)-3-(morpholin-4-ylmethyl)-3,4-dihydroisoquinolin-2 (1H)-yl] carbonyl}phenyl)-N-(2-methoxybenzyl)-1,2-dimethyl-N-(4-{[2-(trimethylsilylethoxy] methoxy}phenyl)-1H-pyrrole-3-carboxamide (P162)

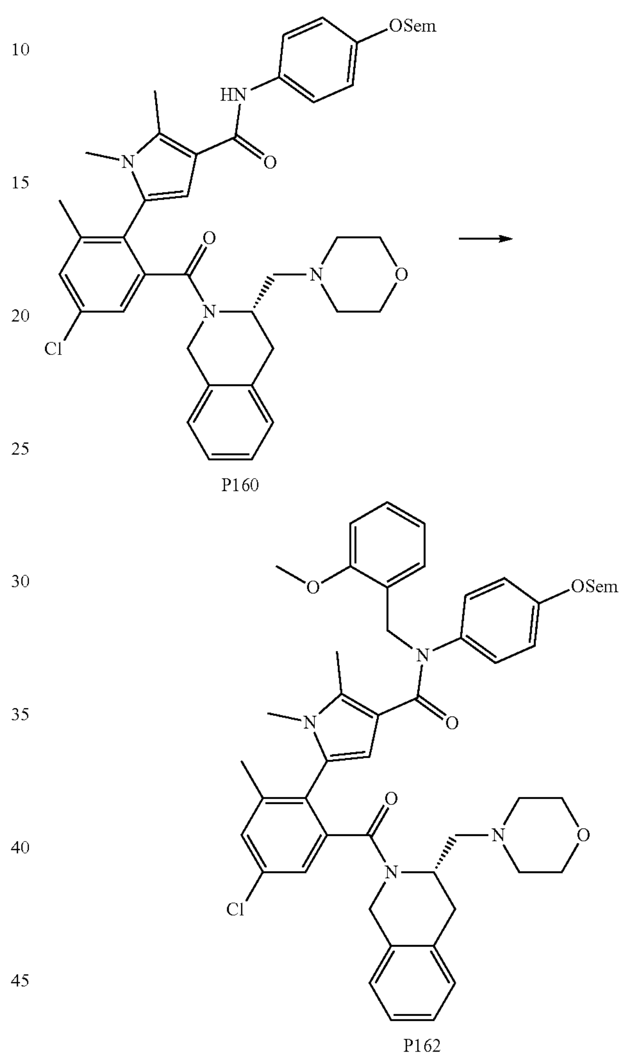

P160

P162

Preparation 5-(4-Chloro-2-methyl-6-{[(3S)-3-(morpholin-4-ylmethyl)-3,4-dihydroisoquinolin-2 (1H)-yl]carbonyl}phenyl)-N-(2-methoxybenzyl)-1,2-dimethyl-N-(4-{[2-(trimethylsilylethoxy] methoxy}phenyl)-1H-pyrrole-3-carboxamide (P162)

A mixture of P160 (80 mg, 0.112 mmol), tert-BuOK (48 mg 0.448 mmol), and tert-BuOH (9 mL) was stirred at 50° C. for 30 min, then 2-methoxylbenzyl methanesulfonate (34 mg, 0.224 mmol) was added. The reaction mixture was stirred at 60° C. for 1 h and then partitioned between EtOAc and water. The organic layer was separated, washed with brine, dried over $Na_2SO_4$, filtered, and concentrated under reduced pressure. The residue was subjected to silica flash chromatography eluting with a mixture of EtOAc (0→100%) and DCM to afford 30 mg (21%).

Methyl 2-bromo-4-fluorobenzoate (P163)

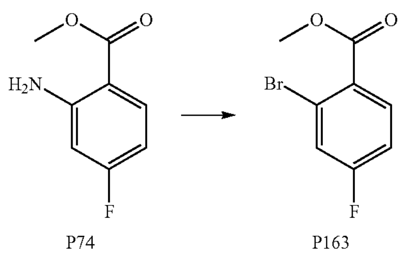

P74 P163

Preparation 163. Methyl 2-bromo-4-fluorobenzoate (P163)

To a solution of P74 (2.2 g, 13.92 mmol) and tert-butyl nitrite (2.59 g, 25.06 mmol) in acetonitrile (50 ml) was added CuBr2 (5.69 g, 25.06 mmol) at 0° C. and the reaction mixture was stirred at rt overnight. The reaction mixture was treated with water and extracted with EtOAc. The combined organic layers were dried over anhydrous sodium sulfate, filtered and the filtrate was evaporated under reduced pressure The residue was subjected to a silica gel flash chromatography eluting with a of DCM to afford (1.4 g, 47%) of the title compound. LCMS(ESI+) m/z 234 $[M+H]^+$. $^1$H NMR (400 MHZ, $CDCl_3$), δ: 7.87 (t, J=6.8 Hz, 1H), 7.74 (d, J=5.4 Hz, 1H), 7.39 (t, J=8.8 Hz, 1H), 3.85 (s, 3H). 2-[4-({[4-(benzyloxy)phenyl]amino}carbonyl)-1,5-dimethyl-1H-pyrrol-2-yl]-4-fluorobenzoic acid (P165)

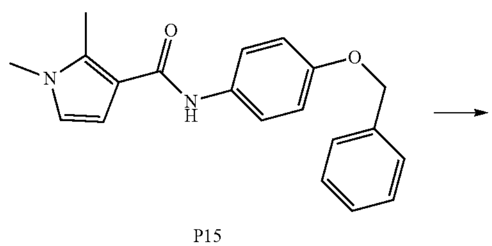

P15

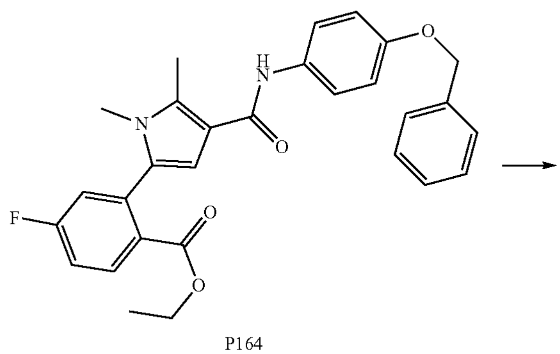

P164

-continued

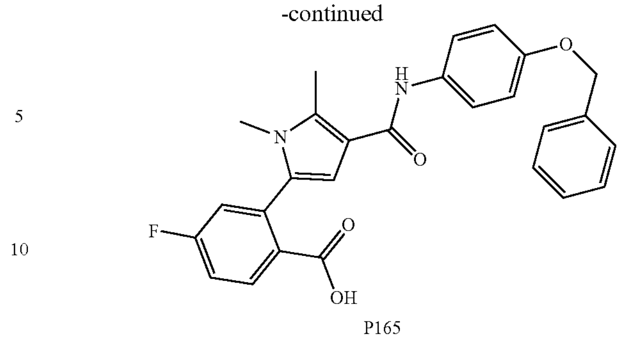

P165

Preparation 164. Ethyl 2-[4-({[4-(benzyloxy)phenyl]amino}carbonyl)-1,5-dimethyl-1H-pyrrol-2-yl]-4-fluorobenzoate (P164)

A mixture of P15 (500 mg, 1.56 mmol), P163 (728 mg, 3.12 mmol), $K_3PO_4$ (1.32 g, 6.24 mmol), pivalic acid (47 mg, 0.38 mmol) in N,N-dimethylacetamide (30 mL) was stirred at 135° C. for 15 min, then $PdCl_2$ $(PPh_3)_2$ (250 mg, 0.31 mmol) was added. The resulting mixture was stirred at 135° C. for 30 min. Upon completion of the reaction mixture was diluted with water (50 mL) and EtOAc (50 mL). The organic layer was separated, washed with brine, dried over sodium sulfate, filtered, and concentrated under reduced pressure. The residue was subjected to silica flash chromatography eluting with a mixture of EtOAc (0→20%) and DCM to afford 215 mg (31%) of the title compound.

Preparation 165. 2-[4-({[4-(Benzyloxy)phenyl]amino}carbonyl)-1,5-dimethyl-1H-pyrrol-2-yl]-4-fluorobenzoic acid (P165)

A solution of P164 (215 mg, 0.45 mmol) and LiOH (109 mg, 4.5 mmol) in a mixture of THF (16 mL) and water (4 mL) was stirred at ambient temperature for 12 h. The volatiles were removed under reduced pressure, and water (20 mL) was added to the residue. The solution was acidified with 6M HCl to pH 1 and extracted with DCM (2×10 mL), the combined organic layers were dried over $Na_2SO_4$ and evaporated to dryness under reduced pressure to afford 116 mg (55%) of the title compound that was pure enough to be used further for the next step.

N-[4-(Benzyloxy)phenyl]-5-(5-fluoro-2-{[(3S)-3-(morpholin-4-ylmethyl)-3,4-dihydroisoquinolin-2(1H)-yl]carbonyl}phenyl)-1,2-dimethyl-1H-pyrrole-3-carboxamide (P166)

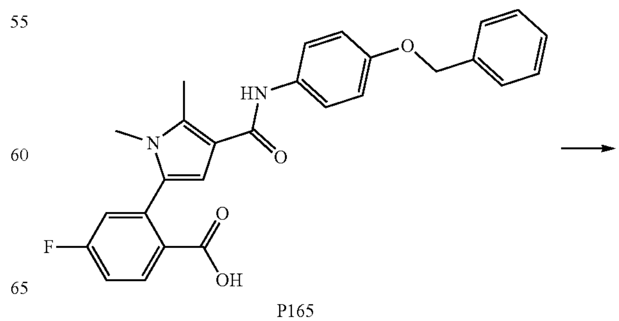

P165

-continued

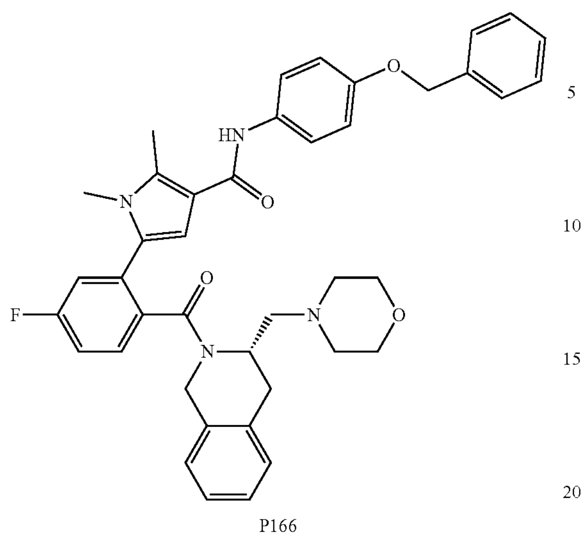

P166

Preparation 166. N-[4-(benzyloxy)phenyl]-5-(5-fluoro-2-{[(3S)-3-(morpholin-4-ylmethyl)-3,4-dihydroisoquinolin-2 (1H)-yl]carbonyl}phenyl)-1,2-dimethyl-1H-pyrrole-3-carboxamide (P166)

A mixture of P165 (116 mg, 0.25 mmol), P43 (71 mg, 0.35 mmol), DIPEA (0.066 mL, 0.75 mmol), and TBTU (97 mg, 0.35 mmol), and DMF (15 mL) was stirred at 60° C. overnight. The reaction mixture was diluted with water (20 mL) and EtOAc (10 ml). The organic layer was separated, washed with brine, dried over $Na_2SO_4$, filtered, and concentrated under reduced pressure. The residue was subjected to silica flash chromatography eluting with a mixture of EtOAc (0→100%) and DCM to afford 100 mg (59%) of the title compound.

N-[4-(benzyloxy)phenyl]-5-(5-fluoro-2-{[(3S)-3-(morpholin-4-ylmethyl)-3,4-dihydroisoquinolin-2 (1H)-yl]carbonyl}phenyl)-N-(2-methoxybenzyl)-1,2-dimethyl-1H-pyrrole-3-carboxamide (P167)

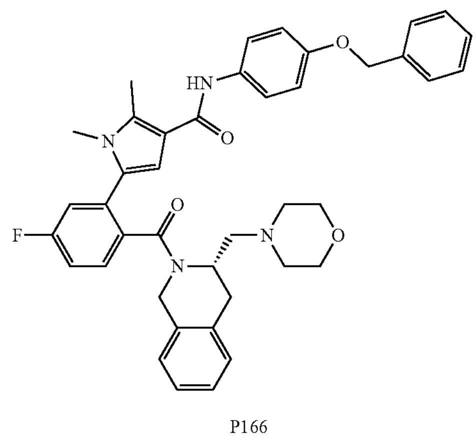

P166

-continued

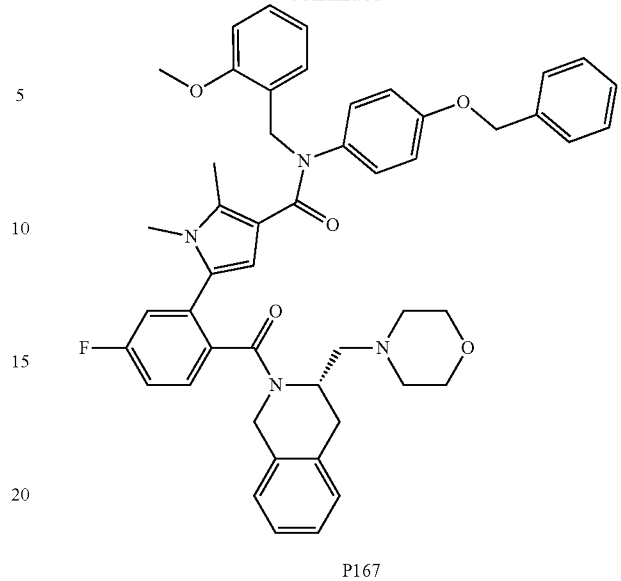

P167

Preparation 167. N-[4-(Benzyloxy)phenyl]-5-(5-fluoro-2-{[(3S)-3-(morpholin-4-ylmethyl)-3,4-dihydroisoquinolin-2 (1H)-yl]carbonyl}phenyl)-N-(2-methoxybenzyl)-1,2-dimethyl-1H-pyrrole-3-carboxamide (P167)

A mixture of P166 (35 mg, 0.052 mmol), tert-BuOK (23 mg 0.208 mmol), and tert-BuOH (9 mL) was stirred at 50° C. for 30 min, then 2-methoxylbenzyl chloride (16 mg, 0.104 mmol) was added. The reaction mixture was stirred at 60° C. for 1 h and then partitioned between EtOAc and water. The organic layer was separated, washed with brine, dried over $Na_2SO_4$, filtered, and concentrated under reduced pressure. The residue was subjected to silica flash chromatography eluting with a mixture of EtOAc (0→100%) and DCM to afford 33 mg (81%).

N-[4-(benzyloxy)phenyl]-5-(5-fluoro-2-{[(3S)-3-(morpholin-4-ylmethyl)-3,4-dihydroisoquinolin-2 (1H)-yl]carbonyl}phenyl)-N-(3-methoxy-2-methylbenzyl)-1,2-dimethyl-1H-pyrrole-3-carboxamide (P168)

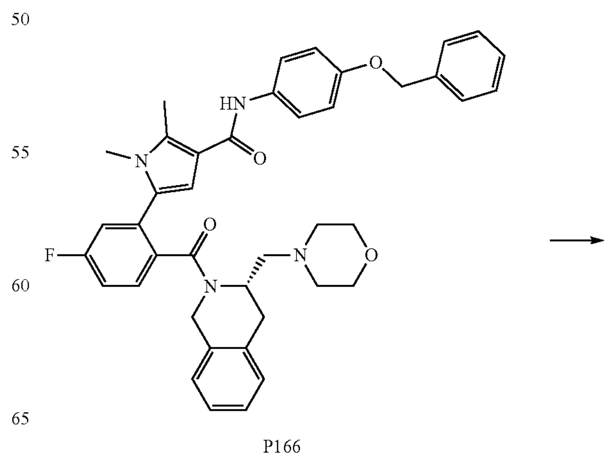

P166

-continued

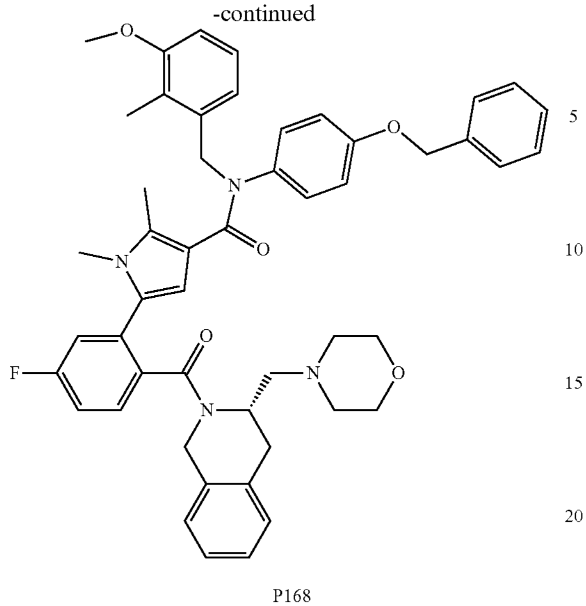

P168

Preparation 168. N-[4-(benzyloxy)phenyl]-5-(5-fluoro-2-{[(3S)-3-(morpholin-4-ylmethyl)-3,4-dihydroisoquinolin-2 (1H)-yl]carbonyl}phenyl)-N-(3-methoxy-2-methylbenzyl)-1,2-dimethyl-1H-pyrrole-3-carboxamide (P168)

A mixture of P166 (100 mg, 0.149 mmol), tert-BuOK (67 mg, 0.576 mmol), and tert-BuOH (15 mL) was stirred at 50° C. for 30 min, then 3-methoxy-2-methylbenzyl methanesulfonate (69 mg, 0.298 mmol) was added. The reaction mixture was stirred at 60° C. for 1 h and then partitioned between EtOAc and water. The organic layer was separated, washed with brine, dried over $Na_2SO_4$, filtered, and concentrated under reduced pressure. The residue was subjected to silica flash chromatography eluting with a mixture of EtOAc (0→100%) and DCM to afford 33 mg (27%) of the title compound.

Examples of the Compound (I)

Example 1:3-(5-Chloro-2-{[(3S)-3-(morpholin-4-ylmethyl)-3,4-dihydroisoquinolin-2 (1H)-yl] carbonyl}phenyl)-N-(4-chlorophenyl)-N-(2-cyanobenzyl)-5,6,7,8-tetrahydroindolizine-1-carboxamide (1)

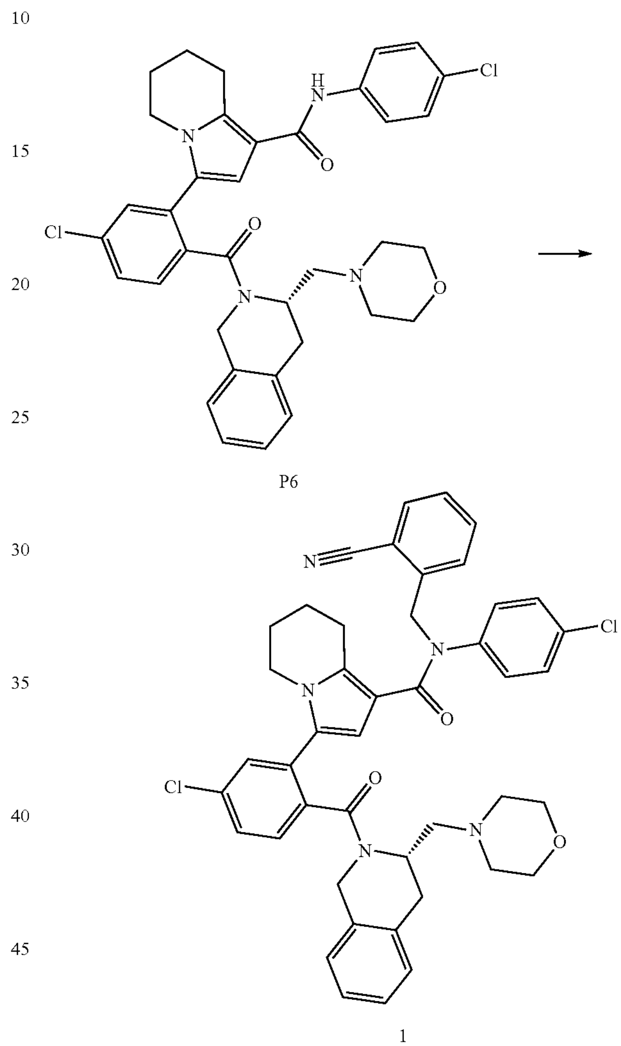

P6

1

A mixture of 3-(5-chloro-2-{[(3S)-3-(morpholin-4-ylmethyl)-3,4-dihydroisoquinolin-2 (1H)-yl]carbonyl}phenyl)-N-(4-chlorophenyl)-5,6,7,8-tetrahydroindolizine-1-carboxamide (P6, 150 mg, 0.23 mmol), tert-BuOK (104 mg 0.9 mmol), and tert-BuOH (5 mL) was stirred at 50° C. for 30 min, then 2-(bromomethyl)benzonitrile (91 mg, 0.46 mmol) was added. The reaction mixture was stirred at 60° C. for 1 h and then partitioned between EtOAc and water. The organic layer was separated, washed with brine, dried over $Na_2SO_4$, filtered, and concentrated under reduced pressure. The residue was subjected to silica flash chromatography eluting with a mixture of EtOAc (0→100%) and DCM to afford 154 mg (87%) of the title compound 1. 1H NMR (400 MHz, DMSO-$d_6$), δ:7.93-7.35 (m, 8H), 7.31-6.85 (m, 8H), 5.37-4.92 (m, 4H), 4.20-3.64 (m, 7H), 3.55-3.24 (m, 6H), 3.18-2.72 (m, 4H), 1.79-0.88 (m, 4H). ESI LCMS $[MH]^+$: 758.

Example 2. 3-(5-Chloro-2-{[(3S)-3-(morpholin-4-ylmethyl)-3,4-dihydroisoquinolin-2 (1H)-yl]carbonyl}phenyl)-N-(4-chlorophenyl)-N-(3-methoxy-2-methylbenzyl)-5,6,7,8-tetrahydroindolizine-1-carboxamide (2)

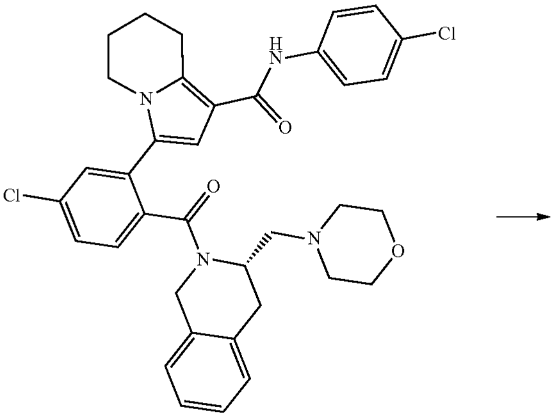

P6

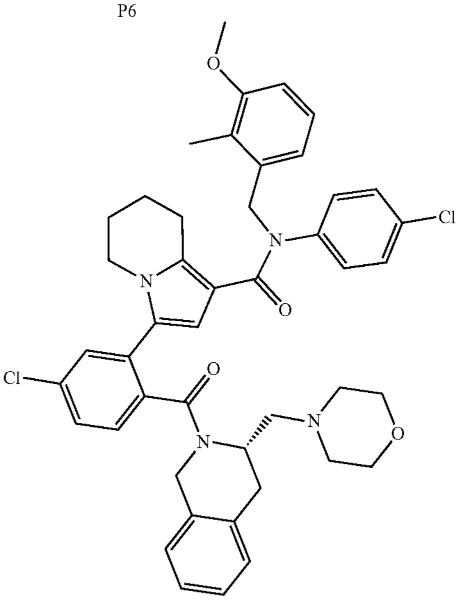

2

A mixture of 3-(5-chloro-2-{[(3S)-3-(morpholin-4-ylmethyl)-3,4-dihydroisoquinolin-2 (1H)-yl]carbonyl}phenyl)-N-(4-chlorophenyl)-5,6,7,8-tetrahydroindolizine-1-carboxamide (P6, 150 mg, 0.23 mmol), tert-BuOK (104 mg 0.9 mmol), and tert-BuOH (5 mL) was stirred at 50° C. for 30 min, then 3-methoxy-2-methylbenzyl methanesulfonate (107 mg, 0.46 mmol) was added. The reaction mixture was stirred at 60° C. for 1 h and then partitioned between EtOAc and water. The organic layer was separated, washed with brine, dried over $Na_2SO_4$, filtered, and concentrated under reduced pressure. The residue was subjected to silica flash chromatography eluting with a mixture of EtOAc (0→100%) and DCM to afford 60 mg (34%) of the title compound 2. 1H NMR (400 MHZ, DMSO-$d_6$), δ:7.61-7.26 (m, 3H), 7.24-6.93 (m, 8H), 6.89-6.73 (m, 2H), 6.71-6.51 (m, 2H), 5.43-4.98 (m, 2H), 4.98-4.65 (m, 2H), 4.28-3.88 (m, 2H), 3.84-3.68 (m, 4H), 3.65-3.38 (m, 6H), 3.04-2.78

(m, 2H), 2.72-2.57 (m, 1H), 2.38-2.25 (m, 2H), 2.21-1.78 (m, 6H), 1.76-1.36 (m, 4H). ESI LCMS $[MH]^+$: 777.

Example 3. 3-(5-Chloro-2-{[(3S)-3-(morpholin-4-ylmethyl)-3,4-dihydroisoquinolin-2 (1H)-yl]carbonyl}phenyl)-N-(2-cyanobenzyl)-N-(4-hydroxyphenyl)-5,6,7,8-tetrahydroindolizine-1-carboxamide (3)

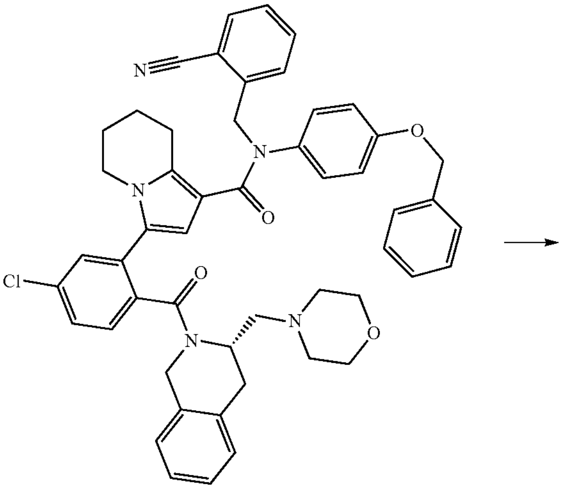

P11

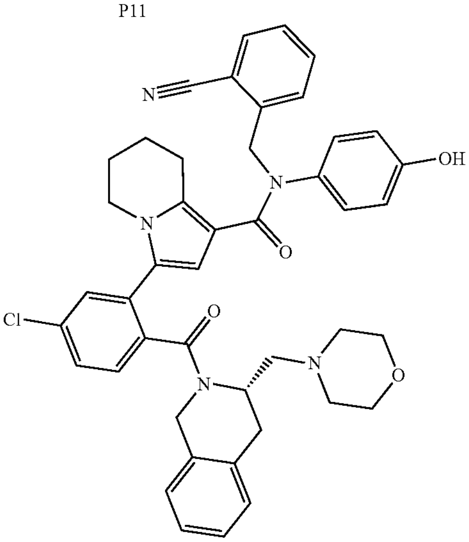

3

A solution of the compound P11 (180 mg, 0.22 mmol) in DCM (5 mL) was cooled to −78° C., and a solution of $BBr_3$ (108 mg, 0.43 mmol) in THF (1 mL) was added over 5 min. The reaction mixture was stirred at to −78° C. C for 1 h and then was diluted with saturated aq. solution of sodium bicarbonate $NaHCO_3$. The organic layer was separated, washed with brine, dried over $Na_2SO_4$, filtered, and concentrated under reduced pressure. The residue was subjected to HPLC purification to afford 73 mg (46%) of the title compound 3. 1H NMR (400 MHZ, DMSO-$d_6$), δ:9.60-9.26 (m, 1H), 7.83-7.25 (m, 7H), 7.21-6.79 (m, 5H), 6.74-6.32 (m, 4H), 5.39-4.71 (m, 4H), 4.34-3.82 (m, 2H), 3.72-3.38

(m, 6H), 3.14-2.77 (m, 2H), 2.75-2.56 (m, 1H), 2.41-2.25 (m, 2H), 2.20-1.82 (m, 2H), 1.80-1.33 (m, 6H). ESI LCMS $[MH]^+$: 740.

Example 4. 3-(5-Chloro-2-{[(3S)-3-(morpholin-4-ylmethyl)-3,4-dihydroisoquinolin-2 (1H)-yl] carbonyl}phenyl)-N-(4-hydroxyphenyl)-N-(3-methoxy-2-methylbenzyl)-5,6,7,8-tetrahydroindolizine-1-carboxamide (4) and N-(4-hydroxyphenyl)-N-(3-methoxy-2-methylbenzyl)-3-(2-{[(3S)-3-(morpholin-4-ylmethyl)-3,4-dihydroisoquinolin-2 (1H)-yl]carbonyl}phenyl)-5,6,7,8-tetrahydroindolizine-1-carboxamide (5)

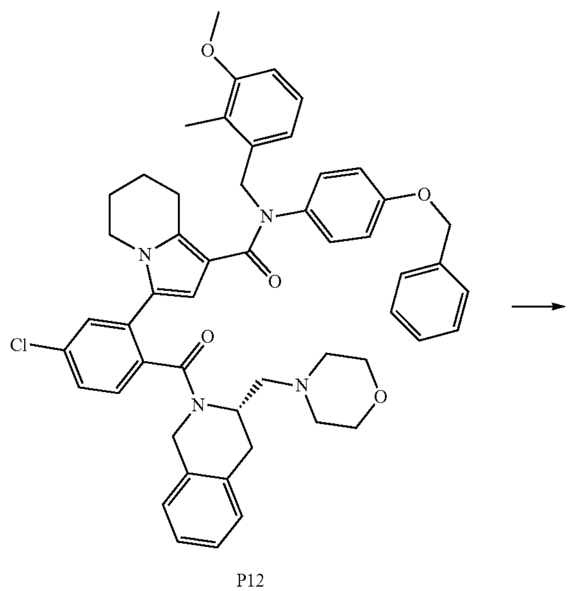

P12

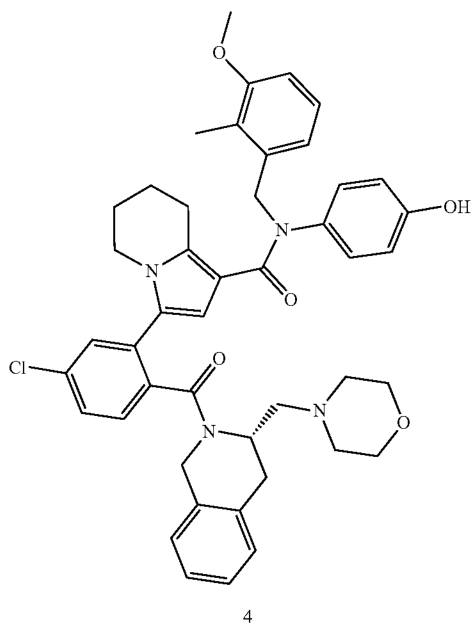

4

+

-continued

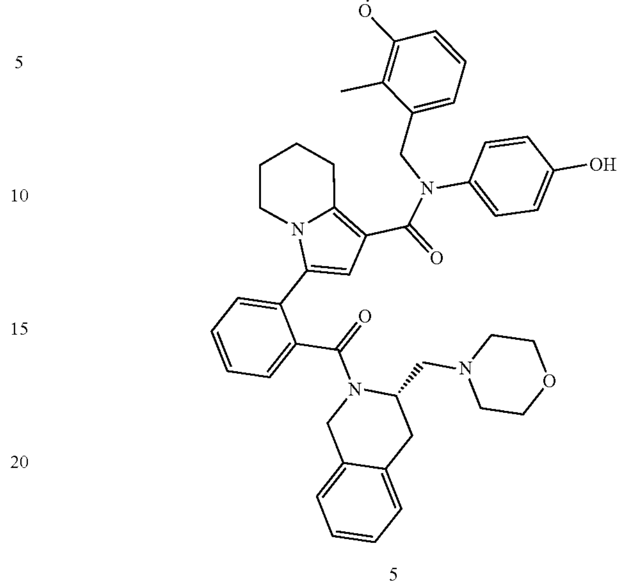

5

A stirred mixture of the compound P12 (200 mg), catalyst (10 mg of 5% Pd on charcoal), and methanol (2 mL) was hydrogenated under $H_2$ atm for 2 h. The catalyst was filtered off, and the filtrate was evaporated to dryness. The residue was subjected to HPLC purification to afford 40 mg (22%) of the compound 4 and 14 mg (8%) of the compound 5. Compound 4: 1H NMR (400 MHz, DMSO-$d_6$), δ:9.49-9.13 (m, 1H), 7.64-7.24 (m, 3H), 7.24-6.71 (m, 8H), 6.71-6.47 (m, 2H), 6.47-6.24 (m, 2H), 5.32-4.52 (m, 4H), 4.28-3.89 (m, 2H), 3.86-3.68 (m, 3H), 3.64-3.37 (m, 6H), 3.08-2.82 (m, 2H), 2.75-2.64 (m, 1H), 2.39-2.23 (m, 2H), 2.23-1.83 (m, 7H), 1.78-1.39 (m, 4H). ESI LCMS $[MH]^+$: 759. Compound 5: 1H NMR (400 MHZ, DMSO-$d_6$), δ: 9.45-9.12 (m, 1H), 7.55-7.32 (m, 3H), 7.32-6.71 (m, 9H), 6.70-6.45 (m, 3H), 6.44-6.22 (m, 2H), 5.27-4.49 (m, 4H), 4.31-3.94 (m, 2H), 3.86-3.68 (m, 3H), 3.68-3.37 (m, 6H), 3.07-2.86 (m, 2H), 2.79-2.56 (m, 1H), 2.37-2.23 (m, 2H), 2.15-1.36 (m, 10H). ESI LCMS $[MH]^+$: 725.

Example 5. 5-(5-Chloro-2-{[(3S)-3-(morpholin-4-ylmethyl)-3,4-dihydroisoquinolin-2 (1H)-yl]carbonyl}phenyl)-N-(2-cyanobenzyl)-N-(4-hydroxyphenyl)-1,2-dimethyl-1H-pyrrole-3-carboxamide (6)

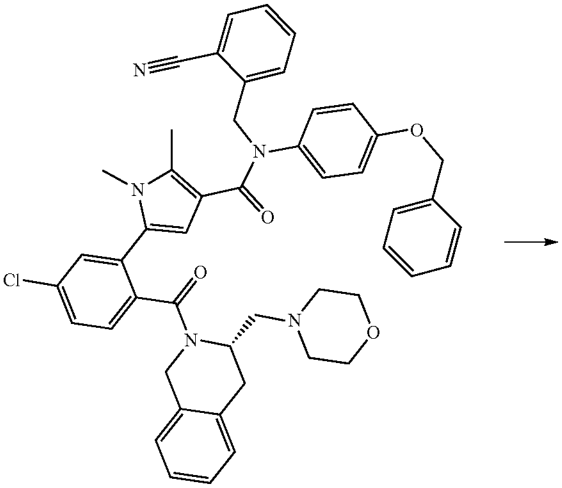

P19

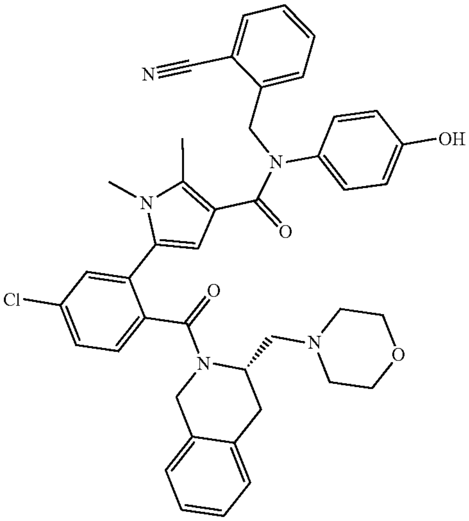

6

A solution of P19 (100 mg, 0.12 mmol) in DCM (5 mL) was cooled to −78° C., and a solution of $BBr_3$ (62 mg, 0.25 mmol) in THF (1 mL) was added over 5 min. The reaction mixture was stirred at to −78° C. C for 1 h and then was diluted with saturated aq. solution of sodium bicarbonate $NaHCO_3$. The organic layer was separated, washed with brine, dried over $Na_2SO_4$, filtered, and concentrated under reduced pressure. The residue was subjected to HPLC purification to afford 60 mg (67%) of the title compound 6.

1H NMR (400 MHZ, DMSO-$d_6$), δ:9.59-9.26 (m, 1H), 7.93-7.65 (m, 2H), 7.62-7.06 (m, 8H), 7.04-6.68 (m, 3H), 6.63-6.32 (m, 3H), 5.54-4.71 (m, 4H), 4.34-3.88 (m, 2H), 3.69-3.39 (m, 5H), 3.18-3.02 (s, 2H), 2.98-2.65 (m, 2H), 2.43-2.25 (m, 3H), 2.25-1.66 (m, 5H). ESI LCMS $[MH]^+$: 714.

Example 6. 5-(5-Chloro-2-{[(3S)-3-(morpholin-4-ylmethyl)-3,4-dihydroisoquinolin-2 (1H)-yl]carbonyl}phenyl)-N-(4-hydroxyphenyl)-N-(3-methoxy-2-methylbenzyl)-1,2-dimethyl-1H-pyrrole-3-carboxamide (7) and N-(4-hydroxyphenyl)-N-(3-methoxy-2-methylbenzyl)-1,2-dimethyl-5-(2-{[(3S)-3-(morpholin-4-ylmethyl)-3,4-dihydroisoquinolin-2 (1H)-yl]carbonyl}phenyl)-1H-pyrrole-3-carboxamide (8)

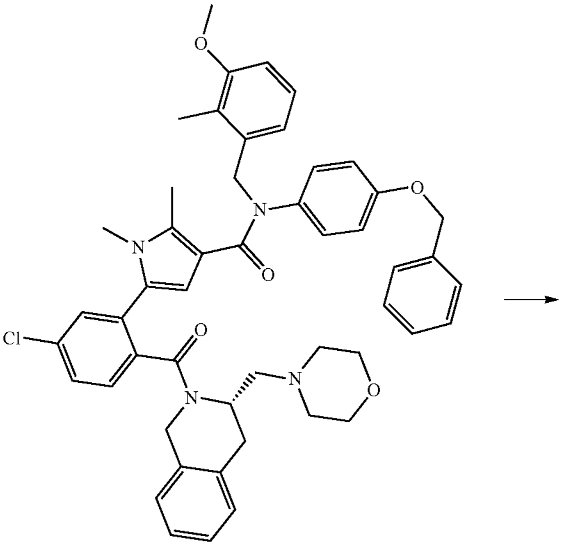

P20

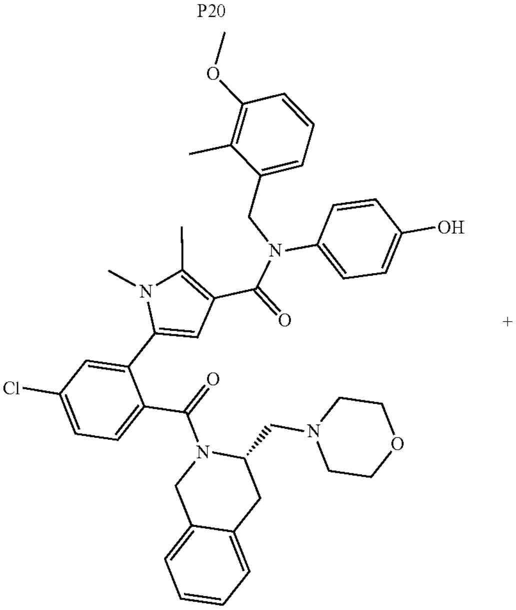

7

-continued

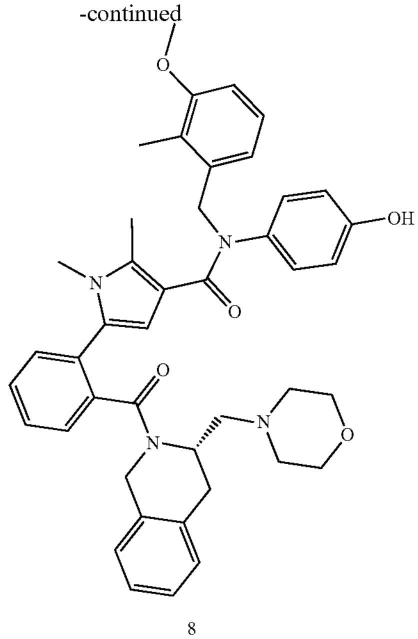

8

A stirred mixture of the compound P20 (120 mg), catalyst (10 mg of 5% Pd on charcoal), and methanol (2 mL) was hydrogenated under $H_2$ atm for 2 h. The catalyst was filtered off, and the filtrate was evaporated to dryness. The residue was subjected to HPLC purification to afford 28 mg (28%) of the compound 7, and 18 mg (13%) of the compound 8. Compound 7: 1H NMR (400 MHz, DMSO-$d_6$), δ:9.48-9.09 (m, 1H), 7.65-7.38 (m, 2H), 7.38-6.91 (m, 7H), 6.91-6.73 (m, 2H), 6.69-6.43 (m, 2H), 6.41-6.26 (s, 2H), 5.46-4.54 (m, 4H), 4.31-3.85 (m, 2H), 3.86-3.69 (m, 3H), 3.65-3.39 (m, 5H), 3.19-3.02 (s, 2H), 3.00-2.63 (m, 1H), 2.43-2.23 (m, 3H), 2.22-1.71 (m, 9H). ESI LCMS $[MH]^+$: 733. Compound δ: $^1H$ NMR (400 MHZ, DMSO-$d_6$), δ:9. 45-9.11 (m, 1H), 7.57-7.25 (m, 3H), 7.26-6.73 (m, 9H), 6.70-6.45 (m, 2H), 6.39-6.20 (s, 2H), 5.47-4.43 (m, 4H), 4.32-3.89 (m, 2H), 3.85-3.66 (m, 3H), 3.65-3.36 (m, 5H), 3.19-2.99 (s, 2H), 2.97-2.65 (m, 1H), 2.38-2.24 (m, 3H), 2.23-1.68 (m, 9H). ESI LCMS $[MH]^+$: 699.

Example 7. (S)—N-(4-chlorophenyl)-5-(4-(difluoromethoxy)-5-fluoro-2-(3-(morpholinomethyl)-1,2,3,4-tetrahydroisoquinoline-2-carbonyl)phenyl)-N-(3-methoxy-2-methylbenzyl)-1,2-dimethyl-1H-pyrrole-3-carboxamide (26)

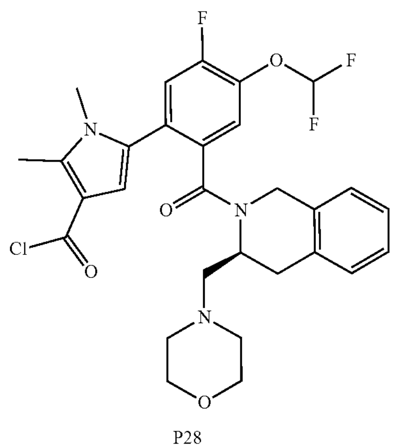

P28

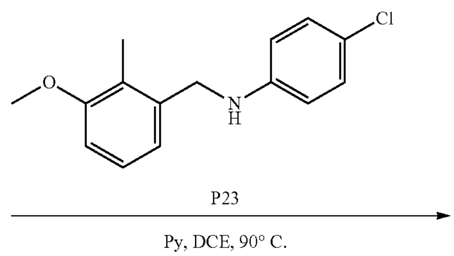

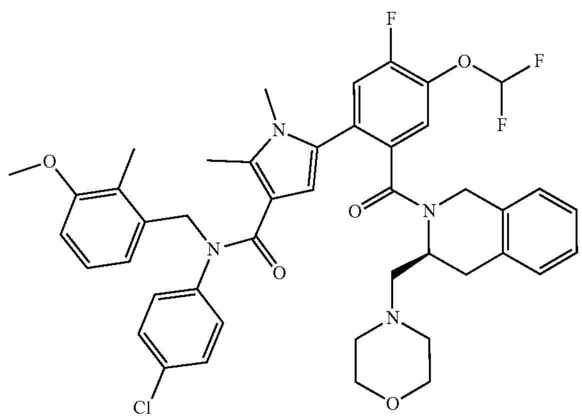

26

To a solution of P23 (56 mg, 0.21 mmol) in dichloroethane (1.0 mL) was added a solution of pyridine (42 μL, 0.53 mmol) and P28 (crude, 0.179 mmol) in dichloroethane (2.0 mL) at rt. The mixture was stirred at 90° C. for 8 h. The reaction was quenched with $NaHCO_{3(aq)}$ and extracted with DCM. The organic layers were dried over $MgSO_{4(s)}$, filtered and concentrated. The crude was purified by reverse phase chromatography (0-100% ACN in $H_2O$) to give compound 26 (23 mg, 23%) as a white powder. $^1H$ NMR (400 MHZ, $CDCl_3$), δ: 7.19-6.44 (m, 15H), 5.62-5.00 (m, 3H), 4.95-4.67 (m, 1H), 4.26-3.98 (m, 1H), 3.84-3.78 (m, 3H), 3.68-3.50 (m, 4H), 3.32-3.11 (m, 3H), 2.76-2.03 (m, 14H); LCMS(ESI) m/z calcd for $C_{44}H_{44}ClF_3N_4O_5$800.30; found, 801.4 $[M+H]^+$; HPLC purity: 99.9%, $t_R$=27.232 min.

Example 8 (S)—N-(4-(benzyloxy)phenyl)-5-(4-(difluoromethoxy)-2-(3-(morpholinomethyl)-1,2,3,4-tetrahydroisoquinoline-2-carbonyl)phenyl)-N-(3-methoxy-2-methylbenzyl)-1,2-dimethyl-1H-pyrrole-3-carboxamide (31)

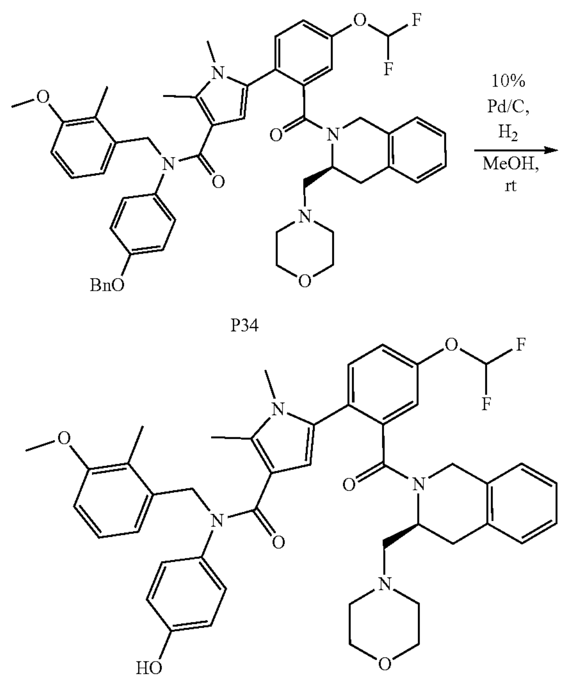

P34

31

To a solution of P34 (24 mg, 0.028 mmol) in MeOH (4.0 mL) was added 10% Pd/C (28 mg) and the solution was degassed with $H_2$ (g). After the mixture was stirred at rt for 30 min under hydrogen (1 atm), the solution was diluted with a solution of 20% MeOH in DCM and filtered through a pad of celite. The filtrate was concentrated under reduced pressure and purified by reverse phase chromatography (0-100% MeOH in $H_2O$ with 1% $NH_4HCO_3$) to give compound 31 (13.3 mg, 62%) as a white solid. $^1H$ NMR (400 MHZ, DMSO-$d_6$), δ:9.39-9.22 (m, 1H), 7.54-7.25 (m, 2H), 7.25-7.04 (m, 6H), 7.03-6.85 (m, 3H), 6.80-6.48 (m, 1H), 6.28 (s, 2H), 5.39-4.96 (m, 2H), 4.94-4.52 (m, 2H), 4.30-4.14 (m, 1H), 4.03-3.89 (m, 1H), 3.82-3.68 (m, 3H), 3.62-3.47 (m, 4H), 3.30-3.27 (m, 1H), 3.07 (s, 2H), 2.96-2.64 (m, 1H), 2.60-2.53 (m, 1H), 2.46-2.24 (m, 4H), 2.23-2.07 (m, 3H), 2.03-1.93 (m, 3H), 1.91-1.68 (m, 2H); LCMS(ESI) m/z calcd for $C_{44}H_{46}F_2N_4O_6$764.34; found, 765.4 $[M+H]^+$; HPLC purity: 98.9%, +R=20.23 min.

Example 9. (S)-5-(5-Chloro-4-(difluoromethoxy)-2-(3-(morpholinomethyl)-1,2,3,4-tetrahydroisoquinoline-2-carbonyl)phenyl)-N-(4-hydroxyphenyl)-N-(3-methoxy-2-methylbenzyl)-1,2-dimethyl-1H-pyrrole-3-carboxamide (36)

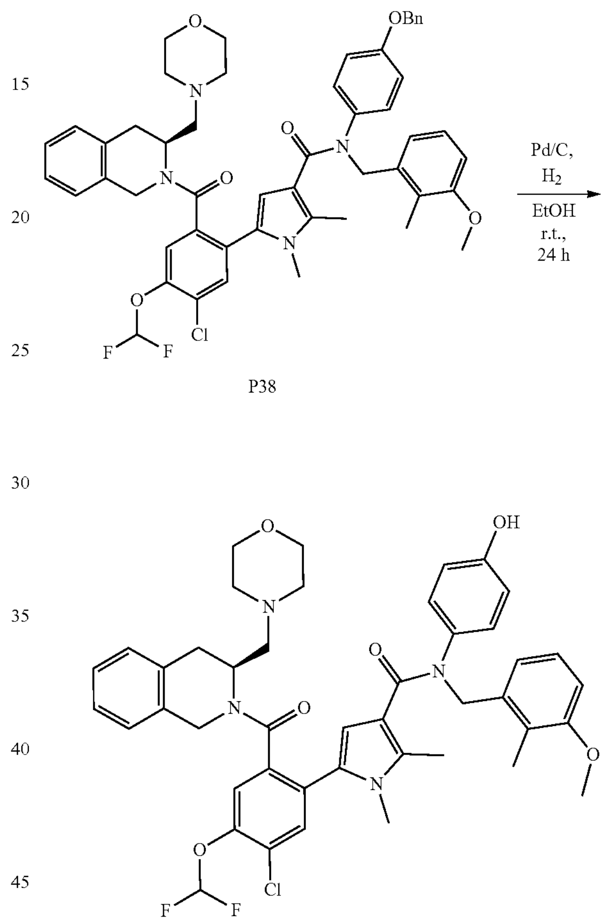

P38

36

To a solution of P38 (40.0 mg, 0.0449 mmol) in ethanol (4.0 mL) was added Pd/C (4.0 mg, 10% w/w) at rt. After the reaction solution was stirred at rt for 24 h under $H_2$ (g) atmosphere, the solution was filtered through a pad of celite and washed with methanol. The filtrate was concentrated under reduced pressure and the residue was purified by C18 flash column chromatography (0-100% methanol in $H_2O$) to give compound 36 (7.4 mg, 20% yield) as a white solid. $^1H$ NMR (400 MHZ, $CDCl_3$), δ: 7.22-6.34 (m, 14H), 5.50-5.33 (m, 1H), 5.12-4.76 (m, 4H), 4.26-3.93 (m, 2H), 3.82-3.78 (m, 3H), 3.67-3.66 (m, 3H), 3.53-3.50 (m, 1H), 3.27 (s, 1H), 3.10 (s, 1H), 2.80-2.14 (m, 10H), 2.06-1.96 (m, 4H); LCMS (ESI) m/z calcd for $C_{44}H_{45}ClF_2N_4O_6$798.30; found, 799.4 $[M+H]^+$; HPLC purity: 97.8%, (R=21.662 min. Example 10. (S)-5-(4-chloro-5-(difluoromethyl)-2-(3-(morpholinomethyl)-1,2,3,4-tetrahydroisoquinoline-2-carbonyl)phenyl)-N-(4-chlorophenyl)-N-(3-methoxy-2-methylbenzyl)-1,2-dimethyl-1H-pyrrole-3-carboxamide (39)

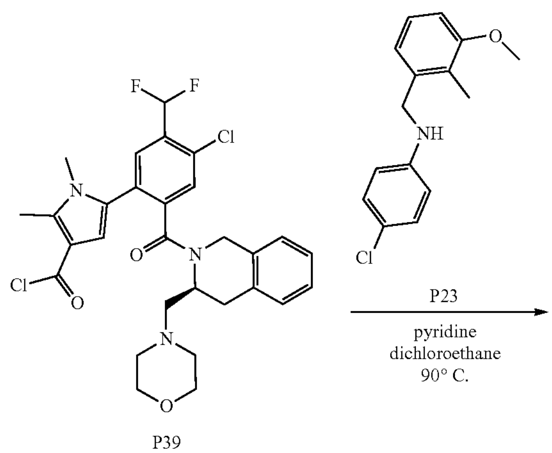

P39

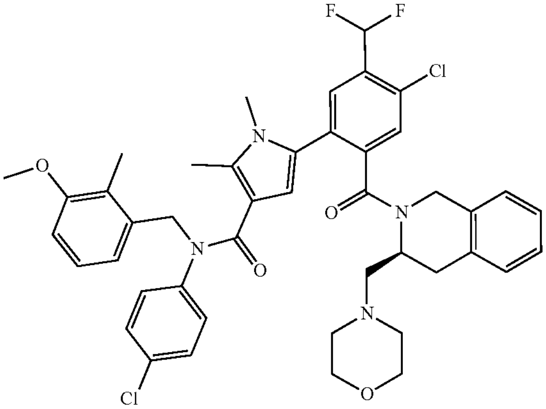

39

To a solution of P39 (0.27 mmol) in dichloroethane (3.0 mL) was added P23 (85 mg, 0.32 mmol, 1.2 eq) and pyridine (65 μL, 0.81 mmol, 3.0 eq). The reaction mixture was stirred at 90° C. for 16 h. The reaction mixture was treated with water and extracted with DCM. The organic layers were dried over $MgSO_{4(s)}$, filtered, and concentrated in vacuo to give a residue. The residue was purified by flash column chromatography (0-2% MeOH in DCM containing 1% $NH_4OH$ (aq)) to give 39 (43.7 mg, 21%) as a brown gum. $^1H$ NMR (400 MHZ, $CDCl_3$), δ: 7.41 (d, J=8.8 Hz, 2H), 7.16-6.71 (m, 11H), 6.53 (d, J=8.8 Hz, 2H), 5.15-4.76 (m, 4H), 4.23-4.19 (m, 1H), 3.99-3.95 (m, 1H), 3.83-3.79 (m, 5H), 3.70-3.55 (m, 4H), 3.28-3.26 (m, 2H), 3.11 (s, 3H), 2.85-2.30 (m, 5H), 2.22-1.95 (m, 6H); LRMS(ESI) m/z 801.4 $[M+H]^+$; HPLC purity: 97.7%, $t_R$=28.195 min.

Example 11. (S)-5-(5-Chloro-4-(difluoromethoxy)-2-(3-(morpholinomethyl)-1,2,3,4-tetrahydroisoquinoline-2-carbonyl)phenyl)-N-(4-cyanophenyl)-N-(3-methoxy-2-methylbenzyl)-1,2-dimethyl-1H-pyrrole-3-carboxamide (40)

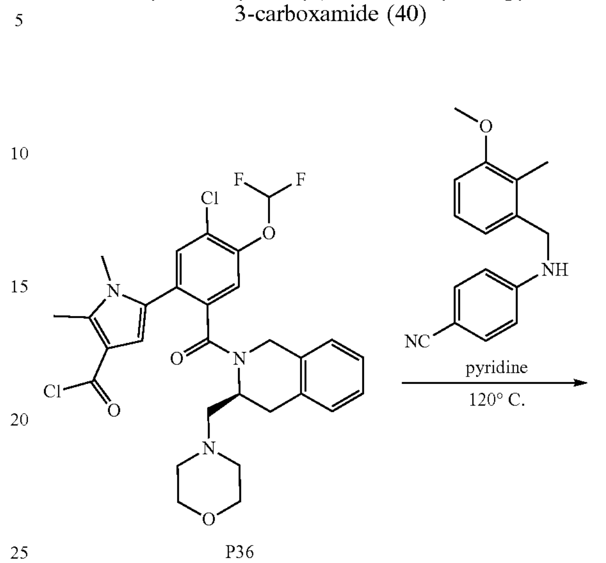

P36

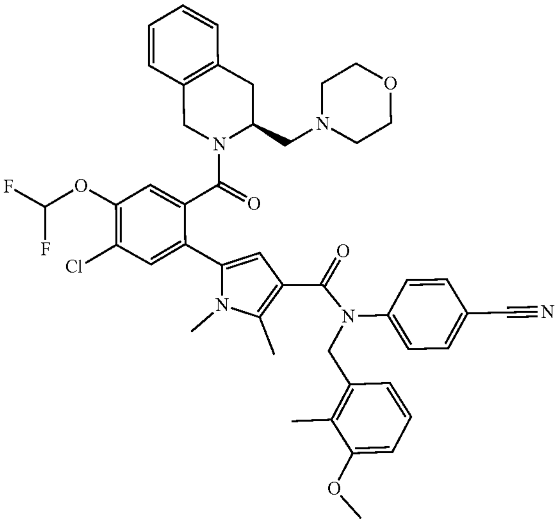

40

To a solution of P36 (0.35 mmol) in pyridine (2.0 mL) was added 4-[(3-methoxy-2-methyl-phenyl)methylamino]benzonitrile (97 mg, 0.39 mmol, 1.1 eq). The reaction mixture was stirred at 120° C. for 2 days. The reaction mixture was treated with water and extracted with DCM. The organic layers were dried over $MgSO_{4(s)}$, filtered, and concentrated in vacuo to give a residue. The residue was purified by flash column chromatography (0-2% MeOH in DCM containing 1% $NH_4OH$ (aq)) and followed by reverse phase HPLC (10-90% acetonitrile in $H_2O$) to give 40 (3.2 mg, 1%) as a brown gum. $^1H$ NMR (400 MHZ, $CDCl_3$), δ: 7.25-6.67 (m, 15H), 5.13-4.79 (m, 4H), 4.22 (m, 1H), 3.99 (m, 1H), 3.84-3.81 (m, 5H), 3.67-3.55 (m, 7H), 3.17 (s, 3H), 2.84-2.00 (m, 14H); LRMS(ESI) m/z 808.3 $[M+H]^+$; HPLC purity: 99.3%, $t_R$=25.188 min.

Example 12. (S)-5-(5-Chloro-4-(difluoromethoxy)-2-(3-(morpholinomethyl)-1,2,3,4-tetrahydroisoquinoline-2-carbonyl)phenyl)-N-(4-cyanophenyl)-N-(3-methoxy-2-methylbenzyl)-1,2-dimethyl-1H-pyrrole-3-carboxamide (43)

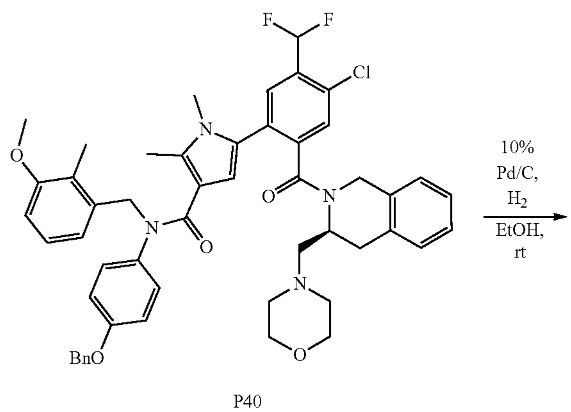

P40

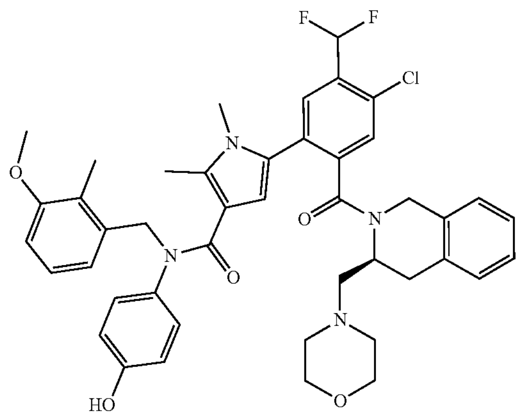

43

To a solution of P40 (65 mg, 0.074 mmol) in EtOH (4.0 mL) was added 10% Pd/C (74 mg) and the solution was degassed with $H_2$ (g). After the mixture was stirred at room temperature for 6 h under hydrogen (1 atm), the solution was diluted with a solution of 20% MeOH in DCM and filtered through a pad of celite. The filtrate was concentrated under reduced pressure and purified by reverse phase chromatography (0-100% ACN in $H_2O$) to give compound 43 (5.4 mg, 9%) as a white solid. $^1H$ NMR (400 MHZ, DMSO-$d_6$), δ:7.63-7.28 (m, 2H), 7.25-6.88 (m, 6H), 6.85-6.63 (m, 4H), 6.55-6.32 (m, 3H), 5.56-4.77 (m, 3H), 4.29-3.88 (m, 1H), 3.84-3.78 (m, 3H), 3.75-3.61 (m, 3H), 3.58-3.47 (m, 2H), 3.27 (s, 1H), 3.08 (s, 2H), 2.83-2.45 (m, 3H), 2.43-2.29 (m, 2H), 2.27-2.14 (m, 3H), 2.11-1.87 (m, 5H); LCMS(ESI) m/z calcd for $C_{44}H_{45}ClF_2N_4O_5$782.30; found, 783.4 $[M+H]^+$; HPLC purity: 98.6%, $t_R$=21.193 min.

Example 13. (S)—N-(4-cyanophenyl)-5-(4-(difluoromethoxy)-5-fluoro-2-(3-(morpholinomethyl)-1,2,3,4-tetrahydroisoquinoline-2-carbonyl)phenyl)-N-(3-methoxy-2-methylbenzyl)-1,2-dimethyl-1H-pyrrole-3-carboxamide (44)

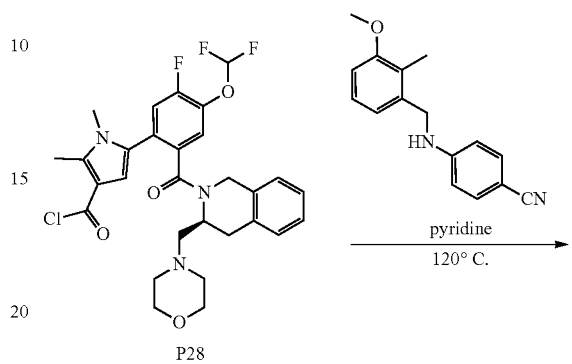

P28

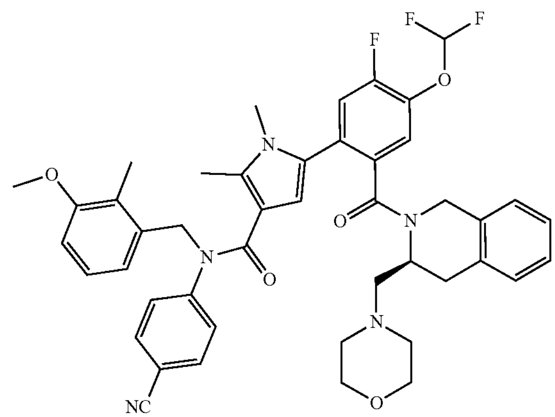

44

To a solution of P28 (0.36 mmol) in pyridine (2.0 mL) was added 4-[(3-methoxy-2-methyl-phenyl)methylamino]benzonitrile (100 mg, 0.40 mmol, 1.1 eq). The reaction mixture was stirred at 120° C. for 2 days. The reaction mixture was treated with water and extracted by DCM. The organic layers were dried over $MgSO_{4(s)}$, filtered, and concentrated in vacuo to give a residue. The residue was purified by flash column chromatography (0-2% MeOH in DCM containing 1% $NH_4OH$ (aq)) and followed by reverse phase HPLC (10-90% acetonitrile in $H_2O$) to give 44 (5.5 mg, 4%) as a brown gum. $^1H$ NMR (400 MHz, $CDCl_3$), δ: 7.28-6.62 (m, 15H), 5.15-4.80 (m, 4H), 4.24-4.22 (m, 1H), 4.01-3.97 (m 1H), 3.84-3.81 (m, 3H), 3.70-3.55 (m, 4H), 3.25-3.17 (m, 3H), 2.81-2.00 (m, 14H); LRMS(ESI) m/z 792.4 $[M+H]^+$; HPLC purity: 98.8%, (R=23.896 min.

Example 14. (S)-5-(5-Chloro-2-(3-(morpholinomethyl)-1,2,3,4-tetrahydroisoquinoline-2-carbonyl)phenyl)-N-(1H-indazol-5-yl)-N-(3-methoxy-2-methylbenzyl)-1,2-dimethyl-1H-pyrrole-3-carboxamide (70)

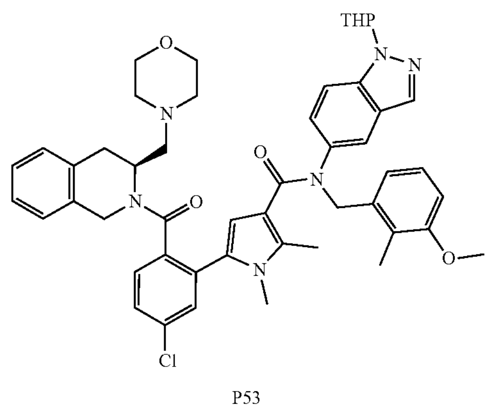

P53

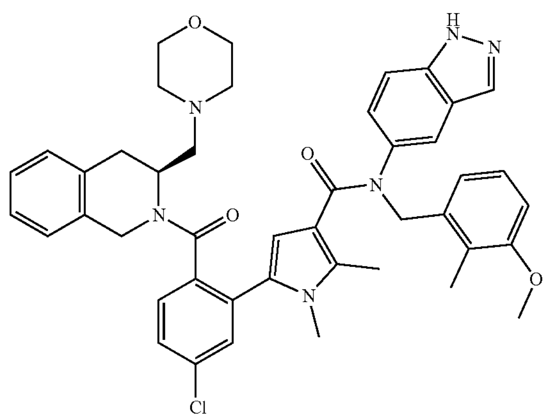

70

To a solution of P53 (100 mg, 0.119 mmol) in DCM (1.0 mL) was added TFA (0.20 ml). The reaction was stirred at rt for 2 h. The mixture was concentrated to remove solvent. The crude was purified by preparative thin layer chromatography (5% MeOH in DCM) to give compound 70 (29 mg, 37%). $^1H$ NMR (400 MHZ, $CDCl_3$), δ: 7.89-7.84 (m, 1H), 7.42-7.28 (m, 2H), 7.22-6.90 (m, 8H), 6.81-6.67 (m, 4H), 5.47 (br s, 1H), 5.25-4.68 (m, 3H), 4.21-4.08 (m, 1H), 3.92-3.60 (m, 7H), 3.53-3.45 (m, 1H), 3.30-3.20 (m, 1H), 3.05 (br s, 2H), 2.78-2.72 (m, 1H), 2.66-2.50 (m, 2H), 2.40-2.32 (m, 1H), 2.24 (br m, 2H), 2.07-2.05 (m, 3H), 1.98-1.82 (m, 1H), 1.67 (br s, 3H);LCMS(ESI) m/z 757.4 $[M+H]^+$.; HPLC purity: 95.1%, $t_R$=19.5 min.

Example 15. (S)-5-(5-Chloro-2-(3-(morpholinomethyl)-1,2,3,4-tetrahydroisoquinoline-2-carbonyl)phenyl)-N-(2-cyanobenzyl)-N-(1H-indazol-5-yl)-1,2-dimethyl-1H-pyrrole-3-carboxamide (68)

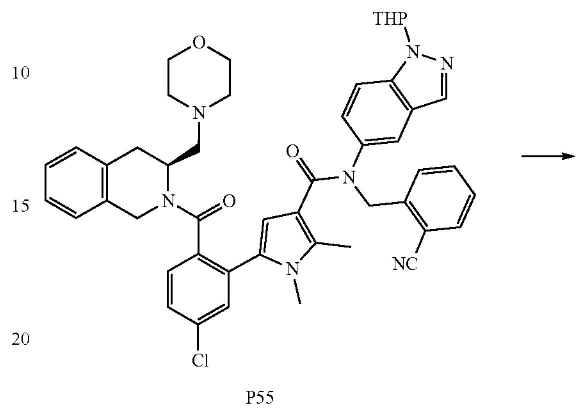

P55

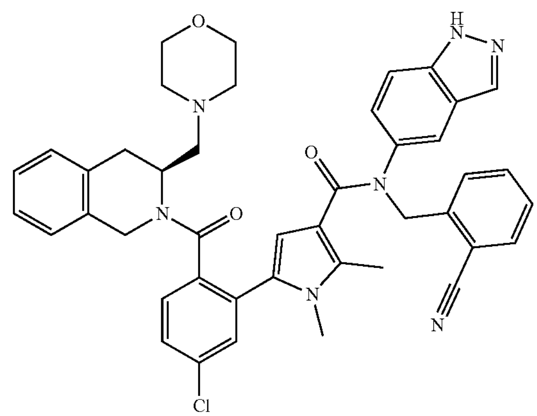

68

To a solution of P55 (40 mg, 0.049 mmol) in DCM (1.0 mL) was added TFA (0.10 ml). The reaction was stirred at rt for 1 h. The mixture was concentrated to remove solvent. The crude was purified by preparative thin layer chromatography (5% MeOH in DCM) to give compound 68 (16 mg, 44%). $^1H$ NMR (400 MHZ, $CDCl_3$), δ: 7.92-7.87 (m, 1H), 7.71-7.63 (m, 1H), 7.51-7.49 (m, 2H), 7.41-7.01 (m, 9H), 6.95-6.92 (m, 1H), 6.82-6.77 (m, 2H), 5.45-5.27 (m, 2H), 5.13-4.95 (m, 2H), 4.21-4.10 (m, 1H), 3.94-3.87 (m, 1H), 3.65 (br m, 5H), 3.50-3.48 (m, 1H), 3.25 (br s, 2H), 3.09 (br s, 2H), 2.75-2.53 (m, 3H), 2.42-2.37 (m, 1H), 2.29 (s, 3H), 2.21-1.84 (m, 1H), 1.28-1.24 (m, 1H); LCMS(ESI) m/z 738.4 $[M+H]^+$.; HPLC purity: 93.8%, $t_R$=17.896 min.

Example 16. (S)-5-(5-Chloro-2-(3-(morpholinomethyl)-1,2,3,4-tetrahydroisoquinoline-2-carbonyl)phenyl)-N-(1H-indazol-5-yl)-N-(2-methoxybenzyl)-1,2-dimethyl-1H-pyrrole-3-carboxamide (69)

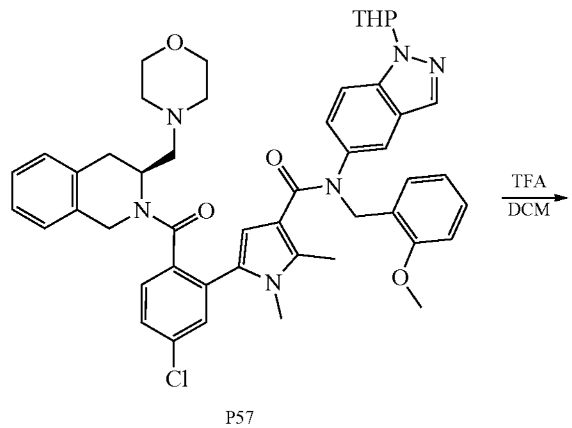

P57

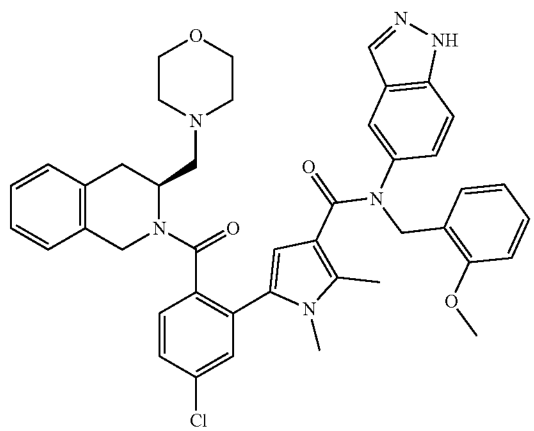

69

To a solution of P57 (265 mg, 0.32 mmol) in DCM (4.0 mL) was added TFA (2.0 mL). The reaction was stirred at rt for overnight and concentrated. The residue was purified by C18 reverse phase column chromatography (0-100% MeOH in water) to give compound 69 (31 mg, 13% yield) as a white solid. $^1$H NMR (400 MHZ, $CDCl_3$), δ: 7.87-7.83 (m, 1H), 7.45-7.28 (m, 3H), 7.24-7.04 (m, 5H), 7.01-6.82 (m, 4H), 6.75-6.70 (m, 2H), 5.56-4.99 (m, 4H), 4.23-4.09 (m, 1H), 3.92-3.87 (m, 1H), 3.65-3.42 (m, 9H), 3.30-3.18 (m, 2H), 3.04-2.46 (m, 5H), 2.43-2.06 (m, 5H), 1.99-1.83 (m, 2H).; LCMS(ESI) m/z calcd for $C_{43}H_{43}ClN_6O_4$ 742.30; found, 743.3 $[M+H]^+$. HPLC purity: 93.5%, $t_R$=18.577 min.

Example 17. 5-(5-chloro-4-cyano-2-[(3R)-3-(morpholinomethyl)-3,4-dihydro-2 (1H)-isoquinolinyl]carbonylphenyl)-$N^3$-(4-hydroxyphenyl)-$N^3$-(3-methoxy-2-methylbenzyl)-1,2-dimethyl-1H-pyrrole-3-carboxamide (9)

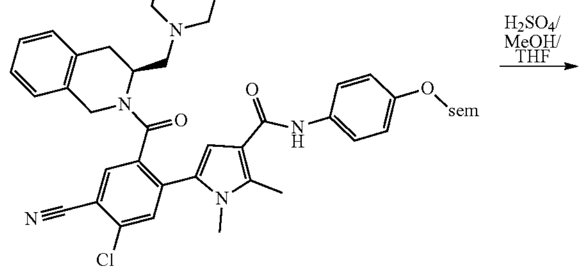

P61

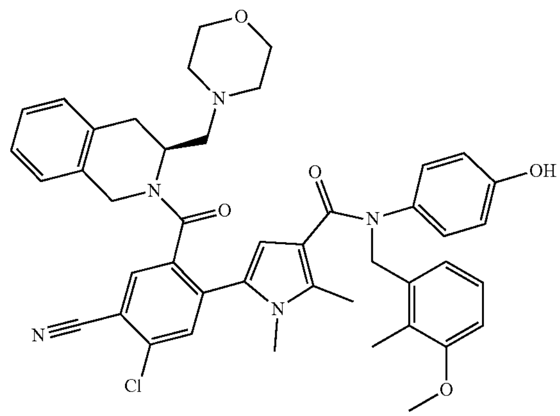

9

A stirred mixture of P61, $H_2SO_4$ (0.1 mL), and methanol/THF (2 mL, 1:1) was stirred at ambient temperature for 2 h. Sodium carbonate 20% water solution was added (pH 7), product was extracted with DCM twice. Combined organic layers were washed with brine, dried over anh. sodium sulfate, and concentrated on a rotary evaporator under reduced pressure. The residue was subjected to a silica gel flash chromatography eluting with a mixture of MeOH (0→2%) and DCM to afford 17 mg (25%) of the title compound. $^1$H NMR (400 MHZ, DMSO-$d_6$), δ:9.32-9.24 (m, 1H), 8.01-7.81 (m, 1H), 7.74-7.58 (m, 1H), 7.24-6.24 (m, 10H), 5.63-5.25 (m, 1H), 5.12-4.54 (m, 4H), 4.28-3.83 (m, 2H), 3.83-3.65 (m, 3H), 3.65-3.36 (m, 6H), 3.13 (s, 2H), 3.00-2.62 (m, 1H), 2.44-2.25 (m, 5H), 2.25-1.61 (m, 7H). LCMS(ESI+) m/z 759 $[M+H]^+$.

Example 18. 5-(5-Chloro-4-methoxy-2-{[(3S)-3-(morpholin-4-ylmethyl)-3,4-dihydroisoquinolin-2(1H)-yl]carbonyl}phenyl)-N-(4-hydroxyphenyl)-N-(3-methoxy-2-methylbenzyl)-1,2-dimethyl-1H-pyrrole-3-carboxamide (11)

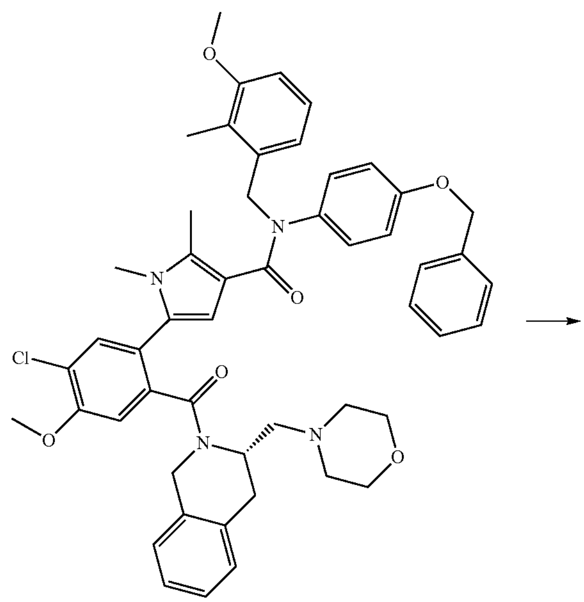

P67

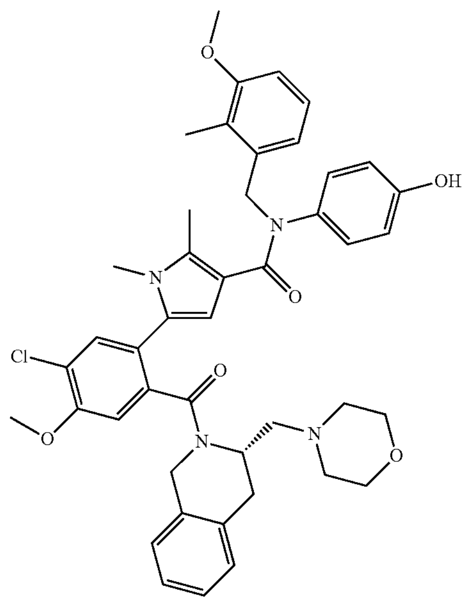

11

A stirred mixture of P67, catalyst (5 mg of 5% Pd on charcoal), and methanol (2 mL) was hydrogenated under $H_2$ atmosphere for 2 h. The catalyst was filtered off, and the filtrate was evaporated to dryness. The residue was subjected to HPLC purification to afford 15 mg (21%). 1H NMR (400 MHZ, DMSO-$d_6$), δ:9.53-9.11 (m, 1H), 7.51-5.98 (m, 12H), 5.45-4.44 (m, 4H), 4.33-3.67 (m, 12H), 3.57 (s, 6H), 3.16-2.64 (m, 3H), 2.38-1.73 (m, 9H). LCMS(ESI+) m/z 764 $[M+H]^+$.

Example 19. 5-(5-Fluoro-4-methoxy-2-{[(3S)-3-(morpholin-4-ylmethyl)-3,4-dihydroisoquinolin-2(1H)-yl]carbonyl}phenyl)-N-(4-hydroxyphenyl)-N-(3-methoxy-2-methylbenzyl)-1,2-dimethyl-1H-pyrrole-3-carboxamide (21)

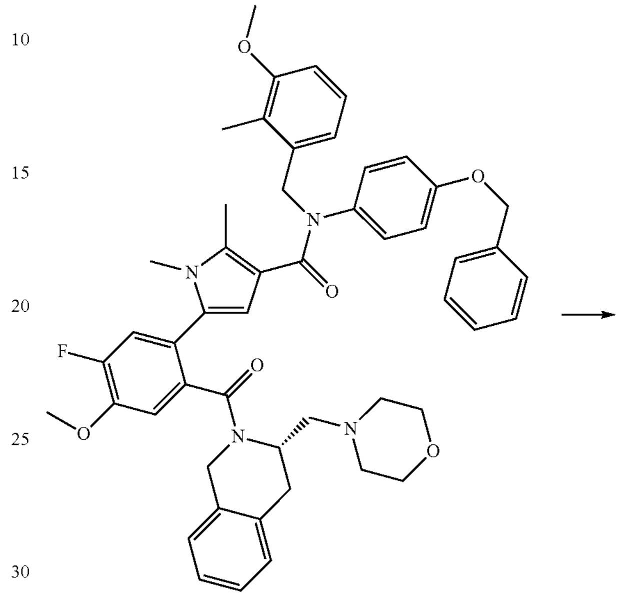

P72

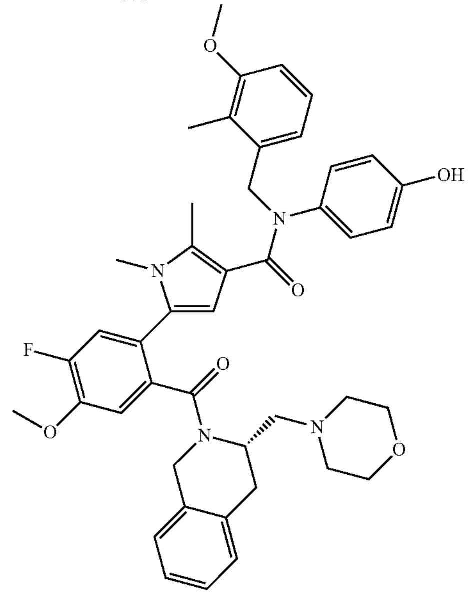

21

A stirred mixture of P72, catalyst (5 mg of 5% Pd on charcoal), and methanol (2 mL) was hydrogenated under $H_2$ atmosphere for 2 h. The catalyst was filtered off, and the filtrate was evaporated to dryness. The residue was subjected to HPLC purification to afford 18 mg (64%) of compound 21. 1H NMR (400 MHZ, DMSO-$d_6$), δ:9.48-9.14 (m, 1H), 7.30-6.71 (m, 9H), 6.71-6.44 (m, 2H), 6.31 (s, 2H), 5.42-4.46 (m, 4H), 4.32-3.68 (m, 10H), 3.66-3.36 (m, 6H), 3.18-2.67 (m, 4H), 2.48-2.27 (m, 3H), 2.22-1.72 (m, 6H). MS(ESI+) m/z 747 $[M+H]^+$.

Example 20. N-(4-chlorophenyl)-5-(4-cyano-5-methoxy-2-{[(3S)-3-(morpholin-4-ylmethyl)-3,4-dihydroisoquinolin-2 (1H)-yl]carbonyl}phenyl)-N-(2-methoxybenzyl)-1,2-dimethyl-1H-pyrrole-3-carboxamide (56), 5-(4-(aminocarbonyl)-5-methoxy-2-{[(3S)-3-(morpholin-4-ylmethyl)-3,4-dihydroisoquinolin-2 (1H)-yl]carbonyl}phenyl)-N-(4-chlorophenyl)-N-(2-methoxybenzyl)-1,2-dimethyl-1H-pyrrole-3-carboxamide (63)

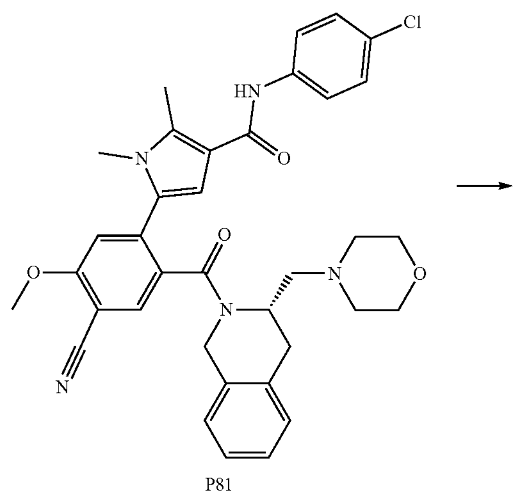

P81

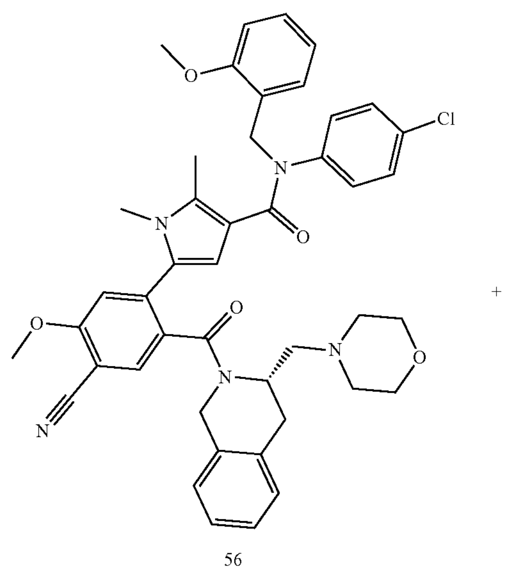

56

-continued

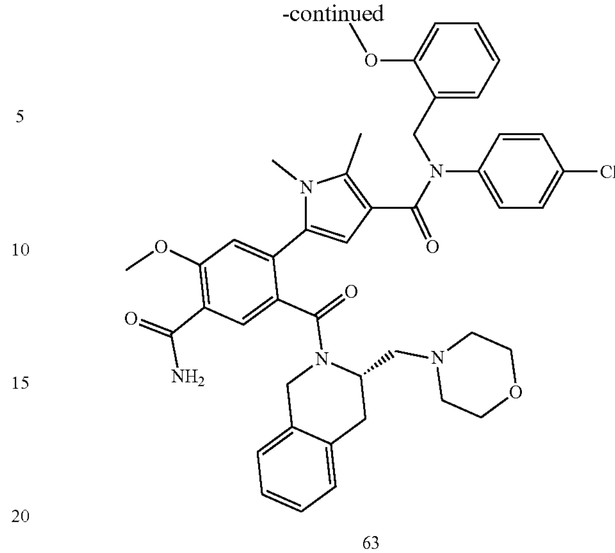

63

A mixture of P81 (100 mg, 0.157 mmol), tert-BuOK (88 mg, 0.8 mmol), and tert-BuOH (25 mL) was stirred at 50° C. for 30 min, then 2-methoxylbenzyl methanesulfonate (60 mg, 0.314 mmol) was added. The reaction mixture was stirred at 60° C. for 1 h and then partitioned between EtOAc and water. The organic layer was separated, washed with brine, dried over $Na_2SO_4$, filtered, and concentrated under reduced pressure. The residue was subjected to HPLC purification to afford 16.0 mg (12%) of compound 56 and 6 mg (4%) of compound 63. Compound 56: 1H NMR (400 MHz, DMSO-$d_6$), δ:7.86-7.59 (m, 1H), 7.34-6.67 (m, 15H), 5.12-4.65 (m, 4H), 4.28-3.85 (m, 5H), 3.76-3.36 (m, 8H), 3.19 (s, 2H), 2.95-2.63 (m, 1H), 2.42-2.25 (m, 2H), 2.20-1.75 (m, 6H). LCMS(ESI+) m/z 759 $[M+H]^+$. Compound 63: LCMS(ESI+) m/z 777 $[M+H]^+$.

Example 21. 5-(5-Chloro-4-fluoro-2-{[(3S)-3-(morpholin-4-ylmethyl)-3,4-dihydroisoquinolin-2 (1H)-yl]carbonyl}phenyl)-N-(4-hydroxyphenyl)-N-(3-methoxy-2-methylbenzyl)-1,2-dimethyl-1H-pyrrole-3-carboxamide (27)

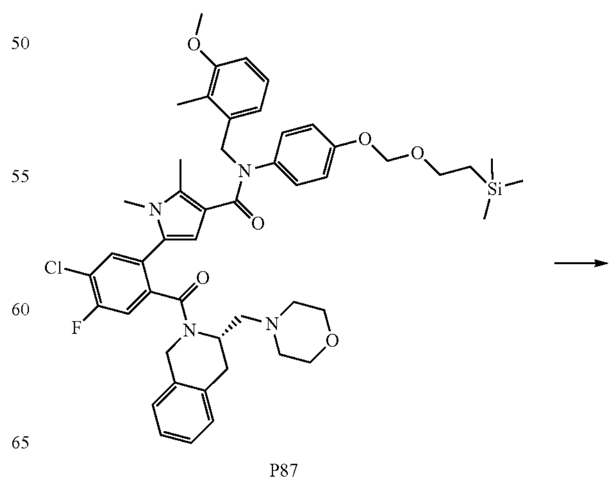

P87

-continued

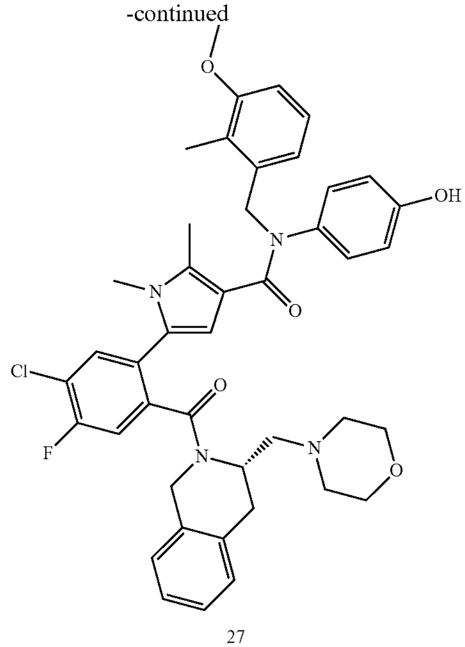

27

A stirred mixture of P87, $H_2SO_4$ (0.15 mL), and methanol/THF (2 mL, 1:1) was stirred at ambient temperature for 1 h. Volatiles were removed under reduced pressure, and the residue was stirred with 20% aqueous solution of $Na_2CO_3$ for 5 min. The product was extracted with DCM (2×10 mL). Combined organic layers were washed with brine, dried over $Na_2SO_4$, and concentrated on rotary evaporator under reduced pressure. The residue was subjected to HPLC purification to afford 40 mg (40%) of the title compound. $^1H$ NMR (400 MHZ, DMSO-$d_6$), δ:9.52-9.15 (m, 1H), 7.65-7.24 (m, 2H), 7.24-6.42 (m, 8H), 6.34 (s, 2H), 5.46-4.60 (m, 4H), 4.33-3.96 (m, 2H), 3.92-3.67 (m, 3H), 3.65-3.39 (m, 6H), 3.17-2.62 (m, 3H), 2.42-2.23 (m, 4H), 2.18-1.81 (m, 9H). LCMS(ESI+) m/z 752 $[M+H]^+$.

Example 22. 5-(4-Cyano-5-methoxy-2-{[(3S)-3-(morpholin-4-ylmethyl)-3,4-dihydroisoquinolin-2(1H)-yl]carbonyl}phenyl)-N-(4-hydroxyphenyl)-N-(3-methoxy-2-methylbenzyl)-1,2-dimethyl-1H-pyrrole-3-carboxamide (58)

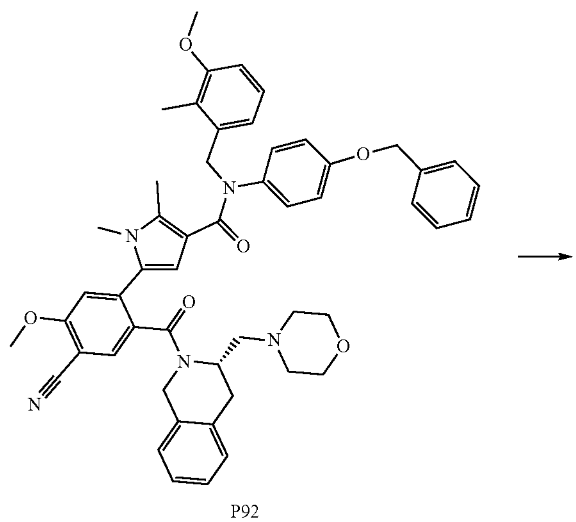

P92

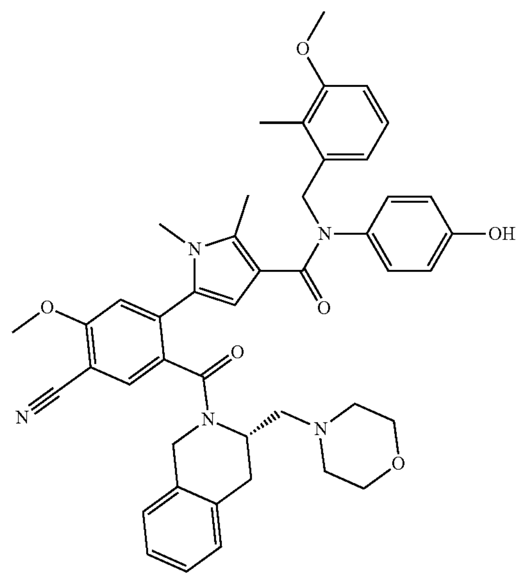

58

A stirred mixture of P92, catalyst (5 mg of 5% Pd on charcoal), and methanol (10 mL) was hydrogenated under $H_2$ atmosphere for 2 h. The catalyst was filtered off, and the filtrate was evaporated to dryness. The residue was subjected to HPLC purification to afford 29 mg (25%) of compound 58. 1H NMR (400 MHZ, DMSO-$d_6$), δ:9.52-9.15 (m, 1H), 7.87-7.46 (m, 1H), 7.29-6.72 (m, 9H), 6.72-6.43 (m, 2H), 6.43-6.27 (m, 2H), 5.25 (s, 1H), 5.07-4.57 (m, 4H), 4.37-3.99 (m, 2H), 3.92 (s, 3H), 3.83-3.69 (m, 3H), 3.62-3.40 (m, 6H), 3.18 (s, 2H), 3.01-2.57 (m, 2H), 2.45-2.22 (m, 3H), 2.20-1.82 (m, 6H). LCMS(ESI+) m/z 754 $[M+H]^+$.

Example 23. 5-(5-nitro-2-[(3R)-3-(morpholinomethyl)-3,4-dihydro-2 (1H)-isoquinolinyl]carbonylphenyl)-$N^3$-(1H-indazol-5-yl)-$N^3$-(3-methoxy-2-methylbenzyl)-1,2-dimethyl-1H-pyrrole-3-carboxamide (65)

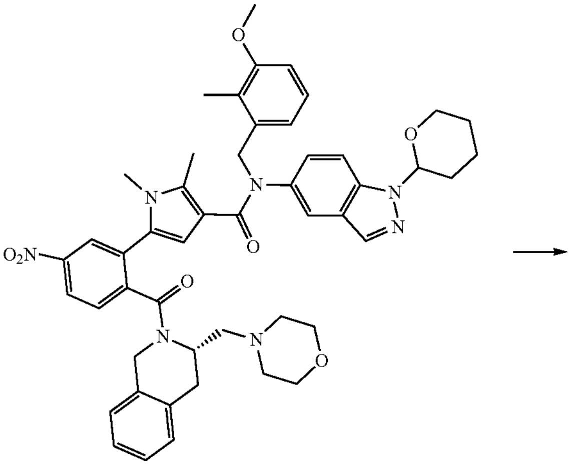

P97

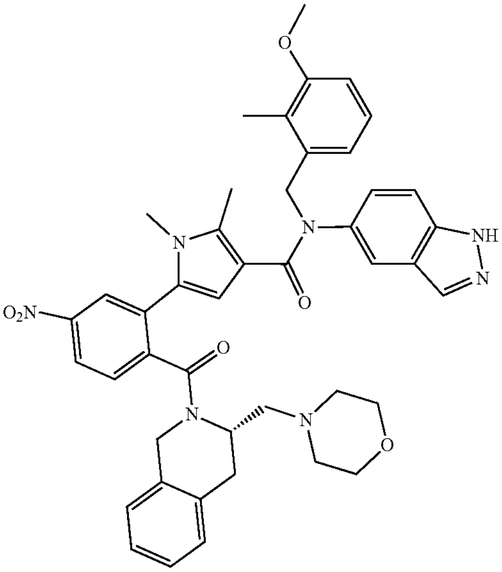

65

A stirred mixture of the crude compound P97 (180 mg) and TFA (0.4 mL) in DCM (3 mL) was stirred at ambient temperature for 3 h. Water solution (20%, $NaHCO_3$) was added (pH 7), product was extracted with DCM (2×6 ml). Combined organic layers were washed with brine, dried over $Na_2SO_4$, and concentrated under reduced pressure. The residue was purified by HPLC to afford 40 mg of compound 65. LCMS(ESI+) m/z 768 $[M+H]^+$. $^1H$ NMR (400 MHZ, DMSO-$d_6$), δ:13.18-12.76 (m, 1H), 8.38-8.08 (m, 1H), 8.00-7.80 (m, 3H), 7.66-6.45 (m, 11H), 5.55-4.68 (m, 4H), 4.40-3.85 (m, 2H), 3.84-3.66 (m, 3H), 3.64-3.37 (m, 6H), 3.08 (s, 2H), 2.81-2.56 (m, 1H), 2.43-2.16 (m, 3H), 2.09-1.71 (m, 8H).

Example 24. 5-(5-Nitro-2-[(3R)-3-(morpholinomethyl)-3,4-dihydro-2 (1H)-isoquinolinyl]carbonylphenyl)-$N^3$-(1H-indazol-5-yl)-$N^3$-(2-cyanobenzyl)-1,2-dimethyl-1H-pyrrole-3-carboxamide (71)

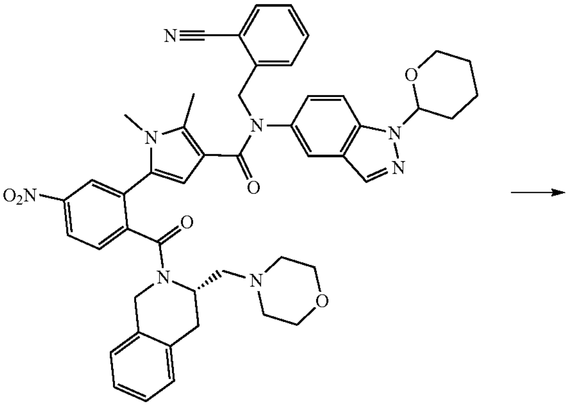

P101

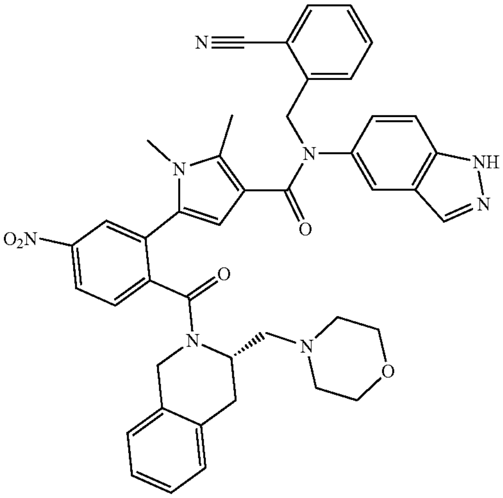

71

A stirred mixture of the crude compound P101 (100 mg) and TFA (0.48 mL) in DCM (2 mL) was stirred at ambient temperature for 3 h. Water solution of $NaHCO_3$ (20%) was added (up to pH 7), product was extracted with DCM. Combined organic layers were washed with brine, dried over $Na_2SO_4$, and concentrated under reduced pressure. The residue was purified by HPLC to afford 56 mg (64%) of compound 71. LCMS(ESI+) m/z 749 $[M+H]^+$. $^1H$ NMR (400 MHZ, DMSO-$d_6$), δ:9. 48-9.09 (m, 1H), 7.65-7.38 (m, 2H), 7.38-6.91 (m, 7H), 6.91-6.73 (m, 2H), 6.69-6.43 (m, 2H), 6.41-6.26 (s, 2H), 5.46-4.54 (m, 4H), 4.31-3.85 (m, 2H), 3.86-3.69 (m, 3H), 3.65-3.39 (m, 5H), 3.19-3.02 (s, 2H), 3.00-2.63 (m, 1H), 2.43-2.23 (m, 3H), 2.22-1.71 (m, 9H).

Example 25. 5-(5-Cyano-2-{[(3S)-3-(morpholin-4-ylmethyl)-3,4-dihydroisoquinolin-2 (1H)-yl]carbonyl}phenyl)-N-(4-hydroxyphenyl)-N-(3-methoxy-2-methylbenzyl)-1,2-dimethyl-1H-pyrrole-3-carboxamide (55)

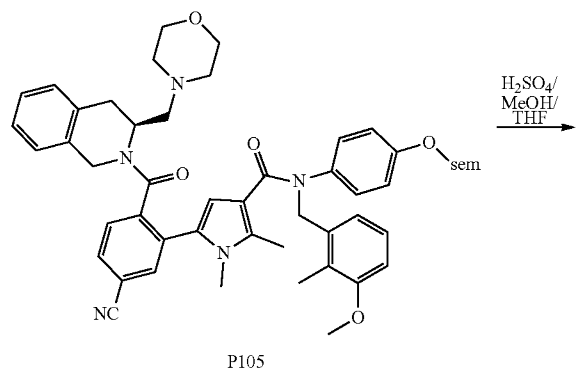

P105

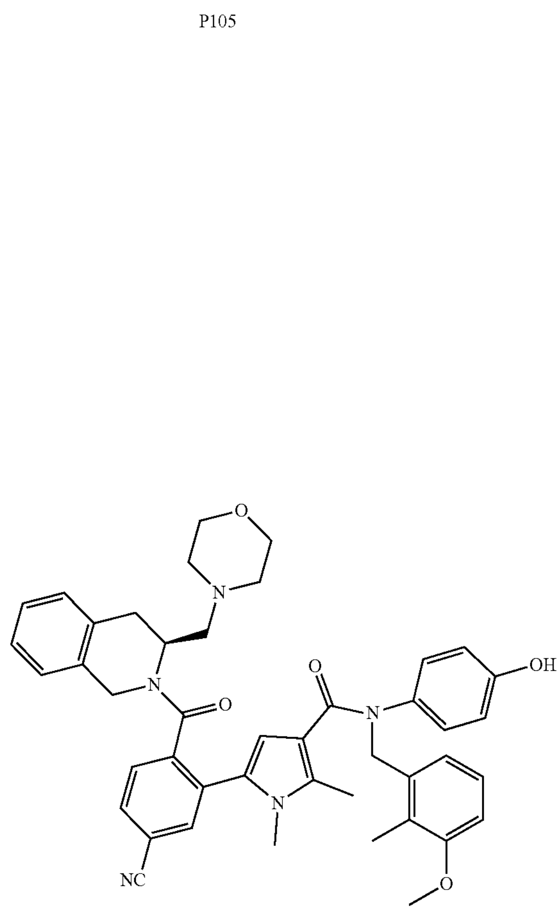

55

A stirred mixture of P105, $H_2SO_4$ (1.2 mL), and methanol/THF (20 mL, 1:1) was stirred at ambient temperature for 2 h. Sodium carbonate 20% water solution was added (pH 7), product was extracted with DCM (2×200 ml). Combined organic layers were washed with brine, dried over anh. sodium sulfate, and concentrated under reduced pressure. The residue was subjected to a silica gel flash chromatography eluting with a mixture of MeOH (0→2%) and DCM to afford 80 mg (86%) of the title compound. $^1$H NMR (400

MHZ, DMSO-$d_6$), δ:9.51-9.10 (m, 1H), 8.10-7.33 (m, 3H), 7.33-6.65 (m, 10H), 6.64-6.29 (m, 3H), 5.60-4.50 (m, 4H), 4.36-3.85 (m, 2H), 3.80-3.40 (m, 8H), 3.10 (s, 2H), 3.00-2.61 (m, 1H), 2.45-2.21 (m, 3H), 2.23-1.74 (m, 6H). LCMS (ESI+) m/z 724 $[M+H]^+$.

Example 26. N-(4-Hydroxyphenyl)-N-(3-methoxy-2-methylbenzyl)-1,2-dimethyl-5-(5-(methylsulfonyl)-2-{[(3S)-3-(morpholin-4-ylmethyl)-3,4-dihydroisoquinolin-2 (1H)-yl]carbonyl}phenyl)-1H-pyrrole-3-carboxamide (49)

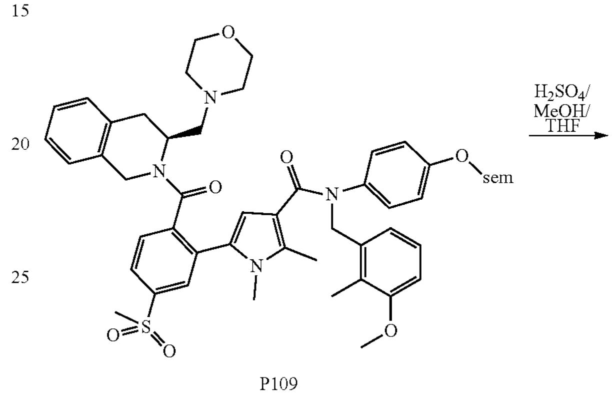

P109

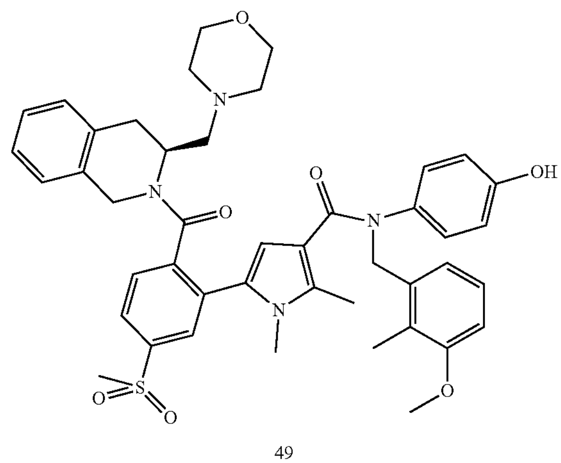

49

A stirred mixture of P109, $H_2SO_4$ (1.5 mL), and methanol/THF (2 mL, 1:1) was stirred at ambient temperature for 2 h. Sodium carbonate 20% water solution was added (pH 7), product was extracted with DCM two times. Combined organic layers were washed with brine, dried over anh. sodium sulfate, and concentrated on a rotary evaporator under reduced pressure. The residue was subjected to a silica gel flash chromatography eluting with a mixture of MeOH (0→2%) and DCM to afford 130 mg (95%) of the title compound. $^1$H NMR (400 MHZ, DMSO-$d_6$), δ:9.48-9.14 (m, 1H), 8.11-7.85 (m, 1H), 7.82-7.43 (m, 2H), 7.29-6.24 (m, 12H), 5.58-4.58 (m, 4H), 4.33-3.90 (m, 2H), 3.87-3.67 (m, 3H), 3.67-3.48 (m, 8H), 3.12 (s, 2H), 3.02-2.66 (m, 1H), 2.43-2.27 (m, 4H), 2.26-1.74 (m, 8H). LCMS(ESI+) m/z 777 $[M+H]^+$.

Example 27. N-1H-indazol-6-yl-N-(3-methoxy-2-methylbenzyl)-1,2-dimethyl-5-(2-{[(3S)-3-(morpholin-4-ylmethyl)-3,4-dihydroisoquinolin-2 (1H)-yl] carbonyl}-5-nitrophenyl)-1H-pyrrole-3-carboxamide (67)

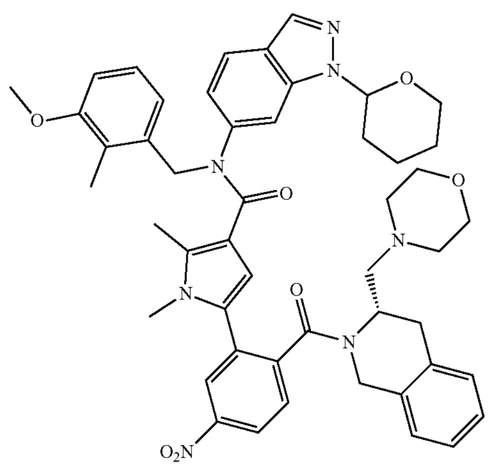

P116

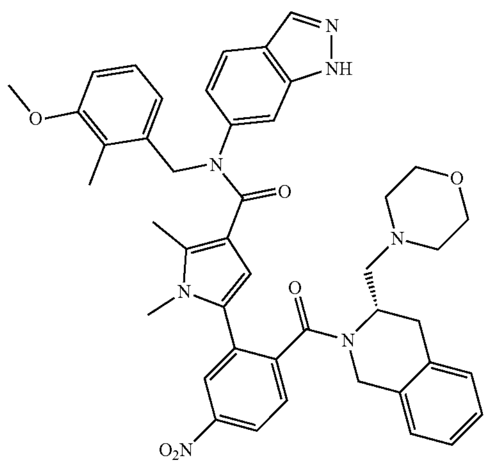

67

A stirred mixture of P116 (230 mg, 0.27 mmol) and TFA (1 mL) in DCM (2 mL) was stirred at ambient temperature for 3 h. $NaHCO_3$20% water solution was added (pH 7), product was extracted with DCM. Combined organic layers were washed with brine, dried over $Na_2SO_4$, and concentrated under reduced pressure. The residue was subjected to silica flash chromatography eluting with a mixture of EtOAc (0→20%) and DCM to afford 23 mg (11%) of the title compound. LCMS(ESI+) m/z 768 $[M+H]^+$. $^1$H NMR (400 MHZ, DMSO-$d_6$), δ:13.01-12.60 (m, 1H), 8.37-8.07 (m, 1H), 8.01-7.78 (m, 2H), 7.72-6.35 (m, 12H), 5.53-4.70 (m, 4H), 4.30-3.82 (m, 2H), 3.84-3.68 (m, 3H), 3.67-3.36 (m, 6H), 3.07 (s, 2H), 2.95-2.62 (m, 1H), 2.43-2.16 (m, 3H), 2.08-1.64 (m, 8H).

Example 28. N-1H-indazol-6-yl-N-(2-methoxybenzyl)-1,2-dimethyl-5-(2-{[(3S)-3-(morpholin-4-ylmethyl)-3,4-dihydroisoquinolin-2 (1H)-yl]carbonyl}-5-nitrophenyl)-1H-pyrrole-3-carboxamide (72)

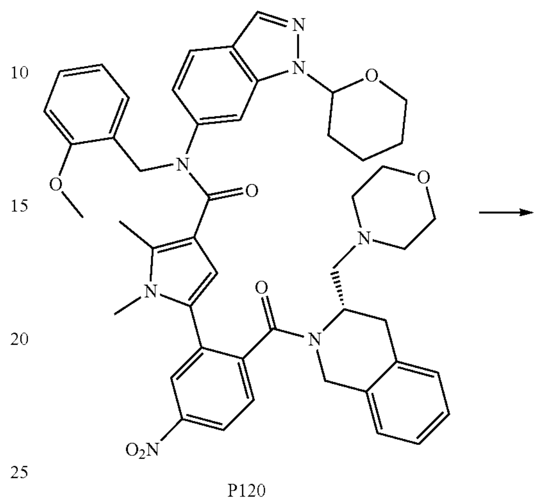

P120

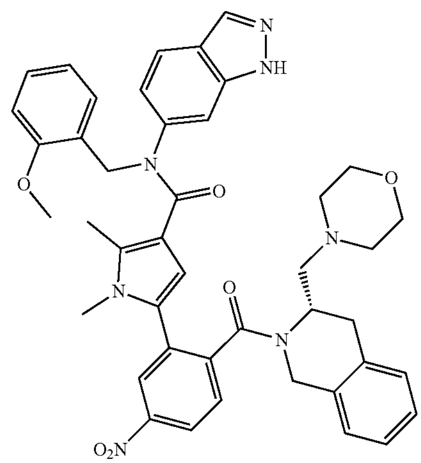

72

A stirred mixture of the crude P120 (350 mg, 0.4 mmol) and TFA (1 mL) in DCM (2 mL) was stirred at ambient temperature for 3 h. $NaHCO_3$20% water solution was added (pH 7), product was extracted with DCM. Combined organic layers were washed with brine, dried over $Na_2SO_4$, and concentrated under reduced pressure. The residue was subjected to silica flash chromatography eluting with a mixture of EtOAc (0→20%) and DCM to afford 6.6 mg (3%) of the title compound. LCMS(ESI+) m/z 754 $[M+H]^+$.

Example 29. N-1H-indazol-6-yl-N-(2-cyanobenzyl)-1,2-dimethyl-5-(2-{[(3S)-3-(morpholin-4-ylmethyl)-3,4-dihydroisoquinolin-2 (1H)-yl]carbonyl}-5-nitrophenyl)-1H-pyrrole-3-carboxamide (66)

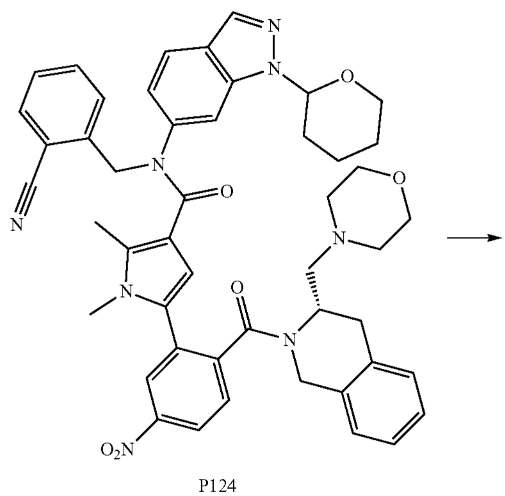

P124

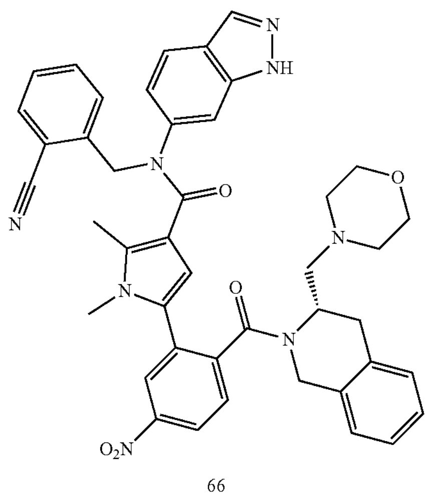

66

A stirred mixture of the crude P124 (350 mg, 0.4 mmol) and TFA (1 mL) in DCM (2 mL) was stirred at ambient temperature for 3 h. $NaHCO_3$20% water solution was added (pH 7), product was extracted with DCM. Combined organic layers were washed with brine, dried over $Na_2SO_4$, and concentrated on rotary evaporator under reduced pressure. The residue was subjected to silica flash chromatography eluting with a mixture of EtOAc (0→20%) and DCM to afford 69 mg (23%) of the title compound. LCMS(ESI+) m/z 749 $[M+H]^+$. $^1H$ NMR (400 MHZ, DMSO-$d_6$), δ:13.11-12.82 (m, 1H), 8.37-8.08 (m, 1H), 8.07-7.84 (m, 2H), 7.83-7.33 (m, 6H), 7.28-6.42 (m, 7H), 5.67-4.74 (m, 4H), 4.33-3.80 (m, 2H), 3.74-3.46 (m, 6H), 3.08 (s, 2H), 2.98-2.58 (m, 1H), 2.39-2.22 (m, 2H), 2.21-1.66 (m, 6H).

Example 30. 5-(5-Chloro-4-fluoro-2-{[(3S)-3-(morpholin-4-ylmethyl)-3,4-dihydroisoquinolin-2 (1H)-yl]carbonyl}phenyl)-N-(4-cyanophenyl)-N-(3-methoxy-2-methylbenzyl)-1,2-dimethyl-1H-pyrrole-3-carboxamide (73)

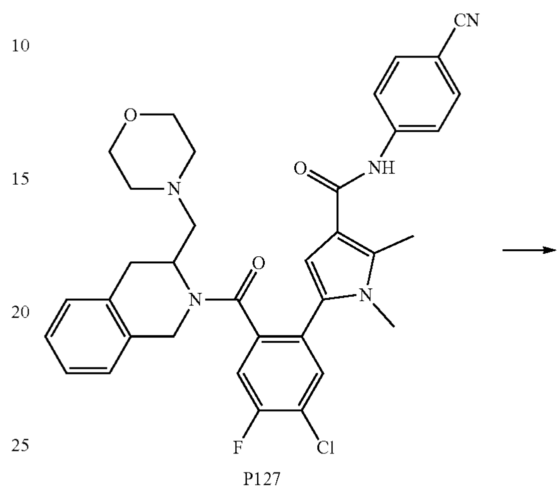

P127

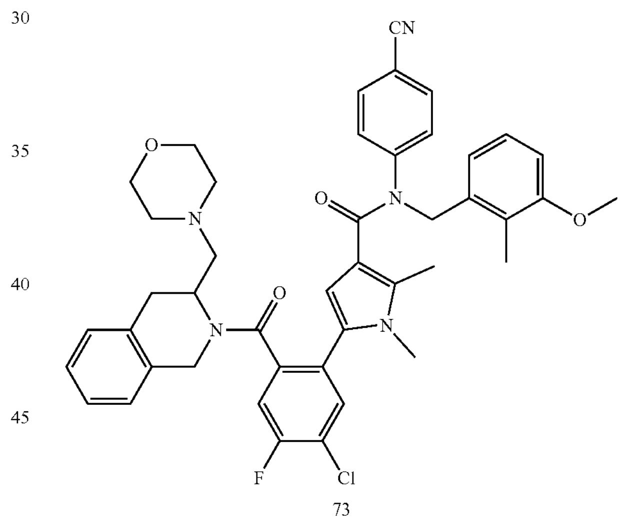

73

A mixture of P127 (90 mg, 0.14 mmol), tert-BuOK (64 mg 0.58 mmol), and tert-BuOH (5 mL) was stirred at 50° C. for 30 min, then 3-methoxy-2-methylbenzyl methanesulfonate (66 mg, 0.29 mmol) was added. The reaction mixture was stirred at 60° C. for 1 h and then partitioned between EtOAc and water. The organic layer was separated, washed with brine, dried over anh. sodium sulfate, filtered, and concentrated under reduced pressure. The residue was subjected to a silica gel flash chromatography eluting with a mixture of EtOAc (0→100%) and DCM to afford 20 mg (20%) of the title compound. $^1H$ NMR (400 MHZ, DMSO-$d_6$), δ:7.82-7.33 (m, 5H), 7.27-6.52 (m, 9H), 5.91-5.48 (m, 1H), 5.33-4.74 (m, 4H), 4.35-3.92 (m, 2H), 3.86-3.67 (m, 3H), 3.67-3.40 (m, 4H), 3.16-2.81 (m, 2H), 2.69 (s, 3H), 2.42-2.14 (m, 3H), 2.09-1.76 (m, 7H). LCMS (ESI) m/z calcd for $C_{44}H_{43}ClFN_5O_4$ 760.32; found, 760.6 $[M+H]^+$.

Example 31. N-(4-chlorophenyl)-5-(4-cyano-5-methoxy-2-{[(3S)-3-(morpholin-4-ylmethyl)-3,4-dihydroisoquinolin-2 (1H)-yl]carbonyl}phenyl)-N-(3-methoxy-2-methylbenzyl)-1,2-dimethyl-1H-pyrrole-3-carboxamide (60)

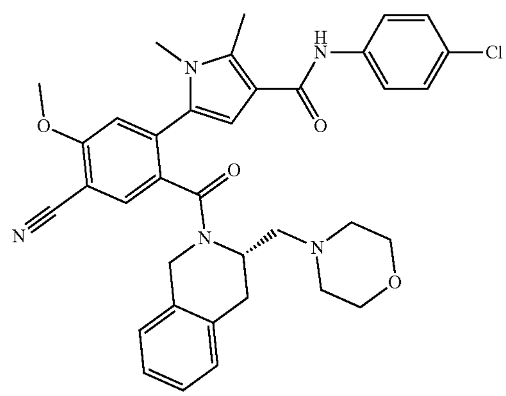

P131

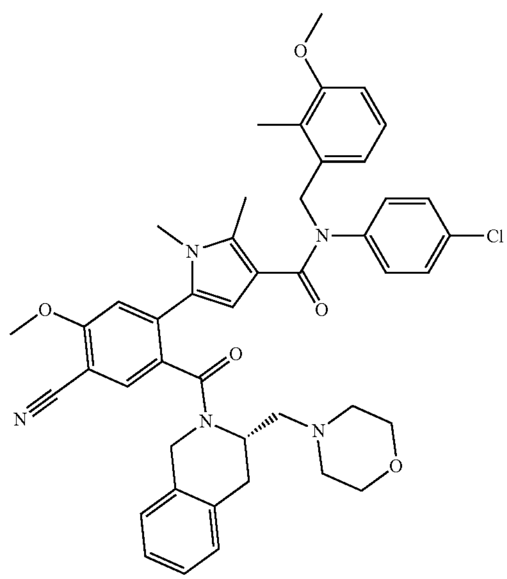

60

A mixture of P131 (95 mg, 0.149 mmol), tert-BuOK (67 mg 0.57 mmol), and tert-BuOH (9 mL) was stirred at 50° C. for 30 min, then 3-methoxy-2-methylbenzyl methanesulfonate (69 mg, 0.29 mmol) was added. The reaction mixture was stirred at 60° C. for 1 h and then partitioned between EtOAc and water. The organic layer was separated, washed with brine, dried over $Na_2SO_4$, filtered, and concentrated under reduced pressure. The residue was subjected to silica flash chromatography eluting with a mixture of EtOAc (0→100%) and DCM to afford 79 mg (68%). $^1H$ NMR (400 MHz, DMSO-$d_6$), δ:7.84-7.53 (m, 1H), 7.26-6.75 (m, 11H), 6.72-6.51 (m, 2H), 5.86-5.26 (m, 1H), 5.14-4.69 (m, 4H), 3.94 (s, 5H), 3.84-3.69 (m, 3H), 3.67-3.37 (m, 6H), 3.19 (s, 2H), 3.04-2.58 (m, 2H), 2.44-2.22 (m, 3H), 2.23-1.68 (m, 6H). LCMS(ESI+) m/z 773 $[M+H]^+$.

Example 32. N-(4-Chlorophenyl)-N-(2-cyanobenzyl)-5-(4-cyano-5-methoxy-2-{[(3S)-3-(morpholin-4-ylmethyl)-3,4-dihydroisoquinolin-2 (1H)-yl] carbonyl}phenyl)-1,2-dimethyl-1H-pyrrole-3-carboxamide (59)

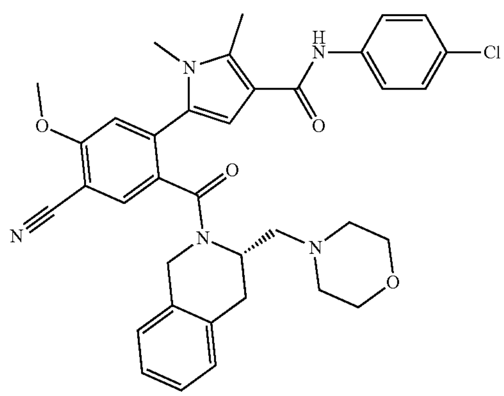

P131

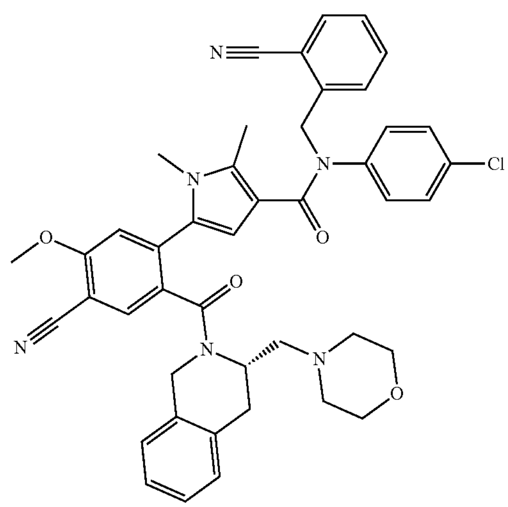

59

A mixture of P131 (190 mg, 0.298 mmol), tert-BuOK (134 mg 1.14 mmol), and tert-BuOH (18 mL) was stirred at 50° C. for 30 min, then 2-(bromomethyl)benzonitrile (117 mg, 0.598 mmol) was added. The reaction mixture was stirred at 60° C. for 1 h and then partitioned between EtOAc and water. The organic layer was separated, washed with brine, dried over $Na_2SO_4$, filtered, and concentrated under reduced pressure. The residue was subjected to silica flash chromatography eluting with a mixture of EtOAc (0→100%) and DCM to afford 63 mg (28%). $^1H$ NMR (400 MHz, DMSO-$d_6$), δ:7.98-7.34 (m, 4H), 7.29-6.69 (m, 10H), 5.44-4.69 (m, 4H), 4.40-3.84 (m, 6H), 3.76-3.39 (m, 6H), 3.19 (s, 2H), 2.99-2.65 (m, 1H), 2.46-2.26 (m, 3H), 2.24-1.81 (m, 5H). LCMS(ESI+) m/z 754 $[M+H]^+$.

Example 33. 5-(5-Cyano-2-[3-(morpholinomethyl)-3,4-dihydro-2 (1H)-isoquinolinyl]carbonylphenyl)-$N^3$-(4-hydroxyphenyl)-$N^3$-(3-methoxy-2-methylbenzyl)-1,2-dimethyl-1H-pyrrole-3-carboxamide (57)

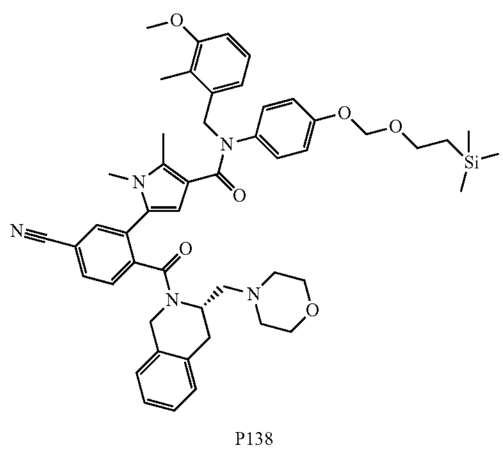

P138

-continued

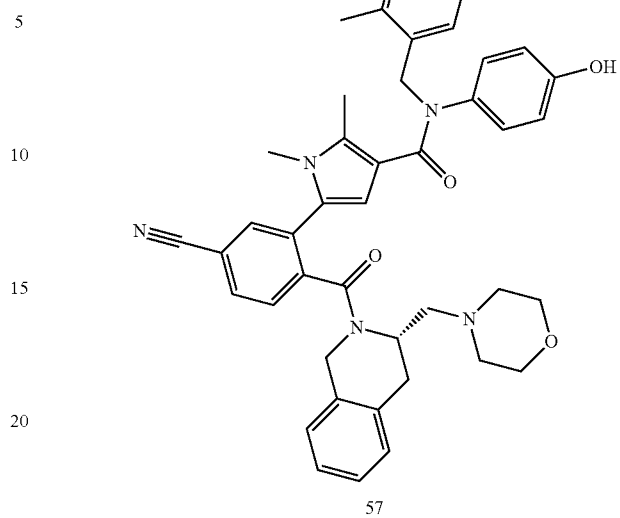

57

A stirred mixture of the P139 (50 mg) and $H_2SO_4$ (0.1 mL) in methanol/THF (2 mL, 1:1) was stirred at ambient temperature for 1 h. $NaHCO_3$20% water solution was added (pH 7), product was extracted with DCM (2×6 ml). Combined organic layers were washed with brine, dried over $Na_2SO_4$, and concentrated under reduced pressure. The residue was subjected to silica flash chromatography eluting with a mixture of MeOH (0→2%) and DCM to afford 20 (50%) mg of compound 57. LCMS(ESI+) m/z 724 $[M+H]^+$. $^1H$ NMR (400 MHZ, DMSO-$d_6$), δ: 9.52-9.12 (m, 1H), 8.05-7.30 (m, 3H), 7.30-6.41 (m, 9H), 6.41-6.24 (m, 3H), 5.33-4.55 (m, 4H), 4.36-3.87 (m, 2H), 3.87-3.66 (m, 3H), 3.66-3.38 (m, 6H), 3.10 (s, 2H), 3.02-2.61 (m, 1H), 2.45-2.12 (m, 3H), 2.09-1.78 (m, 8H).

Example 34. 5-(5-(Aminocarbonyl)-2-[3-(morpholinomethyl)-3,4-dihydro-2 (1H)-isoquinolinyl]carbonylphenyl)-$N^3$-(4-hydroxyphenyl)-$N^3$-(3-methoxy-2-methylbenzyl)-1,2-dimethyl-1H-pyrrole-3-carboxamide (64)

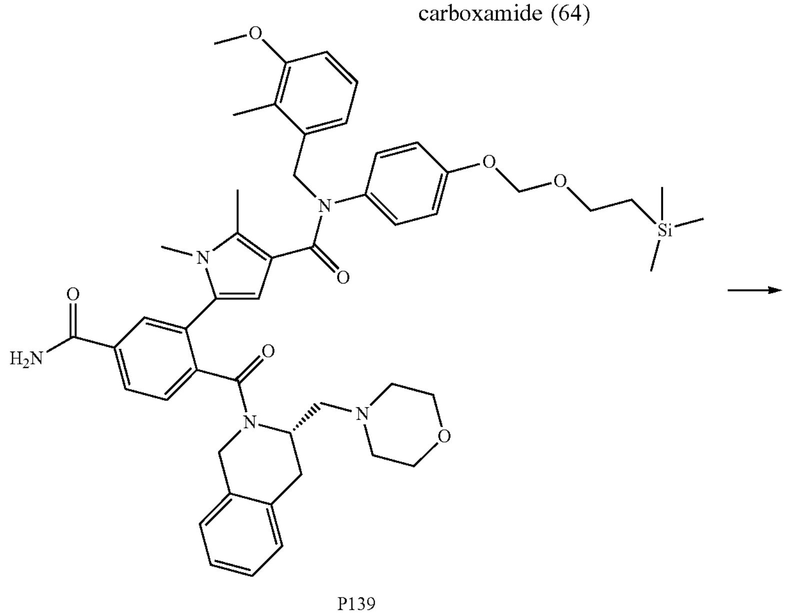

P139

-continued

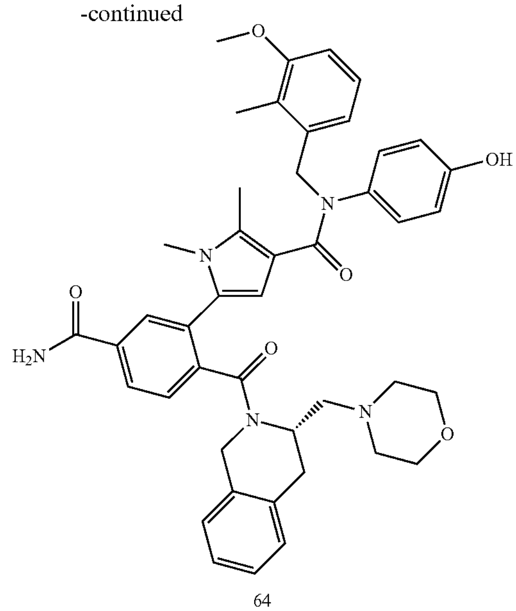

64

A stirred mixture of the compound P139 (70 mg) and $H_2SO_4$ (0.1 mL) in methanol/THF (2 mL, 1:1) was stirred at ambient temperature for 1 h. $NaHCO_3$20% water solution was added (pH 7), product was extracted with DCM (2×6 mL). Combined organic layers were washed with brine, dried over $Na_2SO_4$, and concentrated under reduced pressure. The residue was subjected to silica flash chromatography eluting with a mixture of MeOH (0→2%) and DCM to afford 40 mg (67%) of compound 64. LCMS(ESI+) m/z 742 $[M+H]^+$. $^1H$ NMR (400 MHZ, DMSO-$d_6$), δ: 9.45-9.14 (m, 1H), 8.17-7.34 (m, 6H), 7.26-6.74 (m, 7H), 6.73-6.40 (m, 2H), 6.31 (s, 2H), 5.55-4.53 (m, 4H), 4.33-3.89 (m, 2H), 3.87-3.68 (m, 3H), 3.68-3.36 (m, 4H), 3.09 (s, 2H), 3.05-2.65 (m, 1H), 2.47-2.21 (m, 4H), 2.20-1.72 (m, 9H).

Example 35. 5-[5-Chloro-2-[(3S)-3-(morpholinomethyl)-3,4-dihydro-1H-isoquinoline-2-carbonyl]phenyl]-N-(4-cyanophenyl)-N-[(3-methoxy-2-methyl-phenyl)methyl]-1,2-dimethyl-pyrrole-3-carboxamide (33)

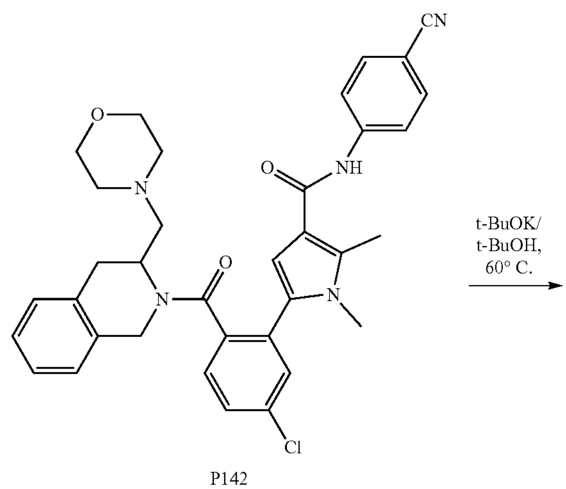

P142

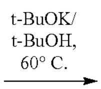

-continued

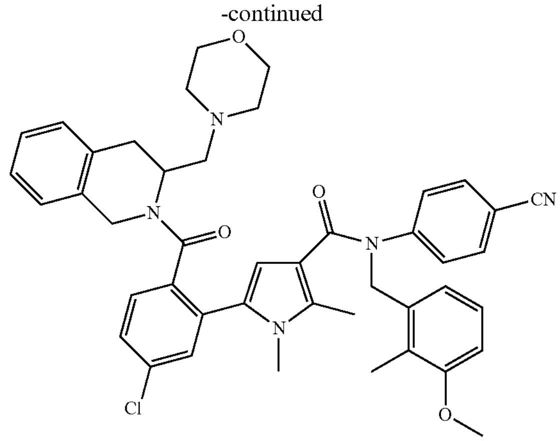

33

A mixture of P142 (170 mg, 0.28 mmol), tert-BuOK (125 mg, 1.1 mmol), and tert-BuOH (5 mL) was stirred at 50° C. for 30 min, then 3-methoxy-2-methylbenzyl methanesulfonate (128 mg, 0.56 mmol) was added. The reaction mixture was stirred at 60° C. for 1 h and then partitioned between EtOAc and water. The organic layer was separated, washed with brine, dried over anh. sodium sulfate, filtered, and was concentrated under reduced pressure. The residue was subjected to a silica gel flash chromatography eluting with a mixture of EtOAc (0→100%) and DCM to afford 17 mg (10%) of the title compound. $^1H$ NMR (400 MHZ, DMSO-$d_6$), δ:7.83-6.47 (m, 15H), 5.87-5.52 (m, 1H), 5.41-4.68 (m, 5H), 4.31-3.91 (m, 2H), 3.87-3.69 (m, 3H), 3.69-3.40 (m, 6H), 3.19-2.62 (m, 3H), 2.41-2.21 (m, 2H), 2.21-1.71 (m, 7H). LCMS(ESI) m/z calcd for $C_{44}H_{44}ClN_5O_4$ 742.32; found, 742.3 $[M+H]^+$.

Example 36. N-(2-cyanobenzyl)-N-(4-hydroxyphenyl)-1,2-dimethyl-5-(2-{[(3S)-3-(morpholin-4-ylmethyl)-3,4-dihydroisoquinolin-2 (1H)-yl]carbonyl}-5-nitrophenyl)-1H-pyrrole-3-carboxamide (62)

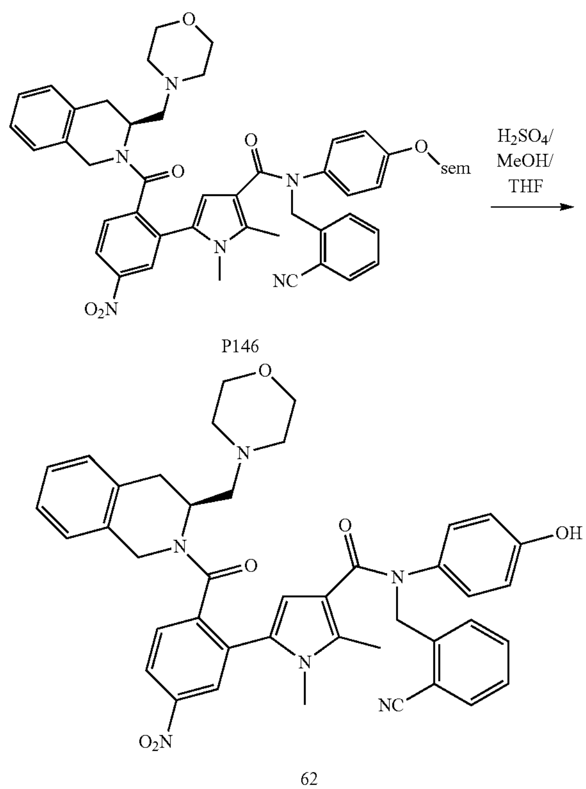

P146

62

A stirred mixture of P146, $H_2SO_4$ (1.4 mL), and methanol/THF (20 mL, 1:1) was stirred at ambient temperature for 2 h. Sodium carbonate 20% water solution was added (pH 7), product was extracted with DCM (2×200 ml). Combined organic layers were washed with brine, dried over anh. sodium sulfate, and concentrated on a rotary evaporator under reduced pressure. The residue was subjected to a silica gel flash chromatography eluting with a mixture of MeOH (0→2%) and DCM to afford 64 mg (63%) of the title compound. $^1$H NMR (400 MHZ, DMSO-$d_6$), δ:9.61-9.28 (m, 1H), 8.48-7.91 (m, 2H), 7.86-7.29 (m, 6H), 7.29-6.81 (m, 5H), 6.62-6.28 (m, 3H), 5.37-4.77 (m, 4H), 4.31-3.88 (m, 2H), 3.74-3.34 (m, 7H), 3.13 (s, 2H), 2.96-2.63 (m, 1H), 2.43-2.17 (m, 3H), 2.17-1.72 (m, 4H). LCMS(ESI+) m/z 725 $[M+H]^+$.

Example 37. N-(4-hydroxyphenyl)-N-(3-methoxy-2-methylbenzyl)-1,2-dimethyl-5-(2-{[(3S)-3-(morpholin-4-ylmethyl)-3,4-dihydroisoquinolin-2 (1H)-yl] carbonyl}-5-nitrophenyl)-1H-pyrrole-3-carboxamide (61)

A stirred mixture of P147, $H_2SO_4$ (1.4 mL), and methanol/THF (20 mL, 1:1) was stirred at ambient temperature for 2 h. Sodium carbonate 20% water solution was added (pH 7), product was extracted with DCM (2×200 ml). Combined organic layers were washed with brine, dried over anh. sodium sulfate, and concentrated under reduced pressure. The residue was subjected to a silica gel flash chromatography eluting with a mixture of MeOH (0→2%) and DCM to afford 96 mg (54%) of the title compound. $^1$H NMR (400 MHZ, DMSO), &: 9.52-9.09 (m, 1H), 8.38-7.40 (m, Hz, 1H), 7.25-6.73 (m, 16H), 6.67-6.46 (m, 5H), 6.33 (s, 5H), 5.54-4.59 (m, 9H), 4.33-4.10 (m, 4H), 3.96 (s, 3H), 3.77 (s, 3H), 3.67-3.49 (m, 7H), 3.13 (s, 3H), 2.96-2.63 (m, 1H), 2.43-2.17 (m, 3H), 2.17-1.72 (m, 4H). LCMS(ESI+) m/z 744 $[M+H]^+$.

Example 38. 5-(5-(acetylamino)-2-{[(3S)-3-(morpholin-4-ylmethyl)-3,4-dihydroisoquinolin-2 (1H)-yl]carbonyl}phenyl)-N-(4-hydroxyphenyl)-N-(3-methoxy-2-methylbenzyl)-1,2-dimethyl-1H-pyrrole-3-carboxamide (48)

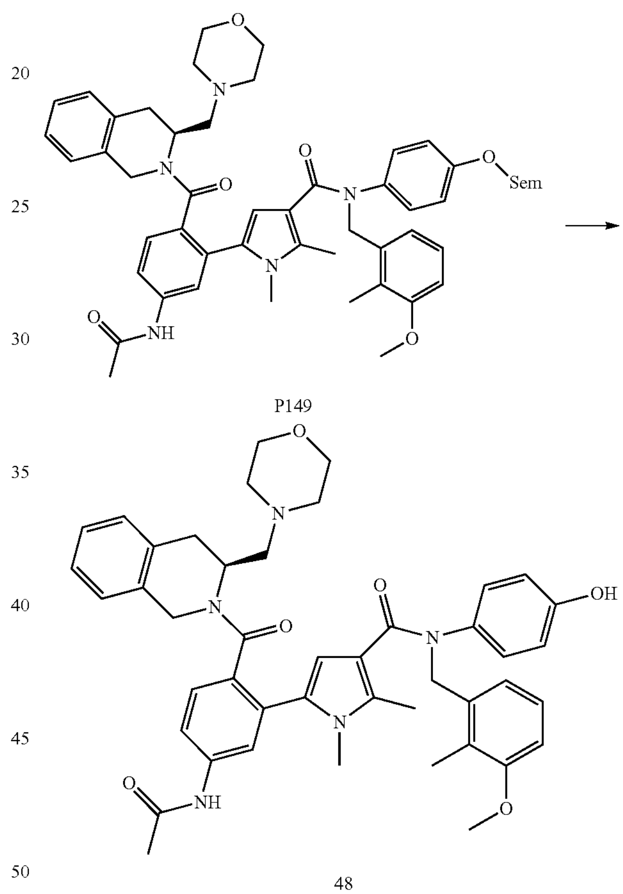

P149

48

A stirred mixture of P149, $H_2SO_4$ (1.7 mL), and methanol/THF (20 mL, 1:1) was stirred at ambient temperature for 2 h. Sodium carbonate 20% water solution was added (pH 7), product was extracted with DCM (2×200 ml). Combined organic layers were washed with brine, dried over anhydrous sodium sulfate, and concentrated under reduced pressure. The residue was subjected to a silica gel flash chromatography eluting with a mixture of MeOH (0→2%) and DCM to afford 15 mg (12%) of the title compound. $^1$H NMR (400 MHZ, DMSO-$d_6$), δ:10.09 (s, 1H), 9.44-9.06 (m, 1H), 7.66-7.31 (m, 2H), 7.25-6.44 (m, 12H), 6.39-6.14 (m, 2H), 5.42-4.52 (m, 4H), 4.34-3.94 (m, 2H), 3.76 (d, J=22.8 Hz, 3H), 3.70-3.38 (m, 6H), 3.08 (s, 2H), 2.96-2.64 (m, 1H), 2.40-2.23 (m, 2H), 2.22-1.71 (m, 11H). LCMS(ESI+) m/z 756 $[M+H]^+$.

Example 39. 5-(4,5-Difluoro-2-{[(3S)-3-(morpholin-4-ylmethyl)-3,4-dihydroisoquinolin-2 (1H)-yl]carbonyl}phenyl)-N-(4-hydroxyphenyl)-N-(3-methoxy-2-methylbenzyl)-1,2-dimethyl-1H-pyrrole-3-carboxamide (51)

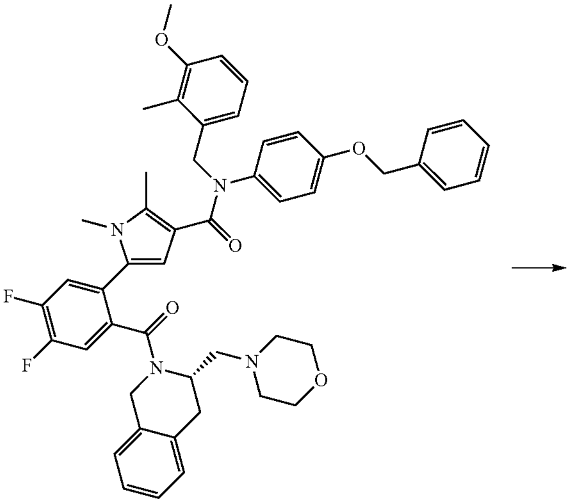

P153

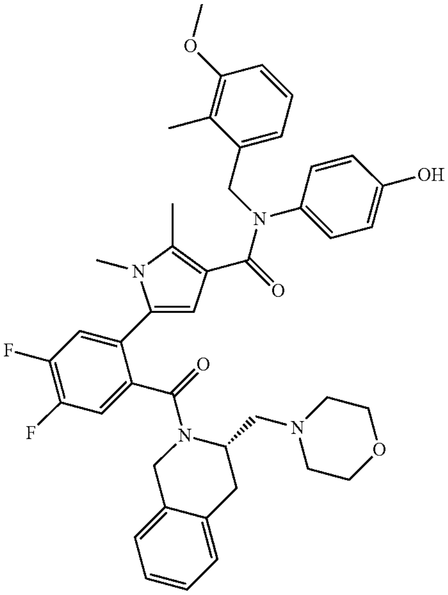

51

A stirred mixture of P153, catalyst (5 mg of 5% Pd on charcoal), and methanol (2 mL) was hydrogenated under $H_2$ atmosphere for 2 h. The catalyst was filtered off, and the filtrate was evaporated to dryness. The residue was subjected to HPLC purification to afford 25 mg (40%) of the title compound. $^1$H NMR (400 MHZ, Chloroform-d), δ: 9.48-9.16 (m, 1H), 7.61-7.24 (m, 2H), 7.24-6.72 (m, 7H), 6.71-6.44 (m, 3H), 6.41-6.21 (m, 2H), 5.45-4.60 (m, 4H), 4.32-3.95 (m, 2H), 3.91-3.70 (m, 3H), 3.68-3.42 (m, 8H), 3.08 (s, 2H), 2.96-2.65 (m, 1H), 2.45-2.22 (m, 3H), 2.22-1.75 (m, 6H). LCMS(ESI+) m/z 735 $[M+H]^+$.

Example 40. N-(2-cyanobenzyl)-5-(4,5-difluoro-2-{[(3S)-3-(morpholin-4-ylmethyl)-3,4-dihydroisoquinolin-2 (1H)-yl]carbonyl}phenyl)-N-(4-hydroxyphenyl)-1,2-dimethyl-1H-pyrrole-3-carboxamide (53)

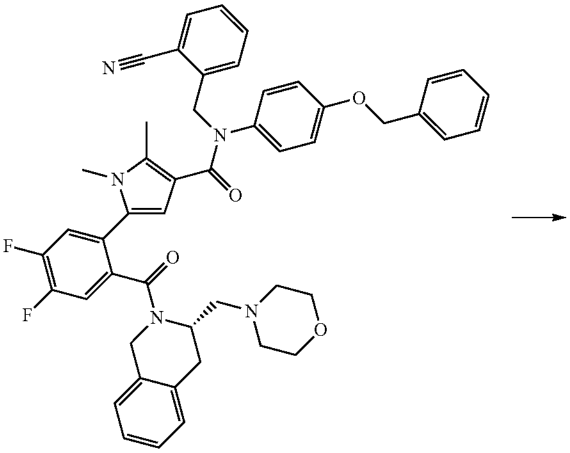

P154

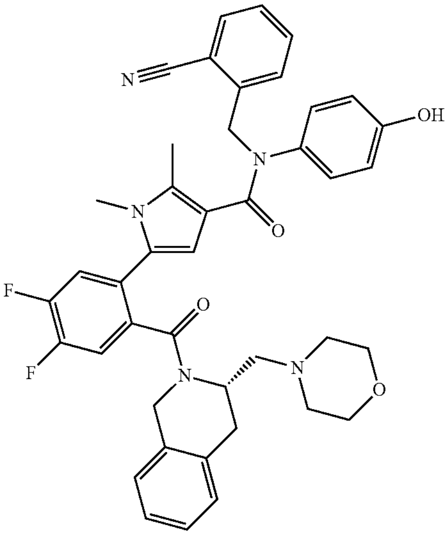

53

A stirred mixture of P154, catalyst (5 mg of 5% Pd on charcoal), and methanol (2 mL) was hydrogenated under $H_2$ atmosphere for 2 h. The catalyst was filtered off, and the filtrate was evaporated to dryness. The residue was subjected to HPLC purification to afford 62 mg (70%) of the title compound. $^1$H NMR (400 MHZ, Chloroform-d), δ: 9.58-9.27 (m, 1H), 7.97-7.26 (m, 7H), 7.22-6.66 (m, 6H), 6.62-6.31 (m, 3H), 5.50-4.69 (m, 4H), 4.35-3.94 (m, 2H), 3.73-3.42 (m, 6H), 3.09 (s, 2H), 2.84-2.57 (m, 1H), 2.41-2.26 (m, 2H), 2.20-1.75 (m, 5H). LCMS (ESI+) m/z 716 $[M+H]^+$.

Example 41. N-(4-Chlorophenyl)-5-(4-cyano-5-methoxy-2-{[(3S)-3-(morpholin-4-ylmethyl)-3,4-dihydroisoquinolin-2 (1H)-yl]carbonyl}phenyl)-N-(3-methoxy-2-methylbenzyl)-1,2-dimethyl-1H-pyrrole-3-carboxamide (50)

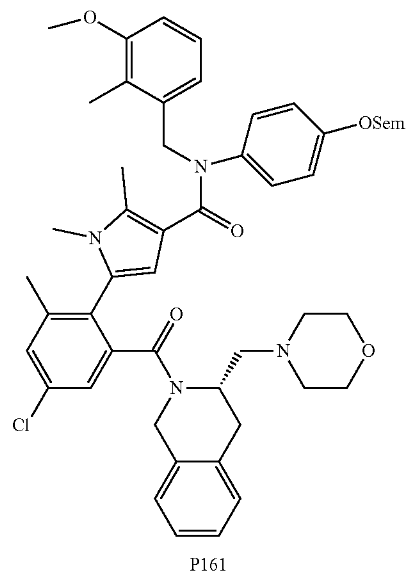

P161

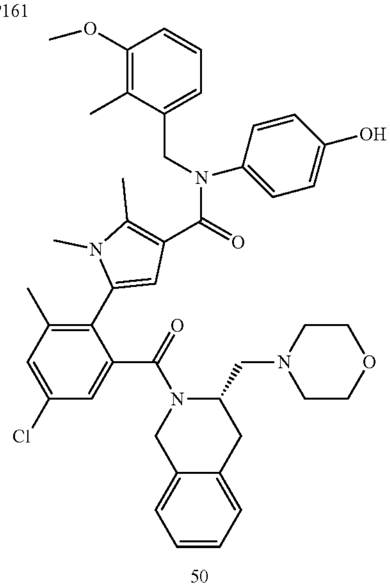

50

A stirred mixture of P161, $H_2SO_4$ (0.03 mL), and methanol/THF (10 mL, 1:1) was stirred at ambient temperature for 2 h. Sodium carbonate 20% water solution was added (pH 7), product was extracted with DCM (2×10 ml). Combined organic layers were washed with brine, dried over anhydrous sodium sulfate, and concentrated on a rotary evaporator under reduced pressure. The residue was subjected to a silica gel flash chromatography eluting with a mixture of MeOH (0→2%) and DCM to afford 4 mg (16%) of the title compound. LCMS(ESI+) m/z 748 $[M+H]^+$. Example 42. 5-(4-chloro-2-methyl-6-{[(3S)-3-(morpholin-4-ylmethyl)-3,4-dihydroisoquinolin-2 (1H)-yl]carbonyl}phenyl)-N-(4-hydroxyphenyl)-N-(2-methoxybenzyl)-1,2-dimethyl-1H-pyrrole-3-carboxamide (74).

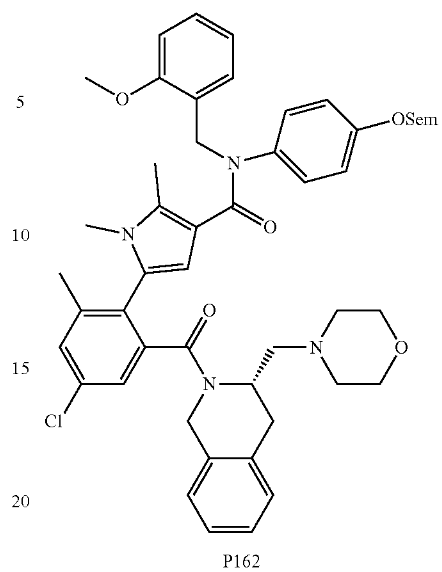

P162

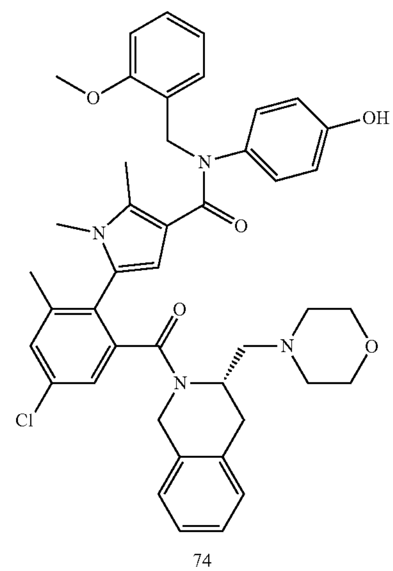

74

A stirred mixture of P162, $H_2SO_4$ (0.03 mL), and methanol/THF (10 mL, 1:1) was stirred at ambient temperature for 2 h. Sodium carbonate 20% water solution was added (pH 7), product was extracted with DCM (2×10 ml). Combined organic layers were washed with brine, dried over anh. sodium sulfate, and concentrated under reduced pressure. The residue was subjected to a silica gel flash chromatography eluting with a mixture of MeOH (0→2%) and DCM to afford 12 mg (8%) of the title compound. LCMS(ESI+) m/z 734 $[M+H]^+$.

Example 43. 5-(5-Fluoro-2-{[(3S)-3-(morpholin-4-ylmethyl)-3,4-dihydroisoquinolin-2 (1H)-yl]carbonyl}phenyl)-N-(4-hydroxyphenyl)-N-(2-methoxybenzyl)-1,2-dimethyl-1H-pyrrole-3-carboxamide (54)

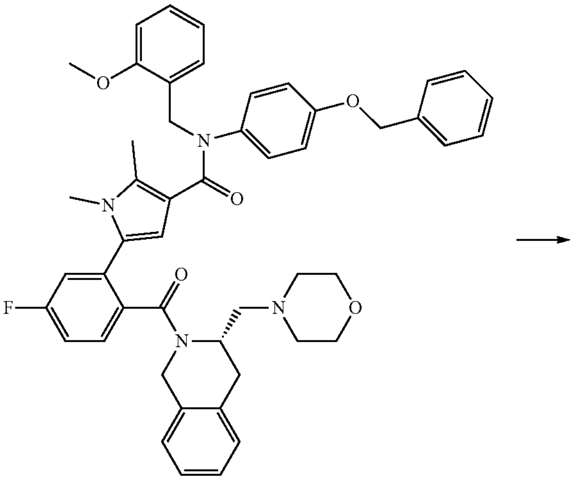

P167

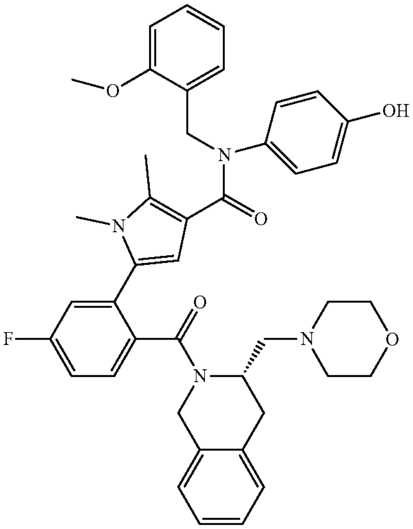

54

A stirred mixture of P167, catalyst (5 mg of 5% Pd on charcoal), and methanol (2 mL) was hydrogenated under $H_2$ atmosphere for 2 h. The catalyst was filtered off, and the filtrate was evaporated to dryness. The residue was subjected to HPLC purification to afford 3 mg (18%) of compound 54. LCMS(ESI+) m/z 703 $[M+H]^+$.

Example 44. 5-(5-Fluoro-2-{[(3S)-3-(morpholin-4-ylmethyl)-3,4-dihydroisoquinolin-2 (1H)-yl]carbonyl}phenyl)-N-(4-hydroxyphenyl)-N-(3-methoxy-2-methylbenzyl)-1,2-dimethyl-1H-pyrrole-3-carboxamide (52)

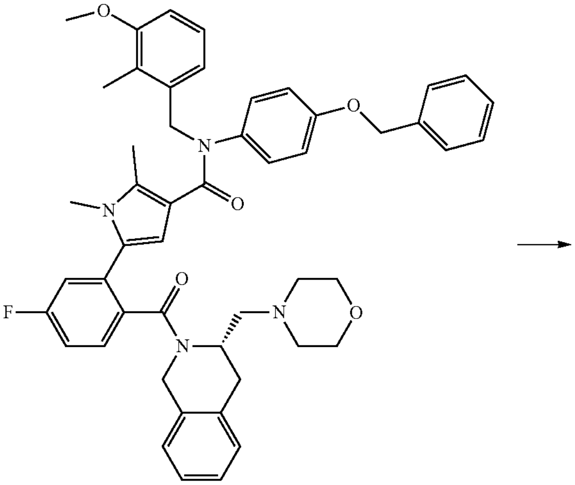

P168

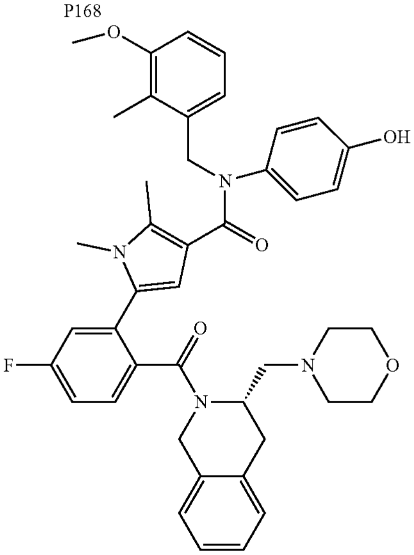

52

A stirred mixture of P168, catalyst (5 mg of 5% Pd on charcoal), and methanol (2 mL) was hydrogenated under $H_2$ atmosphere for 2 h. The catalyst was filtered off, and the filtrate was evaporated to dryness. The residue was subjected to HPLC purification to afford 13 mg (44%). LCMS(ESI+) m/z 717 $[M+H]^+$. $^1H$ NMR (400 MHZ, Chloroform-d), δ: 9.50-9.16 (m, 1H), 7.59-6.71 (m, 10H), 6.71-6.43 (m, 3H), 6.40-6.20 (m, 2H), 5.47-4.46 (m, 4H), 4.28-3.91 (m, 2H), 3.86-3.69 (m, 3H), 3.69-3.39 (m, 6H), 3.11 (s, 2H), 2.97-2.64 (m, 1H), 2.45-2.22 (m, 3H), 2.18-1.72 (m, 8H).

Using procedures described above (directly or slightly modified) and different substrates were obtained other examples of the Compound (I) presented in the Table 3. In the Table 3 presented analytical data for the obtained compounds as well.

TABLE 3
| Examples of the compound of Formula (I) | | | |
|---|---|---|---|
| Comp. # | Structure | $[MH]^+$ Calc. | $[MH]^+$ Found |
| 1 | 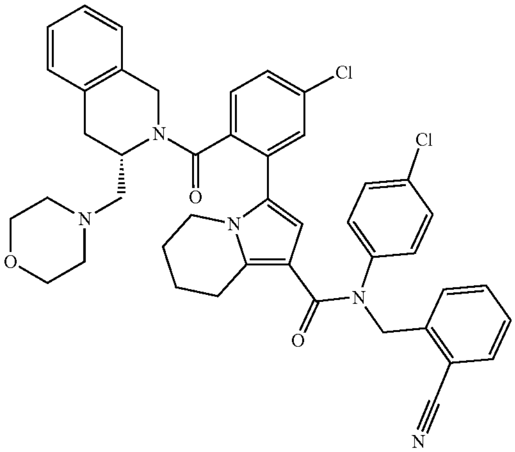 [SMILES: N#Cc1ccccc1CN(C(=O)c1cc(-c2cc(Cl)ccc2C(=O)N2Cc3ccccc3C[C@H]2CN2CCOCC2)n2c1CCCC2)c1ccc(Cl)cc1] | 758.266 | 758 |
| 2 | 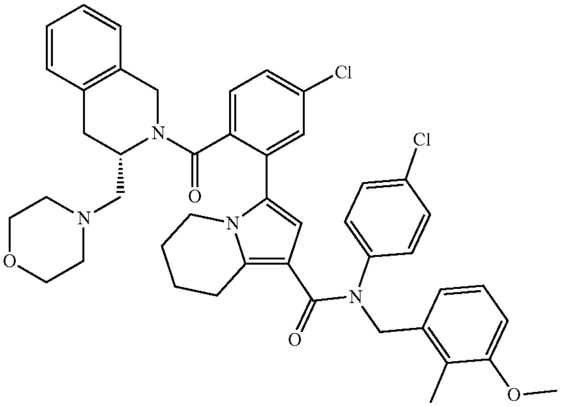 [SMILES: COc1cccc(CN(C(=O)c2cc(-c3cc(Cl)ccc3C(=O)N3Cc4ccccc4C[C@H]3CN3CCOCC3)n3c2CCCC3)c2ccc(Cl)cc2)c1C] | 777.297 | 777 |
| 3 | 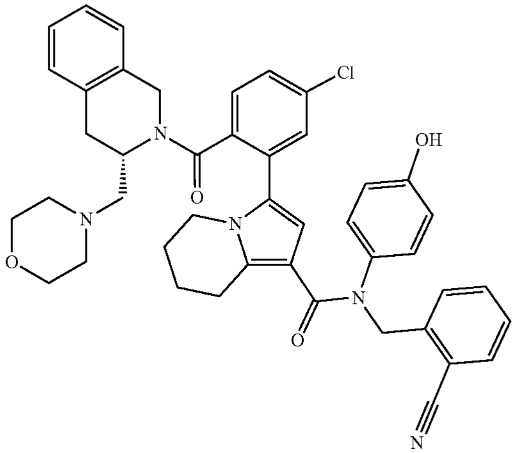 [SMILES: N#Cc1ccccc1CN(C(=O)c1cc(-c2cc(Cl)ccc2C(=O)N2Cc3ccccc3C[C@H]2CN2CCOCC2)n2c1CCCC2)c1ccc(O)cc1] | 740.3 | 740 |

TABLE 3-continued
Examples of the compound of Formula (I)
| Comp. # | Structure | [MH]+ Calc. | [MH]+ Found |
| --- | --- | --- | --- |
| 4 | 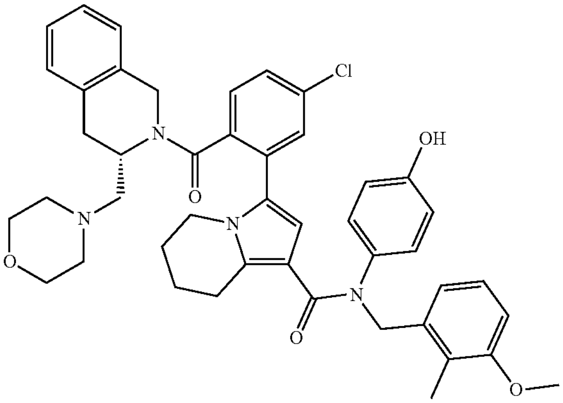 [SMILES: COc1cccc(CN(C(=O)c2cc(-c3cc(Cl)ccc3C(=O)N3Cc4ccccc4C[C@H]3CN3CCOCC3)n3c2CCCC3)c2ccc(O)cc2)c1C] | 759.331 | 759 |
| 5 | 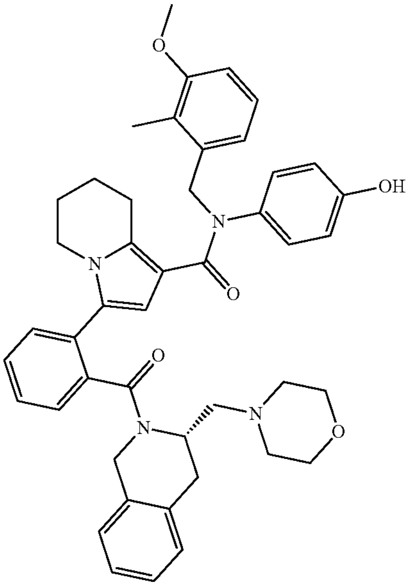 [SMILES: COc1cccc(CN(C(=O)c2cc(-c3ccccc3C(=O)N3Cc4ccccc4C[C@H]3CN3CCOCC3)n3c2CCCC3)c2ccc(O)cc2)c1C] | 725.37 | 725 |
| 6 | 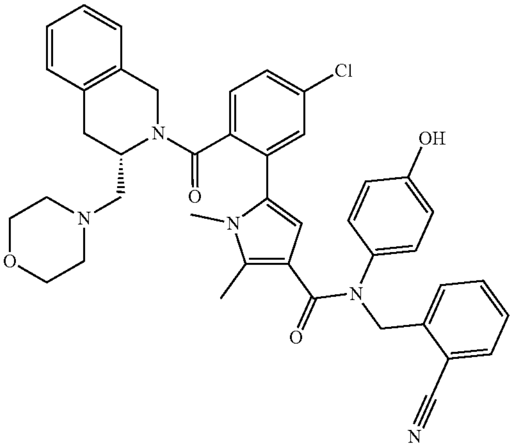 [SMILES: Cc1c(C(=O)N(Cc2ccccc2C#N)c2ccc(O)cc2)cc(-c2cc(Cl)ccc2C(=O)N2Cc3ccccc3C[C@H]2CN2CCOCC2)n1C] | 714.285 | 714 |

TABLE 3-continued
| Examples of the compound of Formula (I) | | | |
|---|---|---|---|
| Comp. # | Structure | [MH]+ Calc. | [MH]+ Found |
| 7 | 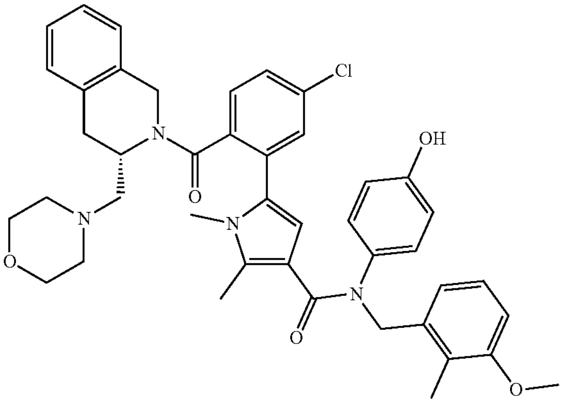 [SMILES: COc1cccc(CN(C(=O)c2cc(-c3cc(Cl)ccc3C(=O)N3Cc4ccccc4C[C@H]3CN3CCOCC3)n(C)c2C)c2ccc(O)cc2)c1C] | 733.316 | 733 |
| 8 | 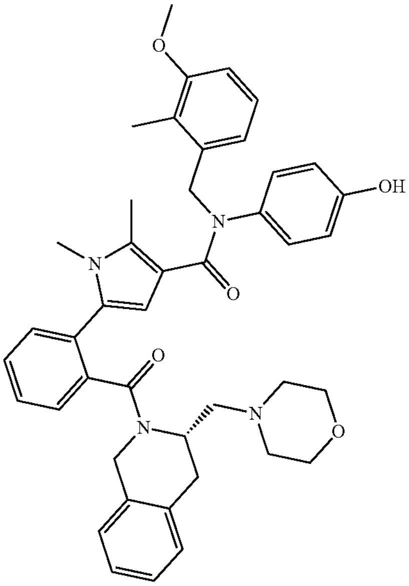 [SMILES: COc1cccc(CN(C(=O)c2cc(-c3ccccc3C(=O)N3Cc4ccccc4C[C@H]3CN3CCOCC3)n(C)c2C)c2ccc(O)cc2)c1C] | 699.355 | 699 |
| 9 | 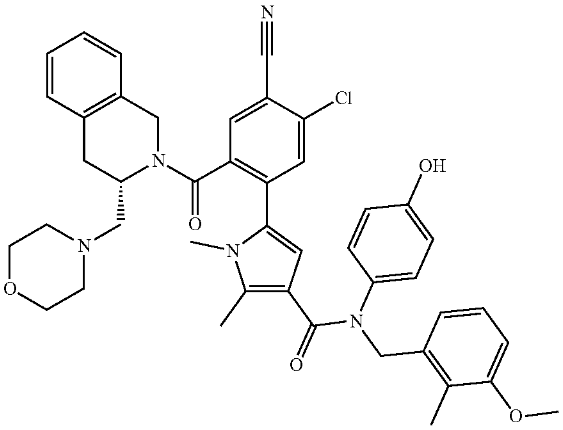 [SMILES: COc1cccc(CN(C(=O)c2cc(-c3cc(Cl)c(C#N)cc3C(=O)N3Cc4ccccc4C[C@H]3CN3CCOCC3)n(C)c2C)c2ccc(O)cc2)c1C] | 758.311 | 758 |

TABLE 3-continued
| Examples of the compound of Formula (I) | | | |
|---|---|---|---|
| Comp. # | Structure | [MH]+ Calc. | [MH]+ Found |
| 10 | 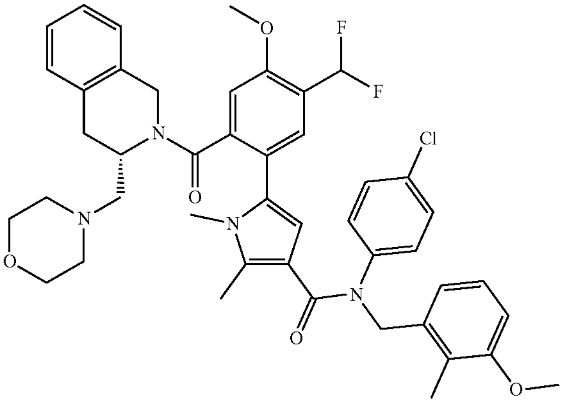 [SMILES: COc1cc(C(=O)N2Cc3ccccc3C[C@H]2CN2CCOCC2)c(-c2cc(C(=O)N(Cc3cccc(OC)c3C)c3ccc(Cl)cc3)c(C)n2C)cc1C(F)F] | 797.328 | 797 |
| 11 | 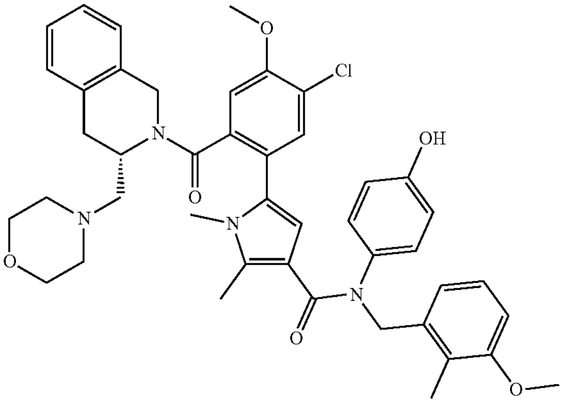 | 763.326 | 763 |
| 12 | 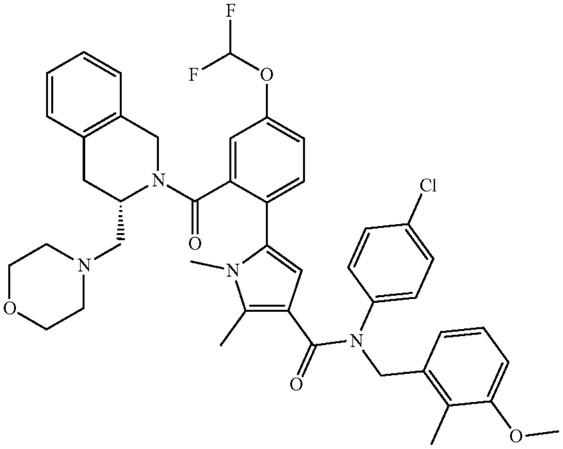 [SMILES: COc1cccc(CN(C(=O)c2cc(-c3ccc(OC(F)F)cc3C(=O)N3Cc4ccccc4C[C@H]3CN3CCOCC3)n(C)c2C)c2ccc(Cl)cc2)c1C] | 783.313 | 783 |

TABLE 3-continued
| Examples of the compound of Formula (I) | | | |
|---|---|---|---|
| Comp. # | Structure | [MH]+ Calc. | [MH]+ Found |
| 13 | 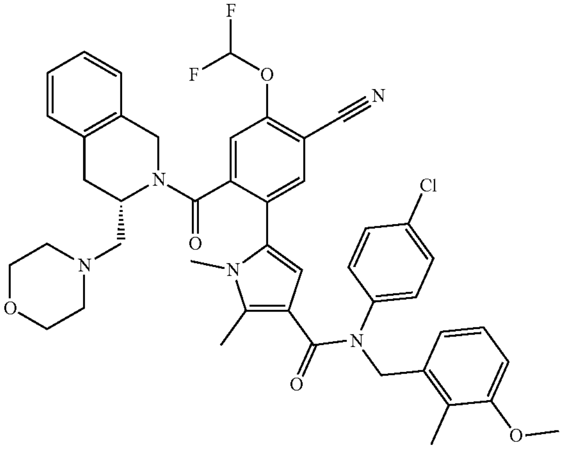 [SMILES: COc1cccc(CN(C(=O)c2cc(-c3cc(C#N)c(OC(F)F)cc3C(=O)N3Cc4ccccc4C[C@H]3CN3CCOCC3)n(C)c2C)c2ccc(Cl)cc2)c1C] | 808.308 | 808 |
| 14 | 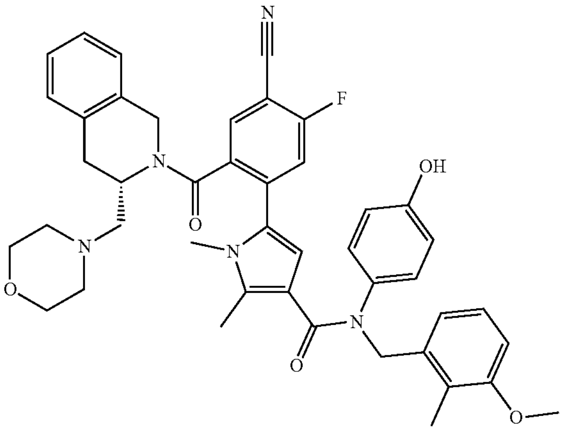 [SMILES: COc1cccc(CN(C(=O)c2cc(-c3cc(F)c(C#N)cc3C(=O)N3Cc4ccccc4C[C@H]3CN3CCOCC3)n(C)c2C)c2ccc(O)cc2)c1C] | 742.341 | 742 |
| 15 | 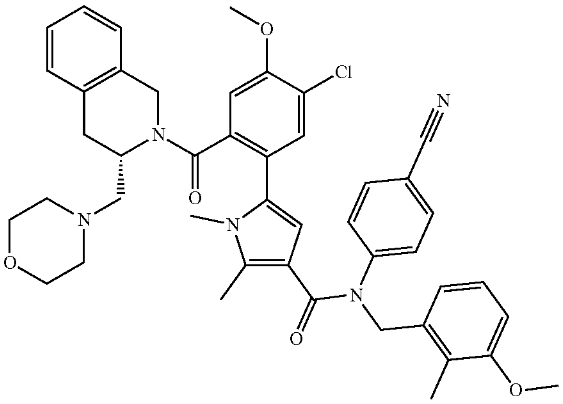 | 772.327 | 772 |

TABLE 3-continued
| Examples of the compound of Formula (I) | | | |
|---|---|---|---|
| Comp. # | Structure | [MH]+ Calc. | [MH]+ Found |
| 16 | 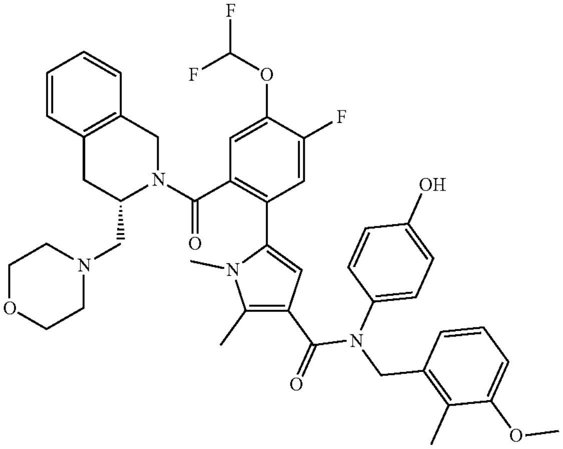 [SMILES: COc1cccc(CN(C(=O)c2cc(-c3cc(F)c(OC(F)F)cc3C(=O)N3Cc4ccccc4C[C@H]3CN3CCOCC3)n(C)c2C)c2ccc(O)cc2)c1C] | 783.337 | 783 |
| 17 | 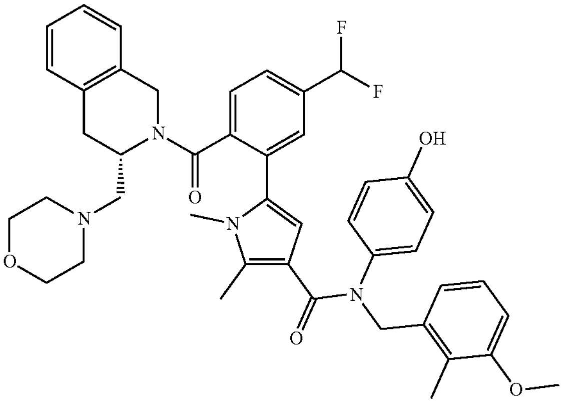 [SMILES: COc1cccc(CN(C(=O)c2cc(-c3cc(C(F)F)ccc3C(=O)N3Cc4ccccc4C[C@H]3CN3CCOCC3)n(C)c2C)c2ccc(O)cc2)c1C] | 749.352 | 749 |
| 18 | 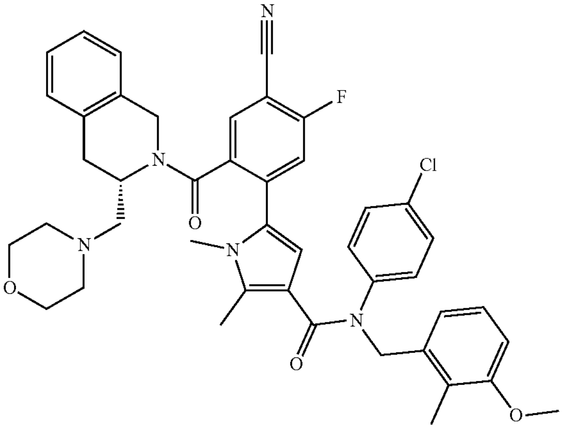 [SMILES: COc1cccc(CN(C(=O)c2cc(-c3cc(F)c(C#N)cc3C(=O)N3Cc4ccccc4C[C@H]3CN3CCOCC3)n(C)c2C)c2ccc(Cl)cc2)c1C] | 760.307 | 760 |

TABLE 3-continued
Examples of the compound of Formula (I)
| Comp. # | Structure | [MH]+ Calc. | [MH]+ Found |
| --- | --- | --- | --- |
| 19 | 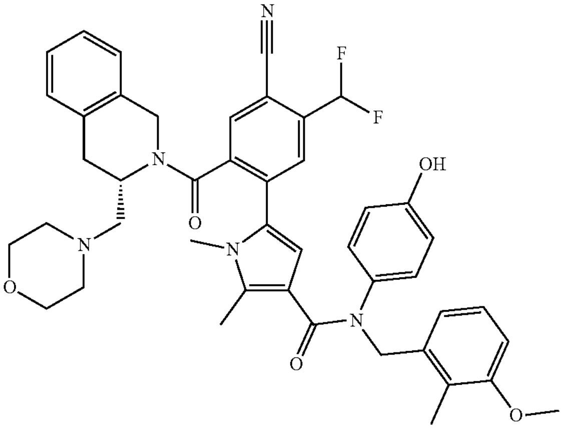 [SMILES: COc1cccc(CN(C(=O)c2cc(-c3cc(C(F)F)c(C#N)cc3C(=O)N3Cc4ccccc4C[C@H]3CN3CCOCC3)n(C)c2C)c2ccc(O)cc2)c1C] | 774.347 | 774 |
| 20 | 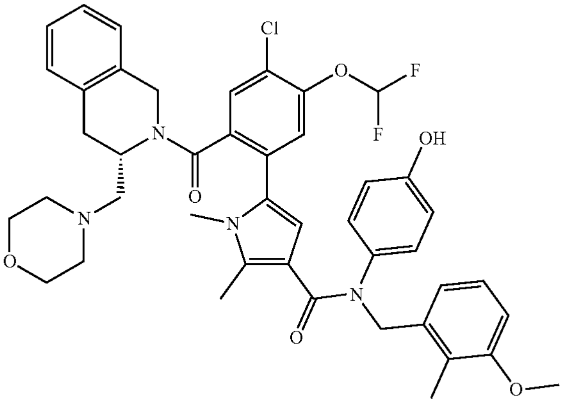 [SMILES: COc1cccc(CN(C(=O)c2cc(-c3cc(OC(F)F)c(Cl)cc3C(=O)N3Cc4ccccc4C[C@H]3CN3CCOCC3)n(C)c2C)c2ccc(O)cc2)c1C] | 799.307 | 799 |
| 21 | 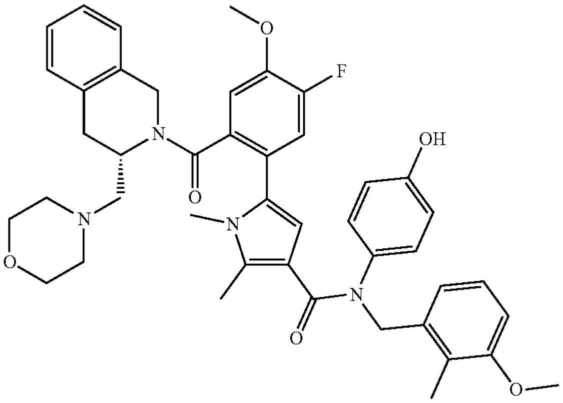 [SMILES: COc1cc(C(=O)N2Cc3ccccc3C[C@H]2CN2CCOCC2)c(-c2cc(C(=O)N(Cc3cccc(OC)c3C)c3ccc(O)cc3)c(C)n2C)cc1F] | 747.356 | 747 |

TABLE 3-continued
| Examples of the compound of Formula (I) | | | |
|---|---|---|---|
| Comp. # | Structure | [MH]+ Calc. | [MH]+ Found |
| 22 | 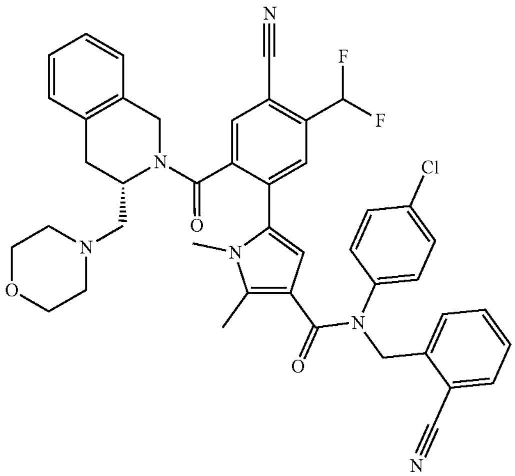 [SMILES: Cc1c(C(=O)N(Cc2ccccc2C#N)c2ccc(Cl)cc2)cc(-c2cc(C(F)F)c(C#N)cc2C(=O)N2Cc3ccccc3C[C@H]2CN2CCOCC2)n1C] | 773.282 | 773 |
| 23 | 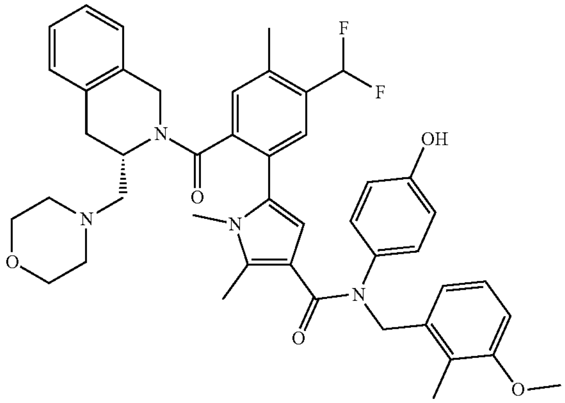 | 763.367 | 763 |
| 24 | 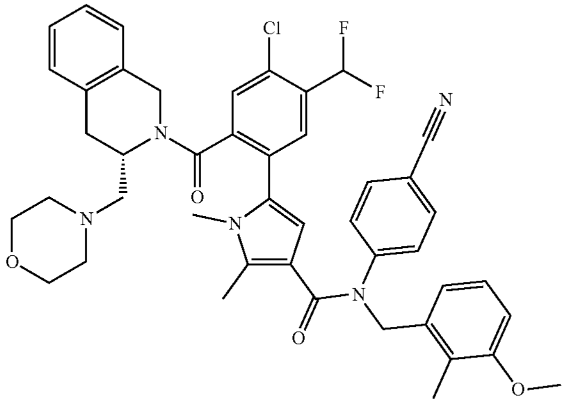 [SMILES: COc1cccc(CN(C(=O)c2cc(-c3cc(C(F)F)c(Cl)cc3C(=O)N3Cc4ccccc4C[C@H]3CN3CCOCC3)n(C)c2C)c2ccc(C#N)cc2)c1C] | 792.313 | 792 |

TABLE 3-continued
| Examples of the compound of Formula (I) | | | |
|---|---|---|---|
| Comp. # | Structure | [MH]+ Calc. | [MH]+ Found |
| 25 | 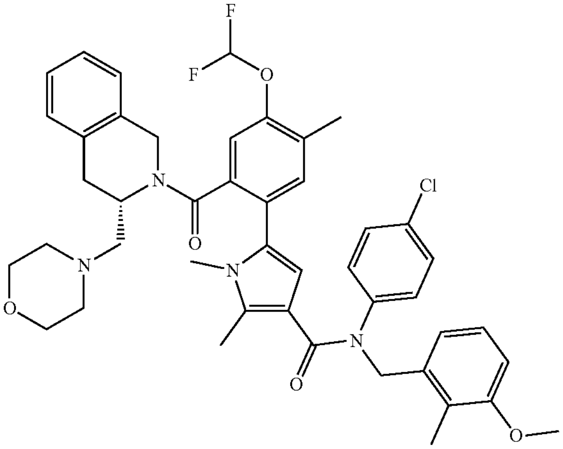 [SMILES: COc1cccc(CN(C(=O)c2cc(-c3cc(C)c(OC(F)F)cc3C(=O)N3Cc4ccccc4C[C@H]3CN3CCOCC3)n(C)c2C)c2ccc(Cl)cc2)c1C] | 797.328 | 797 |
| 26 | 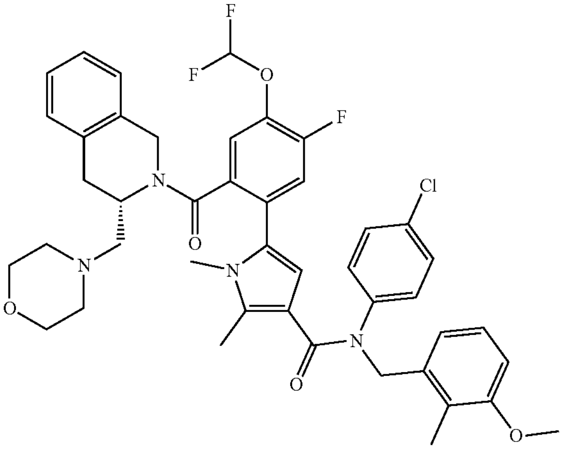 [SMILES: COc1cccc(CN(C(=O)c2cc(-c3cc(F)c(OC(F)F)cc3C(=O)N3Cc4ccccc4C[C@H]3CN3CCOCC3)n(C)c2C)c2ccc(Cl)cc2)c1C] | 801.303 | 801 |
| 27 | 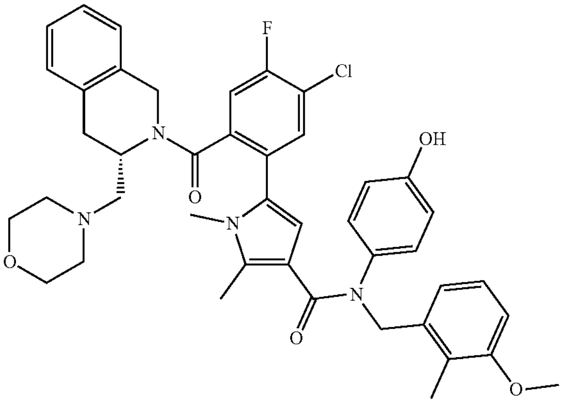 [SMILES: COc1cccc(CN(C(=O)c2cc(-c3cc(Cl)c(F)cc3C(=O)N3Cc4ccccc4C[C@H]3CN3CCOCC3)n(C)c2C)c2ccc(O)cc2)c1C] | 751.306 | 751 |

TABLE 3-continued
| Examples of the compound of Formula (I) | | | |
|---|---|---|---|
| Comp. # | Structure | [MH]+ Calc. | [MH]+ Found |
| 28 | 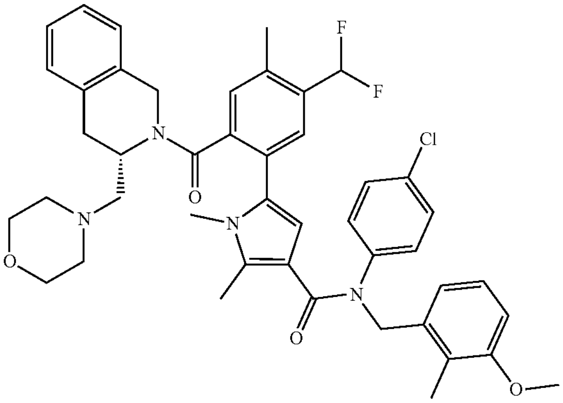 [SMILES: COc1cccc(CN(C(=O)c2cc(-c3cc(C(F)F)c(C)cc3C(=O)N3Cc4ccccc4C[C@H]3CN3CCOCC3)n(C)c2C)c2ccc(Cl)cc2)c1C] | 781.333 | 781 |
| 29 | 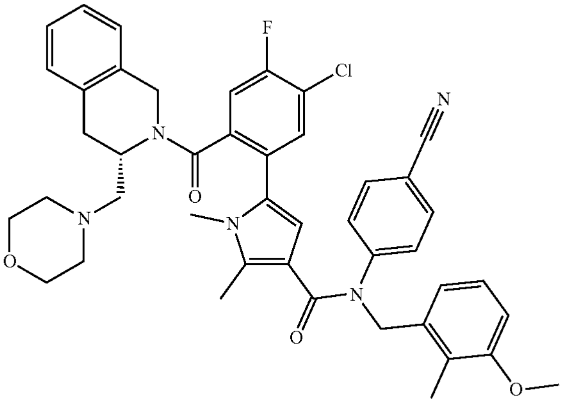 [SMILES: COc1cccc(CN(C(=O)c2cc(-c3cc(Cl)c(F)cc3C(=O)N3Cc4ccccc4C[C@H]3CN3CCOCC3)n(C)c2C)c2ccc(C#N)cc2)c1C] | 760.307 | 760 |
| 30 | 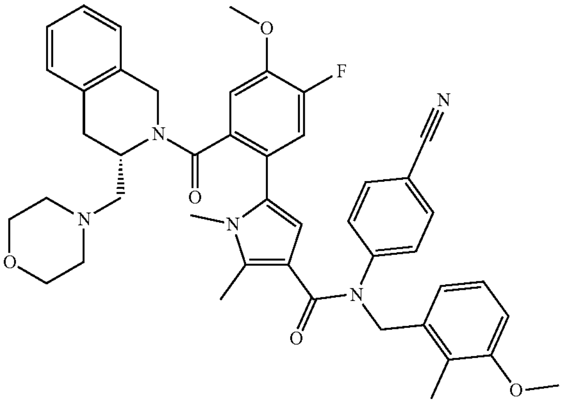 [SMILES: COc1cc(C(=O)N2Cc3ccccc3C[C@H]2CN2CCOCC2)c(-c2cc(C(=O)N(Cc3cccc(OC)c3C)c3ccc(C#N)cc3)c(C)n2C)cc1F] | 756.356 | 756 |

TABLE 3-continued
| Examples of the compound of Formula (I) | | | |
|---|---|---|---|
| Comp. # | Structure | [MH]+ Calc. | [MH]+ Found |
| 31 | 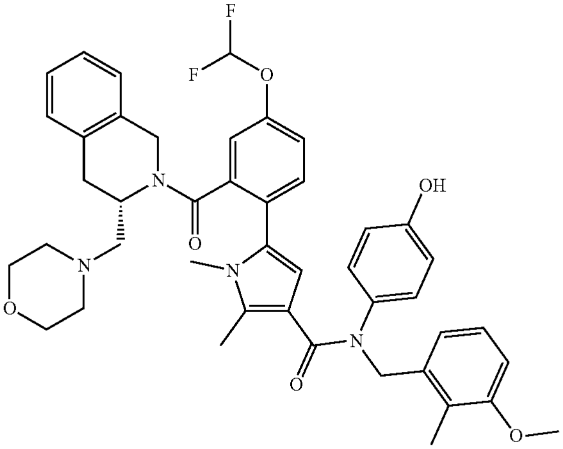 [SMILES: COc1cccc(CN(C(=O)c2cc(-c3ccc(OC(F)F)cc3C(=O)N3Cc4ccccc4C[C@H]3CN3CCOCC3)n(C)c2C)c2ccc(O)cc2)c1C] | 765.346 | 765 |
| 32 | 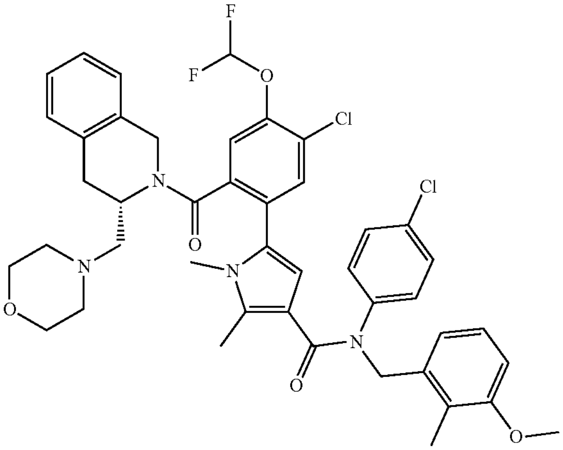 [SMILES: COc1cccc(CN(C(=O)c2cc(-c3cc(Cl)c(OC(F)F)cc3C(=O)N3Cc4ccccc4C[C@H]3CN3CCOCC3)n(C)c2C)c2ccc(Cl)cc2)c1C] | 817.274 | 817 |
| 33 | 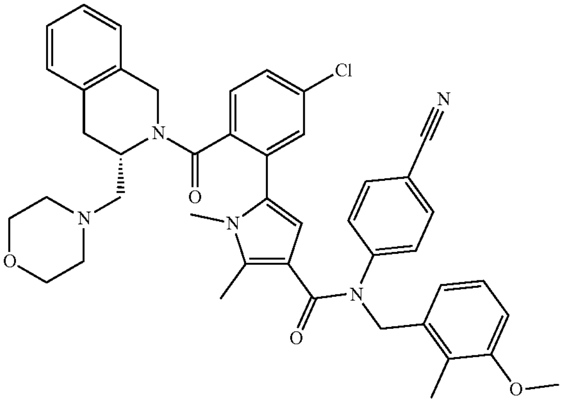 [SMILES: COc1cccc(CN(C(=O)c2cc(-c3cc(Cl)ccc3C(=O)N3Cc4ccccc4C[C@H]3CN3CCOCC3)n(C)c2C)c2ccc(C#N)cc2)c1C] | 742.316 | 742 |

TABLE 3-continued
| Examples of the compound of Formula (I) | | | |
|---|---|---|---|
| Comp. # | Structure | [MH]+ Calc. | [MH]+ Found |
| 34 | 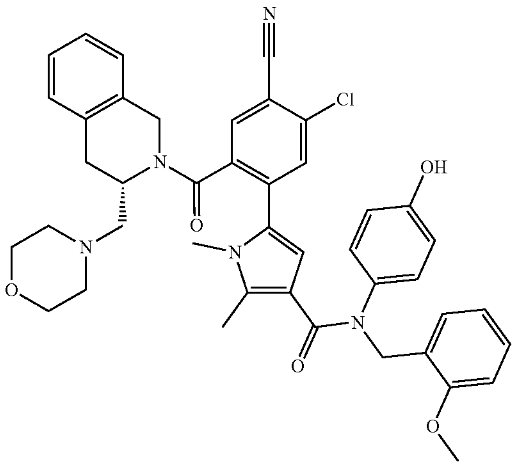 [SMILES: COc1ccccc1CN(C(=O)c1cc(-c2cc(Cl)c(C#N)cc2C(=O)N2Cc3ccccc3C[C@H]2CN2CCOCC2)n(C)c1C)c1ccc(O)cc1] | 744.295 | 744 |
| 35 | 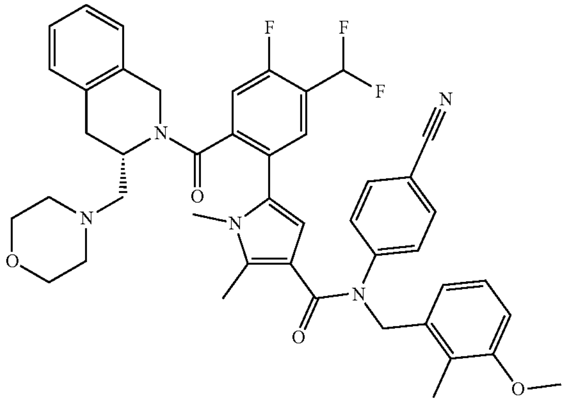 [SMILES: COc1cccc(CN(C(=O)c2cc(-c3cc(C(F)F)c(F)cc3C(=O)N3Cc4ccccc4C[C@H]3CN3CCOCC3)n(C)c2C)c2ccc(C#N)cc2)c1C] | 776.342 | 776 |
| 36 | 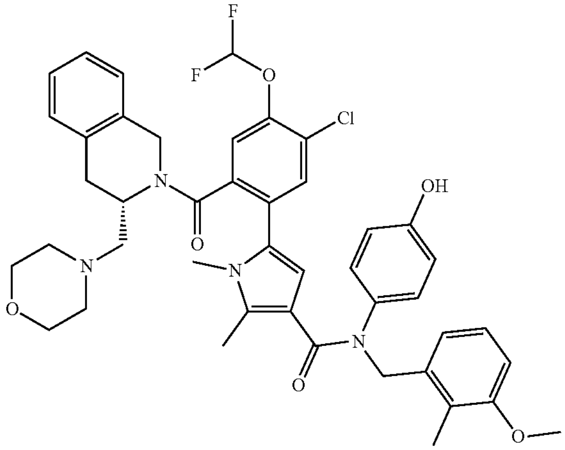 | 799.307 | 799 |

TABLE 3-continued
| Examples of the compound of Formula (I) | | | |
|---|---|---|---|
| Comp. # | Structure | [MH]+ Calc. | [MH]+ Found |
| 37 | 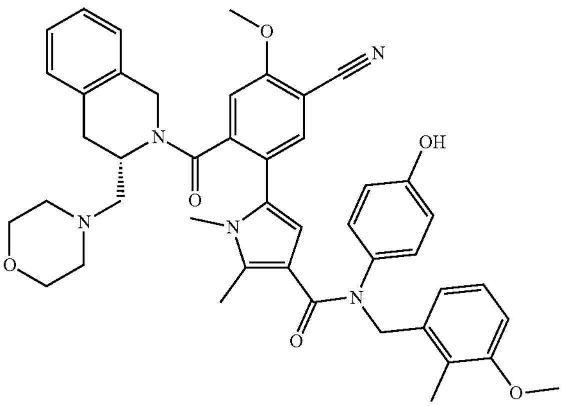 [SMILES: COc1cc(C(=O)N2Cc3ccccc3C[C@H]2CN2CCOCC2)c(-c2cc(C(=O)N(Cc3cccc(OC)c3C)c3ccc(O)cc3)c(C)n2C)cc1C#N] | 754.361 | 754 |
| 38 | 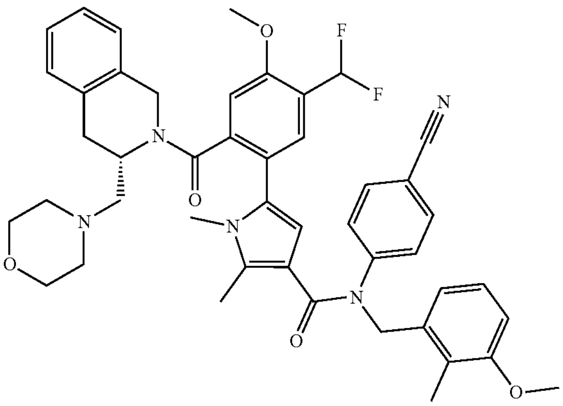 [SMILES: COc1cc(C(=O)N2Cc3ccccc3C[C@H]2CN2CCOCC2)c(-c2cc(C(=O)N(Cc3cccc(OC)c3C)c3ccc(C#N)cc3)c(C)n2C)cc1C(F)F] | 788.362 | 788 |
| 39 | 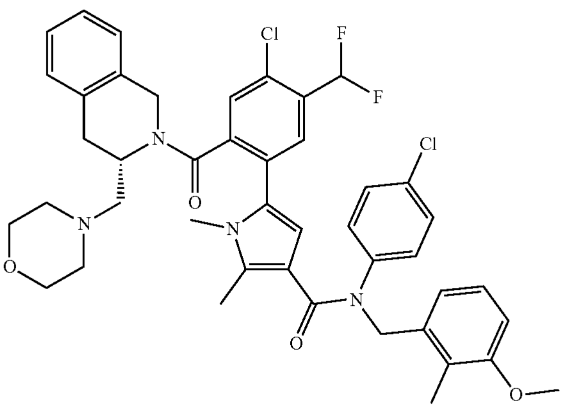 [SMILES: COc1cccc(CN(C(=O)c2cc(-c3cc(C(F)F)c(Cl)cc3C(=O)N3Cc4ccccc4C[C@H]3CN3CCOCC3)n(C)c2C)c2ccc(Cl)cc2)c1C] | 801.279 | 801 |

TABLE 3-continued
| Comp. # | Structure | [MH]+ Calc. | [MH]+ Found |
|---|---|---|---|
| Examples of the compound of Formula (I) | | | |
| 40 | 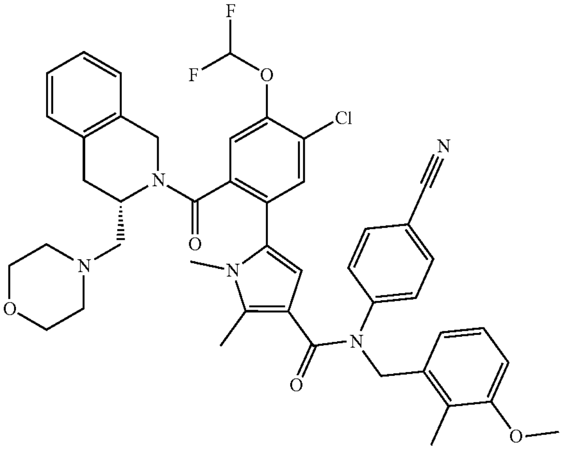 [SMILES: COc1cccc(CN(C(=O)c2cc(-c3cc(Cl)c(OC(F)F)cc3C(=O)N3Cc4ccccc4C[C@H]3CN3CCOCC3)n(C)c2C)c2ccc(C#N)cc2)c1C] | 808.308 | 808 |
| 41 | 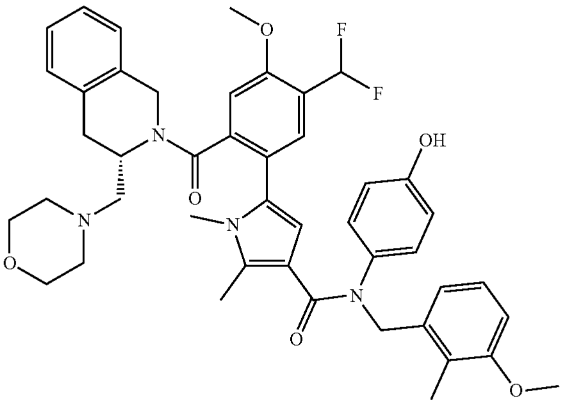 [SMILES: COc1cc(C(=O)N2Cc3ccccc3C[C@H]2CN2CCOCC2)c(-c2cc(C(=O)N(Cc3cccc(OC)c3C)c3ccc(O)cc3)c(C)n2C)cc1C(F)F] | 779.362 | 779 |
| 42 | 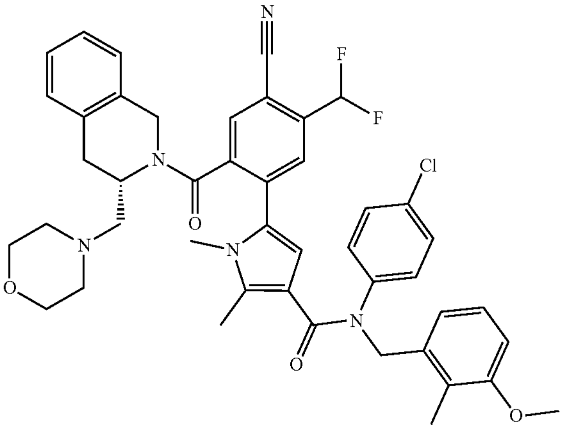 [SMILES: COc1cccc(CN(C(=O)c2cc(-c3cc(C(F)F)c(C#N)cc3C(=O)N3Cc4ccccc4C[C@H]3CN3CCOCC3)n(C)c2C)c2ccc(Cl)cc2)c1C] | 792.313 | 792 |

TABLE 3-continued
| Examples of the compound of Formula (I) | | | |
|---|---|---|---|
| Comp. # | Structure | [MH]+ Calc. | [MH]+ Found |
| 43 | 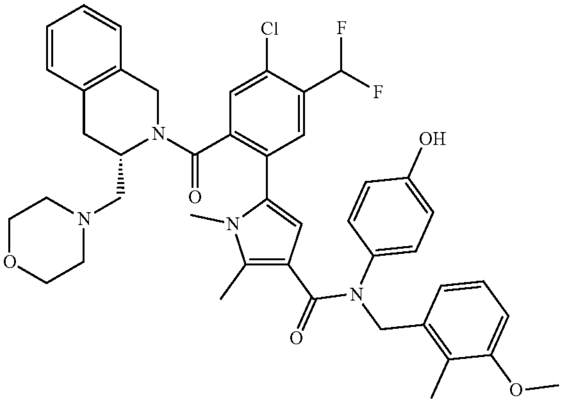 [SMILES: COc1cccc(CN(C(=O)c2cc(-c3cc(C(F)F)c(Cl)cc3C(=O)N3Cc4ccccc4C[C@H]3CN3CCOCC3)n(C)c2C)c2ccc(O)cc2)c1C] | 783.313 | 783 |
| 44 | 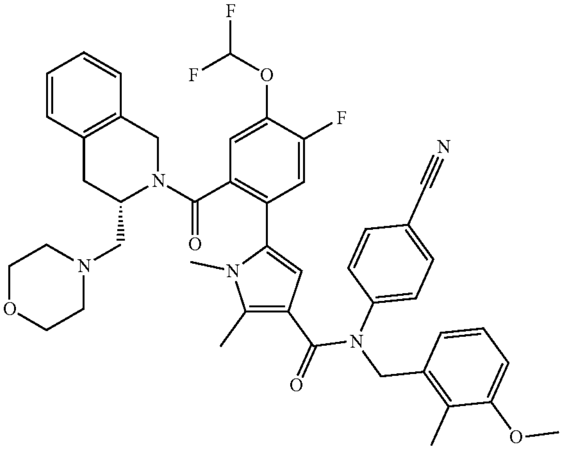 [SMILES: COc1cccc(CN(C(=O)c2cc(-c3cc(F)c(OC(F)F)cc3C(=O)N3Cc4ccccc4C[C@H]3CN3CCOCC3)n(C)c2C)c2ccc(C#N)cc2)c1C] | 792.337 | 792 |
| 45 | 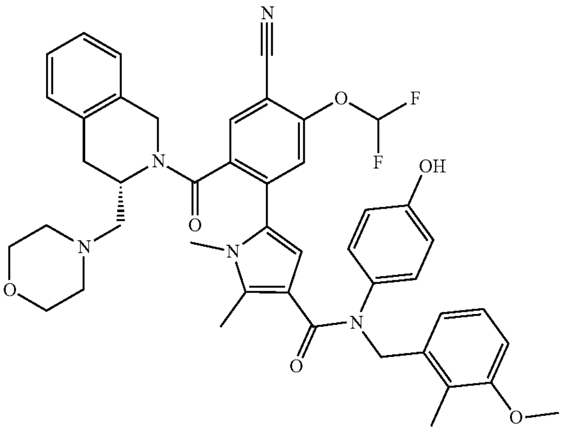 [SMILES: COc1cccc(CN(C(=O)c2cc(-c3cc(OC(F)F)c(C#N)cc3C(=O)N3Cc4ccccc4C[C@H]3CN3CCOCC3)n(C)c2C)c2ccc(O)cc2)c1C] | 790.342 | 790 |

TABLE 3-continued
| Examples of the compound of Formula (I) | | | |
|---|---|---|---|
| Comp. # | Structure | [MH]+ Calc. | [MH]+ Found |
| 46 | 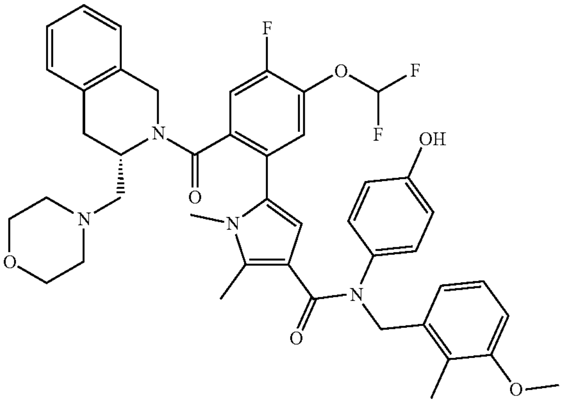 [SMILES: COc1cccc(CN(C(=O)c2cc(-c3cc(OC(F)F)c(F)cc3C(=O)N3Cc4ccccc4C[C@H]3CN3CCOCC3)n(C)c2C)c2ccc(O)cc2)c1C] | 783.337 | 783 |
| 47 | 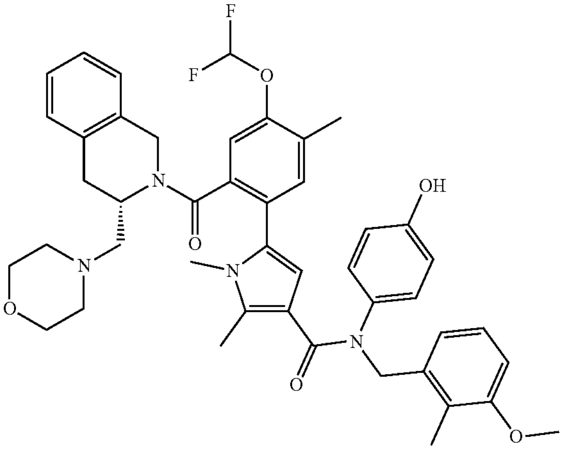 | 779.362 | 779 |
| 48 | 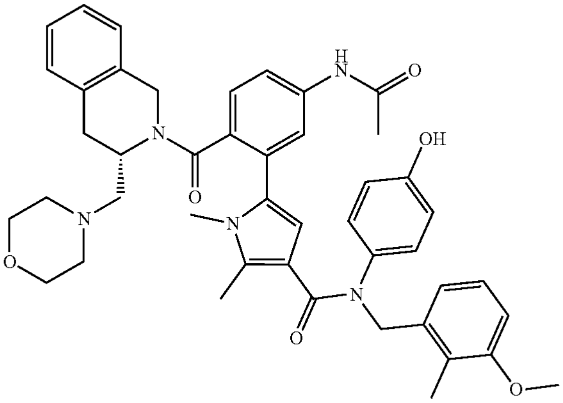 [SMILES: COc1cccc(CN(C(=O)c2cc(-c3cc(NC(C)=O)ccc3C(=O)N3Cc4ccccc4C[C@H]3CN3CCOCC3)n(C)c2C)c2ccc(O)cc2)c1C] | 756.376 | 756 |

TABLE 3-continued
| Examples of the compound of Formula (I) | | | |
|---|---|---|---|
| Comp. # | Structure | $[MH]^+$ Calc. | $[MH]^+$ Found |
| 49 | 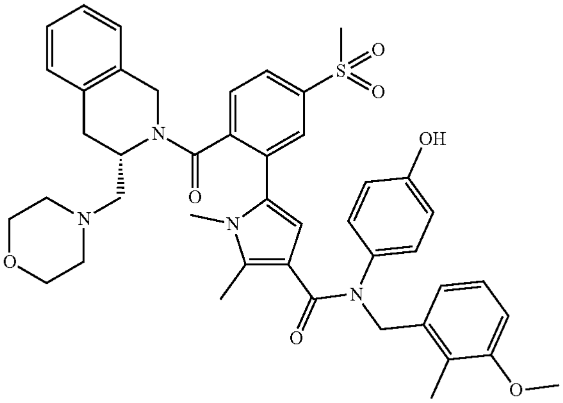 [SMILES: COc1cccc(CN(C(=O)c2cc(-c3cc(S(C)(=O)=O)ccc3C(=O)N3Cc4ccccc4C[C@H]3CN3CCOCC3)n(C)c2C)c2ccc(O)cc2)c1C] | 777.332 | 777 |
| 50 | 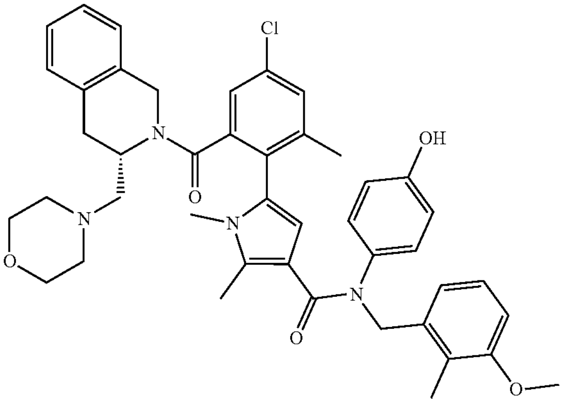 [SMILES: COc1cccc(CN(C(=O)c2cc(-c3c(C)cc(Cl)cc3C(=O)N3Cc4ccccc4C[C@H]3CN3CCOCC3)n(C)c2C)c2ccc(O)cc2)c1C] | 747.331 | 747 |
| 51 | 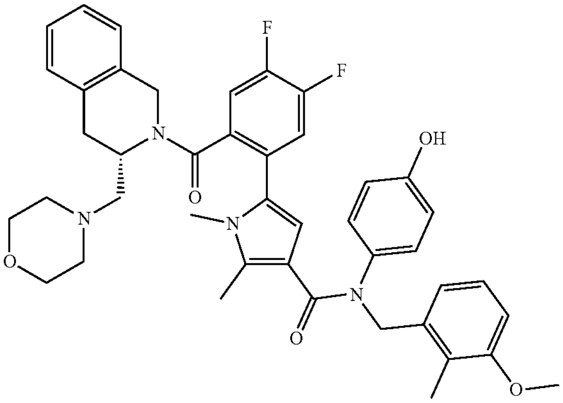 [SMILES: COc1cccc(CN(C(=O)c2cc(-c3cc(F)c(F)cc3C(=O)N3Cc4ccccc4C[C@H]3CN3CCOCC3)n(C)c2C)c2ccc(O)cc2)c1C] | 735.336 | 735 |

TABLE 3-continued
| Examples of the compound of Formula (I) | | | |
|---|---|---|---|
| Comp. # | Structure | [MH]+ Calc. | [MH]+ Found |
| 52 | 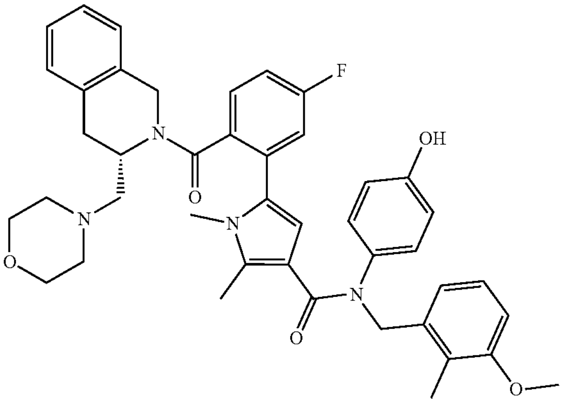 [SMILES: COc1cccc(CN(C(=O)c2cc(-c3cc(F)ccc3C(=O)N3Cc4ccccc4C[C@H]3CN3CCOCC3)n(C)c2C)c2ccc(O)cc2)c1C] | 717.345 | 717 |
| 53 | 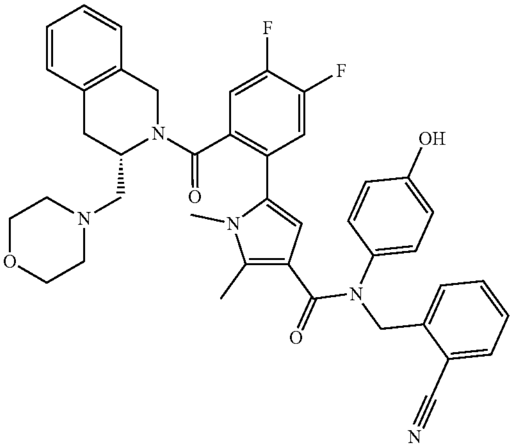 [SMILES: Cc1c(C(=O)N(Cc2ccccc2C#N)c2ccc(O)cc2)cc(-c2cc(F)c(F)cc2C(=O)N2Cc3ccccc3C[C@H]2CN2CCOCC2)n1C] | 716.305 | 716 |
| 54 | 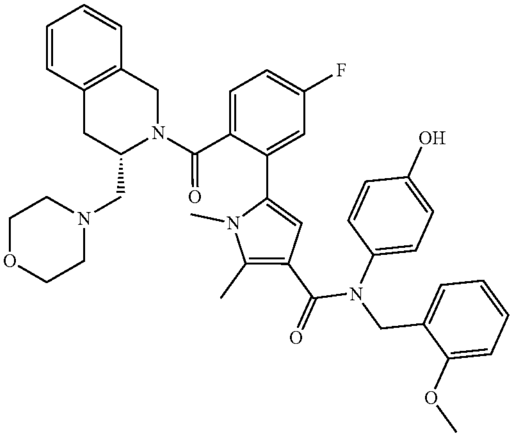 [SMILES: COc1ccccc1CN(C(=O)c1cc(-c2cc(F)ccc2C(=O)N2Cc3ccccc3C[C@H]2CN2CCOCC2)n(C)c1C)c1ccc(O)cc1] | 703.330 | 703 |

TABLE 3-continued
| Examples of the compound of Formula (I) | | | |
|---|---|---|---|
| Comp. # | Structure | [MH]+ Calc. | [MH]+ Found |
| 55 | 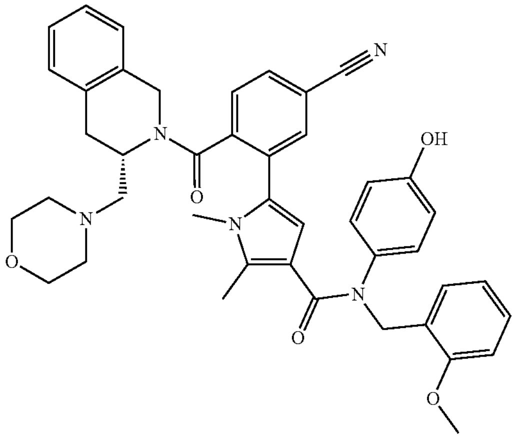 [SMILES: COc1ccccc1CN(C(=O)c1cc(-c2cc(C#N)ccc2C(=O)N2Cc3ccccc3C[C@H]2CN2CCOCC2)n(C)c1C)c1ccc(O)cc1] | 710.334 | 710 |
| 56 | 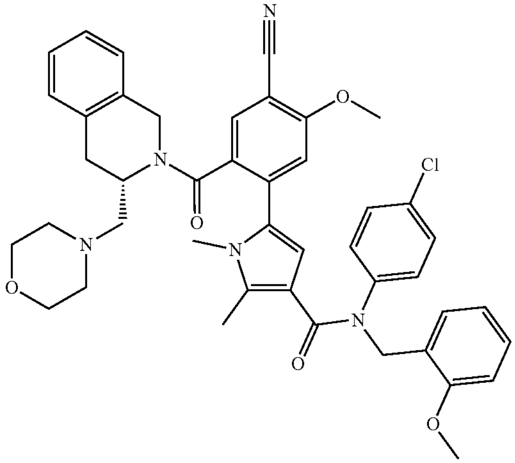 [SMILES: COc1cc(-c2cc(C(=O)N(Cc3ccccc3OC)c3ccc(Cl)cc3)c(C)n2C)c(C(=O)N2Cc3ccccc3C[C@H]2CN2CCOCC2)cc1C#N] | 758.311 | 758 |
| 57 | 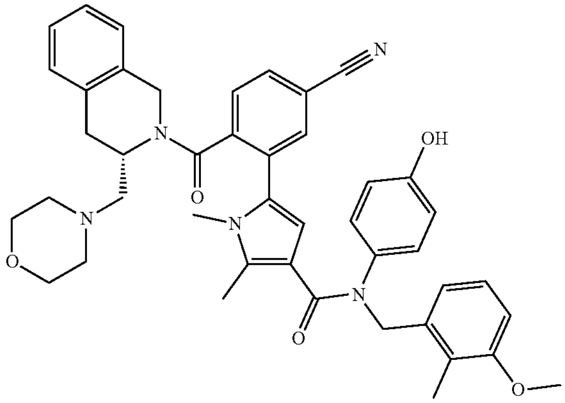 [SMILES: COc1cccc(CN(C(=O)c2cc(-c3cc(C#N)ccc3C(=O)N3Cc4ccccc4C[C@H]3CN3CCOCC3)n(C)c2C)c2ccc(O)cc2)c1C] | 724.350 | 724 |

TABLE 3-continued
| Examples of the compound of Formula (I) | | | |
|---|---|---|---|
| Comp. # | Structure | [MH]+ Calc. | [MH]+ Found |
| 58 | 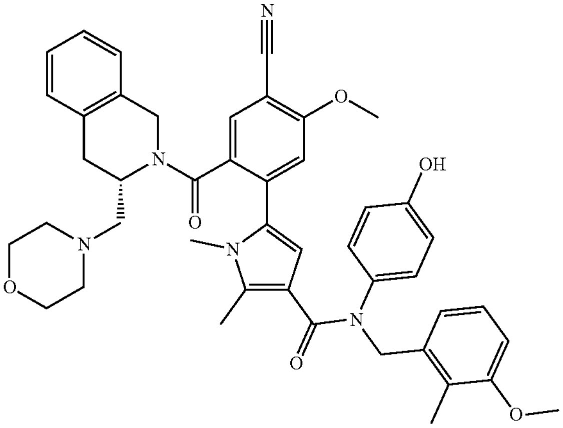 [SMILES: COc1cc(-c2cc(C(=O)N(Cc3cccc(OC)c3C)c3ccc(O)cc3)c(C)n2C)c(C(=O)N2Cc3ccccc3C[C@H]2CN2CCOCC2)cc1C#N] | 754.361 | 754 |
| 59 | 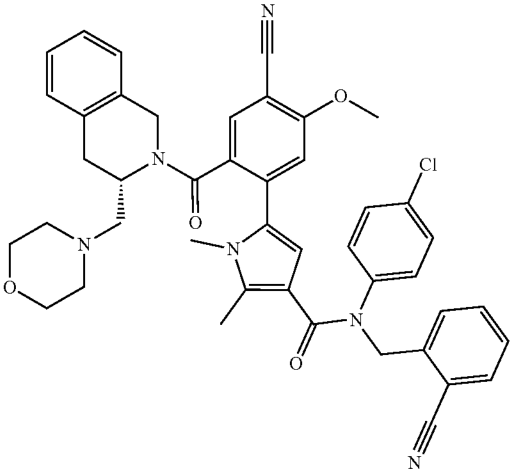 [SMILES: COc1cc(-c2cc(C(=O)N(Cc3ccccc3C#N)c3ccc(Cl)cc3)c(C)n2C)c(C(=O)N2Cc3ccccc3C[C@H]2CN2CCOCC2)cc1C#N] | 753.296 | 753 |
| 60 | 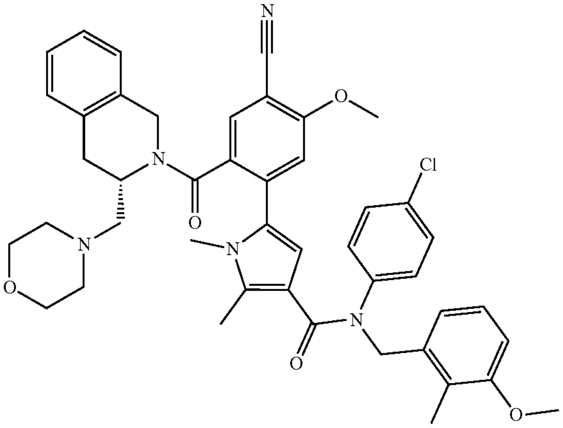 [SMILES: COc1cc(-c2cc(C(=O)N(Cc3cccc(OC)c3C)c3ccc(Cl)cc3)c(C)n2C)c(C(=O)N2Cc3ccccc3C[C@H]2CN2CCOCC2)cc1C#N] | 772.327 | 772 |

TABLE 3-continued
| Examples of the compound of Formula (I) | | | |
|---|---|---|---|
| Comp. # | Structure | [MH]+ Calc. | [MH]+ Found |
| 61 | 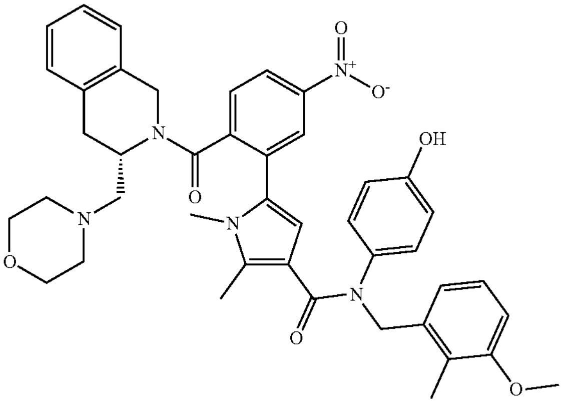 | 744.340 | 744 |
| 62 | 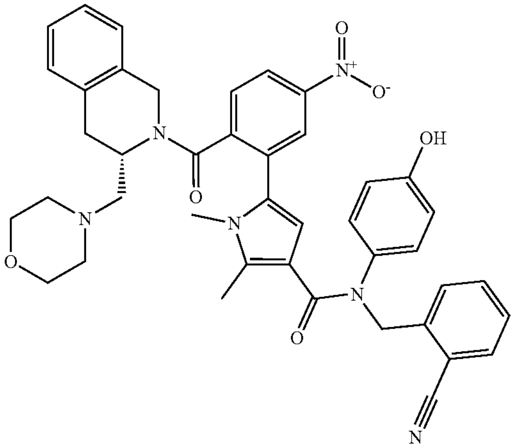 [SMILES: Cc1c(C(=O)N(Cc2ccccc2C#N)c2ccc(O)cc2)cc(-c2cc([N+](=O)[O-])ccc2C(=O)N2Cc3ccccc3C[C@H]2CN2CCOCC2)n1C] | 725.309 | 725 |
| 63 | 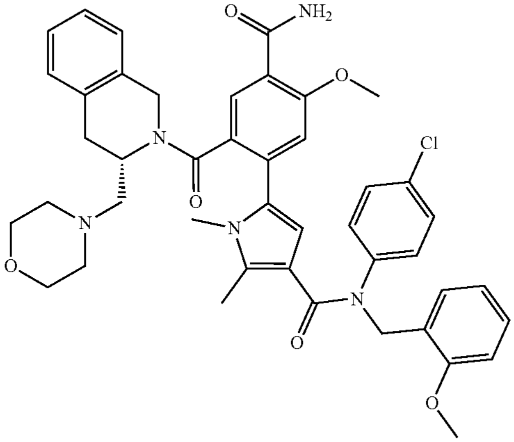 [SMILES: COc1ccccc1CN(C(=O)c1cc(-c2cc(OC)c(C(N)=O)cc2C(=O)N2Cc3ccccc3C[C@H]2CN2CCOCC2)n(C)c1C)c1ccc(Cl)cc1] | 776.322 | 776 |

TABLE 3-continued
| Examples of the compound of Formula (I) | | | |
|---|---|---|---|
| Comp. # | Structure | [MH]+ Calc. | [MH]+ Found |
| 64 | 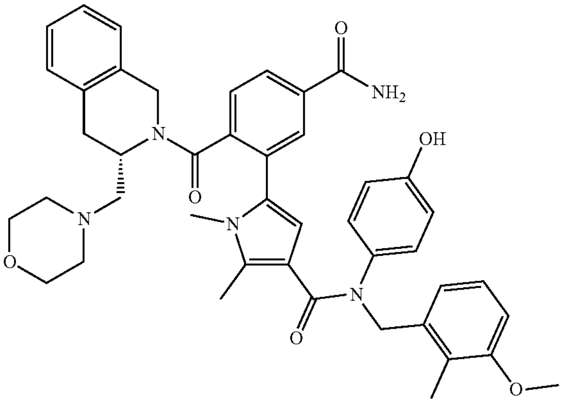 [SMILES: COc1cccc(CN(C(=O)c2cc(-c3cc(C(N)=O)ccc3C(=O)N3Cc4ccccc4C[C@H]3CN3CCOCC3)n(C)c2C)c2ccc(O)cc2)c1C] | 742.361 | 742 |
| 65 | 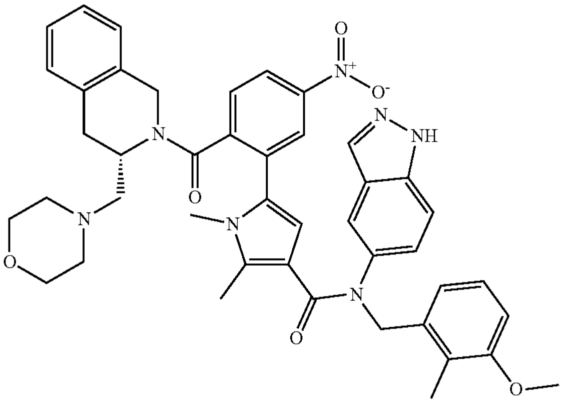 [SMILES: COc1cccc(CN(C(=O)c2cc(-c3cc([N+](=O)[O-])ccc3C(=O)N3Cc4ccccc4C[C@H]3CN3CCOCC3)n(C)c2C)c2ccc3[nH]ncc3c2)c1C] | 768.351 | 768 |
| 66 | 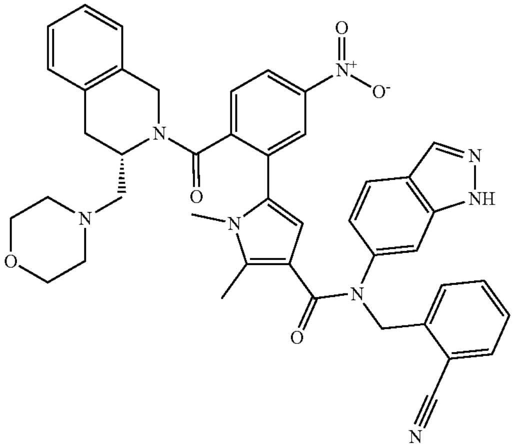 [SMILES: Cc1c(C(=O)N(Cc2ccccc2C#N)c2ccc3cn[nH]c3c2)cc(-c2cc([N+](=O)[O-])ccc2C(=O)N2Cc3ccccc3C[C@H]2CN2CCOCC2)n1C] | 749.32 | 749 |

TABLE 3-continued
| Examples of the compound of Formula (I) | | | |
|---|---|---|---|
| Comp. # | Structure | [MH]+ Calc. | [MH]+ Found |
| 67 | 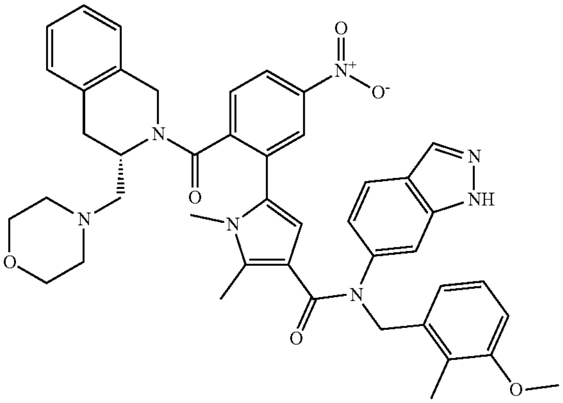 [SMILES: COc1cccc(CN(C(=O)c2cc(-c3cc([N+](=O)[O-])ccc3C(=O)N3Cc4ccccc4C[C@H]3CN3CCOCC3)n(C)c2C)c2ccc3cn[nH]c3c2)c1C] | 768.351 | 768 |
| 68 | 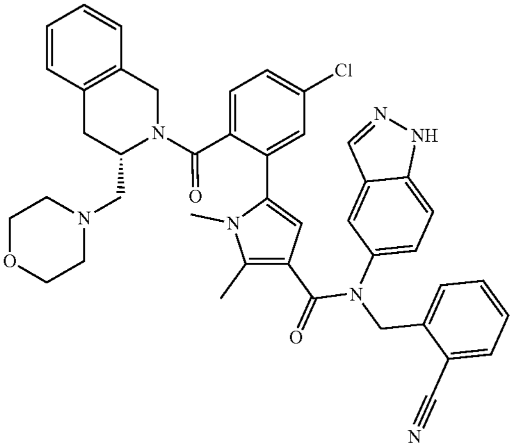 [SMILES: Cc1c(C(=O)N(Cc2ccccc2C#N)c2ccc3[nH]ncc3c2)cc(-c2cc(Cl)ccc2C(=O)N2Cc3ccccc3C[C@H]2CN2CCOCC2)n1C] | 738.296 | 738 |
| 69 | 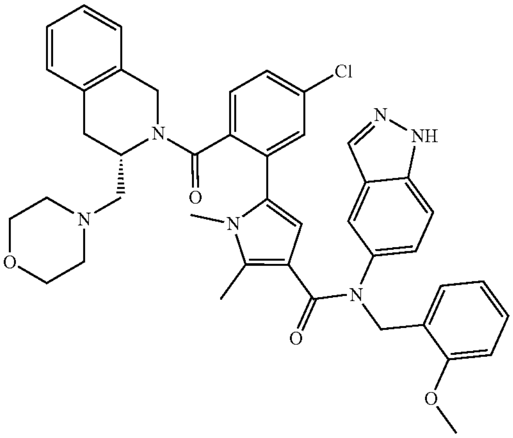 [SMILES: COc1ccccc1CN(C(=O)c1cc(-c2cc(Cl)ccc2C(=O)N2Cc3ccccc3C[C@H]2CN2CCOCC2)n(C)c1C)c1ccc2[nH]ncc2c1] | 743.311 | 743 |

TABLE 3-continued
| Examples of the compound of Formula (I) | | | |
|---|---|---|---|
| Comp. # | Structure | [MH]+ Calc. | [MH]+ Found |
| 70 | 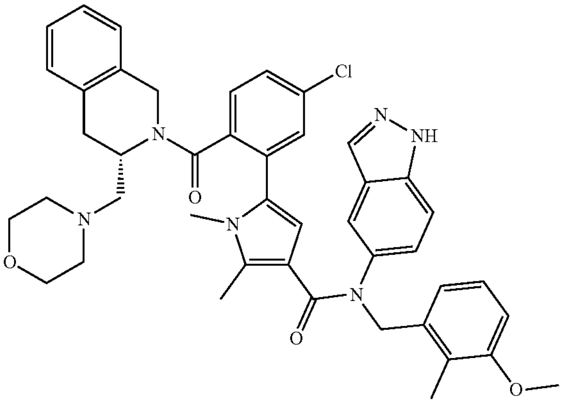 [SMILES: COc1cccc(CN(C(=O)c2cc(-c3cc(Cl)ccc3C(=O)N3Cc4ccccc4C[C@H]3CN3CCOCC3)n(C)c2C)c2ccc3[nH]ncc3c2)c1C] | 757.327 | 757 |
| 71 | 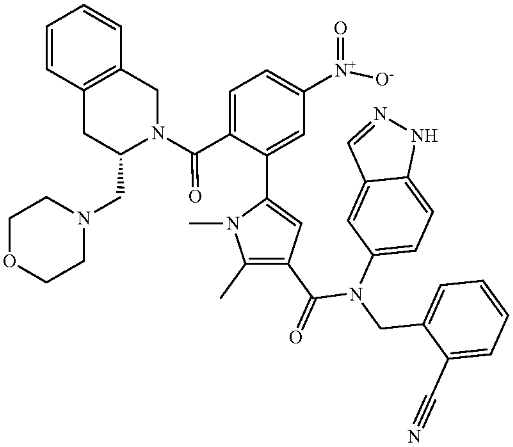 [SMILES: Cc1c(C(=O)N(Cc2ccccc2C#N)c2ccc3[nH]ncc3c2)cc(-c2cc([N+](=O)[O-])ccc2C(=O)N2Cc3ccccc3C[C@H]2CN2CCOCC2)n1C] | 749.32 | 749 |
| 72 | 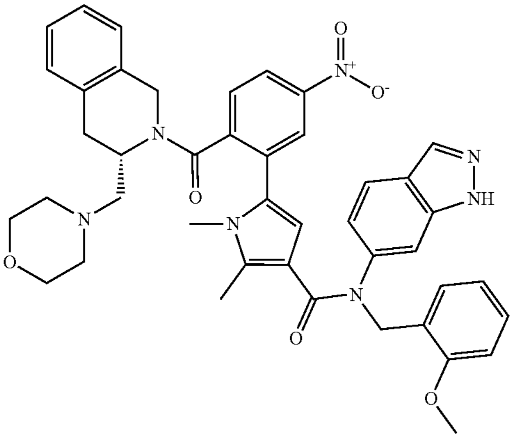 [SMILES: COc1ccccc1CN(C(=O)c1cc(-c2cc([N+](=O)[O-])ccc2C(=O)N2Cc3ccccc3C[C@H]2CN2CCOCC2)n(C)c1C)c1ccc2cn[nH]c2c1] | 754.335 | 754 |

TABLE 3-continued

| Examples of the compound of Formula (I) | | | |
|---|---|---|---|
| Comp. # | Structure | [MH]+ Calc. | [MH]+ Found |
| 73 | 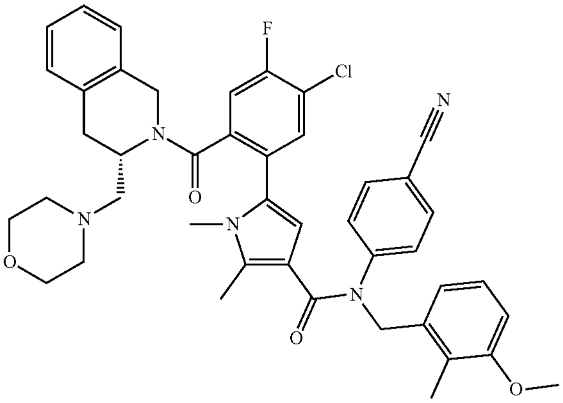 [SMILES: COc1cccc(CN(C(=O)c2cc(-c3cc(Cl)c(F)cc3C(=O)N3Cc4ccccc4C[C@H]3CN3CCOCC3)n(C)c2C)c2ccc(C#N)cc2)c1C] | 760.307 | 760 |
| 74 | 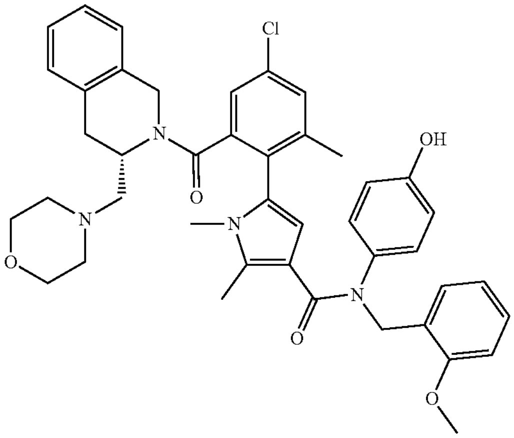 [SMILES: COc1ccccc1CN(C(=O)c1cc(-c2c(C)cc(Cl)cc2C(=O)N2Cc3ccccc3C[C@H]2CN2CCOCC2)n(C)c1C)c1ccc(O)cc1] | 733.316 | 733 |

Biological Assays

Primary PPI Inhibition Assays

Example A. BCL-2 TR-FRET Assay (BPS Bioscience, #50222)

The following assay concentrations and times were used: 3 ng of BCL-2, 5 μL of 1:100 anti-His Tb-labeled donor, 5 μL of 1:100 Dye-labeled acceptor, 5 L of 1:40 BCL-2 Peptide Ligand, and 2 μL of 200× test compound, with 60 min incubation time (final concentration of DMSO 0.5%). The results of the assay were read using a plate reader with the following parameters: TR FRET, 340ex/620 and 665em; 60 usec Delay; and 500 usec integration.

Example B. BCL-xL TR-FRET Assay (BPS Bioscience, #50223)

The following assay concentrations and times were used: 10.5 ng of BCL-xL, 5 μL of 1:120 anti-His Tb-labeled donor, 5 μL of 1:120 Dye-labeled acceptor, 5 μL of 1:96 BCL-xL Peptide Ligand, 2 μL of 200× test compound, with 60 min incubation time (final concentration of DMSO 0.5%). The results of the assay were read using a plate reader with the following parameters: TR FRET, 340ex/620 and 665em; 60 usec Delay; and 500 usec integration.

Example C. BCL-2 [G101V]TR-FRET Assay

The following assay concentrations and times were used: 0.22 ng/μl of BCL-2 (SinoBiological, #10195-H08E1), 5 μL of 1:100 anti-His Tb-labeled donor, 5 μL of 1:100 Dye-labeled acceptor, 5 μL of 1:40 BCL-2 Peptide Ligand (BPS Bioscience, #50223), and 2 μL of 200× test compound, with 60 min incubation time (final concentration of DMSO 0.5%). The results of the assay were read using a plate reader with the following parameters: TR FRET, 340ex/620 and 665em; 60 usec Delay; and 500 usec integration.

Instrumentation: CLARIOstar Plus (BMG LABTECH); Biomek FX for liquid handling (Beckman Coulter).

Table A assigns a code for potency for BCL-2 TR-FRET Assay: A, B, C, or D. According to the code, A represents an $IC_{50}$ value≤5 nM; B represents $IC_{50}$>5 nM and ≤10 nM; C represents $IC_{50}$>10 nM and ≤50 nM D represents $IC_{50}$>50 nM.

Table A assigns a code for potency for BCL-xL TR-FRET Assay: A, B, or C. According to the code, A represents $IC_{50}$ value≤2,000 nM; B represents $IC_{50}$ values>2,000 nM and ≤5,000 nM; C represents $IC_{50}$ values>5,000 nM.

Table A assigns a code for potency for BCL-2 [G101V] TR-FRET Assay: A, B, or C. According to the code, A represents an $IC_{50}$ value≤100 nM; B represents $IC_{50}$>100 nM and ≤ 1,000 nM; C represents $IC_{50}$>1,000 nM.

TABLE A

| Primary PPI inhibition | | | |
|---|---|---|---|
| Compound # | BCL2 IC50, nM | BCLxL IC50, nM | BCL2[G101V] IC50, nM |
| 1 | D | C | C |
| 2 | C | C | C |
| 3 | A | C | A |
| 4 | A | C | B |
| 6 | A | A | A |
| 7 | A | B | A |
| 9 | A | B | B |
| 11 | C | B | B |
| 12 | D | B | — |
| 16 | B | B | C |
| 21 | C | B | B |
| 24 | D | B | — |
| 26 | D | B | — |
| 27 | C | B | — |
| 29 | C | — | — |
| 31 | B | B | C |
| 32 | D | B | — |
| 33 | D | B | — |
| 36 | B | B | B |
| 39 | D | B | — |
| 40 | D | B | — |
| 43 | A | B | B |
| 44 | D | B | — |
| 48 | B | B | B |
| 49 | A | B | A |
| 50 | D | B | — |
| 51 | C | B | B |
| 52 | A | B | A |
| 53 | C | B | — |
| 54 | B | A | A |
| 55 | B | A | — |
| 56 | D | B | |
| 57 | B | B | — |
| 58 | D | B | — |
| 59 | D | B | — |
| 60 | D | B | — |
| 61 | A | C | — |
| 62 | A | C | — |
| 63 | C | — | — |
| 64 | A | C | — |
| 65 | C | C | C |
| 66 | D | C | — |
| 67 | D | C | — |
| 68 | C | C | C |
| 69 | C | C | — |
| 70 | B | C | C |
| 73 | D | B | |

Cell Viability Assays (Cell lines HEK293, RS4-11, MOLT-4)

Example D. Cell Viability Assays (Cell lines HEK293, RS4-11, MOLT-4)

Cells were seeded at a density of 4000 cells per well in the 384-well clear bottom plate (Greiner Cat #781090) to the 45 μL total volume of either DMEM (PanEco, Cat #$C_{420}$, for HEK293) or RPMI (PanEco, Cat #$C_{330}$, for other cell lines) with 10% FBS(HyClone Cat #SV30160.03). Prior to adding compounds, the HEK293 cells were allowed to adhere overnight at 37° C. and 5% $CO_2$. The 500× compounds solutions in DMSO(Sigma Cat #D2650) were dispersed into a 384-well compound plate (Diamond Well Plate, Axigen, Cat #P-384-120 SQ-C—S) including only DMSO control. The 1 μL aliquots of the 500× compounds from the compound plate were added to 49 μL of culture medium in the Dilution plate (Diamond Well Plate, Axigen, Cat #P-384-120 SQ-C—S), mixed and then the 5 μL aliquts of the 10× compound solutions were transferred to cells followed by centrifugation at 100 g for 1 min. Final DMSO concentration was 0.2%. After 3 days of incubation the 10 μL aliquots of CellTiter-Glo (Promega, CAT #G7572) were added to the cells, plate was centrifuged at 100 g for 1 min and the luminescence was measured on the CLARIOstar Plus (BMG LABTECH) instrument.

Cell lines: HEK293, MOLT-4 (ATCC, CRL-1582), RS4-11 (ATCC, CRL-1873)

Instrumentation: CLARIOstar Plus (BMG LABTECH); Biomek FX for liquid handling (Beckman Coulter).

Table B assigns a code for potency for RS4-11 Assay: A, B, or C. According to the code, A represents an $CC_{50}$ value≤0.1 μM; B represents CC50>0.1 μM and ≤0.2 μM; C represents CC50>0.2 μM.

Table B assigns a code for potency for HEK293 Assay: A, B, or C. According to the code, A represents an $CC_{50}$ value≤10 μM; B represents $CC_{50}$>10 μM and ≤25 μM; C represents $CC_{50}$>25 M.

Table B assigns a code for potency for MOLT-4 Assay: A, B, or C. According to the code, A represents an CC50 value≤5 μM; B represents CC50>5 M and ≤10 μM; C represents CC50>10 μM.

TABLE B

| Cellular models efficacy and cytotoxicity | | | |
|---|---|---|---|
| Compound # | RS4-11 CC50, μM | HEK293 CC50, μM | MOLT-4 CC50, μM |
| 3 | B | B | A |
| 4 | A | B | A |
| 6 | B | B | B |
| 7 | A | B | B |
| 9 | C | B | A |
| 11 | B | C | A |
| 12 | C | C | A |
| 16 | C | C | A |
| 21 | B | C | A |
| 24 | C | C | C |
| 26 | C | C | A |
| 27 | B | C | A |
| 29 | B | C | C |
| 31 | C | C | A |
| 32 | C | C | A |
| 36 | C | C | B |
| 39 | C | C | A |
| 43 | C | C | A |
| 49 | A | C | B |
| 51 | B | C | A |
| 52 | A | C | A |
| 53 | B | C | B |
| 54 | B | C | A |
| 55 | B | C | A |
| 56 | C | A | A |
| 57 | A | C | A |
| 58 | C | C | A |
| 61 | A | C | A |
| 62 | A | C | A |
| 63 | B | B | A |
| 64 | A | C | C |
| 65 | C | B | A |
| 68 | C | C | C |
| 69 | C | C | C |
| 70 | C | C | A |
| 73 | C | B | C |

Caspase-3/7 Activation

Example E. Caspase-3/7 Activation

Assay Principle: The Caspase-Glo 3/7 Assay is homogeneous, luminescent assay that measures caspase-3 and -7 activities. The assay provides a luminogenic caspase-3/7 substrate, which contains the tetrapeptide sequence DEVD, in a reagent optimized for caspase activity.

Assay Procedure: Incubate RS4-11 (ATCC, CRL-1873) cells in the 384-well white plate (Corning, #3570) with varying concentrations of test compounds for 3.5 h in a humidified incubator at 37° C. and 5% $CO_2$ for 30 min at rt. Add 15 μL of the Caspase-Glo (Promega, #8212) reagent to each well and to incubate the plate for 30 min at rt. Read on the CLARIOstar Plus (BMG LABTECH) instrument.

Instrumentation: CLARIOstar Plus (BMG LABTECH); Biomek FX for liquid handling (Beckman Coulter).

Table C assigns a code for potency for Cas-3/7 Assay: A, B, or C. According to the code, A represents an $EC_{50}$ value≤0.2 μM; B represents $EC_{50}$>0.2 μM and ≤0.5 μM; C represents $EC_{50}$>0.5 μM.

TABLE C

Caspase-3/7 activation.

| Compound # | Cas-3/7 EC50, μM |
|---|---|
| 1 | C |
| 2 | C |
| 3 | B |
| 4 | A |
| 6 | B |
| 7 | A |
| 9 | C |
| 11 | A |
| 12 | C |
| 16 | B |
| 21 | A |
| 24 | C |
| 26 | C |
| 27 | B |
| 29 | C |
| 31 | C |
| 32 | C |
| 36 | C |
| 39 | C |
| 43 | C |
| 51 | B |
| 52 | B |
| 53 | B |
| 54 | C |
| 55 | B |
| 56 | C |
| 57 | A |
| 58 | C |
| 61 | B |
| 62 | A |
| 63 | C |
| 64 | C |
| 65 | C |
| 68 | C |
| 69 | C |
| 70 | C |
| 73 | C |

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

What is claimed is:

1. A compound of Formula (I):

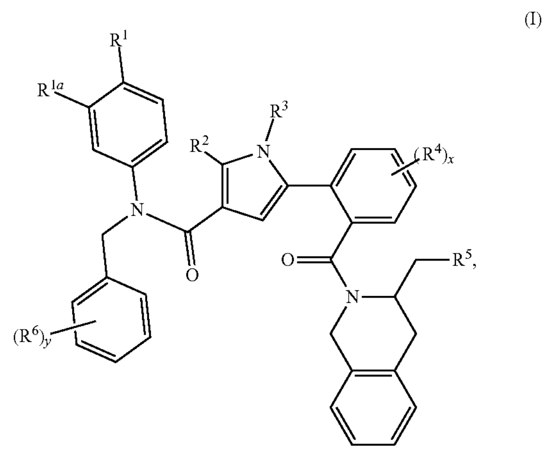

or a pharmaceutically acceptable salt, stereoisomer, solvate, or tautomer thereof, wherein:

$R^1$ is selected from halogen, —OH, —CN, and —$CONH_2$;

$R^{1a}$ is H;

or $R^1$ and $R^{1a}$, together with the atom to which they are attached, come together to form a 3- to 10-membered heteroaryl ring further comprising 1, 2, or 3 heteroatoms selected from N, O, and S;

$R^2$ and $R^3$ each independently selected from $C_1$-$C_6$ alkyl;

or $R^2$ and $R^3$, together with the atom to which they are attached, come together to form a 3- to 10-membered heterocyclyl ring further comprising 1, 2, or 3 heteroatoms selected from N, O, and S;

each $R^4$ is independently selected from halogen, —OH, —CN, —$NO_2$, —COOH, —$CH_2CN$, $CH_2N(R^8)_2$, $C_1$-$C_6$ alkyl, $C_1$-$C_6$ alkoxy, $C_1$-$C_6$ halogenalkyl, $C_1$-$C_6$ halogenalkoxy, —O—($C_2$-$C_6$ alkenyl), —O—($C_2$-$C_6$ alkynyl), $C_2$-$C_6$ alkenyl, $C_2$-$C_6$ alkynyl, —OH, —OP(O)$(OH)_2$, —OC(O)($C_1$-$C_6$ alkyl), —C(O)($C_1$-$C_6$ alkyl), —OC(O)O($C_1$-$C_6$ alkyl), —$NH_2$, —NH($C_1$-$C_6$ alkyl), —N$(C_1$-$C_6$ alkyl$)_2$, —NHC(O)($C_1$-$C_6$ alkyl), —C(O)$NH_2$, —C(O)NH($C_1$-$C_6$ alkyl), —S$(O)_2$($C_1$-$C_6$ alkyl), —S(O)NH($C_1$-$C_6$ alkyl), and S(O)N$(C_1$-$C_6$ alkyl$)_2$;

$R^5$ is selected from

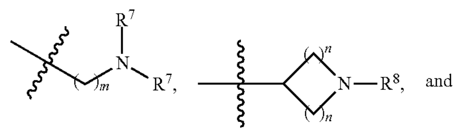

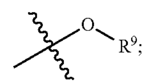

each $R^6$ is independently selected from halogen, —OH, —CN, —COOH, —$CH_2CN$, —$CH_2N(R^8)_2$, $C_1$-$C_6$ alkyl, $C_1$-$C_6$ alkoxy, $C_1$-$C_6$ halogenalkyl, $C_1$-$C_6$ halogenalkoxy, —O—($C_2$-$C_6$) alkenyl, —O—($C_2$-$C_6$) alkynyl, $C_2$-$C_6$ alkenyl, $C_2$-$C_6$ alkynyl, —OH, —OP(O)$(OH)_2$, —OC(O)($C_1$-$C_6$) alkyl, —C(O)($C_1$-$C_6$) alkyl, —OC(O)O($C_1$-$C_6$) alkyl, —$NH_2$, —NH($C_1$-$C_6$ alkyl), —N($C_1$-$C_6$ alkyl$)_2$, —NHC(O)($C_1$-$C_6$) alkyl, —C(O)NH($C_1$-$C_6$)alkyl, —S(O)$_2$($C_1$-$C_6$) alkyl, —S(O)NH($C_1$-$C_6$) alkyl, and S(O)N($C_1$-$C_6$ alkyl$)_2$;

each $R^7$ is independently selected from H, $C_{1-6}$ alkyl, $C_{2-6}$ alkenyl, $C_{2-6}$ alkynyl, aryl;

wherein alkyl or aryl is optionally substituted with one or more substituents independently selected from halogen, —OH, —CN, —COOH, —$CH_2CN$, —$CH_2N(R^8)_2$, C1-$C_6$ alkyl, $C_1$-$C_6$ alkoxy, $C_1$-$C_6$ halogenalkyl, $C_1$-$C_6$ halogenalkoxy, —O—($C_2$-$C_6$) alkenyl, —O—($C_2$-$C_6$) alkynyl, $C_2$-$C_6$ alkenyl, $C_2$-$C_6$ alkynyl, —OH, —OP(O) $(OH)_2$, —OC(O) ($C_1$-$C_6$) alkyl, —C(O) ($C_1$-$C_6$) alkyl, —OC(O) O($C_1$-$C_6$) alkyl, —$NH_2$, —NH($C_1$-$C_6$ alkyl), —N($C_1$-$C_6$ alkyl$)_2$, —NHC(O) ($C_1$-$C_6$) alkyl, —C(O) NH($C_1$-$C_6$) alkyl, —S(O)$_2$($C_1$-$C_6$) alkyl, —S(O)NH($C_1$-$C_6$) alkyl, and S(O)N($C_1$-$C_6$ alkyl$)_2$;

or two $R^7$ together with the nitrogen atom to which they are bound and any intervening atoms, form a heterocycle;

wherein heterocycle is optionally substituted with one or more substituents independently selected from halogen, —OH, —CN, —COOH, —$CH_2CN$, —$CH_2N(R^8)_2$, $C_1$-$C_6$ alkyl, $C_1$-$C_6$ alkoxy, $C_1$-$C_6$ halogenalkyl, $C_1$-$C_6$ halogenalkoxy, —O—($C_2$-$C_6$) alkenyl, —O—($C_2$-$C_6$) alkynyl, $C_2$-$C_6$ alkenyl, $C_2$-$C_6$ alkynyl, —OH, —OP(O)$(OH)_2$, —OC(O)($C_1$-$C_6$) alkyl, —C(O) ($C_1$-$C_6$) alkyl, —OC(O)O($C_1$-$C_6$) alkyl, —$NH_2$, —NH($C_1$-$C_6$ alkyl), —N($C_1$-$C_6$ alkyl$)_2$, —NHC(O)($C_1$-$C_6$) alkyl, —C(O)NH($C_1$-$C_6$) alkyl, —S(O)$_2$($C_1$-$C_6$) alkyl, —S(O)NH($C_1$-$C_6$) alkyl, and S(O)N($C_1$-$C_6$ alkyl$)_2$;

$R^8$ is selected from H, $C_{1-6}$ alkyl, $C_{3-8}$ cycloalkyl, aryl, $C_{1-6}$ halogenalkyl;

$R^9$ is selected from $C_{1-6}$ alkyl, $C_{2-6}$ alkenyl, $C_{2-6}$ alkynyl, —$(CH_2)_{1-6}OR_8$, $C_{3-8}$ cycloalkyl, aryl, heterocycle;

wherein alkyl, cycloalkyl, aryl or heterocycle are optionally substituted with one or more substituents independently selected from halogen, —OH, —CN, —COOH, —$CH_2CN$, $C_1$-$C_6$ alkyl, $C_1$-$C_6$ alkoxy, $C_1$-$C_6$ halogenalkyl, $C_1$-$C_6$ halogenalkoxy, —O—($C_2$-$C_6$) alkenyl, —O—($C_2$-$C_6$) alkynyl, $C_2$-$C_6$ alkenyl, $C_2$-$C_6$ alkynyl, —OH, —OP(O)$(OH)_2$, —OC(O)($C_1$-$C_6$) alkyl, —C(O)($C_1$-$C_6$) alkyl, —OC(O)O($C_1$-$C_6$) alkyl, —$NH_2$, —NH($C_1$-$C_6$ alkyl), —N($C_1$-$C_6$ alkyl$)_2$, —NHC(O)($C_1$-$C_6$) alkyl, —C(O)NH($C_1$-$C_6$) alkyl, —S(O)$_2$($C_1$-$C_6$) alkyl, —S(O)NH($C_1$-$C_6$) alkyl, and S(O)N($C_1$-$C_6$ alkyl$)_2$;

wherein, x is an integer selected from 0, 1, 2, 3;

y is an integer selected from 0, 1, 2, 3;

m is an integer selected from 0, 1, and 2;

each n is an integer independently selected from 1, 2, 3;

aryl is cyclic, aromatic hydrocarbon groups that have 1 to 3 aromatic rings;

heterocycle is saturated or partially unsaturated 3-10 membered monocyclic, 7-12 membered bicyclic (fused, bridged, or spiro rings), or 11-14 membered tricyclic ring system (fused, bridged, or spiro rings) having one or more heteroatoms selected from O, N, S, P, Se, and B.

2. The compound of claim 1, wherein compound has Formula (I'):

(I')

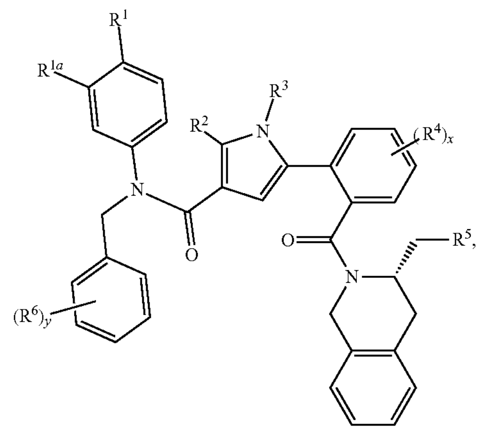

or a pharmaceutically acceptable salt, stereoisomer, solvate, or tautomer thereof.

3. The compound of claim 1, wherein compound is compound of Formula (II):

(II)

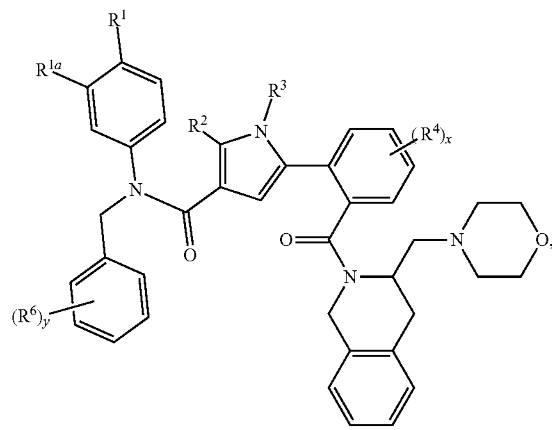

or a pharmaceutically acceptable salt, stereoisomer, solvate, or tautomer thereof.

4. The compound of claim 1, wherein compound is compound of Formula (II'):

(II')

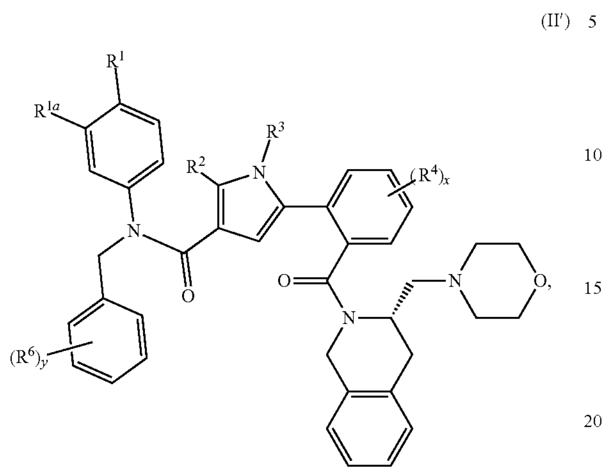

or a pharmaceutically acceptable salt, stereoisomer, solvate, or tautomer thereof.

5. The compound of claim 1, wherein compound of Formula (II-A):

(II-A)

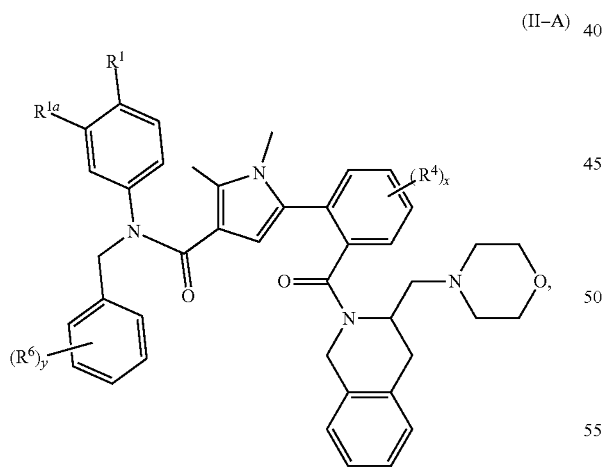

or a pharmaceutically acceptable salt, stereoisomer, solvate, or tautomer thereof.

6. The compound of claim 1, wherein compound is of Formula (II'):

(II-B)

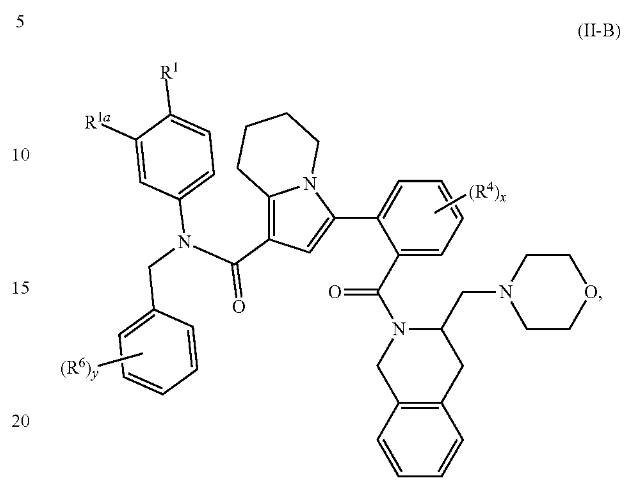

or a pharmaceutically acceptable salt, stereoisomer, solvate, or tautomer thereof.

7. The compound of claim 1, wherein compound is of Formula (II-A-A), Formula (II-A-B), or Formula (II-A-C):

(II-A-A)

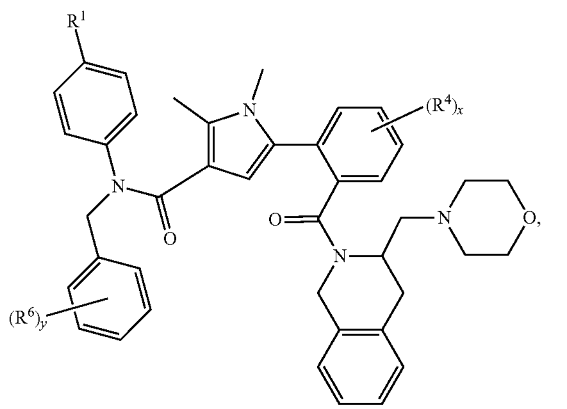

(II-A-B)

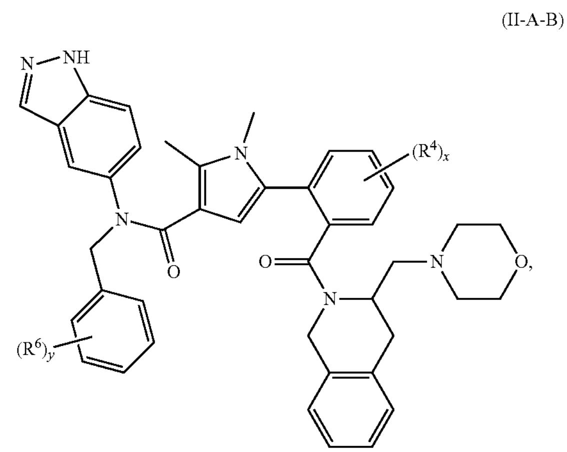

-continued (II-A-C)

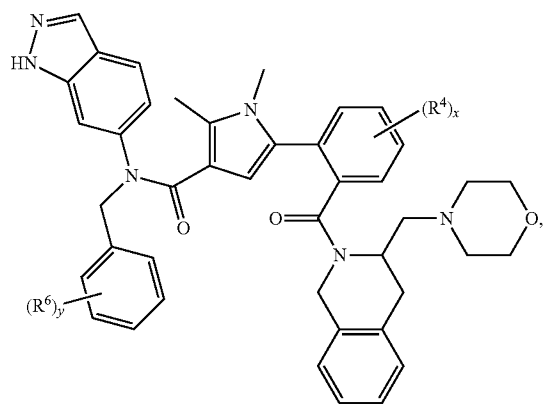

or a pharmaceutically acceptable salt, stereoisomer, solvate, or tautomer thereof.

8. The compound of claim 1, wherein compound is of Formula (II-B-A), Formula (II-B-B), Formula (II-B-C):

(II-B-A)

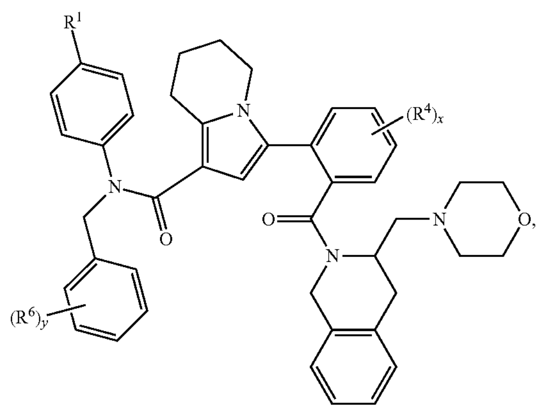

-continued (II-B-B)

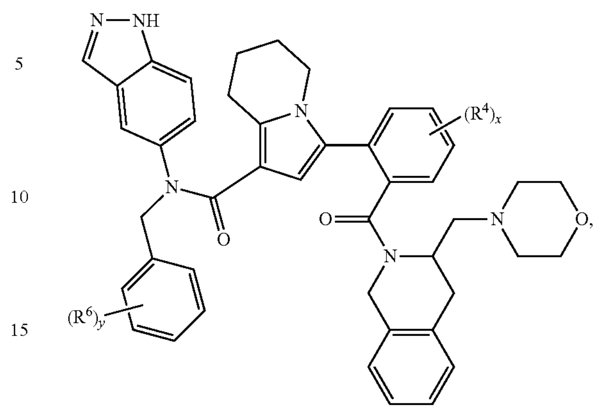

(II-B-C)

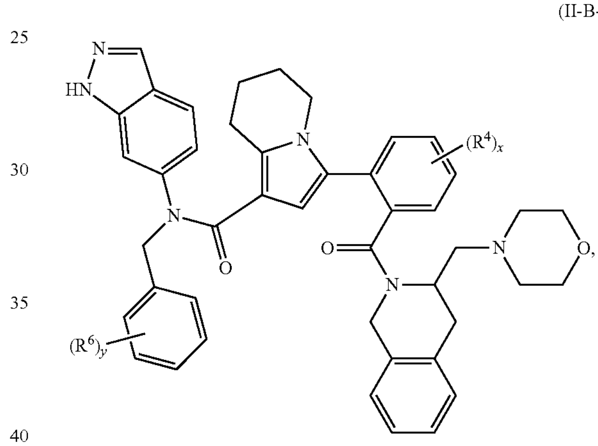

or a pharmaceutically acceptable salt, stereoisomer, solvate, or tautomer thereof.

9. A compound selected from:

| Cmpd # | Structure | IUPAC name |
|---|---|---|
| 1 | 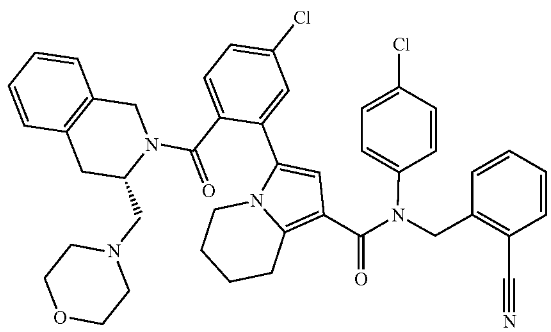 [SMILES: N#Cc1ccccc1CN(C(=O)c1cc(-c2cc(Cl)ccc2C(=O)N2Cc3ccccc3C[C@H]2CN2CCOCC2)n2c1CCCC2)c1ccc(Cl)cc1] | 3-[5-chloro-2-[(3S)-3-(morpholinomethyl)-3,4-dihydro-1H-isoquinoline-2-carbonyl]phenyl]-N-(4-chlorophenyl)-N-[(2-cyanophenyl)methyl]-5,6,7,8-tetrahydroindolizine-1-carboxamide |

-continued

| Cmpd # | Structure | IUPAC name |
|---|---|---|
| 2 | 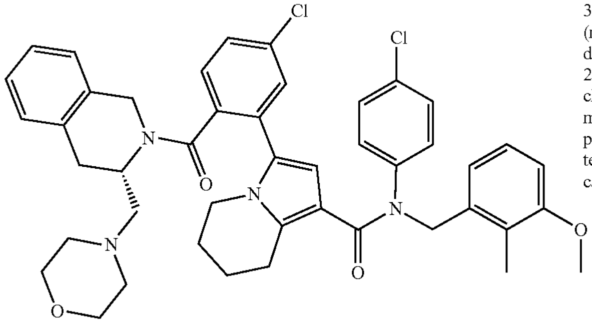 [SMILES: COc1cccc(CN(C(=O)c2cc(-c3cc(Cl)ccc3C(=O)N3Cc4ccccc4C[C@H]3CN3CCOCC3)n3c2CCCC3)c2ccc(Cl)cc2)c1C] | 3-[5-chloro-2-[(3S)-3-(morpholinomethyl)-3,4-dihydro-1H-isoquinoline-2-carbonyl]phenyl]-N-(4-chlorophenyl)-N-[(3-methoxy-2-methyl-phenyl)methyl]-5,6,7,8-tetrahydroindolizine-1-carboxamide |
| 3 | 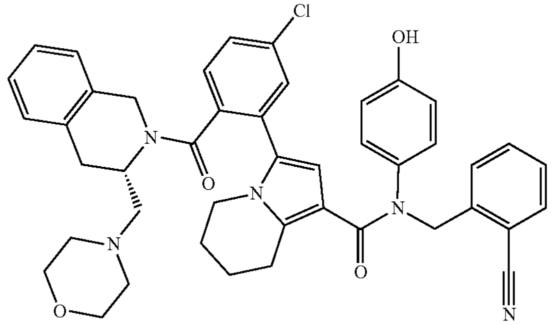 [SMILES: N#Cc1ccccc1CN(C(=O)c1cc(-c2cc(Cl)ccc2C(=O)N2Cc3ccccc3C[C@H]2CN2CCOCC2)n2c1CCCC2)c1ccc(O)cc1] | 3-[5-chloro-2-[(3S)-3-(morpholinomethyl)-3,4-dihydro-1H-isoquinoline-2-carbonyl]phenyl]-N-[(2-cyanopenyl)methyl]-N-(4-hydroxyphenyl)-5,6,7,8-tetrahydroindolizine-1-carboxamide |
| 4 | 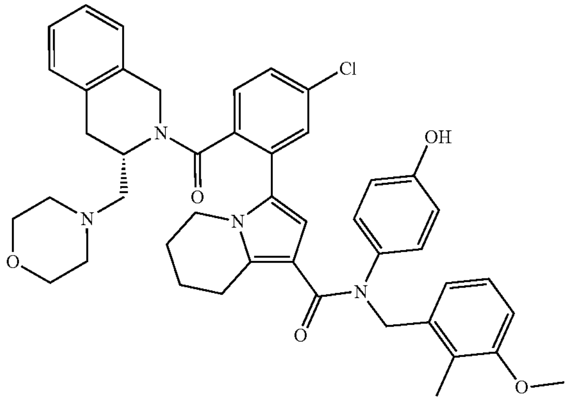 [SMILES: COc1cccc(CN(C(=O)c2cc(-c3cc(Cl)ccc3C(=O)N3Cc4ccccc4C[C@H]3CN3CCOCC3)n3c2CCCC3)c2ccc(O)cc2)c1C] | 3-[5-chloro-2-[(3S)-3-(morpholinomethyl)-3,4-dihydro-1H-isoquinoline-2-carbonyl]phenyl]-N-(4-hydroxyphenyl)-N-[(3-methoxy-2-methyl-phenyl)methyl]-5,6,7,8-tetrahydroindolizine-1-carboxamide |
| 5 | 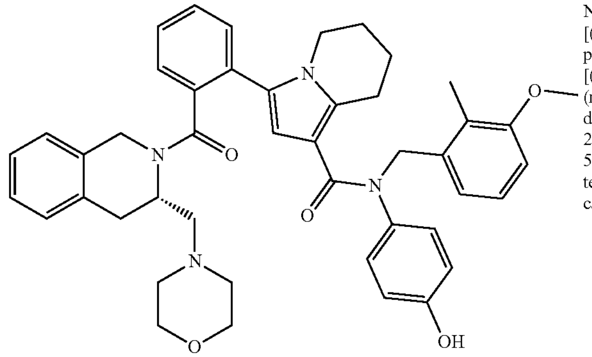 | N-(4-hydroxyphenyl)-N-[(3-methoxy-2-methyl-phenyl)methyl]-3-[2-[(3S)-3-(morpholinomethyl)-3,4-dihydro-1H-isoquinoline-2-carbonyl]phenyl]-5,6,7,8-tetrahydroindolizine-1-carboxamide |

-continued

| Cmpd # | Structure | IUPAC name |
|---|---|---|
| 6 | 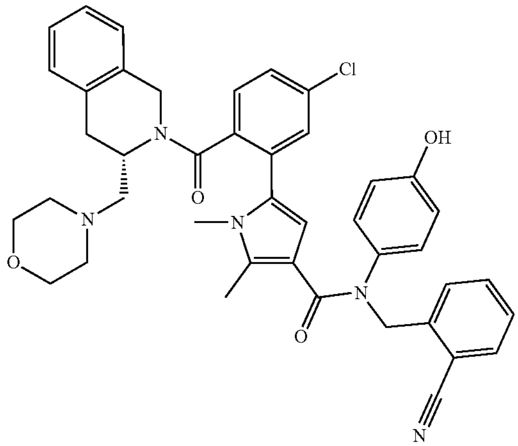 [SMILES: Cc1c(C(=O)N(Cc2ccccc2C#N)c2ccc(O)cc2)cc(-c2cc(Cl)ccc2C(=O)N2Cc3ccccc3C[C@H]2CN2CCOCC2)n1C] | 5-[5-chloro-2-[(3S)-3-(morpholinomethyl)-3,4-dihydro-1H-isoquinoline-2-carbonyl]phenyl]-N-[(2-cyanophenyl)methyl]-N-(4-hydroxyphenyl)-1,2-dimethyl-pyrrole-3-carboxamide |
| 7 | 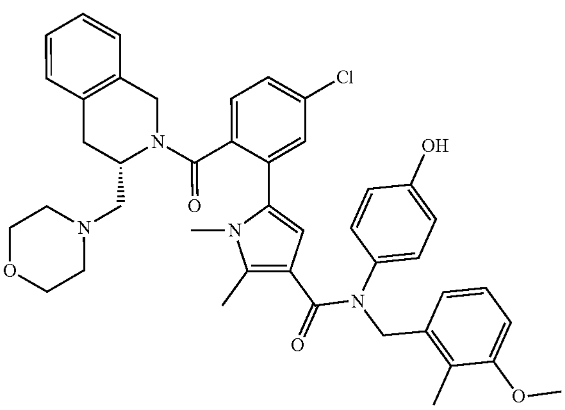 | 5-[5-chloro-2-[(3S)-3-(morpholinomethyl)-3,4-dihydro-1H-isoquinoline-2-carbonyl]phenyl]-N-(4-hydroxyphenyl)-N-[(3-methoxy-2-methyl-phenyl)methyl]-1,2-dimethyl-pyrrole-3-carboxamide |
| 8 | 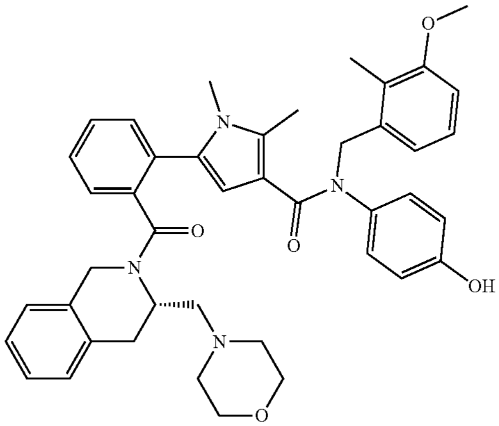 [SMILES: COc1cccc(CN(C(=O)c2cc(-c3ccccc3C(=O)N3Cc4ccccc4C[C@H]3CN3CCOCC3)n(C)c2C)c2ccc(O)cc2)c1C] | N-(4-hydroxyphenyl)-N-[(3-methoxy-2-methyl-phenyl)methyl]-1,2-dimethyl-5-[2-[(3S)-3-(morpholinomethyl)-3,4-dihydro-1H-isoquinoline-2-carbonyl]phenyl]pyrrole-3-carboxamide |

-continued

| Cmpd # | Structure | IUPAC name |
| --- | --- | --- |
| 9 | 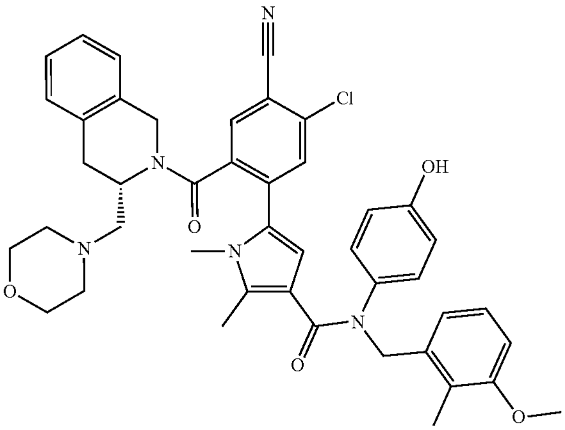 [SMILES: COc1cccc(CN(C(=O)c2cc(-c3cc(Cl)c(C#N)cc3C(=O)N3Cc4ccccc4C[C@H]3CN3CCOCC3)n(C)c2C)c2ccc(O)cc2)c1C] | 5-[5-chloro-4-cyano-2-[(3S)-3-(morpholinomethyl)-3,4-dihydro-1H-isoquinoline-2-carbonyl]phenyl]-N-(4-hydroxyphenyl)-N-[(3-methoxy-2-methyl-phenyl)methyl]-1,2-dimethyl-pyrrole-3-carboxamide |
| 10 | 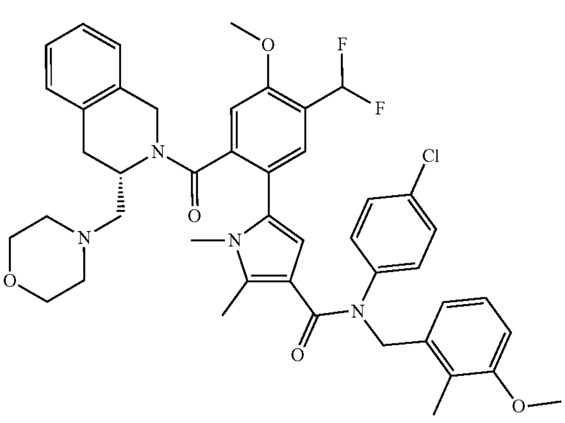 [SMILES: COc1cc(C(=O)N2Cc3ccccc3C[C@H]2CN2CCOCC2)c(-c2cc(C(=O)N(Cc3cccc(OC)c3C)c3ccc(Cl)cc3)c(C)n2C)cc1C(F)F] | N-(4-chlorophenyl)-5-[5-(difluoromethyl)-4-methoxy-2-[(3S)-3-(morpholinomethyl)-3,4-dihydro-1H-isoquinoline-2-carbonyl]phenyl]-N-[(3-methoxy-2-methyl-phenyl)methyl]-1,2-dimethyl-pyrrole-3-carboxamide |
| 11 | 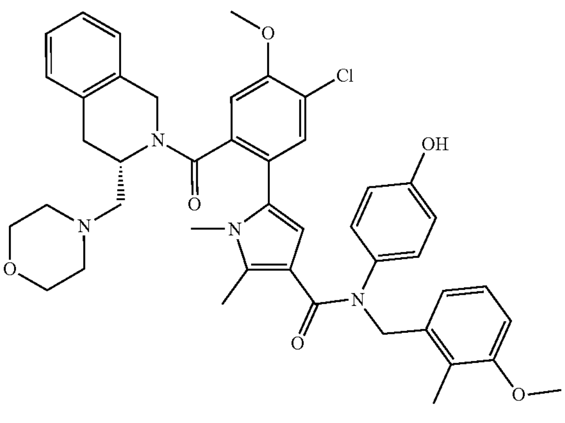 [SMILES: COc1cc(C(=O)N2Cc3ccccc3C[C@H]2CN2CCOCC2)c(-c2cc(C(=O)N(Cc3cccc(OC)c3C)c3ccc(O)cc3)c(C)n2C)cc1Cl] | 5-[5-chloro-4-methoxy-2-[(3S)-3-(morpholinomethyl)-3,4-dihydro-1H-isoquinoline-2-carbonyl]phenyl]-N-(4-hydroxyphenyl)-N-[(3-methoxy-2-methyl-phenyl)methyl]-1,2-dimethyl-pyrrole-3-carboxamide |

-continued

| Cmpd # | Structure | IUPAC name |
| --- | --- | --- |
| 12 | 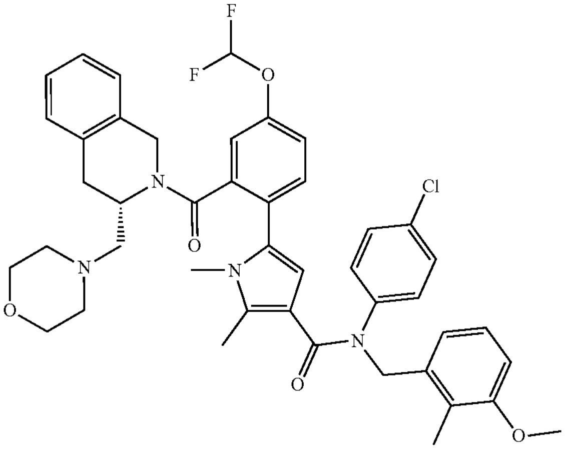 [SMILES: COc1cccc(CN(C(=O)c2cc(-c3ccc(OC(F)F)cc3C(=O)N3Cc4ccccc4C[C@H]3CN3CCOCC3)n(C)c2C)c2ccc(Cl)cc2)c1C] | N-(4-chlorophenyl)-5-[4-(difluoromethoxy)-2-[(3S)-3-(morpholinomethyl)-3,4-dihydro-1H-isoquinoline-2-carbonyl]phenyl]-N-[(3-methoxy-2-methyl-phenyl)methyl]-1,2-dimethyl-pyrrole-3-carboxamide |
| 13 | 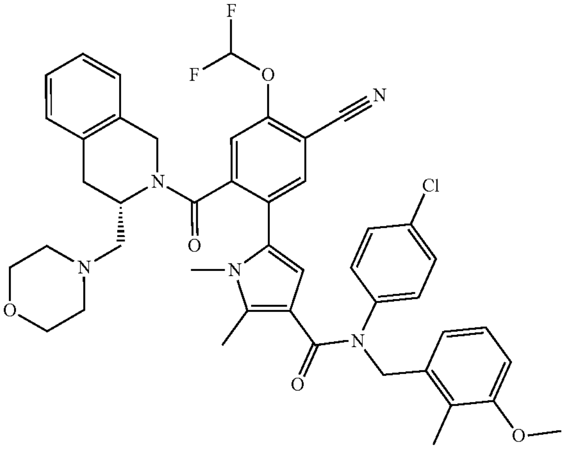 [SMILES: COc1cccc(CN(C(=O)c2cc(-c3cc(C#N)c(OC(F)F)cc3C(=O)N3Cc4ccccc4C[C@H]3CN3CCOCC3)n(C)c2C)c2ccc(Cl)cc2)c1C] | N-(4-chlorophenyl)-5-[5-cyano-4-(difluoromethoxy)-2-[(3S)-3-(morpholinomethyl)-3,4-dihydro-1H-isoquinoline-2-carbonyl]phenyl]-N-[(3-methoxy-2-methyl-phenyl)methyl]-1,2-dimethyl-pyrrole-3-carboxamide |
| 14 | 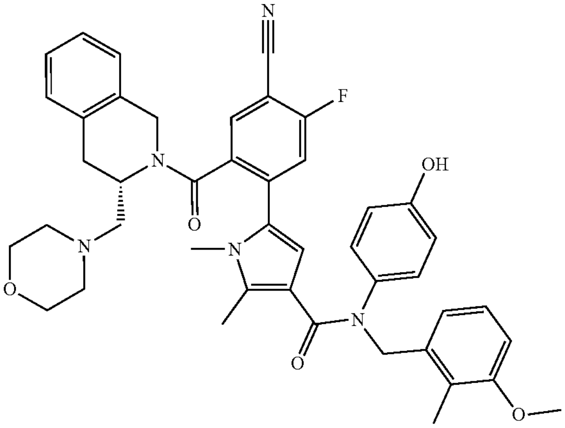 [SMILES: COc1cccc(CN(C(=O)c2cc(-c3cc(F)c(C#N)cc3C(=O)N3Cc4ccccc4C[C@H]3CN3CCOCC3)n(C)c2C)c2ccc(O)cc2)c1C] | 5-[4-cyano-5-fluoro-2-[(3S)-3-(morpholinomethyl)-3,4-dihydro-1H-isoquinoline-2-carbonyl]phenyl]-N-(4-hydroxyphenyl)-N-[(3-methoxy-2-methyl-phenyl)methyl]-1,2-dimethyl-pyrrole-3-carboxamide |

-continued

| Cmpd # | Structure | IUPAC name |
|---|---|---|
| 15 | 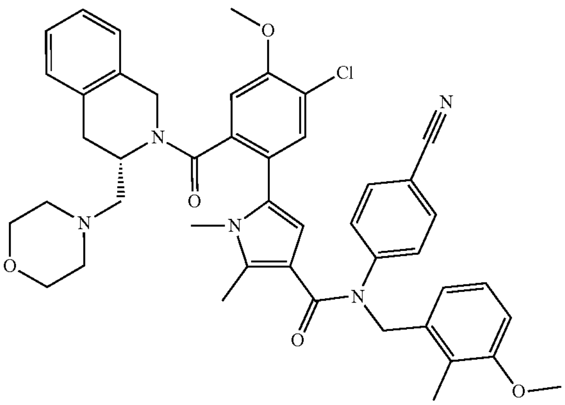 [SMILES: COc1cc(C(=O)N2Cc3ccccc3C[C@H]2CN2CCOCC2)c(-c2cc(C(=O)N(Cc3cccc(OC)c3C)c3ccc(C#N)cc3)c(C)n2C)cc1Cl] | 5-[5-chloro-4-methoxy-2-[(3S)-3-(morpholinomethyl)-3,4-dihydro-1H-isoquinoline-2-carbonyl]phenyl]-N-(4-cyanophenyl)-N-[(3-methoxy-2-methyl-phenyl)methyl]-1,2-dimethyl-pyrrole-3-carboxamide |
| 16 | 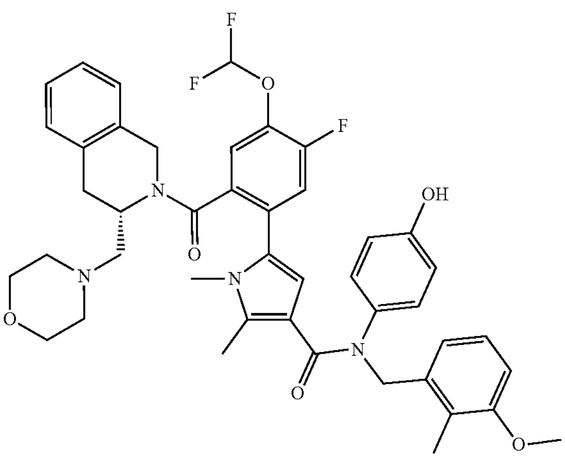 | 5-[4-(difluoromethoxy)-5-fluoro-2-[(3S)-3-(morpholinomethyl)-3,4-dihydro-1H-isoquinoline-2-carbonyl]phenyl]-N-(4-hydroxyphenyl)-N-[(3-methoxy-2-methyl-phenyl)methyl]-1,2-dimethyl-pyrrole-3-carboxamide |
| 17 | 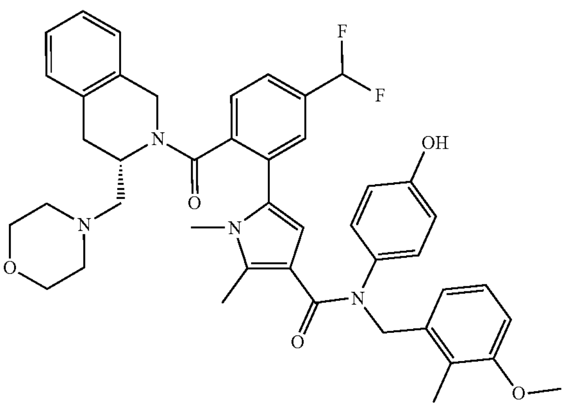 [SMILES: COc1cccc(CN(C(=O)c2cc(-c3cc(C(F)F)ccc3C(=O)N3Cc4ccccc4C[C@H]3CN3CCOCC3)n(C)c2C)c2ccc(O)cc2)c1C] | 5-[5-(difluoromethyl)-2-[(3S)-3-(morpholinomethyl)-3,4-dihydro-1H-isoquinoline-2-carbonyl]phenyl]-N-(4-hydroxyphenyl)-N-[(3-methoxy-2-methyl-phenyl)methyl]-1,2-dimethyl-pyrrole-3-carboxamide |

-continued

| Cmpd # | Structure | IUPAC name |
|---|---|---|
| 18 | 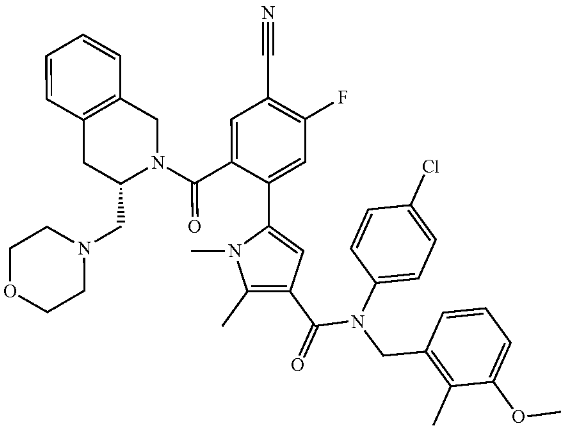 [SMILES: COc1cccc(CN(C(=O)c2cc(-c3cc(F)c(C#N)cc3C(=O)N3Cc4ccccc4C[C@H]3CN3CCOCC3)n(C)c2C)c2ccc(Cl)cc2)c1C] | N-(4-chlorophenyl)-5-[4-cyano-5-fluoro-2-[(3S)-3-(morpholinomethyl)-3,4-dihydro-1H-isoquinoline-2-carbonyl]phenyl]-N-[(3-methoxy-2-methyl-phenyl)methyl]-1,2-dimethyl-pyrrole-3-carboxamide |
| 19 | 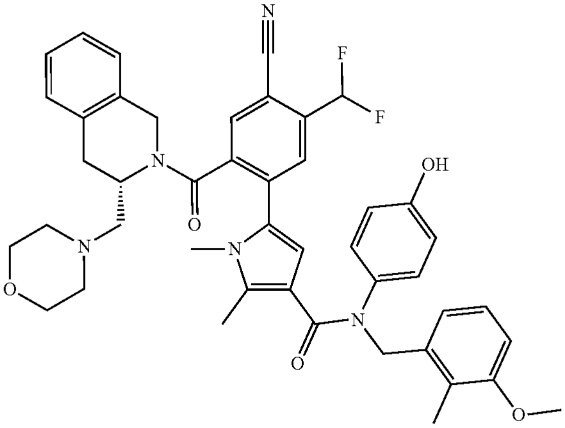 [SMILES: COc1cccc(CN(C(=O)c2cc(-c3cc(C(F)F)c(C#N)cc3C(=O)N3Cc4ccccc4C[C@H]3CN3CCOCC3)n(C)c2C)c2ccc(O)cc2)c1C] | 5-[4-cyano-5-(difluoromethyl)-2-[(3S)-3-(morpholinomethyl)-3,4-dihydro-1H-isoquinoline-2-carbonyl]phenyl]-N-(4-hydroxyphenyl)-N-[(3-methoxy-2-methyl-phenyl)methyl]-1,2-dimethyl-pyrrole-3-carboxamide |
| 20 | 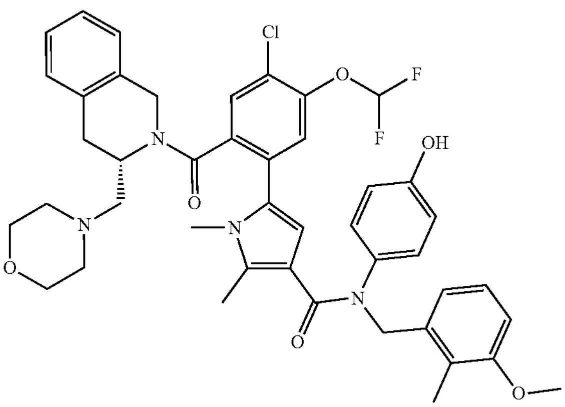 | 5-[4-chloro-5-(difluoromethoxy)-2-[(3S)-3-(morpholinomethyl)-3,4-dihydro-1H-isoquinoline-2-carbonyl]phenyl]-N-(4-hydroxyphenyl)-N-[(3-methoxy-2-methyl-phenyl)methyl]-1,2-dimethyl-pyrrole-3-carboxamide |

-continued

| Cmpd # | Structure | IUPAC name |
| --- | --- | --- |
| 21 | 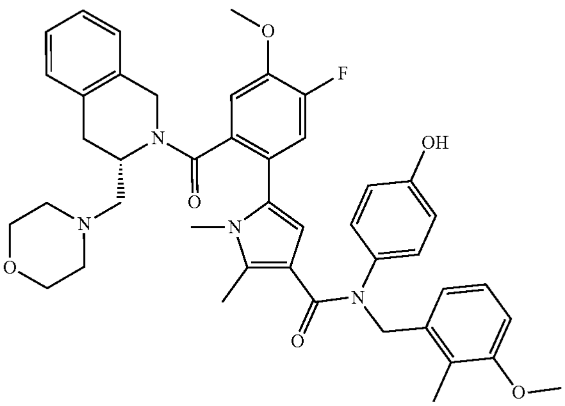 [SMILES: COc1cc(C(=O)N2Cc3ccccc3C[C@H]2CN2CCOCC2)c(-c2cc(C(=O)N(Cc3cccc(OC)c3C)c3ccc(O)cc3)c(C)n2C)cc1F] | 5-[5-fluoro-4-methoxy-2-[(3S)-3-(morpholinomethyl)-3,4-dihydro-1H-isoquinoline-2-carbonyl]phenyl]-N-(4-hydroxyphenyl)-N-[(3-methoxy-2-methyl-phenyl)methyl]-1,2-dimethyl-pyrrole-3-carboxamide |
| 22 | 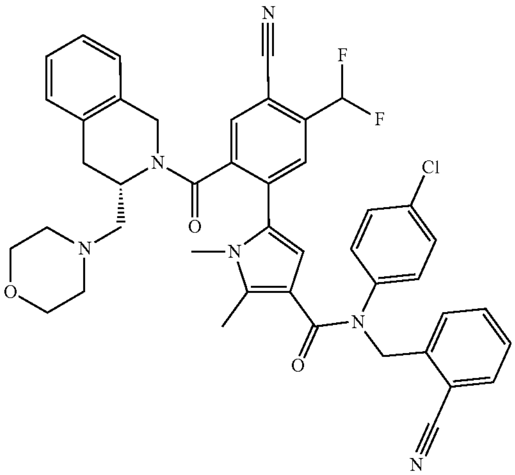 [SMILES: Cc1c(C(=O)N(Cc2ccccc2C#N)c2ccc(Cl)cc2)cc(-c2cc(C(F)F)c(C#N)cc2C(=O)N2Cc3ccccc3C[C@H]2CN2CCOCC2)n1C] | N-(4-chlorophenyl)-5-[4-cyano-5-(difluoromethyl)-2-[(3S)-3-(morpholinomethyl)-3,4-dihydro-1H-isoquinoline-2-carbonyl]phenyl]-N-[(2-cyanophenyl)methyl]-1,2-dimethyl-pyrrole-3-carboxamide |
| 23 | 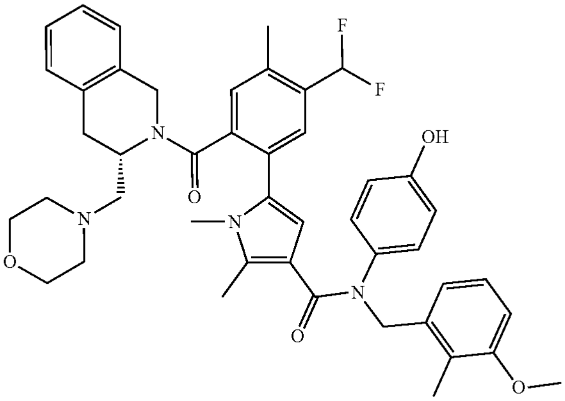 [SMILES: COc1cccc(CN(C(=O)c2cc(-c3cc(C(F)F)c(C)cc3C(=O)N3Cc4ccccc4C[C@H]3CN3CCOCC3)n(C)c2C)c2ccc(O)cc2)c1C] | 5-[5-(difluoromethyl)-4-methyl-2-[(3S)-3-(morpholinomethyl)-3,4-dihydro-1H-isoquinoline-2-carbonyl]phenyl]-N-(4-hydroxyphenyl)-N-[(3-methoxy-2-methyl-phenyl)methyl]-1,2-dimethyl-pyrrole-3-carboxamide |

-continued

| Cmpd # | Structure | IUPAC name |
|---|---|---|
| 24 | 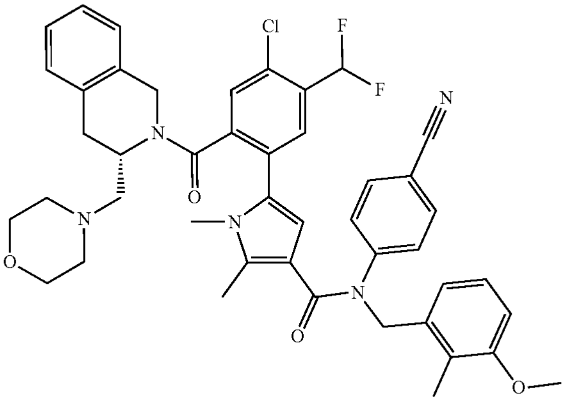 | 5-[4-chloro-5-(difluoromethyl)-2-[(3S)-3-(morpholinomethyl)-3,4-dihydro-1H-isoquinoline-2-carbonyl]phenyl]-N-(4-cyanophenyl)-N-[(3-methoxy-2-methyl-phenyl)methyl]-1,2-dimethyl-pyrrole-3-carboxamide |
| 25 | 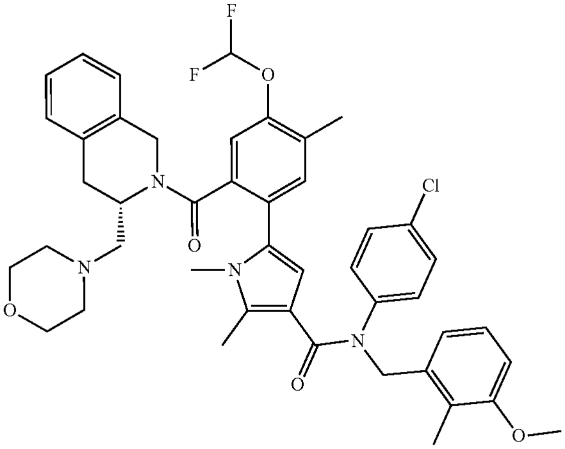 [SMILES: COc1cccc(CN(C(=O)c2cc(-c3cc(C)c(OC(F)F)cc3C(=O)N3Cc4ccccc4C[C@H]3CN3CCOCC3)n(C)c2C)c2ccc(Cl)cc2)c1C] | N-(4-chlorophenyl)-5-[4-(difluoromethoxy)-5-methyl-2-[(3S)-3-(morpholinomethyl)-3,4-dihydro-1H-isoquinoline-2-carbonyl]phenyl]-N-[(3-methoxy-2-methyl-phenyl)methyl]-1,2-dimethyl-pyrrole-3-carboxamide |
| 26 | 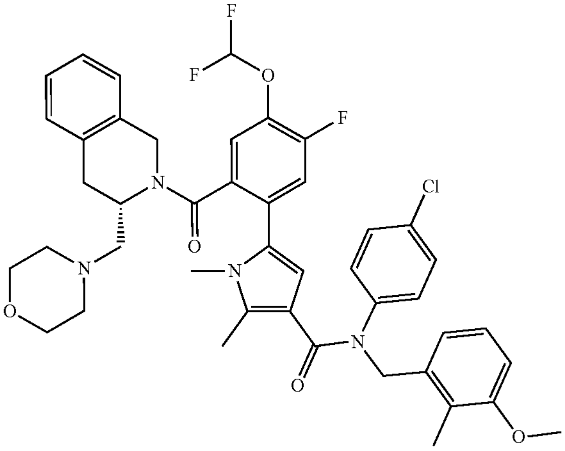 [SMILES: COc1cccc(CN(C(=O)c2cc(-c3cc(F)c(OC(F)F)cc3C(=O)N3Cc4ccccc4C[C@H]3CN3CCOCC3)n(C)c2C)c2ccc(Cl)cc2)c1C] | N-(4-chlorophenyl)-5-[4-(difluoromethoxy)-5-fluoro-2-[(3S)-3-(morpholinomethyl)-3,4-dihydro-1H-isoquinoline-2-carbonyl]phenyl]-N-[(3-methoxy-2-methyl-phenyl)methyl]-1,2-dimethyl-pyrrole-3-carboxamide |

-continued

| Cmpd # | Structure | IUPAC name |
|---|---|---|
| 27 | 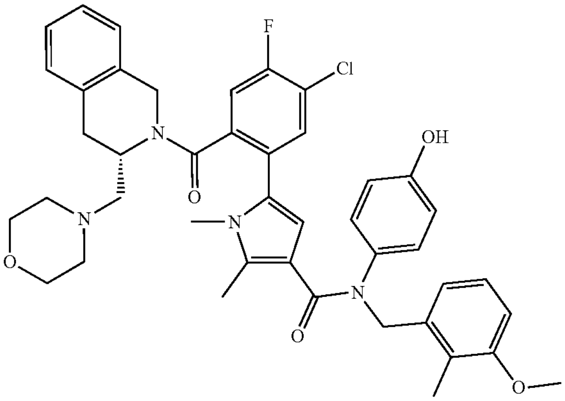 | 5-[5-chloro-4-fluoro-2-[(3S)-3-(morpholinomethyl)-3,4-dihydro-1H-isoquinoline-2-carbonyl]phenyl]-N-(4-hydroxyphenyl)-N-[(3-methoxy-2-methyl-phenyl)methyl]-1,2-dimethyl-pyrrole-3-carboxamide |
| 28 | 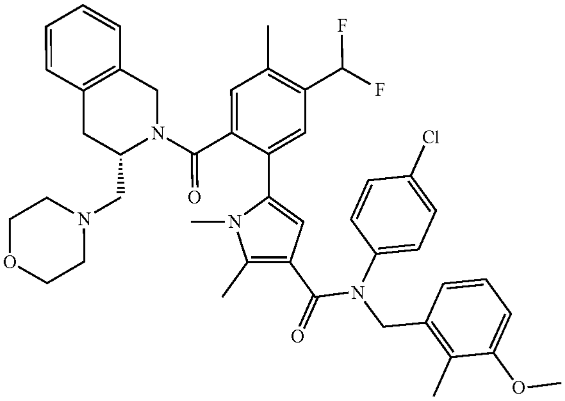 [SMILES: COc1cccc(CN(C(=O)c2cc(-c3cc(C(F)F)c(C)cc3C(=O)N3Cc4ccccc4C[C@H]3CN3CCOCC3)n(C)c2C)c2ccc(Cl)cc2)c1C] | N-(4-chlorophenyl)-5-[5-(difluoromethyl)-4-methyl-2-[(3S)-3-(morpholinomethyl)-3,4-dihydro-1H-isoquinoline-2-carbonyl]phenyl]-N-[(3-methoxy-2-methyl-phenyl)methyl]-1,2-dimethyl-pyrrole-3-carboxamide |
| 29 | 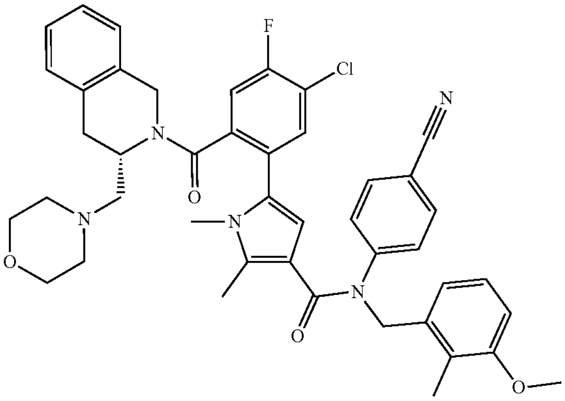 [SMILES: COc1cccc(CN(C(=O)c2cc(-c3cc(Cl)c(F)cc3C(=O)N3Cc4ccccc4C[C@H]3CN3CCOCC3)n(C)c2C)c2ccc(C#N)cc2)c1C] | 5-[5-chloro-4-fluoro-2-[(3S)-3-(morpholinomethyl)-3,4-dihydro-1H-isoquinoline-2-carbonyl]phenyl]-N-(4-cyanophenyl)-N-[(3-methoxy-2-methyl-phenyl)methyl]-1,2-dimethyl-pyrrole-3-carboxamide |

-continued

| Cmpd # | Structure | IUPAC name |
|---|---|---|
| 30 | 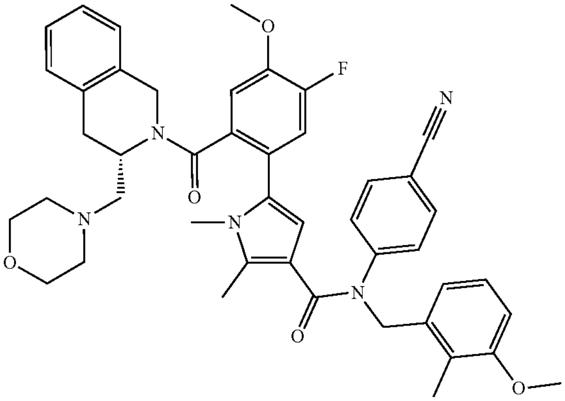 [SMILES: COc1cc(C(=O)N2Cc3ccccc3C[C@H]2CN2CCOCC2)c(-c2cc(C(=O)N(Cc3cccc(OC)c3C)c3ccc(C#N)cc3)c(C)n2C)cc1F] | N-(4-cyanophenyl)-5-[5-fluoro-4-methoxy-2-[(3S)-3-(morpholinomethyl)-3,4-dihydro-1H-isoquinoline-2-carbonyl]phenyl]-N-[(3-methoxy-2-methyl-phenyl)methyl]-1,2-dimethyl-pyrrole-3-carboxamide |
| 31 | 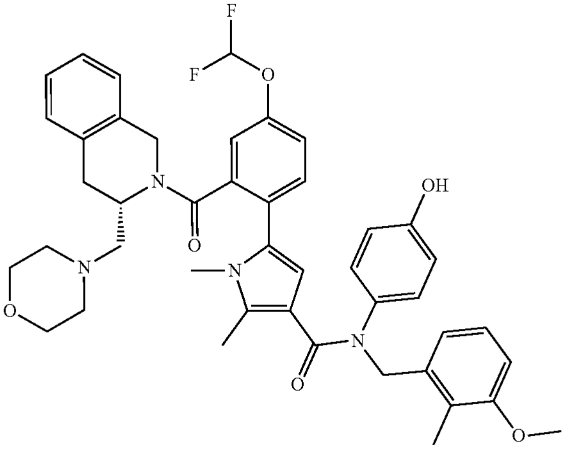 | 5-[4-(difluoromethoxy)-2-[(3S)-3-(morpholinomethyl)-3,4-dihydro-1H-isoquinoline-2-carbonyl]phenyl]-N-(4-hydroxyphenyl)-N-[(3-methoxy-2-methyl-phenyl)methyl]-1,2-dimethyl-pyrrole-3-carboxamide |
| 32 | 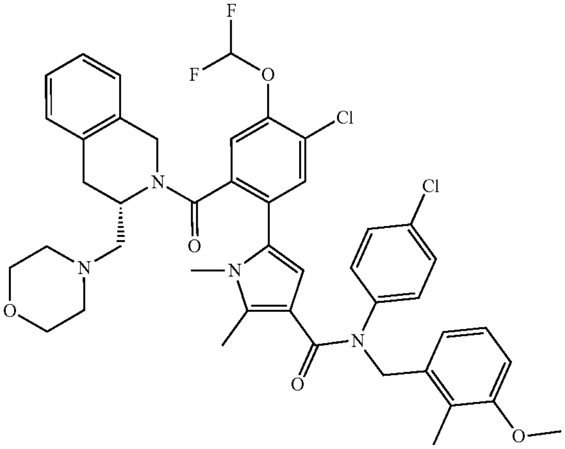 | 5-[5-chloro-4-(difluoromethoxy)-2-[(3S)-3-(morpholinomethyl)-3,4-dihydro-1H-isoquinoline-2-carbonyl]phenyl]-N-(4-chlorophenyl)-N-[(3-methoxy-2-methyl-phenyl)methyl]-1,2-dimethyl-pyrrole-3-carboxamide |

-continued

| Cmpd # | Structure | IUPAC name |
| --- | --- | --- |
| 33 | 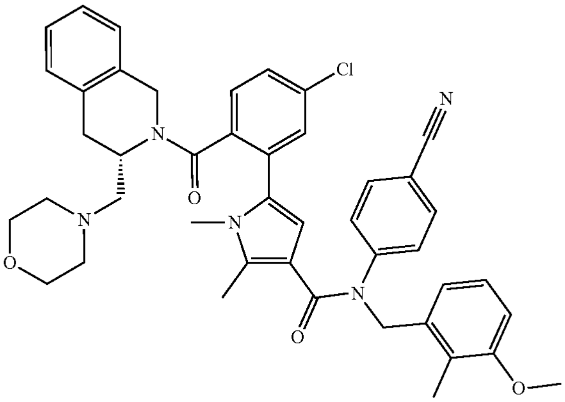 [SMILES: COc1cccc(CN(C(=O)c2cc(-c3cc(Cl)ccc3C(=O)N3Cc4ccccc4C[C@H]3CN3CCOCC3)n(C)c2C)c2ccc(C#N)cc2)c1C] | 5-[5-chloro-2-[(3S)-3-(morpholinomethyl)-3,4-dihydro-1H-isoquinoline-2-carbonyl]phenyl]-N-(4-cyanophenyl)-N-[(3-methoxy-2-methyl-phenyl)methyl]-1,2-dimethyl-pyrrole-3-carboxamide |
| 34 | 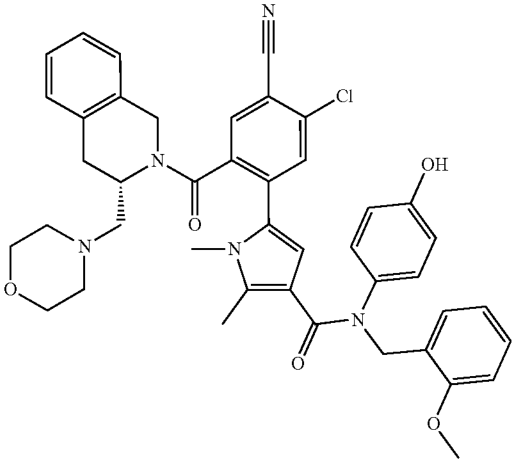 [SMILES: COc1ccccc1CN(C(=O)c1cc(-c2cc(Cl)c(C#N)cc2C(=O)N2Cc3ccccc3C[C@H]2CN2CCOCC2)n(C)c1C)c1ccc(O)cc1] | 5-[5-chloro-4-cyano-2-[(3S)-3-(morpholinomethyl)-3,4-dihydro-1H-isoquinoline-2-carbonyl]phenyl]-N-(4-hydroxyphenyl)-N-[(2-methoxyphenyl)methyl]-1,2-dimethyl-pyrrole-3-carboxamide |
| 35 | 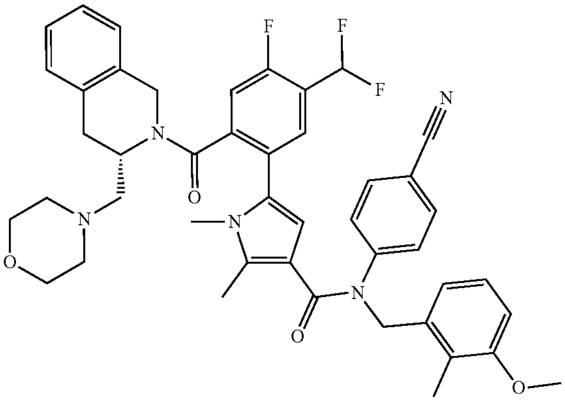 [SMILES: COc1cccc(CN(C(=O)c2cc(-c3cc(C(F)F)c(F)cc3C(=O)N3Cc4ccccc4C[C@H]3CN3CCOCC3)n(C)c2C)c2ccc(C#N)cc2)c1C] | N-(4-cyanophenyl)-5-[5-(difluoromethyl)-4-fluoro-2-[(3S)-3-(morpholinomethyl)-3,4-dihydro-1H-isoquinoline-2-carbonyl]phenyl]-N-[(3-methoxy-2-methyl-phenyl)methyl]-1,2-dimethyl-pyrrole-3-carboxamide |

-continued

| Cmpd # | Structure | IUPAC name |
| --- | --- | --- |
| 36 | 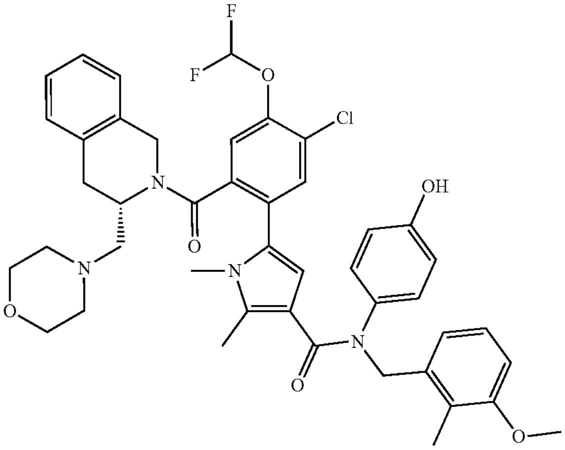 | 5-[5-chloro-4-(difluoromethoxy)-2-[(3S)-3-(morpholinomethyl)-3,4-dihydro-1H-isoquinoline-2-carbonyl]phenyl]-N-(4-hydroxyphenyl)-N-[(3-methoxy-2-methyl-phenyl)methyl]-1,2-dimethyl-pyrrole-3-carboxamide |
| 37 | 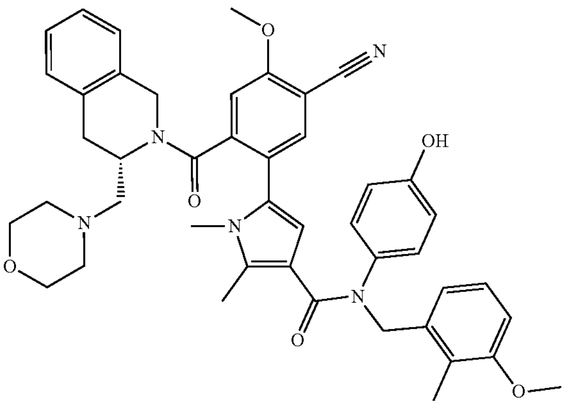 [SMILES: COc1cc(C(=O)N2Cc3ccccc3C[C@H]2CN2CCOCC2)c(-c2cc(C(=O)N(Cc3cccc(OC)c3C)c3ccc(O)cc3)c(C)n2C)cc1C#N] | 5-[5-cyano-4-methoxy-2-[(3S)-3-(morpholinomethyl)-3,4-dihydro-1H-isoquinoline-2-carbonyl]phenyl]-N-(4-hydroxyphenyl)-N-[(3-methoxy-2-methyl-phenyl)methyl]-1,2-dimethyl-pyrrole-3-carboxamide |
| 38 | 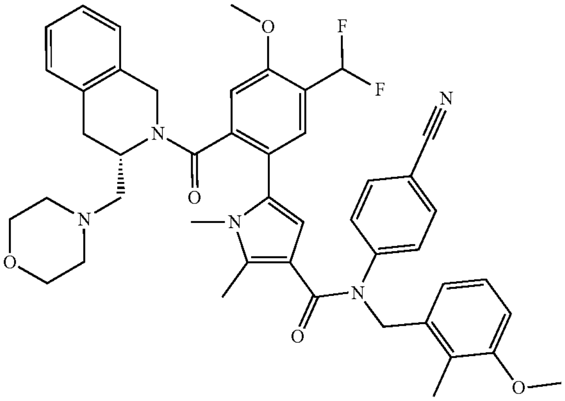 [SMILES: COc1cc(C(=O)N2Cc3ccccc3C[C@H]2CN2CCOCC2)c(-c2cc(C(=O)N(Cc3cccc(OC)c3C)c3ccc(C#N)cc3)c(C)n2C)cc1C(F)F] | N-(4-cyanophenyl)-5-[5-(difluoromethyl)-4-methoxy-2-[(3S)-3-(morpholinomethyl)-3,4-dihydro-1H-isoquinoline-2-carbonyl]phenyl]-N-[(3-methoxy-2-methyl-phenyl)methyl]-1,2-dimethyl-pyrrole-3-carboxamide |

-continued

| Cmpd # | Structure | IUPAC name |
|---|---|---|
| 39 | 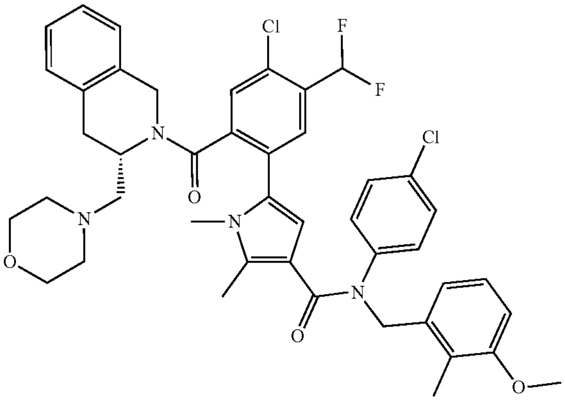 [SMILES: COc1cccc(CN(C(=O)c2cc(-c3cc(C(F)F)c(Cl)cc3C(=O)N3Cc4ccccc4C[C@H]3CN3CCOCC3)n(C)c2C)c2ccc(Cl)cc2)c1C] | 5-[4-chloro-5-(difluoromethyl)-2-[(3S)-3-(morpholinomethyl)-3,4-dihydro-1H-isoquinoline-2-carbonyl]phenyl]-N-(4-chlorophenyl)-N-[(3-methoxy-2-methyl-phenyl)methyl]-1,2-dimethyl-pyrrole-3-carboxamide |
| 40 | 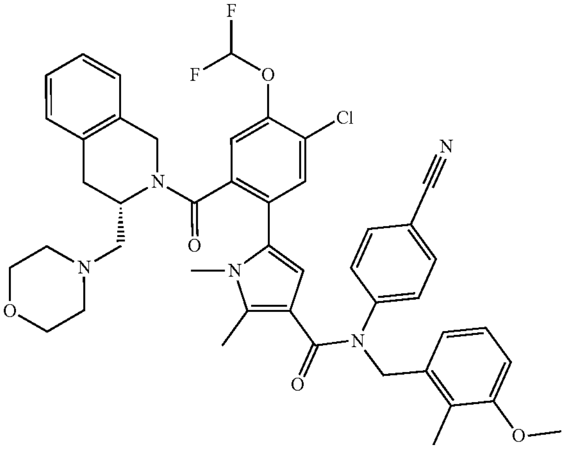 [SMILES: COc1cccc(CN(C(=O)c2cc(-c3cc(Cl)c(OC(F)F)cc3C(=O)N3Cc4ccccc4C[C@H]3CN3CCOCC3)n(C)c2C)c2ccc(C#N)cc2)c1C] | 5-[5-chloro-4-(difluoromethoxy)-2-[(3S)-3-(morpholinomethyl)-3,4-dihydro-1H-isoquinoline-2-carbonyl]phenyl]-N-(4-cyanophenyl)-N-[(3-methoxy-2-methyl-phenyl)methyl]-1,2-dimethyl-pyrrole-3-carboxamide |
| 41 | 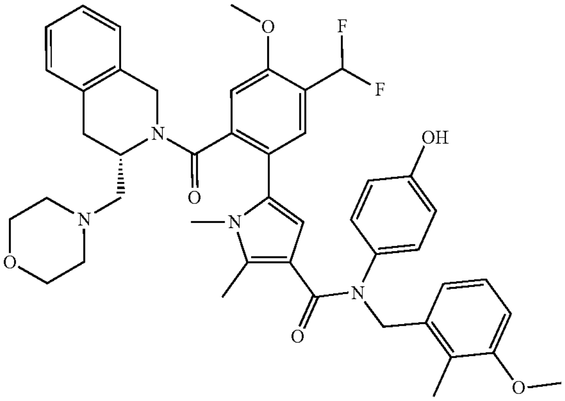 [SMILES: COc1cc(C(=O)N2Cc3ccccc3C[C@H]2CN2CCOCC2)c(-c2cc(C(=O)N(Cc3cccc(OC)c3C)c3ccc(O)cc3)c(C)n2C)cc1C(F)F] | 5-[5-(difluoromethyl)-4-methoxy-2-[(3S)-3-(morpholinomethyl)-3,4-dihydro-1H-isoquinoline-2-carbonyl]phenyl]-N-(4-hydroxyphenyl)-N-[(3-methoxy-2-methyl-phenyl)methyl]-1,2-dimethyl-pyrrole-3-carboxamide |

-continued

| Cmpd # | Structure | IUPAC name |
|---|---|---|
| 42 | 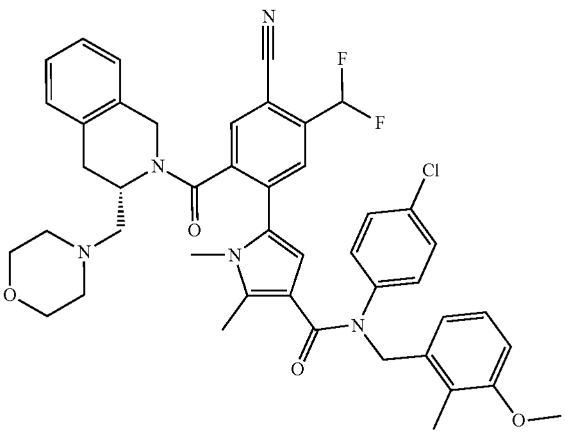 [SMILES: COc1cccc(CN(C(=O)c2cc(-c3cc(C(F)F)c(C#N)cc3C(=O)N3Cc4ccccc4C[C@H]3CN3CCOCC3)n(C)c2C)c2ccc(Cl)cc2)c1C] | N-(4-chlorophenyl)-5-[4-cyano-5-(difluoromethyl)-2-[(3S)-3-(morpholinomethyl)-3,4-dihydro-1H-isoquinoline-2-carbonyl]phenyl]-N-[(3-methoxy-2-methyl-phenyl)methyl]-1,2-dimethyl-pyrrole-3-carboxamide |
| 43 | 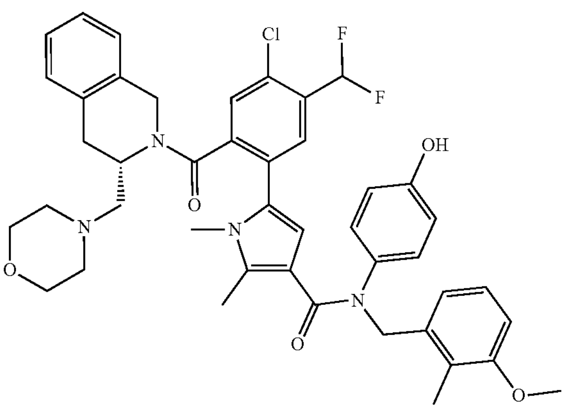 [SMILES: COc1cccc(CN(C(=O)c2cc(-c3cc(C(F)F)c(Cl)cc3C(=O)N3Cc4ccccc4C[C@H]3CN3CCOCC3)n(C)c2C)c2ccc(O)cc2)c1C] | 5-[4-chloro-5-(difluoromethyl)-2-[(3S)-3-(morpholinomethyl)-3,4-dihydro-1H-isoquinoline-2-carbonyl]phenyl]-N-(4-hydroxyphenyl)-N-[(3-methoxy-2-methyl-phenyl)methyl]-1,2-dimethyl-pyrrole-3-carboxamide |
| 44 | 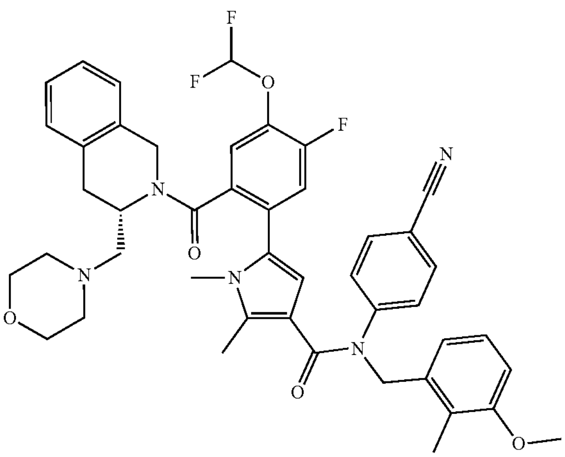 [SMILES: COc1cccc(CN(C(=O)c2cc(-c3cc(F)c(OC(F)F)cc3C(=O)N3Cc4ccccc4C[C@H]3CN3CCOCC3)n(C)c2C)c2ccc(C#N)cc2)c1C] | N-(4-cyanophenyl)-5-[4-(difluoromethoxy)-5-fluoro-2-[(3S)-3-(morpholinomethyl)-3,4-dihydro-1H-isoquinoline-2-carbonyl]phenyl]-N-[(3-methoxy-2-methyl-phenyl)methyl]-1,2-dimethyl-pyrrole-3-carboxamide |

-continued

| Cmpd # | Structure | IUPAC name |
|---|---|---|
| 45 | 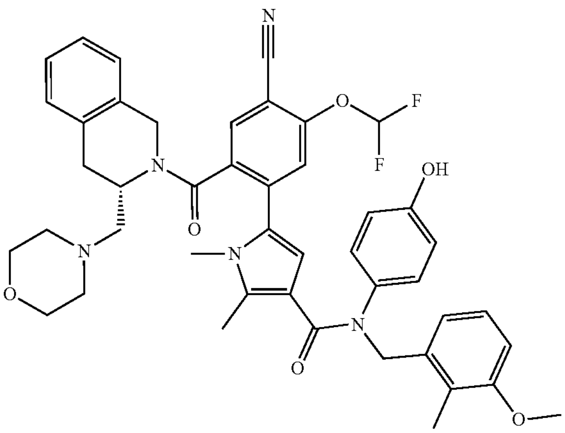 [SMILES: COc1cccc(CN(C(=O)c2cc(-c3cc(OC(F)F)c(C#N)cc3C(=O)N3Cc4ccccc4C[C@H]3CN3CCOCC3)n(C)c2C)c2ccc(O)cc2)c1C] | 5-[4-cyano-5-(difluoromethoxy)-2-[(3S)-3-(morpholinomethyl)-3,4-dihydro-1H-isoquinoline-2-carbonyl]phenyl]-N-(4-hydroxyphenyl)-N-[(3-methoxy-2-methyl-phenyl)methyl]-1,2-dimethyl-pyrrole-3-carboxamide |
| 46 | 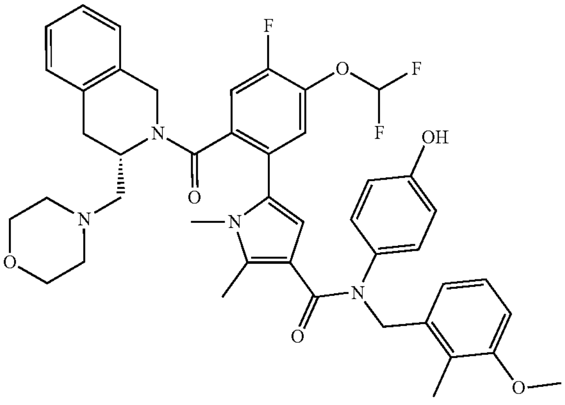 [SMILES: COc1cccc(CN(C(=O)c2cc(-c3cc(OC(F)F)c(F)cc3C(=O)N3Cc4ccccc4C[C@H]3CN3CCOCC3)n(C)c2C)c2ccc(O)cc2)c1C] | 5-[5-(difluoromethoxy)-4-fluoro-2-[(3S)-3-(morpholinomethyl)-3,4-dihydro-1H-isoquinoline-2-carbonyl]phenyl]-N-(4-hydroxyphenyl)-N-[(3-methoxy-2-methyl-phenyl)methyl]-1,2-dimethyl-pyrrole-3-carboxamide |
| 47 | 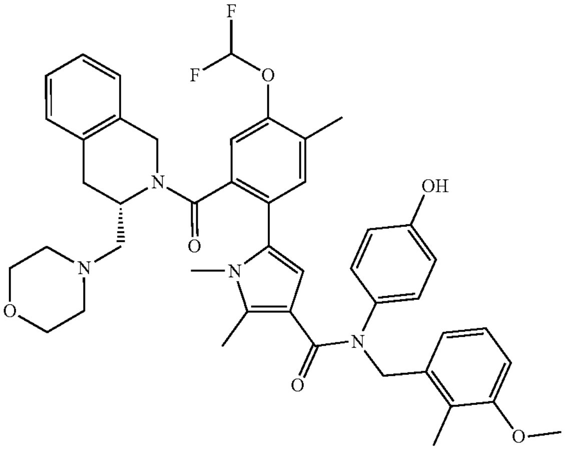 [SMILES: COc1cccc(CN(C(=O)c2cc(-c3cc(C)c(OC(F)F)cc3C(=O)N3Cc4ccccc4C[C@H]3CN3CCOCC3)n(C)c2C)c2ccc(O)cc2)c1C] | 5-[4-(difluoromethoxy)-5-methyl-2-[(3S)-3-(morpholinomethyl)-3,4-dihydro-1H-isoquinoline-2-carbonyl]phenyl]-N-(4-hydroxyphenyl)-N-[(3-methoxy-2-methyl-phenyl)methyl]-1,2-dimethyl-pyrrole-3-carboxamide |

-continued

| Cmpd # | Structure | IUPAC name |
|---|---|---|
| 48 | 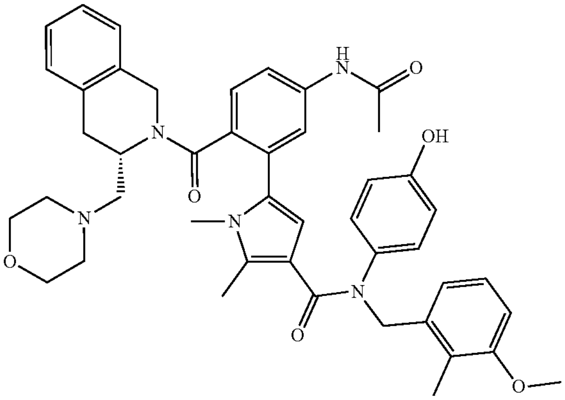 [SMILES: COc1cccc(CN(C(=O)c2cc(-c3cc(NC(C)=O)ccc3C(=O)N3Cc4ccccc4C[C@H]3CN3CCOCC3)n(C)c2C)c2ccc(O)cc2)c1C] | 5-[5-acetamido-2-[(3S)-3-(morpholinomethyl)-3,4-dihydro-1H-isoquinoline-2-carbonyl]phenyl]-N-(4-hydroxyphenyl)-N-[(3-methoxy-2-methyl-phenyl)methyl]-1,2-dimethyl-pyrrole-3-carboxamide |
| 49 | 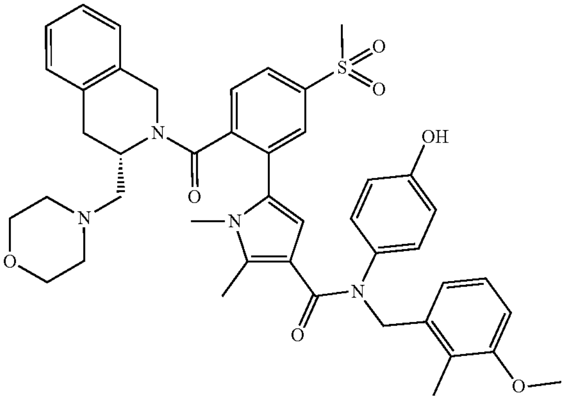 [SMILES: COc1cccc(CN(C(=O)c2cc(-c3cc(S(C)(=O)=O)ccc3C(=O)N3Cc4ccccc4C[C@H]3CN3CCOCC3)n(C)c2C)c2ccc(O)cc2)c1C] | N-(4-hydroxyphenyl)-N-[(3-methoxy-2-methyl-phenyl)methyl]-1,2-dimethyl-5-[5-methylsulfonyl-2-[(3S)-3-(morpholinomethyl)-3,4-dihydro-1H-isoquinoline-2-carbonyl]phenyl]pyrrole-3-carboxamide |
| 50 | 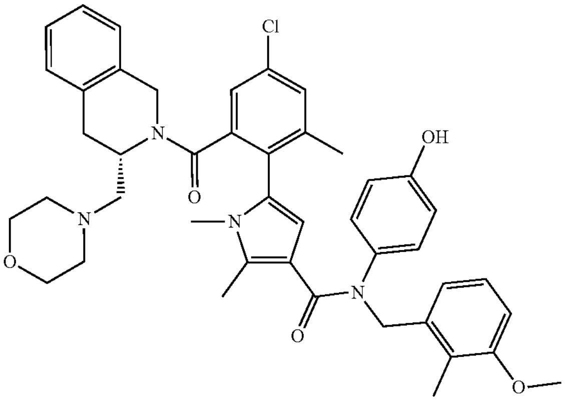 [SMILES: COc1cccc(CN(C(=O)c2cc(-c3c(C)cc(Cl)cc3C(=O)N3Cc4ccccc4C[C@H]3CN3CCOCC3)n(C)c2C)c2ccc(O)cc2)c1C] | 5-[4-chloro-2-methyl-6-[(3S)-3-(morpholinomethyl)-3,4-dihydro-1H-isoquinoline-2-carbonyl]phenyl]-N-(4-hydroxyphenyl)-N-[(3-methoxy-2-methyl-phenyl)methyl]-1,2-dimethyl-pyrrole-3-carboxamide |

-continued

| Cmpd # | Structure | IUPAC name |
|---|---|---|
| 51 | 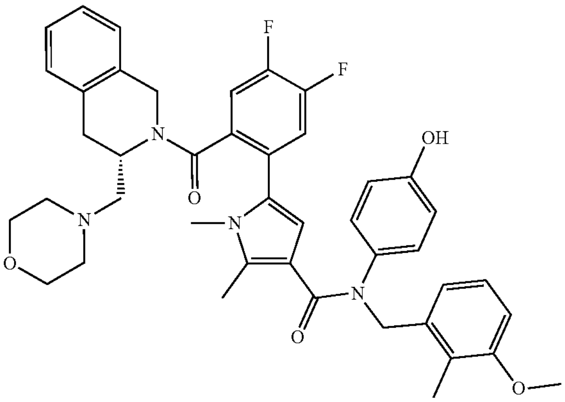 [SMILES: COc1cccc(CN(C(=O)c2cc(-c3cc(F)c(F)cc3C(=O)N3Cc4ccccc4C[C@H]3CN3CCOCC3)n(C)c2C)c2ccc(O)cc2)c1C] | 5-[4,5-difluoro-2-[(3S)-3-(morpholinomethyl)-3,4-dihydro-1H-isoquinoline-2-carbonyl]phenyl]-N-(4-hydroxyphenyl)-N-[(3-methoxy-2-methyl-phenyl)methyl]-1,2-dimethyl-pyrrole-3-carboxamide |
| 52 | 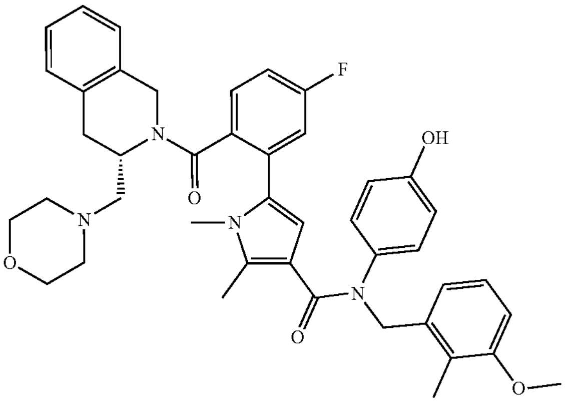 [SMILES: COc1cccc(CN(C(=O)c2cc(-c3cc(F)ccc3C(=O)N3Cc4ccccc4C[C@H]3CN3CCOCC3)n(C)c2C)c2ccc(O)cc2)c1C] | 5-[5-fluoro-2-[(3S)-3-(morpholinomethyl)-3,4-dihydro-1H-isoquinoline-2-carbonyl]phenyl]-N-(4-hydroxyphenyl)-N-[(3-methoxy-2-methyl-phenyl)methyl]-1,2-dimethyl-pyrrole-3-carboxamide |
| 53 | 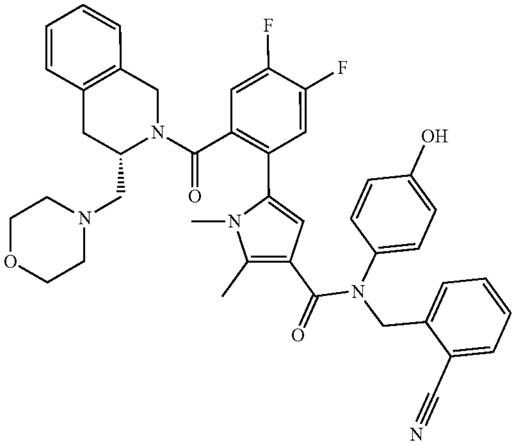 [SMILES: Cc1c(C(=O)N(Cc2ccccc2C#N)c2ccc(O)cc2)cc(-c2cc(F)c(F)cc2C(=O)N2Cc3ccccc3C[C@H]2CN2CCOCC2)n1C] | N-[(2-cyanophenyl)methyl]-5-[4,5-difluoro-2-[(3S)-3-(morpholinomethyl)-3,4-dihydro-1H-isoquinoline-2-carbonyl]phenyl]-N-(4-hydroxyphenyl)-1,2-dimethyl-pyrrole-3-carboxamide |

-continued

| Cmpd # | Structure | IUPAC name |
|---|---|---|
| 54 | 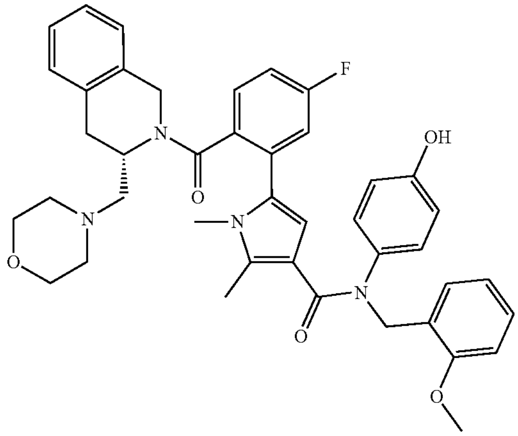 [SMILES: COc1ccccc1CN(C(=O)c1cc(-c2cc(F)ccc2C(=O)N2Cc3ccccc3C[C@H]2CN2CCOCC2)n(C)c1C)c1ccc(O)cc1] | 5-[5-fluoro-2-[(3S)-3-(morpholinomethyl)-3,4-dihydro-1H-isoquinoline-2-carbonyl]phenyl]-N-(4-hydroxyphenyl)-N-[(2-methoxyphenyl)methyl]-1,2-dimethyl-pyrrole-3-carboxamide |
| 55 | 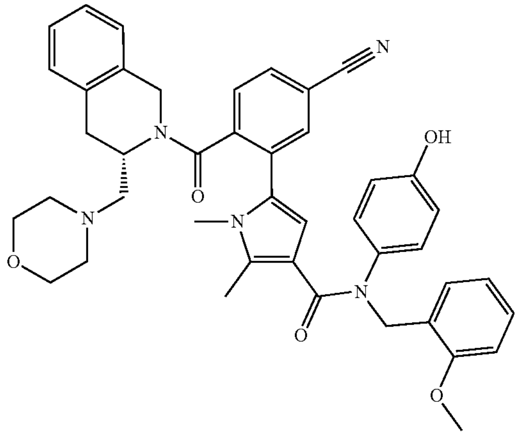 [SMILES: COc1ccccc1CN(C(=O)c1cc(-c2cc(C#N)ccc2C(=O)N2Cc3ccccc3C[C@H]2CN2CCOCC2)n(C)c1C)c1ccc(O)cc1] | 5-[5-cyano-2-[(3S)-3-(morpholinomethyl)-3,4-dihydro-1H-isoquinoline-2-carbonyl]phenyl]-N-(4-hydroxyphenyl)-N-[(2-methoxyphenyl)methyl]-1,2-dimethyl-pyrrole-3-carboxamide |
| 56 | 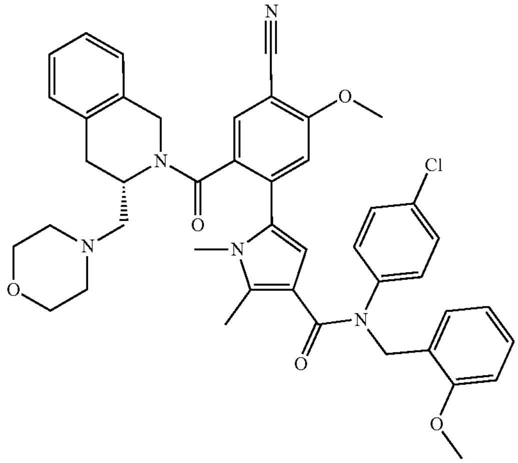 [SMILES: COc1cc(-c2cc(C(=O)N(Cc3ccccc3OC)c3ccc(Cl)cc3)c(C)n2C)c(C(=O)N2Cc3ccccc3C[C@H]2CN2CCOCC2)cc1C#N] | N-(4-chlorophenyl)-5-[4-cyano-5-methoxy-2-[(3S)-3-(morpholinomethyl)-3,4-dihydro-1H-isoquinoline-2-carbonyl]phenyl]-N-[(2-methoxyphenyl)methyl]-1,2-dimethyl-pyrrole-3-carboxamide |

-continued

| Cmpd # | Structure | IUPAC name |
|---|---|---|
| 57 | 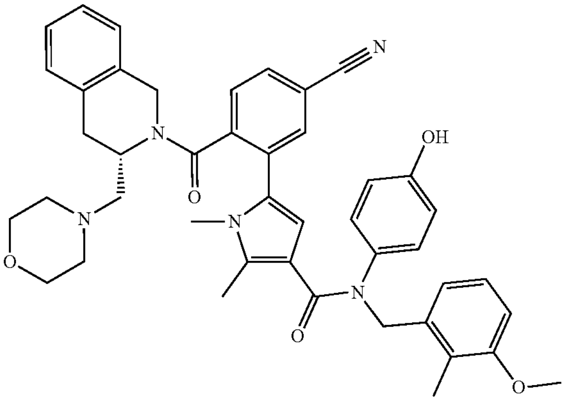 [SMILES: COc1cccc(CN(C(=O)c2cc(-c3cc(C#N)ccc3C(=O)N3Cc4ccccc4C[C@H]3CN3CCOCC3)n(C)c2C)c2ccc(O)cc2)c1C] | 5-[5-cyano-2-[(3S)-3-(morpholinomethyl)-3,4-dihydro-1H-isoquinoline-2-carbonyl]phenyl]-N-(4-hydroxyphenyl)-N-[(3-methoxy-2-methyl-phenyl)methyl]-1,2-dimethyl-pyrrole-3-carboxamide |
| 58 | 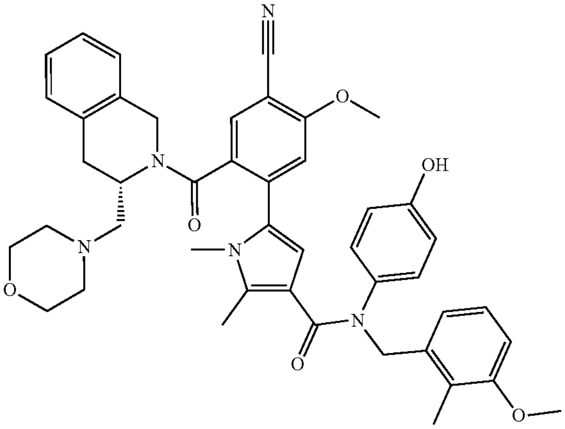 [SMILES: COc1cc(-c2cc(C(=O)N(Cc3cccc(OC)c3C)c3ccc(O)cc3)c(C)n2C)c(C(=O)N2Cc3ccccc3C[C@H]2CN2CCOCC2)cc1C#N] | 5-[4-cyano-5-methoxy-2-[(3S)-3-(morpholinomethyl)-3,4-dihydro-1H-isoquinoline-2-carbonyl]phenyl]-N-(4-hydroxyphenyl)-N-[(3-methoxy-2-methyl-phenyl)methyl]-1,2-dimethyl-pyrrole-3-carboxamide |
| 59 | 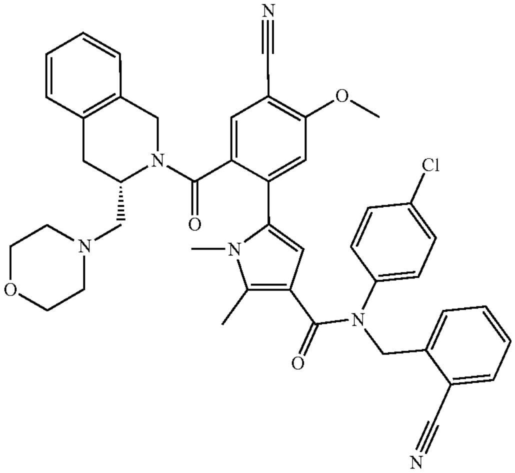 [SMILES: COc1cc(-c2cc(C(=O)N(Cc3ccccc3C#N)c3ccc(Cl)cc3)c(C)n2C)c(C(=O)N2Cc3ccccc3C[C@H]2CN2CCOCC2)cc1C#N] | N-(4-chlorophenyl)-5-[4-cyano-5-methoxy-2-[(3S)-3-(morpholinomethyl)-3,4-dihydro-1H-isoquinoline-2-carbonyl]phenyl]-N-[(2-cyanophenyl)methyl]-1,2-dimethyl-pyrrole-3-carboxamide |

-continued

| Cmpd # | Structure | IUPAC name |
|---|---|---|
| 60 | 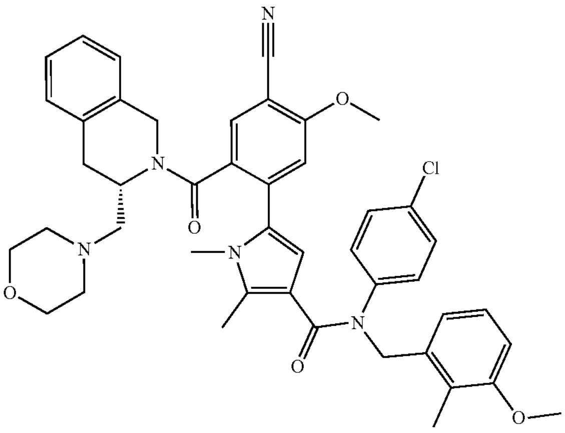 [SMILES: COc1cc(-c2cc(C(=O)N(Cc3cccc(OC)c3C)c3ccc(Cl)cc3)c(C)n2C)c(C(=O)N2Cc3ccccc3C[C@H]2CN2CCOCC2)cc1C#N] | N-(4-chlorophenyl)-5-[4-cyano-5-methoxy-2-[(3S)-3-(morpholinomethyl)-3,4-dihydro-1H-isoquinoline-2-carbonyl]phenyl]-N-[(3-methoxy-2-methyl-phenyl)methyl]-1,2-dimethyl-pyrrole-3-carboxamide |
| 61 | 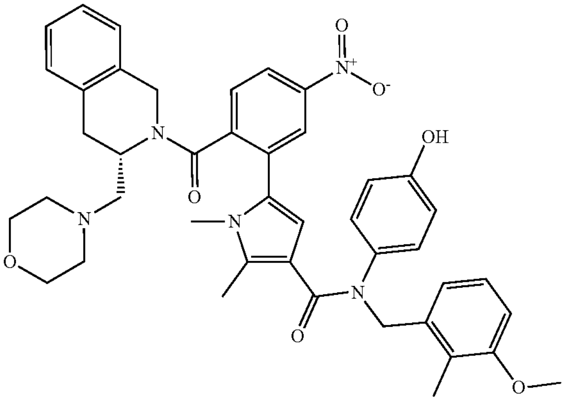 [SMILES: COc1cccc(CN(C(=O)c2cc(-c3cc([N+](=O)[O-])ccc3C(=O)N3Cc4ccccc4C[C@H]3CN3CCOCC3)n(C)c2C)c2ccc(O)cc2)c1C] | N-(4-hydroxyphenyl)-N-[(3-methoxy-2-methyl-phenyl)methyl]-1,2-dimethyl-5-[2-[(3S)-3-(morpholinomethyl)-3,4-dihydro-1H-isoquinoline-2-carbonyl]-5-nitro-phenyl]pyrrole-3-carboxamide |
| 62 | 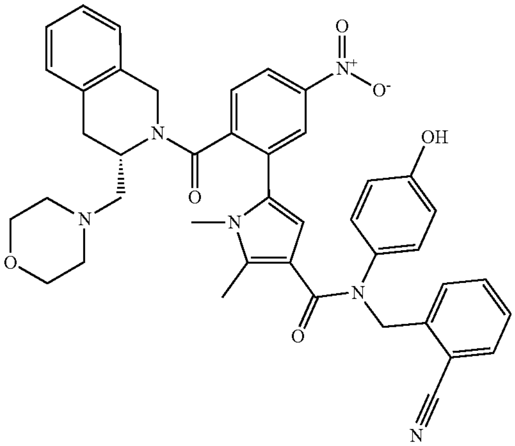 [SMILES: Cc1c(C(=O)N(Cc2ccccc2C#N)c2ccc(O)cc2)cc(-c2cc([N+](=O)[O-])ccc2C(=O)N2Cc3ccccc3C[C@H]2CN2CCOCC2)n1C] | N-[(2-cyanophenyl)methyl]-N-(4-hydroxyphenyl)-1,2-dimethyl-5-[2-[(3S)-3-(morpholinomethyl)-3,4-dihydro-1H-isoquinoline-2-carbonyl]-5-nitro-phenyl]pyrrole-3-carboxamide |

-continued

| Cmpd # | Structure | IUPAC name |
| --- | --- | --- |
| 63 | 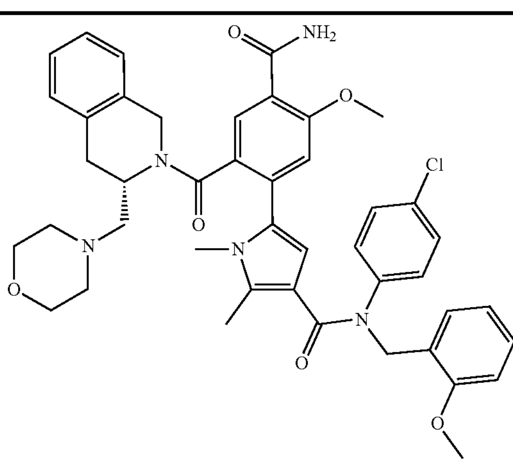 | 5-[4-carbamoyl-5-methoxy-2-[(3S)-3-(morpholinomethyl)-3,4-dihydro-1H-isoquinoline-2-carbonyl]phenyl]-N-(4-chlorophenyl)-N-[(2-methoxyphenyl)methyl]-1,2-dimethyl-pyrrole-3-carboxamide |
| 64 | 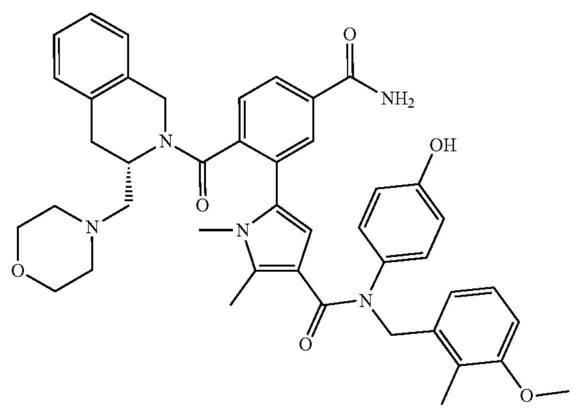 [SMILES: COc1cccc(CN(C(=O)c2cc(-c3cc(C(N)=O)ccc3C(=O)N3Cc4ccccc4C[C@H]3CN3CCOCC3)n(C)c2C)c2ccc(O)cc2)c1C] | 5-[5-carbamoyl-2-[(3S)-3-(morpholinomethyl)-3,4-dihydro-1H-isoquinoline-2-carbonyl]phenyl]-N-(4-hydroxyphenyl)-N-[(3-methoxy-2-methyl-phenyl)methyl]-1,2-dimethyl-pyrrole-3-carboxamide |
| 65 | 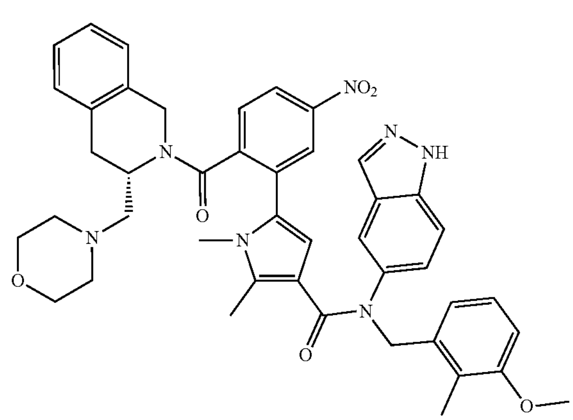 [SMILES: COc1cccc(CN(C(=O)c2cc(-c3cc([N+](=O)[O-])ccc3C(=O)N3Cc4ccccc4C[C@H]3CN3CCOCC3)n(C)c2C)c2ccc3[nH]ncc3c2)c1C] | N-(1H-indazol-5-yl)-N-[(3-methoxy-2-methyl-phenyl)methyl]-1,2-dimethyl-5-[2-[(3S)-3-(morpholinomethyl)-3,4-dihydro-1H-isoquinoline-2-carbonyl]-5-nitro-phenyl]pyrrole-3-carboxamide |

-continued

| Cmpd # | Structure | IUPAC name |
|---|---|---|
| 66 | 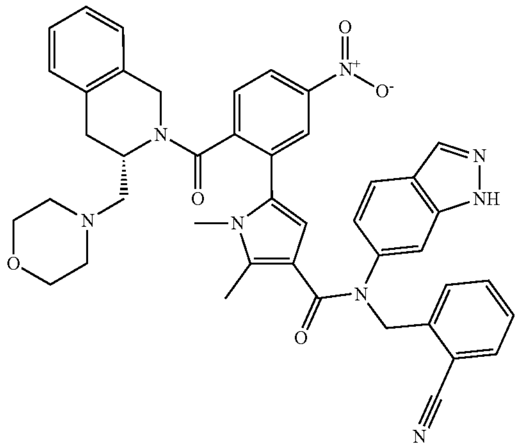 [SMILES: Cc1c(C(=O)N(Cc2ccccc2C#N)c2ccc3cn[nH]c3c2)cc(-c2cc([N+](=O)[O-])ccc2C(=O)N2Cc3ccccc3C[C@H]2CN2CCOCC2)n1C] | N-[(2-cyanophenyl)methyl]-N-(1H-indazol-6-yl)-1,2-dimethyl-5-[2-[(3S)-3-(morpholinomethyl)-3,4-dihydro-1H-isoquinoline-2-carbonyl]-5-nitro-phenyl]pyrrole-3-carboxamide |
| 67 | 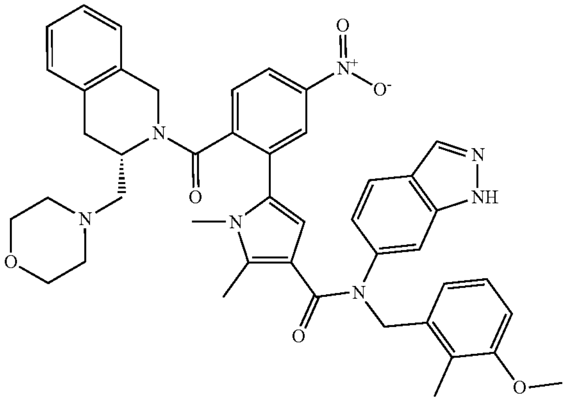 [SMILES: COc1cccc(CN(C(=O)c2cc(-c3cc([N+](=O)[O-])ccc3C(=O)N3Cc4ccccc4C[C@H]3CN3CCOCC3)n(C)c2C)c2ccc3cn[nH]c3c2)c1C] | N-(1H-indazol-6-yl)-N-[(3-methoxy-2-methyl-phenyl)methyl]-1,2-dimethyl-5-[2-[(3S)-3-(morpholinomethyl)-3,4-dihydro-1H-isoquinoline-2-carbonyl]-5-nitro-phenyl]pyrrole-3-carboxamide |
| 68 | 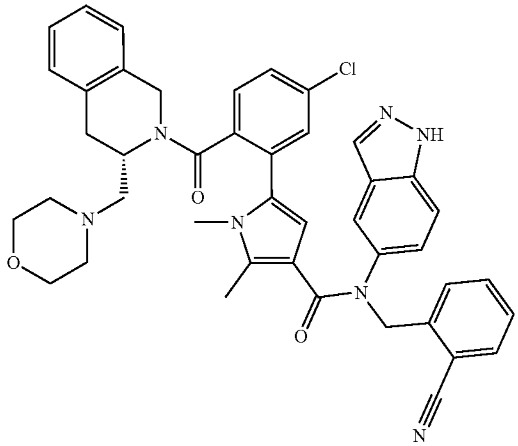 [SMILES: Cc1c(C(=O)N(Cc2ccccc2C#N)c2ccc3[nH]ncc3c2)cc(-c2cc(Cl)ccc2C(=O)N2Cc3ccccc3C[C@H]2CN2CCOCC2)n1C] | 5-[5-chloro-2-[(3S)-3-(morpholinomethyl)-3,4-dihydro-1H-isoquinoline-2-carbonyl]phenyl]-N-[(2-cyanophenyl)methyl]-N-(1H-indazol-5-yl)-1,2-dimethyl-pyrrole-3-carboxamide |

-continued

| Cmpd # | Structure | IUPAC name |
|---|---|---|
| 69 | 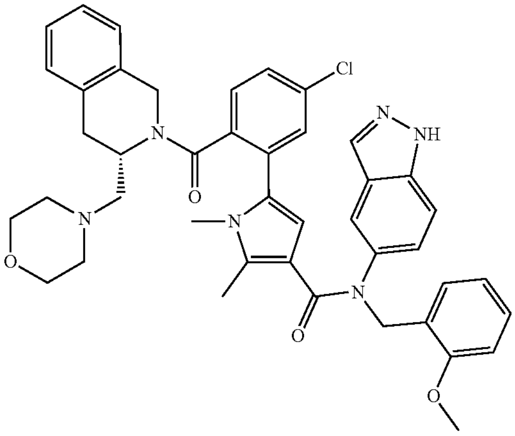 [SMILES: COc1ccccc1CN(C(=O)c1cc(-c2cc(Cl)ccc2C(=O)N2Cc3ccccc3C[C@H]2CN2CCOCC2)n(C)c1C)c1ccc2[nH]ncc2c1] | 5-[5-chloro-2-[(3S)-3-(morpholinomethyl)-3,4-dihydro-1H-isoquinoline-2-carbonyl]phenyl]-N-(1H-indazol-5-yl)-N-[(2-methoxyphenyl)methyl]-1,2-dimethyl-pyrrole-3-carboxamide |
| 70 | 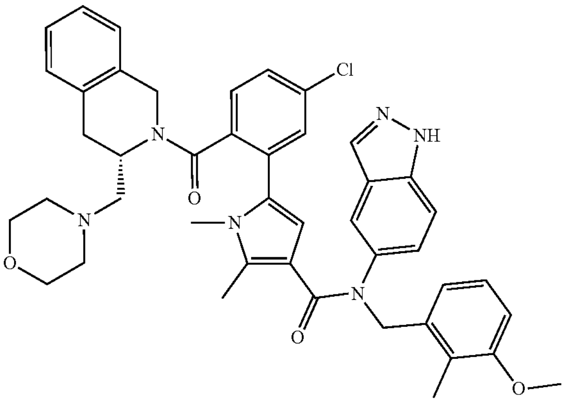 [SMILES: COc1cccc(CN(C(=O)c2cc(-c3cc(Cl)ccc3C(=O)N3Cc4ccccc4C[C@H]3CN3CCOCC3)n(C)c2C)c2ccc3[nH]ncc3c2)c1C] | 5-[5-chloro-2-[(3S)-3-(morpholinomethyl)-3,4-dihydro-1H-isoquinoline-2-carbonyl]phenyl]-N-(1H-indazol-5-yl)-N-[(3-methoxy-2-methyl-phenyl)methyl]-1,2-dimethyl-pyrrole-3-carboxamide |
| 71 | 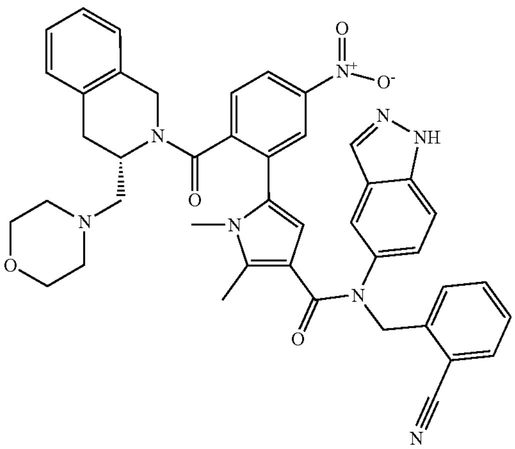 [SMILES: Cc1c(C(=O)N(Cc2ccccc2C#N)c2ccc3[nH]ncc3c2)cc(-c2cc([N+](=O)[O-])ccc2C(=O)N2Cc3ccccc3C[C@H]2CN2CCOCC2)n1C] | N-[(2-cyanophenyl)methyl]-N-(1H-indazol-5-yl)-1,2-dimethyl-5-[2-[(3S)-3-(morpholinomethyl)-3,4-dihydro-1H-isoquinoline-2-carbonyl]-5-nitro-phenyl]pyrrole-3-carboxamide |

-continued

| Cmpd # | Structure | IUPAC name |
|---|---|---|
| 72 | 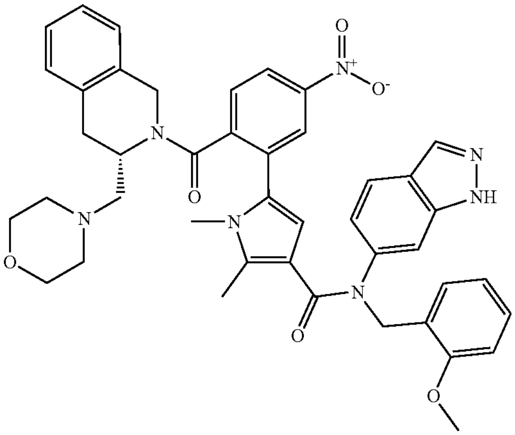 [SMILES: COc1ccccc1CN(C(=O)c1cc(-c2cc([N+](=O)[O-])ccc2C(=O)N2Cc3ccccc3C[C@H]2CN2CCOCC2)n(C)c1C)c1ccc2cn[nH]c2c1] | N-(1H-indazol-6-yl)-N-[(2-methoxyphenyl)methyl]-1,2-dimethyl-5-[2-[(3S)-3-(morpholinomethyl)-3,4-dihydro-1H-isoquinoline-2-carbonyl]-5-nitro-phenyl]pyrrole-3-carboxamide |
| 73 | 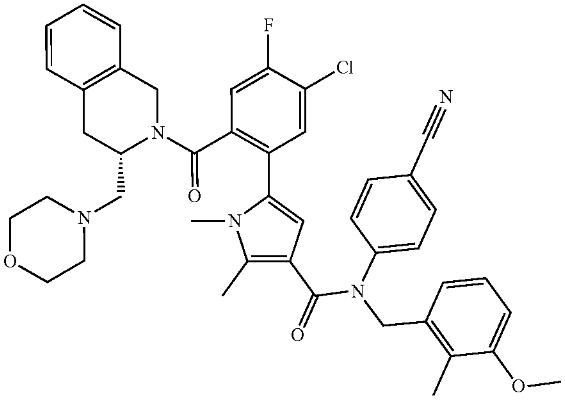 [SMILES: COc1cccc(CN(C(=O)c2cc(-c3cc(Cl)c(F)cc3C(=O)N3Cc4ccccc4C[C@H]3CN3CCOCC3)n(C)c2C)c2ccc(C#N)cc2)c1C] | 5-[5-chloro-4-fluoro-2-[(3S)-3-(morpholinomethyl)-3,4-dihydro-1H-isoquinoline-2-carbonyl]phenyl]-N-(4-cyanophenyl)-N-[(3-methoxy-2-methyl-phenyl)methyl]-1,2-dimethyl-pyrrole-3-carboxamide |
| 74 | 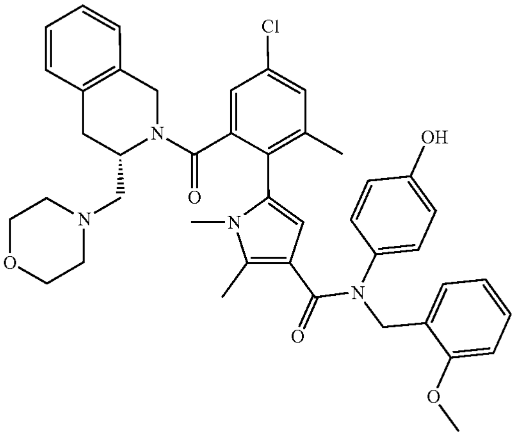 [SMILES: COc1ccccc1CN(C(=O)c1cc(-c2c(C)cc(Cl)cc2C(=O)N2Cc3ccccc3C[C@H]2CN2CCOCC2)n(C)c1C)c1ccc(O)cc1] | 5-[4-chloro-2-methyl-6-[(3S)-3-(morpholinomethyl)-3,4-dihydro-1H-isoquinoline-2-carbonyl]phenyl]-N-(4-hydroxyphenyl)-N-[(2-methoxyphenyl)methyl]-1,2-dimethyl-pyrrole-3-carboxamide |

or a pharmaceutically acceptable salt, stereoisomer, solvate, or tautomer thereof.

10. A pharmaceutical composition comprising the compound of claim 1 or pharmaceutically acceptable salts, solvates, stereoisomers, or tautomers thereof, and a pharmaceutically acceptable carrier.

11. The pharmaceutical composition of claim 10, further comprising an additional pharmaceutically active agent.

12. A method of inhibiting a BCL-2 protein, comprising of administering to a subject in need of a treatment a compound of claim 1.

13. A method of treating a disease or disorder associated with the inhibition of a BCL-2 protein, comprising of administering to a subject in need of a treatment a compound of claim 1.

14. A method of treating cancer, comprising of administering to a subject in need of a treatment for cancer a compound of claim 1.

15. The method of claim 14, wherein the cancer is selected from bladder cancer, bone cancer, brain cancer, breast cancer, cardiac cancer, cervical cancer, colon cancer, colorectal cancer, esophageal cancer, fibrosarcoma, gastric cancer, gastrointestinal cancer, head, spine and neck cancer, Kaposi's sarcoma, kidney cancer, leukemia, liver cancer, lymphoma, melanoma, multiple myeloma, pancreatic cancer, penile cancer, testicular germ cell cancer, thymoma carcinoma, thymic carcinoma, lung cancer, ovarian cancer, and prostate cancer.

16. The method of any one of claims 12-15, wherein the subject is a mammal.

17. The method of claim 16, wherein the subject is a human.

18. The method of any one of claim 12 or 13, wherein the BCL-2 protein is Isoform 1.

19. The method of any one of claim 12 or 13, wherein the BCL-2 protein is Isoform 2.

* * * * *